US009970025B2

(12) United States Patent
Alphey

(10) Patent No.: US 9,970,025 B2
(45) **Date of Patent: *May 15, 2018**

(54) GENE EXPRESSION SYSTEM USING ALTERNATIVE SPLICING IN INSECTS

(71) Applicant: Oxitec Limited, Abingdon, Oxfordshire (GB)

(72) Inventor: Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 44 days.

This patent is subject to a terminal disclaimer.

(21) Appl. No.: 14/991,825

(22) Filed: Jan. 8, 2016

(65) Prior Publication Data

US 2016/0122780 A1 May 5, 2016

Related U.S. Application Data

(63) Continuation of application No. 12/278,849, filed as application No. PCT/GB2007/000488 on Feb. 12, 2007, now abandoned, which is a continuation-in-part of application No. 11/352,177, filed on Feb. 10, 2006, now Pat. No. 9,133,477.

(30) Foreign Application Priority Data

Oct. 25, 2006 (GB) .................................. 0621234.4

(51) Int. Cl.

| | |
|---|---|
| ***C12N 15/00*** | (2006.01) |
| ***C12N 15/90*** | (2006.01) |
| ***C12N 15/85*** | (2006.01) |
| ***A01K 67/033*** | (2006.01) |

(52) U.S. Cl.

CPC ...... *C12N 15/8509* (2013.01); *A01K 67/0335* (2013.01); *A01K 67/0339* (2013.01); *A01K 2217/05* (2013.01); *A01K 2227/703* (2013.01); *A01K 2227/706* (2013.01); *A01K 2267/02* (2013.01); *C12N 2830/003* (2013.01); *C12N 2830/008* (2013.01); *C12N 2830/42* (2013.01); *C12N 2830/75* (2013.01); *C12N 2840/44* (2013.01)

(58) Field of Classification Search

USPC .... 435/3, 6.1, 6.11, 91.1, 91.31, 320.1, 348, 435/455; 536/23.1, 24; 800/8, 21

See application file for complete search history.

(56) References Cited

U.S. PATENT DOCUMENTS

| | | | | |
|---|---|---|---|---|
| 5,254,801 | A | 10/1993 | Dotson et al. | |
| 5,278,057 | A | 1/1994 | Jorgensen | |
| 5,670,353 | A | 9/1997 | Ahlquist et al. | |
| 5,674,747 | A | 10/1997 | Hammock et al. | |
| 5,773,697 | A | 6/1998 | Tomes et al. | |
| 5,851,796 | A | 12/1998 | Schatz | |
| 5,977,441 | A | 11/1999 | Oliver et al. | |
| 6,200,800 | B1 | 3/2001 | Choulika et al. | |
| 6,235,278 | B1 | 5/2001 | Miller et al. | |
| 6,338,040 | B1 | 1/2002 | Buman et al. | |
| 6,962,810 | B2 | 11/2005 | Fraser et al. | |
| 7,998,475 | B2 | 8/2011 | Alphey | |
| 8,124,404 | B2 | 2/2012 | Alphey | |
| 9,121,036 | B2 | 9/2015 | Alphey | |
| 9,125,388 | B2 | 9/2015 | Alphey | |
| 9,133,477 | B2 * | 9/2015 | Alphey | A01K 67/0333 |
| 2003/0015007 | A1 | 8/2003 | Savakis et al. | |
| 2003/0213005 | A1 | 11/2003 | Alphey et al. | |
| 2004/0082032 | A1 | 4/2004 | Bovi et al. | |
| 2005/0221430 | A1 | 10/2005 | Prentice | |
| 2006/0212949 | A1 | 9/2006 | Alphey | |
| 2006/0242717 | A1 | 10/2006 | Alphey | |
| 2006/0275276 | A1 | 12/2006 | Alphey | |
| 2007/0056051 | A1 | 3/2007 | Alphey | |
| 2008/0115233 | A1 | 5/2008 | Alphey et al. | |
| 2009/0170793 | A1 | 7/2009 | Gaur | |
| 2009/0183269 | A1 | 7/2009 | Alphey | |
| 2013/0298266 | A1 | 11/2013 | Alphey et al. | |

FOREIGN PATENT DOCUMENTS

| | | |
|---|---|---|
| EP | 0 636 310 | 2/1995 |
| EP | 0 955 364 | 11/1999 |
| GB | 2355459 | 4/2001 |
| GB | 2 404 382 | 2/2005 |
| GB | 2 443 186 | 4/2008 |
| GB | 2 500 113 | 9/2013 |
| JP | 2008-067678 | 3/2008 |
| WO | WO-90/08830 | 8/1990 |
| WO | WO-94/03619 | 2/1994 |
| WO | WO-96/04393 | 2/1996 |
| WO | WO-96/24605 | 8/1996 |
| WO | WO-97/30162 | 8/1997 |
| WO | WO-98/08960 | 3/1998 |
| WO | WO-99/10488 | 3/1999 |
| WO | WO-00/73510 | 12/2000 |

(Continued)

OTHER PUBLICATIONS

Fryxell et al, Biological and Microbial Control, vol. 88, No. 5, pp. 1221-1232 (1995).*

Adelman et al., "Formation and loss of large, unstable tandem arrays of the piggyBac transposable element in the yellow fever mosquito, Aedes aegypti," Transgenic Res (2004) 13(5):411-425.

Advisory Action for U.S. Appl. No. 11/733,737, dated Aug. 5, 2009, 4 pages.

Advisory Action for U.S. Appl. No. 11/733,737, dated Jun. 3, 2013, 7 pages.

Alignment of SEQ ID No. 22 of D1 (WO 2005/012534) with tTAV, Jul. 4, 2014.

Alphey et al. (2007) "Managing Insecticide Resistance by Mass Release of Engineered Insects" J. Econ. Entomol. 100(5):1642-1649.

Alphey et al. "Dominant Lethality and Insect Population Control," Mol Biochem Parasitol (2002)121(2):173-178.

Alphey et al., "Modeling resistance to genetic control of insects," Journal of Theoretical Biology (2011) 270:42-55.

Appeal Brief for U.S. Appl. No. 11/733,737, filed Feb. 3, 2014, 40 pages.

(Continued)

*Primary Examiner* — Jane Zara

(74) *Attorney, Agent, or Firm* — Morrison & Foerster LLP

(57) ABSTRACT

A polynucleotide expression system is provided that is capable of alternative splicing of RNA transcripts of a polynucleotide sequence to be expressed in an organism.

43 Claims, 59 Drawing Sheets

(56) References Cited

FOREIGN PATENT DOCUMENTS

Figure 1:
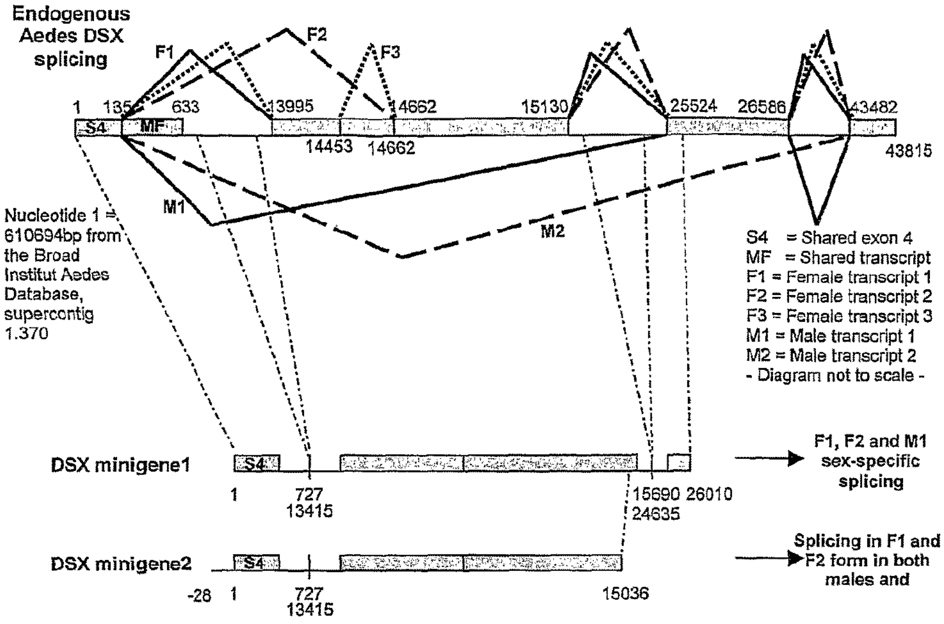

| | | |
|---|---|---|
| WO | WO 01/39599 | 6/2001 |
| WO | WO-01/59088 | 8/2001 |
| WO | WO-01/91802 | 12/2001 |
| WO | WO-02/46444 | 6/2002 |
| WO | WO-02/101061 | 12/2002 |
| WO | WO-04/044150 | 5/2004 |
| WO | WO-04/098278 | 11/2004 |
| WO | WO-04/108933 | 12/2004 |
| WO | WO-05/003364 | 1/2005 |
| WO | WO-05/012534 | 2/2005 |
| WO | WO-07/091099 | 8/2007 |
| WO | WO-2008/134068 | 11/2008 |
| WO | WO-2009/016627 | 2/2009 |
| WO | WO-2009/115569 | 9/2009 |
| WO | WO-2009/157771 | 12/2009 |
| WO | WO-2013/131920 | 9/2013 |

OTHER PUBLICATIONS

Appeal Brief for U.S. Appl. No. 12/278,849, filed Oct. 16, 2014, 31 pages.
Arribas et al., Biochimica et Biophysica Acta (1986) 868:119-127.
Atkinson et al. "Hermes and Other hAT Elements as Gene Vectors in Insects," Insect Transgenesis: Methods and Applications (2000) pp. 219-236.
Atkinson et al., "Genetic transformation systems in insects," Annu Rev Entomol (2001) 46:317-346.
Bello et al., "Spatial and temporal targeting of gene expression in *Drosophila* by means of a tetracycline-dependent transactivator system," Development (1998) 125(12):2193-2202.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Beullens et al., "The isolation of novel inhibitory polypeptides of protein phosphatase 1 from bovine thymus nuclei," J Biol Chem (1992) 267(23):16538-16544.
Bieschke et al. "Doxycycline-Induced Transgene Expression During *Drosophila* Development and Aging," Mol Gen Genet (1998) 258(6):571-579.
Blitvich et al., Insect Molecular Biology (2002) 11(5):431-442.
Boudrez et al., "Identification of MYPT1 and NIPP1 as subunits of protein phosphatase 1 in rat liver cytosol," FEBS Letters 455 (1999) 175-178.
Burcin et al., "A regulatory system for target gene expression," Frontiers in Biosc. (1998) 3:c1-7.
Cabera et al., "Expression Pattern of Ga14 Enhancer Trap Insertions Into the bric a brac Locus Generated by P Element Replacement," Genesis (2002) 34:62-65.
Carriere et al., "Reversing Insect Adaptation to Transgenic Insecticidal Plants," Proc. R. Soc. Lond. B. (2001) 268:1475-1480.
Chen et al. "The Use of Modified Tetracycline Regulatory Expression System with Reduced Basal Level to Develop and in Vivo Biopesticide Expression System," Food Sci Agricult Chem (2000) 2(4):220-225.
Communication pursuant to Article 94(3) EPC for EP 07712717.3, dated Jul. 11, 2014, 8 pages.
Communication pursuant to Article 94(3) EPC for EP 07712717.3, dated Nov. 6, 2015, 4 pages.
Communication pursuant to Article 96(2) EPC for EP 00979774.7, dated Mar. 8, 2006, 4 pages.
Communication pursuant to Article 96(2) EPC for EP 00979774.7, dated Aug. 2, 2005, 4 pages.
Communication pursuant to Article 96(2) EPC for EP 00979774.7, dated Oct. 4, 2004, 4 pages.
Communication pursuant to Article 96(2) EPC for EP 00979774.7, dated Nov. 28, 2003, 5 pages.
Communication under Rule 51(4) EPC, directed to EP 00979774.7, dated May 9, 2007, 4 pages.
Davis et al. "Engineered Underdominance Allows Efficient and Economical Introgression of Traits into Pest Populations," J. Theor. Biol. (2001) 212(1):83-98.
Decision on Further Processing for EP 00979774.7, dated Jan. 29, 2007, 1 page.
Deng et al., "A targeted gene silencing technique shows that *Drosophila myosin* VI is required for egg chamber and imaginal disc morphogenesis," J Cell Science (1999) 112:3677-3690.
Devault et al., "Biotechnology and new integrated pest management approaches," Nature Biotechnology (1996) 14:46-49.
Egloff et al., "Structural basis for the recognition of regulatory subunits by the catalytic subunit of protein phosphatase 1," EMBO J (1997) 16(8):1876-1887.
Elick et al. "Analysis of the Cis-Acting DNA Elements Required for piggyback Transposable Element Excision," Mol. Gen. Genet. (1997) 255:605-610.
Office Action for EP 04743590.4, dated Feb. 16, 2012, 8 pages.
Ernst, U. "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD (1991) (Abstract Only).
Examination Report for European patent application serial No. 04743590.4, dated Nov. 14, 2008, 4 pp.
Examination Report for NZ 519175, dated Nov. 2003, 1 page.
Examination Report for NZ 519175, dated Jul. 9, 2002, 2 pages.
Examiner's Answer to Appeal Brief for U.S. Appl. No. 11/733,737, dated Jul. 18, 2014, 12 pages.
Final Office Action for U.S. Appl. No. 10/148,041, dated Mar. 7, 2006, 9 pages.
Final Office Action for U.S. Appl. No. 10/562,843, dated Aug. 25, 2011, 5 pages.
Final Office Action for U.S. Appl. No. 10/562,843, dated Feb. 3, 2010, 5 pages.
Final Office Action for U.S. Appl. No. 10/566,448, dated Nov. 10, 2009, 18 pages.
Final Office Action for U.S. Appl. No. 10/566,448, dated Feb. 2, 2011, 13 pages.
Final Office Action for U.S. Appl. No. 10/566,448, dated Aug. 14, 2014, 24 pages.
Final Office Action for U.S. Appl. No. 11/352,177, dated Jun. 10, 2009, 14 pages.
Final Office Action for U.S. Appl. No. 11/352,177, dated Oct. 14, 2014, 6 pages.
Final Office Action for U.S. Appl. No. 11/352,177, dated Mar. 16, 2011, 17 pages.
Final Office Action for U.S. Appl. No. 11/733,737, dated Apr. 17, 2009, 16 pages.
Final Office Action for U.S. Appl. No. 11/733,737, dated Aug. 4, 2010, 18 pages.
Final Office Action for U.S. Appl. No. 11/733,737, dated Jan. 7, 2013, 26 pages.
Final Office Action for U.S. Appl. No. 12/278,849, dated Mar. 17, 2014, 24 pages.
Final Office Action for U.S. Appl. No. 12/278,849, dated Oct. 9, 2015, 7 pages.
Final Office Action for U.S. Appl. No. 12/278,849, dated Jun. 6, 2013, 24 pages.
Final Office Action for U.S. Appl. No. 13/942,601, dated Jul. 31, 2014, 23 pages.
Fryxell et al., "Autocidal biological control: a general strategy for insect control based on genetic transformation with a highly conserved gene," J Econ Entomol (1995) 88(5):1221-1232.
Fu et al. "Female-specific insect lethality engineered using alternative splicing", Nature Biotechnology (2007) 25(3):353-357.
Fu et al., "Female-specific flightless phenotype for mosquito control," PNAS (2010) 107(10):4550-4554.
Funaguma et al. The Bmdsx transgene including trimmed introns is sex-specifically spliced in tissues of the silkworm, *Bombyx moil*, Journal of Insect Science (online) (2005), 5(17):1-6.
Further Search Report for GB 9928181.8, dated Apr. 30, 2001.

(56) References Cited

OTHER PUBLICATIONS

Fussenegger et al., "Autoregulated multiscistronic expression vectors provide one-step cloning of regulated product gene expression in mammalian cells," Biotechnol Prog (1997) 13:733-740.
Fussenegger et al., "Regulated Multicistronic Expression Technology for Mammalian Metabolic Engineering," Cytotechnology (1998) 28:111-125.
Fux et al., "Novel Macrolide-Adjustable Bidirectional Expression Modules for Coordinated Expression of Two Different Transgenes in Mice," J Gene Medicine (2003) 5:1067-1079.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Gloor et al. "Targeted Gene Replacement in *Drosophila* Via P Element-Induced Gap Repair," Science (1991) 253:1110-1117.
Golovnin et al., "The su(Hw) insulator can disrupt enhancer-promoter interactions when located more than 20 kilobases away from the *Drosophila* achaete-scute complex," Mol Cell Biol (1999) 19(5):3443-3456.
Gong et al. "A dominant lethal genetic system for autocidal control of the Mediterranean fruitfly", Nature Biotechnology (2005) 23(4):453-456.
Gonzy-Treboul et al. "Enhancer-Trap Targeting at the Broad-Complex Locus of *Drosophila melanogaster*," Genes Dev. (1995) 9:1137-1148.
Gossen et al., "Tetracyclines in the control of gene expression in eukaryotes," Tetracyclines I Biology, Chemistry and Medicine (2001) pp. 139-157.
Guo et al., "Species-specific signals for the splicing of a short *Drosophila intron* in vitro," Mol Cell Biol (1993) 13(2):1104-1118.
Handler et al. "A Current Prospective on Insect Gene Transformation," Insect Biochem. Mol. Biol. (2001) 31(2):111-128.
Handler, A. "Use of piggyback Transposon for Germ-Line Transformation of insects," Insect Biochem Mol Biol (2002) 32:1211-1220.
Harris et al., "Field performance of engineered male mosquitoes," Nature Biotechnology (2011) 29(11):1034-1039.
Heinrich et al. "A Repressible Female-Specific Lethal Genetic System for Making Transgenic Insect Strains Suitable for a Sterile-Release Program," Proc. Nat. Acad. Sci. USA (2000) 97:8229-8232.
Heslip et al. "Targeted Transposition at the vestigial Locus of *Drosophila melanogaster*," Genetics (1994) 138:1127-1135.
Hofmann et al. "Rapid Retroviral Delivery of Tetracycline-Inducible Genes in a Single Autoregulatory Cassette," Proc. Nat. Acad. Sci. USA (1996) 93:5185-5190.
Hondred et al., Plant Physiology (1999) 119:713-723.
Horn et al. "Highly sensitive, fluorescent transformation marker for Drosophil49a transgenesis" Dev Genes Evol (2000) 210:623-629.
Horn et al. "PiggyBac-Based Insertional Metagenesis and Enhancer Detection as a Tool for Functional Insect Genomics," Genetics (2003)163(2):647-661.
Horn et al. "A Transgene-Based Embryo-Specific Lethality System for Insect Pest Management," Nat. Biotechnol. 21(1):64-70.
Horn et al., "Highly sensitive, fluorescent transformation marker for *Drosophila* transgenesis," Dev Genes Evol (2000) 210:623-629.
Horn et al50. "Fluorescent Transformation Markers for Insect Transgenesis," Insect Biochem. Mol. Biol. (2002) 32:1221-1235.
Imai, C. "Control of Insecticide Resistance in a Field Population of Houseflies, *Musca domestica*, by Releasing Susceptible Flies," Res. Popul. Ecol. (1987) 29:129-146.
Inoue et al., "Binding of the *Drosophila* Sex-lethal gene product to the alternative splice site of transformer primary transcript," Nature (1990) 344:461-463.
International Preliminary Examination Report for PCT/GB00/04541, dated Apr. 4, 2002, 2 pages.
International Preliminary Report on Patentability for PCT/GB2004/002021, dated Nov. 18, 2005, 6 pages.
International Preliminary Report on Patentability for PCT/GB2004/002869, dated Jan. 3, 2006, 9 pages.
International Preliminary Report on Patentability for PCT/GB2007/000488, date of search May 5, 2008, 11 pages.
International Search Report for PCT/GB00/04541, dated Dec. 5, 2001.
International Search Report for PCT/GB2004/002021, dated Oct. 6, 2004, 3 pages.
International Search Report for PCT/GB2004/002869, dated Jan. 11, 2005, 5 pages.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Johnson-Schlitz et al. "P-Element-Induced Interallelic Gene Conversion of Insertions and Deletions in *Drosophila melanogaster*," Mol Cell Biol. (1993) 13:70067018.
Krafsur, "Bionomics of the face fly, *Musca autumnalis*," Annu Rev Entomol (1997) 42:503-523 (Abstract).
Lankenau et al. "Comparison of Targeted-Gene Replacement Frequencies in *Drosophila melanogaster* at the Forked and White Loci," Mol. Cell Biol. (1996) 16:35353544.
Louis et al. "A Theoretical Model for the Regulation of Sex-Lethal, a Gene That Controls Sex Determination and Dosage Compensation in *Drosophila melanogaster*," Genetics (2003) 165:1355-1384.
Loukeris et al. "Introduction of the transposable element Minos into the germ line of *Drosophila melanogaster*" Proc. Natl. Acad. Sci. USA (1995) 92:9485-9489.
Munoz et al. (2004) "The AeAct-4 gene is expressed in the developing flight muscles of female Aedes aegypti", Insect Molecular Biology 13(5):563-568.
Namciu et al., "Human matrix attachment regions insulate transgene expression from chromosomal position effects in *Drosophila melanogaster*," Mol Cell Biol (1998) 18(4):2382-2391.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
Notice of Allowance for U.S. Appl. No. 10/566,448, dated Mar. 19, 2015, 10 pages.
Notice of Allowance for U.S. Appl. No. 11/352,177, dated Mar. 17, 2015, 10 pages.
Notice of Allowance for U.S. Appl. No. 11/352,177, dated Jul. 7, 2015, 9 pages.
Notice of Allowance for U.S. Appl. No. 13/942,601, dated Apr. 10, 2015, 11 pages.
Notice of Allowance for U.S. Appl. No. 13/942,601, dated Jul. 7, 2015, 9 pages.
Notice of Appeal for U.S. Appl. No. 10/566,448, filed Feb. 18, 2015, 4 pages.
Notice of Appeal for U.S. Appl. No. 11/733,737, filed Jul. 3, 2013, 1 page.
Notice of Appeal for U.S. Appl. No. 12/278,849, filed Jun. 17, 2014, 1 page.
Notice of Appeal for U.S. Appl. No. 13/942,601, filed Feb. 2, 2015, 1 page.
Noting of loss of rights (R. 69(1) EPC) for EP 00979774.7, dated Jul. 17, 2004, 1 page.
O'Brochta et al., "Gene vector and transposable element behavior in mosquitos," J Exp Biol (2003) 206(Pt 21):3823-3834.
Office Action for AU 17165/01, dated Jul. 13, 2004, 3 pages.
Office Action for CN 00818682.0, fax dated Feb. 4, 2005, 7 pages.
Office Action for IL 149885, dated Apr. 26, 2007, 4 pages.
Office Action for U.S. Appl. No. 10/148,041, dated Jul. 1, 2005, 14 pages.
Office Action for U.S. Appl. No. 10/148,041, dated Oct. 10, 2006, 8 pages.
Office Action for U.S. Appl. No. 10/556,804, dated Feb. 1, 2011, 4 pages.
Office Action for U.S. Appl. No. 10/556,804, dated May 12, 2010, 8 pages.
Office Action for U.S. Appl. No. 10/562,843, dated Nov. 12, 2008, 6 pages.

(56) References Cited

OTHER PUBLICATIONS

Office Action for U.S. Appl. No. 10/562,843, dated Feb. 16, 2011, 4 pages.
Office Action for U.S. Appl. No. 10/562,843, dated Jul. 30, 2010, 7 pages.
Office Action for U.S. Appl. No. 10/562,843, dated Jun. 9, 2009, 5 pages.
Office Action for U.S. Appl. No. 10/566,448, dated Nov. 22, 2013, 24 pages.
Office Action for U.S. Appl. No. 10/566,448, dated Apr. 27, 2010, 12 pages.
Office Action for U.S. Appl. No. 10/566,448, dated Jan. 7, 2009, 14 pages.
Office Action for U.S. Appl. No. 11/352,177, dated Apr. 14, 2010, 15 pages.
Office Action for U.S. Appl. No. 11/352,177, dated Jan. 30, 2014, 17 pages.
Office Action for U.S. Appl. No. 11/733,737, dated Oct. 1, 2009, 21 pages.
Office Action for U.S. Appl. No. 11/733,737, dated Apr. 10, 2008, 8 pages.
Office Action for U.S. Appl. No. 11/733,737, dated Mar. 27, 2012, 17 pages.
Office Action for U.S. Appl. No. 11/733,737, dated Jun. 28, 2011, 14 pages.
Office Action for U.S. Appl. No. 11/733,737, dated Feb. 8, 2011, 6 pages.
Office Action for U.S. Appl. No. 12/278,849, dated Mar. 10, 2015, 18 pages.
Office Action for U.S. Appl. No. 12/278,849, dated Dec. 5, 2014, 15 pages.
Office Action for U.S. Appl. No. 12/278,849, dated Aug. 9, 2013, 22 pages.
Office Action for U.S. Appl. No. 12/278,849, dated Mar. 17, 2014, 24 pages.
Office Action for U.S. Appl. No. 12/278,849, dated Oct. 10, 2012, 12 pages.
Office Action for U.S. Appl. No. 13/942,601, dated Nov. 4, 2013, 16 pages.
Oxitec Nov. 2011 Newsletter, http://www.oxitec.com/our-news/newsletters/november-2011-newsletter/, downloaded Dec. 13, 2011, 6 pages.
Pane et al., "The transformer gene in Ceratitis capitate provides a genetic basis for selecting and remembering the sexual fate," Development (2002) 129:3715-3725.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
Phuc et al., "Late-acting dominant lethal genetic systems and mosquito control," BMC Biology (2007) 5:11, 11 pages.
PiggyBac website, http://piggybac.bio.nd.edu/, Mar. 21, 2006, 5 pp. Raton CRC Press, pp. 219-235.
Rejection for CN 00818682.0, fax dated Jan. 26, 2006, 4 pages.
Reply Brief and Request for Oral Hearing for U.S. Appl. No. 11/733,737, filed Sep. 18, 2014, 16 pages.
Request for Continued Examination for U.S. Appl. No. 10/148,041, filed Sep. 11, 2006, 8 pages.
Request for Continued Examination for U.S. Appl. No. 10/566,448, filed Aug. 2, 2011, 23 pages.
Request for Continued Examination for U.S. Appl. No. 10/566,448, filed Feb. 25, 2010, 21 pages.
Request for Continued Examination for U.S. Appl. No. 11/352,177, filed Jun. 17, 2015, 14 pages.
Request for Continued Examination for U.S. Appl. No. 11/352,177, filed Sep. 16, 2011, 14 pages.
Request for Continued Examination for U.S. Appl. No. 11/733,737, filed Aug. 14, 2009, 1 page.
Request for Further Processing for EP 00979774.7, filed Jan. 4, 2007, 4 pages.
Response for U.S. Appl. No. 10/562,843, filed Feb. 24, 2009, 13 pages.
Response for U.S. Appl. No. 10/562,843, filed Nov. 30, 2010, 8 pages.
Response for U.S. Appl. No. 10/562,843, filed Oct. 5, 2009, 10 pages.
Response to Communication for EP 00979774.7, filed Apr. 14, 2005, 7 pages.
Response to Communication for EP 00979774.7, filed Sep. 20, 2004, 8 pages.
Response to Communication for EP 00979774.7, filed Feb. 13, 2006, 8 pages.
Response to Final Office Action for U.S. Appl. No. 10/566,448, filed Dec. 15, 2014, 9 pages.
Response to Final Office Action for U.S. Appl. No. 11/352,177, filed Dec. 3, 2014, 8 pages.
Response to Final Office Action for U.S. Appl. No. 11/733,737, filed Jul. 17, 2009, 26 pages.
Response to Final Office Action for U.S. Appl. No. 11/733,737, filed Dec. 6, 2010, 26 pages.
Response to Final Office Action for U.S. Appl. No. 11/733,737, filed Apr. 8, 2013, 25 pages.
Response to Final Office Action in U.S. Appl. No. 10/562,843, filed Nov. 21, 2011, 6 pages.
Response to Office Action for EP 07712717.3, filed Mar. 16, 2016, 19 pages.
Response to Office Action for U.S. Appl. No. 10/148,041, filed Dec. 5, 2005, 11 pages.
Response to Office Action for U.S. Appl. No. 10/556,804, filed Nov. 12, 2010, 12 pages.
Response to Office Action for U.S. Appl. No. 10/556,804, filed Mar. 25, 2011, 9 pages.
Response to Office Action for U.S. Appl. No. 10/562,843, filed Jun. 16, 2011, 9 pages.
Response to Office Action for U.S. Appl. No. 10/566,448, filed Apr. 22, 2014, 17 pages.
Response to Office Action for U.S. Appl. No. 10/566,448, filed Oct. 27, 2010, 20 pages.
Response to Office Action for U.S. Appl. No. 10/566,448, filed Aug. 28, 2009, 15 pages.
Response to Office Action for U.S. Appl. No. 10/566,448, filed Jul. 7, 2009, 15 pages.
Response to Office Action for U.S. Appl. No. 11/352,177, filed Dec. 10, 2009, 20 pages.
Response to Office Action for U.S. Appl. No. 11/352,177, filed Oct. 14, 2010, 13 pages.
Response to Office Action for U.S. Appl. No. 11/352,177, filed May 28, 2014, 14 pages.
Response to Office Action for U.S. Appl. No. 11/733,737, filed Oct. 10, 2008, 8 pages.
Response to Office Action for U.S. Appl. No. 11/733,737, filed Feb. 18, 2011, 11 pages.
Response to Office Action for U.S. Appl. No. 11/733,737, filed Oct. 28, 2011, 27 pages.
Response to Office Action for U.S. Appl. No. 11/733,737, filed Jan. 29, 2010, 23 pages.
Response to Office Action for U.S. Appl. No. 11/733,737, filed Aug. 9, 2012, 24 pages.
Response to Office Action for U.S. Appl. No. 12/278,849, filed Jan. 9, 2014, 21 pages.
Response to Office Action for U.S. Appl. No. 12/278,849, filed Aug. 7, 2015, 24 pages.
Response to Office Action for U.S. Appl. No. 12/278,849, filed Apr. 10, 2013, 19 pages.
Response to Office Action for U.S. Appl. No. 13/942,601, filed Feb. 4, 2014, 45 pages.
Response to Restriction Requirement for U.S. Appl. No. 10/148,041, filed Apr. 13, 2005, 10 pages.
Response to Restriction Requirement for U.S. Appl. No. 10/556,804, filed Jun. 29, 2009, 2 pages.

(56) References Cited

OTHER PUBLICATIONS

Response to Restriction Requirement for U.S. Appl. No. 10/562,843, filed Jun. 27, 2008, 2 pages.
Response to Restriction Requirement for U.S. Appl. No. 10/566,448, filed Dec. 1, 2008, 9 pages.
Response to Restriction Requirement for U.S. Appl. No. 10/566,448, filed Feb. 8, 2008, 9 pages.
Response to Restriction Requirement for U.S. Appl. No. 11/352,177, filed Mar. 13, 2009, 12 pages.
Response to Restriction Requirement for U.S. Appl. No. 11/352,177, filed Nov. 3, 2008, 8 pages.
Response to Restriction Requirement for U.S. Appl. No. 11/352,177, filed Jun. 9, 2008, 9 pages.
Response to Restriction Requirement for U.S. Appl. No. 11/733,737, filed Jan. 26, 2009, 8 pages.
Response to Restriction Requirement for U.S. Appl. No. 12/278,849, filed Sep. 28, 2010, 13 pages.
Restriction Requirement for U.S. Appl. No. 10/148,041, dated Mar. 10, 2005, 5 pages.
Restriction Requirement for U.S. Appl. No. 10/556,804, dated May 28, 2009, 5 pages.
Restriction Requirement for U.S. Appl. No. 10/562,843, dated Jun. 12, 2008, 6 pages.
Restriction Requirement for U.S. Appl. No. 10/566,448, dated Aug. 29, 2008, 7 pages.
Restriction Requirement for U.S. Appl. No. 10/566,448, dated Jan. 9, 2008, 5 pages.
Restriction Requirement for U.S. Appl. No. 11/352,177, dated Jan. 13, 2009, 10 pages.
Restriction Requirement for U.S. Appl. No. 11/352,177, dated Sep. 2, 2008, 5 pages.
Restriction Requirement for U.S. Appl. No. 11/352,177, dated Mar. 31, 2008,8 pages.
Restriction Requirement for U.S. Appl. No. 11/733,737, dated Dec. 31, 2008, 9 pages.
Restriction Requirement for U.S. Appl. No. 12/278,849, dated May 28, 2010, 7 pages.
Robinson et al. "Mutations and Their Use in Insect Control," Mutation Research (2002) 511(2):113-132.
Ronaldson et al., "Two independent cis-acting elements regulate the sex- and tissue-specific expression of yp3 in *Drosophila melanogaster*," Genet Res. (1995) 66(1):9-17.
Rong et al. "Gene Targeting by Homologous Recombination in *Drosophila*," Science (2000) 288:2013-2018.
Rong et al. "A Targeted Gene Knockout in *Drosophila*," Genetics (2001)157:13071312.
Russ et al. "Self-Deleting Retrovirus Vectors for Gene Therapy," J. Virol. (1996) 70:4927-4932.
Saccone et al. "Sex Determination in Medfly: A Molecular Approach," In; Area-Wide Control of Fruit Flies and Other Pest Insects, Tan, K.H. ed., Penerbit USM, Penag, (2000) pp. 491-496.
Scali et al. "Identification of sex-specific transcripts of the Anopheles gambiae doublesex gene", Journal of Experimental Biology (2005) 208(19):3701-3709.
Schwechheimer et al., "Transactivation of a target gene through feedforward loop activation in plants," Funct Integr Genomics (2000) 1:35-43.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report corresponding to International Application No. PCT/GB2007/000488, dated Jun. 6, 2007.
Search Report Corresponding to International Application No. PCT/GB2004/003263, dated May 11, 2004.
Second Office Action for AU 17165/01, dated Mar. 21, 2006, 2 pages.
Second Office Action for CN 00818682.0, dated Jul. 28, 2006, 4 pages.
Sepp et al. "Conversion of lacZ Enhanced Trap Lines to GAL4 Lines Using Targeted Transposition in *Drosophila melanogaster*," Genetics (1999) 151:1093-1101.
Shelton et al. "Field Tests on Managing Resistance to Bt-Engineered Plants", Nature Biotechnology (2000) 18(3):339-342.
Shockett et al. "A Modified Tetracycline-Regulated System Provides Autoregulatory, Inducible Gene Expression in Cultured Cells and Transgenic Mice," Proc. Nat. Acad. Sci. USA (1995) 92:6522-6526.
Simmons et al., "Field Performance of a Genetically Engineered Strain of Pink Bollworm," PLoS One (2011) 6(9):1-11.
Sondergaard et al., "Nutritional response in a *Drosophila* yolk protein gene promoter," Mol Gen Genet (1995) 248(1):25-32.
Spradling et al., "Transposition of cloned P elements into *Drosophila* germ line chromosomes," Science (1982) 218(4570):341-347.
Stadtfeld et al., "Without a trace? PiggyBac-ing toward pluripotency," Nat Methods (2009) 6(5):329-330.
Stebbins et al. "Adaptable Doxycycline-Regulated Gene Expression Systems for *Drosophila*," Gene (2001) 270:103-111.
Stebbins et al. "Tetracycline-Inducible Systems for *Drosophila*," Proc. Nat. Acad. Sci. USA. (2001) 98:10775-10780.
Steiner et al. "Homologous Recombination as the Main Mechanism for DNA Integration and Cause of Rearrangements in the Filamentous Ascomycete Ashbya gossypii," Genetics (1995)140:973-987.
Summary of Office Action for MX PA/a/2002/005337, dated Jan. 3, 2007, 2 pages.
Supplemental response to Office Action for U.S. Appl. No. 11/352,177, dated Oct. 21, 2010, 15 pages.
Thomas et al. "Insect Population Control Using Dominant, Repressible, Lethal Genetic System," Science (2000) 287:2474-2476.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Wobus et al. "A New Transposable Element in Chironomus thummi," Mol. General Genet. (1990) 222:311-316.
Woltjen et al., "PiggyBac transposition reprograms fibroblasts to induced pluripotent stem cells," Nature (2009) 458(7239):766-770.
Wool et al., "Genetically-Induced Susceptibility to Malathion in Tribolium Castaneum Despite Selection for Resistance," Ent. Exp. & Appl. (1980) 28:183190.
Written Opinion corresponding to International Application No. PCT/GB2007/000488, parent of the present application.
Written Opinion for PCT/GB2004/002021, dated Oct. 4, 2004, 5 pages.
Written Opinion for PCT/GB2004/002869, dated Jan. 12, 2005, 8 pages.
Written Opinion for PCT/GB2004/003263, dated Nov. 5, 2004, 5 pages.
Wu et al. "Expression of Highly Controllable Genes in Insect Cells Using a Modified Tetracycline-Regulated Gene Expression System," J. Biotechnol (2000) 80(1):7583.
Communication under Rule 71(3) EPC for EP 07 712 717.3, dated Jun. 20, 2016, 7 pages.

(56) References Cited

OTHER PUBLICATIONS

Formal Report (translation) for BR PI0707579-0, dated Jun. 21, 2016, 2 pages.
Formal Report (translation) for BR PI0413024-3, dated Jun. 7, 2016, 10 pages.
Allen et al., "Flight muscle-specific expression of act88F: GFP in transgenic Culex quinquefasciatus Say (Diptera: Culicidae)," Parasitology Int (2004) 53(4):307-314.
Allen et al., "PiggyBac transformation of the New World screwworm, *Cochliomyia hominivorax*, produces multiple distinct mutant strains," Med. Vet. Entomol (2004) 18:1-9.
Allen et al., "Stable, germ-line transformation of Culex quinquefasciatus (Diptera: Culicidae)," J Med Entomol (2001) 38(5):701-710.
Alphey et al., "Malaria control with genetically manipulated insect vectors," Science (2002) 298:119-21.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique," BMC Biology (2012) 10:51, 8 pages.
Arama et al., "Caspase activity and a specific cytochrome C are required for sperm differentiation in *Drosophila*," Dev Cell (2003) 4(5):687-97.
Barreau et al., "Post-meiotic transcription in *Drosophila* testes," Development (2008) 135(11):1897-1902.
Bauer Dumont et al., "Recurrent positive selection at bgcn, a key determinant of germ line differentiation, does not appear to be driven by simple coevolution with its partner protein bam," Mol Biol Evol (2007) 24(1):182-191.
Beall et al., "Discovery of tMAC: a *Drosophila* testis-specific meiotic arrest complex paralogous to Myb-Muv B," Genes Dev (2007) 21(8):904-919.
Berghammer et al., "A universal marker for transgenic insects," Nature (1999) 402(6760):370-371.
Beumer et al., "Efficient gene targeting in *Drosophila* with zinc-finger nucleases," Genetics (2006)172(4):2391-2403.
Bibikova et al., "Targeted chromosomal cleavage and mutagenesis in *Drosophila* using zinc-finger nucleases," Genetics (2002)161(3):1169-1175.
Black et al., "Why RIDL is not SIT," Trends Parasitol (2011) 27(8):362-370.
Brand et al., "Ectopic expression in *Drosophila*," Methods Cell Biol (1994)44:635-654.
Brand et al., "Targeted gene expression as a means of altering cell fates and generating dominant phenotypes," Development (1993) 118(2):401-415.
Burn et al., "Alternative 5C actin transcripts are localized in different patterns during *Drosophila* embryogenesis," Dev Biol (1989) 131(2):345-355.
Burt et al., "Site-specific selfish genes as tools for the control and genetic engineering of natural populations," Proc Biol Sci (2003) 270:921-928.
Caceres et al., "Mass rearing of temperature sensitive genetic sexing strains in the Mediterranean fruit fly (*Ceratitis capitata*)," Genetica (2002) 115(1):107-116.
Cagan et al., "Spermatogenesis: Borrowing the Apoptotic Machinery," Curr Biol (2003)13:R600-R602.
Catteruccia et al., "An Anopheles transgenic sexing strain for vector control," Nat Biotechnol, (2005) 23(11):1414-1417.
Catteruccia et al., "Impact of genetic manipulation on the fitness of *Anopheles stephensi* mosquitoes," Science (2003) 299(5610)1225-1227.
Catteruccia et al., "Stable germline transformation of the malaria mosquito *Anopheles stephensi*," Nature (2000) 405(6789):959-962.
Catteruccia et al., "Transgenic technologies to induce sterility," Malaria Journal (2009)8 (Supp2)S7.
Cenik et al., "Genome analysis reveals interplay between 5'UTR introns and nuclear mRNA export for secretory and mitochondrial genes," PLoS Genet (2011) 794:e1001366.
Cha et al., "Expression of green fluorescent protein in insect larvae and its application for heterologous protein production," Biotechnol Bioeng (1997) 56(3):239-247.
Chalfie et al., "Green fluorescent protein as a marker for gene expression," Science (1994) 263(5148):802-805.
Chen et al., "Apoptotic Activity of REAPER is Distinct from Signaling by the Tumor Necrosis Factor Receptor 1 Death Domain," The Journal of Biological Chemistry (1996) 271(42):25735-25737.
Cheng et al., "Cellular transformation by Simian Virus 40 and Murine Polyoma Virus T antigens," Semin Cancer Biol (2009) 19(4):218-228.
Chintapalli et al., "Using FlyAtlas to identify better *Drosophila melanogaster* models of human disease," Nature Genetics (2007) 39(6)715-720.
Cho, "Enhancers," WIREs Dev Biol (2012) 1:469-478.
Zimowska et al., "The beta2-tubulin gene from three tephritid fruit fly species and use of its promoter for sperm marking," Insect Biochem Mol Biol (2009) 39(8):508-515.
Definition of "pest" from the Concise Oxford American Dictionary (2006) p. 661.
Deredec et al., "The population genetics of using homing endonuclease genes in vector and pest management," Genetics (2008) 179(4):2013-2026.
Dhillon et al., "The melon fruit fly, *Bactrocera cucurbitae*: A review of its biology and management," J Insect Sci (2005) 5:40.
Flaminia et al., "Transgenic technologies to induce sterility," Malar J. (2009) 8 Suppl 2:S7.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Franz, "Recombination between homologous autosomes in medfly (*Ceratitis capitata*) males: type-1 recombination and the implications for the stability of genetic sexing strains," Genetica (2002) 116(1):73-84.
Fraser,"Insect transgenesis: current applications and future prospects," Annu Rev Entomol (2012) 57:267-289.
Fuller, "Spermatogenesis," in: The Development of *Drosophila melanogaster*, Bate et al., Cold Spring Harbor Laboratory Press (1993) pp. 71-147.
Fussenegger et al., "Streptogramin-based gene regulation systems for mammalian cells," Nat Biotechnol (2000) 18(11):1203-1208.
Fussenegger et al., "The impact of mammalian gene regulation concepts on functional genomic research, metabolic engineering, and advanced gene therapies," Biotechnol Prog (2001) 17(1):1-51.
Ghosh et al., "Transcription factor binding and induced transcription alter chromosomal c-myc replicator activity," Mol Cell Biol (2004) 24(23):10193-10207.
Gonczy et al., "Bag-of-marbles and benign gonial cell neoplasm act in the germline to restrict proliferation during *Drosophila* spermatogenesis," Development (1997) 124(21):4361-4371.
Gong et al., "Ends-out, or replacement, gene targeting in *Drosophila*," Proc Natl Acad Sci (USA) (2003) 100(5):2556-2561.
Gossen et al., "Studying gene function in eukaryotes by conditional gene inactivation," Annu Rev Genet (2002) 36:153-173.
Gossen et al., "Tight control of gene expression in mammalian cells by tetracycline-responsive promoters," Proc Natl Acad Sci (USA) (1992) 89(12):5547-5551.
Graham et al., "Larval diets containing dyes for tagging pink bollworm moth internally," J Econ Entomol (1971) 64:376-379.
Great Britain Application No. 1303932.6, filed Mar. 5, 2013, 42 pages.
Hagler et al., "Methods for marking insects: current techniques and future prospects," Annu. Rev. Entomol. (2001) 46:511-543.
Hagler et al., "An Alternative to conventional insect marking procedures; detection of a protein mark on pink bollworm by ELISA," Entomol Exp Appl (2002) 103(1):1-9.
Han et al., PNAS (2011) 108:9673-9678.

(56) References Cited

OTHER PUBLICATIONS

Handler et al., "Germline transformation of *Drosophila melanogaster* with the piggyBac transposon vector," Insect Mol Biol (1999) 8(4):449-457.
Handler et al., "Polyubiquitin-regulated DsRed marker for transgenic insects," BioTechniques (2001) 31:820-828.
Handler et al., "Prospects for using genetic transformation for improved SIT and new biocontrol methods," Genetics (2002) 116:137-149.
Handler et al., "The lepidopteran transposon vector, piggyBac, mediates germ-line transformation in the Mediterranean fruit fly," PNAS (1998) 95:7520-7525.
He et al., "The actin gene family in the oriental fruit fly *Bactrocera dorsalis*. Muscle specific actins," Insect Biochem Mol Biol (1994) 24(9):891-906.
Hiller et al., "Testis-specific TAF homologs collaborate to control a tissue-specific transcription program," Development (2004) 131:5297-5308.
Hockemeyer et al., "Genetic engineering of human pluripotent cells using TALE nucleases," Nat Biotechnol (2011) 29(8):731-734.
International Preliminary Report on Patentability for PCT/EP2014/054290, dated Sep. 8, 2015, 7 pages.
International Preliminary Report on Patentability for PCT/GB2004/003263, dated Jan. 30, 2006, 6 pages.
International Search Report and Written Opinion for PCT/EP2013/054417, dated Jul. 12, 2013, 14 pages.
International Search Report and Written Opinion for PCT/EP2014/054290, dated Jun. 18, 2014, 11 pages.
International Search Report and Written Opinion for PCT/GB2015/051633, dated Oct. 8, 2015, 11 pages.
International Search Report for PCT/GB2000/04541, dated Nov. 19, 2001, 5 pages.
International Search Report for PCT/GB2004/003263, dated Nov. 5, 2004, 3 pages.
International Search Report for PCT/GB2007/000488, dated Jun. 6, 2007, 3 pages.
Irvin et al., "Assessing fitness costs for transgenic Aedes aegypti expressing the GFP marker and transposase genes," Proc Natl Acad Sci U.S.A. (2004) 101(3):891-896.
Jattani et al., "Deficiency screen identifies a novel role for beta 2 tubulin in salivary gland and myoblast migration in the *Drosophila* embryo," Dev Dyn (2009) 238(4):853-863.
Jiang et al., "Tombola, a tesmin/TSO1-family protein, regulates transcriptional activation in the *Drosophila* male germline and physically interacts with always early," Development (2007) 134(8):1549-1559.
Jiang et al., "Transcriptional activation in *Drosophila* spermatogenesis involves the mutually dependent function of aly and a novel meiotic arrest gene cookie monster," Development (2003) 130(3):563-573.
Jin et al., "Engineered female-specific lethality for control of pest lepidoptera," ACS Synthetic Biology, ACS (2013) 1(3):160-66.
Kawase et al., "Gbb/Bmp signaling is essential for maintaining germline stem cells and for repressing bam transcription in the *Drosophila* testis," Development (2004) 131(6):1365-1375.
Kelly et al., "*Drosophila* MEF2 is a direct regulator of Actin57B transcription in cardiac, skeletal, and visceral muscle lineages," Mech Dev (2002) 110(1-2):39-50.
Kim et al., "Hybrid restriction enzymes: zinc finger fusions to Fok I cleavage domain," Proc Natl Acad Sci (USA) (1996) 93:1156-1160.
Klassen, "History of the Sterile Insect Technique," in: Sterile Insect Technique, Principles and Practice in Area-Wide Integrated Pest Management, Curits et al., (eds) The Netherlands, Springer (2005) pp. 3-36.
Knipling et al., "Possibilities of Insect Control or Eradication Through the Use of Sexually Sterile Males," J Econ Entomol (1955) 48:459-462.
Koukidou et al., "Germ line transformation of the olive fly *Bactrocera oleae* using a versatile transgenesis marker," Insect Mol Biol (2006) 15(1):95-103.
Loew et al., "Improved tet-responsive promoters with minimized background expression," BMC Biotechnology (2010) 10:81.
Loukeris et al., "Gene transfer into the medfly, *Ceratitis capitata*, with a *Drosophila hydei* transposable element," Science (1999) 270(5244):2002-2005.
Lycett et al., "Conditional expression in the malaria mosquito *Anopheles stephensi* with Tet-On and Tet-Off systems," Genetics (2004) 167(4):1781-1790.
Mahfouz et al., "De novo-engineered transcription activator-like effector (TALE) hybrid nuclease with novel DNA binding specificity creates double-strand breaks," Proc Natl Acad Sci (USA) (2011) 101(6):2623-2628.
Malacrida et al., "A transgenic sperm marking system in the medfly, as a tool for pest control strategies and sperm use analysis," Entomological Research (2007) 37:A56.
Marrelli et al., "Mosquito transgenesis: what is the fitness cost?" Trends Parasitol (2006) 22(5):197-202.
Mattox et al., "Alternative splicing of the sex determination gene transformer-2 is sex-specific in tile germ line but not in the soma," Genes & Development (1990) 4(5):789-805.
Mattox et al., "Autoregulation of the splicing of transcripts from the transformer-2 gene of *Drosophila*," Genes & Development (1991) 5:786-796.
Matz et al., "Fluorescent proteins from nonbioluminescent *Anthozoa* species," Nat Biotechnol (1999) 17(10):969-973.
Maynard-Smith et al., "A directed approach for engineering conditional protein stability using biologically silent small molecules," J Biol Chem (2007) 282(34):24866-24872.
Miller et al., "A TALE nuclease architecture for efficient genome editing," Nat Biotechnol (2011) 29(2):143-148.
Miller., "An improved zinc-finger nuclease architecture for highly specific genome editing," Nat Biotechnol (2007) 25(7):778-785.
Mishra, "Understanding Forest Biology," Discovery publishing house (2009) 3 pages.
Morrison et al., "Genetic Improvements to the sterile insect technique for agricultural pests," Asia Pacific J Mol Biol and Biotechnol (2010) 18(2):275-295.
Mounier et al., "Insect muscle actins differ distinctly from invertebrate and vertebrate cytoplasmic actins," J Mol Evol (1992) 34(5):406-415.
Nielsen et al., "Axoneme-specific beta-tubulin specialization: a conserved C-terminal motif specifies the central pair," Curr Biol (2001) 11(7):529-533.
Nongthomba et al., "Expression and function of the *Drosophila* ACT88F actin isoform is not restricted to the indirect flight muscles," Journal of Muscle Research and Cell Motility (2001) 22:111-119.
Ohshima et al., "Reassessment of 79B actin gene expression in the abdomen of adult *Drosophila melanogaster*," Insect Molecular Biology (1997) 6(3):227-231.
Osanai-Futahasi et al., "A visible dominant marker for insect transgenesis," Nature Communications (2012) 3:1295.
Osterwalder et al., "A conditional tissue-specific transgene expression system using inducible GAL4," Proc Natl Acad Sci (USA) (2001) 98(22):12596-12601.
Papathanos et al., "Sex separation strategies: past experience and new approaches," Malar J. (2009) 8 Supp 2:S5.
Parker, "Mass-rearing for sterile insect release," The Netherlands, Springer (2005) pp. 209-232.
Peloquin et al., "Germ-line transformation of pink bollworm (*Lepidoptera: gelechiidae*) mediated by the piggyBac transposable element," Insect Mol Biol (2000) 9(3):323-333.
Perera et al., "Germ-line transformation of the South American malaria vector, *Anopheles albimanus*, with a piggyBac/EGFP transposon vector is routine and highly efficient," Insect Mol Biol (2002) 11(4):291-297.
Perezgasga et al., "Regulation of transcription of meiotic cell cycle and terminal differentiation genes by the testis-specific Zn-finger protein matotopetli," Development (2004) 131(8):1691-1702.

(56) References Cited

OTHER PUBLICATIONS

Perrin et al., "The actin gene family: function follows isoform," Cytoskeleton (2010) 67(10):630-634.
Pinkerton et al., "Green fluorescent protein as a genetic marker in transgenic Aedes aegypti," Insect Mol Biol (2000) 9(1):1-10.
Prasher et al., "Primary structure of the Aequorea victoria green-fluorescent protein," Gene (1992) 111(2):229-233.
Qin et al., "Systematic comparison of constitutive promoters and the Doxycycline-inducible promoter," PLOS One (2010) 5(5):e10611.
Raja et al., "Replacement by *Drosophila melanogaster* Protamines and Mst77F of Histones during Chromatin Condensation in Late Spermatids and Role of Sesame in the Removal of These Proteins from the Male Pronucleus," (2005) Mol Cell Biol 25(14):6165-6177.
Remy et al., "Zinc-finger nucleases: a powerful tool for genetic engineering of animals," Transgenic Res (2010) 19:363-371.
Rendon et al., "Medfly (*Diptera: tephritidae*) genetic sexing: large-scale field comparison of males-only and bisexual sterile fly releases in Guatemala," J Econ Entomol (2004) 97(5):1547-1553.
Robinson et al., "Ceratitis capitata—a suitable case for genetic sexing," Genetica (1982) 58(3):229-237.
Robinson et al., "Prospects for the future development and application of the sterile insect technique," The Netherlands, Springer (2005) pp. 727-760.
Robinson, "Genetic Basis of the Sterile Insect Technique," in: Sterile Insect Technique, Principles and Practice in Area-Wide Integrated Pest Management, Dyck et al., (eds.), The Netherland, Springer (2005) pp. 95-114.
Rong et al., "A targeted gene knockout in *Drosophila*," Genetics (2001) 157(3):1307-1312.
Rong et al., "Targeted mutagenesis by homologous recombination in *D. melanogaster*," Genes Dev (2002) 16:1568-1581.
Roper et al., "Contribution of sequence variation in *Drosophila* actins to their incorporation into actin-based structures in vivo," Journal of Cell Science (2005) 118:3937-3948.
Rossler, "The genetics of the Mediterranean fruit fly: a "white pupae" mutant," Annals of the Entomological Society of America (1979) 72:583-585.
Rubin et al., "Genetic transformation of *Drosophila* with transposable element vectors," Science (1982) 218(4570):348-353.
Saccone et al., "Sex determination in flies, fruit flies and butterflies," Genetica (2002) 116:15-23.
Santel et al., "The *Drosophila* don juan (dj) gene encodes a novel sperm specific protein component characterized by an unusual domain of a repetitive amino acid motif," Mech Dev (1997) 64(1-2):19-30.
Schetelig et al., "Strategy for enhanced transgenic strain development for embryonic conditional lethality in Anastrepha suspensa," Pro Natl Acad Sci (USA) (2012) 24: 9348-9353.
Shah et al., "Cardiac remodeling in *Drosophila* arises from changes in actin gene expression and from a contribution of lymph gland-like cells to the heart musculature," Mech Dev (2011) 128(3-4):222-233.
Smith et al., "Testis-specific expression of the beta2 tubulin promoter of Aedes aegypti and its application as a genetic sex-separation marker," Insect Mol Biol (2007) 16(1):16-71.
Spradling et al., "P element-mediated transformation," *Drosophila* a practical approach (1986) Chapter 8:175-197.
Tamura et al., "Germline transformation of the silkworm *Bombyx mori* L. using a piggyBac transposon-derived vector," Nat Biotechnol (2000) 18(1):81-84.
Theodoraki et al., "cDNA cloning, heat shock regulation and developmental expression of the hsp83 gene in the Mediterranean fruit fly *Ceratitis capitata*," Insect Mol Biol (2006) 15(6):839-852.
Urnov et al., "Highly efficient endogenous human gene correction using designed zinc-finger nucleases," Nature (2005) 435:646-651.
Viktorinova et al., "Comparative analysis of binary expression systems for directed gene expression in transgenic insects," Insect Biochem Mol Biol (2007) 37:246-254.
Vivinus et al., Eur. J. Biochem. (2001) 268:1908-1917.
Webster et al., Cell (1988) 52:169-178.
White-Cooper et al., "Transcription of meiotic cell cycle and terminal differentiation genes depends on a conserved chromatin associated protein, whose nuclear localisation is regulated," Development (2000) 127:5463-5473.
Wilson et al., "Position effects on eukaryotic gene expression," Annu Rev Cell Biol (1990) 6:679-714.
Wilson et al., "Sperm plasma membrane breakdown during *Drosophila* fertilization requires sneaky, an acrosomal membrane protein," Development (2006) 133(24):4871-4879.
Windbichler et al., "A synthetic homing endonuclease-based gene drive system in the human malaria mosquito," Nature (2011) 473(7346):212-215.
Windbichler et al., "Homing endonuclease mediated gene targeting in Anopheles gambiae cells and embryos," Nucleic Acids Res (2007) 35:5922-5933.
Windbichler et al., "Targeting the X chromosome during spermatogenesis induces Y chromosome transmission ratio distortion and early dominant embryo lethality in Anopheles gambiae," PLoS Genet (2008) 4(12):e1000291.
Zhao et al., "Male germ cell specification and differentiation," Dev Cell (2002) 2(5):537-547.
Non-final Rejection for U.S. Appl. No. 14/839,683, dated Jun. 16, 2017, 27 pages.
Final Rejection for U.S. Appl. No. 14/839,683, dated Nov. 30, 2017, 17 pages.

* cited by examiner

```
PBW-dsx         GTCCAATCGATCACAATGTATCACAACGTTGCGAATTCAGTTTCACAATCACACGCAACA 3910
Bombyx-dsx      G--CGATTATTTA-ATTCTATAT--ATTTTTCAAATTCAGTTTCTATTCCACTAACAATG 1170
codling-dsx     TTACAAACAAT-GTACGGAGCTACAACGTTGCAAGTTCGGTCCCCACACAAC--ACAATG 3034
                   * *    *   *             *  ** * * *** **  *       **   ***

PBW-dsx         AA-CRCGRCACGT------------TACAAATTAGTTACTT-TGAATCGATCGATTA-TG 3955
bombyx-dsx      TA-CACTACACGTACACA-------TACACACAACAAAATAGTGAATCGATAAATTAGTG 1222
codling-dsx     TGTCATAACACATTAACAACATTGTTACACACCCACACATACAAATTTGCTAAGTTGATA 3094
                   *    *** *            **** *          *    * * * *   **  *

PBW-dsx         ATGCGGCCGACTCARCGGCCCC-CG--GCAGCACTAACC-AGTAGTGATTTCCACTTTGC 4011
bombyx-dsx      GTCGAATAATCGGAATGGTTCG-CATCACACTACTAACC-AGTCGTGATTTCCACTTTAC 1280
codling-dsx     AAAGAGTGGTGTGTCCGACGAATCAGAACATCACTAACCCAGTCGTGATTTCATTTCCAC 3154
                                *      *    **  ******* *** ********    *   *

PBW-dsx         AGTGACCGGACCAA-------AACTTCGAAATTCGAATTGTAAAGTGACAGTTC--ATTT 4062
bombyx-dsx      AGTGACCGGACGAAGGTGGAGAAATTCGAAATTTAAATATAAAAGTGACAATTCGAATTT 1340
codling-dsx     AGTGACCGGACGAAGGTGGAGAAGTTCCAAATTTAAA---AAAAGTGACCACAT---TTT 3208
                *********** **        ** *********  **    ********         ***

PBW-dsx         CC-CGC-------CAAGTGTTGTGCCAGTGTC---ATGTCGATATT-TATTTTATTTTCT 4110
bombyx-dsx      CCACGCGCGCGCTCTAGTGATGTGCCAGTGTGTGAATATCAATATTATTTTTTATTTTCT 1400
codling-dsx     ATTTAA--------TAGTGATGTGCAAGTG-----ATAC---TATTTTTATTTGTTTTTT 3252
                              **** ***** ****      **      **** *  ***  *** *

PBW-dsx         TTTTTGTAGGAAAATGCTGAGCGAAATTAATAATATAAGTGGTGTACTATCGTCGTCCAT 4170
bombyx-dsx      TTTTTGTAGGAAAATGCTG---GAAATTAATAATATAAGTGGTGTACTGTCTTCGTCAAT 1457
codling-dsx     CTTTTGTAGGAAAATGCTGAGCGAAATAAATAATTTTAGTGGTGTGCTATCGTCATCGAT 3312
                 *****************   ***** ****** * ******** ** ** ** ** **

PBW-dsx         GAAGTTATTTTGCGAATGATACTTTGTTTTGTATGTGCTGTGTGTTGTGTGGACTTTTGC 4230
bombyx-dsx      GAAGTTATTTTGCGAATGATACTTAGTTTTACAAGTGCCGTGGTGTGTGTTGACACTTGC 1517
codling-dsx     GAAGTTGTTTTGCGAATGATACTATGTTCTTCAAGTGCTGTGTTTTGTG-GACTGTGGGG 3371
                ****** ***************  *** *  * **** ***   ****          *
```

FIG. 6A

```
PBW-dsx         TGTGCGTTGCTGTT--TGCGATGGAAGGACTAT-TGTGTCGTCGCCACGCTGGACTATTC 4287
bombyx-dsx      TGTGCGATGCTGTG--CGAATTTCAACGGAAATATTTGTTGTCGTAACATTGGATCTATG 1575
codling-dsx     TGACTGTTCCTGTAAATAAGCTTCGTTGGACAT-TGTGTC-TCAC-ACATCGGATCTCAT 3428
                **   * * ****        *     *   ** * ***  **   **   ***

PBW-dsx         GGTGAGTGG------TAGAATAATA-TTTTATCTA-------------TTTCATCGCGGT 4327
bombyx-dsx      GGTAAGTT-------TAGTATAATAACTTTACTCT-------------GTTCACATTAGT 1615
codling-dsx     GGTAAGTGCTAGTGCTAGCATYRMAACTTAACTCTCTGAGCGAATTCCTTTGACTCTAAA 3488
                *** ***        *** **   *  ** *                  ** *

PBW-dsx         ACAATTGACTTTTTATTACTACTCACTGCTATGGAGGAATCTCAGGAACAT----CGTAA 4383
bombyx-dsx      GAAACATACATTTG--TAAAATTTG-TGTTTT--ACTAATGTGAAATTTAT----TTTTG 1666
codling-dsx     GTCACACGRACAGCCATACAATCAA-AGCTACGCTCTAATTTTAAGATGACAWTCTGTAA 3547
                   *            **  *      * *       *** * *     *       *
```

FIG. 6B plasmid LA3582

#3581,2 AttB-3xP3DsRed2-teto21-hsp-adh-michxc plasmid LA3576

#3575,6 AttB-3xP3DsRed2-teto21-hsp-adh-dsred

Figure 18:
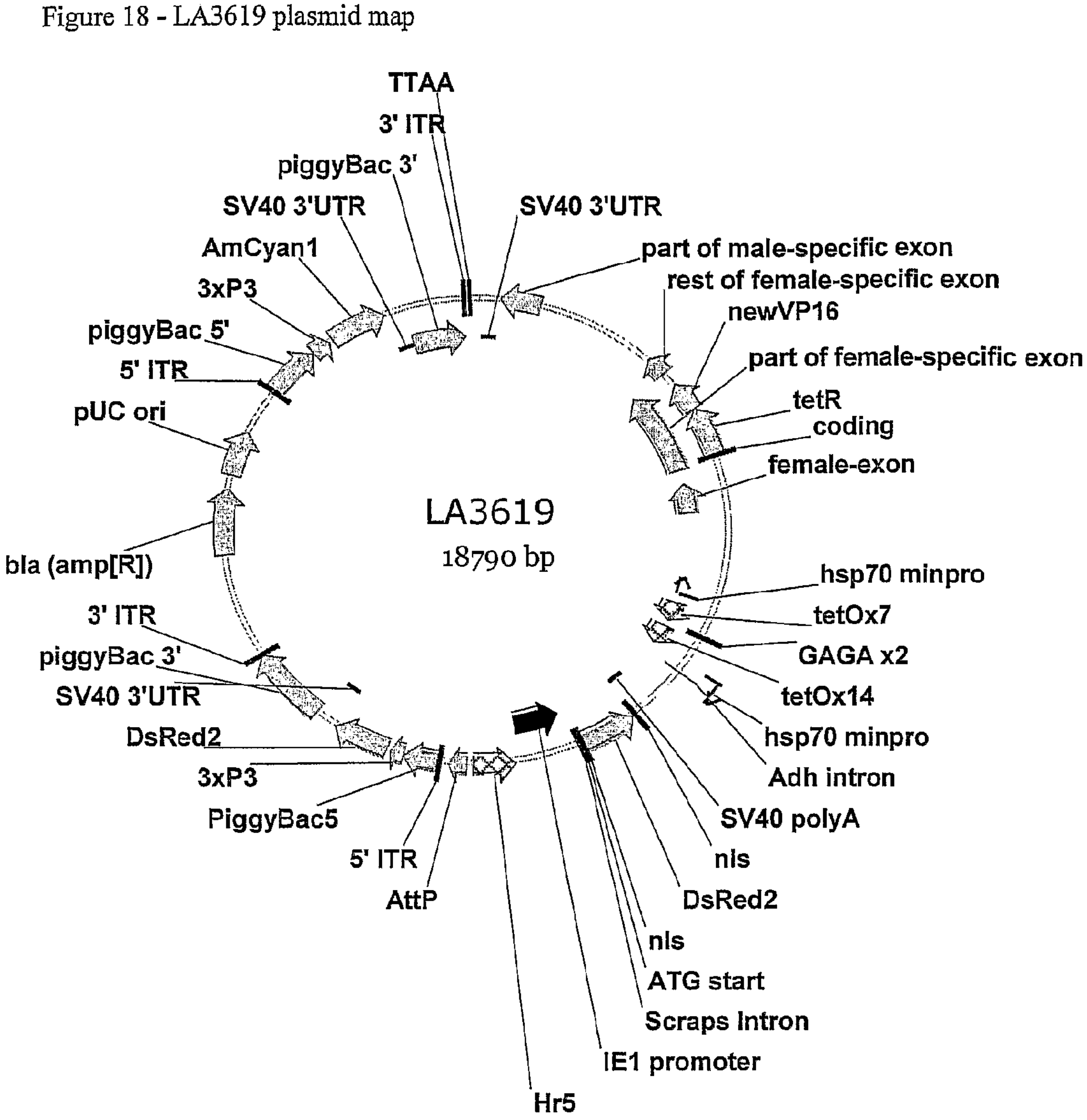

Figure 18 - LA3619 plasmid map

Native: CGTAGATTTG¦GT...intron...AG¦GTGAAGGCTC

LA1188: CTACTG¦GCACGT...intron...AG¦GTGAAGAATA

LA3077: AACGAAGTTG¦GT...intron...AG¦GTATTGAGGG

LA3097: AGCCACCATG¦GT...intron...AG¦GTCAGCCGCC

| LA# | NT Males | NT Females | TET Males | TET Females |
|---|---|---|---|---|
| 3077A | 111 | 32 | 73 | 44 |
| 3077B | 314 | 157 | 132 | 121 |
| 3077C | 161 | 116 | 60 | 84 |
| 3077D | 445 | 85 | 194 | 190 |
| | | | | |
| 3097A | 179 | 5 | 89 | 90 |
| 3097B | 440 | 0 | 59 | 27 |
| 3097C | 172 | 0 | 46 | 44 |
| | | | | |
| 3233A | 457 | 1 | 79 | 58 |
| 3233B | 171 | 0 | 14 | 13 |
| | | | | |
| 3014;1217 | 136 | 0 | 48 | 10 |
| 3166;1217 | 64 | 0 | 5 | 7 |

Figure 35

| | NT males | NTfemales | TET males | TET females |
|---|---|---|---|---|
| 3097A | 136 | 0 | 21 | 19 |
| 3097B | 295 | 11 | 14 | 11 |
| 3097C | 96 | 12 | 22 | 21 |
| 3097D | 103 | 15 | 82 | 67 |
| 3233A | 78 | 6 | 32 | 5 |

Figure 52:
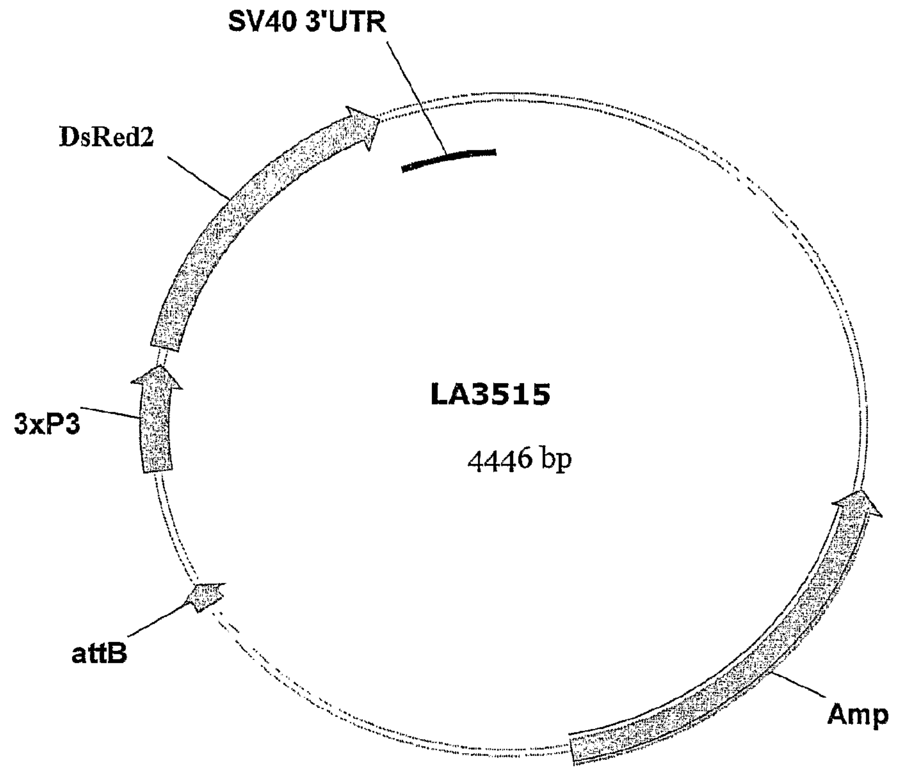

Figure 52- LA3515 Plasmid map

Figure 53:
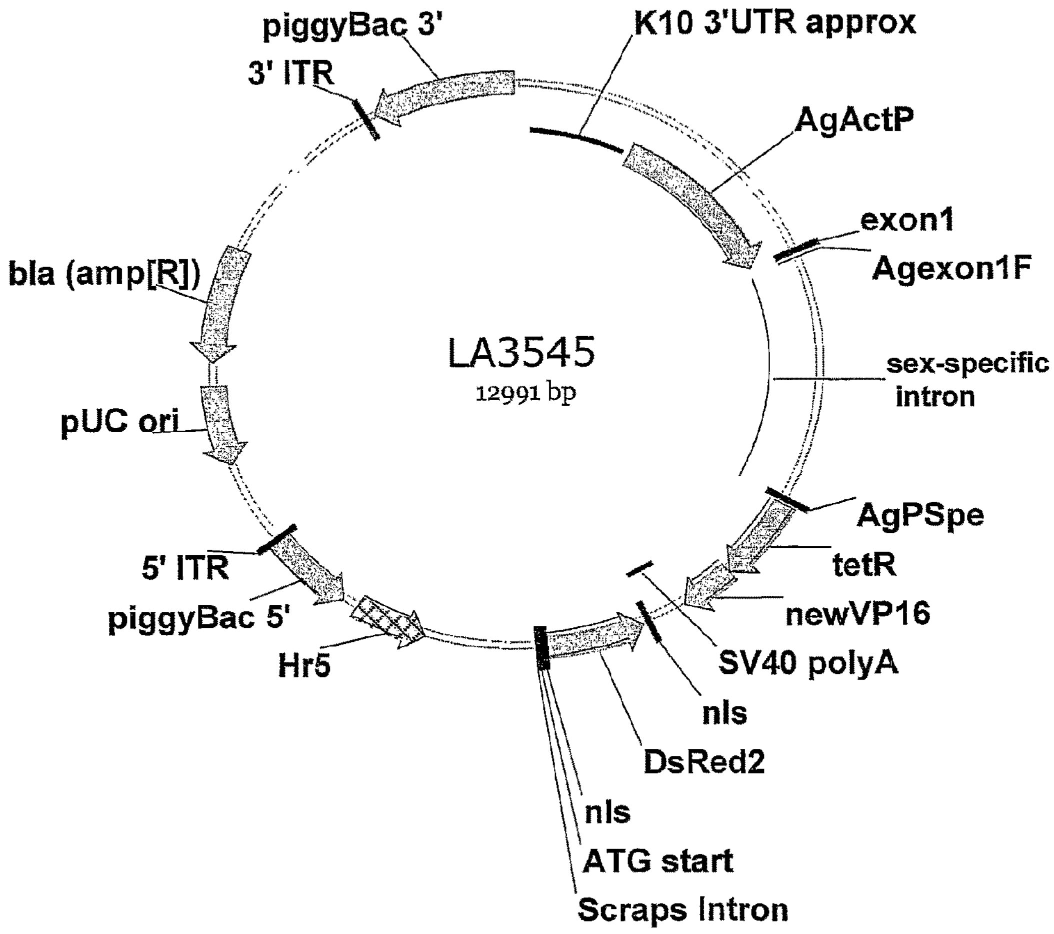

Figure 53 LA3545 Plasmid map

Figure 54:
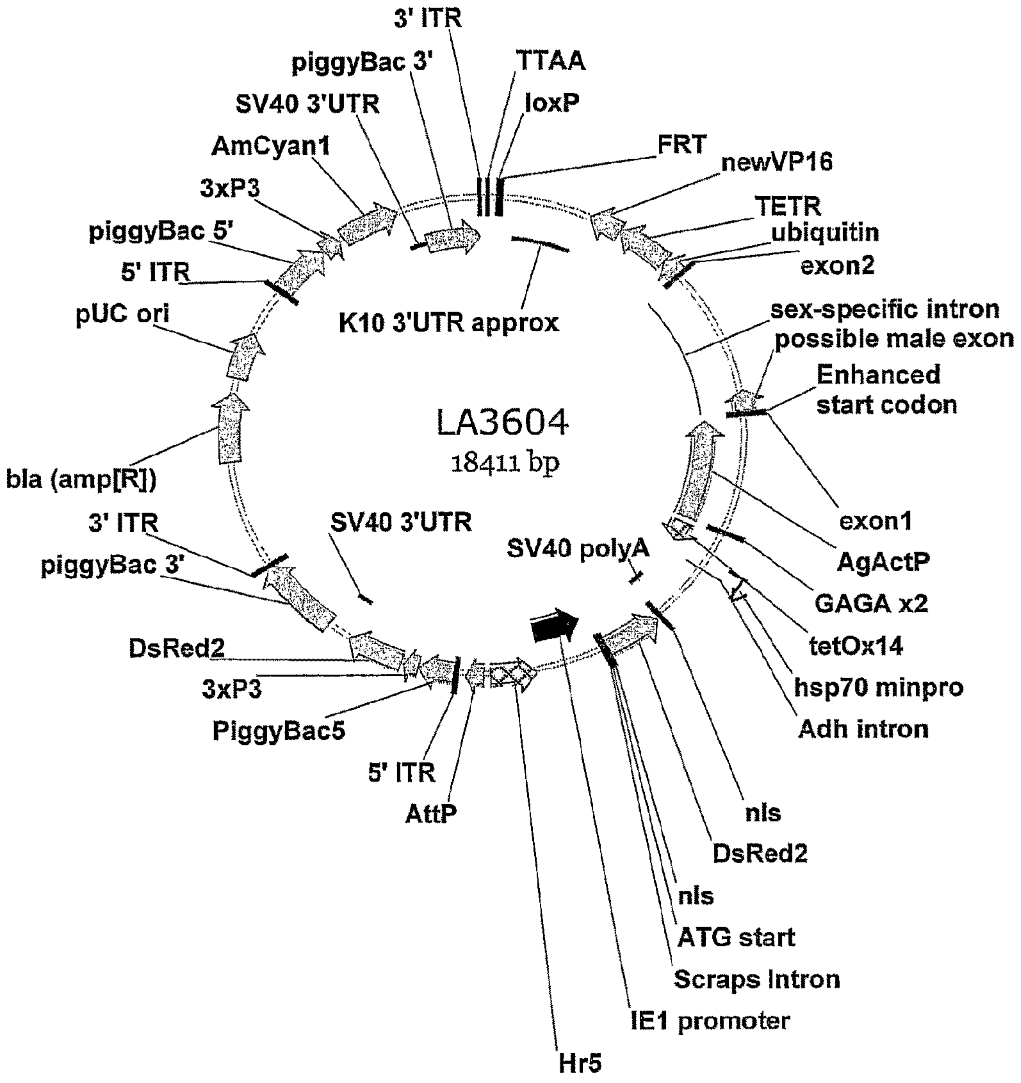

Figure 54 LA3604 Plasmid map

Figure 55:
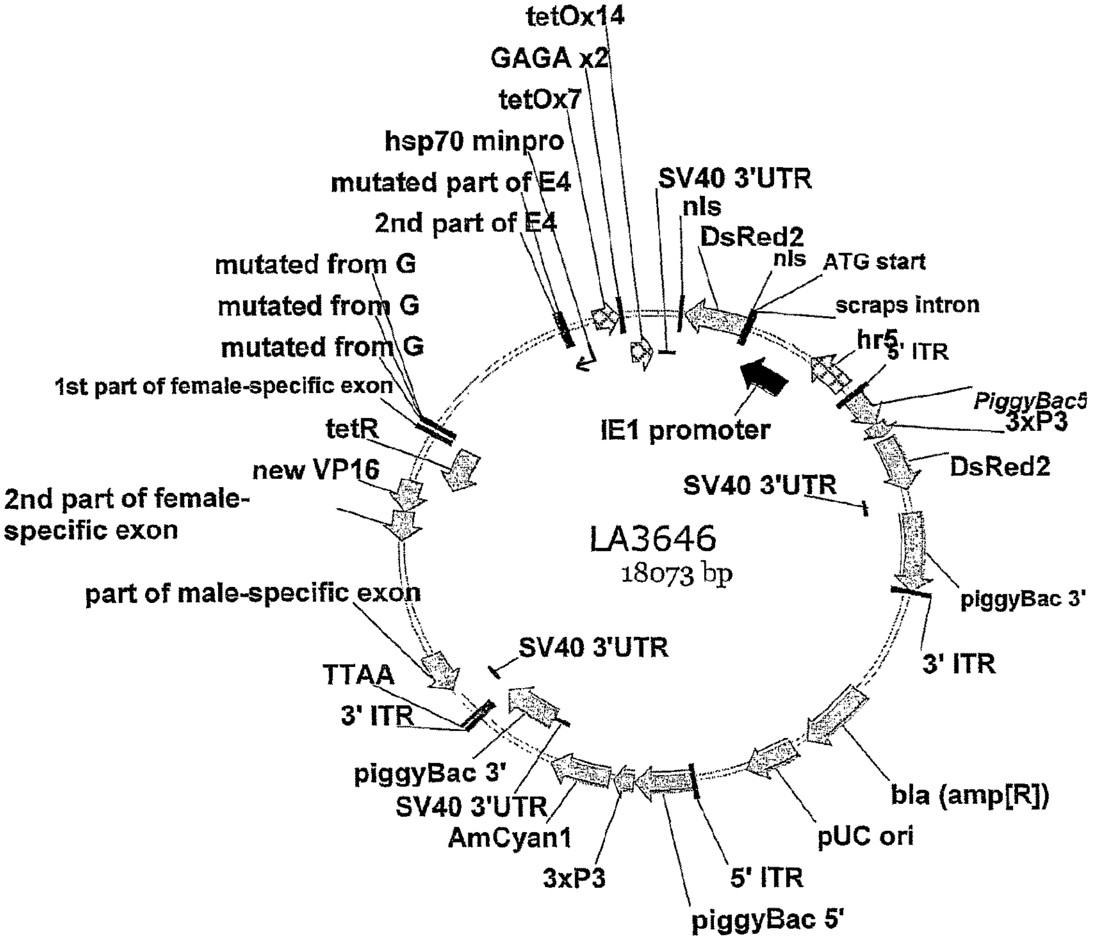

Figure 55 LA3646 Plasmid map

A

Figure 58
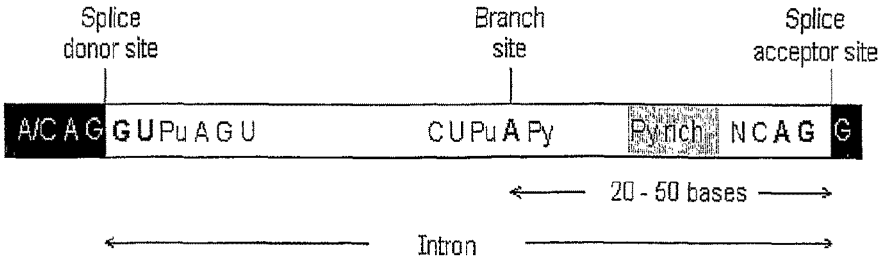
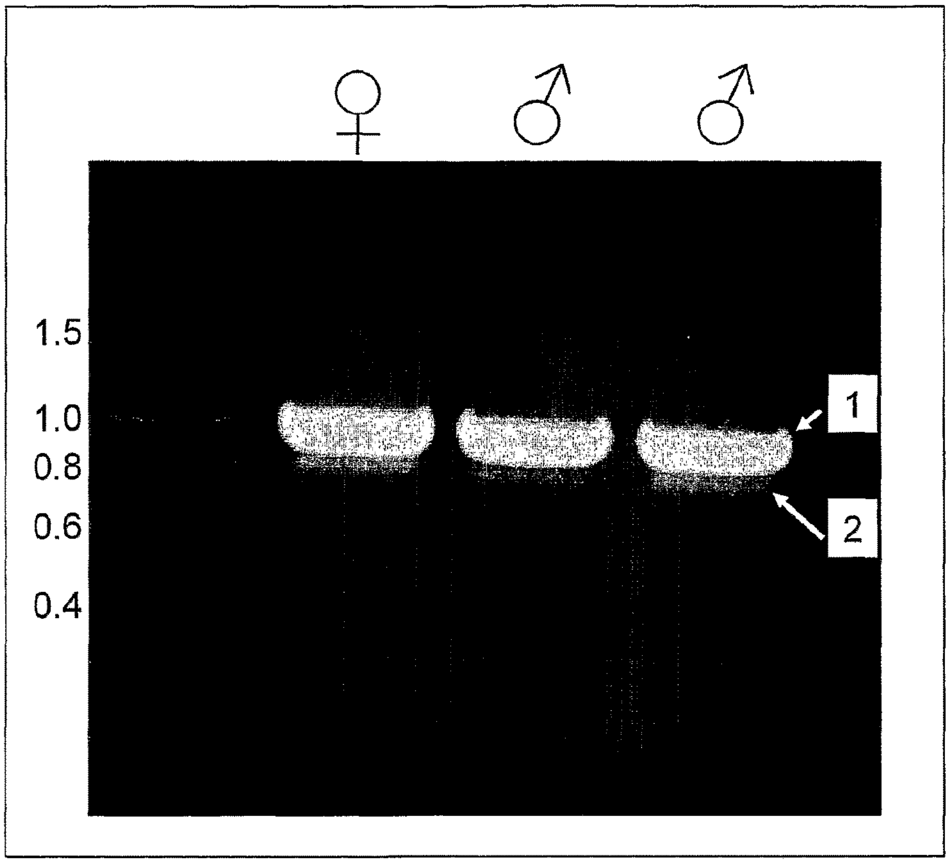
Figure 59

SEQUENCE LISTING

```
<160> NUMBER OF SEQ ID NOS: 168

<210> SEQ ID NO 1
<211> LENGTH: 13
<212> TYPE: DNA
<213> ORGANISM: artificial
<220> FEATURE:
<223> OTHER INFORMATION: Ceratitis capitata tra consensus sequence

<400> SEQUENCE: 1

tcwwcratca aca                                                       13


<210> SEQ ID NO 2
<211> LENGTH: 10
<212> TYPE: DNA
<213> ORGANISM: Artificial
<220> FEATURE:
<223> OTHER INFORMATION: LA3097 flanking sequence

<400> SEQUENCE: 2

agccaccatg                                                           10
```

<210> SEQ ID NO 3
<211> LENGTH: 10
<212> TYPE: DNA
<213> ORGANISM: artificial
<220> FEATURE:
<223> OTHER INFORMATION: LA3097 flanking sequence

<400> SEQUENCE: 3
gtcagccgcc 10

<210> SEQ ID NO 4
<211> LENGTH: 21
<212> TYPE: DNA
<213> ORGANISM: artificial
<220> FEATURE:
<223> OTHER INFORMATION: primer 688 - ie1-transcr

<400> SEQUENCE: 4
gttgcaagtt gacactggcg g 21

<210> SEQ ID NO 5
<211> LENGTH: 21
<212> TYPE: DNA
<213> ORGANISM: artificial
<220> FEATURE:
<223> OTHER INFORMATION: primer 790 - Aedsx-m-r2

<400> SEQUENCE: 5
ccactgtgta aggcttcctc c 21

<210> SEQ ID NO 6
<211> LENGTH: 21
<212> TYPE: DNA
<213> ORGANISM: artificial
<220> FEATURE:
<223> OTHER INFORMATION: primer 761 - Aedsx-fem-r

<400> SEQUENCE: 6
ggatggttgg ttgaagatcc g 21

<210> SEQ ID NO 7
<211> LENGTH: 21
<212> TYPE: DNA
<213> ORGANISM: artificial
<220> FEATURE:
<223> OTHER INFORMATION: primer AedsxR1

<400> SEQUENCE: 7
actgcgcaac tctacaccgt c 21

<210> SEQ ID NO 8
<211> LENGTH: 13
<212> TYPE: RNA
<213> ORGANISM: artificial
<220> FEATURE:
<223> OTHER INFORMATION: Pane et al consensus sequence

<400> SEQUENCE: 8
ucwwcrauca aca 13

<210> SEQ ID NO 9
<211> LENGTH: 13
<212> TYPE: RNA
<213> ORGANISM: artificial
<220> FEATURE:

-continued

<223> OTHER INFORMATION: Scali et al 2005 consensus sequence

<400> SEQUENCE: 9
ucwwcaauca aca 13

<210> SEQ ID NO 10
<211> LENGTH: 13
<212> TYPE: DNA
<213> ORGANISM: Drosophila sp.

<400> SEQUENCE: 10
tcaacaagca aca 13

<210> SEQ ID NO 11
<211> LENGTH: 13
<212> TYPE: DNA
<213> ORGANISM: Drosophila sp.

<400> SEQUENCE: 11
ttatcaaaca aca 13

<210> SEQ ID NO 12
<211> LENGTH: 13
<212> TYPE: DNA
<213> ORGANISM: Drosophila sp.

<400> SEQUENCE: 12
tcatcaatta aaa 13

<210> SEQ ID NO 13
<211> LENGTH: 13
<212> TYPE: DNA
<213> ORGANISM: Drosophila sp.

<400> SEQUENCE: 13
tcatcaatca aac 13

<210> SEQ ID NO 14
<211> LENGTH: 13
<212> TYPE: DNA
<213> ORGANISM: Drosophila sp.

<400> SEQUENCE: 14
tcttcaacca acc 13

<210> SEQ ID NO 15
<211> LENGTH: 13
<212> TYPE: DNA
<213> ORGANISM: Drosophila sp.

<400> SEQUENCE: 15
cctacaatct aca 13

<210> SEQ ID NO 16
<211> LENGTH: 13
<212> TYPE: DNA
<213> ORGANISM: Drosophila sp.

<400> SEQUENCE: 16
tcttagatca aaa 13

<210> SEQ ID NO 17
<211> LENGTH: 13

<212> TYPE: DNA
<213> ORGANISM: Drosophila sp.

<400> SEQUENCE: 17
tcttcgatca tta 13

<210> SEQ ID NO 18
<211> LENGTH: 13
<212> TYPE: DNA
<213> ORGANISM: Drosophila sp.

<400> SEQUENCE: 18
ccaacaatct aca 13

<210> SEQ ID NO 19
<211> LENGTH: 13
<212> TYPE: DNA
<213> ORGANISM: Drosophila sp.

<400> SEQUENCE: 19
tcaaagatca cca 13

<210> SEQ ID NO 20
<211> LENGTH: 13
<212> TYPE: DNA
<213> ORGANISM: Drosophila sp.

<400> SEQUENCE: 20
tcttcggtcg acg 13

<210> SEQ ID NO 21
<211> LENGTH: 13
<212> TYPE: DNA
<213> ORGANISM: Drosophila sp.

<400> SEQUENCE: 21
tcgacaaaca aaa 13

<210> SEQ ID NO 22
<211> LENGTH: 13
<212> TYPE: DNA
<213> ORGANISM: Drosophila sp.

<400> SEQUENCE: 22
tattcaaaca acg 13

<210> SEQ ID NO 23
<211> LENGTH: 13
<212> TYPE: DNA
<213> ORGANISM: Drosophila sp.

<400> SEQUENCE: 23
ttttcgataa aaa 13

<210> SEQ ID NO 24
<211> LENGTH: 13
<212> TYPE: DNA
<213> ORGANISM: Drosophila sp.

<400> SEQUENCE: 24
tcttcagtct gca 13

<210> SEQ ID NO 25

-continued

<211> LENGTH: 13
<212> TYPE: DNA
<213> ORGANISM: Drosophila sp.

<400> SEQUENCE: 25
gattcaatca tca 13

<210> SEQ ID NO 26
<211> LENGTH: 13
<212> TYPE: DNA
<213> ORGANISM: Drosophila sp.

<400> SEQUENCE: 26
ttatcgagca aaa 13

<210> SEQ ID NO 27
<211> LENGTH: 13
<212> TYPE: DNA
<213> ORGANISM: Drosophila sp.

<400> SEQUENCE: 27
tcataactca aga 13

<210> SEQ ID NO 28
<211> LENGTH: 13
<212> TYPE: DNA
<213> ORGANISM: Drosophila sp.

<400> SEQUENCE: 28
tcagaaatca aaa 13

<210> SEQ ID NO 29
<211> LENGTH: 13
<212> TYPE: DNA
<213> ORGANISM: Drosophila sp.

<400> SEQUENCE: 29
tctttaattt aca 13

<210> SEQ ID NO 30
<211> LENGTH: 13
<212> TYPE: DNA
<213> ORGANISM: Drosophila sp.

<400> SEQUENCE: 30
tttacaatcc tca 13

<210> SEQ ID NO 31
<211> LENGTH: 13
<212> TYPE: DNA
<213> ORGANISM: Drosophila sp.

<400> SEQUENCE: 31
tcatagatca gga 13

<210> SEQ ID NO 32
<211> LENGTH: 13
<212> TYPE: DNA
<213> ORGANISM: Drosophila sp.

<400> SEQUENCE: 32
acctcaaaca aca 13

<210> SEQ ID NO 33
<211> LENGTH: 13
<212> TYPE: DNA
<213> ORGANISM: Drosophila sp.

<400> SEQUENCE: 33
tcatcgaaca ccc 13

<210> SEQ ID NO 34
<211> LENGTH: 1014
<212> TYPE: DNA
<213> ORGANISM: artificial
<220> FEATURE:
<223> OTHER INFORMATION: Open reading frame of tTAV construct

<400> SEQUENCE: 34
atgggcagcc gcctggataa gtccaaagtc atcaactccg cgttggagct gttgaacgaa 60
gttggcattg agggactgac gacccgcaag ttggcgcaga agctgggcgt ggagcagccc 120
accctctact ggcacgtgaa gaataagcgg gcgctgctgg atgccctggc catcgagatg 180
ctcgaccgcc accacacgca tttttgcccg ttggaaggcg agtcctggca ggacttcctc 240
cgcaataacg ccaagtcgtt ccgctgcgct ctgctgtccc accgagacgg tgccaaagtc 300
catctcggca cgcgcccgac cgaaaagcaa tacgagacac tggagaacca gctcgcgttc 360
ctgtgccagc aaggcttcag cctggaaaat gctctctacg ctctgagcgc cgtcggtcac 420
tttaccctgg gctgcgtgct ggaggaccaa gagcatcaag tcgcaaaaga ggagcgcgag 480
accccaacaa ccgattcgat gcccccactg ctgcgtcagg caatcgagct gttcgatcat 540
caaggagccg agccggcatt cctgttcggc ttggagctga ttatctgcgg attggaaaag 600
caactgaaat gcgagtcggg ctcgggcccc gcgtacagcc gcgcgcgtac gaaaaacaat 660
tacgggtcta ccatcgaggg cctgctcgat ctcccggacg acgacgcccc cgaagaggcg 720
gggctggcgg ctccgcgcct gtcctttctc cccgcgggac acacgcgcag actgtcgacg 780
gcccccccga ccgatgtcag cctgggggac gagctccact tagacggcga ggacgtggcg 840
atggcgcatg ccgacgcgct agacgatttc gatctggaca tgttggggga cggggattcc 900
ccgggtccgg gatttacccc ccacgactcc gccccctacg gcgctctgga tatggccgac 960
ttcgagtttg agcagatgtt taccgatgcc cttggaattg acgagtacgg tggg 1014

<210> SEQ ID NO 35
<211> LENGTH: 338
<212> TYPE: PRT
<213> ORGANISM: artificial
<220> FEATURE:
<223> OTHER INFORMATION: Protein sequence of tTAV

<400> SEQUENCE: 35

Met Gly Ser Arg Leu Asp Lys Ser Lys Val Ile Asn Ser Ala Leu Glu
1 5 10 15

Leu Leu Asn Glu Val Gly Ile Glu Gly Leu Thr Thr Arg Lys Leu Ala
20 25 30

Gln Lys Leu Gly Val Glu Gln Pro Thr Leu Tyr Trp His Val Lys Asn
35 40 45

Lys Arg Ala Leu Leu Asp Ala Leu Ala Ile Glu Met Leu Asp Arg His
50 55 60

His Thr His Phe Cys Pro Leu Glu Gly Glu Ser Trp Gln Asp Phe Leu
65 70 75 80

Arg Asn Asn Ala Lys Ser Phe Arg Cys Ala Leu Leu Ser His Arg Asp

-continued

```
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly


<210> SEQ ID NO 36
<211> LENGTH: 1014
<212> TYPE: DNA
<213> ORGANISM: artificial
<220> FEATURE:
<223> OTHER INFORMATION: Open reading frame of tTAV2

<400> SEQUENCE: 36

atgagccgcc tggataagtc caaagtcatc aactccgcgt tggagctgtt gaacgaagtt      60

ggcattgagg gactgacgac ccgcaagttg gcgcagaagc tgggcgtgga gcagcccacc     120

ctctactggc acgtgaagaa taagcgggcg ctgctggatg ccctggccat cgagatgctc     180

gaccgccacc acacgcattt ttgcccgttg gaaggcgagt cctggcagga cttcctccgc     240

aataacgcca agtcgttccg ctgcgctctg ctgtcccacc gagacggtgc caaagtccat     300

ctcggcacgc gcccgaccga aaagcaatac gagacactgg agaaccagct cgcgttcctg     360

tgccagcaag gcttcagcct ggaaaatgct ctctacgctc tgagcgccgt cggtcacttt     420

accctgggct gcgtgctgga ggaccaagag catcaagtcg caaaagagga gcgcgagacc     480

ccaacaaccg attcgatgcc cccactgctg cgtcaggcaa tcgagctgtt cgatcatcaa     540

ggagccgagc cggcattcct gttcggcttg gagctgatta tctgcggatt ggaaaagcaa     600
```

```
ctgaaatgcg agtcgggctc gggccccgcc tacagccgcg cccgcaccaa gaacaactac     660

ggcagcacca tcgagggcct gctggatctg ccggatgatg atgccccgga ggaggcgggc     720

ctggccgccc cgcgcctgag cttcctgccg gccggacaca cccgccgcct gtcgaccgcc     780

ccgccgaccg acgtgagcct gggcgatgag ctgcacctgg atggcgagga tgtggcgatg     840

gcccacgccg atgccctgga cgacttcgac ctggacatgc tgggcgatgg cgatagcccg     900

ggaccgggat tcaccccgca cgatagcgcc ccctacggcg ccctggatat ggccgatttc     960

gagttcgagc agatgttcac cgacgccctg ggcatcgatg agtacggcgg ctaa          1014


<210> SEQ ID NO 37
<211> LENGTH: 337
<212> TYPE: PRT
<213> ORGANISM: artificial
<220> FEATURE:
<223> OTHER INFORMATION: Protein sequence of tTAV2

<400> SEQUENCE: 37

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
```

-continued

```
    290                 295                 300

Thr Pro His Asp Ser Ala Pro Tyr Gly Ala Leu Asp Met Ala Asp Phe
305                 310                 315                 320

Glu Phe Glu Gln Met Phe Thr Asp Ala Leu Gly Ile Asp Glu Tyr Gly
                325                 330                 335

Gly


<210> SEQ ID NO 38
<211> LENGTH: 1011
<212> TYPE: DNA
<213> ORGANISM: artificial
<220> FEATURE:
<223> OTHER INFORMATION: Open reading frame of tTAV3

<400> SEQUENCE: 38

atgggcagcc gcctggacaa gagcaaggtg atcaacagcg ccctggagct gctgaacgaa     60

gttggtatcg agggcctgac cacccgcaag ctggcccaga agctgggcgt ggaacagccg    120

accctgtact ggcacgtgaa gaacaagcgc gccctgctgg acgccctggc catcgaaatg    180

ctggatcgcc accacaccca cttctgcccg ctggagggcg agagctggca ggatttcctg    240

cgcaacaacg ccaagagctt ccgctgcgcc ctgctgtcgc accgcgatgg cgccaaggtg    300

cacctgggca cccgcccgac cgagaagcag tacgagaccc tggagaacca gctggccttc    360

ctgtgccagc agggcttcag cctggagaac gccctgtacg ccctgagcgc cgtgggccac    420

ttcaccctgg gctgtgtgct ggaggatcag gagcaccagg tggccaagga ggagcgcgag    480

accccgacca ccgatagcat gccgccgctg ctgcgccagg ccatcgagct gttcgatcac    540

cagggcgccg agccggcctt cctgttcggc ctggagctga tcatctgcgg cctggaaaag    600

cagctgaagt gcgagagcgg cagcgcctac agccgcgccc gtaccaagaa caactatggc    660

agcaccatcg agggactgct ggacctgccg gatgacgatg ccccggagga agccggcctg    720

gccgcccccc gcctgagctt cctgcccgcc ggacacacgc gccgcctgag caccgccccg    780

ccgaccgatg tgagcctggg cgacgagctg cacctggatg gagaggatgt ggcaatggcc    840

cacgccgacg ccctggacga tttcgacctg gatatgctgg gcgatggaga tagcccggga    900

ccgggcttca cgccccacga tagcgccccg tacggcgccc tggacatggc cgacttcgag    960

ttcgagcaaa tgttcaccga cgcgctgggc atcgatgagt atggcgggta g            1011


<210> SEQ ID NO 39
<211> LENGTH: 336
<212> TYPE: PRT
<213> ORGANISM: artificial
<220> FEATURE:
<223> OTHER INFORMATION: Protein sequence of tTAV3

<400> SEQUENCE: 39

Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80
```

```
Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335


<210> SEQ ID NO 40
<211> LENGTH: 568
<212> TYPE: DNA
<213> ORGANISM: Pectinophora gossypiella

<400> SEQUENCE: 40

gctagtggag aactgccaca aactgctgga aaagttccac tactcctggg aaatgatgcc      60

cctggtgctg gtcattctaa actacgccgg ctccgacctc gacgaggctt ctagaaaaat     120

tgatgaaggg aagatgatca tcaacgagta cgcgaggaag cacaatctga acatcttcga     180

tggccacgag ctaaggaact cgactcgcca gtacggactt taatacagta atattagttt     240

tctccaacaa cactaaacac gacataacac gctacacgca aaaaatacac gagtctttaa     300

tgttttacac gctcagtaaa ttattcactt acacgcttaa ctaaaatttt acacaatcgg     360

taaaaaaata caacaattta ttatcgtaaa aattacacaa aataaatgag atttaaatgt     420

cgtttaataa aataaaataa aaatagcatc gggaatatct tttcacctat tgccggagaa     480

cagtttaaat ggatactctc atttgaatca ttttaattgt agtagcattt tattttatta     540

ttaatagcaa taagtacaca aacataaa                                        568


<210> SEQ ID NO 41
<211> LENGTH: 610
```

<212> TYPE: DNA
<213> ORGANISM: Pectinophora gossypiella

<400> SEQUENCE: 41
gtagtggaga actgccacaa actgctggaa aagttccact actcctggga aatgatgccc 60
ctggtgctgg tcattctaaa ctacgccggc tccgacctcg acgaggcttc tagaaaaatt 120
gatgaaggga agatgatcat caacgagtac gcgaggaagc acaatctgaa catcttcgat 180
ggccacgagc tgaggaactc gactcgccag tacggacttt aatacagaaa atgctgagcg 240
aaattaataa tataagtggt gtactatcgt cgtccatgaa gttattttgc gaatgatact 300
ttgttttgta tgtgctgtgt gttgtgtgga cttttgctgt gcgttgctgt ttgcgatgga 360
aggactattg tgtcgtcgcc acgctggact attcgcacat tgggtggtcc accagtggcg 420
gatgtacgag cggtcgctgt gctcgctcct ggagctgcaa gcgcgcaaag ggacgtactc 480
ggtgtgctgc tcaccccgct acgtcatcgc gcccgagtac gcgtcacacc tgttgcctct 540
gccgcttacc acgcagagat catccccgcc gcccgcgcac ttgtagcgat gcgaacctgc 600
gccgcgggaa 610

<210> SEQ ID NO 42
<211> LENGTH: 449
<212> TYPE: DNA
<213> ORGANISM: Pectinophora gossypiella
<220> FEATURE:
<221> NAME/KEY: misc_feature
<222> LOCATION: (26)..(26)
<223> OTHER INFORMATION: n is a, c, g, or t

<400> SEQUENCE: 42
gctagtggag aactgccaca aactgntgga aaagttccac tactcctggg aaatgatgcc 60
cctggtgctg gtcattctaa actacgccgg ctccgacctc gacgaggctt ctagaaaaat 120
tgatgaagca cattgggtgg tccaccagtg gcggatgtac gagcggtcgc tgtgctcgct 180
cctggagctg caagcgcgca aagggacgta ctcggtgtgc tgctcacccc gctacgtcat 240
cgcgcccgag tgcgcgtcac acctgttgcc tctgccgctt accacgcaga gatcatcccc 300
gccgcccgcg cacttgtagc gatgcgaacc tgcgccgcgg gaagtaagta ctatttcatt 360
tattattctt tttatttttg gttttaaggt gctgacagac ttgaatttca agcaaatagt 420
gtctgacaaa gagctcaaaa tagacatgt 449

<210> SEQ ID NO 43
<211> LENGTH: 28774
<212> TYPE: DNA
<213> ORGANISM: Aedes aegypti

<400> SEQUENCE: 43
acagtgaaat ttgatcgatc actcatcgaa acgagatcac tttcgattga tcgtgacaat 60
tttttagaat ccatttcaca gtcgttggga ctgttgaccc tgtcacttta aactagctag 120
tgagtagctt tgctctagtg aaagctaact agcactgtta aaaaatctta ggtaaagtgt 180
cagcaaccct gacaactggg ccacctcttg ccgaccataa gcaaatgaaa tcaaatggtt 240
cgctacgaag gttaattggg tttcgatcta cttcgtccta agcgctattt ttcgtcatac 300
ggtggagaac ggctggtatt cgtttacttt agtttaccaa gcgatgcttc caattaaccc 360
aaagctagat gaagcaggat tcgcgataaa aagcagtatg cgaacttaaa atgttctact 420
acattacggc gggtattcaa atttacctgc cacataaatt tattttccaa gtataatttg 480

```
cgaaagctgc aatggttcat gcttgaattt tacaagatga tgtaatgccg cccataagtt      540

taaatggacg gtgtatttaa ataaaaggtt catattaaac gctttcgacg ttaccaagta      600

ccatttgtac acaaacatgt aataaaacta ttgtatttct ataaataact tcagttcaat      660

catccacttt gcacattttc accgaaatcg catggacgaa ggtaaacatg tgtttgtaca      720

ttattttgat aacataaaga tatttattga agtcaagtta gtaggtgaaa cgtgtaaaag      780

tggctttagc gtacctgctt gacgtaccga gcgaaatctg attagcggtc gactaagcca      840

taaaacttct acaattcaca aaattttgaa aaattccctc gctgccacga tactaatgca      900

ctgcatggct cgctttagac taatcgccag ctgattcggt attttgaaga tgttaagtgt      960

tttaaaactt tttaagggag cgacggtgct atgattacgt aatcaaatgt tctttctttt     1020

actttcagac caattgcaga acaagcttta tcctaatcca tctcattttg ggaacagcac     1080

tagccgcgac cattagccgt ttagtttaca agaaagaaaa tgaaagtctg gttaacgtct     1140

tgttcgaaat aggattaggt agagtaaaac ccttgtcgtg atcggcgctg gtaatcggca     1200

tctgcgtaga gaacatgttg tacttcctcg aggacgattg ctcgcgctcg cacggttctt     1260

attgctacca tggtgaaacc actagcgccg aggaagtgct agacgcatct cttgtacaac     1320

atgaaggagc tcctgctaac gagcgcgagc gtgccaagaa taacgatggt accactttgg     1380

tgatcgcggc tccttcacga taccgttgtg aaggttttct gaattgcgca tcgtctccga     1440

agggtgtgtc caggtgcatt gtctcccaac tgacctgttc ccgacaatat cgagcactaa     1500

atggcaacac ttccaaaaga cttaacgcgt agcagaggct tcccacacag gtccacgtaa     1560

cagagggttg actggacaag ggctgttata gctcgtgatt ggtttccatt agagagcagt     1620

atctcgtagt agcgtaggag agtccattag agtgcgatat tccgtgagtt tgtgtgaccg     1680

gcgatagaga agccctgacg ccaaaggtaa tctctcgtca tagagcatca tcgcatcctc     1740

tcaggtaatc tcacgctata aggcactcaa acacactggc cgctatctct tcgggactgc     1800

cgcgcttcaa gacgattgta actcggaaac tgacctgatt agtacataaa aagagaccta     1860

ttgcgtaagc ttataagaaa cgagtttgtc cacacggttg gcgcgaagtt ctgctaacat     1920

tgagcctttg actggactaa tcatgtattt ttctctggat aacgcattcg aatattcttt     1980

gctcaaacag gtgtgccaac atggtttcgc aagatcgctg gatggtaaag atgtccgagg     2040

cagggtacga taaccgggcg gatggcagtg gagcttccag cagcagcctg aacccgcgaa     2100

taccaaagcg ttctagcgac ctaccatttc tacaggctcc gtcccatgct attggcccgc     2160

ctaccgtcac ctcgaaggtc gtcgtcggac ttgggcgctt cgccgccgaa ctgtgcccgc     2220

tgccggaacc acggtcacaa gatcggcctg aagggacaca agcgctattg taagtatcgc     2280

aattgtacct gcgaaaagtg gcggcggctt gacacgggcg acggccttgg tgccagtgtt     2340

ctagccggac ttccctgtgt tcgcgataac attcatagcg ttaacatgga cgcttttcac     2400

ctgcctgacg gccgaacggc agcgggtcat ggccctgcag acggctctcc gaagggcgca     2460

aacccaggac gaacagcggt tgctggtaga cggagaggtg gacggactgc cggcttgccg     2520

tcgcccagta ccgggacgtc tgccgagagg cttcccgcgt ttgggtcctg cttgtcgcca     2580

acgaccatct gcctctccac cccgccgaac cggtacatag ccttcaaata ccaaaattgt     2640

ctgacctaaa agagatgatc cataattctc agcagaggtc gttgatcgac tgcgactcgt     2700

gggcggcttg gccatgtatc ggaagtttat ggttttaaca gactggattt tctctactag     2760

gtattaagag tcgtctccag caactagctg acgctgagca ccaccggctc gatgaactcc     2820

accccgggca gctcgttggt aacgctgtcc cagcaccgaa gatcaccctg ctccgccgcg     2880
```

```
tcggtccacc ccagcgaggc ggtggccgag ctacttgagg tggggcccgt cgagcaacca   2940
ttgcgacagg gtcgtggctt ctagtgggac gaggcggcgc agccaggtgg ggtcgctccg   3000
tcagcaaaac gttgcaggta ggtgtgaggc atatctattt cgttattctc tcaatgtttg   3060
tggagaaccg gccggaattc aacatcgaag tcggtttctg agtcgttttg caacgtccat   3120
ccacactccg tatagataaa gcaataagag agttacaaac acctcttggc cggccttaag   3180
ttgtagcttc agccaaagac ttctattgat ttatgataaa tttctctcaa atgtttgcgc   3240
ggagggtgga tttttgagag ctgagtggtg tagaaacgaa atgggcatca aacgttatgc   3300
aagataacta aatactattt aaagagagtt tacaaacgcg cctcccacct aaaaactctc   3360
gactcaccac atctttgctt tacccgtagt ttgcaatacg ggcgctgctt gaaacaggtt   3420
tatgttaggg gtttcctgtg tttcatacag tcaccccatt gttatgtata gcacacagat   3480
atggataaaa gttggattaa ccgcgacgaa ctttgtccaa atacaatccc caaaggacac   3540
aaagtatgtc agtggggtaa caatacatat cgtgtgtcta tacctatttt caacctaatt   3600
gcagtgaata tcccatcaaa tagagttgca attgagtaga acacatttta ccaacgtata   3660
aagcatcgta atcaattata atatacttaa gcaaaataca cgtcacttat agggtagttt   3720
atctcaacgt taactcatct tgtgtaaaat ggttgcatat ttcgtagcat tagttaatat   3780
tatatgaatt cgttttatgt atggggaaat aatttgtcaa ccacatttct agaaaagttg   3840
attcatacat gtgtgctttt gaaagccata taccacatta tgtttgattc atatctctta   3900
taccccttta ttaaacagtt ggtgtaaaga tcttttcaac taagtatgta cacacgaaaa   3960
ctttcggtat atggtgtaat acaaactaag tatagagaat taatatgagt cgatttatcg   4020
cgaaattttt caaaatgtcc tatgtaccaa tgaaagatac tctcttatct cgctctgttt   4080
tgaacataac aactgaaact attatactca gctaaatagc gctttaaaaa gttttacagg   4140
atacatggtt actttctatg agagaataga gcgagacaaa acttgtattg ttgactttga   4200
tttgggaagt ttttcactat agataaaaaa atgtccttga ctagcgtttc atacaaaaaa   4260
aaaaaaaaac gcaaccaaaa atgttaatgt ggttcagtga aaacccttca aaaagtgata   4320
tctatttttt tacaggaact gatcgcaaag tatgtttttt tttttttttg cgttggtttt   4380
tacaattaca ccaagtcact ttgattaaag aggaagtaaa ctaagatagt gtctcaatgt   4440
tggataggtc atttagaaaa ggtccgcgag attggatcca taataatgat tctcctctct   4500
aactaatttc tccttcattt gattctatca cagagttaca acctatccag taaatctttt   4560
ccaggcgctc taacctaggt attattacta agaggagaga cactgatccg catctgtggg   4620
atggacaacg tttgtaattt ctatcggtat cgaaaataat cgcgcatttt cgggcgtatt   4680
ccagaaaaca acaatgaaat gtgactaggc gtagacaccc tacctgttgc aaacattaaa   4740
gatagccata gcttttatta gcgcgtaaaa gcccgcataa ggtcttttgt tgttacttta   4800
atactgaagc aaatgtgcac aattttcatt acatgatatt attcaatggg gtaggtgggc   4860
gacaaaatag attcattaat gttggataat aggggcgttt tatgacttcg tttacacgtg   4920
ttaaaagtaa tgtactataa taagttaccc catccacccg ctgttttatc taagtaatta   4980
caacctatta tccccgcaaa gtcattatcc ctaaatgctc cacctcagct ggtggccccg   5040
tcagtcagtt gatcgggaaa gcagcaatca atccggagac aggtcgacct ccatcgaaca   5100
cagtaatagg gatttacgag gtggagtcga ccaccggggc agtcagtcaa ctagcccttt   5160
cgtcgttagt taggcctctg tccagctgga ggtagcttgt ggaaccgaac aacactagat   5220
```

-continued

```
gttcgatttc taacgaccga ctaagaacat cgtcggaagc gtctggttca ttcgacgagc   5280
cggaaggggt tcatctttcg ccttggcttg ttgtgatcta caagctaaag attgctggct   5340
gattcttgta gcagccttcg cagaccaagt aagctgctcg gccttcccca agtagaaagc   5400
ctcgtcgtcg aacgaatagc tgctgctaca cttcgcgtcg ttatcgtcgt cgggggattg   5460
gtgtttgtaa ctgcgcactc gtttatacat tgttgtttgc gagcagcagc ttgcttatcg   5520
acgacgatgt gaagcgcagc aatagcagca gccccctaac cacaaacatt gacgcgtgag   5580
caaatatgta acaacaaacg cgatcggcgg gcgctgtaac tgcctgcagt cacgcgttca   5640
ttcgcagtcg ttgtcgtagt catacacacg ccgtcgttcc tttgtatcag ctgtgtagca   5700
gctagccgcc cgcgacattg acggacgtca gtgcgcaagt aagcgtcagc aacagcatca   5760
gtatgtgtgc ggcagcaagg aaacatagtc gacacatcgt tttagtggtg ttacaacatt   5820
gagctacttt ttgcgtttcg ctttcgtgct gcggcggcgg cggcgggact tcgctgcact   5880
gataggaacg gaatgcatgc aaatcaccac aatgttgtaa ctcgatgaaa aacgcaaagc   5940
gaaagcacga cgccgccgcc gccgccctga agcgacgtga ctatccttgc cttacgtacg   6000
tgctccggtt gaagagagct ctgcgccact tgtggcgggt ttcactcaaa aggcatcgtc   6060
gcgtcgcaac aaagtgcgca cattcgacgc gtaactgtaa acgaggccaa cttctctcga   6120
gacgcggtga acaccgccca aagtgagttt tccgtagcag cgcagcgttg tttcacgcgt   6180
gtaagctgcg cattgacatt gtaaatagaa agactttggt gcgtttagaa aaagggtcac   6240
aaagggtggc aagtgagtat gtatgtgagc tcatttcatt ctcgatggca ttgagacgta   6300
catttatctt tctgaaacca cgcaaatctt tttcccagtg tttcccaccg ttcactcata   6360
catacactcg agtaaagtaa gagctaccgt aactctgcat atctattctg agaacgaaag   6420
ttcaatggat gcattttatg caatgccacc ggaattttcc tatgaactgc tttcacactt   6480
cttttaagaa aattttgcag tagataagac tcttgctttc aagttaccta cgtaaaatac   6540
gttacggtgg ccttaaaagg atacttgacg aaagtgtgaa gaaaattctt ttaaaacgtc   6600
atttaattta ttcactccat ttagttctga cgtaacattc cagataacac acttcaaagt   6660
catggtcagt tcatgttgaa cgaatgtgca ccgcgatcca taaattaaat aagtgaggta   6720
aatcaagact gcattgtaag gtctattgtg tgaagtttca gtaccagtca agtacaactt   6780
gcttacacgt ggcgctaggt cgcagaacga ttccatgtct taatgtcgtc acttatcata   6840
taatcaccca gtttttgccc cacttaaaaa aacgatgtcc actttttatc tgagtttctt   6900
gcgtcttgct aaggtacaga attacagcag tgaatagtat attagtgggt caaaaacggg   6960
gtgaattttt ttgctacagg tgaaaaatag actcaaagaa tctcctctct tttcagccaa   7020
ccactccagc ggaacccctg aacccggaaa catggtacca ggtgagttcg ctgttgaaat   7080
actaatttgc agaaaacata agaggagaga aaagtcggtt ggtgaggtcg ccttggggac   7140
ttgggccttt gtaccatggt ccactcaagc gacaacttta tgattaaacg tcttttgtat   7200
agaaattttg ctaccgattt accataactg gaatcgaaga caatatgact tcatcacacc   7260
agcagtaaac acggcgtaaa aatgattcat caggacccgc tctttaaaac gatggctaaa   7320
tggtattgac cttagcttct gttatactga agtagtgtgg tcgtcatttg tgccgcattt   7380
ttactaagta gtcctgggcg tcaatagccc tgtttttcca cgctcatctt gggtttcaca   7440
tcggtgaaca ccacttggag acgttttcac acaatgttca tgttcttctt tgagtaaatg   7500
agttatcggg acaaaaaggt gcgagtagaa cccaaagtgt agccacttgt ggtgaacctc   7560
tgcaaaagtg tgttacaagt acaagaagaa actcatttac aagttatgcg tggtcccgtg   7620
```

-continued

```
ctcatcaaga tagtgtgcca cacataagaa ttatcttaat tgaggccttc tgcgggccgt   7680
gagcttgttt gctacgccct ttcaatacgc accagggcac gagtagttct atcacacggt   7740
gtgtattctt aatagaatta actccggaag acgcccggca ctcgaacaaa cgatgcggga   7800
tccttggcgt tgagttttag tttctttgac agagaaagac ttttgataat ctactttctg   7860
cagctacgac ctttctctga actatttgga aaattataac aggaaccgca actcaaaatc   7920
aaagaaactg tctctttctg aaaactatta gatgaaagac gtcgatgctg gaaagagact   7980
tgataaacct tttaatattg ttatgttgac aatatttatc ccttcgatta acaaaaaact   8040
tcaagccagg gaaacatcca gtgtgaaaac actaagcggc gcactttggt tcatttcatt   8100
aatacaactg ttataaatag ggaagctaat tgttttttga agttcggtcc ctttgtaggt   8160
cacacttttg tgattcgccg cgtgaaacca agtaaagtaa cgtatcgatc actcttaatt   8220
caagatgaca aagtggttga gtagtagagt acgtggctca caatcggaag gttcttggct   8280
cgaatctcaa tgtatgctat gcatagctag tgagaattaa gttctactgt ttcaccaact   8340
catcatctca tgcaccgagt gttagccttc caagaaccga gcttagagtt acatacgata   8400
ttttaacttt ttttttattt tgtcgatcat aaacggatgc gcgactcagc atttttggca   8460
tttgaatcat gattccgagt aatcagctac aaaaacctaa aaaattgaaa aaaaaataaa   8520
acagctagta tttgcctacg cgctgagtcg taaaaaccgt aaacttagta ctaaggctca   8580
ttagtcgatg tttttggatt cgcgtgtgtt gcgttacggc aatctgactc atgatatcat   8640
gagtccaaat catggtgtat tttcataaga cgaaaacacg ctggaatcat gatatcatga   8700
gcgcacacaa cgcaatgccg ttagactgag tactatagta ctcaggttta gtaccacata   8760
aaagtattct gcttttgtgc gaccttagta ctatagtact gtaataatct tgtttttgga   8820
ttctgatttc tacccgtgca tttctaaagt ttgcaaagaa ggaagcttca aaaaacttcc   8880
aaaagcttat gttacagaag cattattaga acaaaaacct aagactaaag atgggcacgt   8940
aaagatttca aacgtttctt ccttcgaagt tttttgaagg ttttcgaata caatgtcttc   9000
cttggaaagc ttaagttaca gcagtttccg taccagaacg ttggaaagct tatattacga   9060
aacagtaata gggtttctat gcggtggaag tgctgttata gaacctttcg aattcaatgt   9120
cgtcaaaggc atggtcttgc aacctttcga atataatgct ttgtcattat cccaaagata   9180
cgccaccttc acgacaatat tggcgtgtaa gcatttataa tacatctggg tatcatcgaa   9240
atcattagaa aaaatgcggt ataagtttca cttgaattca gatcagtgat cgattgttac   9300
accgcacatt cgtaaatatt atgtagaccc atagtagctt tagtaatctt ttttacgcca   9360
tattcaaagt gaacttaagt ctagtcacta gctaacaatg agttcaaata gatccaaata   9420
tatgagggtg aaacgtcatt gcgatccact gtgaactgca gttgattggc cgcaatttca   9480
aaatatgtac acccgagtga tcaagtttat ctaggtttat atactcccac tttgcagtaa   9540
cgctaggtga cacttgacgt caactaaccg gcgttaaagt tttatacatg tgggctcact   9600
tctgcacggc tgttcagctg acatccttca ttgtcccagt cgttcataca aacttgcccg   9660
tcaagatcaa ggaagttggc gcttgatcaa tgttctgttt agacgtgccg acaagtcgac   9720
tgtaggaagt aacagggtca gcaagtatgt ttgaacgggc agttctagtt ccttcaaccg   9780
cgaactagtt acaagacaaa catttctttt ttcttaagta gtattgggcg ctgcggtcac   9840
ctcatttatc tttttgaaat tgtttcggaa ataatgcacg agatgcaata acggttcttg   9900
gtaaagaaaa aagaattcat cataacccgc gacgccagtg gagtaaatag aaaaacttta   9960
```

-continued

```
acaaagcctt tattacgtgc tctacgttat tgccaagaac aacatagtca tgtagaacct  10020
tacaaatgat cagaattgat ttgatcaatt catttccagc tttcaaactg acgatcgccc  10080
aatgctaccg tccatcacga ttgtatcagt acatcttgga atgtttacta gtcttaacta  10140
aactagttaa gtaaaggtcg aaagtttgac tgctagcggg ttacgatggc aggtagtgct  10200
tattccacgc actggctgtc atgttccctg ccagatttac gtagtgttct tttgtaaagg  10260
caacactgct gcactgctcc aagtcactcc aagcttcatc ataaggtgcg tgaccgacag  10320
tacaagggac ggtctaaatg catcacaaga aaacatttcc gttgtgacga cgtgacgagg  10380
ttcagtgagg ttcgaagtag tgcgagttga agcaaactgt gaaggattga tattttgaat  10440
taaatcaagc tctcgcgttg caggcagctg taacttgcca ccaagtatga tcggtcttcc  10500
acgctcaact tcgtttgaca cttcctaact ataaaactta atttagttcg agagcgcaac  10560
gtccgtcgac attgaacggt ggttcatact agccagaagg gacttcgttc cataaaaagt  10620
ggaatgctcc tcgtccgatt tccagaaaca gtcggttatg caataaaaca ggatcaggtt  10680
cgatgactct tggcgatatc ctgaagcaag gtatttttca ccttacgagg agcaggctaa  10740
aggtctttgt cagccaatac gttattttgt cctagtccaa gctactgaga accgctatag  10800
tgaattggag tcgttaccta tcccccgata aagatatcct ctcgcaattc gagggggatt  10860
aggattagaa accgtttgct gatatttgcg agatataaaa acttaacctc agcaatggat  10920
agggggctat ttctatagga gagcgttaag ctccccctaa tcctaatctt tggcaaacga  10980
ctataaacgc tctatatttt actaataaaa tcttcaattc gctaaaagca cttcaattct  11040
tgttttctct tctggtttca gttgaccccc atatgcgagt gcagcatcac ggaccggact  11100
tgattatttt agaagttaag cgattttcgt gaagttaaga acaaaagaga agaccaaagt  11160
caactggggg tatacgctca cgtcgtagtg cctggcctga caggaacagg tgcgtacttc  11220
cttaacttca ctatcaataa aaccgtacct cctccagtcc atcgaaacaa caataaaata  11280
ctgcaccgat cagctggaat gtccttgtcc acgcatgaag gaattgaagt gatagttatt  11340
ttggcatgga ggaggtcagg tagctttgtt gttattttat gacgtggcta gtcgacctta  11400
ttctatcccg ggaggtccaa tcgctacaat ttatgcacat ttaattccac tggagccatg  11460
tgcgttcggg catcttatca ggcgttcggg aattgaaact aagatagggc cctccaggtt  11520
agcgatgtta aatacgtgta aattaaggtg acctcggtac acgcaagccc gtagaatagt  11580
ccgcaagccc ttaactttga ttacgacctc atttgtcatt aacgggatgc attcgtacgc  11640
agtcagcgtc ttatcggcat atatgcggta gccccccgag tgacaattaa accatggagc  11700
aatgctggag taaacagtaa ttgccctacg taagcatgcg tcagtcgcag aatagccgta  11760
tatacgccat cggggggctc actgttaatt tggtacctcg cgaaaccaat ttcacagcgg  11820
tccaccaact accgaatgcg atgcattttt atacgacagt ggcgttacta ggtgcttaac  11880
atatcaaaac ttggaagctt gctttggtta aagtgtcgcc aggtggttga tggcttacgc  11940
tacgtaaaaa tatgctgtca ccgcaatgat ccacgaattg tatagttttg aaccttcgaa  12000
cctttcaaaa gcttgcaaag cttccttcca ggagcttgga aagcttcctt ccaggagctt  12060
ggaaagcttc cttccaggag cttggaaagc ttccttccag ggaaagtttt cgaacgtttc  12120
gaaggaaggt cctcgaacct ttcgaaggaa ggtcctcgaa cctttcgaag gaaggtcctc  12180
gaacctttcg aaggaaggtc gagcttggaa agcttccttc caggagcttg gaaagcttcc  12240
ttccagtagc ttggaaagct tccttccagg agcttggaaa gcttccttcc aggagcttgg  12300
ctcgaacctt tcgaaggaag gtcctcgaac ctttcgaagg aaggtcatcg aacctttcga  12360
```

-continued

```
aggaaggtcc tcgaaccttt cgaaggaagg tcctcgaacc aaagcttcct tccaggagct  12420
tggaaagctt ccttccagga gcttggaaag cttccttcca ggagcttgga aagcttcctt  12480
ccaggagctt ggaaagcttc tttcgaagga aggtcctcga acctttcgaa ggaaggtcct  12540
cgaacctttc gaaggaaggt cctcgaacct ttcgaaggaa ggtcctcgaa cctttcgaag  12600
cttccaggag cttggaaagc ttccttccag gagcttggaa agcttccttc caggagcttg  12660
gaaagcttcc ttccaggagc ttggaaagct tccttccagg gaaggtcctc gaacctttcg  12720
aaggaaggtc ctcgaacctt tcgaaggaag gtcctcgaac ctttcgaagg aaggtcctcg  12780
aacctttcga aggaaggtcc agcttggaaa gcttccttcc aggagcttgg aaagcttcct  12840
tccaggagct tggaaagctt ccttccagga gcttggaaag cttccttcca ggagcttgga  12900
tcgaaccttt cgaaggaagg tcctcgaacc tttcgaagga aggtcctcga acctttcgaa  12960
ggaaggtcct cgaacctttc gaaggaaggt cctcgaacct aagcttcctt ccaggagctt  13020
ggaaagcttc cttccaggag cttggaaagc ttccttccag gagcttggaa agcttccttc  13080
caggagcttg gaaagcttcc ttcgaaggaa ggtcctcgaa cctttcgaag gaaggtcctc  13140
gaacctttcg aaggaaggtc ctcgaacctt tcgaaggaag gtcctcgaac ctttcgaagg  13200
ttccaggagt ggaaaagatt cctgaaaagt acttggagaa attcctcgag ttatttcagt  13260
aaagattata ctggaggaac caatggtgga atcacttgag aaggtcctca ccttttctaa  13320
ggacttttca tgaacctctt taaggagctc aataaagtca tttctaatat gacctccttg  13380
gttaccacct tagtgaactc gcatttcggc agaaatccct ggcaaaatcg ctatggaaaa  13440
atccctgcaa aaaatcctgg aataatcctt gccggaatct catgaggaac tcctggtaaa  13500
cgtaaagccg tctttaggga ccgttttagc gataccttt tagggacgtt ttttaggacc  13560
ttattaggaa cggccttaga gtactccttg aggaccattt attctttaac aaatttctgt  13620
ttattttctc tacaaagtta cagctccttt accgtgccga ttggccagaa atgaccccaa  13680
agactcatgg ggtacgatct taagaaattg tttaaagaca aataaaagag atgtttcaat  13740
gtcgaggaaa tggcacggct aaccggtctt tactggggtt tctgagtacc ccatgctaga  13800
tatttctgcc aaatatactg tatgtttgtt tctttctgat atgcttttaa gctcaatttt  13860
ctttggaatg gtggagattt gttttggcct ccaatatact ataaagacgg tttatatgac  13920
atacaaacaa agaaagacta tacgaaaatt cgagttaaaa gaaaccttac cacctctaaa  13980
caaaaccgga ggttatatga tgctagctcg tagttcgtac ctgaagtcaa ctcctcaatt  14040
cctaaatgct acaataatat ataaaatttt aggaaataac tgcaaaatat tctgaaggcc  14100
acgatcgagc atcaagcatg gacttcagtt gaggagttaa ggatttacga tgttattata  14160
tattttaaaa tcctttattg acgttttata agacttccgg atgtcttgat ctatcttgat  14220
gtatctaata tgtaatccca gaagcattct agttttttct gataatctgt gaaataagtt  14280
gtttttacga actttgactt tacagaacta gatagaacta catagattat acattagggt  14340
cttcgtaaga tcaaaaaaga ctattagaca ctttattcaa caaaaatgct tgaaactgaa  14400
ttcgggattt gaggtacaag ctttcaaata tattggaggt tctgcgatat taacttcaat  14460
gaattattgg aaattagaaa tcgtcttgtg catacgggtt aagccctaaa ctccatgttc  14520
gaaagtttat ataacctcca agacgctata attgaagtta cttaataacc tttaatcttt  14580
agcagaacac gtatgcccaa aatcgatttt agtctctggt agatttcgag agggaatgtc  14640
tgaagaaatt ttctgaccta catgtgaagt attgtctgtc aaattcaaaa tattttctgt  14700
```

-continued

```
ttagctaaaa tcagagacca tctaaagctc tcccttacag acttctttaa aagactggat  14760
gtacacttca taacagacag tttaagtttt ataaaagaca aggaaattaa aattttttgg  14820
ggaaaactcg aaactccttg gatatccaag gaaacaaaaa aaaaagaaat atctgaagaa  14880
gtgcatcgtc ctttttcctt tcctttaatt ttaaaaaacc ccttttgagc tttgaggaac  14940
ctataggttc ctttgttttt tttttcttta tagacttctt cacgtagcag gaaaaaggaa  15000
aattattgtt ttaattaact aatagttctg ctagaaaggt ttttggcaga accccaaaat  15060
gatattcaaa gcaactaaca gctcgatttc ccctcgtttc ttaataacaa aattaattga  15120
ttatcaagac gatctttcca aaaaccgtct tggggtttta ctataagttt cgttgattgt  15180
cgagctaaag gggagcaaag caatttcaga cgacgaactt gtcaaacgat ctcaatggct  15240
cctggagaag ctgcgatacc cctgggagat gatgcccctg atgtacgtga tactgaaagg  15300
gttaaagtct gctgcttgaa cagtttgcta gagttaccga ggacctcttc gacgctatgg  15360
ggaccctcta ctacggggac tacatgcact atgactttcc cgccgacgga gacgtcaata  15420
aagcgcgcca acggattgac gaaggtatgg gggttcttac cggttgggac tgtttccgag  15480
gtatcgatcg ggtgtcactc gcggctgcct ctgcagttat ttcgcgcggt tgcctaactg  15540
cttccatacc cccaagaatg gccaaccctg acaaaggctc catagctagc ccacagtgag  15600
acttcctggg tgctcccatt ttgtaactgc taacgcttat tattgagttt caggacatct  15660
gggatcttcg gtcgacggag tctattccca acagtgccct tgaaggaccc acgagggtaa  15720
aacattgacg attgcgaata ataactcaaa gtcctgtaga ccctagaagc cagctgcctc  15780
agataagggt tgtcacggga ggatcaaaca ctgccatcat gcagtttccg tagcctgttg  15840
ggctacgctc cccgacttga catcccccat tcttatcaaa caacaactca aggcctgaga  15900
cctagtttgt gacggtagta cgtcaaaggc atcggacaac ccgatgcgag gggctgaact  15960
gtagggggta agaatagttt gttgttgagt tccggactct caacgagtgg tggaatttgc  16020
gcacgaagtc attggtttgt cctggtaaaa gttaaaaggg ttaactggag ggttaattga  16080
cacggtttca actgatggcc gttgctcacc accttaaacg cgtgcttcag taaccaaaca  16140
ggaccatttt caattttccc aattgacctc ccaattaact gtgccaaagt tgactaccgg  16200
ttattgacac acggatgaaa gacttgcacg cttgaccttc tgtctgtact aataaaagtt  16260
acgttggctg ggttttgggg tcataatggc cccaaaatcg aataactgtg tgcctacttt  16320
ctgaacgtgc gaactggaag acagacatga ttattttcaa tgcaaccgac ccaaaacccc  16380
agtattaccg gggttttagc aatcgtcata acttcttgaa atacaactca cgtttaagac  16440
cattcaagag tattagatca tcgtctataa tagcagattt gaaatttact tcacatttcg  16500
ttagcagtat tgaagaactt tatgttgagt gcaaattctg gtaagttctc ataatctagt  16560
agcagatatt atcgtctaaa ctttaaatga agtgtaaagc gtattgcagt gccccttgct  16620
tccacaatgg aattagttaa agtttcgaga gcattgtcaa tatcaagtgt tgttagcaaa  16680
caaatgctaa catcaagatt cataacgtca cggggaacga aggtgttacc ttaatcaatt  16740
tcaaagctct cgtaacagtt atagttcaca acaatcgttt gtttacgatt gtagttctaa  16800
actatcgatg tttgattcac atgtattcca atcagctcgt aaaaaatgga aagtggagct  16860
gatagggttg agaatcgctt catgggataa ttggaaacag tgatagctac aaactaagtg  16920
tacataaggt tagtcgagca ttttttacct ttcacctcga ctatcccaac tcttagcgaa  16980
gtaccctatt aacctttgtc ggacatgatc agaatgaaaa tcagcgtgag taaccagttg  17040
actacaaaga tgactagagt cggttaagaa aaattcaagt agggctatca ggttattgaa  17100
```

```
cctgtactag tcttactttt agtcgcactc attggtcaac tgatgtttct actgatctca  17160
gccaattctt tttaagttca tcccgatagt ccaataactt ttgaaaaata tcccgaaggg  17220
ccctcatcaa ttaaaatttt gcctttggaa atgtttggca ttcaagtagc aaattttaac  17280
atactgcgat tcgatttccg aactttttat agggcttccc gggagtagtt aattttaaaa  17340
cggaaacctt tacaaaccgt aagttcatcg tttaaaattg tatgacgcta agctaaaggc  17400
caagttagtt tgaaacaaat taacttgcta cccagtgcat taaaaaggca agtaggcagc  17460
tttggaagta taaacttagc tgtgttttaa cagaagcact gttcaatcaa actttgttta  17520
attgaacgat gggtcacgta atttttccgt tcatccgtcg aaaccttcat atttgaatcg  17580
acacaaaatt gtcttcgtga cgcaagtttc aaaaattttg gtttcgaatg acaaaaaaag  17640
ttgatgttat atacgcctat tgaatgatga ttccagttga tcatttcgac aaacaaaaaa  17700
gcgttcaaag tttttaaaac caaagcttac tgttttttc aactacaata tatgcggata  17760
acttactact aaggtcaact agtaaagctg tttgtttttt gaatctcttt tgatttcaga  17820
tccaggattc aaataacatt ccgttatcag ataaagggtt aatgccacaa tcgtgtggtc  17880
cattatcccc ggaaacttca cttagagaaa actaaagtct aggtcctaag tttattgtaa  17940
ggcaatagtc tatttcccaa ttacggtgtt agcacaccag gtaatagggg cctttgaagt  18000
caccgtcaca ctcgatccag atctgatgtg atctctgccg tcgggcgcct cagaagcgaa  18060
aaccacattc gcccgcgctc tccggaatta tgtcgtaaaa gtggcagtgt gagctaggtc  18120
tagactacac tagagacggc agcccgcgga gtcttcgctt ttggtgtaag cgggcgcgag  18180
aggccttaat acagcatttt taaaacttta caaccataat tattcagaac ttcgacgact  18240
gcgcgatgac ttggccgcgg tgtgcctgct tgggatggac ctccgagcac tgaaagcagt  18300
attttgaaat gttggtatta ataagtcttg aagctgctga cgcgctactg aaccggcgcc  18360
acacggacga accctacctg gaggctcgtg actttcgtca ggtttgtaca aattgaatgg  18420
gctatttgaa attaattggg ctgcgataac ttcaaagtgt gacatcaaaa tggtgtgagt  18480
tttttactgc acaaattcca ccaaacatgt ttaacttacc cgataaactt taattaaccc  18540
gacgctattg aagtttcaca ctgtagtttt accacactca aaaaatgacg tgtttaaggt  18600
agttatttcc tacttcatat caatcggagc tccaggagtg aagatccaaa ttaccaagct  18660
tggccatttc gtatgaaaaa cggcaaaatg atcttttttt tcaataaagg atgaagtata  18720
gttagcctcg aggtcctcac ttctaggttt aatggttcga accggtaaag catacttttt  18780
gccgttttac tagaaaaaaa cgccagtcac tgtatctcat gatccagatg agataaaaaa  18840
gttcgagtct tcgacaaagt tgttttggaa gtcatggaca ttcttaagca aacaacttag  18900
gcggtcagtg acatagagta ctaggtctac tctatttttt caagctcaga agctgtttca  18960
acaaaacctt cagtacctgt aagaattcgt ttgttgaatc ttttgccact aggtggcgcc  19020
agtaagcata ttcgtcatca aacgtcaaca tcccaccgca aaatcgctag tgtttggagg  19080
ggattttaac ctccaaattg aaaacggtga tccaccgcgg tcattcgtat aagcagtagt  19140
ttgcagttgt agggtggcgt tttagcgatc acaaacctcc cctaaaattg gaggtttaac  19200
ccaaataacc tccaaatcat cacctccaag ttagttctaa tacactccgt tatatgaaat  19260
atggtggtgc gtcgatcgtc gcaagtttat cgttaaacag ggtttattgg aggtttagta  19320
gtggaggttc aatcaagatt atgtgaggca atatacttta taccaccacg cagctagcag  19380
cgttcaaata gcaatttgtc tcaataaaat gagcatttta tatcgtgata catatgagaa  19440
```

```
gatagaggtt tcaattaaaa caaatccaca tggtgtcgct aataaaattg tgcattttaa  19500
agttatttta ctcgtaaaat atagcactat gtatactctt ctatctccaa agttaatttt  19560
gtttaggtgt accacagcga ttattttaac acgtaaaatt gcgagttata tcctctgatc  19620
aagataaaat agaaaattcg atttttgaat attcaattat aagagcctga ataactacaa  19680
catgtagtga atcgaaactg cgctcaatat aggagactag ttctatttta tcttttaagc  19740
taaaaactta taagttaata ttctcggact tattgatgtt gtacatcact tagctttgac  19800
atttatgacg gtttgtgaag gttacacgtc ctaagcattt ggattcaaga aaagcaagag  19860
atatgacgaa tgtaaacttt atcgtatcaa tgaagtaact taaatactgc caaacacttc  19920
caatgtgcag gattcgtaaa cctaagttct tttcgttctc tatactgctt acatttgaaa  19980
tagcatagtt acttcattga agcgtccaga acagtacaaa ccaacatcgt accgtcgtat  20040
tccactccgg tcgttgcaat atctctaggt ccaccgaaaa acactcatga ccaagatcgt  20100
tcgcaggtct tgtcatgttt ggttgtagca tggcagcata aggtgaggcc agcaacgtta  20160
tagagatcca ggtggctttt tgtgagtact ggttctagca gtcgtcgatc ttggtccacc  20220
gaaacaccga tgtccatatc gtttcgtcga acttggacca acgattcatg caactgatga  20280
caacgcggcc cccgggtcgt cagcagctag aaccaggtgg ctttgtggct acaggtatag  20340
caaagcagct tgaacctggt tgctaagtac gttgactact gttgcgccgg gggcccagca  20400
accaatatcc gaaaaatcca actgttcttc tctgcctcgc aggtcaagcc gtggtcaatg  20460
aatactcacg attgcacaat ctgaacatgt tcgacggtgt tggttatagg ctttttaggt  20520
tgacaagaag agacggagcg tccagttcgg caccagttac ttatgagtgc taacgtgtta  20580
gacttgtaca agctgccaca agagttgcgc agtacgacgc gccagtccgg atgatagact  20640
ttttacacga tcagcacgac ccactgcgct gcggcaaagg tcgaaccgaa acaagaataa  20700
tctcaacgcg tcatgctgcg cggtcaggcc tactatctga aaaatgtgct agtcgtgctg  20760
ggtgacgcga cgccgtttcc agcttggctt tgttcttatt accacgaaga tcagatcgat  20820
tcgacggaag aagcaatcga atgcaaagaa gaatcggaac gaagaaaact ctaaagcatc  20880
gcatatttac aaagcataac tggtgcttct agtctagcta agctgccttc ttcgttagct  20940
tacgtttctt cttagccttg cttcttttga gatttcgtag cgtataaatg tttcgtattg  21000
ggaaaacccg caagttcaaa ctagtgatta gtgtaagatg aagcaaagca gaaatgtagt  21060
atctagattt ttcgacgtta gtttacaaag ataaaaaatg ccttttgggc gttcaagttt  21120
gatcactaat cacattctac ttcgtttcgt ctttacatca tagatctaaa aagctgcaat  21180
caaatgtttc tattttttac aggttggaca tacaatcgtg ggtattcgtc tgagttcgtc  21240
acaactgcac cggaaactgt gaaacagaat agagccaacc tgtgcgcgga gaatgttgag  21300
tccaacctgt atgttagcac ccataagcag actcaagcag tgttgacgtg gcctttgaca  21360
ctttgtctta tctcggttgg acacgcgcct cttacaactc gtcattataa gcttccttag  21420
catccacggg tgaaagtcga tcgacggaag cctgcaagac tctgtcgatg ggctttcgtc  21480
ctagaagaat aagattaaac cagtaatatt cgaaggaatc gtaggtgccc actttcagct  21540
agctgccttc ggacgttctg agacagctac ccgaaagcag gatcttctta ttctaatttg  21600
ctgaaatgta ttctcccgtg gaatggtttc atttgagtaa ttctgtatct tctccttccc  21660
aattccacga acgcgacgaa ctctaataca aacaacataa gactttacat aagagggcac  21720
cttaccaaag taaactcatt aagacataga agaggaaggg ttaaggtgct tgcgctgctt  21780
gagattatgt ttgttgtatt tgaccacagt gcaaatgctg tttaacgata atagcgacat  21840
```

-continued

```
gcagccattc tggggctacc acgtgtagct ctacttgtga gacagcgttc ctaaagagtg  21900
actggtgtca cgtttacgac aaattgctat tatcgctgta cgtcggtaag accccgatgg  21960
tgcacatcga gatgaacact ctgtcgcaag gatttctcac tgaaagtgca aacaagtgat  22020
gaaaccaata gtgcaaagca agtttagagg gaaaatttaa aaaatgcaaa acagcagtag  22080
tacttaactt ttaagattgt actttcacgt ttgttcacta ctttggttat cacgtttcgt  22140
tcaaatctcc cttttaaatt ttttacgttt tgtcgtcatc atgaattgaa aattctaaca  22200
gtttcgaaag ccgaagtgtg ttccatctgc caccggaaaa aaacgacgac agcagaatca  22260
tcaacaagca acatccatcc gaaaaaatcc gggaaaccgg caaagctttc ggcttcacac  22320
aaggtagacg gtggcctttt tttgctgctg tcgtcttagt agttgttcgt tgtaggtagg  22380
ctttttttagg ccctttggcc atcttcaacc aaccatccta caatctacaa accagagatt  22440
atatctcttc aatcgtttcc gacatcggtc ggtttcggtg cccaaaatga tctgataaac  22500
tagaagttgg ttggtaggat gttagatgtt tggtctctaa tatagagaag ttagcaaagg  22560
ctgtagccag ccaaagccac gggttttact agactatttg acttatctct ctgtagcttg  22620
catgccattg cgagcgtatt ttggtagctg gccgttgcca aacggctccg acaggtactg  22680
ctattggagg ttgtgcacga tgaatagaga gacatcgaac gtacggtaac gctcgcataa  22740
aaccatcgac cggcaacggt ttgccgaggc tgtccatgac gataacctcc aacacgtgct  22800
ccacgttgag tttgcctttt gagttggaga gtgtgtcttt tcgtcatata tttggccttt  22860
tcaagggtga ttttcaggct gcgtaaagat tgtatagttt ggtgcaactc aaacggaaaa  22920
ctcaacctct cacacagaaa agcagtatat aaaccggaaa agttcccact aaaagtccga  22980
cgcatttcta acatatcaaa aaccagctaa aacatattga tgacaagttc tatttcagca  23040
ccacaaacaa gcctgttaat gtctctcacc gcaaccattg ttctgcgcgc gttataatca  23100
ttggtcgatt ttgtataact actgttcaag ataaagtcgt ggtgtttgtt cggacaatta  23160
cagagagtgg cgttggtaac aagacgcgcg caatattagt gcatagaagt ttattttctt  23220
tgggatgatt caaatattac gtgacgcaaa gtttgccaat tttagaaccc ctccctcctc  23280
cacgtaacgg cttttgtgtg cgtatcttca aataaaagaa accctactaa gtttataatg  23340
cactgcgttt caaacggtta aaatcttggg gagggaggag gtgcattgcc gaaaacacac  23400
aaaaatttaa attttgtgta tagaccgtag catttcggaa gaccccctcc cttactctgt  23460
tgagttacgt aaaatttcaa cgatcctttt gtagttctga tttttaaatt taaaacacat  23520
atctggcatc gtaaagcctt ctgggggagg gaatgagaca actcaatgca ttttaaagtt  23580
gctaggaaaa catcaagact attttatatc agcgtgcagt gttatgaaga tatccacagt  23640
ataaaatatt attttatttt aaattctatg ctgattatca atgtgttact agtggctttt  23700
taaaatatag tcgcacgtca caatacttct ataggtgtca tattttataa taaaataaaa  23760
tttaagatac gactaatagt tacacaatga tcaccgaaaa catactcatg ttgcgagctc  23820
gatttggcgc acggggtcat ctacacctga tacctttagg gtcgttgggg gaccacttag  23880
cgtgcacgta cggacattca gtatgagtac aacgctcgag ctaaaccgcg tgccccagta  23940
gatgtggact atggaaatcc cagcaacccc ctggtgaatc gcacgtgcat gcctgtaagt  24000
aaatgttgtt caaatttttt tcttaccaag acgagcactt tacaatgaca aactctggct  24060
ctgctctggc tctgctctgg ctctgctctg gctctgctct tttacaacaa gtttaaaaaa  24120
agaatggttc tgctcgtgaa atgttactgt ttgagaccga gacgagaccg agacgagacc  24180
```

-continued

```
gagacgagac cgagacgaga ggctctgctc tggctctgct ctggctctgc tctggctctg  24240
ctctggctct gctctggctc tgctctggct ctgctctggc tctgctctgg ctctgctctg  24300
ccgagacgag accgagacga gaccgagacg agaccgagac gagaccgaga cgagaccgag  24360
acgagaccga gacgagaccg agacgagacc gagacgagac gctctgctct ggctctgctc  24420
tggctctgct ctggctctgc tctggctctg ctctggctct gctctggctc tgctctggct  24480
ctgctctggc tctgctctgg cgagacgaga ccgagacgag accgagacga gaccgagacg  24540
agaccgagac gagaccgaga cgagaccgag acgagaccga gacgagaccg agacgagacc  24600
ctctgctctg caaaatgctc tggattaatt tattgctcac actcttttgc tgttggacca  24660
ctattcattt caaatcttca atatgttcct attacccccca gagacgagac gttttacgag  24720
acctaattaa ataacgagtg tgagaaaacg acaacctggt gataagtaaa gtttagaagt  24780
tatacaagga taatgggggt aacacggtcc acacggatcg atttcaacta actccactct  24840
cgtatgcata ttttgtgtat aaattttgaa taatcgaaaa gggttgctgc aaatgttaat  24900
ttgtgccagg tgtgcctagc taaagttgat tgaggtgaga gcatacgtat aaaacacata  24960
tttaaaactt attagctttt cccaacgacg tttacaatta attttttccc tctacccccct  25020
cactctgtcg ttggcgttgg aaaaaaatca ccactgcata caaaacactc attggttggg  25080
tggaaggacg gtttagcaga taaaaaaggg agatggggga gtgagacagc aaccgcaacc  25140
ttttttttagt ggtgacgtat gttttgtgag taaccaaccc accttcctgc caaatcgtct  25200
gttgctaaat tttccatatc acgctgattg atttgtgatt aaaaataaat ataaatagaa  25260
aatgaataat tcccacatgt gtttcggtat taggcaccgg caacgattta aaaggtatag  25320
tgcgactaac taaacactaa tttttattta tatttatctt ttacttatta agggtgtaca  25380
caaagccata atccgtggcc catggggcgg cgaagtgcag acggttctag ttctcattat  25440
ttggcatcga ttggcggtca aactacaacc tccatggaga aacaggcccc atccgtactt  25500
gtaccccgcc gcttcacgtc tgccaagatc aagagtaata aaccgtagct aaccgccagt  25560
ttgatgttgg aggtacctct ttgtccgggg taggcatgaa agttattaat aaataacaat  25620
gatttgaatt tgaatcattc atgctgcggc gtggctgatt tcggtgaatt gttgttctct  25680
tagagaaaga gggggatttg tcaataatta tttattgtta ctaaacttaa acttagtaag  25740
tacgacgccg caccgactaa agccacttaa caacaagaga atctctttct cccccctaaac  25800
aatttggacg agtaaataac attgaatatt acactttatg actaatcacc agtaatgaaa  25860
caacacgggt gatgatttca aaagcttcat tctaaatgca ttaaacctgc tcatttattg  25920
taacttataa tgtgaaatac tgattagtgg tcattacttt gttgtgccca ctactaaagt  25980
tttcgaagta agatttacgt tggttcactt ttggtggcag atttaaaact cttatcttcc  26040
tcttttcttc aacaggtttc acgccatcaa agacgcttgg cagccgcttc catttgcgta  26100
accaagtgaa aaccaccgtc taaattttga gaatagaagg agaaaagaag ttgtccaaag  26160
tgcggtagtt tctgcgaacc gtcggcgaag gtaaacgcat gcaaacgtat gttaacctta  26220
ggttttaatg ttaaaagtat caccaaaaat caagtcccaa gacttctgca agaatggttt  26280
atgctgaatt tattcgaaat cgtttgcata caattggaat ccaaaattac aattttcata  26340
gtggttttta gttcagggtt ctgaagacgt tcttaccaaa tacgacttaa ataagcttta  26400
ggttttattt tcatcgaaac atgtgtgatg taggctacta ttttggtaaa accgttggca  26460
acgactgtat ttaaactcac aaaatttgaa ccaaacttat ccaaaataaa agtagctttg  26520
tacacactac atccgatgat aaaaccattt tggcaaccgt tgctgacata aatttgagtg  26580
```

```
ttttaaactt ggtttgaata aattgtaact tttaattgag taaacatagg cgaaagagag  26640
tgattcaaat gggattcgga atcgaacggt tcttctaagt aagacaaacg aaaaaaacaa  26700
ttaacattga aaattaactc atttgtatcc gctttctctc actaagttta ccctaagcct  26760
tagcttgcca agaagattca ttctgtttgc tttttttgtt ccaaacgagt caaagctgca  26820
aaaacttcaa gtttgaactg tgatatcaat gaaattaaat acgaactatg tatcaagatt  26880
acagtaaaat ttaaagaaga ggtttgctca gtttcgacgt ttttgaagtt caaacttgac  26940
actatagtta ctttaattta tgcttgatac atagttctaa tgtcatttta aatttcttct  27000
ctttcaacgc atgaaacagg agggtggcaa ccgaaaagtg actgaatcaa ttgcgggtta  27060
tcattcgaga tatccagggg ttgaattgtg agaaaacttc gaaagttgcg tactttgtcc  27120
tcccaccgtt ggcttttcac tgacttagtt aacgcccaat agtaagctct ataggtcccc  27180
aacttaacac tcttttgaag ttcttcttct tattcttggc aatacgtcct cactgggata  27240
gagtctgctt cctaacttca tgttcaatga ccacttccac agttattaac tgagagcttt  27300
aagaagaaga ataagaaccg ttatgcagga gtgaccctat ctcagacgaa ggattgaagt  27360
acaagttact ggtgaaggtg tcaataattg actctcgaaa ctttgccaaa gttgccattt  27420
tcgcattcgt atatcgtgtg gcagcagtgt tgtgaaaaac tcaatttctc ataactaacg  27480
cttgagattt ttcatgcgtg gaaacggttt caacggtaaa agcgtaagca tatagcacac  27540
cgtcgtcaca acacttttg agttaaagag tattgattgc gaactctaaa aagtacgcac  27600
agttgtcaat cacgcaactc agcagtcaaa attttccaca gtatacttac acacggcaat  27660
aatttcttgc tagtctggta aaattatagt aatcttttct tcaacagtta gtgcgttgag  27720
tcgtcagttt taaaaggtgt catatgaatg tgtgccgtta ttaaagaacg atcagaccat  27780
tttaatatca ttagaaaaga aacgtaaaca acaaaattcg ggtttcaaga gtttttgacg  27840
ggagcaagca aaataggatt tagaattttg catgagacga agtttgaaaa ttttattgtc  27900
ttgcatttgt tgttttaagc ccaaagttct caaaaactgc cctcgttcgt tttatcctaa  27960
atcttaaaac gtactctgct tcaaactttt aaaataacag aaatttagta tcggttcaat  28020
cgaattttcg aacacaattg taggctctat ataaactaca tttattccct tattttgcca  28080
gatacaatac tcgcataact tttaaatcat agccaagtta gcttaaaagc ttgtgttaac  28140
atccgagata tatttgatgt aaataaggga ataaaacggt ctatgttatg agcgtattga  28200
tgagatctcg cctaaaaagc cattggtaac cgagtgtgta gctctttgtt tctaagccaa  28260
ttaatggacc tggatgaaaa ctatcatcac tgggaaatag actctagagc ggatttttcg  28320
gtaaccattg gctcacacat cgagaaacaa agattcggtt aattacctgg acctactttt  28380
gatagtagtg accctttatc aggaggaact tgtctttatc gtagcattgt taaataacgt  28440
gtaaacccat ttgtttcctc ggtagctgca agctacacac tcgattacca atggctttta  28500
tcctccttga acagaaatag catcgtaaca atttattgca catttgggta aacaaaggag  28560
ccatcgacgt tcgatgtgtg agctaatggt taccgaaaat gggcgagatc acaagttatg  28620
cgagaatact tcccgaaatc accacctttt acccttttaa ataacgaaat tactacaaac  28680
ttcgttaccc gctctagtgt tcaatacgct cttatgaagg gctttagtgg tggaaaatgg  28740
gaaaatttat tgctttaatg atgtttgaag caat                              28774
```

<210> SEQ ID NO 44
<211> LENGTH: 3399
<212> TYPE: DNA

<213> ORGANISM: Cydia pomonella
<220> FEATURE:
<221> NAME/KEY: misc_feature
<222> LOCATION: (1179)..(1184)
<223> OTHER INFORMATION: n is a, c, g, or t

<400> SEQUENCE: 44

```
catcagacgg gcccaggctc aggatgaagc tagagcgcgg gcggcggacg cagggctcca     60
ccctcccggg atcgagctag atcggcctga gccgccagtg gtgaaagcgc cgaggagtcc    120
cgtgatcccg ccgccgccgc cgcgctccat gggatcggcg agctgcgact ccgttccggg    180
atcgcccggg gtatcgccgt atgcgccgaa cccgccgtcc gctccgcctc cgccgatgcc    240
gccgctcccg cctccgcaac cagtggccct ggactccctg gtagaaaact gccacaagct    300
gctggaaaaa ttccactaca gttgggagat gatgccgctc gtgctggtca tcctcaacta    360
cgccggctcc gacctggagg aggcctcgcg gaagattgac gaaggtaagt ttaaatttaa    420
gtacataaca atgcttacag acgaattgaa agggaatgtg actcggctaa tccaccagga    480
tataattttg tagagtgcgc taaagaattc tagcaacgga cgctgttatt ctgccaccgc    540
cgttgatgcc gccgtcttct gatagtgata ctttaagatc cgtatactac gctcacttcc    600
attcacttat gtcgtacgga gtattaatat gggtaaactc gcggacacga aacgattacg    660
aaaacgcaga gtacttagat tggagcaaag cccagggatt cgccgagact tttttgttac    720
ggaagattga tgaaggtaag caagttggga ctgtggcgag ttgacacatg aaacaagtca    780
aggtcacagc tggagttcca ttaaagctgg atgctaccgc tagtcatcct gaggccggct    840
ccgacttcgt gcaatgaggt attaagctgc tggaattgaa tggaatatag tggtgaaaca    900
ctactactag gtttaagcgt ttagttatat ggttgttttc ttatttttaa tttttaaatg    960
ctctgctaag ctaaaacggc waatgtctat ttttgattat aaagacttat ataaaacaac   1020
ttgtttagct tctttkacgt ctttttgtta agctgtgccc tggttttaaa wkgggcgaac   1080
acytcacgaa taagacgtaa ttttaaaaag aaaatagata tcggccctct tggttcgcat   1140
ttatacatat gtattgctgc ccgtgcgaat gttggggann nnnnaaacag tacccctagt   1200
gtaartaaat tcgatttcga aacgtgacgt acgcgtttgc gtttagtctc mwtttgtatt   1260
ggatttagaa agagcgcgcc aagcgggacg ttttggaaac tcaaaatcct atacaaaatg   1320
agacttaacg caaasgcgtt tcgtcacgtt atgatgtcga tcaaatttac actaggggta   1380
cagaggtatt gcagtaactg tacaaatact aaactaaatt aataaattag ctaaatctaa   1440
aatataccct tcaggcattg tactaaggat gctggcggaa ttacttgtgc gaggaagccg   1500
ccagcttttc ggtcaccatt tacgagtacg tataccaaac gcttcgttgc tgcaaaaaag   1560
tttcaacgcc aaatggtaca aaatgcttta tattgttctc tatatattat attaacacat   1620
cgttatttta acctaggtct tagttatgta caaggttaca taaaatagat gttcctagtc   1680
cattcctccg tgtatgttgt gtctattata aagcaaggct gcattttgta atcagtcaat   1740
ttcaatataa aaaagttgca tcgttttttt ttactkttcg acaattaaat tcaagtagca   1800
aaaaataacc caccttaatt tgtcatggtc ataatgaaac aatgacaarg ttttttttat   1860
cgcccgatac atgtacgtgt tctccaaaat gcagtctccg cgccgccaag cgaacgttca   1920
aactgtgcga tttccgttgt ccccaggcaa aatgatcatc aacgattacg ccaggaagca   1980
taatctgaac atcttcgacg ggctcgagct gaggaactcg acacgccact ccatttcgga   2040
tggcgatgaa aaacgcccac cgcaacctaa gcaagtctca aagtaaggtt ccatttaaat   2100
catctcaaaa ccgttagaaa cactcaaaaa gaaaccaaaa ttctgttcgg aaaccgacct   2160
```

```
ttgtttttta cacacactta gaccgaattt gcaaatttta accccttatt cctaaaacta   2220
gcaatggtaa gctcggctga atttcacata caaacggagt ttcgttctca ttataaaact   2280
gcgtgttgga ttgtaatgga actttgcaca tacaatgaca tgaggtatgt ctagggctga   2340
aattagttta tacttggtat ctgaggctac ataaactaat tacagcctta gacttggagg   2400
atttaacaac tggaaacacc ttgtctgtaa ttctctgtac aacgatttta cgggggagga   2460
gcaaatatgt cagttaaacg tcagtccaaa caatacatat gactattggc cgtggtattt   2520
cgacggaggg gtaataagct cttaaaggcg actccgatat gcctaatcct attgttagta   2580
caaagtttca gagcaattta gctagtcgtt ttaaaatgag agcgtaacta cgttagcttg   2640
ctcttcttcc tcctgctctt atcccacgtt atgtggggtc ggcacaacat gttcctctct   2700
tctcactcct ttctttctca tatcctcttt cacacaatcc atccatcgtt tacttacaac   2760
cgagcttgct ggggaccgtt aaggcgccgc gagttcaggt tcttctctca ctctcactct   2820
cactggtgtg agcggagcga gacagcgttt tattttcgcc ttatcgaggt tccactgtat   2880
tataaataac ttacatttat aaagacgctg taatcgataa gaagttgagt cacgcttacg   2940
tcgcttacgt actacgtata gtaacgtagc ctgccgttta caaacaatgt acggagctac   3000
aacgttgcaa gttcggtccc cacacaacac aatgtgtcat aacacattaa caacattgtt   3060
acacacccac acatacaaat ttgctaagtt gataaaagag tggtgtgtcc gacgaatcag   3120
aacatcacta acccagtcgt gatttcattt ccacagtgac cggacgaagg tggagaagtt   3180
cgaaatttaa aaaaagtgac cacattttat ttaatagtga tgtgcaagtg atactatttt   3240
tattttgttt ttcttttgta ggaaaatgct gagcgaaata aataatttta gtggtgtgct   3300
atcgtcatcg atgaagttgt tttgcgaatg atactatgtt cttcaagtgc tgtgttttgt   3360
ggactgtggg gtgactgttc ctgtaaataa gcttcgttg                          3399
```

<210> SEQ ID NO 45
<211> LENGTH: 996
<212> TYPE: DNA
<213> ORGANISM: Cydia pomonella

<400> SEQUENCE: 45

```
catcagacgg gcccaggctc aggatgaagc tagagcgcgg gcggcggacg cagggctcca     60
ccctcccggg atcgagctag atcggcctga gccgccagtg gtgaaagcgc cgaggagtcc    120
cgtgatcccg ccgccgccgc cgcgctccat gggatcggcg agctgcgact ccgttccggg    180
atcgcccggg gtatcgccgt atgcgccgca cccgccgtcc gctccgcctc cgccgatgcc    240
gccgctcccg cctccgcaac cagtggcctt ggactccctg gtagaaaact gccacaagct    300
gctggaaaaa ttccactaca gttgggagat gatgccgctc gtgctggtca tcctcaacta    360
cgccggctcc gacctggagg aggcctcgcg gaagattgac gaagcctcct gggtggtgca    420
ccagtggcgg ctgtacgagc gctcactgtg ctcgctgctg gagctgcaag cgcgcaaaga    480
gtcgttttgc tgctcgccgc gctatgtgct gtcgcgcgag tacgcgccgc acctgcccgt    540
gccgctcatg cgctcgccgc cgccagcgca cttgtagccc cacaccgcgc cgcgacagac    600
ggcgcacgag cccactgagc catctacttc ggccaaaccc gagtaggccc gaggccgacc    660
cgagcccgac ccgagaggac ccgagtgggc tattccggac tttacctagt tttatatgtg    720
ctatacgtgt tacaacacgc atatttgtat attatcacgg acattaagtt ggagagcggt    780
taccttatct tgttaacccg gtccttgaag taattattcc cagatatatt aagaaaacca    840
```

gtgaatactt tgcctgatgt ataattaaca gttgttaagc aaccatgaga attatggtat 900
ttcttgtgga catgttgcag ctagaaattt catatcatcg gtgataaaat ttaaccacac 960
tgtggttggc ggaaaaccac attgtttgta atattg 996

<210> SEQ ID NO 46
<211> LENGTH: 6751
<212> TYPE: DNA
<213> ORGANISM: artificial
<220> FEATURE:
<223> OTHER INFORMATION: Sequence of pLA3435-Bombyx mori-dsx
construct/plasmid.
<220> FEATURE:
<221> NAME/KEY: misc_feature
<222> LOCATION: (1617)..(1622)
<223> OTHER INFORMATION: n is a, c, g, or t

<400> SEQUENCE: 46
ggccgcatgg tacccattgc ttgtcattta ttaatttgga tgatgtcatt tgtttttaaa 60
attgaactgg ctttacgagt agaattctac gcgtaaaaca caatcaagta tgagtcataa 120
tctgatgtca tgttttgtac acggctcata accgaactgg ctttacgagt agaattctac 180
ttgtaatgca cgatcagtgg atgatgtcat ttgtttttca aatcgagatg atgtcatgtt 240
ttgcacacgg ctcataaact cgctttacga gtagaattct acgtgtaacg cacgatcgat 300
tgatgagtca tttgttttgc aatatgatat catacaatat gactcatttg tttttcaaaa 360
ccgaacttga tttacgggta gaattctact tgtaaagcac aatcaaaaag atgatgtcat 420
ttgtttttca aaactgaact cgctttacga gtagaattct acgtgtaaaa cacaatcaag 480
aaatgatgtc atttgttata aaaataaaag ctgatgtcat gttttgcaca tggctcataa 540
ctaaactcgc tttacgggta gaattctacg cgtaaaacat gattgataat taaataattc 600
atttgcaagc tatacgttaa atcaaacgga cgctcgaggt tgcacaacac tattatcgat 660
ttgcagttcg ggacataaat gtttaaatat atcgatgtct ttgtgatgcg cgcgacattt 720
ttgtaggtta ttgataaaat gaacggatac gttgcccgac attatcatta aatccttggc 780
gtagaatttg tcgggtccat tgtccgtgtg cgctagcatg cccgtaacgg acctcgtact 840
tttggcttca aaggttttgc gcacagacaa aatgtgccac acttgcagct ctgcatgtgt 900
gcgcgttacc acaaatccca acggcgcagt gtacttgttg tatgcaaata aatctcgata 960
aaggcgcggc gcgcgaatgc agctgatcac gtacgctcct cgtgttccgt tcaaggacgg 1020
tgttatcgac ctcagattaa tgtttatcgg ccgactgttt tcgtatccgc tcaccaaacg 1080
cgtttttgca ttaacattgt atgtcggcgg atgttctata tctaatttga ataaataaac 1140
gataaccgcg ttggttttag agggcataat aaaagaaata ttgttatcgt gttcgccatt 1200
agggcagtat aaattgacgt tcatgttgga tattgtttca gttgcaagtt gacactggcg 1260
gcgacaagca attctaattg gggtaagttt tcccgttctt ttctgggttc ttcccttttg 1320
ctcatccttg ctgcactacc ttcaggtgca agttgagatt caggccacca tgggagatcc 1380
caccccaccc aagaagaagc gcaaaccggt ccgtcccctc ggagacgctt gtggagaact 1440
gtcacagact cctcgagaag ttccattact cgtgggagat gatgccgctt gtgctcgtca 1500
tcatgaacta cgcccgcagc gacttggatg aggcttcaag gaaaatctac gaaggtaccg 1560
aatgtgtaaa tacgagtgta gcgttgatta gaaaacggac attgttcgtg agtttannnn 1620
nnggtctctc tggccagcaa gacatttgaa acactgtaaa aaaattcatt gaaaaaaaag 1680
aacactgtaa tgaaaatatt ctgaatgctt aatctggtat ttcagggatt aaactgattg 1740

-continued

```
tgatgaaaag tgattaaact attttcttta agtaccaaat taaccgaaca ggtttgggtc   1800
tttcctttca gtaacaaaca aaatctatcg aaggtaagaa ataaacaaca ggatattttc   1860
ttttactaaa aatcaataag gagactgcac tatttcaatg ttcaacttcc tttatcgaat   1920
gcatgaaaaa tttaattgtc taaaaatcta aattactaat taacgcaaag gaacctttgc   1980
ctaaaaaaaa aaataagcta ttaaacgaat gcctaaaata cgtaacagtg ttgccagttg   2040
taaaaattgc gaatccgaga agtgcagttt cctgaaatgc ccagcgatac gaatttccta   2100
tgttagagtc ttgtccgcag ggaagatgat cgtcgacgag tacgcgagga agcacaactt   2160
gaacgtgttc gacggactag aactaaggaa ctcgacacgc caggcgcgcc ggatccggcc   2220
ggccgaaaat gctggaaatt aataatataa gtggtgtact gtcttcgtca atgaagttat   2280
tttgcgaatg atacttagtt ttacaagtgc cgtggtgtgt gttgacactt gctgtgcgat   2340
gctgtgcgaa tttcaacgga aatatttgtt gtcgtaacat tggatctatg ggtaagttta   2400
gtataataac tttactctgt tcacattagt gaaacataca tttgtaaaat ttgtgtttta   2460
ctaatgtgaa atttattttt ggaaattcac gttaacacta ttgaataaaa aaaaatcgat   2520
aatgtaattt aaaaaaaata caaaaatata gttttcgctt attgttagaa agaaaatttt   2580
acatacgcca ttttgaataa ttccttccgg gtacattggg ccctaaacca gcgatcgggg   2640
aacttttta attattaccc taaaatattt ttatgtaagt tgatattacc gatggcgaag   2700
aacaacaaaa aaaaaaacga aatcgcttct ttttagcatc tttcatatta tagaccccac   2760
gataatttta aatcacaacg attataaaga agtttcactt caatatatac tttttactca   2820
caaaagtttc atttttaccc catttgggat aatttagccc ggttcccccc ccgaccgctg   2880
gcctaaacgt atcaccgaca atagctaaaa taacaaggta cgttcgattt gccgagctga   2940
actaacatta cacagctttg cattattcat atgtacattg cgactgaaac gtccggaccg   3000
ttacaggtta ttggatgatg catcaatggc gattgcagca gtattcgttg tgctacggag   3060
cgctggagtt gtcggcgcgc aaggatgtgg ccgcgctatg ttgcctccga gatacgtgct   3120
ggcgcccgag gtcccgccgc gtctggtgcc cctccagctg atctagataa ctgatcataa   3180
tcagccatac cacatttgta gaggttttac ttgctttaaa aaacctccca cacctccccc   3240
tgaacctgaa acataaaatg aatgcaattg ttgttgttaa cttgtttatt gcagcttata   3300
atggttacaa ataaagcaat agcatcacaa atttcacaaa taaagcattt ttttcactgc   3360
attctagttg tggtttgtcc aaactcatca atgtatctta acgcgagtta attaagtgcg   3420
cgtaaattgt aagcgttaat attttgttaa aattcgcgtt aaatttttgt taaatcagct   3480
catttttaa ccaataggcc gaaatcggca aaatccctta taaatcaaaa gaatagaccg   3540
agatagggtt gagtgttgtt ccagtttgga acaagagtcc actattaaag aacgtggact   3600
ccaacgtcaa agggcgaaaa accgtctatc agggcgatgg cccactacgt gaaccatcac   3660
cctaatcaag ttttttgggg tcgaggtgcc gtaaagcact aaatcggaac cctaaaggga   3720
gcccccgatt tagagcttga cggggaaagc cggcgaacgt ggcgagaaag gaagggaaga   3780
aagcgaaagg agcgggcgct agggcgctgg caagtgtagc ggtcacgctg cgcgtaacca   3840
ccacacccgc cgcgcttaat gcgccgctac agggcgcgtc aggtggcact tttcggggaa   3900
atgtgcgcgg aacccctatt tgtttatttt tctaaataca ttcaaatatg tatccgctca   3960
tgagacaata accctgataa atgcttcaat aatattgaaa aaggaagagt cctgaggcgg   4020
aaagaaccag ctgtggaatg tgtgtcagtt agggtgtgga aagtccccag gctccccagc   4080
aggcagaagt atgcaaagca tgcatctcaa ttagtcagca accaggtgtg gaaagtcccc   4140
```

```
aggctcccca gcaggcagaa gtatgcaaag catgcatctc aattagtcag caaccatagt   4200
cccgccccta actccgccca tcccgcccct aactccgccc agttccgccc attctccgcc   4260
ccatggctga ctaatttttt ttatttatgc agaggccgag gccgcctcgg cctctgagct   4320
attccagaag tagtgaggag gcttttttgg aggcctaggc ttttgcaaag atcgatcaag   4380
agacaggatg aggatcgttt cgcatgattg aacaagatgg attgcacgca ggttctccgg   4440
ccgcttgggt ggagaggcta ttcggctatg actgggcaca acagacaatc ggctgctctg   4500
atgccgccgt gttccggctg tcagcgcagg ggcgcccggt tctttttgtc aagaccgacc   4560
tgtccggtgc cctgaatgaa ctgcaagacg aggcagcgcg gctatcgtgg ctggccacga   4620
cgggcgttcc ttgcgcagct gtgctcgacg ttgtcactga agcgggaagg gactggctgc   4680
tattgggcga agtgccgggg caggatctcc tgtcatctca ccttgctcct gccgagaaag   4740
tatccatcat ggctgatgca atgcggcggc tgcatacgct tgatccggct acctgcccat   4800
tcgaccacca agcgaaacat cgcatcgagc gagcacgtac tcggatggaa gccggtcttg   4860
tcgatcagga tgatctggac gaagagcatc aggggctcgc gccagccgaa ctgttcgcca   4920
ggctcaaggc gagcatgccc gacggcgagg atctcgtcgt gacccatggc gatgcctgct   4980
tgccgaatat catggtggaa aatggccgct tttctggatt catcgactgt ggccggctgg   5040
gtgtggcgga ccgctatcag gacatagcgt tggctacccg tgatattgct gaagagcttg   5100
gcggcgaatg ggctgaccgc ttcctcgtgc tttacggtat cgccgctccc gattcgcagc   5160
gcatcgcctt ctatcgcctt cttgacgagt tcttctgagc gggactctgg ggttcgaaat   5220
gaccgaccaa gcgacgccca acctgccatc acgagatttc gattccaccg ccgccttcta   5280
tgaaaggttg ggcttcggaa tcgttttccg ggacgccggc tggatgatcc tccagcgcgg   5340
ggatctcatg ctggagttct tcgcccaccc taggggagg ctaactgaaa cacggaagga   5400
gacaataccg gaaggaaccc gcgctatgac ggcaataaaa agacagaata aaacgcacgg   5460
tgttgggtcg tttgttcata aacgcggggt tcggtcccag ggctggcact ctgtcgatac   5520
cccaccgaga ccccattggg gccaatacgc ccgcgtttct tccttttccc caccccaccc   5580
cccaagttcg ggtgaaggcc cagggctcgc agccaacgtc ggggcggcag gccctgccat   5640
agcctcaggt tactcatata tactttagat tgatttaaaa cttcattttt aatttaaaag   5700
gatctaggtg aagatccttt ttgataatct catgaccaaa atcccttaac gtgagttttc   5760
gttccactga gcgtcagacc ccgtagaaaa gatcaaagga tcttcttgag atcctttttt   5820
tctgcgcgta atctgctgct tgcaaacaaa aaaaccaccg ctaccagcgg tggtttgttt   5880
gccggatcaa gagctaccaa ctctttttcc gaaggtaact ggcttcagca gagcgcagat   5940
accaaatact gtccttctag tgtagccgta gttaggccac cacttcaaga actctgtagc   6000
accgcctaca tacctcgctc tgctaatcct gttaccagtg gctgctgcca gtggcgataa   6060
gtcgtgtctt accgggttgg actcaagacg atagttaccg gataaggcgc agcggtcggg   6120
ctgaacgggg ggttcgtgca cacagcccag cttggagcga acgacctaca ccgaactgag   6180
atacctacag cgtgagctat gagaaagcgc cacgcttccc gaagggagaa aggcggacag   6240
gtatccggta agcggcaggg tcggaacagg agagcgcacg agggagcttc caggggggaaa   6300
cgcctggtat ctttatagtc ctgtcgggtt tcgccacctc tgacttgagc gtcgattttt   6360
gtgatgctcg tcaggggggc ggagcctatg gaaaaacgcc agcaacgcgg cctttttacg   6420
gttcctggcc ttttgctggc cttttgctca catgttcttt cctgcgttat cccctgattc   6480
```

-continued

```
tgtggataac cgtattaccg ccatgcatta gttattaata gtaatcaatt acggggtcat   6540

tagttcatag cccatatatg gagttccgcg ttacataact tacggtaaat ggcccgcctg   6600

gctgaccgcc caacgacccc cgcccattga cgtcaataat gacgtatgtt cccatagtaa   6660

cgccaatagg gactttccat tgacgtcaat gggtggagta tttacggtaa actgcccact   6720

tggcagtaca tcaagtgtat catagcgatg c                                  6751
```

```
<210> SEQ ID NO 47
<211> LENGTH: 8183
<212> TYPE: DNA
<213> ORGANISM: artificial
<220> FEATURE:
<223> OTHER INFORMATION: Sequence of pLA3359-Anopheles gambiae dsx
      construct

<400> SEQUENCE: 47

ccggtgctgc tgttgctgat gctacgatcc tcgacagtga ttggaaacgc ctggagatgg     60

tgggaaaaaa tcaaacacaa aaacggtcct aatgaacatc gtgtgttctc attcgctgcc    120

acgattgaca ccttcgataa gacgcacata atgagctaaa ggagagggga cagggtcttg    180

tctttgccac gagcgataag attgcaatca ctcgtgagcg tgtgctgctg ggctgaagaa    240

gaaacacttt ccacagcagt aggtgggaag tgggattgtg gaacgtggca ttgaaaagaa    300

cctattttct aaagcccgag agcccgttct cgaactggaa aacgagatgc agaagttttt    360

tattgtcccc cgccaggaaa acaaatgtat ttaatgcttt ctctgccttt tccgccccgt    420

ttcagacgac gagctagtga agcgagccca atggctgttg gagaaactcg gctacccgtg    480

ggagatgatg cccctgatgt acgtcatact gaagagcgcc gatggcgatg tacaaaaagc    540

acaccagcgg atcgacgaag gtaagctggc gatgatggtg tcgttcgaca tcactttcat    600

caccgtgtca gacatctact gtgcctagca ccggtccagt ggtcacaggg tgtagcaaaa    660

acgtgttctt ttttgcgaga gactctacct catgatgcag ctgttaagga aaggtttcag    720

atgaagacaa tttttcctag gataatatga tcttaagtta cctgcgtatg agtgtttaac    780

attgtcgtct caactccaag gaatgtttta accgtctagg gctagtttat ttatactgtt    840

ctcattgaaa tgtcgttaaa tccaacatgt taagttagct agctcagaca cgagaagtta    900

ggagtatctg catcttgaag gtagcggcat atggtgttat gccacgttca ctgacttcaa    960

aattcgatac aaaaaaaaac aaaatcaaaa acaaaattgt gaattccgtc agccagcagc   1020

agtgaccttc aaagccttac ctttccattc atttatgttt aacacaggtc aagcggtggt   1080

caacgaatac tcacgattgc ataatctgaa catgtttgat ggcgtggagt tgcgcaatac   1140

cacccgtcag agtggatgat aaactttccg caccactgta actgtccgta tctttgtatg   1200

tgggtgtgtg tatgtgtgtt tggtgaaacg aattcaattg ttctgtgcta ttttaaatca   1260

agccgcgtgc gcaactgatg ccgataagtt caaactagtg tttaaggagt ggagagagag   1320

agccgcacca cggtacagaa gggcagcaga atgggtcggc agcctagctg cactggtgcg   1380

gtgcgtccgg cgtctcgggg ggagggcggg gaaattctag tgttaaatcg gagcagcaaa   1440

aacaaaacag tggtcgtccc gttcaagaaa cggcctgtac acacacagaa aacactgcag   1500

catgtttgta catagtagat cctagagcag gtggtcgttg ctcctcgaac gctctggacg   1560

cacggcttcg cgcgtacttg cgtagcgttc caccgatcgt gggtattcgt actgccacaa   1620

gcccgctttc tcccatgcaa tctctgcaac caaaccaaca aacaacaaca aaataccaat   1680

cgacacaatg aatcacaccc cttttgtatc atctgtatat tcttgttctt tgcgttcttt   1740
```

-continued

```
tccatgtggc ccacgccccg gcgggtacgt aattgcgtcg aaaaccccga aaaccccggc   1800
acatacagtg tacatacggt ttgaggacaa ctttgacctg cagcccttct ggggctgcca   1860
cgtgtagcta tacttgtgag atcgggcgcc gacggtgtaa agcgcgaatg gccgccacac   1920
agtgtgtcca ctccaacact acccctctgg aactaccccg tccagggatg caccggctcg   1980
gctcatgccc ctgcaaaaca gtccgggctc cactgtagta gctccggcgt tgctctgaga   2040
gaaggatgcc cttcgaagtg tcgaaagcgt gcattgggcg ttcaagtgtg tgtctgtgtt   2100
aggtttagcg agaaacagca gcagttgcgt gtgctgaaaa gcgaaggagt aatagagtgc   2160
ataatgaaaa tgaaaatgaa aatgaagcaa aagtagaagg cggaggagag caacctgtgt   2220
tccactagta gcgaatagtt tagtctagtt tcgtcaccaa tcaaccttcc aaccatcgtt   2280
caaccaatac ctgagtcaac atcgtcatcg ttatcgtgcc acaactttat taaaaatgaa   2340
ccttgtccgc gccaccgtag ggtgatctga ggcgaccttt cttacgggcg cgactcacat   2400
gccatcgtca ccttctccaa tcaaaaccaa cagcctgtac cgatggtgtg caattgtgcg   2460
tgcgtgtgtg ttattagcaa aaaaagagaa agagacggcg agagagagat agatcgagat   2520
cgagagtaca aaagagcagt agaaatgttc gttgtttgtt ttccgtaaca cagttgttta   2580
gccaaaatgg gaatttccaa taatcccggg ggcggggaaa tgcgggaata ctgcgtacac   2640
acatacatca atcaaaaaga aaaatccttg cgctacatca ctaccgtttg cgcggtgctg   2700
atctagagca gaccactttc cacgccattc tacaatcaat caatctgtgc agaaggtatg   2760
gtaagacggc ctttgagcga gtcacggtcg ccaccataac gccgtccgac gagggctgaa   2820
tgcgaacttt gctaatcgat tttccgcttt ctttttatcc cacccccctt tctctctctc   2880
tcttttgcac cgccccttgt aacccccaaa aaggtaaacg acacattaag acctacgaag   2940
cgctggtgaa gtcatcgctc gatccgaaca gcgaccggct gacggaagac gacgacgagg   3000
acgagaacat ctcggtgacc cgcaccaact ccaccattcg gtcgaggtcc agctcgctgt   3060
cgcggtcccg gtcctgctcg cgccaggccg aaactccccg ggccgacgat cgggccctga   3120
accttgacac caaatagatc tcgacccaag aaaaagcgga aggtggagga cccgtaagat   3180
ccaccggatc tagataactg atcataatca gccataccac atttgtagag gttttacttg   3240
ctttaaaaaa cctcccacac ctccccctga acctgaaaca taaaatgaat gcaattgttg   3300
ttgttaactt gtttattgca gcttataatg gttacaaata aagcaatagc atcacaaatt   3360
tcacaaataa agcatttttt tcactgcatt ctagttgtgg tttgtccaaa ctcatcaatg   3420
tatcttaacg cgagttaatt aagtgcgcgt aaattgtaag cgttaatatt ttgttaaaat   3480
tcgcgttaaa tttttgttaa atcagctcat tttttaacca ataggccgaa atcggcaaaa   3540
tcccttataa atcaaaagaa tagaccgaga tagggttgag tgttgttcca gtttggaaca   3600
agagtccact attaaagaac gtggactcca acgtcaaagg gcgaaaaacc gtctatcagg   3660
gcgatggccc actacgtgaa ccatcaccct aatcaagttt tttggggtcg aggtgccgta   3720
aagcactaaa tcggaaccct aaagggagcc cccgatttag agcttgacgg ggaaagccgg   3780
cgaacgtggc gagaaaggaa gggaagaaag cgaaaggagc gggcgctagg gcgctggcaa   3840
gtgtagcggt cacgctgcgc gtaaccacca cacccgccgc gcttaatgcg ccgctacagg   3900
gcgcgtcagg tggcactttt cggggaaatg tgcgcggaac ccctatttgt ttatttttct   3960
aaatacattc aaatatgtat ccgctcatga gacaataacc ctgataaatg cttcaataat   4020
attgaaaaag gaagagtcct gaggcggaaa gaaccagctg tggaatgtgt gtcagttagg   4080
gtgtggaaag tccccaggct ccccagcagg cagaagtatg caaagcatgc atctcaatta   4140
```

-continued

```
gtcagcaacc aggtgtggaa agtccccagg ctccccagca ggcagaagta tgcaaagcat   4200
gcatctcaat tagtcagcaa ccatagtccc gcccctaact ccgcccatcc cgcccctaac   4260
tccgcccagt tccgcccatt ctccgcccca tggctgacta atttttttta tttatgcaga   4320
ggccgaggcc gcctcggcct ctgagctatt ccagaagtag tgaggaggct tttttggagg   4380
cctaggcttt tgcaaagatc gatcaagaga caggatgagg atcgtttcgc atgattgaac   4440
aagatggatt gcacgcaggt tctccggccg cttgggtgga gaggctattc ggctatgact   4500
gggcacaaca gacaatcggc tgctctgatg ccgccgtgtt ccggctgtca gcgcaggggc   4560
gcccggttct ttttgtcaag accgacctgt ccggtgccct gaatgaactg caagacgagg   4620
cagcgcggct atcgtggctg gccacgacgg gcgttccttg cgcagctgtg ctcgacgttg   4680
tcactgaagc gggaagggac tggctgctat tgggcgaagt gccggggcag gatctcctgt   4740
catctcacct tgctcctgcc gagaaagtat ccatcatggc tgatgcaatg cggcggctgc   4800
atacgcttga tccggctacc tgcccattcg accaccaagc gaaacatcgc atcgagcgag   4860
cacgtactcg gatggaagcc ggtcttgtcg atcaggatga tctggacgaa gagcatcagg   4920
ggctcgcgcc agccgaactg ttcgccaggc tcaaggcgag catgcccgac ggcgaggatc   4980
tcgtcgtgac ccatggcgat gcctgcttgc cgaatatcat ggtggaaaat ggccgctttt   5040
ctggattcat cgactgtggc cggctgggtg tggcggaccg ctatcaggac atagcgttgg   5100
ctacccgtga tattgctgaa gagcttggcg gcgaatgggc tgaccgcttc ctcgtgcttt   5160
acggtatcgc cgctcccgat tcgcagcgca tcgccttcta tcgccttctt gacgagttct   5220
tctgagcggg actctggggt tcgaaatgac cgaccaagcg acgcccaacc tgccatcacg   5280
agatttcgat tccaccgccg ccttctatga aaggttgggc ttcggaatcg ttttccggga   5340
cgccggctgg atgatcctcc agcgcgggga tctcatgctg gagttcttcg cccaccctag   5400
ggggaggcta actgaaacac ggaaggagac aataccggaa ggaacccgcg ctatgacggc   5460
aataaaaaga cagaataaaa cgcacggtgt tgggtcgttt gttcataaac gcggggttcg   5520
gtcccagggc tggcactctg tcgatacccc accgagaccc cattggggcc aatacgcccg   5580
cgtttcttcc ttttccccac cccacccccc aagttcgggt gaaggcccag ggctcgcagc   5640
caacgtcggg gcggcaggcc ctgccatagc ctcaggttac tcatatatac tttagattga   5700
tttaaaactt catttttaat ttaaaaggat ctaggtgaag atcctttttg ataatctcat   5760
gaccaaaatc ccttaacgtg agttttcgtt ccactgagcg tcagaccccg tagaaaagat   5820
caaaggatct tcttgagatc ctttttttct gcgcgtaatc tgctgcttgc aaacaaaaaa   5880
accaccgcta ccagcggtgg tttgtttgcc ggatcaagag ctaccaactc tttttccgaa   5940
ggtaactggc ttcagcagag cgcagatacc aaatactgtc cttctagtgt agccgtagtt   6000
aggccaccac ttcaagaact ctgtagcacc gcctacatac ctcgctctgc taatcctgtt   6060
accagtggct gctgccagtg gcgataagtc gtgtcttacc gggttggact caagacgata   6120
gttaccggat aaggcgcagc ggtcgggctg aacggggggt tcgtgcacac agcccagctt   6180
ggagcgaacg acctacaccg aactgagata cctacagcgt gagctatgag aaagcgccac   6240
gcttcccgaa gggagaaagg cggacaggta tccggtaagc ggcagggtcg gaacaggaga   6300
gcgcacgagg gagcttccag ggggaaacgc ctggtatctt tatagtcctg tcgggtttcg   6360
ccacctctga cttgagcgtc gatttttgtg atgctcgtca ggggggcgga gcctatggaa   6420
aaacgccagc aacgcggcct ttttacggtt cctggccttt tgctggcctt ttgctcacat   6480
```

```
gttctttcct gcgttatccc ctgattctgt ggataaccgt attaccgcca tgcattagtt   6540

attaatagta atcaattacg gggtcattag ttcatagccc atatatggag ttccgcgtta   6600

cataacttac ggtaaatggc ccgcctggct gaccgcccaa cgacccccgc ccattgacgt   6660

caataatgac gtatgttccc atagtaacgc caatagggac tttccattga cgtcaatggg   6720

tggagtattt acggtaaact gcccacttgg cagtacatca agtgtatcat agcgatgcgg   6780

ccgcatggta cccattgctt gtcatttatt aatttggatg atgtcatttg tttttaaaat   6840

tgaactggct ttacgagtag aattctacgc gtaaaacaca atcaagtatg agtcataatc   6900

tgatgtcatg ttttgtacac ggctcataac cgaactggct ttacgagtag aattctactt   6960

gtaatgcacg atcagtggat gatgtcattt gtttttcaaa tcgagatgat gtcatgtttt   7020

gcacacggct cataaactcg ctttacgagt agaattctac gtgtaacgca cgatcgattg   7080

atgagtcatt tgttttgcaa tatgatatca tacaatatga ctcatttgtt tttcaaaacc   7140

gaacttgatt tacgggtaga attctacttg taaagcacaa tcaaaaagat gatgtcattt   7200

gtttttcaaa actgaactcg ctttacgagt agaattctac gtgtaaaaca caatcaagaa   7260

atgatgtcat ttgttataaa aataaaagct gatgtcatgt tttgcacatg gctcataact   7320

aaactcgctt tacgggtaga attctacgcg taaaacatga ttgataatta aataattcat   7380

ttgcaagcta tacgttaaat caaacggacg ctcgaggttg cacaacacta ttatcgattt   7440

gcagttcggg acataaatgt ttaaatatat cgatgtcttt gtgatgcgcg cgacattttt   7500

gtaggttatt gataaaatga acggatacgt tgcccgacat tatcattaaa tccttggcgt   7560

agaatttgtc gggtccattg tccgtgtgcg ctagcatgcc cgtaacggac ctcgtacttt   7620

tggcttcaaa ggttttgcgc acagacaaaa tgtgccacac ttgcagctct gcatgtgtgc   7680

gcgttaccac aaatcccaac ggcgcagtgt acttgttgta tgcaaataaa tctcgataaa   7740

ggcgcggcgc gcgaatgcag ctgatcacgt acgctcctcg tgttccgttc aaggacggtg   7800

ttatcgacct cagattaatg tttatcggcc gactgttttc gtatccgctc accaaacgcg   7860

tttttgcatt aacattgtat gtcggcggat gttctatatc taatttgaat aaataaacga   7920

taaccgcgtt ggttttagag ggcataataa aagaaatatt gttatcgtgt tcgccattag   7980

ggcagtataa attgacgttc atgttggata ttgtttcagt tgcaagttga cactggcggc   8040

gacaagcaat tctaattggg gtaagttttc ccgttctttt ctgggttctt ccccttttgct   8100

catccttgct gcactacctt caggtgcaag ttgagattca ggccaccatg ggagatccca   8160

ccccacccaa gaagaagcgc aaa                                          8183
```

<210> SEQ ID NO 48
<211> LENGTH: 7342
<212> TYPE: DNA
<213> ORGANISM: artificial
<220> FEATURE:
<223> OTHER INFORMATION: Sequence of pLA3433-Agdsx (Anopheles gambiae) construct with exon 2 included

<400> SEQUENCE: 48

```
ctagtgtcga cgatgtaggt cacggtctcg aagccgcggt gcgggtgcca gggcgtgccc     60

ttgggctccc cgggcgcgta ctccacctca cccatctggt ccatcatgat gaacgggtcg    120

aggtggcggt agttgatccc ggcgaacgcg cggcgcaccg ggaagccctc gccctcgaaa    180

ccgctgggcg cggtggtcac ggtgagcacg ggacgtgcga cggcgtcggc gggtgcggat    240

acgcggggca gcgtcagcgg gttctcgacg gtcacggcgg gcatgtcgac cgccggcgcc    300
```

-continued

```
ttaattaact cgcgttaaga tacattgatg agtttggaca aaccacaact agaatgcagt    360
gaaaaaaatg ctttatttgt gaaatttgtg atgctattgc tttatttgta accattataa    420
gctgcaataa acaagttaac aacaacaatt gcattcattt tatgtttcag gttcaggggg    480
aggtgtggga ggttttttaa agcaagtaaa acctctacaa atgtggtatg gctgattatg    540
atcagttatc tagatccggt ggatcttacg ggtcctccac cttccgcttt ttcttgggtc    600
gagatctgag tccggaatcc tcgtcgctac cgatggcgct ggtgatgcgg ggcacgctgt    660
gggcgtaggt cacctcgcgc tggcacacgt ggtcgcgctt gtcgctggtg tccctcatct    720
gcttggtgat gatggtcacg aagtgggggc cggggatctt gatggcgcgg ctgccgttga    780
aggtcatctt gctgtcgaag tggcccatca tcaggccgcc gtcggcggtg gtgaagccga    840
tgaaggccag ctggcgcacg gcgttggggc cgtgggggaa catgtgggtc tcgttgggca    900
ggatgtccac cagctggtcg cgcatgatgg ggccgtcggg ctggaagccg tcgcagttca    960
cggtgatgcg gctgaccacg caggtgccgt ccagctcgta ggtgtggtgg ctggtcatgg   1020
tgccgtcgtt ctcgaagcgc acggtgcggt cgatgctcag gccctcgggg aagcactcct   1080
gggcgaagtg gctgatgccg ttggggtagc gggcgaagaa gggctcgccg tactggatca   1140
ggtggcagat gggcttccag ctcatgggca gcttgccggt ctcgcacacg gcgtgcacgt   1200
tgaagtcgcc gtgggggaac ttgctgctgc cgtcggccac gatggtgaac ttctggccgt   1260
tcacctcgcc gtcgatgaag attttgaagg tcatgtcgct ctggaacagg gcggggccgc   1320
cctctgaacc atcctcgtcc atggtggcga ccggtttgcg cttcttcttg ggtggggtgg   1380
gatccaccag agacaggttg cggcggcggt tggatggcgt gggcgcgttg gcgttgttgg   1440
accggctcat gttgtgtcgc tgtaacagat gctgttcaac tgtgtttacc agatcgttgc   1500
gggctgtatt tataggcgcg ataagcggga cgggcgcctc gtgtccggtc acgcgcatga   1560
gataacgcgc ggctgatatg gaggcgcgtc ctgttccgat aaggagttgc gtccggctgc   1620
ggttagcaac acaggaagct ggcgtcctgt cacgataaga caacactcgt ccggtccgat   1680
aatgtgattc gtacgtgaca ggacgcgacc cgataaggcc ggcctacgtg actgccgaca   1740
cgtacttttt tgcactgcaa aaaggttcaa tgtgtggtag tgtatttgga gcgtatacaa   1800
cggtgtagac tatttatgta aaatagtcta cgaaacgtag agtttgtact atgtatgggc   1860
ccgcgtgcaa aagcgtgttt ttttgcagtg caaaaaagtt ggtggtgggg aggccaccga   1920
gtatggtacc atgcggccgc gtacgcgccc ggggagccca agggcacgcc ctggcacccg   1980
tccggtgctt atctagagcg cgcttggcgt aatcatggtc atagctgttt cctgtgtgaa   2040
attgttatcc gctcacaatt ccacacaaca tacgagccgg aagcataaag tgtaaagcct   2100
ggggtgccta atgagtgagc taactcacat taattgcgtt gcgctcactg cccgctttcc   2160
agtcgggaaa cctgtcgtgc cagctgcatt aatgaatcgg ccaacgcgcg gggagaggcg   2220
gtttgcgtat tgggcgctct tccgcttcct cgctcactga ctcgctgcgc tcggtcgttc   2280
ggctgcggcg agcggtatca gctcactcaa aggcggtaat acggttatcc acagaatcag   2340
gggataacgc aggaaagaac atgtgagcaa aaggccagca aaaggccagg aaccgtaaaa   2400
aggccgcgtt gctggcgttt ttccataggc tccgcccccc tgacgagcat cacaaaaatc   2460
gacgctcaag tcagaggtgg cgaaacccga caggactata aagataccag gcgtttcccc   2520
ctggaagctc cctcgtgcgc tctcctgttc cgaccctgcc gcttaccgga tacctgtccg   2580
cctttctccc ttcgggaagc gtggcgcttt ctcatagctc acgctgtagg tatctcagtt   2640
cggtgtaggt cgttcgctcc aagctgggct gtgtgcacga accccccgtt cagcccgacc   2700
```

-continued

```
gctgcgcctt atccggtaac tatcgtcttg agtccaaccc ggtaagacac gacttatcgc   2760
cactggcagc agccactggt aacaggatta gcagagcgag gtatgtaggc ggtgctacag   2820
agttcttgaa gtggtggcct aactacggct acactagaag gacagtattt ggtatctgcg   2880
ctctgctgaa gccagttacc ttcggaaaaa gagttggtag ctcttgatcc ggcaaacaaa   2940
ccaccgctgg tagcggtggt ttttttgttt gcaagcagca gattacgcgc agaaaaaaag   3000
gatctcaaga agatcctttg atcttttcta cggggtctga cgctcagtgg aacgaaaact   3060
cacgttaagg gattttggtc atgagattat caaaaaggat cttcacctag atccttttaa   3120
attaaaaatg aagttttaaa tcaatctaaa gtatatatga gtaaacttgg tctgacagtt   3180
accaatgctt aatcagtgag gcacctatct cagcgatctg tctatttcgt tcatccatag   3240
ttgcctgact ccccgtcgtg tagataacta cgatacggga gggcttacca tctggcccca   3300
gtgctgcaat gataccgcga gacccacgct caccggctcc agatttatca gcaataaacc   3360
agccagccgg aagggccgag cgcagaagtg gtcctgcaac tttatccgcc tccatccagt   3420
ctattaattg ttgccgggaa gctagagtaa gtagttcgcc agttaatagt ttgcgcaacg   3480
ttgttgccat tgctacaggc atcgtggtgt cacgctcgtc gtttggtatg gcttcattca   3540
gctccggttc ccaacgatca aggcgagtta catgatcccc catgttgtgc aaaaaagcgg   3600
ttagctcctt cggtcctccg atcgttgtca gaagtaagtt ggccgcagtg ttatcactca   3660
tggttatggc agcactgcat aattctctta ctgtcatgcc atccgtaaga tgcttttctg   3720
tgactggtga gtactcaacc aagtcattct gagaatagtg tatgcggcga ccgagttgct   3780
cttgcccggc gtcaatacgg gataataccg cgccacatag cagaacttta aaagtgctca   3840
tcattggaaa acgttcttcg gggcgaaaac tctcaaggat cttaccgctg ttgagatcca   3900
gttcgatgta acccactcgt gcacccaact gatcttcagc atcttttact ttcaccagcg   3960
tttctgggtg agcaaaaaca ggaaggcaaa atgccgcaaa aaagggaata agggcgacac   4020
ggaaatgttg aatactcata ctcttccttt ttcaatatta ttgaagcatt tatcagggtt   4080
attgtctcat gagcggatac atatttgaat gtatttagaa aaataaacaa ataggggttc   4140
cgcgcacatt tccccgaaaa gtgccaccta aattgtaagc gttaatattt tgttaaaatt   4200
cgcgttaaat ttttgttaaa tcagctcatt ttttaaccaa taggccgaaa tcggcaaaat   4260
cccttataaa tcaaaagaat agaccgagat agggttgagt gttgttccag tttggaacaa   4320
gagtccacta ttaaagaacg tggactccaa cgtcaaaggg cgaaaaaccg tctatcaggg   4380
cgatggccca ctacgtgaac catcacccta atcaagtttt ttggggtcga ggtgccgtaa   4440
agcactaaat cggaacccta aagggagccc ccgatttaga gcttgacggg gaaagccggc   4500
gaacgtggcg agaaaggaag ggaagaaagc gaaaggagcg ggcgctaggg cgctggcaag   4560
tgtagcggtc acgctgcgcg taaccaccac acccgccgcg cttaatgcgc cgctacaggg   4620
cgcgtcccat tcgccattca ggctgcgcaa ctgttgggaa gggcgatcgg tgcgggcctc   4680
ttcgctatta cgccagctgg cgaaaggggg atgtgctgca aggcgattaa gttgggtaac   4740
gccagggttt tcccagtcac gacgttgtaa aacgacggcc agtgagcgcg ctagcgttta   4800
aacgagctct aagatacatt gatgagtttg gacaaaccac aactagaatg cagtgaaaaa   4860
aatgctttat ttgtgaaatt tgtgatgcta ttgctttatt tgtaaccatt ataagctgca   4920
ataaacaagt taacaacaac aattgcattc attttatgtt tcaggttcag ggggaggtgt   4980
gggaggtttt ttaaagcaag taaaacctct acaaatgtgg tatggctgat tatgatcctg   5040
```

-continued

```
cagctacgcc gctacgtctt ccgtgccgtc ctgggcgtcg tcttcgtcgt cgtcggtcgg   5100
cggcttcgcc cacgtgatcg aagcgcgctt ctcgatgggc gttccctgcc ccctgcccgt   5160
agtcgacttc gtgacaacga tcttgtctac gaagagcccg acgaacacgc gcttgtcgtc   5220
tactgacgcg cgccccccacc acgacttagg gccggtcggg tcagcgtcgg cgtcttcggg   5280
gaaccattgg tcaaggggaa gcttcggggc ttcggcggct tcaagttcgg caagccgctc   5340
ttccgcccct tgctgccgga gcgtcagcgc tgcctgttgc ttccggaagt gcttcctgcc   5400
aacgggtccg tcgtacgcgc ctgccgcgcg gtcttcgtac agctcttcaa gggcgttcag   5460
ggcgtcggcg cgctccgcaa caaggttcgc ccgttcgccg ctcttctcag gcgcctcagt   5520
gagcttgccg aagcgtcggg cggcttccca cagaagcgcc aacgtctctt cgtcgccttc   5580
ggcgtgcctg atcttgttga agatgcgttc cgcaacgaac ttgtcgagtg ccgccatgct   5640
gacgttgcac gtgccttcgt gctgcccagg tgcggacggg tcgaccacct tccggcgacg   5700
gcagcggtaa gagtccttga tcgattcttc cccgcgcttc gaagtcatga cggcgccaca   5760
ctcgcagtac agcttgtcca tggcggacag aatggcttgc ccccgggaaa gccccttgcc   5820
gcgcccccctg ccgtccaacc acgcctgaag ctcataccac tcagcgggct cgatgatcgg   5880
tccgcaatca agctcgaccg gccggagcgt gatcgggtcg cgctgaatgc ggtaaccctc   5940
aatcttcgtg gtcggcgtgc cgtccggctt cttcttgtag atcacctcag cggcgaagcc   6000
cgcaatacgc gggtcccgaa ggattcgcat aacggttgcc gggtcccagg cgcttgaagc   6060
ggtcttcttc ccaatcgtct cgccccgggt cggcacggcg tcagcgtcca tgcgcttaca   6120
aagccccgtg atgctgcccg ggtgaatggc ggcttgactg cccggcttga agggaaggtg   6180
tttgtgcgtc ttgatctcac gccaccacca ccggattacg tcgggctcga actcgaaggg   6240
tccggtaagg ggagtggtcg agtgcgcaag cttgttgatg acgacattga ccattcggcc   6300
gttgcgcgtg atctccttcg tctccgaaac aagctcgaag ccgtaaggcg ccttcccgcc   6360
gacgtacccg cccaattcgc gctgaaggtt cttcgtgtcg agaatcttcg ccgacttcag   6420
cgaagattct ttgtgcgacg cgtcgagccg cataatcagg tgaatcaggt ccatgacgtt   6480
tccctgccgg aagacgcctt cctgagtgga aacaatcgtc acgcccaggg cgagcaattc   6540
cgagacaatc ggaatcgcgt ccatgacctt caggcgcgag aagcgcgaca cgtcatagac   6600
aatgatcatg ttgagccgcc cggcgcggca ttcgttcagg atgcgttcga actccgggcg   6660
ctccgccgtc ccgaacgccg acgtgcccgg cgcttcgctg aaatgcccga cgaacctgaa   6720
ccggccccccg tcgcgctcga cttcgcgctg aaggtcggcc gccttgtctt cgttggcgct   6780
acgctgtgtc gctgggcttg ctgcgctcga attctcgcgc tcgcgcgact gacggtcgta   6840
agcacccgcg tacgtgtcca tggcggatcc gtgtcgctgt aacagatgct gttcaactgt   6900
gtttaccaga tcgttgcggg ctgtatttat aggcgcgata agcgggacgg gcgcctcgtg   6960
tccggtcacg cgcatgagat aacgcgcggc tgatatggag gcgcgtcctg ttccgataag   7020
gagttgcgtc cggctgcggt tagcaacaca ggaagctggc gtcctgtcac gataagacaa   7080
cactcgtccg gtccgataat gtgattcgta cgtgacagga cgcgacccga taaggccggc   7140
ctacgtgact gccgacacgt actttttgc actgcaaaaa ggttcaatgt gtggtagtgt   7200
atttggagcg tatacaacgg tgtagactat ttatgtaaaa tagtctacga aacgtagagt   7260
ttgtactatg tatgggcccg cgtgcaaaag cgtgtttttt tgcagtgcaa aaaagttggt   7320
ggtggggagg ccaccgagta ta                                            7342
```

<210> SEQ ID NO 49
<211> LENGTH: 11868
<212> TYPE: DNA
<213> ORGANISM: artificial
<220> FEATURE:
<223> OTHER INFORMATION: 49 Sequence of pLA1188-cctra intron construct

<400> SEQUENCE: 49
gtggtttttg tcaaacgaag attctatgac gtgtttaaag tttaggtcga gtaaagcgca 60
aatctttttt aaccctagaa agatagtctg cgtaaaattg acgcatgcat tcttgaaata 120
ttgctctctc tttctaaata gcgcgaatcc gtcgctgtgc atttaggaca tctcagtcgc 180
cgcttggagc tcccgtgagg cgtgcttgtc aatgcggtaa gtgtcactga ttttgaacta 240
taacgaccgc gtgagtcaaa atgacgcatg attatctttt acgtgacttt taagatttaa 300
ctcatacgat aattatattg ttatttcatg ttctacttac gtgataactt attatatata 360
tattttcttg ttatagatat cgtgactaat atataataaa atgggtagtt ctttagacga 420
tgagcatatc ctctctgctc ttctgcaaag cgatgacgag cttgttggtg aggattctga 480
cagtgaaata tcagatcacg taagtgaaga tgacgtccag agcgatacag aagaagcgtt 540
tatagatgag gtacatgaag tgcagccaac gtcaagcggt agtgaaatat tagacgaaca 600
aaatgttatt gaacaaccag gttcttcatt ggcttctaac agaatcttga ccttgccaca 660
gaggactatt agaggtaaga ataaacattg ttggtcaact tcaaagtcca cgaggcgtag 720
ccgagtctct gcactgaaca ttgtcagatc ggcccgggcg gccgtttttc ttgaaatatt 780
gctctctctt tctaaatagc gcgaatccgt cgctgtgcat ttaggacatc tcagtcgccg 840
cttggagctc ccaaacgcgc cagtggtagt acacagtact gtgggtgttc agtttgaaat 900
cctcttgctt ctccattgtc tcggttacct ttggtcaaat ccatgggttc tattgcctat 960
atactcttgc gattaccagt gattgcgcta ttagctatta gatggattgt tggccaaact 1020
tgtcgcttaa gtggctggga attgtaaccg taggcccgag tgtaatgatc ccccataaaa 1080
agttttcgca atgcctttat tttttgttgc aaatctctct ttattctgcg gtattcttca 1140
ttattgcggg gatggggaaa gtgtttatat agaagcaact tacgattgaa cccaaatgca 1200
cctgacaagc aaggtcaaag ggccagattt ttaaatatat tatttagtct taggactctc 1260
tatttgcaat taaattactt tgctacctga gggttaaatc ttccccattg ataataataa 1320
ttccactata tgttcaattg ggtttcaccg cgcttagtta catgacgagc cctaatgagc 1380
cgtcggtggt ctataaactg tgccttacaa atacttgcaa ctcttctcgt tttgaagtca 1440
gcagagttat tgctaattgc taattgctaa ttgcttttaa ctgatttctt cgaaattggt 1500
gctatgttta tggcgctatt aacaagtatg aatgtcaggt ttaaccaggg gatgcttaat 1560
tgtgttctca acttcaaagg cagaaatgtt tactcttgac catgggttta ggtataatgt 1620
tatcaagctc ctcgagttaa cgttacgtta acgttaacgt tcgaggtcga ctctagaact 1680
acccaccgta ctcgtcaatt ccaagggcat cggtaaacat ctgctcaaac tcgaagtcgg 1740
ccatatccag agcgccgtag ggggcggagt cgtgggggt aaatcccgga cccggggaat 1800
ccccgtcccc caacatgtcc agatcgaaat cgtctagcgc gtcggcatgc gccatcgcca 1860
cgtcctcgcc gtctaagtgg agctcgtccc ccaggctgac atcggtcggg ggggccgtcg 1920
acagtctgcg cgtgtgtccc gcggggagaa aggacaggcg cggagccgcc agccccgcct 1980
cttcgggggc gtcgtcgtcc gggagatcga gcaggccctc gatggtagac ccgtaattgt 2040
ttttcgtacg cgcgcggctg tacgcggggc ccgagcccga ctcgcatttc agttgctttt 2100

-continued

```
ccaatccgca gataatcagc tccaagccga acaggaatgc cggctcggct ccttgatgat   2160
cgaacagctc gattgcctga cgcagcagtg ggggcatcga atcggttgtt ggggtctcgc   2220
gctcctcttt tgcgacttga tgctcttggt cctccagcac gcagcccagg gtaaagtgac   2280
cgacggcgct cagagcgtag agagcatttt ccaggctgaa gccttgctgg cacaggaacg   2340
cgagctggtt ctccagtgtc tcgtattgct tttcggtcgg gcgcgtgccg agatggactt   2400
tggcaccgtc tcggtgggac agcagagcgc agcggaacga cttggcgtta ttgcggagga   2460
agtcctgcca ggactcgcct tccaacgggc aaaaatgcgt gtggtggcgg tcgagcatct   2520
cgatggccag ggcatccagc agcgcccgct tattcttcac ctatagatac catagatgta   2580
tggattagta tcatatacat acaaaggcta tttttgggac atattaatat taacaatttc   2640
cgtgatagtt ttcaccattt ttgttgaatg ttacgttgaa aatttaaatt tgttttaaat   2700
taattttacc agtcatgtgt tcttaaaagt ttttatgatt gaaacggcat aaagtggttc   2760
aaaaatttat caagaaaggc tttccttttt taaatcttat ctttttctct taaaaatcac   2820
tagtcaattc attattaatt tgttaacttg aatttggaat gtctatttac tttcagataa   2880
attaaagcaa gaaacttaat attcgaaaaa aattgattct aaatggaatt tcacttgatc   2940
ttcatgtatg catatcaatt tttatttaca ttgtataata agtttcgagt tgattgttgt   3000
aatccacagg tgtcccagag aattaaattc caaattaccc aagtttattg aatgttgatt   3060
gtagtttcag ttgctttgtt gctgcaacaa tggcttgttg attgtagata ttttcccttt   3120
ccttggttta cttattacat agactgaaaa agaggtttac ttttttgata cttatgaaaa   3180
atttctatta gtgattacta accaatcgct atatgtttac tagaaaacaa ataaactctt   3240
tacattaaca ttcaataatg tttgctctgt aaccgacaat tgaaggcgtt acagcaacag   3300
taatataact agcttcttaa ccctcatcta ttaaccccat cgtttaaaac actatgttaa   3360
atggtctaac aaatctagat actaatagat gtcttattac ttagcagcca cagctgcaac   3420
atccaagaca atttttgaaa cttcttattg agctcttggc agcagaaatg ttggtatttt   3480
tcacagcttt ctgaaagacc ggcaccttcc tccggttccc gtttctgaat tcaagaggat   3540
ttccgacccc caattaatcc cgaaacaaat aaggtatatt caaaatgatg gaaaagtcat   3600
ggctgctgac cttattttta ttcctattga tagaatatta ttcccctttt aaatacactg   3660
tactaagagg tccggctata attttactca cttgtcgatt atcccataga atgttgattg   3720
tagttggttg cttttccagg tgagagttga tcaagtcaca aaagttagcg tgtgttgatt   3780
gtagatttga aggtaaaata atttttgcac ccattcatcg ggtaaaacgt tctccataga   3840
atacatttcc atcgataatt gataacttat gaatttcaaa gaaaaaaata tgcttttaaa   3900
attacgtgcc agtagagggt gggctgctcc acgcccagct tctgcgccaa cttgcgggtc   3960
gtcagtccct caatgccaac ttcgttcaac agctccaacg cggagttgat gactttggac   4020
ttatccaggc ggctgcccat ggtggtttct aaaggtgtta taaatcaaat tagttttgtt   4080
ttttcttgaa aactttgcgt ttcctttgat caacttaccg ccagggtacc gcagattgtt   4140
tagcttgttc agctgcgctt gtttatttgc ttagctttcg cttagcgacg tgttcacttt   4200
gcttgtttga attgaattgt cgctccgtag acgaagcgcc tctatttata ctccggcgct   4260
cgttttcgag tttaccactc cctatcagtg atagagaaaa gtgaaagtcg agtttaccac   4320
tccctatcag tgatagagaa aagtgaaagt cgagtttacc actccctatc agtgatagag   4380
aaaagtgaaa gtcgagttta ccactcccta tcagtgatag agaaaagtga aagtcgagtt   4440
taccactccc tatcagtgat agagaaaagt gaaagtcgag tttaccactc cctatcagtg   4500
```

```
atagagaaaa gtgaaagtcg agtttaccac tccctatcag tgatagagaa aagtgaaagt   4560
cgaaacctgg cgcgccccgg ccatcgagaa agagagagag aagagaagag agagaacatt   4620
cgagaaagag agagagaaga gaagagagag aacatactcc ctatcagtga tagagaagtc   4680
cctatcagtg atagagatgt ccctatcagt gatagagagt tccctatcag tgatagagac   4740
gtccctatca gtgatagaga agtccctatc agtgatagag agatccctat cagtgataga   4800
gatttcccta tcagtgatag agaggtccct atcagtgata gagacttccc tatcagtgat   4860
agagaaatcc ctatcagtga tagagacatc cctatcagtg atagagaact ccctatcagt   4920
gatagagacc tccctatcag tgatagagat cgatgcggcc gcatggtacc cattgcttgt   4980
catttattaa tttggatgat gtcatttgtt tttaaaattg aactggcttt acgagtagaa   5040
ttctacgcgt aaaacacaat caagtatgag tcataatctg atgtcatgtt ttgtacacgg   5100
ctcataaccg aactggcttt acgagtagaa ttctacttgt aatgcacgat cagtggatga   5160
tgtcatttgt ttttcaaatc gagatgatgt catgttttgc acacggctca taaactcgct   5220
ttacgagtag aattctacgt gtaacgcacg atcgattgat gagtcatttg ttttgcaata   5280
tgatatcata caatatgact catttgtttt tcaaaaccga acttgattta cgggtagaat   5340
tctacttgta aagcacaatc aaaaagatga tgtcatttgt ttttcaaaac tgaactcgct   5400
ttacgagtag aattctacgt gtaaaacaca atcaagaaat gatgtcattt gttataaaaa   5460
taaaagctga tgtcatgttt tgcacatggc tcataactaa actcgcttta cgggtagaat   5520
tctacgcgta aaacatgatt gataattaaa taattcattt gcaagctata cgttaaatca   5580
aacggacgct cgaggttgca caacactatt atcgatttgc agttcgggac ataaatgttt   5640
aaatatatcg atgtctttgt gatgcgcgcg acatttttgt aggttattga taaaatgaac   5700
ggatacgttg cccgacatta tcattaaatc cttggcgtag aatttgtcgg gtccattgtc   5760
cgtgtgcgct agcatgcccg taacggacct cgtacttttg gcttcaaagg ttttgcgcac   5820
agacaaaatg tgccacactt gcagctctgc atgtgtgcgc gttaccacaa atcccaacgg   5880
cgcagtgtac ttgttgtatg caaataaatc tcgataaagg cgcggcgcgc gaatgcagct   5940
gatcacgtac gctcctcgtg ttccgttcaa ggacggtgtt atcgacctca gattaatgtt   6000
tatcggccga ctgttttcgt atccgctcac caaacgcgtt tttgcattaa cattgtatgt   6060
cggcggatgt tctatatcta atttgaataa ataaacgata accgcgttgg ttttagaggg   6120
cataataaaa gaaatattgt tatcgtgttc gccattaggg cagtataaat tgacgttcat   6180
gttggatatt gtttcagttg caagttgaca ctggcggcga caagcaattc taattggggt   6240
aagttttccc gttcttttct gggttcttcc cttttgctca tccttgctgc actaccttca   6300
ggtgcaagtt gagattcagg ccaccatggg agatcccacc ccacccaaga agaagcgcaa   6360
accggtcgcc accatggcct cctccgagaa cgtcatcacc gagttcatgc gcttcaaggt   6420
gcgcatggag ggcaccgtga acggccacga gttcgagatc gagggcgagg gcgagggccg   6480
cccctacgag ggccacaaca ccgtgaagct gaaggtgacc aagggcggcc ccctgccctt   6540
cgcctgggac atcctgtccc cccagttcca gtacggctcc aaggtgtacg tgaagcaccc   6600
cgccgacatc cccgactaca agaagctgtc cttccccgag ggcttcaagt gggagcgcgt   6660
gatgaacttc gaggacggcg gcgtggcgac cgtgacccag gactcctccc tgcaggacgg   6720
ctgcttcatc tacaaggtga agttcatcgg cgtgaacttc ccctccgacg gccccgtgat   6780
gcagaagaag accatgggct gggaggcctc caccgagcgc ctgtaccccc gcgacggcgt   6840
```

-continued

```
gctgaagggc gagacccaca aggccctgaa gctgaaggac ggcggccact acctggtgga   6900
gttcaagtcc atctacatgg ccaagaagcc cgtgcagctg cccggctact actacgtgga   6960
cgccaagctg gacatcacct cccacaacga ggactacacc atcgtggagc agtacgagcg   7020
caccgagggc cgccaccacc tgttcctgag atctcgaccc aagaaaaagc ggaaggtgga   7080
ggacccgtaa gatccaccgg atctagataa ctgatcataa tcagccatac cacatttgta   7140
gaggttttac ttgctttaaa aaacctccca cacctccccc tgaacctgaa acataaaatg   7200
aatgcaattg ttgttgttaa cttgtttatt gcagcttata atggttacaa ataaagcaat   7260
agcatcacaa atttcacaaa taaagcattt ttttcactgc attctagttg tggtttgtcc   7320
aaactcatca atgtatctta acgcgagtta attaaggccg ctcatttaaa tctggccggc   7380
cgcaaccatt gtgggaaccg tgcgatcaaa caaacgcgag ataccggaag tactgaaaaa   7440
cagtcgctcc aggccagtgg gaacatcgat gttttgtttt gacggacccc ttactctcgt   7500
ctcatataaa ccgaagccag ctaagatggt atacttatta tcatcttgtg atgaggatgc   7560
ttctatcaac gaaagtaccg gtaaaccgca aatggttatg tattataatc aaactaaagg   7620
cggagtggac acgctagacc aaatgtgttc tgtgatgacc tgcagtagga agacgaatag   7680
gtggcctatg gcattattgt acggaatgat aaacattgcc tgcataaatt cttttattat   7740
atacagccat aatgtcagta gcaagggaga aaaggtccaa agtcgcaaaa aatttatgag   7800
aaacctttac atgagcctga cgtcatcgtt tatgcgtaag cgtttagaag ctcctacttt   7860
gaagagatat ttgcgcgata atatctctaa tattttgcca aatgaagtgc ctggtacatc   7920
agatgacagt actgaagagc cagtaatgaa aaaacgtact tactgtactt actgccccctc   7980
taaaataagg cgaaaggcaa atgcatcgtg caaaaaaatgc aaaaaagtta tttgtcgaga   8040
gcataatatt gatatgtgcc aaagttgttt ctgactgact aataagtata atttgtttct   8100
attatgtata agttaagcta attacttatt ttataataca acatgactgt ttttaaagta   8160
caaaataagt ttatttttgt aaaagagaga atgtttaaaa gttttgttac tttatagaag   8220
aaattttgag tttttgtttt tttttaataa ataaataaac ataaataaat tgtttgttga   8280
atttattatt agtatgtaag tgtaaatata ataaaactta atatctattc aaattaataa   8340
ataaacctcg atatacagac cgataaaaca catgcgtcaa ttttacgcat gattatcttt   8400
aacgtacgtc acaatatgat tatctttcta gggttaaata atagtttcta atttttttat   8460
tattcagcct gctgtcgtga ataccgtata tctcaacgct gtctgtgaga ttgtcgtatt   8520
ctagcctttt tagtttttcg ctcatcgact tgatattgtc cgacacattt tcgtcgattt   8580
gcgttttgat caaagacttg agcagagaca cgttaatcaa ctgttcaaat tgatccatat   8640
taacgatatc aacccgatgc gtatatggtg cgtaaaatat attttttaac cctcttatac   8700
tttgcactct gcgttaatac gcgttcgtgt acagacgtaa tcatgttttc tttttggat   8760
aaaactccta ctgagtttga cctcatatta gaccctcaca agttgcaaaa cgtggcattt   8820
tttaccaatg aagaatttaa agttatttta aaaaatttca tcacagattt aaagaagaac   8880
caaaaattaa attatttcaa cagtttaatc gaccagttaa tcaacgtgta cacagacgcg   8940
tcggcaaaaa acacgcagcc cgacgtgttg gctaaaatta ttaaatcaac ttgtgttata   9000
gtcacggatt tgccgtccaa cgtgttcctc aaaaagttga agaccaacaa gtttacggac   9060
actattaatt atttgatttt gccccacttc attttgtggg atcacaattt tgttatattt   9120
taaacaaagc ttggcactgg ccgtcgtttt acaacgtcgt gactgggaaa accctggcgt   9180
tacccaactt aatcgccttg cagcacatcc ccctttcgcc agctggcgta atagcgaaga   9240
```

```
ggcccgcacc gatcgccctt cccaacagtt gcgcagcctg aatggcgaat ggcgcctgat   9300
gcggtatttt ctccttacgc atctgtgcgg tatttcacac cgcatatggt gcactctcag   9360
tacaatctgc tctgatgccg catagttaag ccagccccga cacccgccaa cacccgctga   9420
cgcgccctga cgggcttgtc tgctcccggc atccgcttac agacaagctg tgaccgtctc   9480
cgggagctgc atgtgtcaga ggttttcacc gtcatcaccg aaacgcgcga gacgaaaggg   9540
cctcgtgata cgcctatttt tataggttaa tgtcatgata ataatggttt cttagacgtc   9600
aggtggcact tttcggggaa atgtgcgcgg aacccctatt tgtttatttt tctaaataca   9660
ttcaaatatg tatccgctca tgagacaata accctgataa atgcttcaat aatattgaaa   9720
aaggaagagt atgagtattc aacatttccg tgtcgccctt attccctttt ttgcggcatt   9780
ttgccttcct gtttttgctc acccagaaac gctggtgaaa gtaaaagatg ctgaagatca   9840
gttgggtgca cgagtgggtt acatcgaact ggatctcaac agcggtaaga tccttgagag   9900
ttttcgcccc gaagaacgtt ttccaatgat gagcactttt aaagttctgc tatgtggcgc   9960
ggtattatcc cgtattgacg ccgggcaaga gcaactcggt cgccgcatac actattctca  10020
gaatgacttg gttgagtact caccagtcac agaaaagcat cttacggatg gcatgacagt  10080
aagagaatta tgcagtgctg ccataaccat gagtgataac actgcggcca acttacttct  10140
gacaacgatc ggaggaccga aggagctaac cgcttttttg cacaacatgg gggatcatgt  10200
aactcgcctt gatcgttggg aaccggagct gaatgaagcc ataccaaacg acgagcgtga  10260
caccacgatg cctgtagcaa tggcaacaac gttgcgcaaa ctattaactg gcgaactact  10320
tactctagct tcccggcaac aattaataga ctggatggag gcggataaag ttgcaggacc  10380
acttctgcgc tcggcccttc cggctggctg gtttattgct gataaatctg gagccggtga  10440
gcgtgggtct cgcggtatca ttgcagcact ggggccagat ggtaagccct cccgtatcgt  10500
agttatctac acgacgggga gtcaggcaac tatggatgaa cgaaatagac agatcgctga  10560
gataggtgcc tcactgatta agcattggta actgtcagac caagtttact catatatact  10620
ttagattgat ttaaaacttc atttttaatt taaaaggatc taggtgaaga tcctttttga  10680
taatctcatg accaaaatcc cttaacgtga gttttcgttc cactgagcgt cagaccccgt  10740
agaaaagatc aaaggatctt cttgagatcc tttttttctg cgcgtaatct gctgcttgca  10800
aacaaaaaaa ccaccgctac cagcggtggt ttgtttgccg gatcaagagc taccaactct  10860
ttttccgaag gtaactggct tcagcagagc gcagatacca aatactgtcc ttctagtgta  10920
gccgtagtta ggccaccact tcaagaactc tgtagcaccg cctacatacc tcgctctgct  10980
aatcctgtta ccagtggctg ctgccagtgg cgataagtcg tgtcttaccg ggttggactc  11040
aagacgatag ttaccggata aggcgcagcg gtcgggctga acggggggtt cgtgcacaca  11100
gcccagcttg gagcgaacga cctacaccga actgagatac ctacagcgtg agcattgaga  11160
aagcgccacg cttcccgaag ggagaaaggc ggacaggtat ccggtaagcg gcagggtcgg  11220
aacaggagag cgcacgaggg agcttccagg gggaaacgcc tggtatcttt atagtcctgt  11280
cgggtttcgc cacctctgac ttgagcgtcg atttttgtga tgctcgtcag gggggcggag  11340
cctatggaaa aacgccagca acgcggcctt tttacggttc ctggcctttt gctggccttt  11400
tgctcacatg ttctttcctg cgttatcccc tgattctgtg gataaccgta ttaccgcctt  11460
tgagtgagct gataccgctc gccgcagccg aacgaccgag cgcagcgagt cagtgagcga  11520
ggaagcggaa gagcgcccaa tacgcaaacc gcctctcccc gcgcgttggc cgattcatta  11580
```

-continued

```
atgcagctgg cacgacaggt ttcccgactg gaaagcgggc agtgagcgca acgcaattaa  11640

tgtgagttag ctcactcatt aggcacccca ggctttacac tttatgcttc cggctcgtat  11700

gttgtgtgga attgtgagcg gataacaatt tcacacagga aacagctatg accatgatta  11760

cgaatttcga cctgcaggca tgcaagcttg catgcctgca ggtcgacgct cgcgcgactt  11820

ggtttgccat tctttagcgc gcgtcgcgtc acacagcttg gccacaat              11868
```

<210> SEQ ID NO 50
<211> LENGTH: 11868
<212> TYPE: DNA
<213> ORGANISM: artificial
<220> FEATURE:
<223> OTHER INFORMATION: Sequence of pLA3077-a Cctra intron-tTAV construct.

<400> SEQUENCE: 50

```
gtggtttttg tcaaacgaag attctatgac gtgtttaaag tttaggtcga gtaaagcgca     60

aatctttttt aaccctagaa agatagtctg cgtaaaattg acgcatgcat tcttgaaata    120

ttgctctctc tttctaaata gcgcgaatcc gtcgctgtgc atttaggaca tctcagtcgc    180

cgcttggagc tcccgtgagg cgtgcttgtc aatgcggtaa gtgtcactga ttttgaacta    240

taacgaccgc gtgagtcaaa atgacgcatg attatctttt acgtgacttt taagatttaa    300

ctcatacgat aattatattg ttatttcatg ttctacttac gtgataactt attatatata    360

tattttcttg ttatagatat cgtgactaat atataataaa atgggtagtt ctttagacga    420

tgagcatatc ctctctgctc ttctgcaaag cgatgacgag cttgttggtg aggattctga    480

cagtgaaata tcagatcacg taagtgaaga tgacgtccag agcgatacag aagaagcgtt    540

tatagatgag gtacatgaag tgcagccaac gtcaagcggt agtgaaatat tagacgaaca    600

aaatgttatt gaacaaccag gttcttcatt ggcttctaac agaatcttga ccttgccaca    660

gaggactatt agaggtaaga ataaacattg ttggtcaact tcaaagtcca cgaggcgtag    720

ccgagtctct gcactgaaca ttgtcagatc ggcccgggcg ccgtttttct tgaaatattg    780

ctctctcttt ctaaatagcg cgaatccgtc gctgtgcatt taggacatct cagtcgccgc    840

ttggagctcc caaacgcgcc agtggtagta cacagtactg tgggtgttca gtttgaaatc    900

ctcttgcttc tccattgtct cggttacctt tggtcaaatc catgggttct attgcctata    960

tactcttgcg attaccagtg attgcgctat tagctattag atggattgtt ggccaaactt   1020

gtcgcttaag tggctgggaa ttgtaaccgt aggcccgagt gtaatgatcc cccataaaaa   1080

gttttcgcaa tgcctttatt ttttgttgca aatctctctt tattctgcgg tattcttcat   1140

tattgcgggg atggggaaag tgtttatata gaagcaactt acgattgaac ccaaatgcac   1200

ctgacaagca aggtcaaagg gccagatttt taaatatatt atttagtctt aggactctct   1260

atttgcaatt aaattacttt gctacctgag ggttaaatct tccccattga taataataat   1320

tccactatat gttcaattgg gtttcaccgc gcttagttac atgacgagcc ctaatgagcc   1380

gtcggtggtc tataaactgt gccttacaaa tacttgcaac tcttctcgtt ttgaagtcag   1440

cagagttatt gctaattgct aattgctaat tgcttttaac tgatttcttc gaaattggtg   1500

ctatgtttat ggcgctatta acaagtatga atgtcaggtt taaccagggg atgcttaatt   1560

gtgttctcaa cttcaaaggc agaaatgttt actcttgacc atgggtttag gtataatgtt   1620

atcaagctcc tcgagttaac gttacgttaa cgttaacgtt cgaggtcgac tctagaacta   1680

cccaccgtac tcgtcaattc caagggcatc ggtaaacatc tgctcaaact cgaagtcggc   1740
```

-continued

```
catatccaga gcgccgtagg gggcggagtc gtggggggta aatcccggac ccggggaatc   1800
cccgtccccc aacatgtcca gatcgaaatc gtctagcgcg tcggcatgcg ccatcgccac   1860
gtcctcgccg tctaagtgga gctcgtcccc caggctgaca tcggtcgggg gggccgtcga   1920
cagtctgcgc gtgtgtcccg cggggagaaa ggacaggcgc ggagccgcca gccccgcctc   1980
ttcgggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacg tgccagtaga gggtgggctg   2580
ctccacgccc agcttctgcg ccaacttgcg ggtcgtcagt ccctcaatac ctatagatac   2640
catagatgta tggattagta tcatatacat acaaaggcta tttttgggac atattaatat   2700
taacaatttc cgtgatagtt ttcaccattt ttgttgaatg ttacgttgaa aatttaaatt   2760
tgttttaaat taattttacc agtcatgtgt tcttaaaagt tttatgatt gaaacggcat    2820
aaagtggttc aaaaatttat caagaaaggc tttcctttt taaatcttat ctttttctct    2880
taaaaatcac tagtcaattc attattaatt tgttaacttg aatttggaat gtctatttac   2940
tttcagataa attaaagcaa gaaacttaat attcgaaaaa aattgattct aaatggaatt   3000
tcacttgatc ttcatgtatg catatcaatt tttatttaca ttgtataata agtttcgagt   3060
tgattgttgt aatccacagg tgtcccagag aattaaattc caaattaccc aagtttattg   3120
aatgttgatt gtagtttcag ttgctttgtt gctgcaacaa tggcttgttg attgtagata   3180
ttttcccttt ccttggttta cttattacat agactgaaaa agaggtttac ttttttgata   3240
cttatgaaaa atttctatta gtgattacta accaatcgct atatgtttac tagaaaacaa   3300
ataaactctt tacattaaca ttcaataatg tttgctctgt aaccgacaat tgaaggcgtt   3360
acagcaacag taatataact agcttcttaa ccctcatcta ttaaccccat cgtttaaaac   3420
actatgttaa atggtctaac aaatctagat actaatagat gtcttattac ttagcagcca   3480
cagctgcaac atccaagaca atttttgaaa cttcttattg agctcttggc agcagaaatg   3540
ttggtatttt tcacagcttt ctgaaagacc ggcaccttcc tccggttccc gtttctgaat   3600
tcaagaggat ttccgacccc caattaatcc cgaaacaaat aaggtatatt caaaatgatg   3660
gaaaagtcat ggctgctgac cttattttta ttcctattga tagaatatta ttccccctttt  3720
aaatacactg tactaagagg tccggctata attttactca cttgtcgatt atcccataga   3780
atgttgattg tagttggttg cttttccagg tgagagttga tcaagtcaca aaagttagcg   3840
tgtgttgatt gtagatttga aggtaaaata atttttgcac ccattcatcg ggtaaaacgt   3900
tctccataga atacatttcc atcgataatt gataacttat gaatttcaaa gaaaaaaata   3960
tgcttttaaa attaccaact tcgttcaaca gctccaacgc ggagttgatg actttggact   4020
tatccaggcg gctgcccatg gtggtttcta aaggtgttat aaatcaaatt agttttgttt   4080
tttcttgaaa actttgcgtt tcctttgatc aacttaccgc cagggtacct gcagattgtt   4140
```

tagcttgttc agctgcgctt gtttatttgc ttagctttcg cttagcgacg tgttcacttt 4200
gcttgtttga attgaattgt cgctccgtag acgaagcgcc tctatttata ctccggcgct 4260
cgttttcgag tttaccactc cctatcagtg atagagaaaa gtgaaagtcg agtttaccac 4320
tccctatcag tgatagagaa aagtgaaagt cgagtttacc actccctatc agtgatagag 4380
aaaagtgaaa gtcgagttta ccactcccta tcagtgatag agaaaagtga aagtcgagtt 4440
taccactccc tatcagtgat agagaaaagt gaaagtcgag tttaccactc cctatcagtg 4500
atagagaaaa gtgaaagtcg agtttaccac tccctatcag tgatagagaa aagtgaaagt 4560
cgaaacctgg cgcgccccgg ccatcgagaa agagagagag aagagaagag agagaacatt 4620
cgagaaagag agagagaaga gaagagagag aacatactcc ctatcagtga tagagaagtc 4680
cctatcagtg atagagatgt ccctatcagt gatagagagt tccctatcag tgatagagac 4740
gtccctatca gtgatagaga agtccctatc agtgatagag agatccctat cagtgataga 4800
gatttcccta tcagtgatag agaggtccct atcagtgata gagacttccc tatcagtgat 4860
agagaaatcc ctatcagtga tagagacatc cctatcagtg atagagaact ccctatcagt 4920
gatagagacc tccctatcag tgatagagat cgatgcggcc gcatggtacc cattgcttgt 4980
catttattaa tttggatgat gtcatttgtt tttaaaattg aactggcttt acgagtagaa 5040
ttctacgcgt aaaacacaat caagtatgag tcataatctg atgtcatgtt ttgtacacgg 5100
ctcataaccg aactggcttt acgagtagaa ttctacttgt aatgcacgat cagtggatga 5160
tgtcatttgt ttttcaaatc gagatgatgt catgttttgc acacggctca taaactcgct 5220
ttacgagtag aattctacgt gtaacgcacg atcgattgat gagtcatttg ttttgcaata 5280
tgatatcata caatatgact catttgtttt tcaaaaccga acttgattta cgggtagaat 5340
tctacttgta aagcacaatc aaaaagatga tgtcatttgt ttttcaaaac tgaactcgct 5400
ttacgagtag aattctacgt gtaaaacaca atcaagaaat gatgtcattt gttataaaaa 5460
taaaagctga tgtcatgttt tgcacatggc tcataactaa actcgcttta cgggtagaat 5520
tctacgcgta aaacatgatt gataattaaa taattcattt gcaagctata cgttaaatca 5580
aacggacgct cgaggttgca caacactatt atcgatttgc agttcgggac ataaatgttt 5640
aaatatatcg atgtctttgt gatgcgcgcg acatttttgt aggttattga taaaatgaac 5700
ggatacgttg cccgacatta tcattaaatc cttggcgtag aatttgtcgg gtccattgtc 5760
cgtgtgcgct agcatgcccg taacggacct cgtacttttg gcttcaaagg ttttgcgcac 5820
agacaaaatg tgccacactt gcagctctgc atgtgtgcgc gttaccacaa atcccaacgg 5880
cgcagtgtac ttgttgtatg caaataaatc tcgataaagg cgcggcgcgc gaatgcagct 5940
gatcacgtac gctcctcgtg ttccgttcaa ggacggtgtt atcgacctca gattaatgtt 6000
tatcggccga ctgttttcgt atccgctcac caaacgcgtt tttgcattaa cattgtatgt 6060
cggcggatgt tctatatcta atttgaataa ataaacgata accgcgttgg ttttagaggg 6120
cataataaaa gaaatattgt tatcgtgttc gccattaggg cagtataaat tgacgttcat 6180
gttggatatt gtttcagttg caagttgaca ctggcggcga caagcaattc taattggggt 6240
aagttttccc gttcttttct gggttcttcc cttttgctca tccttgctgc actaccttca 6300
ggtgcaagtt gagattcagg ccaccatggg agatcccacc ccacccaaga agaagcgcaa 6360
accggtcgcc accatggcct cctccgagaa cgtcatcacc gagttcatgc gcttcaaggt 6420
gcgcatggag ggcaccgtga acggccacga gttcgagatc gagggcgagg gcgagggccg 6480

-continued

```
cccctacgag ggccacaaca ccgtgaagct gaaggtgacc aagggcggcc ccctgccctt   6540
cgcctgggac atcctgtccc cccagttcca gtacggctcc aaggtgtacg tgaagcaccc   6600
cgccgacatc cccgactaca agaagctgtc cttccccgag ggcttcaagt gggagcgcgt   6660
gatgaacttc gaggacggcg gcgtggcgac cgtgacccag gactcctccc tgcaggacgg   6720
ctgcttcatc tacaaggtga agttcatcgg cgtgaacttc ccctccgacg gccccgtgat   6780
gcagaagaag accatgggct gggaggcctc caccgagcgc ctgtaccccc gcgacggcgt   6840
gctgaagggc gagacccaca aggccctgaa gctgaaggac ggcggccact acctggtgga   6900
gttcaagtcc atctacatgg ccaagaagcc cgtgcagctg cccggctact actacgtgga   6960
cgccaagctg gacatcacct cccacaacga ggactacacc atcgtggagc agtacgagcg   7020
caccgagggc cgccaccacc tgttcctgag atctcgaccc aagaaaaagc ggaaggtgga   7080
ggacccgtaa gatccaccgg atctagataa ctgatcataa tcagccatac cacatttgta   7140
gaggttttac ttgctttaaa aaacctccca cacctccccc tgaacctgaa acataaaatg   7200
aatgcaattg ttgttgttaa cttgtttatt gcagcttata atggttacaa ataaagcaat   7260
agcatcacaa atttcacaaa taaagcattt ttttcactgc attctagttg tggtttgtcc   7320
aaactcatca atgtatctta acgcgagtta attaaggccg ctcatttaaa tctggccggc   7380
cgcaaccatt gtgggaaccg tgcgatcaaa caaacgcgag ataccggaag tactgaaaaa   7440
cagtcgctcc aggccagtgg gaacatcgat gttttgtttt gacggacccc ttactctcgt   7500
ctcatataaa ccgaagccag ctaagatggt atacttatta tcatcttgtg atgaggatgc   7560
ttctatcaac gaaagtaccg gtaaaccgca aatggttatg tattataatc aaactaaagg   7620
cggagtggac acgctagacc aaatgtgttc tgtgatgacc tgcagtagga agacgaatag   7680
gtggcctatg gcattattgt acggaatgat aaacattgcc tgcataaatt cttttattat   7740
atacagccat aatgtcagta gcaagggaga aaaggtccaa agtcgcaaaa aatttatgag   7800
aaacctttac atgagcctga cgtcatcgtt tatgcgtaag cgtttagaag ctcctacttt   7860
gaagagatat ttgcgcgata atatctctaa tattttgcca aatgaagtgc ctggtacatc   7920
agatgacagt actgaagagc cagtaatgaa aaaacgtact tactgtactt actgcccctc   7980
taaaataagg cgaaaggcaa atgcatcgtg caaaaaatgc aaaaaagtta tttgtcgaga   8040
gcataatatt gatatgtgcc aaagttgttt ctgactgact aataagtata atttgtttct   8100
attatgtata agttaagcta attacttatt ttataataca acatgactgt ttttaaagta   8160
caaaataagt ttatttttgt aaaagagaga atgtttaaaa gttttgttac tttatagaag   8220
aaattttgag tttttgtttt tttttaataa ataaataaac ataaataaat tgtttgttga   8280
atttattatt agtatgtaag tgtaaatata ataaaactta atatctattc aaattaataa   8340
ataaacctcg atatacagac cgataaaaca catgcgtcaa ttttacgcat gattatcttt   8400
aacgtacgtc acaatatgat tatctttcta gggttaaata atagtttcta atttttttat   8460
tattcagcct gctgtcgtga ataccgtata tctcaacgct gtctgtgaga ttgtcgtatt   8520
ctagcctttt tagtttttcg ctcatcgact tgatattgtc cgacacattt tcgtcgattt   8580
gcgttttgat caaagacttg agcagagaca cgttaatcaa ctgttcaaat tgatccatat   8640
taacgatatc aacccgatgc gtatatggtg cgtaaaatat attttttaac cctcttatac   8700
tttgcactct gcgttaatac gcgttcgtgt acagacgtaa tcatgttttc tttttttggat   8760
aaaactccta ctgagtttga cctcatatta gaccctcaca agttgcaaaa cgtggcattt   8820
tttaccaatg aagaatttaa agttatttta aaaaatttca tcacagattt aaagaagaac   8880
```

caaaaattaa attatttcaa cagtttaatc gaccagttaa tcaacgtgta cacagacgcg 8940
tcggcaaaaa acacgcagcc cgacgtgttg gctaaaatta ttaaatcaac ttgtgttata 9000
gtcacggatt tgccgtccaa cgtgttcctc aaaaagttga agaccaacaa gtttacggac 9060
actattaatt atttgatttt gccccacttc attttgtggg atcacaattt tgttatattt 9120
taaacaaagc ttggcactgg ccgtcgtttt acaacgtcgt gactgggaaa accctggcgt 9180
tacccaactt aatcgccttg cagcacatcc ccctttcgcc agctggcgta atagcgaaga 9240
ggcccgcacc gatcgccctt cccaacagtt gcgcagcctg aatggcgaat ggcgcctgat 9300
gcggtatttt ctccttacgc atctgtgcgg tatttcacac cgcatatggt gcactctcag 9360
tacaatctgc tctgatgccg catagttaag ccagccccga cacccgccaa cacccgctga 9420
cgcgccctga cgggcttgtc tgctcccggc atccgcttac agacaagctg tgaccgtctc 9480
cgggagctgc atgtgtcaga ggttttcacc gtcatcaccg aaacgcgcga gacgaaaggg 9540
cctcgtgata cgcctatttt tataggttaa tgtcatgata ataatggttt cttagacgtc 9600
aggtggcact tttcggggaa atgtgcgcgg aacccctatt tgtttatttt tctaaataca 9660
ttcaaatatg tatccgctca tgagacaata accctgataa atgcttcaat aatattgaaa 9720
aaggaagagt atgagtattc aacatttccg tgtcgccctt attccctttt ttgcggcatt 9780
ttgccttcct gtttttgctc acccagaaac gctggtgaaa gtaaaagatg ctgaagatca 9840
gttgggtgca cgagtgggtt acatcgaact ggatctcaac agcggtaaga tccttgagag 9900
ttttcgcccc gaagaacgtt ttccaatgat gagcactttt aaagttctgc tatgtggcgc 9960
ggtattatcc cgtattgacg ccgggcaaga gcaactcggt cgccgcatac actattctca 10020
gaatgacttg gttgagtact caccagtcac agaaaagcat cttacggatg gcatgacagt 10080
aagagaatta tgcagtgctg ccataaccat gagtgataac actgcggcca acttacttct 10140
gacaacgatc ggaggaccga aggagctaac cgcttttttg cacaacatgg gggatcatgt 10200
aactcgcctt gatcgttggg aaccggagct gaatgaagcc ataccaaacg acgagcgtga 10260
caccacgatg cctgtagcaa tggcaacaac gttgcgcaaa ctattaactg gcgaactact 10320
tactctagct tcccggcaac aattaataga ctggatggag gcggataaag ttgcaggacc 10380
acttctgcgc tcggcccttc cggctggctg gtttattgct gataaatctg gagccggtga 10440
gcgtgggtct cgcggtatca ttgcagcact ggggccagat ggtaagccct cccgtatcgt 10500
agttatctac acgacgggga gtcaggcaac tatggatgaa cgaaatagac agatcgctga 10560
gataggtgcc tcactgatta agcattggta actgtcagac caagtttact catatatact 10620
ttagattgat ttaaaacttc atttttaatt taaaaggatc taggtgaaga tcctttttga 10680
taatctcatg accaaaatcc cttaacgtga gttttcgttc cactgagcgt cagaccccgt 10740
agaaaagatc aaaggatctt cttgagatcc tttttttctg cgcgtaatct gctgcttgca 10800
aacaaaaaaa ccaccgctac cagcggtggt ttgtttgccg gatcaagagc taccaactct 10860
ttttccgaag gtaactggct tcagcagagc gcagatacca aatactgtcc ttctagtgta 10920
gccgtagtta ggccaccact tcaagaactc tgtagcaccg cctacatacc tcgctctgct 10980
aatcctgtta ccagtggctg ctgccagtgg cgataagtcg tgtcttaccg ggttggactc 11040
aagacgatag ttaccggata aggcgcagcg gtcgggctga acggggggtt cgtgcacaca 11100
gcccagcttg gagcgaacga cctacaccga actgagatac ctacagcgtg agcattgaga 11160
aagcgccacg cttcccgaag ggagaaaggc ggacaggtat ccggtaagcg gcagggtcgg 11220

-continued

```
aacaggagag cgcacgaggg agcttccagg gggaaacgcc tggtatcttt atagtcctgt  11280

cgggtttcgc cacctctgac ttgagcgtcg atttttgtga tgctcgtcag gggggcggag  11340

cctatggaaa aacgccagca acgcggcctt tttacggttc ctggcctttt gctggccttt  11400

tgctcacatg ttctttcctg cgttatcccc tgattctgtg gataaccgta ttaccgcctt  11460

tgagtgagct gataccgctc gccgcagccg aacgaccgag cgcagcgagt cagtgagcga  11520

ggaagcggaa gagcgcccaa tacgcaaacc gcctctcccc gcgcgttggc cgattcatta  11580

atgcagctgg cacgacaggt ttcccgactg gaaagcgggc agtgagcgca acgcaattaa  11640

tgtgagttag ctcactcatt aggcacccca ggctttacac tttatgcttc cggctcgtat  11700

gttgtgtgga attgtgagcg gataacaatt tcacacagga aacagctatg accatgatta  11760

cgaatttcga cctgcaggca tgcaagcttg catgcctgca ggtcgacgct cgcgcgactt  11820

ggtttgccat tctttagcgc gcgtcgcgtc acacagcttg gccacaat              11868
```

<210> SEQ ID NO 51
<211> LENGTH: 11788
<212> TYPE: DNA
<213> ORGANISM: artificial
<220> FEATURE:
<223> OTHER INFORMATION: 51 Sequence of pLA3097-a Cctra intron-tTAV construct.

<400> SEQUENCE: 51

```
gggcggccgt ttttcttgaa atattgctct ctctttctaa atagcgcgaa tccgtcgctg     60

tgcatttagg acatctcagt cgccgcttgg agctcccaaa cgcgccagtg gtagtacaca    120

gtactgtggg tgttcagttt gaaatcctct tgcttctcca ttgtctcggt tacctttggt    180

caaatccatg ggttctattg cctatatact cttgcgatta ccagtgattg cgctattagc    240

tattagatgg attgttggcc aaacttgtcg cttaagtggc tgggaattgt aaccgtaggc    300

ccgagtgtaa tgatccccca taaaaagttt tcgcaatgcc tttatttttt gttgcaaatc    360

tctctttatt ctgcggtatt cttcattatt gcggggatgg ggaaagtgtt tatatagaag    420

caacttacga ttgaacccaa atgcacctga caagcaaggt caaagggcca gatttttaaa    480

tatattattt agtcttagga ctctctattt gcaattaaat tactttgcta cctgagggtt    540

aaatcttccc cattgataat aataattcca ctatatgttc aattgggttt caccgcgctt    600

agttacatga cgagccctaa tgagccgtcg gtggtctata aactgtgcct tacaaatact    660

tgcaactctt ctcgttttga agtcagcaga gttattgcta attgctaatt gctaattgct    720

tttaactgat ttcttcgaaa ttggtgctat gtttatggcg ctattaacaa gtatgaatgt    780

caggtttaac caggggatgc ttaattgtgt tctcaacttc aaaggcagaa atgtttactc    840

ttgaccatgg gtttaggtat aatgttatca agctcctcga gttaacgtta cgttaacgtt    900

aacgttcgag gtcgactcta gaactaccca ccgtactcgt caattccaag ggcatcggta    960

aacatctgct caaactcgaa gtcggccata tccagagcgc cgtagggggc ggagtcgtgg   1020

ggggtaaatc ccggacccgg ggaatccccg tcccccaaca tgtccagatc gaaatcgtct   1080

agcgcgtcgg catgcgccat cgccacgtcc tcgccgtcta agtggagctc gtcccccagg   1140

ctgacatcgg tcggggggc cgtcgacagt ctgcgcgtgt gtcccgcggg gagaaaggac   1200

aggcgcggag ccgccagccc cgcctcttcg gggcgtcgt cgtccgggag atcgagcagg   1260

ccctcgatgg tagacccgta attgtttttc gtacgcgcgc ggctgtacgc ggggcccgag   1320

cccgactcgc atttcagttg cttttccaat ccgcagataa tcagctccaa gccgaacagg   1380
```

-continued

```
aatgccggct cggctccttg atgatcgaac agctcgattg cctgacgcag cagtgggggc   1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgcttttcg   1620
gtcgggcgcg tgccgagatg gactttggca ccgtctcggt gggacagcag agcgcagcgg   1680
aacgacttgg cgttattgcg gaggaagtcc tgccaggact cgccttccaa cgggcaaaaa   1740
tgcgtgtggt ggcggtcgag catctcgatg gccagggcat ccagcagcgc ccgcttattc   1800
ttcacgtgcc agtagagggt gggctgctcc acgcccagct tctgcgccaa cttgcgggtc   1860
gtcagtccct caatgccaac ttcgttcaac agctccaacg cggagttgat gactttggac   1920
ttatccaggc ggctgaccta tagataccat agatgtatgg attagtatca tatacataca   1980
aaggctattt ttgggacata ttaatattaa caatttccgt gatagttttc accatttttg   2040
ttgaatgtta cgttgaaaat ttaaatttgt tttaaattaa ttttaccagt catgtgttct   2100
taaaagtttt tatgattgaa acggcataaa gtggttcaaa aatttatcaa gaaaggcttt   2160
cctttttaa atcttatctt tttctcttaa aaatcactag tcaattcatt attaatttgt   2220
taacttgaat ttggaatgtc tatttacttt cagataaatt aaagcaagaa acttaatatt   2280
cgaaaaaaat tgattctaaa tggaatttca cttgatcttc atgtatgcat atcaattttt   2340
atttacattg tataataagt ttcgagttga ttgttgtaat ccacaggtgt cccagagaat   2400
taaattccaa attacccaag tttattgaat gttgattgta gtttcagttg ctttgttgct   2460
gcaacaatgg cttgttgatt gtagatattt tccctttcct tggtttactt attacataga   2520
ctgaaaaaga ggtttacttt tttgatactt atgaaaaatt tctattagtg attactaacc   2580
aatcgctata tgtttactag aaaacaaata aactctttac attaacattc aataatgttt   2640
gctctgtaac cgacaattga aggcgttaca gcaacagtaa tataactagc ttcttaaccc   2700
tcatctatta accccatcgt ttaaaacact atgttaaatg gtctaacaaa tctagatact   2760
aatagatgtc ttattactta gcagccacag ctgcaacatc caagacaatt tttgaaactt   2820
cttattgagc tcttggcagc agaaatgttg gtatttttca cagctttctg aaagaccggc   2880
accttcctcc ggttcccgtt tctgaattca agaggatttc cgacccccaa ttaatcccga   2940
aacaaataag gtatattcaa aatgatggaa aagtcatggc tgctgacctt atttttattc   3000
ctattgatag aatattattc cccttttaaa tacactgtac taagaggtcc ggctataatt   3060
ttactcactt gtcgattatc ccatagaatg ttgattgtag ttggttgctt ttccaggtga   3120
gagttgatca agtcacaaaa gttagcgtgt gttgattgta gatttgaagg taaaataatt   3180
tttgcaccca ttcatcgggt aaaacgttct ccatagaata catttccatc gataattgat   3240
aacttatgaa tttcaaagaa aaaaatatgc ttttaaaatt accatggtgg ctagcgcaga   3300
ttgtttagct tgttcagctg cgcttgttta tttgcttagc tttcgcttag cgacgtgttc   3360
actttgcttg tttgaattga attgtcgctc cgtagacgaa gcgcctctat ttatactccg   3420
gcgctcgttt tcgagtttac cactccctat cagtgataga gaaaagtgaa agtcgagttt   3480
accactccct atcagtgata gagaaaagtg aaagtcgagt ttaccactcc ctatcagtga   3540
tagagaaaag tgaaagtcga gtttaccact ccctatcagt gatagagaaa agtgaaagtc   3600
gagtttacca ctccctatca gtgatagaga aaagtgaaag tcgagtttac cactccctat   3660
cagtgataga gaaaagtgaa agtcgagttt accactccct atcagtgata gagaaaagtg   3720
aaagtcgaaa cctggcgcgc cccggccatc gagaaagaga gagagaagag aagagagaga   3780
```

```
acattcgaga aagagagaga gaagagaaga gagagaacat actccctatc agtgatagag   3840
aagtccctat cagtgataga gatgtcccta tcagtgatag agagttccct atcagtgata   3900
gagacgtccc tatcagtgat agagaagtcc ctatcagtga tagagagatc cctatcagtg   3960
atagagattt ccctatcagt gatagagagg tccctatcag tgatagagac ttccctatca   4020
gtgatagaga aatccctatc agtgatagag acatccctat cagtgataga gaactcccta   4080
tcagtgatag agacctccct atcagtgata gagatcgatg cggccgcatg gtacccattg   4140
cttgtcattt attaatttgg atgatgtcat ttgtttttaa aattgaactg gctttacgag   4200
tagaattcta cgcgtaaaac acaatcaagt atgagtcata atctgatgtc atgttttgta   4260
cacggctcat aaccgaactg gctttacgag tagaattcta cttgtaatgc acgatcagtg   4320
gatgatgtca tttgtttttc aaatcgagat gatgtcatgt tttgcacacg gctcataaac   4380
tcgctttacg agtagaattc tacgtgtaac gcacgatcga ttgatgagtc atttgttttg   4440
caatatgata tcatacaata tgactcattt gtttttcaaa accgaacttg atttacgggt   4500
agaattctac ttgtaaagca caatcaaaaa gatgatgtca tttgtttttc aaaactgaac   4560
tcgctttacg agtagaattc tacgtgtaaa acacaatcaa gaaatgatgt catttgttat   4620
aaaaataaaa gctgatgtca tgttttgcac atggctcata actaaactcg ctttacgggt   4680
agaattctac gcgtaaaaca tgattgataa ttaaataatt catttgcaag ctatacgtta   4740
aatcaaacgg acgctcgagg ttgcacaaca ctattatcga tttgcagttc gggacataaa   4800
tgtttaaata tatcgatgtc tttgtgatgc gcgcgacatt tttgtaggtt attgataaaa   4860
tgaacggata cgttgcccga cattatcatt aaatccttgg cgtagaattt gtcgggtcca   4920
ttgtccgtgt gcgctagcat gcccgtaacg gacctcgtac ttttggcttc aaaggttttg   4980
cgcacagaca aaatgtgcca cacttgcagc tctgcatgtg tgcgcgttac cacaaatccc   5040
aacggcgcag tgtacttgtt gtatgcaaat aaatctcgat aaaggcgcgg cgcgcgaatg   5100
cagctgatca cgtacgctcc tcgtgttccg ttcaaggacg gtgttatcga cctcagatta   5160
atgtttatcg gccgactgtt ttcgtatccg ctcaccaaac gcgtttttgc attaacattg   5220
tatgtcggcg gatgttctat atctaatttg aataaataaa cgataaccgc gttggtttta   5280
gagggcataa taaaagaaat attgttatcg tgttcgccat tagggcagta taaattgacg   5340
ttcatgttgg atattgtttc agttgcaagt tgacactggc ggcgacaagc aattctaatt   5400
ggggtaagtt ttcccgttct tttctgggtt cttccctttt gctcatcctt gctgcactac   5460
cttcaggtgc aagttgagat tcaggccacc atgggagatc ccaccccacc caagaagaag   5520
cgcaaaccgg tcgccaccat ggcctcctcc gagaacgtca tcaccgagtt catgcgcttc   5580
aaggtgcgca tggagggcac cgtgaacggc cacgagttcg agatcgaggg cgagggcgag   5640
ggccgcccct acgagggcca caacaccgtg aagctgaagg tgaccaaggg cggccccctg   5700
cccttcgcct gggacatcct gtccccccag ttccagtacg gctccaaggt gtacgtgaag   5760
caccccgccg acatccccga ctacaagaag ctgtccttcc ccgagggctt caagtgggag   5820
cgcgtgatga acttcgagga cggcggcgtg gcgaccgtga cccaggactc ctccctgcag   5880
gacggctgct tcatctacaa ggtgaagttc atcggcgtga acttcccctc cgacggcccc   5940
gtgatgcaga agaagaccat gggctgggag gcctccaccg agcgcctgta cccccgcgac   6000
ggcgtgctga agggcgagac ccacaaggcc ctgaagctga aggacggcgg ccactacctg   6060
gtggagttca agtccatcta catggccaag aagcccgtgc agctgcccgg ctactactac   6120
```

-continued

```
gtggacgcca agctggacat cacctcccac aacgaggact acaccatcgt ggagcagtac   6180
gagcgcaccg agggccgcca ccacctgttc ctgagatctc gacccaagaa aaagcggaag   6240
gtggaggacc cgtaagatcc accggatcta gataactgat cataatcagc cataccacat   6300
ttgtagaggt tttacttgct ttaaaaaacc tcccacacct ccccctgaac ctgaaacata   6360
aaatgaatgc aattgttgtt gttaacttgt ttattgcagc ttataatggt tacaaataaa   6420
gcaatagcat cacaaatttc acaaataaag catttttttc actgcattct agttgtggtt   6480
tgtccaaact catcaatgta tcttaacgcg agttaattaa ggccgctcat ttaaatctgg   6540
ccggccgcaa ccattgtggg aaccgtgcga tcaaacaaac gcgagatacc ggaagtactg   6600
aaaaacagtc gctccaggcc agtgggaaca tcgatgtttt gttttgacgg accccttact   6660
ctcgtctcat ataaaccgaa gccagctaag atggtatact tattatcatc ttgtgatgag   6720
gatgcttcta tcaacgaaag taccggtaaa ccgcaaatgg ttatgtatta taatcaaact   6780
aaaggcggag tggacacgct agaccaaatg tgttctgtga tgacctgcag taggaagacg   6840
aataggtggc ctatggcatt attgtacgga atgataaaca ttgcctgcat aaattctttt   6900
attatataca gccataatgt cagtagcaag ggagaaaagg tccaaagtcg caaaaaattt   6960
atgagaaacc tttacatgag cctgacgtca tcgtttatgc gtaagcgttt agaagctcct   7020
actttgaaga gatatttgcg cgataatatc tctaatattt tgccaaatga agtgcctggt   7080
acatcagatg acagtactga agagccagta atgaaaaaac gtacttactg tacttactgc   7140
ccctctaaaa taaggcgaaa ggcaaatgca tcgtgcaaaa aatgcaaaaa agttatttgt   7200
cgagagcata atattgatat gtgccaaagt tgtttctgac tgactaataa gtataatttg   7260
tttctattat gtataagtta agctaattac ttattttata atacaacatg actgttttta   7320
aagtacaaaa taagtttatt tttgtaaaag agagaatgtt taaaagtttt gttactttat   7380
agaagaaatt ttgagttttt gttttttttt aataaataaa taaacataaa taaattgttt   7440
gttgaattta ttattagtat gtaagtgtaa atataataaa acttaatatc tattcaaatt   7500
aataaataaa cctcgatata cagaccgata aaacacatgc gtcaatttta cgcatgatta   7560
tctttaacgt acgtcacaat atgattatct ttctagggtt aaataatagt ttctaatttt   7620
tttattattc agcctgctgt cgtgaatacc gtatatctca acgctgtctg tgagattgtc   7680
gtattctagc ctttttagtt tttcgctcat cgacttgata ttgtccgaca cattttcgtc   7740
gatttgcgtt ttgatcaaag acttgagcag agacacgtta atcaactgtt caaattgatc   7800
catattaacg atatcaaccc gatgcgtata tggtgcgtaa aatatatttt ttaaccctct   7860
tatactttgc actctgcgtt aatacgcgtt cgtgtacaga cgtaatcatg ttttcttttt   7920
tggataaaac tcctactgag tttgacctca tattagaccc tcacaagttg caaaacgtgg   7980
catttttttac caatgaagaa tttaaagtta ttttaaaaaa tttcatcaca gatttaaaga   8040
agaaccaaaa attaaattat ttcaacagtt taatcgacca gttaatcaac gtgtacacag   8100
acgcgtcggc aaaaaacacg cagcccgacg tgttggctaa aattattaaa tcaacttgtg   8160
ttatagtcac ggatttgccg tccaacgtgt tcctcaaaaa gttgaagacc aacaagttta   8220
cggacactat taattatttg attttgcccc acttcatttt gtgggatcac aattttgtta   8280
tattttaaac aaagcttggc actggccgtc gttttacaac gtcgtgactg ggaaaaccct   8340
ggcgttaccc aacttaatcg ccttgcagca catccccctt tcgccagctg gcgtaatagc   8400
gaagaggccc gcaccgatcg cccttcccaa cagttgcgca gcctgaatgg cgaatggcgc   8460
ctgatgcggt attttctcct tacgcatctg tgcggtattt cacaccgcat atggtgcact   8520
```

-continued

```
ctcagtacaa tctgctctga tgccgcatag ttaagccagc cccgacaccc gccaacaccc   8580
gctgacgcgc cctgacgggc ttgtctgctc ccggcatccg cttacagaca agctgtgacc   8640
gtctccggga gctgcatgtg tcagaggttt tcaccgtcat caccgaaacg cgcgagacga   8700
aagggcctcg tgatacgcct atttttatag gttaatgtca tgataataat ggtttcttag   8760
acgtcaggtg gcacttttcg gggaaatgtg cgcggaaccc ctatttgttt atttttctaa   8820
atacattcaa atatgtatcc gctcatgaga caataaccct gataaatgct tcaataatat   8880
tgaaaaagga agagtatgag tattcaacat ttccgtgtcg cccttattcc cttttttgcg   8940
gcattttgcc ttcctgtttt tgctcaccca gaaacgctgg tgaaagtaaa agatgctgaa   9000
gatcagttgg gtgcacgagt gggttacatc gaactggatc tcaacagcgg taagatcctt   9060
gagagttttc gccccgaaga acgttttcca atgatgagca cttttaaagt tctgctatgt   9120
ggcgcggtat tatcccgtat tgacgccggg caagagcaac tcggtcgccg catacactat   9180
tctcagaatg acttggttga gtactcacca gtcacagaaa agcatcttac ggatggcatg   9240
acagtaagag aattatgcag tgctgccata accatgagtg ataacactgc ggccaactta   9300
cttctgacaa cgatcggagg accgaaggag ctaaccgctt ttttgcacaa catgggggat   9360
catgtaactc gccttgatcg ttgggaaccg gagctgaatg aagccatacc aaacgacgag   9420
cgtgacacca cgatgcctgt agcaatggca acaacgttgc gcaaactatt aactggcgaa   9480
ctacttactc tagcttcccg gcaacaatta atagactgga tggaggcgga taaagttgca   9540
ggaccacttc tgcgctcggc ccttccggct ggctggttta ttgctgataa atctggagcc   9600
ggtgagcgtg ggtctcgcgg tatcattgca gcactggggc cagatggtaa gccctcccgt   9660
atcgtagtta tctacacgac ggggagtcag gcaactatgg atgaacgaaa tagacagatc   9720
gctgagatag gtgcctcact gattaagcat tggtaactgt cagaccaagt ttactcatat   9780
atactttaga ttgatttaaa acttcatttt taatttaaaa ggatctaggt gaagatcctt   9840
tttgataatc tcatgaccaa aatcccttaa cgtgagtttt cgttccactg agcgtcagac   9900
cccgtagaaa agatcaaagg atcttcttga gatccttttt ttctgcgcgt aatctgctgc   9960
ttgcaaacaa aaaaaccacc gctaccagcg gtggtttgtt tgccggatca agagctacca  10020
actctttttc cgaaggtaac tggcttcagc agagcgcaga taccaaatac tgtccttcta  10080
gtgtagccgt agttaggcca ccacttcaag aactctgtag caccgcctac atacctcgct  10140
ctgctaatcc tgttaccagt ggctgctgcc agtggcgata agtcgtgtct taccgggttg  10200
gactcaagac gatagttacc ggataaggcg cagcggtcgg gctgaacggg gggttcgtgc  10260
acacagccca gcttggagcg aacgacctac accgaactga gatacctaca gcgtgagcat  10320
tgagaaagcg ccacgcttcc cgaagggaga aaggcggaca ggtatccggt aagcggcagg  10380
gtcggaacag gagagcgcac gagggagctt ccagggggaa acgcctggta tctttatagt  10440
cctgtcgggt ttcgccacct ctgacttgag cgtcgatttt tgtgatgctc gtcagggggg  10500
cggagcctat ggaaaaacgc cagcaacgcg gcctttttac ggttcctggc cttttgctgg  10560
ccttttgctc acatgttctt tcctgcgtta tcccctgatt ctgtggataa ccgtattacc  10620
gcctttgagt gagctgatac cgctcgccgc agccgaacga ccgagcgcag cgagtcagtg  10680
agcgaggaag cggaagagcg cccaatacgc aaaccgcctc tccccgcgcg ttggccgatt  10740
cattaatgca gctggcacga caggtttccc gactggaaag cgggcagtga gcgcaacgca  10800
attaatgtga gttagctcac tcattaggca ccccaggctt tacactttat gcttccggct  10860
```

-continued

```
cgtatgttgt gtggaattgt gagcggataa caatttcaca caggaaacag ctatgaccat  10920

gattacgaat ttcgacctgc aggcatgcaa gcttgcatgc ctgcaggtcg acgctcgcgc  10980

gacttggttt gccattcttt agcgcgcgtc gcgtcacaca gcttggccac aatgtggttt  11040

ttgtcaaacg aagattctat gacgtgttta aagtttaggt cgagtaaagc gcaaatcttt  11100

tttaacccta gaaagatagt ctgcgtaaaa ttgacgcatg cattcttgaa atattgctct  11160

ctctttctaa atagcgcgaa tccgtcgctg tgcatttagg acatctcagt cgccgcttgg  11220

agctcccgtg aggcgtgctt gtcaatgcgg taagtgtcac tgattttgaa ctataacgac  11280

cgcgtgagtc aaaatgacgc atgattatct tttacgtgac ttttaagatt taactcatac  11340

gataattata ttgttatttc atgttctact tacgtgataa cttattatat atatattttc  11400

ttgttataga tatcgtgact aatatataat aaaatgggta gttctttaga cgatgagcat  11460

atcctctctg ctcttctgca aagcgatgac gagcttgttg gtgaggattc tgacagtgaa  11520

atatcagatc acgtaagtga agatgacgtc cagagcgata cagaagaagc gtttatagat  11580

gaggtacatg aagtgcagcc aacgtcaagc ggtagtgaaa tattagacga acaaaatgtt  11640

attgaacaac caggttcttc attggcttct aacagaatct tgaccttgcc acagaggact  11700

attagaggta agaataaaca ttgttggtca acttcaaagt ccacgaggcg tagccgagtc  11760

tctgcactga acattgtcag atcggccc                                    11788
```

<210> SEQ ID NO 52
<211> LENGTH: 13292
<212> TYPE: DNA
<213> ORGANISM: artificial
<220> FEATURE:
<223> OTHER INFORMATION: Sequence of pLA3233-Cctra-intron-tTAV2
      construct.

<400> SEQUENCE: 52

```
gggcggccgt ttttcttgaa atattgctct ctctttctaa atagcgcgaa tccgtcgctg     60

tgcatttagg acatctcagt cgccgcttgg agctcccaaa cgcgccagtg gtagtacaca    120

gtactgtggg tgttcagttt gaaatcctct tgcttctcca ttgtctcggt tacctttggt    180

caaatccatg ggttctattg cctatatact cttgcgatta ccagtgattg cgctattagc    240

tattagatgg attgttggcc aaacttgtcg cttaagtggc tgggaattgt aaccgtaggc    300

ccgagtgtaa tgatccccca taaaaagttt tcgcaatgcc tttatttttt gttgcaaatc    360

tctctttatt ctgcggtatt cttcattatt gcggggatgg ggaaagtgtt tatatagaag    420

caacttacga ttgaacccaa atgcacctga caagcaaggt caaagggcca gatttttaaa    480

tatattattt agtcttagga ctctctattt gcaattaaat tactttgcta cctgagggtt    540

aaatcttccc cattgataat aataattcca ctatatgttc aattgggttt caccgcgctt    600

agttacatga cgagccctaa tgagccgtcg gtggtctata aactgtgcct tacaaatact    660

tgcaactctt ctcgttttga agtcagcaga gttattgcta attgctaatt gctaattgct    720

tttaactgat ttcttcgaaa ttggtgctat gtttatggcg ctattaacaa gtatgaatgt    780

caggtttaac caggggatgc ttaattgtgt tctcaacttc aaaggcagaa atgtttactc    840

ttgaccatgg gtttaggtat aatgttatca agctcctcga gttaacgtta cgttaacgtt    900

aacgttcgag gtcgactcta gacaccggtg ttagccgccg tactcatcga tgcccagggc    960

gtcggtgaac atctgctcga actcgaaatc ggccatatcc agggcgccgt agggggcgct   1020

atcgtgcggg gtgaatcccg gtcccgggct atcgccatcg cccagcatgt ccaggtcgaa   1080
```

-continued

```
gtcgtccagg gcatcggcgt gggccatcgc cacatcctcg ccatccaggt gcagctcatc   1140
gcccaggctc acgtcggtcg gcggggcggt cgacaggcgg cgggtgtgtc cggccggcag   1200
gaagctcagg cgcggggcgg ccaggcccgc ctcctccggg gcatcatcat ccggcagatc   1260
cagcaggccc tcgatggtgc tgccgtagtt gttcttggtg cgggcgcggc tgtaggcggg   1320
gcccgagccc gactcgcatt tcagttgctt ttccaatccg cagataatca gctccaagcc   1380
gaacaggaat gccggctcgg ctccttgatg atcgaacagc tcgattgcct gacgcagcag   1440
tgggggcatc gaatcggttg ttggggtctc gcgctcctct tttgcgactt gatgctcttg   1500
gtcctccagc acgcagccca gggtaaagtg accgacggcg ctcagagcgt agagagcatt   1560
ttccaggctg aagccttgct ggcacaggaa cgcgagctgg ttctccagtg tctcgtattg   1620
cttttcggtc gggcgcgtgc cgagatggac tttggcaccg tctcggtggg acagcagagc   1680
gcagcggaac gacttggcgt tattgcggag gaagtcctgc caggactcgc cttccaacgg   1740
gcaaaaatgc gtgtggtggc ggtcgagcat ctcgatggcc agggcatcca gcagcgcccg   1800
cttattcttc acgtgccagt agagggtggg ctgctccacg cccagcttct gcgccaactt   1860
gcgggtcgtc agtccctcaa tgccaacttc gttcaacagc tccaacgcgg agttgatgac   1920
tttggactta tccaggcggc tgacctatag ataccataga tgtatggatt agtatcatat   1980
acatacaaag gctatttttg ggacatatta atattaacaa tttccgtgat agttttcacc   2040
atttttgttg aatgttacgt tgaaaattta aatttgtttt aaattaattt taccagtcat   2100
gtgttcttaa aagtttttat gattgaaacg gcataaagtg gttcaaaaat ttatcaagaa   2160
aggctttcct tttttaaatc ttatcttttt ctcttaaaaa tcactagtca attcattatt   2220
aatttgttaa cttgaatttg gaatgtctat ttactttcag ataaattaaa gcaagaaact   2280
taatattcga aaaaaattga ttctaaatgg aatttcactt gatcttcatg tatgcatatc   2340
aatttttatt tacattgtat aataagtttc gagttgattg ttgtaatcca caggtgtccc   2400
agagaattaa attccaaatt acccaagttt attgaatgtt gattgtagtt tcagttgctt   2460
tgttgctgca acaatggctt gttgattgta gatattttcc ctttccttgg tttacttatt   2520
acatagactg aaaaagaggt ttactttttt gatacttatg aaaaatttct attagtgatt   2580
actaaccaat cgctatatgt ttactagaaa acaaataaac tctttacatt aacattcaat   2640
aatgtttgct ctgtaaccga caattgaagg cgttacagca acagtaatat aactagcttc   2700
ttaaccctca tctattaacc ccatcgttta aaacactatg ttaaatggtc taacaaatct   2760
agatactaat agatgtctta ttacttagca gccacagctg caacatccaa gacaattttt   2820
gaaacttctt attgagctct tggcagcaga aatgttggta tttttcacag ctttctgaaa   2880
gaccggcacc ttcctccggt tcccgtttct gaattcaaga ggatttccga cccccaatta   2940
atcccgaaac aaataaggta tattcaaaat gatggaaaag tcatggctgc tgaccttatt   3000
tttattccta ttgatagaat attattcccc ttttaaatac actgtactaa gaggtccggc   3060
tataatttta ctcacttgtc gattatccca tagaatgttg attgtagttg gttgcttttc   3120
caggtgagag ttgatcaagt cacaaaagtt agcgtgtgtt gattgtagat ttgaaggtaa   3180
aataattttt gcacccattc atcgggtaaa acgttctcca tagaatacat ttccatcgat   3240
aattgataac ttatgaattt caaagaaaaa aatatgcttt taaaattacc atggtggcta   3300
gcgcagattg tttagcttgt tcagctgcgc ttgtttattt gcttagcttt cgcttagcga   3360
cgtgttcact ttgcttgttt gaattgaatt gtcgctccgt agacgaagcg cctctattta   3420
tactccggcg ctcgttttcg agtttaccac tccctatcag tgatagagaa aagtgaaagt   3480
```

-continued

```
cgagtttacc actccctatc agtgatagag aaaagtgaaa gtcgagttta ccactcccta   3540
tcagtgatag agaaaagtga aagtcgagtt taccactccc tatcagtgat agagaaaagt   3600
gaaagtcgag tttaccactc cctatcagtg atagagaaaa gtgaaagtcg agtttaccac   3660
tccctatcag tgatagagaa aagtgaaagt cgagtttacc actccctatc agtgatagag   3720
aaaagtgaaa gtcgaaacct ggcgcgcccc ggccatcgag aaagagagag agaagagaag   3780
agagagaaca ttcgagaaag agagagagaa gagaagagag agaacatact ccctatcagt   3840
gatagagaag tccctatcag tgatagagat gtccctatca gtgatagaga gttccctatc   3900
agtgatagag acgtccctat cagtgataga gaagtcccta tcagtgatag agagatccct   3960
atcagtgata gagatttccc tatcagtgat agagaggtcc ctatcagtga tagagacttc   4020
cctatcagtg atagagaaat ccctatcagt gatagagaca tccctatcag tgatagagaa   4080
ctccctatca gtgatagaga cctccctatc agtgatagag atcgatgcgg ccgcatggta   4140
cccattgctt gtcatttatt aatttggatg atgtcatttg tttttaaaat tgaactggct   4200
ttacgagtag aattctacgc gtaaaacaca atcaagtatg agtcataatc tgatgtcatg   4260
ttttgtacac ggctcataac cgaactggct ttacgagtag aattctactt gtaatgcacg   4320
atcagtggat gatgtcattt gtttttcaaa tcgagatgat gtcatgtttt gcacacggct   4380
cataaactcg ctttacgagt agaattctac gtgtaacgca cgatcgattg atgagtcatt   4440
tgttttgcaa tatgatatca tacaatatga ctcatttgtt tttcaaaacc gaacttgatt   4500
tacgggtaga attctacttg taaagcacaa tcaaaaagat gatgtcattt gtttttcaaa   4560
actgaactcg ctttacgagt agaattctac gtgtaaaaca caatcaagaa atgatgtcat   4620
ttgttataaa aataaaagct gatgtcatgt tttgcacatg gctcataact aaactcgctt   4680
tacgggtaga attctacgcg taaaacatga ttgataatta aataattcat ttgcaagcta   4740
tacgttaaat caaacggacg ctcgaggttg cacaacacta ttatcgattt gcagttcggg   4800
acataaatgt ttaaatatat cgatgtcttt gtgatgcgcg cgacattttt gtaggttatt   4860
gataaaatga acggatacgt tgcccgacat tatcattaaa tccttggcgt agaatttgtc   4920
gggtccattg tccgtgtgcg ctagcatgcc cgtaacggac ctcgtacttt tggcttcaaa   4980
ggttttgcgc acagacaaaa tgtgccacac ttgcagctct gcatgtgtgc gcgttaccac   5040
aaatcccaac ggcgcagtgt acttgttgta tgcaaataaa tctcgataaa ggcgcggcgc   5100
gcgaatgcag ctgatcacgt acgctcctcg tgttccgttc aaggacggtg ttatcgacct   5160
cagattaatg tttatcggcc gactgttttc gtatccgctc accaaacgcg tttttgcatt   5220
aacattgtat gtcggcggat gttctatatc taatttgaat aaataaacga taaccgcgtt   5280
ggttttagag ggcataataa aagaaatatt gttatcgtgt tcgccattag ggcagtataa   5340
attgacgttc atgttggata ttgtttcagt tgcaagttga cactggcggc gacaagcaat   5400
tctaattggg gtaagttttc ccgttctttt ctgggttctt cccttttgct catccttgct   5460
gcactacctt caggtgcaag ttgagattca ggccaccatg ggagatccca ccccacccaa   5520
gaagaagcgc aaaccggtcg ccaccatgga cgaggatggt tcagagggcg gccccgccct   5580
gttccagagc gacatgacct tcaaaatctt catcgacggc gaggtgaacg gccagaagtt   5640
caccatcgtg gccgacggca gcagcaagtt cccccacggc gacttcaacg tgcacgccgt   5700
gtgcgagacc ggcaagctgc ccatgagctg gaagcccatc tgccacctga tccagtacgg   5760
cgagcccttc ttcgcccgct accccaacgg catcagccac ttcgcccagg agtgcttccc   5820
```

```
cgagggcctg agcatcgacc gcaccgtgcg cttcgagaac gacggcacca tgaccagcca   5880
ccacacctac gagctggacg gcacctgcgt ggtcagccgc atcaccgtga actgcgacgg   5940
cttccagccc gacggcccca tcatgcgcga ccagctggtg gacatcctgc ccaacgagac   6000
ccacatgttc ccccacggcc ccaacgccgt gcgccagctg gccttcatcg gcttcaccac   6060
cgccgacggc ggcctgatga tgggccactt cgacagcaag atgaccttca acggcagccg   6120
cgccatcaag atccccggcc cccacttcgt gaccatcatc accaagcaga tgagggacac   6180
cagcgacaag cgcgaccacg tgtgccagcg cgaggtgacc tacgcccaca gcgtgccccg   6240
catcaccagc gccatcggta gcgacgagga ttccggactc agatctcgac ccaagaaaaa   6300
gcggaaggtg gaggacccgt aagatccacc ggatctagat aactgatcat aatcagccat   6360
accacatttg tagaggtttt acttgcttta aaaaacctcc cacacctccc cctgaacctg   6420
aaacataaaa tgaatgcaat tgttgttgtt aacttgttta ttgcagctta taatggttac   6480
aaataaagca atagcatcac aaatttcaca aataaagcat ttttttcact gcattctagt   6540
tgtggtttgt ccaaactcat caatgtatct taacgcgagt taattaacac cgaaatcgta   6600
attcacggca tcattacaaa atattttgac gttttggacc tcgtccctaa tgacaccata   6660
acggtggcct tgaagtatat ttaaccctag aaagatagtc tgcgtaaaat tgacgcatgc   6720
attcttgaaa tattgctctc tctttctaaa tagcgcgaat ccgtcgctgt gcatttagga   6780
catctcagtc gccgcttgga gctcccgtga ggcgtgcttg tcaatgcggt aagtgtcact   6840
gattttgaac tataacgacc gcgtgagtca aaatgacgca tgattatctt ttacgtgact   6900
tttaagattt aactcatacg ataattatat tgttatttca tgttctactt acgtgataac   6960
ttattatata tatattttct tgttatagat atcgtgacta atatataata aaatgggtag   7020
ttctttagac gatgagcata tcctctctgc tcttctgcaa agcgatgacg agcttgttgg   7080
tgaggattct gacagtgaaa tatcagatca cgtaagtgaa gatgacgtcc aggaaatctg   7140
gccggccgca accattgtgg gaaccgtgcg atcaaacaaa cgcgagatac cggaagtact   7200
gaaaaacagt cgctccaggc cagtgggaac atcgatgttt tgttttgacg gacccctac    7260
tctcgtctca tataaaccga agccagctaa gatggtatac ttattatcat cttgtgatga   7320
ggatgcttct atcaacgaaa gtaccggtaa accgcaaatg gttatgtatt ataatcaaac   7380
taaaggcgga gtggacacgc tagaccaaat gtgttctgtg atgacctgca gtaggaagac   7440
gaataggtgg cctatggcat tattgtacgg aatgataaac attgcctgca taaattcttt   7500
tattatatac agccataatg tcagtagcaa gggagaaaag gtccaaagtc gcaaaaaatt   7560
tatgagaaac ctttacatga gcctgacgtc atcgtttatg cgtaagcgtt tagaagctcc   7620
tactttgaag agatatttgc gcgataatat ctctaatatt ttgccaaatg aagtgcctgg   7680
tacatcagat gacagtactg aagagccagt aatgaaaaaa cgtacttact gtacttactg   7740
cccctctaaa ataaggcgaa aggcaaatgc atcgtgcaaa aaatgcaaaa aagttatttg   7800
tcgagagcat aatattgata tgtgccaaag ttgtttctga ctgactaata agtataattt   7860
gtttctatta tgtataagtt aagctaatta cttattttat aatacaacat gactgttttt   7920
aaagtacaaa ataagtttat ttttgtaaaa gagagaatgt ttaaaagttt tgttacttta   7980
tagaagaaat tttgagtttt tgtttttttt taataaataa ataaacataa ataaattgtt   8040
tgttgaattt attattagta tgtaagtgta aatataataa aacttaatat ctattcaaat   8100
taataaataa acctcgatat acagaccgat aaaacacatg cgtcaatttt acgcatgatt   8160
atctttaacg tacgtcacaa tatgattatc tttctagggt taaataatag tttctaattt   8220
```

```
ttttattatt cagcctgctg tcgtgaatac cgtatatctc aacgctgtct gtgagattgt   8280
cgtattctag cctttttagt ttttcgctca tcgacttgat attgtccgac acattttcgt   8340
cgatttgcgt tttgatcaaa gacttgagca gagacacgtt aatcaactgt tcaaattgat   8400
ccatattaac gatatcaacc cgatgcgtat atggtgcgta aaatatattt tttaaccctc   8460
ttatactttg cactctgcgt taatacgcgt tcgtgtacag acgtaatcat gttttctttt   8520
ttggataaaa ctcctactga gtttgacctc atattagacc ctcacaagtt gcaaaacgtg   8580
gcattttttta ccaatgaaga atttaaagtt attttaaaaa atttcatcac agatttaaag   8640
aagaaccaaa aattaaatta tttcaacagt ttaatcgacc agttaatcaa cgtgtacaca   8700
gacgcgtcgg caaaaaacac gcagcccgac gtgttggcta aaattattaa atcaacttgt   8760
gttatagtca cggatttgcc gtccaacgtg ttcctcaaaa agttgaagac caacaagttt   8820
acggacacta ttaattattt gattttgccc cacttcattt tgtgggatca caattttgtt   8880
atattttaaa caaagcttgg cactggccgt cgttttacaa cgtcgtgact gggaaaaccc   8940
tggcgttacc caacttaatc gccttgcagc acatccccct ttcgccagct ggcgtaatag   9000
cgaagaggcc cgcaccgatc gcccttccca acagttgcgc agcctgaatg gcgaatggcg   9060
cctgatgcgg tattttctcc ttacgcatct gtgcggtatt tcacaccgca tatggtgcac   9120
tctcagtaca atctgctctg atgccgcata gttaagccag ccccgacacc cgccaacacc   9180
cgctgacgcg ccctgacggg cttgtctgct cccggcatcc gcttacagac aagctgtgac   9240
cgtctccggg agctgcatgt gtcagaggtt ttcaccgtca tcaccgaaac gcgcgagacg   9300
aaagggcctc gtgatacgcc tatttttata ggttaatgtc atgataataa tggtttctta   9360
gacgtcaggt ggcacttttc ggggaaatgt gcgcggaacc cctatttgtt tatttttcta   9420
aatacattca aatatgtatc cgctcatgag acaataaccc tgataaatgc ttcaataata   9480
ttgaaaaagg aagagtatga gtattcaaca tttccgtgtc gcccttattc cctttttttgc   9540
ggcattttgc cttcctgttt ttgctcaccc agaaacgctg gtgaaagtaa aagatgctga   9600
agatcagttg ggtgcacgag tgggttacat cgaactggat ctcaacagcg gtaagatcct   9660
tgagagtttt cgccccgaag aacgttttcc aatgatgagc acttttaaag ttctgctatg   9720
tggcgcggta ttatcccgta ttgacgccgg gcaagagcaa ctcggtcgcc gcatacacta   9780
ttctcagaat gacttggttg agtactcacc agtcacagaa aagcatctta cggatggcat   9840
gacagtaaga gaattatgca gtgctgccat aaccatgagt gataacactg cggccaactt   9900
acttctgaca acgatcggag gaccgaagga gctaaccgct tttttgcaca acatggggga   9960
tcatgtaact cgccttgatc gttgggaacc ggagctgaat gaagccatac caaacgacga  10020
gcgtgacacc acgatgcctg tagcaatggc aacaacgttg cgcaaactat taactggcga  10080
actacttact ctagcttccc ggcaacaatt aatagactgg atggaggcgg ataaagttgc  10140
aggaccactt ctgcgctcgg cccttccggc tggctggttt attgctgata aatctggagc  10200
cggtgagcgt gggtctcgcg gtatcattgc agcactgggg ccagatggta agccctcccg  10260
tatcgtagtt atctacacga cggggagtca ggcaactatg gatgaacgaa atagacagat  10320
cgctgagata ggtgcctcac tgattaagca ttggtaactg tcagaccaag tttactcata  10380
tatactttag attgatttaa aacttcattt ttaatttaaa aggatctagg tgaagatcct  10440
ttttgataat ctcatgacca aaatccctta acgtgagttt tcgttccact gagcgtcaga  10500
ccccgtagaa aagatcaaag gatcttcttg agatcctttt tttctgcgcg taatctgctg  10560
```

```
cttgcaaaca aaaaaaccac cgctaccagc ggtggtttgt ttgccggatc aagagctacc  10620
aactcttttt ccgaaggtaa ctggcttcag cagagcgcag ataccaaata ctgtccttct  10680
agtgtagccg tagttaggcc accacttcaa gaactctgta gcaccgccta catacctcgc  10740
tctgctaatc ctgttaccag tggctgctgc cagtggcgat aagtcgtgtc ttaccgggtt  10800
ggactcaaga cgatagttac cggataaggc gcagcggtcg ggctgaacgg ggggttcgtg  10860
cacacagccc agcttggagc gaacgaccta caccgaactg agatacctac agcgtgagca  10920
ttgagaaagc gccacgcttc ccgaagggag aaaggcggac aggtatccgg taagcggcag  10980
ggtcggaaca ggagagcgca cgagggagct tccaggggga aacgcctggt atctttatag  11040
tcctgtcggg tttcgccacc tctgacttga gcgtcgattt ttgtgatgct cgtcaggggg  11100
gcggagccta tggaaaaacg ccagcaacgc ggccttttta cggttcctgg ccttttgctg  11160
gccttttgct cacatgttct ttcctgcgtt atcccctgat tctgtggata accgtattac  11220
cgcctttgag tgagctgata ccgctcgccg cagccgaacg accgagcgca gcgagtcagt  11280
gagcgaggaa gcggaagagc gcccaatacg caaaccgcct ctccccgcgc gttggccgat  11340
tcattaatgc agctggcacg acaggtttcc cgactggaaa gcgggcagtg agcgcaacgc  11400
aattaatgtg agttagctca ctcattaggc accccaggct ttacacttta tgcttccggc  11460
tcgtatgttg tgtggaattg tgagcggata acaatttcac acaggaaaca gctatgacca  11520
tgattacgaa tttcgacctg caggcatgca agcttgcatg cctgcaggtc gacgctcgcg  11580
cgacttggtt tgccattctt tagcgcgcgt cgcgtcacac agcttggcca caatgtggtt  11640
tttgtcaaac gaagattcta tgacgtgttt aaagtttagg tcgagtaaag cgcaaatctt  11700
ttttaaccct agaaagatag tctgcgtaaa attgacgcat gcattcttga aatattgctc  11760
tctctttcta aatagcgcga atccgtcgct gtgcatttag gacatctcag tcgccgcttg  11820
gagctcccgt gaggcgtgct tgtcaatgcg gtaagtgtca ctgattttga actataacga  11880
ccgcgtgagt caaaatgacg catgattatc ttttacgtga cttttaagat ttaactcata  11940
cgataattat attgttattt catgttctac ttacgtgata acttattata tatatatttt  12000
cttgttatag atatcgtgac taatatataa taaaatgggt agttctttag acgatgagca  12060
tatcctctct gctcttctgc aaagcgatga cgagcttgtt ggtgaggatt ctgacagtga  12120
aatatcagat cacgtaagtg aagatgacgt ccagagcgat acagaagaag cgtttataga  12180
tgaggtacat gaagtgcagc caacgtcaag cggtagtgaa atattagacg aacaaaatgt  12240
tattgaacaa ccaggttctt cattggcttc taacagaatc ttgaccttgc cacagaggac  12300
tattagaggt aagaataaac attgttggtc aacttcaaag tccacgaggc gtagccgagt  12360
ctctgcactg aacattgtca gatcggcccg gcggagtgga cacgctagac caaatgtgtt  12420
ctgtgatgac ctgcagtagg aagacgaata ggtggcctat ggcattattg tacggaatga  12480
taaacattgc ctgcataaat tcttttatta tatacagcca taatgtcagt agcaagggag  12540
aaaaggtcca aagtcgcaaa aaatttatga gaaacccttta catgagcctg acgtcatcgt  12600
ttatgcgtaa gcgtttagaa gctcctactt tgaagagata tttgcgcgat aatatctcta  12660
atattttgcc aaatgaagtg cctggtacat cagatgacag tactgaagag ccagtaatga  12720
aaaaacgtac ttactgtact tactgcccct ctaaaataag gcgaaaggca aatgcatcgt  12780
gcaaaaaatg caaaaaagtt atttgtcgag agcataatat tgatatgtgc caaagttgtt  12840
tctgactgac taataagtat aatttgtttc tattatgtat aagttaagct aattacttat  12900
tttataatac aacatgactg tttttaaagt acaaaataag tttatttttg taaaagagag  12960
```

aatgtttaaa agttttgtta ctttatagaa gaaattttga gtttttgttt ttttttaata 13020
aataaataaa cataaataaa ttgtttgttg aatttattat tagtatgtaa gtgtaaatat 13080
aataaaactt aatatctatt caaattaata aataaacctc gatatacaga ccgataaaac 13140
acatgcgtca attttacgca tgattatctt taacgtacgt cacaatatga ttatctttct 13200
agggttaaaa tgaatgtaag cactttatta acgaaatctt tgggaatatt tcgctcatca 13260
gcattttatt tgagcaggag tccgagatgc cc 13292

<210> SEQ ID NO 53
<211> LENGTH: 14713
<212> TYPE: DNA
<213> ORGANISM: artificial
<220> FEATURE:
<223> OTHER INFORMATION: Sequence of pLA3014-Cctra-intron-Ubiquitin-reaperKR construct.

<400> SEQUENCE: 53
cgcgccggac gcggcaagtc tgcgagctta tatttacgtg gatctccggt gtgtccatga 60
ttcggcatca tatcataaac gacgaattcc aataaaaact ttgcttgttg ataacacctg 120
atgttcagag atgcccgata aaatcacagc tgttctggtt cacagtcacc agaaataaaa 180
aatattggaa ttgagatgta cacaattaac gatatttata aatatcttcc gatagtctat 240
cgtccggtta atcaaaataa agtgcgacga attaacatat tttcaaaatt aagacgcttt 300
gatagatgta tttgtataga gatagaaatt aaggttaaaa taacataaat gccaaagttt 360
agagcactat tcaataattc tcttgatttc aaattgaaat aatacacaat ataacatttt 420
ctaacactac aaagtcacga tattcttcca ccaaccgata gtatcgcaca cttgccattc 480
gcctcatcac gcacacgccc gcttcacaat tcaaacgaac ggcattttat tttcacagga 540
tcccgggagt cgtgaatgtt ttacccaata tcgactttca ttgttaactg accaaaattg 600
taatctgttc tgttagttgt cgagtgcctg tgccgcgatc gctatgggca tatgttgcca 660
aactctaaac caaatactca ttctgatgtt ttaaatgatt tgccctccca tatgtccttc 720
cgagtgagag acacaaaaaa ttccaacaca ctattgcaat gaaaataaat ttcctttatt 780
agccagaagt cagatgctca aggggcttca tgatgtcccc ataatttttg gcagagggaa 840
aaagatctca gtggtatttg tgagccaggg cattggccac accagccacc accttctgat 900
aggcagcctg cacctgagga gtgaattctt tgccaaaatg atgagacagc acaacaacca 960
gcacgttgcc caggagctgt aggaaagaga agaaggcatg aacatggtta gcagaggggc 1020
ccggtttgga ctcagagtat tttatcctca tctcaaacag tgtatatcat tgtaaccata 1080
aagagaaagg caggatgatg accagggtgt agttgtttct accaataaga atatttccac 1140
gccagccaga atttatatgc agaaatattc taccttatca tttaattata acaattgttc 1200
tctaaaactg tgctgaagta caatataata taccctgatt gccttgaaaa aaaagtgatt 1260
agagaaagta cttacaatct gacaaataaa caaaagtgaa tttaaaaatt cgttacaaat 1320
gcaagctaaa gtttaacgaa aaagttacag aaaatgaaaa gaaaataaga ggagacaatg 1380
gttgtcaaca gagtagaaag tgaaagaaac aaaattatca tgagggtcca tggtgataca 1440
agggacatct tcccattcta aacaacaccc tgaaaacttt gccccctcca tataacatga 1500
attttacaat agcgaaaaag aaagaacaat caagggtccc caaactcacc ctgaagttct 1560
cagctctaga cgcgtttcac tacccaccgt actcgtcaat tccaagggca tcggtaaaca 1620
tctgctcaaa ctcgaagtcg gccatatcca gagcgccgta gggggcggag tcgtgggggg 1680

```
taaatcccgg acccggggaa tccccgtccc ccaacatgtc cagatcgaaa tcgtctagcg   1740
cgtcggcatg cgccatcgcc acgtcctcgc cgtctaagtg gagctcgtcc cccaggctga   1800
catcggtcgg gggggccgtc gacagtctgc gcgtgtgtcc cgcggggaga aaggacaggc   1860
gcggagccgc cagccccgcc tcttcggggg cgtcgtcgtc cgggagatcg agcaggccct   1920
cgatggtaga cccgtaattg tttttcgtac gcgcgcggct gtacgcggac ccactttcac   1980
atttaagttg tttttctaat ccgcatatga tcaattcaag gccgaataag aaggctggct   2040
ctgcaccttg gtgatcaaat aattcgatag cttgtcgtaa taatggcggc atactatcag   2100
tagtaggtgt ttccctttct tctttagcga cttgatgctc ttgatcttcc aatacgcaac   2160
ctaaagtaaa atgccccaca gcgctgagtg catataatgc attctctagt gaaaaacctt   2220
gttggcataa aaaggctaat tgattttcga gagtttcata ctgtttttct gtaggccgtg   2280
tacctaaatg tacttttgct ccatcgcgat gacttagtaa agcacatcta aaacttttag   2340
cgttattacg taaaaaatct tgccagcttt ccccttctaa agggcaaaag tgagtatggt   2400
gcctatctaa catctcaatg gctaaggcgt cgagcaaagc ccgcttattt tttacatgcc   2460
aatacaatgt aggctgctct acacctagct tctgggcgag tttacgggtt gttaaacctt   2520
cgattccgac ctcattaagc agctctaatg cgctgttaat cactttactt ttatctaatc   2580
tcaattccat ggtggcaacc tgcaaggcga atgaataaac aagattgtgg cgaacagtgt   2640
aatgcgaaga acccacctct gctccaattc ccaattccct attcagctcg agcggggatc   2700
cccgggtacc gagctcgaat tcggggccgc ggaggctgga tcggtcccgg tgtcttctat   2760
ggaggtcaaa acagcgtgga tggcgtctcc aggcgatctg acggttcact aaacgagctc   2820
tgcttatata ggcctcccac cgtacacgcc tacctcgacc cgggtaccga gctcgacttt   2880
cacttttctc tatcactgat agggagtggt aaactcgact ttcacttttc tctatcactg   2940
atagggagtg gtaaactcga ctttcacttt tctctatcac tgatagggag tggtaaactc   3000
gactttcact tttctctatc actgataggg agtggtaaac tcgactttca cttttctcta   3060
tcactgatag ggagtggtaa actcgacttt cacttttctc tatcactgat agggagtggt   3120
aaactcgact ttcacttttc tctatcactg atagggagtg gtaaactcga aatgtcgact   3180
atgcggaccg agcgccggag tataaataga ggcgcttcgt ctacggagcg acaattcaat   3240
tcaaacaagc aaagtgaaca cgtcgctaag cgaaagctaa gcaaataaac aagcgcagct   3300
gaacaagcta aacaatctgc gctagccacc atggttgtta ttaaacgtag atttggtaat   3360
tttaaaagca tatttttttc tttgaaattc ataagttatc aattatcgat ggaaatgtat   3420
tctatggaga acgttttacc cgatgaatgg gtgcaaaaat tattttacct tcaaatctac   3480
aatcaacaca cgctaacttt tgtgacttga tcaactctca cctggaaaag caaccaacta   3540
caatcaacat tctatgggat aatcgacaag tgagtaaaat tatagccgga cctcttagta   3600
cagtgtattt aaaaggggaa taatattcta tcaataggaa taaaaataag gtcagcagcc   3660
atgacttttc catcattttg aatatacctt atttgtttcg ggattaattg ggggtcggaa   3720
atcctcttga attcagaaac gggaaccgga ggaaggtgcc ggtctttcag aaagctgtga   3780
aaaataccaa catttctgct gccaagagct caataagaag tttcaaaaat tgtcttggat   3840
gttgcagctg tggctgctaa gtaataagac atctattagt atctagattt gttagaccat   3900
ttaacatagt gttttaaacg atggggttaa tagatgaggg ttaagaagct agttatatta   3960
ctgttgctgt aacgccttca attgtcggtt acagagcaaa cattattgaa tgttaatgta   4020
```

-continued

```
aagagtttat ttgttttcta gtaaacatat agcgattggt tagtaatcac taatagaaat   4080
ttttcataag tatcaaaaaa gtaaacctct ttttcagtct atgtaataag taaaccaagg   4140
aaagggaaaa tatctacaat caacaagcca ttgttgcagc aacaaagcaa ctgaaactac   4200
aatcaacatt caataaactt gggtaatttg gaatttaatt ctctgggaca cctgtggatt   4260
acaacaatca actcgaaact tattatacaa tgtaaataaa aattgatatg catacatgaa   4320
gatcaagtga aattccattt agaatcaatt tttttcgaat attaagtttc ttgctttaat   4380
ttatctgaaa gtaaatagac attccaaatt caagttaaca aattaataat gaattgacta   4440
gtgattttta agagaaaaag ataagattta aaaaaggaaa gcctttcttg ataaattttt   4500
gaaccacttt atgccgtttc aatcataaaa acttttaaga acacatgact ggtaaaatta   4560
atttaaaaca aatttaaatt ttcaacgtaa cattcaacaa aaatggtgaa aactatcacg   4620
gaaattgtta atattaatat gtcccaaaaa tagcctttgt atgtatatga tactaatcca   4680
tacatctatg gtatctatag gtgaaggctc aaagcctctg atgcagatct ttgtgaagac   4740
tttgaccgga aagaccatca ccctcgaggt agagccatcg gacaccattg agaatgtaaa   4800
ggccaagatt caggataagg agggaatccc cccagatcag cagcgtctga tcttcgctgg   4860
caagcaactg gaagacggac gcaccctgtc cgattacaac atccagaagg agtccaccct   4920
tcacttggtc cttcgtctcc gtggtggcgc cgtggccttc tacatcccgg atcaggccac   4980
cctgctgcgc gaggccgagc agcgcgagca gcagatcctg cgcctgcgcg agagccagtg   5040
gcgcttcctg gccaccgtgg tgctggagac cctgcgccag tacaccagct gccacccgcg   5100
caccggccgc cgcagcggcc gttaccgccg tccgagccag taacaccggt gatcataatc   5160
agccatacca catttgtaga ggttttactt gctttaaaaa acctcccaca cctccccctg   5220
aacctgaaac ataaaatgaa tgcaattgtt gttgttaact tgtttattgc agcttataat   5280
ggttacaaat aaagcaatag catcacaaat ttcacaaata aagcattttt ttcactgcat   5340
tctagttgtg gtttgtccaa actcatcaat gtatcttaac gcgagtttaa acgcgtccgc   5400
atacgtccgc tcacgttaag ttccgcagag agaagttgtt gaaaacataa acagaatcac   5460
ttgttgcact ctttgagaaa actggggcta ttgcggaaaa aaccaactaa aaatattgca   5520
ggttaggggt actacgctcg attggcgtac ggccaccact tttgcgactt cactgttaac   5580
cgctaccttc atagagactt ttacccgata aatgttatgt agtttgactt tctctgttaa   5640
tcacaagaaa aaatattgtg gaaattaaaa ttatctcaaa ctcaataagg aaataataat   5700
atatacacct atgttttata gaagtcaaca gtaaataagt tatttggaaa accattgtag   5760
ccgtttaaat aaatctcctt gagtgtgttt taaataacgg tcattaagta tattacttgg   5820
ccctctgaat ttcttgaatt acaccatttt ttgaaataaa tcaatccaaa agactacttt   5880
ttggtggcaa atgaactgca taaaaagtaa caaaagaaat atgtttttga aataacagta   5940
tagctgaagt gtattaaaaa ataccgtcat atgagcgacc cgctgttacc gcttcgctgc   6000
gaatgacaaa acgggctgag caagaaaatg gcgtagaagg cgacgaaaat tcgtttcact   6060
cgtgaagaaa acctcgataa ctgaggaata cagctgggat ttaaagagca tattcgaact   6120
acaagcagag atgtttcctg gtggaaacgg aaacgccgat ttgggctaca acaagcatgc   6180
ccacgtccat ggacttggac aacatggcca tgggcacaac cataatcaca atcagttcct   6240
gcgcagcccc caccaccccc cacacatttt tcactgccct ccgggggcgg tcagggcatg   6300
gtgacgccca tggtagccgc cggcctgccg ctcgccatgc agggtggcgt tggcatcgat   6360
tggcgcagct cgcccagcaa tggattaatt aactcgcgtt aagatacatt gatgagtttg   6420
```

-continued

```
gacaaaccac aactagaatg cagtgaaaaa aatgctttat ttgtgaaatt tgtgatgcta   6480
ttgctttatt tgtaaccatt ataagctgca ataaacaagt taacaacaac aattgcattc   6540
attttatgtt tcaggttcag ggggaggtgt gggaggtttt ttaaagcaag taaaacctct   6600
acaaatgtgg tatggctgat tatgatcagt tatctagatc cggtggatct tacgggtcct   6660
ccaccttccg ctttttcttg ggtcgagatc tcaggaacag gtggtggcgg ccctcggtgc   6720
gctcgtactg ctccacgatg gtgtagtcct cgttgtggga ggtgatgtcc agcttggcgt   6780
ccacgtagta gtagccgggc agctgcacgg gcttcttggc catgtagatg gacttgaact   6840
ccaccaggta gtggccgccg tccttcagct tcagggcctt gtgggtctcg cccttcagca   6900
cgccgtcgcg ggggtacagg cgctcggtgg aggcctccca gcccatggtc ttcttctgca   6960
tcacggggcc gtcggagggg aagttcacgc cgatgaactt caccttgtag atgaagcagc   7020
cgtcctgcag ggaggagtcc tgggtcacgg tcgccacgcc gccgtcctcg aagttcatca   7080
cgcgctccca cttgaagccc tcggggaagg acagcttctt gtagtcgggg atgtcggcgg   7140
ggtgcttcac gtacaccttg gagccgtact ggaactgggg ggacaggatg tcccaggcga   7200
agggcagggg gccgcccttg gtcaccttca gcttcacggt gttgtggccc tcgtaggggc   7260
ggccctcgcc ctcgccctcg atctcgaact cgtggccgtt cacggtgccc tccatgcgca   7320
ccttgaagcg catgaactcg gtgatgacgt tctcggagga ggccatggtg gcgaccggtt   7380
tgcgcttctt cttgggtggg gtgggatccc cgatctgcat tttggattat tctgcgggtc   7440
aaaatagaga tgtggaaaat tagtacgaaa tcaaatgagt ttcgttgaaa ttacaaaact   7500
attgaaacta acttcctggc tggggaataa aaatgggaaa cttatttatc gacgccaact   7560
ttgttgagaa acccctatta accctctacg aatattggaa caaaggaaag cgaagaaaca   7620
ggaacaaagg tagttgagaa acctgttccg ttgctcgtca tcgttttcat aatgcgagtg   7680
tgtgcatgta tatatacaca gctgaaacgc atgcatacac attattttgt gtgtatatgg   7740
tgacgtcaca actactaagc aataagaaat tttccagacg tggctttcgt ttcaagcaac   7800
ctactctatt tcagctaaaa ataagtggat ttcgttggta aaatacttca attaagcaaa   7860
gaactaacta actaataaca tgcacacaaa tgctcgagtg cgttcgtgat ttctcgaatt   7920
ttcaaatgcg tcactgcgaa tttcacaatt tgccaataaa tcttggcgaa aatcaacacg   7980
caagttttat ttatagattt gtttgcgttt tgatgccaat tgattgggaa aacaagatgc   8040
gtggctgcca atttcttatt ttgtaattac gtagagcgtt gaataaaaaa aaaatggccg   8100
aacaaagacc ttgaaatgca gtttttcttg aaattactca acgtcttgtt gctcttatta   8160
ctaattggta acagcgagtt aaaaacttac gtttcttgtg actttcgaga atgttctttt   8220
aattgtactt taatcaccaa caattaagta taaatttttc gctgattgcg ctttactttc   8280
tgcttgtact tgctgctgca aatgtcaatt ggttttgaag gcgaccgttc gcgaacgctg   8340
tttatatacc ttcggtgtcc gttgaaaatc actaaaaaat accgtagtgt tcgtaacact   8400
ttagtacaga gaaaaaaaat tgtgccgaaa tgtttttgat acgtacgaat accttgtatt   8460
aaaatttttt atgatttctg tgtatcactt tttttttgtg tttttcgttt aaactcacca   8520
cagtacaaaa caataaaata tttttaagac aatttcaaat tgagaccttt ctcgtactga   8580
cttgaccggc tgaatgagga tttctaccta gacgacctac ttcttaccat gacattgaat   8640
gcaatgccac ctttgatcta aacttacaaa agtccaaggc ttgttaggat tggtgtttat   8700
ttagtttgct tttgaaatag cactgtcttc tctaccggct ataattttga aactcgcagc   8760
```

-continued

```
ttgactggaa atttaaaaag taattctgtg taggtaaagg gtgttttaaa agtgtgatgt   8820
gttgagcgtt gcggcaacga ctgctattta tgtatatatt ttcaaaactt attgtttttg   8880
aagtgtttta aatggagcta tctggcaacg ctgcgcataa tcttacacaa gcttttctta   8940
atccattttt aagtgaaatt tgtttttact ctttcggcaa ataattgtta aatcgcttta   9000
agtgggctta catctggata agtaatgaaa acctgcatat tataatatta aaacatataa   9060
tccactgtgc tttccccgtg tgtggccata tacctaaaaa agtttatttt cgcagagccc   9120
cgcacggtca cactacggtt cggcgatttt cgattttgga cagtactgat tgcaagcgca   9180
ccgaaagcaa aatggagctg gagattttga acgcgaagaa cagcaagccg tacggcaagg   9240
tgaaggtgcc ctccggcgcc acgcccatcg gcgatctgcg cgccctaatt cacaagaccc   9300
tgaagcagac cccacacgcg aatcgccagt cgcttcgtct ggaactgaag ggcaaaagcc   9360
tgaaagatac ggacacattg gaatctctgt cgctgcgttc cggcgacaag atcggggtac   9420
catgcggccg ctcatttaaa tctggccggc ctggccgatc tgacaatgtt cagtgcagag   9480
actcggctac gcctcgtgga ctttgaagtt gaccaacaat gtttattctt acctctaata   9540
gtcctctgtg gcaaggtcaa gattctgtta gaagccaatg aagaacctgg ttgttcaata   9600
acattttgtt cgtctaatat ttcactaccg cttgacgttg gctgcacttc atgtacctca   9660
tctataaacg cttcttctgt atcgctctgg acgtcatctt cacttacgtg atctgatatt   9720
tcactgtcag aatcctcacc aacaagctcg tcatcgcttt gcagaagagc agagaggata   9780
tgctcatcgt ctaaagaact acccatttta ttatatatta gtcacgatat ctataacaag   9840
aaaatatata tataataagt tatcacgtaa gtagaacatg aaataacaat ataattatcg   9900
tatgagttaa atcttaaaag tcacgtaaaa gataatcatg cgtcattttg actcacgcgg   9960
tcgttatagt tcaaaatcag tgacacttac cgcattgaca agcacgcctc acgggagctc  10020
caagcggcga ctgagatgtc ctaaatgcac agcgacggat tcgcgctatt tagaaagaga  10080
gagcaatatt tcaagaatgc atgcgtcaat tttacgcaga ctatctttct agggttaaaa  10140
aagatttgcg ctttactcga cctaaacttt aaacacgtca tagaatcttc gtttgacaaa  10200
aaccacattg tggccaagct gtgtgacgcg acgcgcgcta aagaatggca aaccaagtcg  10260
cgcgagcgtc gacctgcagg catgcaagct tgcatgcctg caggtcgaaa ttcgtaatca  10320
tggtcatagc tgtttcctgt gtgaaattgt tatccgctca caattccaca caacatacga  10380
gccggaagca taaagtgtaa agcctggggt gcctaatgag tgagctaact cacattaatt  10440
gcgttgcgct cactgcccgc tttccagtcg ggaaacctgt cgtgccagct gcattaatga  10500
atcggccaac gcgcggggag aggcggtttg cgtattgggc gctcttccgc ttcctcgctc  10560
actgactcgc tgcgctcggt cgttcggctg cggcgagcgg tatcagctca ctcaaaggcg  10620
gtaatacggt tatccacaga atcaggggat aacgcaggaa agaacatgtg agcaaaaggc  10680
cagcaaaagg ccaggaaccg taaaaaggcc gcgttgctgg cgtttttcca taggctccgc  10740
ccccctgacg agcatcacaa aaatcgacgc tcaagtcaga ggtggcgaaa cccgacagga  10800
ctataaagat accaggcgtt tccccctgga agctccctcg tgcgctctcc tgttccgacc  10860
ctgccgctta ccggatacct gtccgccttt ctcccttcgg gaagcgtggc gctttctcaa  10920
tgctcacgct gtaggtatct cagttcggtg taggtcgttc gctccaagct gggctgtgtg  10980
cacgaacccc ccgttcagcc cgaccgctgc gccttatccg gtaactatcg tcttgagtcc  11040
aacccggtaa gacacgactt atcgccactg gcagcagcca ctggtaacag gattagcaga  11100
gcgaggtatg taggcggtgc tacagagttc ttgaagtggt ggcctaacta cggctacact  11160
```

-continued

```
agaaggacag tatttggtat ctgcgctctg ctgaagccag ttaccttcgg aaaaagagtt  11220
ggtagctctt gatccggcaa acaaaccacc gctggtagcg gtggtttttt tgtttgcaag  11280
cagcagatta cgcgcagaaa aaaaggatct caagaagatc ctttgatctt ttctacgggg  11340
tctgacgctc agtggaacga aaactcacgt taagggattt tggtcatgag attatcaaaa  11400
aggatcttca cctagatcct tttaaattaa aaatgaagtt ttaaatcaat ctaaagtata  11460
tatgagtaaa cttggtctga cagttaccaa tgcttaatca gtgaggcacc tatctcagcg  11520
atctgtctat ttcgttcatc catagttgcc tgactccccg tcgtgtagat aactacgata  11580
cgggagggct taccatctgg ccccagtgct gcaatgatac cgcgagaccc acgctcaccg  11640
gctccagatt tatcagcaat aaaccagcca gccggaaggg ccgagcgcag aagtggtcct  11700
gcaactttat ccgcctccat ccagtctatt aattgttgcc gggaagctag agtaagtagt  11760
tcgccagtta atagtttgcg caacgttgtt gccattgcta caggcatcgt ggtgtcacgc  11820
tcgtcgtttg gtatggcttc attcagctcc ggttcccaac gatcaaggcg agttacatga  11880
tcccccatgt tgtgcaaaaa agcggttagc tccttcggtc ctccgatcgt tgtcagaagt  11940
aagttggccg cagtgttatc actcatggtt atggcagcac tgcataattc tcttactgtc  12000
atgccatccg taagatgctt ttctgtgact ggtgagtact caaccaagtc attctgagaa  12060
tagtgtatgc ggcgaccgag ttgctcttgc ccggcgtcaa tacgggataa taccgcgcca  12120
catagcagaa ctttaaaagt gctcatcatt ggaaaacgtt cttcggggcg aaaactctca  12180
aggatcttac cgctgttgag atccagttcg atgtaaccca ctcgtgcacc caactgatct  12240
tcagcatctt ttactttcac cagcgtttct gggtgagcaa aaacaggaag gcaaaatgcc  12300
gcaaaaaagg gaataagggc gacacggaaa tgttgaatac tcatactctt cctttttcaa  12360
tattattgaa gcatttatca gggttattgt ctcatgagcg gatacatatt tgaatgtatt  12420
tagaaaaata aacaaatagg ggttccgcgc acatttcccc gaaaagtgcc acctgacgtc  12480
taagaaacca ttattatcat gacattaacc tataaaaata ggcgtatcac gaggcccttt  12540
cgtctcgcgc gtttcggtga tgacggtgaa aacctctgac acatgcagct cccggagacg  12600
gtcacagctt gtctgtaagc ggatgccggg agcagacaag cccgtcaggg cgcgtcagcg  12660
ggtgttggcg ggtgtcgggg ctggcttaac tatgcggcat cagagcagat tgtactgaga  12720
gtgcaccata tatgcggtgt gaaataccgc acagatgcgt aaggagaaaa taccgcatca  12780
ggcgccattc gccattcagg ctgcgcaact gttgggaagg gcgatcggtg cgggcctctt  12840
cgctattacg ccagctggcg aaagggggat gtgctgcaag gcgattaagt tgggtaacgc  12900
cagggttttc ccagtcacga cgttgtaaaa cgacggccag tgccaagctt tgtttaaaat  12960
ataacaaaat tgtgatccca caaaatgaag tggggcaaaa tcaaataatt aatagtgtcc  13020
gtaaacttgt tggtcttcaa ctttttgagg aacacgttgg acggcaaatc cgtgactata  13080
acacaagttg atttaataat tttagccaac acgtcgggct gcgtgttttt tgccgacgcg  13140
tctgtgtaca cgttgattaa ctggtcgatt aaactgttga aataatttaa tttttggttc  13200
ttctttaaat ctgtgatgaa attttttaaa ataactttaa attcttcatt ggtaaaaaat  13260
gccacgtttt gcaacttgtg agggtctaat atgaggtcaa actcagtagg agttttatcc  13320
aaaaaagaaa acatgattac gtctgtacac gaacgcgtat taacgcagag tgcaaagtat  13380
aagagggtta aaaaatatat tttacgcacc atatacgcat cgggttgata tcgttaatat  13440
ggatcaattt gaacagttga ttaacgtgtc tctgctcaag tctttgatca aaacgcaaat  13500
```

```
cgacgaaaat gtgtcggaca atatcaagtc gatgagcgaa aaactaaaaa ggctagaata  13560
cgacaatctc acagacagcg ttgagatata cggtattcac gacagcaggc tgaataataa  13620
aaaaattaga aactattatt taaccctaga aagataatca tattgtgacg tacgttaaag  13680
ataatcatgc gtaaaattga cgcatgtgtt ttatcggtct gtatatcgag gtttatttat  13740
taatttgaat agatattaag ttttattata tttacactta catactaata ataaattcaa  13800
caaacaattt atttatgttt atttatttat taaaaaaaaa caaaaactca aaatttcttc  13860
tataaagtaa caaaactttt aaacattctc tcttttacaa aaataaactt attttgtact  13920
ttaaaaacag tcatgttgta ttataaaata agtaattagc ttaacttata cataatagaa  13980
acaaattata cttattagtc agtcagaaac aactttggca catatcaata ttatgctctc  14040
gacaaataac ttttttgcat tttttgcacg atgcatttgc ctttcgcctt attttagagg  14100
ggcagtaagt acagtaagta cgttttttca ttactggctc ttcagtactg tcatctgatg  14160
taccaggcac ttcatttggc aaaatattag agatattatc gcgcaaatat ctcttcaaag  14220
taggagcttc taaacgctta cgcataaacg atgacgtcag gctcatgtaa aggtttctca  14280
taaatttttt gcgactttgg accttttctc ccttgctact gacattatgg ctgtatataa  14340
taaaagaatt tatgcaggca atgtttatca ttccgtacaa taatgccata ggccacctat  14400
tcgtcttcct actgcaggtc atcacagaac acatttggtc tagcgtgtcc actccgcctt  14460
tagtttgatt ataatacata accatttgcg gtttaccggt actttcgttg atagaagcat  14520
cctcatcaca agatgataat aagtatacca tcttagctgg cttcggttta tatgagacga  14580
gagtaagggg tccgtcaaaa caaaacatcg atgttcccac tggcctggag cgactgtttt  14640
tcagtacttc cggtatctcg cgtttgtttg atcgcacggt tcccacaatg gttgcggcca  14700
gcccgggcta tgg                                                     14713
```

<210> SEQ ID NO 54
<211> LENGTH: 15848
<212> TYPE: DNA
<213> ORGANISM: artificial
<220> FEATURE:
<223> OTHER INFORMATION: Sequence of pLA3166-Cctra intron-Ubiquitin-
reaperKR construct.

<400> SEQUENCE: 54

```
gggcggccgt ttttcttgaa atattgctct ctctttctaa atagcgcgaa tccgtcgctg     60
tgcatttagg acatctcagt cgccgcttgg agctcccaaa cgcgccagtg gtagtacaca    120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaaagttt tcgcaatgcc tttatttttt gttgcaaatc    360
tctctttatt ctgcggtatt cttcattatt gcggggatgg ggaaagtgtt tatatagaag    420
caacttacga ttgaacccaa atgcacctga caagcaaggt caaagggcca gatttttaaa    480
tatattattt agtcttagga ctctctattt gcaattaaat tactttgcta cctgagggtt    540
aaatcttccc cattgataat aataattcca ctatatgttc aattgggttt caccgcgctt    600
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
```

-continued

```
caggtttaac caggggatgc ttaattgtgt tctcaacttc aaaggcagaa atgtttactc    840
ttgaccatgg gtttaggtat aatgttatca agctcctcga gttaacgtta cgttaacgtt    900
aacgttcgag gtcgactcta gaactaccca ccgtactcgt caattccaag ggcatcggta    960
aacatctgct caaactcgaa gtcggccata tccagagcgc cgtagggggc ggagtcgtgg   1020
ggggtaaatc ccggacccgg ggaatccccg tcccccaaca tgtccagatc gaaatcgtct   1080
agcgcgtcgg catgcgccat cgccacgtcc tcgccgtcta agtggagctc gtcccccagg   1140
ctgacatcgg tcgggggggc cgtcgacagt ctgcgcgtgt gtcccgcggg gagaaaggac   1200
aggcgcggag ccgccagccc cgcctcttcg gggcgtcgt cgtccgggag atcgagcagg   1260
ccctcgatgg tagacccgta attgtttttc gtacgcgcgc ggctgtacgc ggggcccgag   1320
cccgactcgc atttcagttg cttttccaat ccgcagataa tcagctccaa gccgaacagg   1380
aatgccggct cggctccttg atgatcgaac agctcgattg cctgacgcag cagtgggggc   1440
atcgaatcgg ttgttggggt ctcgcgctcc tcttttgcga cttgatgctc ttggtcctcc   1500
agcacgcagc ccagggtaaa gtgaccgacg gcgctcagag cgtagagagc attttccagg   1560
ctgaagcctt gctggcacag gaacgcgagc tggttctcca gtgtctcgta ttgcttttcg   1620
gtcgggcgcg tgccgagatg gactttggca ccgtctcggt gggacagcag agcgcagcgg   1680
aacgacttgg cgttattgcg gaggaagtcc tggaaatggg atagatattg gtgttattgt   1740
tcatgtggca tataaaggac aagcaacaaa aaacgaacat aacatgagag atggttctga   1800
atcagaactt ctgaatatta tcctcccaaa agggttaaag tttttattaa gcatattacg   1860
ttttatacca cttccttatg taaaattttc ttcgtagttt aatatcatgt gaaatcatat   1920
ataatttcta tcgaacgttt gttcaaattg aatgatgtca tttttgaat aattggttat   1980
aattttataa catctcccga cttcgacatg tggttggtac taatgattgc gaaatcgccc   2040
tccgagaatg agaacaaccg aggtccaccg tctggtcgag attaaaacac ttgaggagtg   2100
ctttggtgac tcgatcaata ggtacagggc tcgttgccaa caatctggcc agctggacat   2160
ccgggacctc gttcccccct ggggtatcaa aatttttgta gtgtaaatag tagtacactc   2220
ttaaaaataa tgaaaattac tgcggacgta attcacatta tgattgaatg acactatcat   2280
tgacatttcc cgaatcagac accatcgtat ttaaaatgtg acacaaattc acctcatttg   2340
gctcgcttct tttatgtgca tccaaaagac gtaaaatcgc atgatttttt cggagtgtgt   2400
agtaagattg tcaaatttta attttaaata accagagccc ataaagcaaa gcaacactag   2460
gaaaaaaccc acaaactcaa cctgtccaaa aaaaaatata acaatcaaag ttgagggaat   2520
cggggtcaaa cgtcatgtaa aaatattttt tgtaaaaacc aaaccaggaa taaatatgaa   2580
tttaatcgga aaaaattgca aaatcgcata atttaatcct ccaactgtac tttatccagc   2640
ctgttgcaga aatgatgttt aaaggttcta atctgtaatt gttattagcc ttcaatactg   2700
atgtagtatt tatttcttat tgaaacattg agagctttat tttccaaagt tgtcattttc   2760
tcattcgtat atcgtaatat gtatattcgt aaatggcaag cacaatgata cttagggtag   2820
tcaaggatat ttcaattacg aaaagatcct gaaacgaccg ggaatcgaac ccttcagcat   2880
ggttttgctt tgtagctgct gaatctaacc actaggctga tgaagatccc attttagggt   2940
tgcaagttct caaagagcaa gaatgccaaa atagtgtcaa aagaagccct atttgacgat   3000
ataccttta gtctctacgt taatttgcta tgataattta tcatcaatta attggcaaag   3060
cctgatgcac gaaaagatct tcttctaaaa tttcagttgt tcttttcaac acattatgta   3120
atcataaaat ttaattaata aacctttttt ttttgtaact atccacagtt gatcaggcat   3180
```

aattttcttg gaaagtaaag tccatattta ggttgatgtt gaataaaaaa actttcaatt 3240
cactcttctg tttcacttca gaacttacgt aatacgacat tatgcatggt gcacacggaa 3300
caggataaga cgttcacaag ggatcaacat cacatcggat cgtaatcact ggatctggaa 3360
cacatatgac gccacaagac agcacatttt acacgatcac cagacgtgaa caaggaactg 3420
gatccacaag acgtcacagg aagacggcac atttccaacg gcttcgatgg aacttttctc 3480
gagtcttttt ccaccaatca taaacaccga cctgccagga ctcgccttcc aacgggcaaa 3540
aatgcgtgtg gtggcggtcg agcatctcga tggccagggc atccagcagc gcccgcttat 3600
tcttcacgtg ccagtagagg gtgggctgct ccacgcccag cttctgcgcc aacttgcggg 3660
tcgtcagtcc ctcaatgcca acttcgttca acagctccaa cgcggagttg atgactttgg 3720
acttatccag gcggctgccc atggtggttt ctaaaggtgt tataaatcaa attagttttg 3780
tttttcttg aaaactttgc gtttcctttg atcaacttac cgccagggta ccgcagattg 3840
tttagcttgt tcagctgcgc ttgtttattt gcttagcttt cgcttagcga cgtgttcact 3900
ttgcttgttt gaattgaatt gtcgctccgt agacgaagcg cctctattta tactccggcg 3960
ctcgttttcg agtttaccac tccctatcag tgatagagaa aagtgaaagt cgagtttacc 4020
actccctatc agtgatagag aaaagtgaaa gtcgagttta ccactcccta tcagtgatag 4080
agaaaagtga aagtcgagtt taccactccc tatcagtgat agagaaaagt gaaagtcgag 4140
tttaccactc cctatcagtg atagagaaaa gtgaaagtcg agtttaccac tccctatcag 4200
tgatagagaa aagtgaaagt cgagtttacc actccctatc agtgatagag aaaagtgaaa 4260
gtcgaaacct ggcgcgcccc ggccatcgag aaagagagag agaagagaag agagagaaca 4320
ttcgagaaag agagagagaa gagaagagag agaacatact ccctatcagt gatagagaag 4380
tccctatcag tgatagagat gtccctatca gtgatagaga gttccctatc agtgatagag 4440
acgtccctat cagtgataga gaagtcccta tcagtgatag agagatccct atcagtgata 4500
gagatttccc tatcagtgat agagaggtcc ctatcagtga tagagacttc cctatcagtg 4560
atagagaaat ccctatcagt gatagagaca tccctatcag tgatagagaa ctccctatca 4620
gtgatagaga cctccctatc agtgatagag atcgatgcgg ccgcatggta cccattgctt 4680
gtcatttatt aatttggatg atgtcatttg tttttaaaat tgaactggct ttacgagtag 4740
aattctacgc gtaaaacaca atcaagtatg agtcataatc tgatgtcatg ttttgtacac 4800
ggctcataac cgaactggct ttacgagtag aattctactt gtaatgcacg atcagtggat 4860
gatgtcattt gtttttcaaa tcgagatgat gtcatgtttt gcacacggct cataaactcg 4920
ctttacgagt agaattctac gtgtaacgca cgatcgattg atgagtcatt tgttttgcaa 4980
tatgatatca tacaatatga ctcatttgtt tttcaaaacc gaacttgatt tacgggtaga 5040
attctacttg taaagcacaa tcaaaaagat gatgtcattt gtttttcaaa actgaactcg 5100
ctttacgagt agaattctac gtgtaaaaca caatcaagaa atgatgtcat ttgttataaa 5160
aataaaagct gatgtcatgt tttgcacatg gctcataact aaactcgctt tacgggtaga 5220
attctacgcg taaaacatga ttgataatta aataattcat ttgcaagcta tacgttaaat 5280
caaacggacg ctcgaggttg cacaacacta ttatcgattt gcagttcggg acataaatgt 5340
ttaaatatat cgatgtcttt gtgatgcgcg cgacattttt gtaggttatt gataaaatga 5400
acggatacgt tgcccgacat tatcattaaa tccttggcgt agaatttgtc gggtccattg 5460
tccgtgtgcg ctagcatgcc cgtaacggac ctcgtacttt tggcttcaaa ggttttgcgc 5520

-continued

```
acagacaaaa tgtgccacac ttgcagctct gcatgtgtgc gcgttaccac aaatcccaac   5580
ggcgcagtgt acttgttgta tgcaaataaa tctcgataaa ggcgcggcgc gcgaatgcag   5640
ctgatcacgt acgctcctcg tgttccgttc aaggacggtg ttatcgacct cagattaatg   5700
tttatcggcc gactgttttc gtatccgctc accaaacgcg tttttgcatt aacattgtat   5760
gtcggcggat gttctatatc taatttgaat aaataaacga taaccgcgtt ggttttagag   5820
ggcataataa aagaaatatt gttatcgtgt tcgccattag ggcagtataa attgacgttc   5880
atgttggata ttgtttcagt tgcaagttga cactggcggc gacaagcaat tctaattggg   5940
gtaagttttc ccgttctttt ctgggttctt cccttttgct catccttgct gcactacctt   6000
caggtgcaag ttgagattca ggccaccatg ggagatccca ccccacccaa gaagaagcgc   6060
aaaccggtcg ccaccatgga cgaggatggt tcagagggcg gccccgccct gttccagagc   6120
gacatgacct tcaaaatctt catcgacggc gaggtgaacg gccagaagtt caccatcgtg   6180
gccgacggca gcagcaagtt cccccacggc gacttcaacg tgcacgccgt gtgcgagacc   6240
ggcaagctgc ccatgagctg gaagcccatc tgccacctga tccagtacgg cgagcccttc   6300
ttcgcccgct accccaacgg catcagccac ttcgcccagg agtgcttccc cgagggcctg   6360
agcatcgacc gcaccgtgcg cttcgagaac gacggcacca tgaccagcca ccacacctac   6420
gagctggacg gcacctgcgt ggtcagccgc atcaccgtga actgcgacgg cttccagccc   6480
gacggcccca tcatgcgcga ccagctggtg gacatcctgc ccaacgagac ccacatgttc   6540
ccccacggcc ccaacgccgt gcgccagctg gccttcatcg gcttcaccac cgccgacggc   6600
ggcctgatga tgggccactt cgacagcaag atgaccttca acggcagccg cgccatcaag   6660
atccccggcc cccacttcgt gaccatcatc accaagcaga tgagggacac cagcgacaag   6720
cgcgaccacg tgtgccagcg cgaggtgacc tacgcccaca gcgtgccccg catcaccagc   6780
gccatcggta gcgacgagga ttccggactc agatctcgac ccaagaaaaa gcggaaggtg   6840
gaggacccgt aagatccacc ggatctagat aactgatcat aatcagccat accacatttg   6900
tagaggtttt acttgcttta aaaaacctcc cacacctccc cctgaacctg aaacataaaa   6960
tgaatgcaat tgttgttgtt aacttgttta ttgcagctta taatggttac aaataaagca   7020
atagcatcac aaatttcaca aataaagcat ttttttcact gcattctagt tgtggtttgt   7080
ccaaactcat caatgtatct taacgcgagt taattaatcc attgctgggc gagctgcgcc   7140
aatcgatgcc aacgccaccc tgcatggcga gcggcaggcc ggcggctacc atgggcgtca   7200
ccatgccctg accgccccg gagggcagtg aaaaatgtgt gggggggtggt gggggctgcg   7260
caggaactga ttgtgattat ggttgtgccc atggccatgt tgtccaagtc catggacgtg   7320
ggcatgcttg ttgtagccca aatcggcgtt tccgtttcca ccaggaaaca tctctgcttg   7380
tagttcgaat atgctcttta aatcccagct gtattcctca gttatcgagg ttttcttcac   7440
gagtgaaacg aattttcgtc gccttctacg ccattttctt gctcagcccg ttttgtcatt   7500
cgcagcgaag cggtaacagc gggtcgctca tatgacggta ttttttaata cacttcagct   7560
atactgttat ttcaaaaaca tatttctttt gttacttttt atgcagttca tttgccacca   7620
aaaagtagtc ttttggattg atttatttca aaaaatggtg taattcaaga aattcagagg   7680
gccaagtaat atacttaatg accgttattt aaaacacact caaggagatt tatttaaacg   7740
gctacaatgg ttttccaaat aacttattta ctgttgactt ctataaaaca taggtgtata   7800
tattattatt tccttattga gtttgagata attttaattt ccacaatatt ttttcttgtg   7860
attaacagag aaagtcaaac tacataacat ttatcgggta aaagtctcta tgaaggtagc   7920
```

```
ggttaacagt gaagtcgcaa aagtggtggc cgtacgccaa tcgagcgtag taccccctaac   7980
ctgcaatatt tttagttggt tttttccgca atagccccag ttttctcaaa gagtgcaaca   8040
agtgattctg tttatgtttt caacaacttc tctctgcgga acttaacgtg agcggacgta   8100
tgcggacgcg tttaaactcg cgttaagata cattgatgag tttggacaaa ccacaactag   8160
aatgcagtga aaaaaatgct ttatttgtga aatttgtgat gctattgctt tatttgtaac   8220
cattataagc tgcaataaac aagttaacaa caacaattgc attcatttta tgtttcaggt   8280
tcagggggag gtgtgggagg ttttttaaag caagtaaaac ctctacaaat gtggtatggc   8340
tgattatgat caccggtgtt actggctcgg acggcggtaa cggccgctgc ggcggccggt   8400
gcgcgggtgg cagctggtgt actggcgcag ggtctccagc accacggtgg ccaggaagcg   8460
ccactggctc tcgcgcaggc gcaggatctg ctgctcgcgc tgctcggcct cgcgcagcag   8520
ggtggcctga tccgggatgt agaaggccac ggcgccacca cggagacgaa ggaccaagtg   8580
aagggtggac tccttctgga tgttgtaatc ggacagggtg cgtccgtctt ccagttgctt   8640
acctatagat accatagatg tatggattag tatcatatac atacaaaggc tatttttggg   8700
acatattaat attaacaatt tccgtgatag ttttcaccat ttttgttgaa tgttacgttg   8760
aaaatttaaa tttgttttaa attaatttta ccagtcatgt gttcttaaaa gtttttatga   8820
ttgaaacggc ataaagtggt tcaaaaattt atcaagaaag gctttccttt tttaaatctt   8880
atctttttct cttaaaaatc actagtcaat tcattattaa tttgttaact tgaatttgga   8940
atgtctattt actttcagat aaattaaagc aagaaactta atattcgaaa aaaattgatt   9000
ctaaatggaa tttcacttga tcttcatgta tgcatatcaa tttttattta cattgtataa   9060
taagtttcga gttgattgtt gtaatccaca ggtgtcccag agaattaaat tccaaattac   9120
ccaagtttat tgaatgttga ttgtagtttc agttgcttg ttgctgcaac aatggcttgt   9180
tgattgtaga tattttccct ttccttggtt tacttattac atagactgaa aaagaggttt   9240
actttttga tacttatgaa aaatttctat tagtgattac taaccaatcg ctatatgttt   9300
actagaaaac aaataaactc tttacattaa cattcaataa tgtttgctct gtaaccgaca   9360
attgaaggcg ttacagcaac agtaatataa ctagcttctt aaccctcatc tattaacccc   9420
atcgtttaaa acactatgtt aaatggtcta acaaatctag atactaatag atgtcttatt   9480
acttagcagc cacagctgca acatccaaga caatttttga aacttcttat tgagctcttg   9540
gcagcagaaa tgttggtatt tttcacagct ttctgaaaga ccggcacctt cctccggttc   9600
ccgtttctga attcaagagg atttccgacc cccaattaat cccgaaacaa ataaggtata   9660
ttcaaaatga tggaaaagtc atggctgctg accttatttt tattcctatt gatagaatat   9720
tattcccctt ttaaatacac tgtactaaga ggtccggcta taattttact cacttgtcga   9780
ttatcccata gaatgttgat tgtagttggt tgcttttcca ggtgagagtt gatcaagtca   9840
caaaagttag cgtgtgttga ttgtagattt gaaggtaaaa taatttttgc acccattcat   9900
cgggtaaaac gttctccata gaatacattt ccatcgataa ttgataactt atgaatttca   9960
aagaaaaaaa tatgctttta aaattaccag cgaagatcag acgctgctga tctgggggga  10020
ttccctcctt atcctgaatc ttggccttta cattctcaat ggtgtccgat ggctctacct  10080
cgagggtgat ggtctttccg gtcaaagtct tcacaaagat ctgcattttg gattgctagc  10140
gcagattgtt tagcttgttc agctgcgctt gtttatttgc ttagctttcg cttagcgacg  10200
tgttcacttt gcttgtttga attgaattgt cgctccgtag acgaagcgcc tctatttata  10260
```

```
ctccggcgct cggtccgcat agtcgacatt tcgagtttac cactccctat cagtgataga  10320
gaaaagtgaa agtcgagttt accactccct atcagtgata gagaaaagtg aaagtcgagt  10380
ttaccactcc ctatcagtga tagagaaaag tgaaagtcga gtttaccact ccctatcagt  10440
gatagagaaa agtgaaagtc gagtttacca ctccctatca gtgatagaga aaagtgaaag  10500
tcgagtttac cactccctat cagtgataga gaaaagtgaa agtcgagttt accactccct  10560
atcagtgata gagaaaagtg aaagtcgagc tcggtacccg ggtcgaggta ggcgtgtacg  10620
gtgggaggaa atctggccgg ccgcaaccat tgtgggaacc gtgcgatcaa acaaacgcga  10680
gataccggaa gtactgaaaa acagtcgctc caggccagtg ggaacatcga tgttttgttt  10740
tgacggaccc cttactctcg tctcatataa accgaagcca gctaagatgg tatacttatt  10800
atcatcttgt gatgaggatg cttctatcaa cgaaagtacc ggtaaaccgc aaatggttat  10860
gtattataat caaactaaag gcggagtgga cacgctagac caaatgtgtt ctgtgatgac  10920
ctgcagtagg aagacgaata ggtggcctat ggcattattg tacggaatga taaacattgc  10980
ctgcataaat tcttttatta tatacagcca taatgtcagt agcaagggag aaaaggtcca  11040
aagtcgcaaa aaatttatga gaaaccttta catgagcctg acgtcatcgt ttatgcgtaa  11100
gcgtttagaa gctcctactt tgaagagata tttgcgcgat aatatctcta atattttgcc  11160
aaatgaagtg cctggtacat cagatgacag tactgaagag ccagtaatga aaaaacgtac  11220
ttactgtact tactgcccct ctaaaataag gcgaaaggca aatgcatcgt gcaaaaaatg  11280
caaaaaagtt atttgtcgag agcataatat tgatatgtgc caaagttgtt tctgactgac  11340
taataagtat aatttgtttc tattatgtat aagttaagct aattacttat tttataatac  11400
aacatgactg tttttaaagt acaaaataag tttatttttg taaaagagag aatgtttaaa  11460
agttttgtta ctttatagaa gaaattttga gtttttgttt tttttaata aataaataaa  11520
cataaataaa ttgtttgttg aatttattat tagtatgtaa gtgtaaatat aataaaactt  11580
aatatctatt caaattaata aataaacctc gatatacaga ccgataaaac acatgcgtca  11640
attttacgca tgattatctt taacgtacgt cacaatatga ttatctttct agggttaaat  11700
aatagtttct aattttttta ttattcagcc tgctgtcgtg aataccgtat atctcaacgc  11760
tgtctgtgag attgtcgtat tctagccttt ttagtttttc gctcatcgac ttgatattgt  11820
ccgacacatt ttcgtcgatt tgcgttttga tcaaagactt gagcagagac acgttaatca  11880
actgttcaaa ttgatccata ttaacgatat caacccgatg cgtatatggt gcgtaaaata  11940
tatttttaa ccctcttata ctttgcactc tgcgttaata cgcgttcgtg tacagacgta  12000
atcatgtttt ctttttgga taaaactcct actgagtttg acctcatatt agaccctcac  12060
aagttgcaaa acgtggcatt ttttaccaat gaagaattta aagttatttt aaaaaatttc  12120
atcacagatt taaagaagaa ccaaaaatta aattatttca acagtttaat cgaccagtta  12180
atcaacgtgt acacagacgc gtcggcaaaa aacacgcagc ccgacgtgtt ggctaaaatt  12240
attaaatcaa cttgtgttat agtcacggat ttgccgtcca acgtgttcct caaaaagttg  12300
aagaccaaca agtttacgga cactattaat tatttgattt tgccccactt cattttgtgg  12360
gatcacaatt ttgttatatt ttaaacaaag cttggcactg gccgtcgttt tacaacgtcg  12420
tgactgggaa aaccctggcg ttacccaact taatcgcctt gcagcacatc cccctttcgc  12480
cagctggcgt aatagcgaag aggcccgcac cgatcgccct tcccaacagt tgcgcagcct  12540
gaatggcgaa tggcgcctga tgcggtattt tctccttacg catctgtgcg gtatttcaca  12600
ccgcatatgg tgcactctca gtacaatctg ctctgatgcc gcatagttaa gccagccccg  12660
```

-continued

```
acacccgcca acacccgctg acgcgccctg acgggcttgt ctgctcccgg catccgctta  12720
cagacaagct gtgaccgtct ccgggagctg catgtgtcag aggttttcac cgtcatcacc  12780
gaaacgcgcg agacgaaagg gcctcgtgat acgcctattt ttataggtta atgtcatgat  12840
aataatggtt tcttagacgt caggtggcac ttttcgggga aatgtgcgcg gaacccctat  12900
ttgtttattt ttctaaatac attcaaatat gtatccgctc atgagacaat aaccctgata  12960
aatgcttcaa taatattgaa aaaggaagag tatgagtatt caacatttcc gtgtcgccct  13020
tattcccttt tttgcggcat tttgccttcc tgtttttgct cacccagaaa cgctggtgaa  13080
agtaaaagat gctgaagatc agttgggtgc acgagtgggt tacatcgaac tggatctcaa  13140
cagcggtaag atccttgaga gttttcgccc cgaagaacgt tttccaatga tgagcacttt  13200
taaagttctg ctatgtggcg cggtattatc ccgtattgac gccgggcaag agcaactcgg  13260
tcgccgcata cactattctc agaatgactt ggttgagtac tcaccagtca cagaaaagca  13320
tcttacggat ggcatgacag taagagaatt atgcagtgct gccataacca tgagtgataa  13380
cactgcggcc aacttacttc tgacaacgat cggaggaccg aaggagctaa ccgctttttt  13440
gcacaacatg ggggatcatg taactcgcct tgatcgttgg gaaccggagc tgaatgaagc  13500
cataccaaac gacgagcgtg acaccacgat gcctgtagca atggcaacaa cgttgcgcaa  13560
actattaact ggcgaactac ttactctagc ttcccggcaa caattaatag actggatgga  13620
ggcggataaa gttgcaggac cacttctgcg ctcggccctt ccggctggct ggtttattgc  13680
tgataaatct ggagccggtg agcgtgggtc tcgcggtatc attgcagcac tggggccaga  13740
tggtaagccc tcccgtatcg tagttatcta cacgacgggg agtcaggcaa ctatggatga  13800
acgaaataga cagatcgctg agataggtgc ctcactgatt aagcattggt aactgtcaga  13860
ccaagtttac tcatatatac tttagattga tttaaaactt catttttaat ttaaaaggat  13920
ctaggtgaag atcctttttg ataatctcat gaccaaaatc ccttaacgtg agttttcgtt  13980
ccactgagcg tcagaccccg tagaaaagat caaaggatct tcttgagatc cttttttct  14040
gcgcgtaatc tgctgcttgc aaacaaaaaa accaccgcta ccagcggtgg tttgtttgcc  14100
ggatcaagag ctaccaactc tttttccgaa ggtaactggc ttcagcagag cgcagatacc  14160
aaatactgtc cttctagtgt agccgtagtt aggccaccac ttcaagaact ctgtagcacc  14220
gcctacatac ctcgctctgc taatcctgtt accagtggct gctgccagtg gcgataagtc  14280
gtgtcttacc gggttggact caagacgata gttaccggat aaggcgcagc ggtcgggctg  14340
aacggggggt tcgtgcacac agcccagctt ggagcgaacg acctacaccg aactgagata  14400
cctacagcgt gagcattgag aaagcgccac gcttcccgaa gggagaaagg cggacaggta  14460
tccggtaagc ggcagggtcg gaacaggaga gcgcacgagg gagcttccag ggggaaacgc  14520
ctggtatctt tatagtcctg tcgggtttcg ccacctctga cttgagcgtc gatttttgtg  14580
atgctcgtca ggggggcgga gcctatggaa aaacgccagc aacgcggcct ttttacggtt  14640
cctggccttt tgctggcctt ttgctcacat gttctttcct gcgttatccc ctgattctgt  14700
ggataaccgt attaccgcct ttgagtgagc tgataccgct cgccgcagcc gaacgaccga  14760
gcgcagcgag tcagtgagcg aggaagcgga agagcgccca atacgcaaac cgcctctccc  14820
cgcgcgttgg ccgattcatt aatgcagctg gcacgacagg tttcccgact ggaaagcggg  14880
cagtgagcgc aacgcaatta atgtgagtta gctcactcat taggcacccc aggctttaca  14940
ctttatgctt ccggctcgta tgttgtgtgg aattgtgagc ggataacaat ttcacacagg  15000
```

```
aaacagctat gaccatgatt acgaatttcg acgctcgcgc gacttggttt gccattcttt  15060
agcgcgcgtc gcgtcacaca gcttggccac aatgtggttt ttgtcaaacg aagattctat  15120
gacgtgttta aagtttaggt cgagtaaagc gcaaatcttt tttaacccta gaaagatagt  15180
ctgcgtaaaa ttgacgcatg cattcttgaa atattgctct ctctttctaa atagcgcgaa  15240
tccgtcgctg tgcatttagg acatctcagt cgccgcttgg agctcccgtg aggcgtgctt  15300
gtcaatgcgg taagtgtcac tgattttgaa ctataacgac cgcgtgagtc aaaatgacgc  15360
atgattatct tttacgtgac ttttaagatt taactcatac gataattata ttgttatttc  15420
atgttctact tacgtgataa cttattatat atatattttc ttgttataga tatcgtgact  15480
aatatataat aaaatgggta gttctttaga cgatgagcat atcctctctg ctcttctgca  15540
aagcgatgac gagcttgttg gtgaggattc tgacagtgaa atatcagatc acgtaagtga  15600
agatgacgtc cagagcgata cagaagaagc gtttatagat gaggtacatg aagtgcagcc  15660
aacgtcaagc ggtagtgaaa tattagacga acaaaatgtt attgaacaac caggttcttc  15720
attggcttct aacagaatct tgaccttgcc acagaggact attagaggta agaataaaca  15780
ttgttggtca acttcaaagt ccacgaggcg tagccgagtc tctgcactga acattgtcag  15840
atcggccc                                                           15848
```

<210> SEQ ID NO 55
<211> LENGTH: 17802
<212> TYPE: DNA
<213> ORGANISM: artificial
<220> FEATURE:
<223> OTHER INFORMATION: Sequence of pLA3376-Bztra intron-reaperKR and Bztra-intron-tTAV3.

<400> SEQUENCE: 55

```
gggcggccgt ttttcttgaa atattgctct ctctttctaa atagcgcgaa tccgtcgctg     60
tgcatttagg acatctcagt cgccgcttgg agctcccaaa cgcgccagtg gtagtacaca    120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaaagttt tcgcaatgcc tttatttttt gttgcaaatc    360
tctctttatt ctgcggtatt cttcattatt gcggggatgg ggaaagtgtt tatatagaag    420
caacttacga ttgaacccaa atgcacctga caagcaaggt caaagggcca gatttttaaa    480
tatattattt agtcttagga ctctctattt gcaattaaat tactttgcta cctgagggtt    540
aaatcttccc cattgataat aataattcca ctatatgttc aattgggttt caccgcgctt    600
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
caggtttaac caggggatgc ttaattgtgt tctcaacttc aaaggcagaa atgtttactc    840
ttgaccatgg gtttaggtat aatgttatca agctcctcga gttaacgtta cgttaacgtt    900
aacgttcgag gtcgactcta gacaccggtg ttagccgccg tactcatcga tgcccagggc    960
gtcggtgaac atctgctcga actcgaaatc ggccatatcc agggcgccgt agggggcgct   1020
atcgtgcggg gtgaatcccg gtcccgggct atcgccatcg cccagcatgt ccaggtcgaa   1080
gtcgtccagg gcatcggcgt gggccatcgc cacatcctcg ccatccaggt gcagctcatc   1140
```

-continued gcccaggctc acgtcggtcg gcggggcggt cgacaggcgg cgggtgtgtc cggccggcag 1200
gaagctcagg cgcggggcgg ccaggcccgc ctcctccggg gcatcatcat ccggcagatc 1260
cagcaggccc tcgatggtgc tgccgtagtt gttcttggtg cgggcgcggc tgtaggcggg 1320
gcccgagccc gactcgcatt tcagttgctt ttccaatccg cagataatca gctccaagcc 1380
gaacaggaat gccggctcgg ctccttgatg atcgaacagc tcgattgcct gacgcagcag 1440
tgggggcatc gaatcggttg ttggggtctc gcgctcctct tttgcgactt gatgctcttg 1500
gtcctccagc acgcagccca gggtaaagtg accgacggcg ctcagagcgt agagagcatt 1560
ttccaggctg aagccttgct ggcacaggaa cgcgagctgg ttctccagtg tctcgtattg 1620
cttttcggtc gggcgcgtgc cgagatggac tttggcaccg tctcggtggg acagcagagc 1680
gcagcggaac gacttggcgt tattgcggag gaagtcctgc caggactcgc cttccaacgg 1740
gcaaaaatgc gtgtggtggc ggtcgagcat ctcgatggcc agggcatcca gcagcgcccg 1800
cttattcttc acgtgccagt agagggtggg ctgctccacg cccagcttct gcgccaactt 1860
gcgggtcgtc agtccctcaa tgccaacttc gttcaacagc tccaacgcgg agttgatgac 1920
tttggactta tccaggcggc tgacctatag ataccataga tgtatggatt agtatcatat 1980
acatacaaag gctatttttg ggacatatta atattaacaa tttccgtgat agttttcacc 2040
atttttgttg aatgttacgt tgaaaattta aatttgtttt aaattaattt taccagtcat 2100
gtgttcttaa aagtttttat gattgaaacg gcataaagtg gttcaaaaat ttatcaagaa 2160
aggctttcct tttttaaatc ttatcttttt ctcttaaaaa tcactagtca attcattatt 2220
aatttgttaa cttgaatttg gaatgtctat ttactttcag ataaattaaa gcaagaaact 2280
taatattcga aaaaaattga ttctaaatgg aatttcactt gatcttcatg tatgcatatc 2340
aatttttatt tacattgtat aataagtttc gagttgattg ttgtaatcca caggtgtccc 2400
agagaattaa attccaaatt acccaagttt attgaatgtt gattgtagtt tcagttgctt 2460
tgttgctgca acaatggctt gttgattgta gatattttcc ctttccttgg tttacttatt 2520
acatagactg aaaaagaggt ttactttttt gatacttatg aaaaatttct attagtgatt 2580
actaaccaat cgctatatgt ttactagaaa acaaataaac tctttacatt aacattcaat 2640
aatgtttgct ctgtaaccga caattgaagg cgttacagca acagtaatat aactagcttc 2700
ttaaccctca tctattaacc ccatcgttta aaacactatg ttaaatggtc taacaaatct 2760
agatactaat agatgtctta ttacttagca gccacagctg caacatccaa gacaattttt 2820
gaaacttctt attgagctct tggcagcaga aatgttggta tttttcacag ctttctgaaa 2880
gaccggcacc ttcctccggt tcccgtttct gaattcaaga ggatttccga cccccaatta 2940
atcccgaaac aaataaggta tattcaaaat gatggaaaag tcatggctgc tgaccttatt 3000
tttattccta ttgatagaat attattcccc ttttaaatac actgtactaa gaggtccggc 3060
tataatttta ctcacttgtc gattatccca tagaatgttg attgtagttg gttgcttttc 3120
caggtgagag ttgatcaagt cacaaaagtt agcgtgtgtt gattgtagat ttgaaggtaa 3180
aataattttt gcacccattc atcgggtaaa acgttctcca tagaatacat ttccatcgat 3240
aattgataac ttatgaattt caaagaaaaa aatatgcttt taaaattacc atggtggcta 3300
gcgcagattg tttagcttgt tcagctgcgc ttgtttattt gcttagcttt cgcttagcga 3360
cgtgttcact ttgcttgttt gaattgaatt gtcgctccgt agacgaagcg cctctattta 3420
tactccggcg ctcgttttcg agtttaccac tccctatcag tgatagagaa aagtgaaagt 3480
cgagtttacc actccctatc agtgatagag aaaagtgaaa gtcgagttta ccactcccta 3540

-continued

```
tcagtgatag agaaaagtga aagtcgagtt taccactccc tatcagtgat agagaaaagt   3600
gaaagtcgag tttaccactc cctatcagtg atagagaaaa gtgaaagtcg agtttaccac   3660
tccctatcag tgatagagaa aagtgaaagt cgagtttacc actccctatc agtgatagag   3720
aaaagtgaaa gtcgaaacct gcgcgccgtt taaactcgcg ttaagataca ttgatgagtt   3780
tggacaaacc acaactagaa tgcagtgaaa aaaatgcttt atttgtgaaa tttgtgatgc   3840
tattgcttta tttgtaacca ttataagctg caataaacaa gttaacaaca acaattgcat   3900
tcattttatg tttcaggttc agggggaggt gtgggaggtt ttttaaagca agtaaaacct   3960
ctacaaatgt ggtatggctg attatgatcg ctctagacac cggtgctacc cgccatactc   4020
atcgatgccc agcgcgtcgg tgaacatttg ctcgaactcg aagtcggcca tgtccagggc   4080
gccgtacggg gcgctatcgt ggggcgtgaa gcccggtccc gggctatctc catcgcccag   4140
catatccagg tcgaaatcgt ccagggcgtc ggcgtgggcc attgccacat cctctccatc   4200
caggtgcagc tcgtcgccca ggctcacatc ggtcggcggg gcggtgctca ggcggcgcgt   4260
gtgtccggcg ggcaggaagc tcaggcgggg ggcggccagg ccggcttcct ccggggcatc   4320
gtcatccggc aggtccagca gtccctcgat ggtgctgcca tagttgttct tggtacgggc   4380
gcggctgtag gcgctgccgc tctcgcactt cagctgcttt tccaggccgc agatgatcag   4440
ctccaggccg aacaggaagg ccggctcggc gccctggtga tcgaacagct cgatggcctg   4500
gcgcagcagc ggcggcatgc tatcggtggt cggggtctcg cgctcctcct tggccacctg   4560
gtgctcctga tcctccagca cacagcccag ggtgaagtgg cccacggcgc tcagggcgta   4620
cagggcgttc tccaggctga agccctgctg gcacaggaag gccagctggt tctccagggt   4680
ctcgtactgc ttctcggtcg ggcgggtgcc caggtgcacc ttggcgccat cgcggtgcga   4740
cagcagggcg cagcggaagc tcttggcgtt gttgcgcagg aaatcctgcc agctctcgcc   4800
ctccagcggg cagaagtggg tgtggtggcg atccagcatt tcgatggcca gggcgtccag   4860
cagggcgcgc ttgttcttca cgtgccagta cagggtcggc tgttccacgc ccagcttctg   4920
ggccagcttg cgggtggtca ggccctcgat accaacttcg ttcagcagct ccagggcgct   4980
gttgatcacc ttgctcttgt ccaggcggct gacctgtgaa tacggttaat gtcactatta   5040
gtgatttata aaaataaatt tgatttatat atcaacaatt tttcatcgca gccttcagct   5100
ttttgttgaa taattataat gatattttt acgattcaaa tcatttaatt gttactcaac   5160
gaaataagtt taattcaaat tttaaaacaa gattatatat taagattaga ataagaaaga   5220
actttgttag attatttaat taaaaagatt aaaatttaag tctccagtca ctatttaaag   5280
atcatctttc aaacgttaaa gtgaattcaa acgagacgtt caaatttcga ttaaacagta   5340
attaactcta aatttctatc acgaattaag ttattgaata tgaaggttta tatttattta   5400
catcatctaa taggtttgag ttgattgttg taatccgcat gtgccagaag atatcaattt   5460
ccaaattgtc cgagttcatg gaatgttgat tgttgtttgt gttgctttgt aattgttgca   5520
gggagtattt atggtttgtt gattgtagta taaggctgtt tctaaaggct agaaaataat   5580
tttatttatt tgaaaataag taaatataca taatattact aacaataggt cgtcctattt   5640
tttgatattc tgcacaaatt tttaaaacac aaagattgca atacttttag acactaatac   5700
tgcacactct gaaaaattat taaattattt ttaaaaactt accttaatac tttagagaaa   5760
aatattatac cgcacctttc tactttatac tcactttatt ataccagttg catgttgatt   5820
gtagttcttt gacaagaaaa tattccatat tgctccaaat tatcttggta agttgattgg   5880
```

-continued

```
tgcgtcattt gagcaagcta acaccttgtc tcatttaagt tcgcctcaag atctcatagc   5940
atttttaaat atcactatat ttagtaagta attagaatta ccatggtggt ttgctagccg   6000
ttctatcaga tgtgctccgg gaaacagaaa tgttcaacta agttctggcg gacgacgcaa   6060
cacctttata tactttgcca agcgcacagg tagaaaggac ctattttggg gattaaaaaa   6120
catctgcctg ttttattgcc atacccgcga aaattcgcga aatccgctac tttacctact   6180
ggggttcctg gaaaatgggc gaagaacggc aaagaactgg tactttccgt caataattgt   6240
ttagaagaga gagaacatac tccctatcag tgatagagaa gtccctatca gtgatagaga   6300
tgtccctatc agtgatagag agttccctat cagtgataga gacgtcccta tcagtgatag   6360
agaagtccct atcagtgata gagagatccc tatcagtgat agagatttcc ctatcagtga   6420
tagagaggtc cctatcagtg atagagactt ccctatcagt gatagagaaa tccctatcag   6480
tgatagagac atccctatca gtgatagaga actccctatc agtgatagag acctccctat   6540
cagtgataga gatcgatgcg gccgcatggt acccattgct tgtcatttat taatttggat   6600
gatgtcattt gtttttaaaa ttgaactggc tttacgagta gaattctacg cgtaaaacac   6660
aatcaagtat gagtcataat ctgatgtcat gttttgtaca cggctcataa ccgaactggc   6720
tttacgagta gaattctact tgtaatgcac gatcagtgga tgatgtcatt tgtttttcaa   6780
atcgagatga tgtcatgttt tgcacacggc tcataaactc gctttacgag tagaattcta   6840
cgtgtaacgc acgatcgatt gatgagtcat ttgttttgca atatgatatc atacaatatg   6900
actcatttgt ttttcaaaac cgaacttgat ttacgggtag aattctactt gtaaagcaca   6960
atcaaaaaga tgatgtcatt tgtttttcaa aactgaactc gctttacgag tagaattcta   7020
cgtgtaaaac acaatcaaga aatgatgtca tttgttataa aaataaaagc tgatgtcatg   7080
ttttgcacat ggctcataac taaactcgct ttacgggtag aattctacgc gtaaaacatg   7140
attgataatt aaataattca tttgcaagct atacgttaaa tcaaacggac gctcgaggtt   7200
gcacaacact attatcgatt tgcagttcgg gacataaatg tttaaatata tcgatgtctt   7260
tgtgatgcgc gcgacatttt tgtaggttat tgataaaatg aacggatacg ttgcccgaca   7320
ttatcattaa atccttggcg tagaatttgt cgggtccatt gtccgtgtgc gctagcatgc   7380
ccgtaacgga cctcgtactt ttggcttcaa aggttttgcg cacagacaaa atgtgccaca   7440
cttgcagctc tgcatgtgtg cgcgttacca caaatcccaa cggcgcagtg tacttgttgt   7500
atgcaaataa atctcgataa aggcgcggcg cgcgaatgca gctgatcacg tacgctcctc   7560
gtgttccgtt caaggacggt gttatcgacc tcagattaat gtttatcggc cgactgtttt   7620
cgtatccgct caccaaacgc gtttttgcat taacattgta tgtcggcgga tgttctatat   7680
ctaatttgaa taaataaacg ataaccgcgt tggttttaga gggcataata aaagaaatat   7740
tgttatcgtg ttcgccatta gggcagtata aattgacgtt catgttggat attgtttcag   7800
ttgcaagttg acactggcgg cgacaagcaa ttctaattgg ggtaagtttt cccgttcttt   7860
tctgggttct tccctttttgc tcatccttgc tgcactacct tcaggtgcaa gttgagattc   7920
aggccaccat gggagatccc accccaccca agaagaagcg caaaccggtc gccaccatgg   7980
agagcgacga gagcggcctg cccgccatgg agatcgagtg ccgcatcacc ggcaccctga   8040
acggcgtgga gttcgagctg gtgggcggcg gagagggcac ccccgagcag ggccgcatga   8100
ccaacaagat gaagagcacc aaaggcgccc tgaccttcag cccctacctg ctgagccacg   8160
tgatgggcta cggcttctac cacttcggca cctaccccag cggctacgag aaccccttcc   8220
tgcacgccat caacaacggc ggctacacca acacccgcat cgagaagtac gaggacggcg   8280
```

-continued

```
gcgtgctgca cgtgagcttc agctaccgct acgaggccgg ccgcgtgatc ggcgacttca   8340
aggtgatggg caccggcttc cccgaggaca gcgtgatctt caccgacaag atcatccgca   8400
gcaacgccac cgtggagcac ctgcacccca tgggcgataa cgatctggat ggcagcttca   8460
cccgcacctt cagcctgcgc gacggcggct actacagctc cgtggtggac agccacatgc   8520
acttcaagag cgccatccac cccagcatcc tgcagaacgg gggccccatg ttcgccttcc   8580
gccgcgtgga ggaggatcac agcaacaccg agctgggcat cgtggagtac cagcacgcct   8640
tcaagacccc ggatgcagat gccggtgaag aaagatctcg acccaagaaa aagcggaagg   8700
tggaggaccc gtaagatcca ccggatctag ataactgatc ataatcagcc ataccacatt   8760
tgtagaggtt ttacttgctt taaaaaacct cccacacctc cccctgaacc tgaaacataa   8820
aatgaatgca attgttgttg ttaacttgtt tattgcagct tataatggtt acaaataaag   8880
caatagcatc acaaatttca caaataaagc atttttttca ctgcattcta gttgtggttt   8940
gtccaaactc atcaatgtat cttaacgcga gttatcgcgc tcgcgcgact gacggtcgta   9000
agcacccgcg tacgtgtcca ccccggtcac aacccccttgt gtcatgtcgg cgaccctacg   9060
cccccaactg agagaactca aaggttaccc cagttggggc actactcccg aaaaccgctt   9120
ctgacctggg aaaacgtgaa gccccggggc atccgctgag ggttgccgcc ggggcttcgg   9180
tgtgtccgtc agtacttaat taacaccgaa atcgtaattc acggcatcat tacaaaatat   9240
tttgacgttt tggacctcgt ccctaatgac accataacgg tggccttgaa gtatatttaa   9300
ccctagaaag atagtctgcg taaaattgac gcatgcattc ttgaaatatt gctctctctt   9360
tctaaatagc gcgaatccgt cgctgtgcat ttaggacatc tcagtcgccg cttggagctc   9420
ccgtgaggcg tgcttgtcaa tgcggtaagt gtcactgatt ttgaactata acgaccgcgt   9480
gagtcaaaat gacgcatgat tatcttttac gtgactttta agatttaact catacgataa   9540
ttatattgtt atttcatgtt ctacttacgt gataacttat tatatatata ttttcttgtt   9600
atagatatcg tgactaatat ataataaaat gggtagttct ttagacgatg agcatatcct   9660
ctctgctctt ctgcaaagcg atgacgagct tgttggtgag gattctgaca gtgaaatatc   9720
agatcacgta agtgaagatg acgtccagga aatctggccg gccgcaacca ttgtgggaac   9780
cgtgcgatca aacaaacgcg agataccgga agtactgaaa aacagtcgct ccaggccagt   9840
gggaacatcg atgttttgtt ttgacggacc ccttactctc gtctcatata aaccgaagcc   9900
agctaagatg gtatacttat tatcatcttg tgatgaggat gcttctatca acgaaagtac   9960
cggtaaaccg caaatggtta tgtattataa tcaaactaaa ggcggagtgg acacgctaga  10020
ccaaatgtgt tctgtgatga cctgcagtag gaagacgaat aggtggccta tggcattatt  10080
gtacggaatg ataaacattg cctgcataaa ttcttttatt atatacagcc ataatgtcag  10140
tagcaaggga gaaaaggtcc aaagtcgcaa aaaatttatg agaaaccttt acatgagcct  10200
gacgtcatcg tttatgcgta agcgtttaga agctcctact ttgaagagat atttgcgcga  10260
taatatctct aatattttgc caaatgaagt gcctggtaca tcagatgaca gtactgaaga  10320
gccagtaatg aaaaaacgta cttactgtac ttactgcccc tctaaaataa ggcgaaaggc  10380
aaatgcatcg tgcaaaaaat gcaaaaaagt tatttgtcga gagcataata ttgatatgtg  10440
ccaaagttgt ttctgactga ctaataagta taatttgttt ctattatgta taagttaagc  10500
taattactta ttttataata caacatgact gtttttaaag tacaaaataa gtttattttt  10560
gtaaaagaga gaatgtttaa aagttttgtt actttataga agaaattttg agtttttgtt  10620
```

-continued

```
tttttttaat aaataaataa acataaataa attgtttgtt gaatttatta ttagtatgta  10680
agtgtaaata taataaaact taatatctat tcaaattaat aaataaacct cgatatacag  10740
accgataaaa cacatgcgtc aattttacgc atgattatct ttaacgtacg tcacaatatg  10800
attatctttc tagggttaaa taatagtttc taattttttt attattcagc ctgctgtcgt  10860
gaataccgta tatctcaacg ctgtctgtga gattgtcgta ttctagcctt tttagttttt  10920
cgctcatcga cttgatattg tccgacacat tttcgtcgat ttgcgttttg atcaaagact  10980
tgagcagaga cacgttaatc aactgttcaa attgatccat attaacgata tcaacccgat  11040
gcgtatatgg tgcgtaaaat atattttta accctcttat actttgcact ctgcgttaat  11100
acgcgttcgt gtacagacgt aatcatgttt tctttttgg ataaaactcc tactgagttt  11160
gacctcatat tagaccctca caagttgcaa aacgtggcat tttttaccaa tgaagaattt  11220
aaagttattt taaaaaattt catcacagat ttaaagaaga accaaaaatt aaattatttc  11280
aacagtttaa tcgaccagtt aatcaacgtg tacacagacg cgtcggcaaa aaacacgcag  11340
cccgacgtgt tggctaaaat tattaaatca acttgtgtta tagtcacgga tttgccgtcc  11400
aacgtgttcc tcaaaaagtt gaagaccaac aagtttacgg acactattaa ttatttgatt  11460
ttgccccact tcattttgtg ggatcacaat tttgttatat tttaaacaaa gcttggcact  11520
ggccgtcgtt ttacaacgtc gtgactggga aaaccctggc gttacccaac ttaatcgcct  11580
tgcagcacat ccccctttcg ccagctggcg taatagcgaa gaggcccgca ccgatcgccc  11640
ttcccaacag ttgcgcagcc tgaatggcga atggcgcctg atgcggtatt ttctccttac  11700
gcatctgtgc ggtatttcac accgcatatg gtgcactctc agtacaatct gctctgatgc  11760
cgcatagtta agccagcccc gacacccgcc aacacccgct gacgcgccct gacgggcttg  11820
tctgctcccg gcatccgctt acagacaagc tgtgaccgtc tccgggagct gcatgtgtca  11880
gaggttttca ccgtcatcac cgaaacgcgc gagacgaaag ggcctcgtga tacgcctatt  11940
tttataggtt aatgtcatga taataatggt ttcttagacg tcaggtggca cttttcgggg  12000
aaatgtgcgc ggaaccccta tttgtttatt tttctaaata cattcaaata tgtatccgct  12060
catgagacaa taaccctgat aaatgcttca ataatattga aaaaggaaga gtatgagtat  12120
tcaacatttc cgtgtcgccc ttattccctt ttttgcggca ttttgccttc ctgtttttgc  12180
tcacccagaa acgctggtga aagtaaaaga tgctgaagat cagttgggtg cacgagtggg  12240
ttacatcgaa ctggatctca acagcggtaa gatccttgag agttttcgcc ccgaagaacg  12300
ttttccaatg atgagcactt ttaaagttct gctatgtggc gcggtattat cccgtattga  12360
cgccgggcaa gagcaactcg gtcgccgcat acactattct cagaatgact tggttgagta  12420
ctcaccagtc acagaaaagc atcttacgga tggcatgaca gtaagagaat tatgcagtgc  12480
tgccataacc atgagtgata acactgcggc caacttactt ctgacaacga tcggaggacc  12540
gaaggagcta accgcttttt tgcacaacat gggggatcat gtaactcgcc ttgatcgttg  12600
ggaaccggag ctgaatgaag ccataccaaa cgacgagcgt gacaccacga tgcctgtagc  12660
aatggcaaca acgttgcgca aactattaac tggcgaacta cttactctag cttcccggca  12720
acaattaata gactggatgg aggcggataa agttgcagga ccacttctgc gctcggccct  12780
tccggctggc tggtttattg ctgataaatc tggagccggt gagcgtgggt ctcgcggtat  12840
cattgcagca ctggggccag atggtaagcc ctcccgtatc gtagttatct acacgacggg  12900
gagtcaggca actatggatg aacgaaatag acagatcgct gagataggtg cctcactgat  12960
taagcattgg taactgtcag accaagttta ctcatatata ctttagattg atttaaaact  13020
```

tcatttttaa tttaaaagga tctaggtgaa gatccttttt gataatctca tgaccaaaat 13080
cccttaacgt gagttttcgt tccactgagc gtcagacccc gtagaaaaga tcaaaggatc 13140
ttcttgagat cctttttttc tgcgcgtaat ctgctgcttg caaacaaaaa aaccaccgct 13200
accagcggtg gtttgtttgc cggatcaaga gctaccaact ctttttccga aggtaactgg 13260
cttcagcaga gcgcagatac caaatactgt ccttctagtg tagccgtagt taggccacca 13320
cttcaagaac tctgtagcac cgcctacata cctcgctctg ctaatcctgt taccagtggc 13380
tgctgccagt ggcgataagt cgtgtcttac cgggttggac tcaagacgat agttaccgga 13440
taaggcgcag cggtcgggct gaacgggggg ttcgtgcaca cagcccagct tggagcgaac 13500
gacctacacc gaactgagat acctacagcg tgagcattga gaaagcgcca cgcttcccga 13560
agggagaaag gcggacaggt atccggtaag cggcagggtc ggaacaggag agcgcacgag 13620
ggagcttcca gggggaaacg cctggtatct ttatagtcct gtcgggtttc gccacctctg 13680
acttgagcgt cgatttttgt gatgctcgtc aggggggcgg agcctatgga aaaacgccag 13740
caacgcggcc tttttacggt tcctggcctt ttgctggcct tttgctcaca tgttctttcc 13800
tgcgttatcc cctgattctg tggataaccg tattaccgcc tttgagtgag ctgataccgc 13860
tcgccgcagc cgaacgaccg agcgcagcga gtcagtgagc gaggaagcgg aagagcgccc 13920
aatacgcaaa ccgcctctcc ccgcgcgttg gccgattcat taatgcagct ggcacgacag 13980
gtttcccgac tggaaagcgg gcagtgagcg caacgcaatt aatgtgagtt agctcactca 14040
ttaggcaccc caggctttac actttatgct tccggctcgt atgttgtgtg gaattgtgag 14100
cggataacaa tttcacacag gaaacagcta tgaccatgat tacgaatttc gacctgcagg 14160
catgcaagct tgcatgcctg caggtcgacg ctcgcgcgac ttggtttgcc attctttagc 14220
gcgcgtcgcg tcacacagct tggccacaat gtggtttttg tcaaacgaag attctatgac 14280
gtgtttaaag tttaggtcga gtaaagcgca aatctttttt aaccctagaa agatagtctg 14340
cgtaaaattg acgcatgcat tcttgaaata ttgctctctc tttctaaata gcgcgaatcc 14400
gtcgctgtgc atttaggaca tctcagtcgc cgcttggagc tcccgtgagg cgtgcttgtc 14460
aatgcggtaa gtgtcactga ttttgaacta taacgaccgc gtgagtcaaa atgacgcatg 14520
attatctttt acgtgacttt taagatttaa ctcatacgat aattatattg ttatttcatg 14580
ttctacttac gtgataactt attatatata tattttcttg ttatagatat cgtgactaat 14640
atataataaa atgggtagtt ctttagacga tgagcatatc ctctctgctc ttctgcaaag 14700
cgatgacgag cttgttggtg aggattctga cagtgaaata tcagatcacg taagtgaaga 14760
tgacgtccag agcgatacag aagaagcgtt tatagatgag gtacatgaag tgcagccaac 14820
gtcaagcggt agtgaaatat tagacgaaca aaatgttatt gaacaaccag gttcttcatt 14880
ggcttctaac agaatcttga ccttgccaca gaggactatt agaggtaaga ataaacattg 14940
ttggtcaact tcaaagtcca cgaggcgtag ccgagtctct gcactgaaca ttgtcagatc 15000
ggcccggcgg agtggacacg ctagaccaaa tgtgttctgt gatgacctgc agtaggaaga 15060
cgaataggtg gcctatggca ttattgtacg gaatgataaa cattgcctgc ataaattctt 15120
ttattatata cagccataat gtcagtagca agggagaaaa ggtccaaagt cgcaaaaaat 15180
ttatgagaaa cctttacatg agcctgacgt catcgtttat gcgtaagcgt ttagaagctc 15240
ctactttgaa gagatatttg cgcgataata tctctaatat tttgccaaat gaagtgcctg 15300
gtacatcaga tgacagtact gaagagccag taatgaaaaa acgtacttac tgtacttact 15360

-continued

```
gcccctctaa aataaggcga aaggcaaatg catcgtgcaa aaaatgcaaa aaagttattt  15420
gtcgagagca taatattgat atgtgccaaa gttgtttctg actgactaat aagtataatt  15480
tgtttctatt atgtataagt taagctaatt acttatttta taatacaaca tgactgtttt  15540
taaagtacaa aataagttta tttttgtaaa agagagaatg tttaaaagtt ttgttacttt  15600
atagaagaaa ttttgagttt ttgttttttt ttaataaata aataaacata aataaattgt  15660
ttgttgaatt tattattagt atgtaagtgt aaatataata aaacttaata tctattcaaa  15720
ttaataaata aacctcgata tacagaccga taaaacacat gcgtcaattt tacgcatgat  15780
tatctttaac gtacgtcaca atatgattat ctttctaggg ttaaaatgaa tgtaagcact  15840
ttattaacga aatctttggg aatatttcgc tcatcagcat tttatttgag caggagtccg  15900
agatgcccgg ccgcgccggc catcgagaaa gagagagaga agagaagaga gagaacattc  15960
gagaaagaga gagagaagag aagagagaga acatactccc tatcagtgat agagaagtcc  16020
ctatcagtga tagagatgtc cctatcagtg atagagagtt ccctatcagt gatagagacg  16080
tccctatcag tgatagagaa gtccctatca gtgatagaga gatccctatc agtgatagag  16140
atttccctat cagtgataga gaggtcccta tcagtgatag agacttccct atcagtgata  16200
gagaaatccc tatcagtgat agagacatcc ctatcagtga tagagaactc cctatcagtg  16260
atagagacct ccctatcagt gatagagatc gatccgtcta cctgagcgat atataaacta  16320
atgcctgttg caattgttca gtcagtcacg agtttgttac cactgcgaca agctagcaac  16380
caccatggcg gtaattctaa ttacttacta aatatagtga tatttaaaaa tgctatgaga  16440
tcttgaggcg aacttaaatg agacaaggtg ttagcttgct caaatgacgc accaatcaac  16500
ttaccaagat aatttggagc aatatggaat attttcttgt caaagaacta caatcaacat  16560
gcaactggta taataaagtg agtataaagt agaaaggtgc ggtataatat ttttctctaa  16620
agtattaagg taagttttta aaaataattt aataattttt cagagtgtgc agtattagtg  16680
tctaaaagta ttgcaatctt tgtgttttaa aaatttgtgc agaatatcaa aaaataggac  16740
gacctattgt tagtaatatt atgtatattt acttattttc aaataaataa aattattttc  16800
tagcctttag aaacagcctt atactacaat caacaaacca taaatactcc ctgcaacaat  16860
tacaaagcaa cacaaacaac aatcaacatt ccatgaactc ggacaatttg gaaattgata  16920
tcttctggca catgcggatt acaacaatca actcaaacct attagatgat gtaaataaat  16980
ataaaccttc atattcaata acttaattcg tgatagaaat ttagagttaa ttactgttta  17040
atcgaaattt gaacgtctcg tttgaattca ctttaacgtt tgaaagatga tctttaaata  17100
gtgactggag acttaaattt taatcttttt aattaaataa tctaacaaag ttctttctta  17160
ttctaatctt aatatataat cttgttttaa aatttgaatt aaacttattt cgttgagtaa  17220
caattaaatg atttgaatcg taaaaaatat cattataatt attcaacaaa aagctgaagg  17280
ctgcgatgaa aaattgttga tatataaatc aaatttattt ttataaatca ctaatagtga  17340
cattaaccgt attcacaggt ggccttctac atcccggatc aggccaccct gctgcgcgag  17400
gccgagcagc gcgagcagca gatcctgcgc ctgcgcgaga gccagtggcg cttcctggcc  17460
accgtggtgc tggagaccct gcgccagtac accagctgcc acccgcgcac cggccgccgc  17520
agcggccgtt accgccgtcc gagccagtaa caccggtgat cataatcagc cataccacat  17580
ttgtagaggt tttacttgct ttaaaaaacc tcccacacct ccccctgaac ctgaaacata  17640
aaatgaatgc aattgttgtt gttaacttgt ttattgcagc ttataatggt tacaaataaa  17700
gcaatagcat cacaaatttc acaaataaag catttttttc actgcattct agttgtggtt  17760
```

tgtccaaact catcaatgta tcttaacgcg agtttaggcg cg 17802

<210> SEQ ID NO 56
<211> LENGTH: 15134
<212> TYPE: DNA
<213> ORGANISM: artificial
<220> FEATURE:
<223> OTHER INFORMATION: Sequence of pLA3242-Crtra intron-reaperKR construct.

<400> SEQUENCE: 56
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gaactaccca ccgtactcgt caattccaag ggcatcggta 960
aacatctgct caaactcgaa gtcggccata tccagagcgc cgtagggggc ggagtcgtgg 1020
ggggtaaatc ccggacccgg ggaatccccg tcccccaaca tgtccagatc gaaatcgtct 1080
agcgcgtcgg catgcgccat cgccacgtcc tcgccgtcta agtggagctc gtcccccagg 1140
ctgacatcgg tcgggggggc cgtcgacagt ctgcgcgtgt gtcccgcggg gagaaaggac 1200
aggcgcggag ccgccagccc cgcctcttcg gggcgtcgt cgtccgggag atcgagcagg 1260
ccctcgatgg tagacccgta attgtttttc gtacgcgcgc ggctgtacgc ggggcccgag 1320
cccgactcgc atttcagttg cttttccaat ccgcagataa tcagctccaa gccgaacagg 1380
aatgccggct cggctccttg atgatcgaac agctcgattg cctgacgcag cagtgggggc 1440
atcgaatcgg ttgttggggt ctcgcgctcc tcttttgcga cttgatgctc ttggtcctcc 1500
agcacgcagc ccagggtaaa gtgaccgacg gcgctcagag cgtagagagc attttccagg 1560
ctgaagcctt gctggcacag gaacgcgagc tggttctcca gtgtctcgta ttgcttttcg 1620
gtcgggcgcg tgccgagatg gactttggca ccgtctcggt gggacagcag agcgcagcgg 1680
aacgacttgg cgttattgcg gaggaagtcc tgccaggact cgccttccaa cgggcaaaaa 1740
tgcgtgtggt ggcggtcgag catctcgatg gccagggcat ccagcagcgc ccgcttattc 1800
ttcacgtgcc agtagagggt gggctgctcc acgcccagct tctgcgccaa cttgcgggtc 1860
gtcagtccct caatgccaac ttcgttcaac agctccaacg cggagttgat gactttggac 1920
ttatccaggc ggctgaccta tagataccat agatgtatgg attagtatca tatacataca 1980

-continued

```
aaggctattt ttgggacata ttaatattaa caatttccgt gatagttttc accatttttg   2040
ttgaatgtta cgttgaaaat ttaaatttgt tttaaattaa ttttaccagt catgtgttct   2100
taaaagtttt tatgattgaa acggcataaa gtggttcaaa aatttatcaa gaaaggcttt   2160
ccttttttaa atcttatctt tttctcttaa aaatcactag tcaattcatt attaatttgt   2220
taacttgaat ttggaatgtc tatttacttt cagataaatt aaagcaagaa acttaatatt   2280
cgaaaaaaat tgattctaaa tggaatttca cttgatcttc atgtatgcat atcaattttt   2340
atttacattg tataataagt ttcgagttga ttgttgtaat ccacaggtgt cccagagaat   2400
taaattccaa attacccaag tttattgaat gttgattgta gtttcagttg ctttgttgct   2460
gcaacaatgg cttgttgatt gtagatattt tccctttcct tggtttactt attacataga   2520
ctgaaaaaga ggtttacttt tttgatactt atgaaaaatt tctattagtg attactaacc   2580
aatcgctata tgtttactag aaaacaaata aactctttac attaacattc aataatgttt   2640
gctctgtaac cgacaattga aggcgttaca gcaacagtaa tataactagc ttcttaaccc   2700
tcatctatta accccatcgt ttaaaacact atgttaaatg gtctaacaaa tctagatact   2760
aatagatgtc ttattactta gcagccacag ctgcaacatc caagacaatt tttgaaactt   2820
cttattgagc tcttggcagc agaaatgttg gtatttttca cagctttctg aaagaccggc   2880
accttcctcc ggttcccgtt tctgaattca agaggatttc cgacccccaa ttaatcccga   2940
aacaaataag gtatattcaa aatgatggaa aagtcatggc tgctgacctt atttttattc   3000
ctattgatag aatattattc cccttttaaa tacactgtac taagaggtcc ggctataatt   3060
ttactcactt gtcgattatc ccatagaatg ttgattgtag ttggttgctt ttccaggtga   3120
gagttgatca agtcacaaaa gttagcgtgt gttgattgta gatttgaagg taaaataatt   3180
tttgcaccca ttcatcgggt aaaacgttct ccatagaata catttccatc gataattgat   3240
aacttatgaa tttcaaagaa aaaaatatgc ttttaaaatt accatggtgg ctagcgcaga   3300
ttgtttagct tgttcagctg cgcttgttta tttgcttagc tttcgcttag cgacgtgttc   3360
actttgcttg tttgaattga attgtcgctc cgtagacgaa gcgcctctat ttatactccg   3420
gcgctcgttt tcgagtttac cactccctat cagtgataga gaaaagtgaa agtcgagttt   3480
accactccct atcagtgata gagaaaagtg aaagtcgagt ttaccactcc ctatcagtga   3540
tagagaaaag tgaaagtcga gtttaccact ccctatcagt gatagagaaa agtgaaagtc   3600
gagtttacca ctccctatca gtgatagaga aaagtgaaag tcgagtttac cactccctat   3660
cagtgataga gaaaagtgaa agtcgagttt accactccct atcagtgata gagaaaagtg   3720
aaagtcgaaa cctggcgcgc ctaaactcgc gttaagatac attgatgagt ttggacaaac   3780
cacaactaga atgcagtgaa aaaaatgctt tatttgtgaa atttgtgatg ctattgcttt   3840
atttgtaacc attataagct gcaataaaca agttaacaac aacaattgca ttcattttat   3900
gtttcaggtt cagggggagg tgtgggaggt tttttaaagc aagtaaaacc tctacaaatg   3960
tggtatggct gattatgatc accggtgtta ctggctcgga cggcggtaac ggccgctgcg   4020
gcggccggtg cgcgggtggc agctggtgta ctggcgcagg gtctccagca ccacggtggc   4080
caggaagcgc cactggctct cgcgcaggcg caggatctgc tgctcgcgct gctcggcctc   4140
gcgcagcagg gtggcctgat ccgggatgta gaaggccacc taaagatacc atggatgtat   4200
gaattagtat catatacata taaatgcttt tttttttggc atattaatgt taaaaatatc   4260
aacaatttcc gtgatagttt ttaccatttt tgttgaatgt ttactttgaa aacttaaata   4320
```

-continued

```
tttttaact aattttacca gtcatgtgtt attaaaagta tttatgaata aaactgcaag   4380
taaagcgttt caaaaattta tcaagtaaaa ctttactttt tttaaatctt aactgtcaat   4440
tcattattaa tttattaatt taaatttgca atgtctattt actttaagac aaattaaagc   4500
aagaaactaa atattcgaat caattctttt ttaaatgaaa ttttacttca tcatcatgta   4560
tgtgtgtatc aatttttatt tacattgtat aataagtttc gagttgattg ttgtaatccg   4620
caggtgtccc gaagtattaa attccgaatt cccaagttta ttgaatgttg attgtagttt   4680
cagttgtttt gttattgcaa caatggcttg ttgattggag atattttcct tttccttggt   4740
ttacttacta catagactga aaaagatgtt tgactttttt gatactattg taaaatttct   4800
attagtgatt actaaccaat cgctataagt ttaatagaaa acaaataaac tctttgcatc   4860
cagatatacc tagcttctta acccttatct attaactcca ttgcttgtaa caaatctaga   4920
tattaataga tgtctaatta cttagcaaaa cttctttttg attaagcagc cacagctgtc   4980
gattttggtc atatttaaag gaaataaatg cgtttaaaat aataattaat ataagttttg   5040
aaacttttta ctaacacttg gcagcaggaa gtaggtgttt ttcacagctt tctgaaccac   5100
cggcaccttc cccggtctcc gttgtcggag ttcagcagga tttccggccc ccaattaacc   5160
ccgaaacaaa acatgtctta ttaataaggt gtattcaaaa tagtgggaat gtcatgactg   5220
ctgaccttat ttttattcct attgtaagtg ttccggctat aattttactc acttgtccat   5280
tatcccatag aatgttatgt tgattgtagt tgtttgcttt tccaggtgag agttgatcaa   5340
gtcgcaaaag ttagcgtgtg ttgattgtag atttgaaggt aaaataattt tgtacacatt   5400
catcaggcaa aacgttctcc atcgaataaa cttccatcga taattgatag cttatgaatt   5460
tcaaaaaaaa atatgctttt aaaattaccg ccatggtggt tgctagcttg tcgcagtggt   5520
aacaaactcg tgactgactg aacaattgca acaggcatta gtttatatat cgctcaggta   5580
gacggatcga tctctatcac tgatagggag gtctctatca ctgataggga gttctctatc   5640
actgataggg atgtctctat cactgatagg gatttctcta tcactgatag ggaagtctct   5700
atcactgata gggacctctc tatcactgat agggaaatct ctatcactga tagggatctc   5760
tctatcactg atagggactt ctctatcact gatagggacg tctctatcac tgatagggaa   5820
ctctctatca ctgataggga catctctatc actgataggg acttctctat cactgatagg   5880
gagtatgttc tctctcttct cttctctctc tctttctcga atgttctctc tcttctcttc   5940
tctctctctt tctcgatggc cggcctggct taattaactc gcgttaagat acattgatga   6000
gtttggacaa accacaacta gaatgcagtg aaaaaaatgc tttatttgtg aaatttgtga   6060
tgctattgct ttatttgtaa ccattataag ctgcaataaa caagttaaca acaacaattg   6120
cattcatttt atgtttcagg ttcaggggga ggtgtgggag gtttttttaaa gcaagtaaaa   6180
cctctacaaa tgtggtatgg ctgattatga tcagttatct agatccggtg gatcttacgg   6240
gtcctccacc ttccgctttt tcttgggtcg agatctgagt ccggaatcct cgtcgctacc   6300
gatggcgctg gtgatgcggg gcacgctgtg ggcgtaggtc acctcgcgct ggcacacgtg   6360
gtcgcgcttg tcgctggtgt ccctcatctg cttggtgatg atggtcacga agtgggggcc   6420
ggggatcttg atggcgcggc tgccgttgaa ggtcatcttg ctgtcgaagt ggcccatcat   6480
caggccgccg tcggcggtgg tgaagccgat gaaggccagc tggcgcacgg cgttggggcc   6540
gtgggggaac atgtgggtct cgttgggcag gatgtccacc agctggtcgc gcatgatggg   6600
gccgtcgggc tggaagccgt cgcagttcac ggtgatgcgg ctgaccacgc aggtgccgtc   6660
cagctcgtag gtgtggtggc tggtcatggt gccgtcgttc tcgaagcgca cggtgcggtc   6720
```

gatgctcagg ccctcgggga agcactcctg ggcgaagtgg ctgatgccgt tggggtagcg 6780
ggcgaagaag ggctcgccgt actggatcag gtggcagatg ggcttccagc tcatgggcag 6840
cttgccggtc tcgcacacgg cgtgcacgtt gaagtcgccg tgggggaact tgctgctgcc 6900
gtcggccacg atggtgaact tctggccgtt cacctcgccg tcgatgaaga ttttgaaggt 6960
catgtcgctc tggaacaggg cggggccgcc ctctgaacca tcctcgtcca tggtggcgac 7020
cggtttgcgc ttcttcttgg gtggggtggg atctcccatg gtggcctgaa tctcaacttg 7080
cacctgaagg tagtgcagca aggatgagca aaagggaaga acccagaaaa gaacgggaaa 7140
acttacccca attagaattg cttgtcgccg ccagtgtcaa cttgcaactg aaacaatatc 7200
caacatgaac gtcaatttat actgccctaa tggcgaacac gataacaata tttcttttat 7260
tatgccctct aaaaccaacg cggttatcgt ttatttattc aaattagata tagaacatcc 7320
gccgacatac aatgttaatg caaaaacgcg tttggtgagc ggatacgaaa acagtcggcc 7380
gataaacatt aatctgaggt cgataacacc gtccttgaac ggaacacgag gagcgtacgt 7440
gatcagctgc attcgcgcgc cgcgccttta tcgagattta tttgcataca acaagtacac 7500
tgcgccgttg ggatttgtgg taacgcgcac acatgcagag ctgcaagtgt ggcacatttt 7560
gtctgtgcgc aaaacctttg aagccaaaag tacgaggtcc gttacgggca tgctagcgca 7620
cacggacaat ggacccgaca aattctacgc caaggattta atgataatgt cgggcaacgt 7680
atccgttcat tttatcaata acctacaaaa atgtcgcgcg catcacaaag acatcgatat 7740
atttaaacat ttatgtcccg aactgcaaat cgataatagt gttgtgcaac ctcgagcgtc 7800
cgtttgattt aacgtatagc ttgcaaatga attatttaat tatcaatcat gttttacgcg 7860
tagaattcta cccgtaaagc gagtttagtt atgagccatg tgcaaaacat gacatcagct 7920
tttattttta taacaaatga catcatttct tgattgtgtt ttacacgtag aattctactc 7980
gtaaagcgag ttcagttttg aaaaacaaat gacatcatct tttgattgt gctttacaag 8040
tagaattcta cccgtaaatc aagttcggtt ttgaaaaaca aatgagtcat attgtatgat 8100
atcatattgc aaaacaaatg actcatcaat cgatcgtgcg ttacacgtag aattctactc 8160
gtaaagcgag tttatgagcc gtgtgcaaaa catgacatca tctcgatttg aaaaacaaat 8220
gacatcatcc actgatcgtg cattacaagt agaattctac tcgtaaagcc agttcggtta 8280
tgagccgtgt acaaaacatg acatcagatt atgactcata cttgattgtg ttttacgcgt 8340
agaattctac tcgtaaagcc agttcaattt taaaaacaaa tgacatcatc caaattaata 8400
aatgacaagc aatgggtacc atgcggccgc accgaaatcg taattcacgg catcattaca 8460
aaatatttg acgttttgga cctcgtccct aatgacacca taacggtggc cttgaagtat 8520
atttaaccct agaaagatag tctgcgtaaa attgacgcat gcattcttga aatattgctc 8580
tctctttcta aatagcgcga atccgtcgct gtgcatttag gacatctcag tcgccgcttg 8640
gagctcccgt gaggcgtgct tgtcaatgcg gtaagtgtca ctgattttga actataacga 8700
ccgcgtgagt caaaatgacg catgattatc ttttacgtga cttttaagat ttaactcata 8760
cgataattat attgttattt catgttctac ttacgtgata acttattata tatatatttt 8820
cttgttatag atatcgtgac taatatataa taaaatgggt agttctttag acgatgagca 8880
tatcctctct gctcttctgc aaagcgatga cgagcttgtt ggtgaggatt ctgacagtga 8940
aatatcagat cacgtaagtg aagatgacgt ccaggaaatc tggccggccg caaccattgt 9000
gggaaccgtg cgatcaaaca aacgcgagat accggaagta ctgaaaaaca gtcgctccag 9060

-continued

```
gccagtggga acatcgatgt tttgttttga cggacccctt actctcgtct catataaacc   9120
gaagccagct aagatggtat acttattatc atcttgtgat gaggatgctt ctatcaacga   9180
aagtaccggt aaaccgcaaa tggttatgta ttataatcaa actaaaggcg gagtggacac   9240
gctagaccaa atgtgttctg tgatgacctg cagtaggaag acgaataggt ggcctatggc   9300
attattgtac ggaatgataa acattgcctg cataaattct tttattatat acagccataa   9360
tgtcagtagc aagggagaaa aggtccaaag tcgcaaaaaa tttatgagaa acctttacat   9420
gagcctgacg tcatcgttta tgcgtaagcg tttagaagct cctactttga agagatattt   9480
gcgcgataat atctctaata ttttgccaaa tgaagtgcct ggtacatcag atgacagtac   9540
tgaagagcca gtaatgaaaa aacgtactta ctgtacttac tgcccctcta aaataaggcg   9600
aaaggcaaat gcatcgtgca aaaaatgcaa aaaagttatt tgtcgagagc ataatattga   9660
tatgtgccaa agttgtttct gactgactaa taagtataat ttgtttctat tatgtataag   9720
ttaagctaat tacttatttt ataatacaac atgactgttt ttaaagtaca aaataagttt   9780
atttttgtaa aagagagaat gtttaaaagt tttgttactt tatagaagaa attttgagtt   9840
tttgtttttt tttaataaat aaataaacat aaataaattg tttgttgaat ttattattag   9900
tatgtaagtg taaatataat aaaacttaat atctattcaa attaataaat aaacctcgat   9960
atacagaccg ataaaacaca tgcgtcaatt ttacgcatga ttatctttaa cgtacgtcac  10020
aatatgatta tctttctagg gttaaataat agtttctaat tttttatta ttcagcctgc  10080
tgtcgtgaat accgtatatc tcaacgctgt ctgtgagatt gtcgtattct agccttttta  10140
gtttttcgct catcgacttg atattgtccg acacattttc gtcgatttgc gttttgatca  10200
aagacttgag cagagacacg ttaatcaact gttcaaattg atccatatta acgatatcaa  10260
cccgatgcgt atatggtgcg taaaatatat tttttaaccc tcttatactt tgcactctgc  10320
gttaatacgc gttcgtgtac agacgtaatc atgttttctt ttttggataa aactcctact  10380
gagtttgacc tcatattaga ccctcacaag ttgcaaaacg tggcattttt taccaatgaa  10440
gaatttaaag ttattttaaa aaatttcatc acagatttaa agaagaacca aaaattaaat  10500
tatttcaaca gtttaatcga ccagttaatc aacgtgtaca cagacgcgtc ggcaaaaaac  10560
acgcagcccg acgtgttggc taaaattatt aaatcaactt gtgttatagt cacggatttg  10620
ccgtccaacg tgttcctcaa aaagttgaag accaacaagt ttacggacac tattaattat  10680
ttgattttgc cccacttcat tttgtgggat cacaattttg ttatatttta aacaaagctt  10740
ggcactggcc gtcgttttac aacgtcgtga ctgggaaaac cctggcgtta cccaacttaa  10800
tcgccttgca gcacatcccc ctttcgccag ctggcgtaat agcgaagagg cccgcaccga  10860
tcgcccttcc caacagttgc gcagcctgaa tggcgaatgg cgcctgatgc ggtattttct  10920
ccttacgcat ctgtgcggta tttcacaccg catatggtgc actctcagta caatctgctc  10980
tgatgccgca tagttaagcc agccccgaca cccgccaaca cccgctgacg cgccctgacg  11040
ggcttgtctg ctcccggcat ccgcttacag acaagctgtg accgtctccg ggagctgcat  11100
gtgtcagagg ttttcaccgt catcaccgaa acgcgcgaga cgaaagggcc tcgtgatacg  11160
cctattttta taggttaatg tcatgataat aatggtttct tagacgtcag gtggcacttt  11220
tcggggaaat gtgcgcggaa cccctatttg tttatttttc taaatacatt caaatatgta  11280
tccgctcatg agacaataac cctgataaat gcttcaataa tattgaaaaa ggaagagtat  11340
gagtattcaa catttccgtg tcgcccttat tccctttttt gcggcatttt gccttcctgt  11400
ttttgctcac ccagaaacgc tggtgaaagt aaaagatgct gaagatcagt tgggtgcacg  11460
```

-continued

```
agtgggttac atcgaactgg atctcaacag cggtaagatc cttgagagtt ttcgccccga  11520
agaacgtttt ccaatgatga gcacttttaa agttctgcta tgtggcgcgg tattatcccg  11580
tattgacgcc gggcaagagc aactcggtcg ccgcatacac tattctcaga atgacttggt  11640
tgagtactca ccagtcacag aaaagcatct tacggatggc atgacagtaa gagaattatg  11700
cagtgctgcc ataaccatga gtgataacac tgcggccaac ttacttctga caacgatcgg  11760
aggaccgaag gagctaaccg cttttttgca caacatgggg gatcatgtaa ctcgccttga  11820
tcgttgggaa ccggagctga atgaagccat accaaacgac gagcgtgaca ccacgatgcc  11880
tgtagcaatg gcaacaacgt tgcgcaaact attaactggc gaactactta ctctagcttc  11940
ccggcaacaa ttaatagact ggatggaggc ggataaagtt gcaggaccac ttctgcgctc  12000
ggcccttccg gctggctggt ttattgctga taaatctgga gccggtgagc gtgggtctcg  12060
cggtatcatt gcagcactgg ggccagatgg taagccctcc cgtatcgtag ttatctacac  12120
gacggggagt caggcaacta tggatgaacg aaatagacag atcgctgaga taggtgcctc  12180
actgattaag cattggtaac tgtcagacca agtttactca tatatacttt agattgattt  12240
aaaacttcat ttttaattta aaaggatcta ggtgaagatc ctttttgata atctcatgac  12300
caaaatccct taacgtgagt tttcgttcca ctgagcgtca gaccccgtag aaaagatcaa  12360
aggatcttct tgagatcctt tttttctgcg cgtaatctgc tgcttgcaaa caaaaaaacc  12420
accgctacca gcggtggttt gtttgccgga tcaagagcta ccaactcttt ttccgaaggt  12480
aactggcttc agcagagcgc agataccaaa tactgtcctt ctagtgtagc cgtagttagg  12540
ccaccacttc aagaactctg tagcaccgcc tacatacctc gctctgctaa tcctgttacc  12600
agtggctgct gccagtggcg ataagtcgtg tcttaccggg ttggactcaa gacgatagtt  12660
accggataag gcgcagcggt cgggctgaac ggggggttcg tgcacacagc ccagcttgga  12720
gcgaacgacc tacaccgaac tgagatacct acagcgtgag cattgagaaa gcgccacgct  12780
tcccgaaggg agaaaggcgg acaggtatcc ggtaagcggc agggtcggaa caggagagcg  12840
cacgagggag cttccagggg gaaacgcctg gtatctttat agtcctgtcg ggtttcgcca  12900
cctctgactt gagcgtcgat ttttgtgatg ctcgtcaggg gggcggagcc tatggaaaaa  12960
cgccagcaac gcggcctttt tacggttcct ggccttttgc tggccttttg ctcacatgtt  13020
ctttcctgcg ttatcccctg attctgtgga taaccgtatt accgcctttg agtgagctga  13080
taccgctcgc cgcagccgaa cgaccgagcg cagcgagtca gtgagcgagg aagcggaaga  13140
gcgcccaata cgcaaaccgc ctctccccgc gcgttggccg attcattaat gcagctggca  13200
cgacaggttt cccgactgga aagcgggcag tgagcgcaac gcaattaatg tgagttagct  13260
cactcattag gcaccccagg ctttacactt tatgcttccg gctcgtatgt tgtgtggaat  13320
tgtgagcgga taacaatttc acacaggaaa cagctatgac catgattacg aatttcgacc  13380
tgcaggcatg caagcttgca tgcctgcagg tcgacgctcg cgcgacttgg tttgccattc  13440
tttagcgcgc gtcgcgtcac acagcttggc cacaatgtgg tttttgtcaa acgaagattc  13500
tatgacgtgt ttaaagttta ggtcgagtaa agcgcaaatc ttttttaacc ctagaaagat  13560
agtctgcgta aaattgacgc atgcattctt gaaatattgc tctctctttc taaatagcgc  13620
gaatccgtcg ctgtgcattt aggacatctc agtcgccgct tggagctccc gtgaggcgtg  13680
cttgtcaatg cggtaagtgt cactgatttt gaactataac gaccgcgtga gtcaaaatga  13740
cgcatgatta tcttttacgt gacttttaag atttaactca tacgataatt atattgttat  13800
```

ttcatgttct acttacgtga taacttatta tatatatatt ttcttgttat agatatcgtg 13860
actaatatat aataaaatgg gtagttcttt agacgatgag catatcctct ctgctcttct 13920
gcaaagcgat gacgagcttg ttggtgagga ttctgacagt gaaatatcag atcacgtaag 13980
tgaagatgac gtccagagcg atacagaaga agcgtttata gatgaggtac atgaagtgca 14040
gccaacgtca agcggtagtg aaatattaga cgaacaaaat gttattgaac aaccaggttc 14100
ttcattggct tctaacagaa tcttgacctt gccacagagg actattagag gtaagaataa 14160
acattgttgg tcaacttcaa agtccacgag gcgtagccga gtctctgcac tgaacattgt 14220
cagatcggcc cggcggagtg gacacgctag accaaatgtg ttctgtgatg acctgcagta 14280
ggaagacgaa taggtggcct atggcattat tgtacggaat gataaacatt gcctgcataa 14340
attcttttat tatatacagc cataatgtca gtagcaaggg agaaaaggtc caaagtcgca 14400
aaaaatttat gagaaacctt tacatgagcc tgacgtcatc gtttatgcgt aagcgtttag 14460
aagctcctac tttgaagaga tatttgcgcg ataatatctc taatattttg ccaaatgaag 14520
tgcctggtac atcagatgac agtactgaag agccagtaat gaaaaaacgt acttactgta 14580
cttactgccc ctctaaaata aggcgaaagg caaatgcatc gtgcaaaaaa tgcaaaaaag 14640
ttatttgtcg agagcataat attgatatgt gccaaagttg tttctgactg actaataagt 14700
ataatttgtt tctattatgt ataagttaag ctaattactt attttataat acaacatgac 14760
tgtttttaaa gtacaaaata agtttatttt tgtaaaagag agaatgttta aaagttttgt 14820
tactttatag aagaaatttt gagtttttgt tttttttaa taaataaata aacataaata 14880
aattgtttgt tgaatttatt attagtatgt aagtgtaaat ataataaaac ttaatatcta 14940
ttcaaattaa taaataaacc tcgatataca gaccgataaa acacatgcgt caattttacg 15000
catgattatc tttaacgtac gtcacaatat gattatcttt ctagggttaa aatgaatgta 15060
agcactttat taacgaaatc tttgggaata tttcgctcat cagcatttta tttgagcagg 15120
agtccgagat gccc 15134

<210> SEQ ID NO 57
<211> LENGTH: 1403
<212> TYPE: DNA
<213> ORGANISM: artificial
<220> FEATURE:
<223> OTHER INFORMATION: SEQ ID NO. 57 Partial sequence of a male transcript generated in Drosophila melanogaster from LA3077 transformants that differs to the sequence generated in Medfly LA3077 lines. T

<400> SEQUENCE: 57
ggccagatct gttgttatta aacgtagatt tggtaatttt aaaagcatat ttttttcttt 60
gaaattcata agttatcaat tatcgatgga aatgtattct atggagaacg ttttacccga 120
tgaatgggtg caaaaattat tttaccttca aatctacaat caacacacgc taacttttgt 180
gacttgatca actctcacct ggaaaagcaa ccaactacaa tcaacattct atgggataat 240
cgacaagtga gtaaaattat agccggacct cttagtacag tgtatttaaa aggggaataa 300
tattctatca ataggaataa aaataaggtc agcagccatg acttttccat cattttgaat 360
ataccttatt tgtttcggga ttaattgggg gtcggaaatc ctcttgaatt cagaaacggg 420
aaccggagga aggtgccggt ctttcagaaa gctgtgaaaa ataccaacat ttctgctgcc 480
aagagctcaa taagaagttt caaaaattgt cttggatgtt gcagctgtgg ctgctaagta 540
ataagacatc tattagtatc tagatttgtt agaccattta acatagtgtt ttaaacgatg 600

```
gggttaatag atgagggtta agaagctagt tatattactg ttgctgtaac gccttcaatt    660

gtcggttaca gagcaaacat tattgaatgt taatgtaaag agtttatttg ttttctagta    720

aacatatagc gattggttag taatcactaa tagaaatttt tcataagtat caaaaaagta    780

aacctctttt tcagtctatg taataagtaa accaaggaaa gggaaaatat ctacaatcaa    840

caagccattg ttgcagcaac aaagcaactg aaactacaat caacattcaa taaacttggg    900

taatttggaa tttaattctc tgggacacct gtggattaca acaatcaact cgaaacttat    960

tatacaatgt aaataaaaat tgatatgcat acatgaagat caagtgaaat tccatttaga   1020

atcaattttt ttcgaatatt aagtttcttg ctttaattta tctgaaagta aatagacatt   1080

ccaaattcaa gttaacaaat taataatgaa ttgactagtg atttttaaga gaaaaagata   1140

agatttaaaa aaggaaagcc tttcttgata aatttttgaa ccactttatg ccgtttcaat   1200

cataaaaact tttaagaaca catgactggt aaaattaatt taaaacaaat ttaaattttc   1260

aacgtaacat tcaacaaaaa tggtgaaaac tatcacggaa attgttaata ttaatatgtc   1320

ccaaaaatag cctttgtatg tatatgatac taatccatac atctatggta tctataggtg   1380

aaggctcaaa gcctctggct agc                                           1403
```

<210> SEQ ID NO 58
<211> LENGTH: 972
<212> TYPE: DNA
<213> ORGANISM: Bactrocera zonata

<400> SEQUENCE: 58

```
cggtaattct aattacttac taaatatagt gatatttaaa aatgctatga gatcttgagg     60

cgaacttaaa tgagacaagg tgttagcttg ctcaaatgac gcaccaatca acttaccaag    120

ataatttgga gcaatatgga atattttctt gtcaaagaac tacaatcaac atgcaactgg    180

tataataaag tgagtataaa gtagaaaggt gcggtataat atttttctct aaagtattaa    240

ggtaagtttt taaaaataat ttaataattt ttcagagtgt gcagtattag tgtctaaaag    300

tattgcaatc tttgtgtttt aaaaatttgt gcagaatatc aaaaaatagg acgacctatt    360

gttagtaata ttatgtatat ttacttattt tcaaataaat aaaattattt tctagccttt    420

agaaacagcc ttatactaca atcaacaaac cataaatact ccctgcaaca attacaaagc    480

aacacaaaca acaatcaaca ttccatgaac tcggacaatt tggaaattga tatcttctgg    540

cacatgcgga ttacaacaat caactcaaac ctattagatg atgtaaataa atataaacct    600

tcatattcaa taacttaatt cgtgatagaa atttagagtt aattactgtt taatcgaaat    660

ttgaacgtct cgtttgaatt cactttaacg tttgaaagat gatctttaaa tagtgactgg    720

agacttaaat tttaatcttt ttaattaaat aatctaacaa agttctttct tattctaatc    780

ttaatatata atcttgtttt aaaatttgaa ttaaacttat ttcgttgagt aacaattaaa    840

tgatttgaat cgtaaaaaat atcattataa ttattcaaca aaaagctgaa ggctgcgatg    900

aaaaattgtt gatatataaa tcaaatttat ttttataaat cactaatagt gacattaacc    960

gtattcacag gt                                                        972
```

<210> SEQ ID NO 59
<211> LENGTH: 1312
<212> TYPE: DNA
<213> ORGANISM: Ceratitis rosa

<400> SEQUENCE: 59

```
tggtaatttt aaaagcatat ttttttttga aattcataag ctatcaatta tcgatggaag     60
```

```
tttattcgat ggagaacgtt ttgcctgatg aatgtgtaca aaattatttt accttcaaat    120

ctacaatcaa cacacgctaa cttttgcgac ttgatcaact ctcacctgga aaagcaaaca    180

actacaatca acataacatt ctatgggata atggacaagt gagtaaaatt atagccggaa    240

cacttacaat aggaataaaa ataaggtcag cagtcatgac attcccacta ttttgaatac    300

accttattaa taagacatgt tttgtttcgg ggttaattgg gggccggaaa tcctgctgaa    360

ctccgacaac ggagaccggg gaaggtgccg gtggttcaga aagctgtgaa aaacacctac    420

ttcctgctgc caagtgttag taaaaagttt caaaacttat attaattatt attttaaacg    480

catttatttc ctttaaatat gaccaaaatc gacagctgtg gctgcttaat caaaaagaag    540

ttttgctaag taattagaca tctattaata tctagatttg ttacaagcaa tggagttaat    600

agataagggt taagaagcta ggtatatctg gatgcaaaga gtttatttgt tttctattaa    660

acttatagcg attggttagt aatcactaat agaaatttta caatagtatc aaaaaagtca    720

aacatctttt tcagtctatg tagtaagtaa accaaggaaa aggaaaatat ctccaatcaa    780

caagccattg ttgcaataac aaaacaactg aaactacaat caacattcaa taaacttggg    840

aattcggaat ttaatacttc gggacacctg cggattacaa caatcaactc gaaacttatt    900

atacaatgta aataaaaatt gatacacaca tacatgatga tgaagtaaaa tttcatttaa    960

aaaagaattg attcgaatat ttagtttctt gctttaattt gtcttaaagt aaatagacat   1020

tgcaaattta aattaataaa ttaataatga attgacagtt aagatttaaa aaaagtaaag   1080

ttttacttga taaatttttg aaacgcttta cttgcagttt tattcataaa tacttttaat   1140

aacacatgac tggtaaaatt agttaaaaaa tatttaagtt ttcaaagtaa acattcaaca   1200

aaaatggtaa aaactatcac ggaaattgtt gatattttta acattaatat gccaaaaaaa   1260

aaagcattta tatgtatatg atactaattc atacatccat ggtatcttta gg           1312
```

<210> SEQ ID NO 60
<211> LENGTH: 21
<212> TYPE: DNA
<213> ORGANISM: artificial
<220> FEATURE:
<223> OTHER INFORMATION: spl-agdsx-e3 primer

<400> SEQUENCE: 60

```
cgagcccaat ggctgttgga g                                              21
```

<210> SEQ ID NO 61
<211> LENGTH: 22
<212> TYPE: DNA
<213> ORGANISM: artificial
<220> FEATURE:
<223> OTHER INFORMATION: spl-agdsx-m primer

<400> SEQUENCE: 61

```
gtcaaggttc agggcccgat cg                                             22
```

<210> SEQ ID NO 62
<211> LENGTH: 21
<212> TYPE: DNA
<213> ORGANISM: artificial
<220> FEATURE:
<223> OTHER INFORMATION: primer spl-agdsx-e3

<400> SEQUENCE: 62

```
cgagcccaat ggctgttgga g                                              21
```

<210> SEQ ID NO 63
<211> LENGTH: 22
<212> TYPE: DNA
<213> ORGANISM: artificial
<220> FEATURE:
<223> OTHER INFORMATION: spl-agdsx-m primer

<400> SEQUENCE: 63
gtcaaggttc agggcccgat cg 22

<210> SEQ ID NO 64
<211> LENGTH: 20
<212> TYPE: DNA
<213> ORGANISM: artificial
<220> FEATURE:
<223> OTHER INFORMATION: aedesxF1 primer

<400> SEQUENCE: 64
tcaatggctc ctggagaagc 20

<210> SEQ ID NO 65
<211> LENGTH: 25
<212> TYPE: DNA
<213> ORGANISM: artificial
<220> FEATURE:
<223> OTHER INFORMATION: aedesxR5 primer

<400> SEQUENCE: 65
accattcttg cagaagtctt gggac 25

<210> SEQ ID NO 66
<211> LENGTH: 19
<212> TYPE: DNA
<213> ORGANISM: artificial
<220> FEATURE:
<223> OTHER INFORMATION: aedesxR2 primer

<400> SEQUENCE: 66
aacattctcc gcgcacagg 19

<210> SEQ ID NO 67
<211> LENGTH: 23
<212> TYPE: DNA
<213> ORGANISM: artificial
<220> FEATURE:
<223> OTHER INFORMATION: Agexon1 primer

<400> SEQUENCE: 67
gacgctcgct ctggtacagt tcg 23

<210> SEQ ID NO 68
<211> LENGTH: 20
<212> TYPE: DNA
<213> ORGANISM: artificial
<220> FEATURE:
<223> OTHER INFORMATION: Tra (tTAV) seq+ primer

<400> SEQUENCE: 68
cctgccagga ctcgccttcc 20

<210> SEQ ID NO 69
<211> LENGTH: 23
<212> TYPE: DNA
<213> ORGANISM: artificial
<220> FEATURE:
<223> OTHER INFORMATION: Agexon1 primer

<400> SEQUENCE: 69
gacgctcgct ctggtacagt tcg 23

<210> SEQ ID NO 70
<211> LENGTH: 26
<212> TYPE: DNA
<213> ORGANISM: artificial
<220> FEATURE:
<223> OTHER INFORMATION: Exon 3 primer

<400> SEQUENCE: 70
gttgtcgctt tgactggcaa tgtcgc 26

<210> SEQ ID NO 71
<211> LENGTH: 632
<212> TYPE: DNA
<213> ORGANISM: Pectinophora gossypiella

<400> SEQUENCE: 71
gaactgccac aaactgctgg aaaagttcca ctactcctgg gaaatgatgc ccctggtgct 60
ggtcattcta aactacgccg gctccgacct cgacgaggct tctagaaaaa ttgatgaagg 120
gaagatgatc atcaacgagt acgcgaggga gcacaatctg aacatcttcg atggccacga 180
gctgaggaac tcgactcgcc agaaaatgct gagcgaaatt aataatataa gtggtgtact 240
atcgtcgtcc atgaagttat tttgcgaatg atactttgtt ttgtatgtgc tgtgtgttgt 300
gtggactttt gctgtgcgtt gctgtttgcg atggaaggac tattgtgtcg tcgccacgct 360
ggactattcg cacattgggt ggtccaccag tggcggatgt acgagcggtc gctgtgctcg 420
ctcctggagc tgcaagcgcg caaagggacg tactcggtgt gctgctcacc ccgctacgtc 480
atcgcgcccg agtacgcgtc acacctgttg cctctgccgc ttaccacgca gagatcatcc 540
ccgccgcccg cgcacttgta gcgatgcgaa cctgcgccgc gggaagcggc gcaagaaccc 600
gccgatgccc cggcgtcgtc gtcgggtgcc ac 632

<210> SEQ ID NO 72
<211> LENGTH: 222
<212> TYPE: DNA
<213> ORGANISM: Drosophila melanogaster

<400> SEQUENCE: 72
atgcagatct ttgtgaagac tttgaccgga aagaccatca ccctcgaggt agagccatcg 60
gacaccattg agaatgtaaa ggccaagatt caggataagg agggaatccc cccagatcag 120
cagcgtctga tcttcgctgg caagcaactg gaagacggac gcaccctgtc cgattacaac 180
atccagaagg agtccaccct tcacttggtc cttcgtctcc gt 222

<210> SEQ ID NO 73
<211> LENGTH: 74
<212> TYPE: PRT
<213> ORGANISM: Drosophila melanogaster

<400> SEQUENCE: 73

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

```
Gln Leu Glu Asp Gly Arg Thr Leu Ser Asp Tyr Asn Ile Gln Lys Glu
    50                  55                  60

Ser Thr Leu His Leu Val Leu Arg Leu Arg
65                  70


<210> SEQ ID NO 74
<211> LENGTH: 34
<212> TYPE: DNA
<213> ORGANISM: artificial
<220> FEATURE:
<223> OTHER INFORMATION: primer

<400> SEQUENCE: 74

caagcaaagt gaacacgtcg ctaagcgaaa gcta                                34


<210> SEQ ID NO 75
<211> LENGTH: 22
<212> TYPE: DNA
<213> ORGANISM: artificial
<220> FEATURE:
<223> OTHER INFORMATION: primer

<400> SEQUENCE: 75

gcgggtggca gctggtgtac tg                                             22


<210> SEQ ID NO 76
<211> LENGTH: 34
<212> TYPE: DNA
<213> ORGANISM: artificial
<220> FEATURE:
<223> OTHER INFORMATION: primer

<400> SEQUENCE: 76

caagcaaagt gaacacgtcg ctaagcgaaa gcta                                34


<210> SEQ ID NO 77
<211> LENGTH: 24
<212> TYPE: DNA
<213> ORGANISM: artificial
<220> FEATURE:
<223> OTHER INFORMATION: primer

<400> SEQUENCE: 77

gcggaacgac ttggcgttat tgcg                                           24


<210> SEQ ID NO 78
<211> LENGTH: 28
<212> TYPE: DNA
<213> ORGANISM: artificial
<220> FEATURE:
<223> OTHER INFORMATION: primer

<400> SEQUENCE: 78

ggaagggtcc ttacgctata gagcgcag                                       28


<210> SEQ ID NO 79
<211> LENGTH: 31
<212> TYPE: DNA
<213> ORGANISM: artificial
<220> FEATURE:
<223> OTHER INFORMATION: primer

<400> SEQUENCE: 79

ccaggcgaag ttgttattaa gcgtagattt g                                   31
```

<210> SEQ ID NO 80
<211> LENGTH: 33
<212> TYPE: DNA
<213> ORGANISM: artificial
<220> FEATURE:
<223> OTHER INFORMATION: primer

<400> SEQUENCE: 80
cgtcgctttg aaacagaggc tttgagcctt ctc 33

<210> SEQ ID NO 81
<211> LENGTH: 48
<212> TYPE: DNA
<213> ORGANISM: artificial
<220> FEATURE:
<223> OTHER INFORMATION: primer

<400> SEQUENCE: 81
gctagcaacc accatggcgg taattctaat tacttactaa atatagtg 48

<210> SEQ ID NO 82
<211> LENGTH: 41
<212> TYPE: DNA
<213> ORGANISM: artificial
<220> FEATURE:
<223> OTHER INFORMATION: primer

<400> SEQUENCE: 82
ccgggatgta gaaggccacc tgtgaatacg gttaatgtca c 41

<210> SEQ ID NO 83
<211> LENGTH: 31
<212> TYPE: DNA
<213> ORGANISM: artificial
<220> FEATURE:
<223> OTHER INFORMATION: primer

<400> SEQUENCE: 83
cagtcagtca cgagtttgtt accactgcga c 31

<210> SEQ ID NO 84
<211> LENGTH: 22
<212> TYPE: DNA
<213> ORGANISM: artificial
<220> FEATURE:
<223> OTHER INFORMATION: primer

<400> SEQUENCE: 84
gcgggtggca gctggtgtac tg 22

<210> SEQ ID NO 85
<211> LENGTH: 21
<212> TYPE: DNA
<213> ORGANISM: artificial
<220> FEATURE:
<223> OTHER INFORMATION: primer

<400> SEQUENCE: 85
cggagcacat ctgatagaac g 21

<210> SEQ ID NO 86
<211> LENGTH: 23
<212> TYPE: DNA
<213> ORGANISM: artificial
<220> FEATURE:
<223> OTHER INFORMATION: primer

<400> SEQUENCE: 86
cgcggctgta ggcgctgccg ctc 23

<210> SEQ ID NO 87
<211> LENGTH: 31
<212> TYPE: DNA
<213> ORGANISM: artificial
<220> FEATURE:
<223> OTHER INFORMATION: primer

<400> SEQUENCE: 87
ccaggcgaag ttgttattaa gcgtagattt g 31

<210> SEQ ID NO 88
<211> LENGTH: 33
<212> TYPE: DNA
<213> ORGANISM: artificial
<220> FEATURE:
<223> OTHER INFORMATION: primer

<400> SEQUENCE: 88
cgtcgctttg aaacagaggc tttgagcctt ctc 33

<210> SEQ ID NO 89
<211> LENGTH: 52
<212> TYPE: DNA
<213> ORGANISM: artificial
<220> FEATURE:
<223> OTHER INFORMATION: primer

<400> SEQUENCE: 89
gctagcaacc accatggcgg taattttaaa agcatatttt tttttgaaat tc 52

<210> SEQ ID NO 90
<211> LENGTH: 41
<212> TYPE: DNA
<213> ORGANISM: artificial
<220> FEATURE:
<223> OTHER INFORMATION: primer

<400> SEQUENCE: 90
ccgggatgta gaaggccacc taaagatacc atggatgtat g 41

<210> SEQ ID NO 91
<211> LENGTH: 31
<212> TYPE: DNA
<213> ORGANISM: artificial
<220> FEATURE:
<223> OTHER INFORMATION: primer

<400> SEQUENCE: 91
cagtcagtca cgagtttgtt accactgcga c 31

<210> SEQ ID NO 92
<211> LENGTH: 22
<212> TYPE: DNA
<213> ORGANISM: artificial
<220> FEATURE:
<223> OTHER INFORMATION: primer

<400> SEQUENCE: 92
gcgggtggca gctggtgtac tg 22

<210> SEQ ID NO 93

<211> LENGTH: 21
<212> TYPE: DNA
<213> ORGANISM: artificial
<220> FEATURE:
<223> OTHER INFORMATION: primer

<400> SEQUENCE: 93
gttgcaagtt gacactggcg g 21

<210> SEQ ID NO 94
<211> LENGTH: 23
<212> TYPE: DNA
<213> ORGANISM: artificial
<220> FEATURE:
<223> OTHER INFORMATION: primer

<400> SEQUENCE: 94
aggtgtggga ggttttttaa agc 23

<210> SEQ ID NO 95
<211> LENGTH: 52
<212> TYPE: DNA
<213> ORGANISM: artificial
<220> FEATURE:
<223> OTHER INFORMATION: primer

<400> SEQUENCE: 95
cctgtaatac gactcactat agggcgtttt tttttttttt tttttttttt tt 52

<210> SEQ ID NO 96
<211> LENGTH: 33
<212> TYPE: DNA
<213> ORGANISM: artificial
<220> FEATURE:
<223> OTHER INFORMATION: primer

<400> SEQUENCE: 96
gcaaacggca atcagacggg cccaggctca gga 33

<210> SEQ ID NO 97
<211> LENGTH: 28
<212> TYPE: DNA
<213> ORGANISM: artificial
<220> FEATURE:
<223> OTHER INFORMATION: primer

<400> SEQUENCE: 97
cctgtaatac gactcactat agggcgtt 28

<210> SEQ ID NO 98
<211> LENGTH: 37
<212> TYPE: DNA
<213> ORGANISM: artificial
<220> FEATURE:
<223> OTHER INFORMATION: primer

<400> SEQUENCE: 98
gggatcgagc tagatcggcc tgagccgcca gtggtga 37

<210> SEQ ID NO 99
<211> LENGTH: 28
<212> TYPE: DNA
<213> ORGANISM: artificial
<220> FEATURE:
<223> OTHER INFORMATION: primer

<400> SEQUENCE: 99
cctgtaatac gactcactat agggcgtt 28

<210> SEQ ID NO 100
<211> LENGTH: 32
<212> TYPE: DNA
<213> ORGANISM: artificial
<220> FEATURE:
<223> OTHER INFORMATION: primer

<400> SEQUENCE: 100
cgctccatgg gatcggcgag ctgcgactcc gt 32

<210> SEQ ID NO 101
<211> LENGTH: 27
<212> TYPE: DNA
<213> ORGANISM: artificial
<220> FEATURE:
<223> OTHER INFORMATION: primer

<400> SEQUENCE: 101
gcaacaacca gcggtgtccc ttgaaac 27

<210> SEQ ID NO 102
<211> LENGTH: 28
<212> TYPE: DNA
<213> ORGANISM: artificial
<220> FEATURE:
<223> OTHER INFORMATION: primer

<400> SEQUENCE: 102
cctgtaatac gactcactat agggcgtt 28

<210> SEQ ID NO 103
<211> LENGTH: 28
<212> TYPE: DNA
<213> ORGANISM: artificial
<220> FEATURE:
<223> OTHER INFORMATION: primer

<400> SEQUENCE: 103
gctagtggag aactgccaca aactgctg 28

<210> SEQ ID NO 104
<211> LENGTH: 34
<212> TYPE: DNA
<213> ORGANISM: artificial
<220> FEATURE:
<223> OTHER INFORMATION: primer

<400> SEQUENCE: 104
caagcaaagt gaacacgtcg ctaagcgaaa gcta 34

<210> SEQ ID NO 105
<211> LENGTH: 25
<212> TYPE: DNA
<213> ORGANISM: artificial
<220> FEATURE:
<223> OTHER INFORMATION: primer

<400> SEQUENCE: 105
gccctcgatg gtagacccgt aattg 25

<210> SEQ ID NO 106
<211> LENGTH: 14874
<212> TYPE: DNA

<213> ORGANISM: artificial
<220> FEATURE:
<223> OTHER INFORMATION: LA1172 nucleotide sequence, including plasmid
      backbone

<400> SEQUENCE: 106
gggctggccg caaccattgt gggaaccgtg cgatcaaaca aacgcgagat accggaagta 60
ctgaaaaaca gtcgctccag gccagtggga acatcgatgt tttgttttga cggacccctt 120
actctcgtct catataaacc gaagccagct aagatggtat acttattatc atcttgtgat 180
gaggatgctt ctatcaacga aagtaccggt aaaccgcaaa tggttatgta ttataatcaa 240
actaaaggcg gagtggacac gctagaccaa atgtgttctg tgatgacctg cagtaggaag 300
acgaataggt ggcctatggc attattgtac ggaatgataa acattgcctg cataaattct 360
tttattatat acagccataa tgtcagtagc aagggagaaa aggtccaaag tcgcaaaaaa 420
tttatgagaa acctttacat gagcctgacg tcatcgttta tgcgtaagcg tttagaagct 480
cctactttga agagatattt gcgcgataat atctctaata ttttgccaaa tgaagtgcct 540
ggtacatcag atgacagtac tgaagagcca gtaatgaaaa aacgtactta ctgtacttac 600
tgcccctcta aaataaggcg aaaggcaaat gcatcgtgca aaaaatgcaa aaaagttatt 660
tgtcgagagc ataatattga tatgtgccaa agttgtttct gactgactaa taagtataat 720
ttgtttctat tatgtataag ttaagctaat tacttatttt ataatacaac atgactgttt 780
ttaaagtaca aaataagttt atttttgtaa aagagagaat gtttaaaagt tttgttactt 840
tatagaagaa attttgagtt tttgtttttt tttaataaat aaataaacat aaataaattg 900
tttgttgaat ttattattag tatgtaagtg taaatataat aaaacttaat atctattcaa 960
attaataaat aaacctcgat atacagaccg ataaaacaca tgcgtcaatt ttacgcatga 1020
ttatctttaa cgtacgtcac aatatgatta tctttctagg gttaaataat agtttctaat 1080
ttttttatta ttcagcctgc tgtcgtgaat accgtatatc tcaacgctgt ctgtgagatt 1140
gtcgtattct agccttttta gtttttcgct catcgacttg atattgtccg acacattttc 1200
gtcgatttgc gttttgatca aagacttgag cagagacacg ttaatcaact gttcaaattg 1260
atccatatta acgatatcaa cccgatgcgt atatggtgcg taaaatatat tttttaaccc 1320
tcttatactt tgcactctgc gttaatacgc gttcgtgtac agacgtaatc atgttttctt 1380
ttttggataa aactcctact gagtttgacc tcatattaga ccctcacaag ttgcaaaacg 1440
tggcattttt taccaatgaa gaatttaaag ttattttaaa aaatttcatc acagatttaa 1500
agaagaacca aaaattaaat tatttcaaca gtttaatcga ccagttaatc aacgtgtaca 1560
cagacgcgtc ggcaaaaaac acgcagcccg acgtgttggc taaaattatt aaatcaactt 1620
gtgttatagt cacggatttg ccgtccaacg tgttcctcaa aaagttgaag accaacaagt 1680
ttacggacac tattaattat ttgattttgc cccacttcat tttgtgggat cacaattttg 1740
ttatatttta aacaaagctt ggcactggcc gtcgttttac aacgtcgtga ctgggaaaac 1800
cctggcgtta cccaacttaa tcgccttgca gcacatcccc ctttcgccag ctggcgtaat 1860
agcgaagagg cccgcaccga tcgcccttcc caacagttgc gcagcctgaa tggcgaatgg 1920
cgcctgatgc ggtattttct ccttacgcat ctgtgcggta tttcacaccg catatatggt 1980
gcactctcag tacaatctgc tctgatgccg catagttaag ccagccccga cacccgccaa 2040
cacccgctga cgcgccctga cgggcttgtc tgctcccggc atccgcttac agacaagctg 2100
tgaccgtctc cgggagctgc atgtgtcaga ggttttcacc gtcatcaccg aaacgcgcga 2160

-continued

```
gacgaaaggg cctcgtgata cgcctatttt tataggttaa tgtcatgata ataatggttt   2220
cttagacgtc aggtggcact tttcggggaa atgtgcgcgg aacccctatt tgtttatttt   2280
tctaaataca ttcaaatatg tatccgctca tgagacaata accctgataa atgcttcaat   2340
aatattgaaa aaggaagagt atgagtattc aacatttccg tgtcgccctt attccctttt   2400
ttgcggcatt ttgccttcct gtttttgctc acccagaaac gctggtgaaa gtaaaagatg   2460
ctgaagatca gttgggtgca cgagtgggtt acatcgaact ggatctcaac agcggtaaga   2520
tccttgagag ttttcgcccc gaagaacgtt ttccaatgat gagcactttt aaagttctgc   2580
tatgtggcgc ggtattatcc cgtattgacg ccgggcaaga gcaactcggt cgccgcatac   2640
actattctca gaatgacttg gttgagtact caccagtcac agaaaagcat cttacggatg   2700
gcatgacagt aagagaatta tgcagtgctg ccataaccat gagtgataac actgcggcca   2760
acttacttct gacaacgatc ggaggaccga aggagctaac cgcttttttg cacaacatgg   2820
gggatcatgt aactcgcctt gatcgttggg aaccggagct gaatgaagcc ataccaaacg   2880
acgagcgtga caccacgatg cctgtagcaa tggcaacaac gttgcgcaaa ctattaactg   2940
gcgaactact tactctagct tcccggcaac aattaataga ctggatggag gcggataaag   3000
ttgcaggacc acttctgcgc tcggcccttc cggctggctg gtttattgct gataaatctg   3060
gagccggtga gcgtgggtct cgcggtatca ttgcagcact ggggccagat ggtaagccct   3120
cccgtatcgt agttatctac acgacgggga gtcaggcaac tatggatgaa cgaaatagac   3180
agatcgctga gataggtgcc tcactgatta agcattggta actgtcagac caagtttact   3240
catatatact ttagattgat ttaaaacttc atttttaatt taaaaggatc taggtgaaga   3300
tcctttttga taatctcatg accaaaatcc cttaacgtga gttttcgttc cactgagcgt   3360
cagaccccgt agaaaagatc aaaggatctt cttgagatcc tttttttctg cgcgtaatct   3420
gctgcttgca aacaaaaaaa ccaccgctac cagcggtggt ttgtttgccg gatcaagagc   3480
taccaactct ttttccgaag gtaactggct tcagcagagc gcagatacca aatactgtcc   3540
ttctagtgta gccgtagtta ggccaccact tcaagaactc tgtagcaccg cctacatacc   3600
tcgctctgct aatcctgtta ccagtggctg ctgccagtgg cgataagtcg tgtcttaccg   3660
ggttggactc aagacgatag ttaccggata aggcgcagcg gtcgggctga acggggggtt   3720
cgtgcacaca gcccagcttg gagcgaacga cctacaccga actgagatac ctacagcgtg   3780
agcattgaga aagcgccacg cttcccgaag ggagaaaggc ggacaggtat ccggtaagcg   3840
gcagggtcgg aacaggagag cgcacgaggg agcttccagg gggaaacgcc tggtatcttt   3900
atagtcctgt cgggtttcgc cacctctgac ttgagcgtcg atttttgtga tgctcgtcag   3960
gggggcggag cctatggaaa aacgccagca acgcggcctt tttacggttc ctggcctttt   4020
gctggccttt tgctcacatg ttctttcctg cgttatcccc tgattctgtg gataaccgta   4080
ttaccgcctt tgagtgagct gataccgctc gccgcagccg aacgaccgag cgcagcgagt   4140
cagtgagcga ggaagcggaa gagcgcccaa tacgcaaacc gcctctcccc gcgcgttggc   4200
cgattcatta atgcagctgg cacgacaggt ttcccgactg gaaagcgggc agtgagcgca   4260
acgcaattaa tgtgagttag ctcactcatt aggcacccca ggctttacac tttatgcttc   4320
cggctcgtat gttgtgtgga attgtgagcg gataacaatt tcacacagga aacagctatg   4380
accatgatta cgaatttcga cctgcaggca tgcaagcttg catgcctgca ggtcgacgct   4440
cgcgcgactt ggtttgccat tctttagcgc gcgtcgcgtc acacagcttg gccacaatgt   4500
ggtttttgtc aaacgaagat tctatgacgt gtttaaagtt taggtcgagt aaagcgcaaa   4560
```

-continued

```
tctttttaa ccctagaaag atagtctgcg taaaattgac gcatgcattc ttgaaatatt   4620
gctctctctt tctaaatagc gcgaatccgt cgctgtgcat ttaggacatc tcagtcgccg   4680
cttggagctc ccgtgaggcg tgcttgtcaa tgcggtaagt gtcactgatt ttgaactata   4740
acgaccgcgt gagtcaaaat gacgcatgat tatcttttac gtgactttta agatttaact   4800
catacgataa ttatattgtt atttcatgtt ctacttacgt gataacttat tatatatata   4860
ttttcttgtt atagatatcg tgactaatat ataataaaat gggtagttct ttagacgatg   4920
agcatatcct ctctgctctt ctgcaaagcg atgacgagct tgttggtgag gattctgaca   4980
gtgaaatatc agatcacgta agtgaagatg acgtccagag cgatacagaa gaagcgttta   5040
tagatgaggt acatgaagtg cagccaacgt caagcggtag tgaaatatta gacgaacaaa   5100
atgttattga acaaccaggt tcttcattgg cttctaacag aatcttgacc ttgccacaga   5160
ggactattag aggtaagaat aaacattgtt ggtcaacttc aaagtccacg aggcgtagcc   5220
gagtctctgc actgaacatt gtcagatcgg ccaggccggc cagatttaaa tgagcggccg   5280
catggtacca tactcggtgg cctccccacc accaactttt ttgcactgca aaaaaacacg   5340
cttttgcacg cgggcccata catagtacaa actctacgtt tcgtagacta ttttacataa   5400
atagtctaca ccgttgtata cgctccaaat acactaccac acattgaacc tttttgcagt   5460
gcaaaaaagt acgtgtcggc agtcacgtag gccggcctta tcgggtcgcg tcctgtcacg   5520
tacgaatcac attatcggac cggacgagtg ttgtcttatc gtgacaggac gccagcttcc   5580
tgtgttgcta accgcagccg gacgcaactc cttatcggaa caggacgcgc ctccatatca   5640
gccgcgcgtt atctcatgcg cgtgaccgga cacgaggcgc ccgtcccgct tatcgcgcct   5700
ataaatacag cccgcaacga tctggtaaac acagttgaac agcatctgtt acagcgacac   5760
aacatgagcc ggtccaacaa cgccaacgcg cccacgccat ccaaccgccg ccgcaacctg   5820
tctctggtgg atcccacccc acccaagaag aagcgcaaac cggtcgccac catggcctcc   5880
tccgagaacg tcatcaccga gttcatgcgc ttcaaggtgc gcatggaggg caccgtgaac   5940
ggccacgagt tcgagatcga gggcgagggc gagggccgcc cctacgaggg ccacaacacc   6000
gtgaagctga aggtgaccaa gggcggcccc ctgcccttcg cctgggacat cctgtccccc   6060
cagttccagt acggctccaa ggtgtacgtg aagcaccccg ccgacatccc cgactacaag   6120
aagctgtcct tccccgaggg cttcaagtgg gagcgcgtga tgaacttcga ggacggcggc   6180
gtggcgaccg tgacccagga ctcctccctg caggacggct gcttcatcta caaggtgaag   6240
ttcatcggcg tgaacttccc ctccgacggc cccgtgatgc agaagaagac catgggctgg   6300
gaggcctcca ccgagcgcct gtacccccgc gacggcgtgc tgaagggcga gacccacaag   6360
gccctgaagc tgaaggacgg cggccactac ctggtggagt tcaagtccat ctacatggcc   6420
aagaagcccg tgcagctgcc cggctactac tacgtggacg ccaagctgga catcacctcc   6480
cacaacgagg actacaccat cgtggagcag tacgagcgca ccgagggccg ccaccacctg   6540
ttcctgagat ctcgacccaa gaaaaagcgg aaggtggagg acccgtaaga tccaccggat   6600
ctagataact gatcataatc agccatacca catttgtaga ggttttactt gctttaaaaa   6660
acctcccaca cctccccctg aacctgaaac ataaaatgaa tgcaattgtt gttgttaact   6720
tgtttattgc agcttataat ggttacaaat aaagcaatag catcacaaat ttcacaaata   6780
aagcattttt ttcactgcat tctagttgtg gtttgtccaa actcatcaat gtatcttaac   6840
gcgagttaat taatccattg ctgggcgagc tgcgccaatc gatgccaacg ccaccctgca   6900
```

-continued

```
tggcgagcgg caggccggcg gctaccatgg gcgtcaccat gccctgaccg cccccggagg   6960
gcagtgaaaa atgtgtgggg ggtggtgggg gctgcgcagg aactgattgt gattatggtt   7020
gtgcccatgg ccatgttgtc caagtccatg gacgtgggca tgcttgttgt agcccaaatc   7080
ggcgtttccg tttccaccag gaaacatctc tgcttgtagt tcgaatatgc tctttaaatc   7140
ccagctgtat tcctcagtta tcgaggtttt cttcacgagt gaaacgaatt ttcgtcgcct   7200
tctacgccat tttcttgctc agcccgtttt gtcattcgca gcgaagcggt aacagcgggt   7260
cgctcatatg acggtatttt ttaatacact tcagctatac tgttatttca aaaacatatt   7320
tcttttgtta ctttttatgc agttcatttg ccaccaaaaa gtagtctttt ggattgattt   7380
atttcaaaaa atggtgtaat tcaagaaatt cagagggcca agtaatatac ttaatgaccg   7440
ttatttaaaa cacactcaag gagatttatt taaacggcta caatggtttt ccaaataact   7500
tatttactgt tgacttctat aaaacatagg tgtatatatt attatttcct tattgagttt   7560
gagataattt taatttccac aatatttttt cttgtgatta acagagaaag tcaaactaca   7620
taacatttat cgggtaaaag tctctatgaa ggtagcggtt aacagtgaag tcgcaaaagt   7680
ggtggccgta cgccaatcga gcgtagtacc cctaacctgc aatattttta gttggttttt   7740
tccgcaatag ccccagtttt ctcaaagagt gcaacaagtg attctgttta tgttttcaac   7800
aacttctctc tgcggaactt aacgtgagcg gacgtatgcg gacgcgccat ggtttaaact   7860
cgctagcact gggaagttga cgttgatata gagccgaatt gaacttcacc gctgcttggt   7920
aattactcta caagttcatt taggagaacc ggattcgaaa gatgattttc cagcgtttag   7980
ctttcagatg gccgcataca ttttgcacca ccaaaccgaa actcactagc gtatccaatc   8040
gttcgttttt tggtgccggt gtgttacgaa ctttagctat caagctaaag caatttgctc   8100
tggtcttccg tgctaaaaag aaaaaaaaac tgtttttttt ttggttttga tatttgcgct   8160
atttttactt gggccttaat tgaacaaact tttgaaagtt tccacagcga aatcgttttc   8220
gacgatgcca tttttggtaa catttgcatt ttcttgctca aattgcttgc aaaacccgtg   8280
aaagacatta atattcgata gtgtcatcca aaatcacgaa aatgattgtt gcaaaacgtt   8340
gaacaattta cacatgtaaa aaacaaccat cgattaatgt ttattcaaac tttttacaag   8400
aagggttatt ctgatcaatg tcaccccgct gatgaatgtt accccggatt acacttctcg   8460
aaaagtggtt caaaatgcta cttgagaatt tttatctgtc aaaggaagca aattcgagtc   8520
gaattaaatg gtatagtcct gaattaggtt tccatttact tacaggtatt ccactaaata   8580
gctggaagat ttattttaca caataatgat aattcgtacc ccaaagagtg tagccctact   8640
tttttctctc tttttttttt gtaaattttc atcgctgcgt gccagcttac cgacatgtcg   8700
cgacagcata aagagcctgt caagagatga agaaaaatga caaggagtca gtggtcaggt   8760
ctctgtatca atatttgacg tcctgacttt ccaatatacc tttccttaaa gagtagagat   8820
catgcgatac gtgaataaat atcgtttgga cttcgaaata gaacataatt taaggtagct   8880
gatcagtagt tgaacatctt cagacttctg ggacaagaag tgtttttttg tttgtagaaa   8940
aggtttttgt taaattatat ttgtaagata attcaatgaa tatatctctg attcagtaat   9000
caatccgtac cacgcaccgt ttaagaaaca ccctgtaggt ttgcatcacg tctcagacaa   9060
aagtgtatcg atgtgcgaac actgcatacc ggcgctttgc aaataatgcc aaatttagat   9120
atgcattaca ttgtcacttc gcaaaacaca cactcccaaa tgcgtcggaa acctcacccg   9180
aacgcacgat cgtaacgcga tcgatcgccg attgattgat cggaattaac tatctcaatc   9240
gatccttcta tggactgatg catgggccgg cacttccgag tataaaaccc cggtaaaccc   9300
```

-continued

```
aaggaatcac tcacaatcgg attttgacgc tcgctctggt acagttcgat acggtctagt   9360
gaaaccgagg ataacgacga aggtttttcc ccattgatcc aggtcggtgt ttatgattgg   9420
tggaaaaaga ctcgagaaaa gttccatcga agccgttgga aatgtgccgt cttcctgtga   9480
cgtcttgtgg atccagttcc ttgttcacgt ctggtgatcg tgtaaaatgt gctgtcttgt   9540
ggcgtcatat gtgttccaga tccagtgatt acgatccgat gtgatgttga tcccttgtga   9600
acgtcttatc ctgttccgtg tgcaccatgc ataatgtcgt attacgtaag ttctgaagtg   9660
aaacagaaga gtgaattgaa agttttttta ttcaacatca acctaaatat ggactttact   9720
ttccaagaaa attatgcctg atcaactgtg gatagttaca aaaaaaaaag gtttattaat   9780
taaattttat gattacataa tgtgttgaaa agaacaactg aaattttaga agaagatctt   9840
ttcgtgcatc aggctttgcc aattaattga tgataaatta tcatagcaaa ttaacgtaga   9900
gactaaaagg tatatcgtca aatagggctt cttttgacac tattttggca ttcttgctct   9960
ttgagaactt gcaaccctaa aatgggatct tcatcagcct agtggttaga ttcagcagct  10020
acaaagcaaa accatgctga agggttcgat tcccggtcgt ttcaggatct tttcgtaatt  10080
gaaatatcct tgactaccct aagtatcatt gtgcttgcca tttacgaata tacatattac  10140
gatatacgaa tgagaaaatg acaactttgg aaaataaagc tctcaatgtt tcaataagaa  10200
ataaatacta catcagtatt gaaggctaat aacaattaca gattagaacc tttaaacatc  10260
atttctgcaa caggctggat aaagtacagt tggaggatta aattatgcga ttttgcaatt  10320
ttttccgatt aaattcatat ttattcctgg tttggttttt acaaaaaaata tttttacatg  10380
acgtttgacc ccgattccct caactttgat tgttatattt ttttttggac aggttgagtt  10440
tgtgggtttt ttcctagtgt tgctttgctt tatgggctct ggttatttaa aattaaaatt  10500
tgacaatctt actacacact ccgaaaaaat catgcgattt tacgtctttt ggatgcacat  10560
aaaagaagcg agccaaatga ggtgaatttg tgtcacattt taaatacgat ggtgtctgat  10620
tcgggaaatg tcaatgatag tgtcattcaa tcataatgtg aattacgtcc gcagtaattt  10680
tcattatttt taagagtgta ctactattta cactacaaaa attttgatac cccagggggg  10740
aacgaggtcc cggatgtcca gctggccaga ttgttggcaa cgagccctgt acctattgat  10800
cgagtcacca aagcactcct caagtgtttt aatctcgacc agacggtgga cctcggttgt  10860
tctcattctc ggagggcgat ttcgcaatca ttagtaccaa ccacatgtcg aagtcgggag  10920
atgttataaa attataacca attattcaaa aaatgacatc attcaatttg aacaaacgtt  10980
cgatagaaat tatatatgat ttcacatgat attaaactac gaagaaaatt ttacataagg  11040
aagtggtata aaacgtaata tgcttaataa aaactttaac ccttttggga ggataatatt  11100
cagaagttct gattcagaac catctctcat gttatgttcg ttttttgttg cttgtccttt  11160
atatgccaca tgaacaataa caccaatatc tatcccattt ccaggaccta acggaccttg  11220
aagcggcgcc aaaacgtgtg acgatgatgc tggtaccctg gcggtaagtt gatcaaagga  11280
aacgcaaagt tttcaagaaa aaacaaaact aatttgattt ataacacctt tagaaaccac  11340
catgggcagc cgcctggata agtccaaagt catcaactcc gcgttggagc tgttgaacga  11400
agttggcatt gagggactga cgacccgcaa gttggcgcag aagctgggcg tggagcagcc  11460
caccctctac tggcacgtga agaataagcg ggcgctgctg gatgccctgg ccatcgagat  11520
gctcgaccgc caccacacgc atttttgccc gttggaaggc gagtcctggc aggacttcct  11580
ccgcaataac gccaagtcgt tccgctgcgc tctgctgtcc caccgagacg gtgccaaagt  11640
```

ccatctcggc acgcgcccga ccgaaaagca atacgagaca ctggagaacc agctcgcgtt 11700
cctgtgccag caaggcttca gcctggaaaa tgctctctac gctctgagcg ccgtcggtca 11760
ctttaccctg ggctgcgtgc tggaggacca agagcatcaa gtcgcaaaag aggagcgcga 11820
gaccccaaca accgattcga tgcccccact gctgcgtcag gcaatcgagc tgttcgatca 11880
tcaaggagcc gagccggcat tcctgttcgg cttggagctg attatctgcg gattggaaaa 11940
gcaactgaaa tgcgagtcgg gctcgggccc cgcgtacagc cgcgcgcgta cgaaaaacaa 12000
ttacgggtct accatcgagg gcctgctcga tctcccggac gacgacgccc ccgaagaggc 12060
ggggctggcg gctccgcgcc tgtcctttct ccccgcggga cacacgcgca gactgtcgac 12120
ggcccccccg accgatgtca gcctgggga cgagctccac ttagacggcg aggacgtggc 12180
gatggcgcat gccgacgcgc tagacgattt cgatctggac atgttggggg acggggattc 12240
cccgggtccg ggatttaccc cccacgactc cgccccctac ggcgctctgg atatggccga 12300
cttcgagttt gagcagatgt ttaccgatgc ccttggaatt gacgagtacg gtgggtagtt 12360
ctagaattgt ccaccgcaag tgcttctaag ccgatcccga ttgtactgat taccataagc 12420
gacattgcca gtgaaagcga caacagcagc atcaaagtac atttgtcata ctgattcggc 12480
tactaccacc atccggaatc agcttgcatc gaacatcaaa tcacgttatt caatgtatct 12540
gtcatccagc tcagacaagt cggagctttt ccagtcgcga aaatctgcga ctccagcgga 12600
aagcaccgaa ccacagagag gactcgtatg aaagccaggg aagaaaccat cattcacctt 12660
gcagcaaata ggaaaaaaaa cggacatctt caacaaacaa aagcccatgc gctaacttgg 12720
tttaggagtt tagtgtgaca ccatgacccc gctgatgatc tttacttagc acaccataac 12780
cacctttatg cgttcgttca tccaaaatct acaggatatc actgcagccg cgagaagaac 12840
tcgtgaacca tcctgttttc ttttttatta tattcttact tttaacttca aattattttc 12900
agtaataaaa cgtctcaaaa taataagttc ataatgagtt taattttacg gaataagaac 12960
aaccatttaa gttattaaat ccttagattt aatggaatta gattgattat atggaaccca 13020
gacttggtaa aaaataaact ccacgttaaa tttctttctg agacttaaaa ttctttcggg 13080
aaagctggga gcaattctcg caccggtgct agggccgcat agtcgacatt tcgagtttac 13140
cactccctat cagtgataga gaaaagtgaa agtcgagttt accactccct atcagtgata 13200
gagaaaagtg aaagtcgagt ttaccactcc ctatcagtga tagagaaaag tgaaagtcga 13260
gtttaccact ccctatcagt gatagagaaa agtgaaagtc gagtttacca ctccctatca 13320
gtgatagaga aaagtgaaag tcgagtttac cactccctat cagtgataga gaaaagtgaa 13380
agtcgagttt accactccct atcagtgata gagaaaagtg aaagtcgagc tcggtacccg 13440
ggtcgaggta ggcgtgtacg gtgggaggcc tatataagca gagctcgttt agtgaaccgt 13500
cagatcgcct ggagacgcca tccacgctgt tttgacctcc atagaagaca ccgggaccga 13560
tccagcctcc gcggccccga attcgagctc ggtacccggg gatccccgct cgaccaccat 13620
gggcgctctc ctgggcctgc ccgaaagcca aacggagctt gataatctta cagaatacaa 13680
cacggcccac aatcggcgca tctcaatgct gggcatcgat gatgatacca atatgcgaaa 13740
gcaaaacgcc ttgaaacagg gacggcgcac tcgaaatgtc acatttaacg atgaggagat 13800
tgtcatcaat cctgaggatg tggatcctaa tgtgggacgc ttcaggaact tggtacaaac 13860
cactgtggtg cccgccaaga gggctcgctg cgacgtcaac cattagtgat aacgcgtcta 13920
gctagagctg agaacttcag ggtgagtttg gggacccttg attgttcttt ctttttcgct 13980
attgtaaaat tcatgttata tggagggggc aaagttttca gggtgttgtt tagaatggga 14040
agatgtccct tgtatcacca tggaccctca tgataatttt gtttctttca ctttctactc 14100
tgttgacaac cattgtctcc tcttattttc ttttcatttt ctgtaacttt ttcgttaaac 14160
tttagcttgc atttgtaacg aatttttaaa ttcacttttg tttatttgtc agattgtaag 14220
tactttctct aatcactttt ttttcaaggc aatcagggta tattatattg tacttcagca 14280
cagttttaga gaacaattgt tataattaaa tgataaggta gaatatttct gcatataaat 14340
tctggctggc gtggaaatat tcttattggt agaaacaact acaccctggt catcatcctg 14400
cctttctctt tatggttaca atgatataca ctgtttgaga tgaggataaa atactctgag 14460
tccaaaccgg gcccctctgc taaccatgtt catgccttct tctctttcct acagctcctg 14520
ggcaacgtgc tggttgttgt gctgtctcat cattttggca aagaattcac tcctcaggtg 14580
caggctgcct atcagaaggt ggtggctggt gtggccaatg ccctggctca caaataccac 14640
tgagatcttt ttccctctgc caaaaattat ggggacatca tgaagcccct tgagcatctg 14700
acttctggct aataaaggaa atttattttc attgcaatag tgtgttggaa tttttttgtgt 14760 ctctcactcg gaaggacata tgggagggca aatcatttaa aacatcagaa tgagtatttg 14820
gtttagagtt tggcaacata tgcccatagc ggccctagcg gcgcgccata gccc 14874

<210> SEQ ID NO 107
<211> LENGTH: 13
<212> TYPE: DNA
<213> ORGANISM: Drosophila sp.

<400> SEQUENCE: 107
tcaataatcg tca 13

<210> SEQ ID NO 108
<211> LENGTH: 13
<212> TYPE: DNA
<213> ORGANISM: Drosophila sp.

<400> SEQUENCE: 108
tcatcaaacg tca 13

<210> SEQ ID NO 109
<211> LENGTH: 13
<212> TYPE: DNA
<213> ORGANISM: Drosophila sp.

<400> SEQUENCE: 109
ttatcgttaa aca 13

<210> SEQ ID NO 110
<211> LENGTH: 13
<212> TYPE: DNA
<213> ORGANISM: Drosophila sp.

<400> SEQUENCE: 110
taaacagtca ata 13

<210> SEQ ID NO 111
<211> LENGTH: 13
<212> TYPE: DNA
<213> ORGANISM: Drosophila sp.

<400> SEQUENCE: 111
tacacgatca gca 13

<210> SEQ ID NO 112
<211> LENGTH: 13
<212> TYPE: DNA
<213> ORGANISM: Drosophila sp.

<400> SEQUENCE: 112
aatacaaaca aca 13

<210> SEQ ID NO 113
<211> LENGTH: 13
<212> TYPE: DNA
<213> ORGANISM: Drosophila sp.

<400> SEQUENCE: 113
tcatcaacaa gca 13

<210> SEQ ID NO 114
<211> LENGTH: 13
<212> TYPE: DNA
<213> ORGANISM: Drosophila sp.

<400> SEQUENCE: 114
tctacaaacc aga 13

<210> SEQ ID NO 115
<211> LENGTH: 13
<212> TYPE: DNA
<213> ORGANISM: Drosophila sp.

<400> SEQUENCE: 115
acatcgattc aca 13

<210> SEQ ID NO 116
<211> LENGTH: 13
<212> TYPE: DNA
<213> ORGANISM: Drosophila sp.

<400> SEQUENCE: 116
cgctcaatca aca 13

<210> SEQ ID NO 117
<211> LENGTH: 13
<212> TYPE: DNA
<213> ORGANISM: Drosophila sp.

<400> SEQUENCE: 117
tctaccataa aaa 13

<210> SEQ ID NO 118
<211> LENGTH: 13
<212> TYPE: DNA
<213> ORGANISM: Drosophila sp.

<400> SEQUENCE: 118
aaatgaatca aca 13

<210> SEQ ID NO 119
<211> LENGTH: 13
<212> TYPE: DNA
<213> ORGANISM: Drosophila sp.

<400> SEQUENCE: 119
acatcgttca acg 13

<210> SEQ ID NO 120
<211> LENGTH: 13
<212> TYPE: DNA
<213> ORGANISM: Drosophila sp.

<400> SEQUENCE: 120
tcttgattca cca 13

<210> SEQ ID NO 121
<211> LENGTH: 13
<212> TYPE: DNA
<213> ORGANISM: Drosophila sp.

<400> SEQUENCE: 121
tctgcagaca aca 13

<210> SEQ ID NO 122
<211> LENGTH: 13
<212> TYPE: DNA
<213> ORGANISM: Drosophila sp.

<400> SEQUENCE: 122
tcttcggtaa tca 13

<210> SEQ ID NO 123
<211> LENGTH: 13
<212> TYPE: DNA
<213> ORGANISM: Drosophila sp.

<400> SEQUENCE: 123
tctataaaca ata 13

<210> SEQ ID NO 124
<211> LENGTH: 13
<212> TYPE: DNA
<213> ORGANISM: Drosophila sp.

<400> SEQUENCE: 124
taaacaataa ata 13

<210> SEQ ID NO 125
<211> LENGTH: 13
<212> TYPE: DNA
<213> ORGANISM: Drosophila sp.

<400> SEQUENCE: 125
taaacaagca aaa 13

<210> SEQ ID NO 126
<211> LENGTH: 13
<212> TYPE: DNA
<213> ORGANISM: Drosophila sp.

<400> SEQUENCE: 126
tcaacgatcg gcg 13

<210> SEQ ID NO 127
<211> LENGTH: 13
<212> TYPE: DNA
<213> ORGANISM: Drosophila sp.

<400> SEQUENCE: 127
tgatccatca tca 13

<210> SEQ ID NO 128
<211> LENGTH: 13
<212> TYPE: DNA
<213> ORGANISM: Drosophila sp.

<400> SEQUENCE: 128
tcaacatgca aga 13

<210> SEQ ID NO 129
<211> LENGTH: 13
<212> TYPE: DNA
<213> ORGANISM: Drosophila sp.

<400> SEQUENCE: 129
tcttaaataa aga 13

<210> SEQ ID NO 130
<211> LENGTH: 13
<212> TYPE: DNA
<213> ORGANISM: Drosophila sp.

<400> SEQUENCE: 130
tcaaagatct ata 13

<210> SEQ ID NO 131
<211> LENGTH: 13
<212> TYPE: DNA
<213> ORGANISM: Drosophila sp.

<400> SEQUENCE: 131
taatgaatta aca 13

<210> SEQ ID NO 132
<211> LENGTH: 13
<212> TYPE: DNA
<213> ORGANISM: Drosophila sp.

<400> SEQUENCE: 132
tttaccatca act 13

<210> SEQ ID NO 133
<211> LENGTH: 13
<212> TYPE: DNA
<213> ORGANISM: Drosophila sp.

<400> SEQUENCE: 133
taatgaaaca aca 13

<210> SEQ ID NO 134
<211> LENGTH: 13
<212> TYPE: DNA
<213> ORGANISM: Drosophila sp.

<400> SEQUENCE: 134
gtttcaatta aaa 13

<210> SEQ ID NO 135
<211> LENGTH: 13
<212> TYPE: DNA
<213> ORGANISM: Drosophila sp.

<400> SEQUENCE: 135
tattcaatta taa 13

<210> SEQ ID NO 136
<211> LENGTH: 13
<212> TYPE: DNA
<213> ORGANISM: Drosophila sp.

<400> SEQUENCE: 136
tcttcaatcg ttt 13

<210> SEQ ID NO 137
<211> LENGTH: 13
<212> TYPE: DNA
<213> ORGANISM: Drosophila sp.

<400> SEQUENCE: 137
tcaacgatcc ttt 13

<210> SEQ ID NO 138
<211> LENGTH: 13
<212> TYPE: DNA
<213> ORGANISM: artificial
<220> FEATURE:
<223> OTHER INFORMATION: Table 2 consensus sequence

<400> SEQUENCE: 138
tcwwcratca aca 13

<210> SEQ ID NO 139
<211> LENGTH: 34
<212> TYPE: DNA
<213> ORGANISM: artificial
<220> FEATURE:
<223> OTHER INFORMATION: primer HSP

<400> SEQUENCE: 139
caagcaaagt gaacacgtcg ctaagcgaaa gcta 34

<210> SEQ ID NO 140
<211> LENGTH: 25
<212> TYPE: DNA
<213> ORGANISM: artificial
<220> FEATURE:
<223> OTHER INFORMATION: VP16 primer

<400> SEQUENCE: 140
gccctcgatg gtagacccgt aattg 25

<210> SEQ ID NO 141
<211> LENGTH: 24
<212> TYPE: DNA
<213> ORGANISM: artificial
<220> FEATURE:
<223> OTHER INFORMATION: primer Agexon1F

<400> SEQUENCE: 141
ggaaaccgag gataacgacg aagg 24

<210> SEQ ID NO 142
<211> LENGTH: 24
<212> TYPE: DNA
<213> ORGANISM: artificial
<220> FEATURE:
<223> OTHER INFORMATION: primer TETRR1

<400> SEQUENCE: 142
gcggaacgac ttggcgttat tgcg 24

<210> SEQ ID NO 143
<211> LENGTH: 6243
<212> TYPE: DNA
<213> ORGANISM: artificial
<220> FEATURE:
<223> OTHER INFORMATION: LA3576 plasmid sequence

<400> SEQUENCE: 143
cctctacaaa tgtggtatgg ctgattatga tcagttatct agatccggtg gatcttacgg 60
gtcctccacc ttccgctttt tcttgggtcg agatctcagg aacaggtggt ggcggccctc 120
ggtgcgctcg tactgctcca cgatggtgta gtcctcgttg tgggaggtga tgtccagctt 180
ggcgtccacg tagtagtagc cgggcagctg cacgggcttc ttggccatgt agatggactt 240
gaactccacc aggtagtggc cgccgtcctt cagcttcagg gccttgtggg tctcgccctt 300
cagcacgccg tcgcgggggt acaggcgctc ggtggaggcc tcccagccca tggtcttctt 360
ctgcatcacg gggccgtcgg aggggaagtt cacgccgatg aacttcacct tgtagatgaa 420
gcagccgtcc tgcagggagg agtcctgggt cacggtcgcc acgccgccgt cctcgaagtt 480
catcacgcgc tcccacttga agccctcggg gaaggacagc ttcttgtagt cggggatgtc 540
ggcggggtgc ttcacgtaca ccttggagcc gtactggaac tgggggggaca ggatgtccca 600
ggcgaagggc agggggccgc ccttggtcac cttcagcttc acggtgttgt ggccctcgta 660
ggggcggccc tcgccctcgc cctcgatctc gaactcgtgg ccgttcacgg tgccctccat 720
gcgcaccttg aagcgcatga actcggtgat gacgttctcg gaggaggcca tggtggcgac 780
cggtttgcgc ttcttcttgg gtggggtggg atctcccatg gtggcctgaa tctcaacttg 840
cacctggcga tcgcctaaag gtgttataaa tcaaattagt tttgtttttt cttgaaaact 900
ttgcgtttcc tttgatcaac ttaccgccag ggtacctgca gattgtttag cttgttcagc 960
tgcgcttgtt tatttgctta gctttcgctt agcgacgtgt tcactttgct tgtttgaatt 1020
gaattgtcgc tccgtagacg aagcgcctct atttatactc cggcgctgtt taaacatcca 1080
ccatgcgccc gcatcgatct ctatcactga tagggaggtc tctatcactg atagggagtt 1140
ctctatcact gatagggatg tctctatcac tgatagggat ttctctatca ctgataggga 1200
agtctctatc actgataggg acctctctat cactgatagg gaaatctcta tcactgatag 1260
ggatctctct atcactgata gggacttctc tatcactgat agggacgtct ctatcactga 1320
tagggaactc tctatcactg atagggacat ctctatcact gatagggact tctctatcac 1380
tgatagggag tatgttctct ctcttctctt ctctctctct ttctcgaatg ttctctctct 1440
tctcttctct ctctctttct cgatggccgg ggcgcgccag gtttcgactt tcacttttct 1500
ctatcactga tagggagtgg taaactcgac tttcactttt ctctatcact gatagggagt 1560
ggtaaactcg actttcactt ttctctatca ctgataggga gtggtaaact cgactttcac 1620
ttttctctat cactgatagg gagtggtaaa ctcgactttc acttttctct atcactgata 1680
gggagtggta aactcgactt tcacttttct ctatcactga tagggagtgg taaactcgac 1740
tttcactttt ctctatcact gatagggagt ggtaaactcg agcggccgcc accgcggtgg 1800
agctccagct tttgttccct ttagtgaggg ttaattgcgc gcttggcgta atcatggtca 1860
tagctgtttc ctgtgtgaaa ttgttatccg ctcacaattc cacacaacat acgagccgga 1920
agcataaagt gtaaagcctg gggtgcctaa tgagtgagct aactcacatt aattgcgttg 1980
cgctcactgc ccgctttcca gtcgggaaac ctgtcgtgcc agctgcatta atgaatcggc 2040
caacgcgcgg ggagaggcgg tttgcgtatt gggcgctctt ccgcttcctc gctcactgac 2100
tcgctgcgct cggtcgttcg gctgcggcga gcggtatcag ctcactcaaa ggcggtaata 2160
cggttatcca cagaatcagg ggataacgca ggaaagaaca tgtgagcaaa aggccagcaa 2220
aaggccagga accgtaaaaa ggccgcgttg ctggcgtttt tccataggct ccgcccccct 2280
gacgagcatc acaaaaatcg acgctcaagt cagaggtggc gaaacccgac aggactataa 2340
agataccagg cgtttccccc tggaagctcc ctcgtgcgct ctcctgttcc gaccctgccg 2400
cttaccggat acctgtccgc ctttctccct tcgggaagcg tggcgctttc tcatagctca 2460
cgctgtaggt atctcagttc ggtgtaggtc gttcgctcca agctgggctg tgtgcacgaa 2520
ccccccgttc agcccgaccg ctgcgcctta tccggtaact atcgtcttga gtccaacccg 2580
gtaagacacg acttatcgcc actggcagca gccactggta acaggattag cagagcgagg 2640
tatgtaggcg gtgctacaga gttcttgaag tggtggccta actacggcta cactagaagg 2700
acagtatttg gtatctgcgc tctgctgaag ccagttacct tcggaaaaag agttggtagc 2760
tcttgatccg gcaaacaaac caccgctggt agcggtggtt tttttgtttg caagcagcag 2820
attacgcgca gaaaaaaagg atctcaagaa gatcctttga tcttttctac ggggtctgac 2880
gctcagtgga acgaaaactc acgttaaggg attttggtca tgagattatc aaaaaggatc 2940
ttcacctaga tccttttaaa ttaaaaatga agttttaaat caatctaaag tatatatgag 3000
taaacttggt ctgacagtta ccaatgctta atcagtgagg cacctatctc agcgatctgt 3060
ctatttcgtt catccatagt tgcctgactc cccgtcgtgt agataactac gatacgggag 3120
ggcttaccat ctggccccag tgctgcaatg ataccgcgag acccacgctc accggctcca 3180
gatttatcag caataaacca gccagccgga agggccgagc gcagaagtgg tcctgcaact 3240
ttatccgcct ccatccagtc tattaattgt tgccgggaag ctagagtaag tagttcgcca 3300
gttaatagtt tgcgcaacgt tgttgccatt gctacaggca tcgtggtgtc acgctcgtcg 3360
tttggtatgg cttcattcag ctccggttcc caacgatcaa ggcgagttac atgatccccc 3420
atgttgtgca aaaaagcggt tagctccttc ggtcctccga tcgttgtcag aagtaagttg 3480
gccgcagtgt tatcactcat ggttatggca gcactgcata attctcttac tgtcatgcca 3540
tccgtaagat gcttttctgt gactggtgag tactcaacca agtcattctg agaatagtgt 3600
atgcggcgac cgagttgctc ttgcccggcg tcaatacggg ataataccgc gccacatagc 3660
agaactttaa aagtgctcat cattggaaaa cgttcttcgg ggcgaaaact ctcaaggatc 3720
ttaccgctgt tgagatccag ttcgatgtaa cccactcgtg cacccaactg atcttcagca 3780
tcttttactt tcaccagcgt ttctgggtga gcaaaaacag gaaggcaaaa tgccgcaaaa 3840
aagggaataa gggcgacacg gaaatgttga atactcatac tcttcctttt tcaatattat 3900
tgaagcattt atcagggtta ttgtctcatg agcggataca tatttgaatg tatttagaaa 3960
aataaacaaa taggggttcc gcgcacattt ccccgaaaag tgccacctaa attgtaagcg 4020
ttaatatttt gttaaaattc gcgttaaatt tttgttaaat cagctcattt tttaaccaat 4080
aggccgaaat cggcaaaatc ccttataaat caaaagaata gaccgagata gggttgagtg 4140
ttgttccagt ttggaacaag agtccactat taaagaacgt ggactccaac gtcaaagggc 4200
gaaaaaccgt ctatcagggc gatggcccac tacgtgaacc atcaccctaa tcaagttttt 4260
tggggtcgag gtgccgtaaa gcactaaatc ggaaccctaa agggagcccc cgatttagag 4320

```
cttgacgggg aaagccggcg aacgtggcga gaaaggaagg gaagaaagcg aaaggagcgg   4380

gcgctagggc gctggcaagt gtagcggtca cgctgcgcgt aaccaccaca cccgccgcgc   4440

ttaatgcgcc gctacagggc gcgtcccatt cgccattcag gctgcgcaac tgttgggaag   4500

ggcgatcggt gcgggcctct tcgctattac gccagctggc gaaaggggga tgtgctgcaa   4560

ggcgattaag ttgggtaacg ccagggtttt cccagtcacg acgttgtaaa acgacggcca   4620

gtgagcgcgc gtaatacgac tcactatagg gcgaattggg taccgggccc cccctcgagg   4680

tcgacgatgt aggtcacggt ctcgaagccg cggtgcgggt gccagggcgt gcccttgggc   4740

tccccgggcg cgtactccac ctcacccatc tggtccatca tgatgaacgg gtcgaggtgg   4800

cggtagttga tcccggcgaa cgcgcggcgc accgggaagc cctcgccctc gaaaccgctg   4860

ggcgcggtgg tcacggtgag cacgggacgt gcgacggcgt cggcgggtgc ggatacgcgg   4920

ggcagcgtca gcgggttctc gacggtcacg gcgggcatgt cgacggtatc gataagcttg   4980

ggccccccct cgaggttccc acaatggtta attcgagctc gcccggggat ctaattcaat   5040

tagagactaa ttcaattaga gctaattcaa ttaggatcca agcttatcga tttcgaaccc   5100

tcgaccgccg gagtataaat agaggcgctt cgtctacgga gcgacaattc aattcaaaca   5160

agcaaagtga acacgtcgct aagcgaaagc taagcaaata aacaagcgca gctgaacaag   5220

ctaaacaatc ggggtaccgc tagagtcgat cccaccccac ccaagaagaa gcgcaaaccg   5280

gtaccatggc ctcctccgag aacgtcatca ccgagttcat gcgcttcaag gtgcgcatgg   5340

agggcaccgt gaacggccac gagttcgaga tcgagggcga gggcgagggc cgcccctacg   5400

agggccacaa caccgtgaag ctgaaggtga ccaagggcgg cccccctgccc ttcgcctggg   5460

acatcctgtc cccccagttc cagtacggct ccaaggtgta cgtgaagcac cccgccgaca   5520

tccccgacta caagaagctg tccttccccg agggcttcaa gtgggagcgc gtgatgaact   5580

tcgaggacgg cggcgtggcg accgtgaccc aggactcctc cctgcaggac ggctgcttca   5640

tctacaaggt gaagttcatc ggcgtgaact tcccctccga cggccccgtg atgcagaaga   5700

agaccatggg ctgggaggcc tccaccgagc gcctgtaccc ccgcgacggc gtgctgaagg   5760

gcgagaccca caaggccctg aagctgaagg acggcggcca ctacctggtg gagttcaagt   5820

ccatctacat ggccaagaag cccgtgcagc tgcccggcta ctactacgtg gacgccaagc   5880

tggacatcac ctcccacaac gaggactaca ccatcgtgga gcagtacgag cgcaccgagg   5940

gccgccacca cctgttcctg tgatgatcat aatcagccat accacatttg tagaggtttt   6000

acttgcttta aaaaacctcc cacacctccc cctgaacctg aaacataaaa tgaatgcaat   6060

tgttgttgtt aacttgttta ttgcagctta taatggttac aaataaagca atagcatcac   6120

aaatttcaca aataaagcat ttttttcact gcattctagt tgtggtttgt ccaaactcat   6180

caatgtatct taacgcgagt taattaaggc cgctcattta tcagcgcttt aaatttgcgc   6240

atg                                                                 6243
```

<210> SEQ ID NO 144
<211> LENGTH: 5746
<212> TYPE: DNA
<213> ORGANISM: artificial
<220> FEATURE:
<223> OTHER INFORMATION: LA3582 plasmid sequence

<400> SEQUENCE: 144

```
cgcctaaagg tgttataaat caaattagtt ttgtttttc ttgaaaactt tgcgtttcct     60

ttgatcaact taccgccagg gtacctgcag attgtttagc ttgttcagct gcgcttgttt    120
```

```
atttgcttag ctttcgctta gcgacgtgtt cactttgctt gtttgaattg aattgtcgct    180
ccgtagacga agcgcctcta tttatactcc ggcgctgttt aaacatccac catgcgcccg    240
catcgatctc tatcactgat agggaggtct ctatcactga tagggagttc tctatcactg    300
atagggatgt ctctatcact gatagggatt tctctatcac tgatagggaa gtctctatca    360
ctgataggga cctctctatc actgataggg aaatctctat cactgatagg gatctctcta    420
tcactgatag ggacttctct atcactgata gggacgtctc tatcactgat agggaactct    480
ctatcactga tagggacatc tctatcactg atagggactt ctctatcact gatagggagt    540
atgttctctc tcttctcttc tctctctctt tctcgaatgt tctctctctt ctcttctctc    600
tctctttctc gatggccggg gcgcgccagg tttcgacttt cacttttctc tatcactgat    660
agggagtggt aaactcgact ttcacttttc tctatcactg atagggagtg gtaaactcga    720
ctttcacttt tctctatcac tgatagggag tggtaaactc gactttcact tttctctatc    780
actgataggg agtggtaaac tcgactttca cttttctcta tcactgatag ggagtggtaa    840
actcgacttt cacttttctc tatcactgat agggagtggt aaactcgact ttcacttttc    900
tctatcactg atagggagtg gtaaactcga gcggccgcca ccgcggtgga gctccagctt    960
ttgttccctt tagtgagggt taattgcgcg cttggcgtaa tcatggtcat agctgtttcc   1020
tgtgtgaaat tgttatccgc tcacaattcc acacaacata cgagccggaa gcataaagtg   1080
taaagcctgg ggtgcctaat gagtgagcta actcacatta attgcgttgc gctcactgcc   1140
cgctttccag tcgggaaacc tgtcgtgcca gctgcattaa tgaatcggcc aacgcgcggg   1200
gagaggcggt ttgcgtattg ggcgctcttc cgcttcctcg ctcactgact cgctgcgctc   1260
ggtcgttcgg ctgcggcgag cggtatcagc tcactcaaag gcggtaatac ggttatccac   1320
agaatcaggg gataacgcag gaaagaacat gtgagcaaaa ggccagcaaa aggccaggaa   1380
ccgtaaaaag gccgcgttgc tggcgttttt ccataggctc cgcccccctg acgagcatca   1440
caaaaatcga cgctcaagtc agaggtggcg aaacccgaca ggactataaa gataccaggc   1500
gtttccccct ggaagctccc tcgtgcgctc tcctgttccg accctgccgc ttaccggata   1560
cctgtccgcc tttctccctt cgggaagcgt ggcgctttct catagctcac gctgtaggta   1620
tctcagttcg gtgtaggtcg ttcgctccaa gctgggctgt gtgcacgaac cccccgttca   1680
gcccgaccgc tgcgccttat ccggtaacta tcgtcttgag tccaacccgg taagacacga   1740
cttatcgcca ctggcagcag ccactggtaa caggattagc agagcgaggt atgtaggcgg   1800
tgctacagag ttcttgaagt ggtggcctaa ctacggctac actagaagga cagtatttgg   1860
tatctgcgct ctgctgaagc cagttacctt cggaaaaaga gttggtagct cttgatccgg   1920
caaacaaacc accgctggta gcggtggttt ttttgtttgc aagcagcaga ttacgcgcag   1980
aaaaaaagga tctcaagaag atcctttgat cttttctacg gggtctgacg ctcagtggaa   2040
cgaaaactca cgttaaggga ttttggtcat gagattatca aaaaggatct tcacctagat   2100
ccttttaaat taaaaatgaa gttttaaatc aatctaaagt atatatgagt aaacttggtc   2160
tgacagttac caatgcttaa tcagtgaggc acctatctca gcgatctgtc tatttcgttc   2220
atccatagtt gcctgactcc ccgtcgtgta gataactacg atacgggagg gcttaccatc   2280
tggccccagt gctgcaatga taccgcgaga cccacgctca ccggctccag atttatcagc   2340
aataaaccag ccagccggaa gggccgagcg cagaagtggt cctgcaactt tatccgcctc   2400
catccagtct attaattgtt gccgggaagc tagagtaagt agttcgccag ttaatagttt   2460
```

-continued

```
gcgcaacgtt gttgccattg ctacaggcat cgtggtgtca cgctcgtcgt ttggtatggc   2520
ttcattcagc tccggttccc aacgatcaag gcgagttaca tgatccccca tgttgtgcaa   2580
aaaagcggtt agctccttcg gtcctccgat cgttgtcaga agtaagttgg ccgcagtgtt   2640
atcactcatg gttatggcag cactgcataa ttctcttact gtcatgccat ccgtaagatg   2700
cttttctgtg actggtgagt actcaaccaa gtcattctga gaatagtgta tgcggcgacc   2760
gagttgctct tgcccggcgt caatacggga taataccgcg ccacatagca gaactttaaa   2820
agtgctcatc attggaaaac gttcttcggg gcgaaaactc tcaaggatct taccgctgtt   2880
gagatccagt tcgatgtaac ccactcgtgc acccaactga tcttcagcat cttttacttt   2940
caccagcgtt tctgggtgag caaaaacagg aaggcaaaat gccgcaaaaa agggaataag   3000
ggcgacacgg aaatgttgaa tactcatact cttccttttt caatattatt gaagcattta   3060
tcagggttat tgtctcatga gcggatacat atttgaatgt atttagaaaa ataaacaaat   3120
aggggttccg cgcacatttc cccgaaaagt gccacctaaa ttgtaagcgt taatattttg   3180
ttaaaattcg cgttaaattt ttgttaaatc agctcatttt ttaaccaata ggccgaaatc   3240
ggcaaaatcc cttataaatc aaaagaatag accgagatag ggttgagtgt tgttccagtt   3300
tggaacaaga gtccactatt aaagaacgtg gactccaacg tcaaagggcg aaaaaccgtc   3360
tatcagggcg atggcccact acgtgaacca tcaccctaat caagtttttt ggggtcgagg   3420
tgccgtaaag cactaaatcg gaaccctaaa gggagccccc gatttagagc ttgacgggga   3480
aagccggcga acgtggcgag aaaggaaggg aagaaagcga aaggagcggg cgctagggcg   3540
ctggcaagtg tagcggtcac gctgcgcgta accaccacac ccgccgcgct taatgcgccg   3600
ctacagggcg cgtcccattc gccattcagg ctgcgcaact gttgggaagg gcgatcggtg   3660
cgggcctctt cgctattacg ccagctggcg aaagggggat gtgctgcaag gcgattaagt   3720
tgggtaacgc cagggttttc ccagtcacga cgttgtaaaa cgacggccag tgagcgcgcg   3780
taatacgact cactataggg cgaattgggt accgggcccc ccctcgaggt cgacgatgta   3840
ggtcacggtc tcgaagccgc ggtgcgggtg ccagggcgtg cccttgggct ccccgggcgc   3900
gtactccacc tcacccatct ggtccatcat gatgaacggg tcgaggtggc ggtagttgat   3960
cccggcgaac gcgcggcgca ccgggaagcc ctcgccctcg aaaccgctgg gcgcggtggt   4020
cacggtgagc acgggacgtg cgacggcgtc ggcgggtgcg gatacgcggg gcagcgtcag   4080
cgggttctcg acggtcacgg cgggcatgtc gacggtatcg ataagcttgg gcccccccctc   4140
gaggttccca caatggttaa ttcgagctcg cccggggatc taattcaatt agagactaat   4200
tcaattagag ctaattcaat taggatccaa gcttatcgat ttcgaaccct cgaccgccgg   4260
agtataaata gaggcgcttc gtctacggag cgacaattca attcaaacaa gcaaagtgaa   4320
cacgtcgcta agcgaaagct aagcaaataa acaagcgcag ctgaacaagc taaacaatcg   4380
gggtaccgct agagtcgatc ccaccccacc caagaagaag cgcaaaccgg taccatggcc   4440
tcctccgaga acgtcatcac cgagttcatg cgcttcaagg tgcgcatgga gggcaccgtg   4500
aacggccacg agttcgagat cgagggcgag ggcgagggcc gcccctacga gggccacaac   4560
accgtgaagc tgaaggtgac caagggcggc cccctgccct tcgcctggga catcctgtcc   4620
ccccagttcc agtacggctc caaggtgtac gtgaagcacc ccgccgacat ccccgactac   4680
aagaagctgt ccttccccga gggcttcaag tgggagcgcg tgatgaactt cgaggacggc   4740
ggcgtggcga ccgtgaccca ggactcctcc ctgcaggacg gctgcttcat ctacaaggtg   4800
aagttcatcg gcgtgaactt cccctccgac ggccccgtga tgcagaagaa gaccatgggc   4860
```

tgggaggcct ccaccgagcg cctgtacccc cgcgacggcg tgctgaaggg cgagacccac 4920
aaggccctga agctgaagga cggcggccac tacctggtgg agttcaagtc catctacatg 4980
gccaagaagc ccgtgcagct gcccggctac tactacgtgg acgccaagct ggacatcacc 5040
tcccacaacg aggactacac catcgtggag cagtacgagc gcaccgaggg ccgccaccac 5100
ctgttcctgt gatgatcata atcagccata ccacatttgt agaggtttta cttgctttaa 5160
aaaacctccc acacctcccc ctgaacctga aacataaaat gaatgcaatt gttgttgtta 5220
acttgtttat tgcagcttat aatggttaca aataaagcaa tagcatcaca aatttcacaa 5280
ataaagcatt tttttcactg cattctagtt gtggtttgtc caaactcatc aatgtatctt 5340
aacgcgagtt aattaaggcc gctcatttat cagcgcttta aatttgcgca tgctagttta 5400
atacaccttt cgcagcaagt agtatagctt gttgcacagc agacatcggg aacgggttgg 5460
gttattttct tgagcgtgac ggaacagaat ctcatgaaag gcctgcacca gatggtagcg 5520
gttgtggtga aggctgactt gcgtcatcgt cggagtcagt ggaggagttg gtggaattga 5580
ctccgttgga cttgttggcg acggtggtgg cgaactgaat tggttctgat tttgctgttg 5640
ttgcattaaa atctgctgct gctgttgcat catttgcaac tgatactgct tctcgatttc 5700
atcatcgatg gcgggaatgt agaatgcgat tgccatggtg ggcgat 5746

<210> SEQ ID NO 145
<211> LENGTH: 15121
<212> TYPE: DNA
<213> ORGANISM: artificial
<220> FEATURE:
<223> OTHER INFORMATION: LA3596 plasmid sequence

<400> SEQUENCE: 145
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatcccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gacaccggtg ctacccgcca tactcatcga tgcccagcgc 960
gtcggtgaac atttgctcga actcgaagtc ggccatgtcc agggcgccgt acggggcgct 1020
atcgtggggc gtgaagcccg gtcccgggct atctccatcg cccagcatat ccaggtcgaa 1080
atcgtccagg gcgtcggcgt gggccattgc cacatcctct ccatccaggt gcagctcgtc 1140

-continued

```
gcccaggctc acatcggtcg gcggggcggt gctcaggcgg cgcgtgtgtc cggcgggcag   1200
gaagctcagg cggggggcgg ccaggccggc ttcctccggg gcatcgtcat ccggcaggtc   1260
cagcagtccc tcgatggtgc tgccatagtt gttcttggta cgggcgcggc tgtaggcgct   1320
gccgctctcg cacttcagct gcttttccag gccgcagatg atcagctcca ggccgaacag   1380
gaaggccggc tcggcgccct ggtgatcgaa cagctcgatg gcctggcgca gcagcggcgg   1440
catgctatcg gtggtcgggg tctcgcgctc ctccttggcc acctggtgct cctgatcctc   1500
cagcacacag cccagggtga agtggcccac ggcgctcagg gcgtacaggg cgttctccag   1560
gctgaagccc tgctggcaca ggaaggccag ctggttctcc agggtctcgt actgcttctc   1620
ggtcgggcgg gtgcccaggt gcaccttggc gccatcgcgg tgcgacagca gggcgcagcg   1680
gaagctcttg gcgttgttgc gcaggaaatc ctgccagctc tcgccctcca gcgggcagaa   1740
gtgggtgtgg tggcgatcca gcatttcgat ggccagggcg tccagcaggg cgcgcttgtt   1800
cttcacgtgc cagtacaggg tcggctgttc cacgcccagc ttctgggcca gcttgcgggt   1860
ggtcaggccc tcgataccaa cttcgttcag cagctccagg gcgctgttga tcaccttgct   1920
cttgtccagg cggctgacct gtgaatacgg ttaatgtcac tattagtgat ttataaaaat   1980
aaatttgatt tatatatcaa caatttttca tcgcagcctt cagctttttg ttgaataatt   2040
ataatgatat tttttacgat tcaaatcatt taattgttac tcaacgaaat aagtttaatt   2100
caaattttaa aacaagatta tatattaaga ttagaataag aaagaacttt gttagattat   2160
ttaattaaaa agattaaaat ttaagtctcc agtcactatt taaagatcat ctttcaaacg   2220
ttaaagtgaa ttcaaacgag acgttcaaat ttcgattaaa cagtaattaa ctctaaattt   2280
ctatcacgaa ttaagttatt gaatatgaag gtttatattt atttacatca tctaataggt   2340
ttgagttgat tgttgtaatc cgcatgtgcc agaagatatc aatttccaaa ttgtccgagt   2400
tcatggaatg ttgattgttg tttgtgttgc tttgtaattg ttgcagggag tatttatggt   2460
ttgttgattg tagtataagg ctgtttctaa aggctagaaa ataattttat ttatttgaaa   2520
ataagtaaat atacataata ttactaacaa taggtcgtcc tattttttga tattctgcac   2580
aaatttttaa aacacaaaga ttgcaatact tttagacact aatactgcac actctgaaaa   2640
attattaaat tatttttaaa aacttacctt aatactttag agaaaaatat tataccgcac   2700
ctttctactt tatactcact ttattatacc agttgcatgt tgattgtagt tctttgacaa   2760
gaaaatattc catattgctc caaattatct tggtaagttg attggtgcgt catttgagca   2820
agctaacacc ttgtctcatt taagttcgcc tcaagatctc atagcatttt taaatatcac   2880
tatatttagt aagtaattag aattaccatg gtggtttgct agcggtacct gcagattgtt   2940
tagcttgttc agctgcgctt gtttatttgc ttagctttcg cttagcgacg tgttcacttt   3000
gcttgtttga attgaattgt cgctccgtag acgaagcgcc tctatttata ctccggcgct   3060
cggtccgact ctctatcact gatagggagt attgtcctct ctatcactga tagggaatgc   3120
tatgttctct atcactgata gggaagttga tagtctctat cactgatagg gagtggtaat   3180
ttctctatca ctgataggga ttagtgatgt ctctatcact gatagggatt ggaatattct   3240
ctatcactga tagggagtgg taatatctct atcactgata gggactggag ttttctctat   3300
cactgatagg gacacgctga ctctctatca ctgataggga taagcttact ctctatcact   3360
gatagggagt attgtcctct ctatcactga tagggaatgc tatgttctct atcactgata   3420
gggaagttga tagtctctat cactgatagg gagtggtaat ttctctatca ctgataggga   3480
ttagtgatgt ctctatcact gatagggatt ggaatattct ctatcactga tagggagtgg   3540
```

-continued

```
taatatctct atcactgata gggactggag ttttctctat cactgatagg gacacgctga   3600
ctctctatca ctgataggga taagcggccg catggtaccc attgcttgtc atttattaat   3660
ttggatgatg tcatttgttt ttaaaattga actggcttta cgagtagaat tctacgcgta   3720
aaacacaatc aagtatgagt cataatctga tgtcatgttt tgtacacggc tcataaccga   3780
actggcttta cgagtagaat tctacttgta atgcacgatc agtggatgat gtcatttgtt   3840
tttcaaatcg agatgatgtc atgttttgca cacggctcat aaactcgctt tacgagtaga   3900
attctacgtg taacgcacga tcgattgatg agtcatttgt tttgcaatat gatatcatac   3960
aatatgactc atttgttttt caaaaccgaa cttgatttac gggtagaatt ctacttgtaa   4020
agcacaatca aaaagatgat gtcatttgtt tttcaaaact gaactcgctt tacgagtaga   4080
attctacgtg taaaacacaa tcaagaaatg atgtcatttg ttataaaaat aaaagctgat   4140
gtcatgtttt gcacatggct cataactaaa ctcgctttac gggtagaatt ctacgcgtaa   4200
aacatgattg ataattaaat aattcatttg caagctatac gttaaatcaa acggacgctc   4260
gaggttgcac aacactatta tcgatttgca gttcgggaca taaatgttta aatatatcga   4320
tgtctttgtg atgcgcgcga catttttgta ggttattgat aaaatgaacg gatacgttgc   4380
ccgacattat cattaaatcc ttggcgtaga atttgtcggg tccattgtcc gtgtgcgcta   4440
gcatgcccgt aacggacctc gtacttttgg cttcaaaggt tttgcgcaca gacaaaatgt   4500
gccacacttg cagctctgca tgtgtgcgcg ttaccacaaa tcccaacggc gcagtgtact   4560
tgttgtatgc aaataaatct cgataaaggc gcggcgcgcg aatgcagctg atcacgtacg   4620
ctcctcgtgt tccgttcaag gacggtgtta tcgacctcag attaatgttt atcggccgac   4680
tgttttcgta tccgctcacc aaacgcgttt ttgcattaac attgtatgtc ggcggatgtt   4740
ctatatctaa tttgaataaa taaacgataa ccgcgttggt tttagagggc ataataaaag   4800
aaatattgtt atcgtgttcg ccattagggc agtataaatt gacgttcatg ttggatattg   4860
tttcagttgc aagttgacac tggcggcgac aagcaattct aattggggta agttttcccg   4920
ttcttttctg ggttcttccc ttttgctcat ccttgctgca ctaccttcag gtgcaagttg   4980
agattcaggc caccatggga gatcccaccc cacccaagaa gaagcgcaaa ccggtcgcca   5040
ccatggagag cgacgagagc ggcctgcccg ccatggagat cgagtgccgc atcaccggca   5100
ccctgaacgg cgtggagttc gagctggtgg gcggcggaga gggcaccccc gagcagggcc   5160
gcatgaccaa caagatgaag agcaccaaag gcgccctgac cttcagcccc tacctgctga   5220
gccacgtgat gggctacggc ttctaccact tcggcaccta ccccagcggc tacgagaacc   5280
ccttcctgca cgccatcaac aacggcggct acaccaacac ccgcatcgag aagtacgagg   5340
acggcggcgt gctgcacgtg agcttcagct accgctacga ggccggccgc gtgatcggcg   5400
acttcaaggt gatgggcacc ggcttccccg aggacagcgt gatcttcacc gacaagatca   5460
tccgcagcaa cgccaccgtg gagcacctgc accccatggg cgataacgat ctggatggca   5520
gcttcacccg caccttcagc ctgcgcgacg gcggctacta cagctccgtg gtggacagcc   5580
acatgcactt caagagcgcc atccacccca gcatcctgca gaacgggggc cccatgttcg   5640
ccttccgccg cgtggaggag gatcacagca acaccgagct gggcatcgtg gagtaccagc   5700
acgccttcaa gaccccggat gcagatgccg gtgaagaaag atctcgaccc aagaaaaagc   5760
ggaaggtgga ggacccgtct ggaggcggtg gatccggcgg tggaggcatg cagatctttg   5820
tgaagacttt gaccggaaag accatcaccc tcgaggtaga gccatcggac accattgaga   5880
```

-continued

```
atgtaaaggc caagattcag gataaggagg gaatccccc agatcagcag cgtctgatct   5940
tcgctggtaa ttttaaaagc atattttttt ctttgaaatt cataagttat caattatcga   6000
tggaaatgta ttctatggag aacgttttac ccgatgaatg ggtgcaaaaa ttattttacc   6060
ttcaaatcta caatcaacac acgctaactt ttgtgacttg atcaactctc acctggaaaa   6120
gcaaccaact acaatcaaca ttctatggga taatcgacaa gtgagtaaaa ttatagccgg   6180
acctcttagt acagtgtatt taaaagggga ataatattct atcaatagga ataaaaataa   6240
ggtcagcagc catgactttt ccatcatttt gaatatacct tatttgtttc gggattaatt   6300
gggggtcgga aatcctcttg aattcagaaa cgggaaccgg aggaaggtgc cggtctttca   6360
gaaagctgtg aaaaatacca acatttctgc tgccaagagc tcaataagaa gtttcaaaaa   6420
ttgtcttgga tgttgcagct gtggctgcta agtaataaga catctattag tatctagatt   6480
tgttagacca tttaacatag tgttttaaac gatggggtta atagatgagg gttaagaagc   6540
tagttatatt actgttgctg taacgccttc aattgtcggt tacagagcaa acattattga   6600
atgttaatgt aaagagttta tttgttttct agtaaacata tagcgattgg ttagtaatca   6660
ctaatagaaa tttttcataa gtatcaaaaa agtaaacctc tttttcagtc tatgtaataa   6720
gtaaaccaag gaaagggaaa atatctacaa tcaacaagcc attgttgcag caacaaagca   6780
actgaaacta caatcaacat tcaataaact tgggtaattt ggaatttaat tctctgggac   6840
acctgtggat tacaacaatc aactcgaaac ttattataca atgtaaataa aaattgatat   6900
gcatacatga agatcaagtg aaattccatt tagaatcaat ttttttcgaa tattaagttt   6960
cttgctttaa tttatctgaa agtaaataga cattccaaat tcaagttaac aaattaataa   7020
tgaattgact agtgattttt aagagaaaaa gataagattt aaaaaaggaa agcctttctt   7080
gataaatttt tgaaccactt tatgccgttt caatcataaa aacttttaag aacacatgac   7140
tggtaaaatt aatttaaaac aaatttaaat tttcaacgta acattcaaca aaaatggtga   7200
aaactatcac ggaaattgtt aatattaata tgtcccaaaa atagcctttg tatgtatatg   7260
atactaatcc atacatctat ggtatctata ggtcgccaac tggaagacgg acgcaccctg   7320
tccgattaca acatccagaa ggagtccacc cttcacttgg tccttcgtct ccgcggtggc   7380
atgcagatcg gggatcccac cccacccaag aagaagcgca aaccggtcgc caccatggcc   7440
tcctccgaga acgtcatcac cgagttcatg cgcttcaagg tgcgcatgga gggcaccgtg   7500
aacggccacg agttcgagat cgagggcgag ggcgagggcc gcccctacga gggccacaac   7560
accgtgaagc tgaaggtgac caagggcggc cccctgccct tcgcctggga catcctgtcc   7620
ccccagttcc agtacggctc caaggtgtac gtgaagcacc ccgccgacat ccccgactac   7680
aagaagctgt ccttccccga gggcttcaag tgggagcgcg tgatgaactt cgaggacggc   7740
ggcgtggcga ccgtgaccca ggactcctcc ctgcaggacg gctgcttcat ctacaaggtg   7800
aagttcatcg gcgtgaactt cccctccgac ggccccgtga tgcagaagaa gaccatgggc   7860
tgggaggcct ccaccgagcg cctgtacccc cgcgacggcg tgctgaaggg cgagacccac   7920
aaggccctga agctgaagga cggcggccac tacctggtgg agttcaagtc catctacatg   7980
gccaagaagc ccgtgcagct gcccggctac tactacgtgg acgccaagct ggacatcacc   8040
tcccacaacg aggactacac catcgtggag cagtacgagc gcaccgaggg ccgccaccac   8100
ctgttcctga gatctcgacc caagaaaaag cggaaggtgg aggacccgta agatccaccg   8160
gatctagata actgatcata atcagccata ccacatttgt agaggtttta cttgctttaa   8220
aaaacctccc acacctcccc ctgaacctga aacataaaat gaatgcaatt gttgttgtta   8280
```

```
acttgtttat tgcagcttat aatggttaca aataaagcaa tagcatcaca aatttcacaa   8340
ataaagcatt tttttcactg cattctagtt gtggtttgtc caaactcatc aatgtatctt   8400
aacgcgagtt aattaacacc gaaatcgtaa ttcacggcat cattacaaaa tattttgacg   8460
ttttggacct cgtccctaat gacaccataa cggtggcctt gaagtatatt taaccctaga   8520
aagatagtct gcgtaaaatt gacgcatgca ttcttgaaat attgctctct ctttctaaat   8580
agcgcgaatc cgtcgctgtg catttaggac atctcagtcg ccgcttggag ctcccgtgag   8640
gcgtgcttgt caatgcggta agtgtcactg attttgaact ataacgaccg cgtgagtcaa   8700
aatgacgcat gattatcttt tacgtgactt ttaagattta actcatacga taattatatt   8760
gttatttcat gttctactta cgtgataact tattatatat atattttctt gttatagata   8820
tcgtgactaa tatataataa aatgggtagt tctttagacg atgagcatat cctctctgct   8880
cttctgcaaa gcgatgacga gcttgttggt gaggattctg acagtgaaat atcagatcac   8940
gtaagtgaag atgacgtcca ggaaatctgg ccggccgcaa ccattgtggg aaccgtgcga   9000
tcaaacaaac gcgagatacc ggaagtactg aaaaacagtc gctccaggcc agtgggaaca   9060
tcgatgtttt gttttgacgg accccttact ctcgtctcat ataaaccgaa gccagctaag   9120
atggtatact tattatcatc ttgtgatgag gatgcttcta tcaacgaaag taccggtaaa   9180
ccgcaaatgg ttatgtatta taatcaaact aaaggcggag tggacacgct agaccaaatg   9240
tgttctgtga tgacctgcag taggaagacg aataggtggc ctatggcatt attgtacgga   9300
atgataaaca ttgcctgcat aaattctttt attatataca gccataatgt cagtagcaag   9360
ggagaaaagg tccaaagtcg caaaaaattt atgagaaacc tttacatgag cctgacgtca   9420
tcgtttatgc gtaagcgttt agaagctcct actttgaaga gatatttgcg cgataatatc   9480
tctaatattt tgccaaatga agtgcctggt acatcagatg acagtactga agagccagta   9540
atgaaaaaac gtacttactg tacttactgc ccctctaaaa taaggcgaaa ggcaaatgca   9600
tcgtgcaaaa aatgcaaaaa agttatttgt cgagagcata atattgatat gtgccaaagt   9660
tgtttctgac tgactaataa gtataatttg tttctattat gtataagtta agctaattac   9720
ttattttata atacaacatg actgttttta aagtacaaaa taagtttatt tttgtaaaag   9780
agagaatgtt taaaagtttt gttactttat agaagaaatt ttgagttttt gttttttttt   9840
aataaataaa taaacataaa taaattgttt gttgaattta ttattagtat gtaagtgtaa   9900
atataataaa acttaatatc tattcaaatt aataaataaa cctcgatata cagaccgata   9960
aaacacatgc gtcaatttta cgcatgatta tctttaacgt acgtcacaat atgattatct  10020
ttctagggtt aaataatagt ttctaatttt tttattattc agcctgctgt cgtgaatacc  10080
gtatatctca acgctgtctg tgagattgtc gtattctagc ctttttagtt tttcgctcat  10140
cgacttgata ttgtccgaca cattttcgtc gatttgcgtt ttgatcaaag acttgagcag  10200
agacacgtta atcaactgtt caaattgatc catattaacg atatcaaccc gatgcgtata  10260
tggtgcgtaa aatatatttt ttaaccctct tatactttgc actctgcgtt aatacgcgtt  10320
cgtgtacaga cgtaatcatg ttttcttttt tggataaaac tcctactgag tttgacctca  10380
tattagaccc tcacaagttg caaaacgtgg catttttttac caatgaagaa tttaaagtta  10440
ttttaaaaaa tttcatcaca gatttaaaga agaaccaaaa attaaattat ttcaacagtt  10500
taatcgacca gttaatcaac gtgtacacag acgcgtcggc aaaaaacacg cagcccgacg  10560
tgttggctaa aattattaaa tcaacttgtg ttatagtcac ggatttgccg tccaacgtgt  10620
```

```
tcctcaaaaa gttgaagacc aacaagttta cggacactat taattatttg attttgcccc  10680

acttcatttt gtgggatcac aattttgtta tattttaaac aaagcttggc actggccgtc  10740

gttttacaac gtcgtgactg ggaaaaccct ggcgttaccc aacttaatcg ccttgcagca  10800

catccccctt tcgccagctg gcgtaatagc gaagaggccc gcaccgatcg cccttcccaa  10860

cagttgcgca gcctgaatgg cgaatggcgc ctgatgcggt attttctcct tacgcatctg  10920

tgcggtattt cacaccgcat atggtgcact ctcagtacaa tctgctctga tgccgcatag  10980

ttaagccagc cccgacaccc gccaacaccc gctgacgcgc cctgacgggc ttgtctgctc  11040

ccggcatccg cttacagaca agctgtgacc gtctccggga gctgcatgtg tcagaggttt  11100

tcaccgtcat caccgaaacg cgcgagacga aagggcctcg tgatacgcct atttttatag  11160

gttaatgtca tgataataat ggtttcttag acgtcaggtg gcacttttcg gggaaatgtg  11220

cgcggaaccc ctatttgttt atttttctaa atacattcaa atatgtatcc gctcatgaga  11280

caataaccct gataaatgct tcaataatat tgaaaaagga agagtatgag tattcaacat  11340

ttccgtgtcg cccttattcc cttttttgcg gcattttgcc ttcctgtttt tgctcaccca  11400

gaaacgctgg tgaaagtaaa agatgctgaa gatcagttgg gtgcacgagt gggttacatc  11460

gaactggatc tcaacagcgg taagatcctt gagagttttc gccccgaaga acgttttcca  11520

atgatgagca cttttaaagt tctgctatgt ggcgcggtat tatcccgtat tgacgccggg  11580

caagagcaac tcggtcgccg catacactat tctcagaatg acttggttga gtactcacca  11640

gtcacagaaa agcatcttac ggatggcatg acagtaagag aattatgcag tgctgccata  11700

accatgagtg ataacactgc ggccaactta cttctgacaa cgatcggagg accgaaggag  11760

ctaaccgctt ttttgcacaa catgggggat catgtaactc gccttgatcg ttgggaaccg  11820

gagctgaatg aagccatacc aaacgacgag cgtgacacca cgatgcctgt agcaatggca  11880

acaacgttgc gcaaactatt aactggcgaa ctacttactc tagcttcccg gcaacaatta  11940

atagactgga tggaggcgga taaagttgca ggaccacttc tgcgctcggc ccttccggct  12000

ggctggttta ttgctgataa atctggagcc ggtgagcgtg ggtctcgcgg tatcattgca  12060

gcactggggc cagatggtaa gccctcccgt atcgtagtta tctacacgac ggggagtcag  12120

gcaactatgg atgaacgaaa tagacagatc gctgagatag gtgcctcact gattaagcat  12180

tggtaactgt cagaccaagt ttactcatat atactttaga ttgatttaaa acttcatttt  12240

taatttaaaa ggatctaggt gaagatcctt tttgataatc tcatgaccaa aatcccttaa  12300

cgtgagtttt cgttccactg agcgtcagac cccgtagaaa agatcaaagg atcttcttga  12360

gatccttttt ttctgcgcgt aatctgctgc ttgcaaacaa aaaaaccacc gctaccagcg  12420

gtggtttgtt tgccggatca agagctacca actctttttc cgaaggtaac tggcttcagc  12480

agagcgcaga taccaaatac tgtccttcta gtgtagccgt agttaggcca ccacttcaag  12540

aactctgtag caccgcctac atacctcgct ctgctaatcc tgttaccagt ggctgctgcc  12600

agtggcgata agtcgtgtct taccgggttg gactcaagac gatagttacc ggataaggcg  12660

cagcggtcgg gctgaacggg gggttcgtgc acacagccca gcttggagcg aacgacctac  12720

accgaactga gatacctaca gcgtgagcat tgagaaagcg ccacgcttcc cgaagggaga  12780

aaggcggaca ggtatccggt aagcggcagg gtcggaacag gagagcgcac gagggagctt  12840

ccagggggaa acgcctggta tctttatagt cctgtcgggt ttcgccacct ctgacttgag  12900

cgtcgatttt tgtgatgctc gtcagggggg cggagcctat ggaaaaacgc cagcaacgcg  12960

gcctttttac ggttcctggc cttttgctgg ccttttgctc acatgttctt tcctgcgtta  13020
```

```
tcccctgatt ctgtggataa ccgtattacc gcctttgagt gagctgatac cgctcgccgc  13080

agccgaacga ccgagcgcag cgagtcagtg agcgaggaag cggaagagcg cccaatacgc  13140

aaaccgcctc tccccgcgcg ttggccgatt cattaatgca gctggcacga caggtttccc  13200

gactggaaag cgggcagtga gcgcaacgca attaatgtga gttagctcac tcattaggca  13260

ccccaggctt tacactttat gcttccggct cgtatgttgt gtggaattgt gagcggataa  13320

caatttcaca caggaaacag ctatgaccat gattacgaat ttcgacctgc aggcatgcaa  13380

gcttgcatgc ctgcaggtcg acgctcgcgc gacttggttt gccattcttt agcgcgcgtc  13440

gcgtcacaca gcttggccac aatgtggttt ttgtcaaacg aagattctat gacgtgttta  13500

aagtttaggt cgagtaaagc gcaaatcttt tttaacccta gaaagatagt ctgcgtaaaa  13560

ttgacgcatg cattcttgaa atattgctct ctctttctaa atagcgcgaa tccgtcgctg  13620

tgcatttagg acatctcagt cgccgcttgg agctcccgtg aggcgtgctt gtcaatgcgg  13680

taagtgtcac tgattttgaa ctataacgac cgcgtgagtc aaaatgacgc atgattatct  13740

tttacgtgac ttttaagatt taactcatac gataattata ttgttatttc atgttctact  13800

tacgtgataa cttattatat atatattttc ttgttataga tatcgtgact aatatataat  13860

aaaatgggta gttctttaga cgatgagcat atcctctctg ctcttctgca aagcgatgac  13920

gagcttgttg gtgaggattc tgacagtgaa atatcagatc acgtaagtga agatgacgtc  13980

cagagcgata cagaagaagc gtttatagat gaggtacatg aagtgcagcc aacgtcaagc  14040

ggtagtgaaa tattagacga acaaaatgtt attgaacaac caggttcttc attggcttct  14100

aacagaatct tgaccttgcc acagaggact attagaggta agaataaaca ttgttggtca  14160

acttcaaagt ccacgaggcg tagccgagtc tctgcactga acattgtcag atcggcccgg  14220

cggagtggac acgctagacc aaatgtgttc tgtgatgacc tgcagtagga agacgaatag  14280

gtggcctatg gcattattgt acggaatgat aaacattgcc tgcataaatt cttttattat  14340

atacagccat aatgtcagta gcaagggaga aaaggtccaa agtcgcaaaa aatttatgag  14400

aaacctttac atgagcctga cgtcatcgtt tatgcgtaag cgtttagaag ctcctacttt  14460

gaagagatat ttgcgcgata atatctctaa tattttgcca aatgaagtgc ctggtacatc  14520

agatgacagt actgaagagc cagtaatgaa aaaacgtact tactgtactt actgcccctc  14580

taaaataagg cgaaaggcaa atgcatcgtg caaaaaaatgc aaaaaagtta tttgtcgaga  14640

gcataatatt gatatgtgcc aaagttgttt ctgactgact aataagtata atttgtttct  14700

attatgtata agttaagcta attacttatt ttataataca acatgactgt ttttaaagta  14760

caaaataagt ttatttttgt aaaagagaga atgtttaaaa gttttgttac tttatagaag  14820

aaattttgag tttttgtttt tttttaataa ataaataaac ataaataaat tgtttgttga  14880

atttattatt agtatgtaag tgtaaatata ataaaactta atatctattc aaattaataa  14940

ataaacctcg atatacagac cgataaaaca catgcgtcaa ttttacgcat gattatcttt  15000

aacgtacgtc acaatatgat tatctttcta gggttaaaat gaatgtaagc actttattaa  15060

cgaaatcttt gggaatattt cgctcatcag cattttattt gagcaggagt ccgagatgcc  15120

c                                                                  15121
```

<210> SEQ ID NO 146
<211> LENGTH: 533
<212> TYPE: DNA
<213> ORGANISM: artificial
<220> FEATURE:

<223> OTHER INFORMATION: 146 PBW dsx fragment (Fig 6)

<400> SEQUENCE: 146
gtccaatcga tcacaatgta tcacaacgtt gcgaattcag tttcacaatc acacgcaaca 60
aacrcgrcac gttacaaatt agttactttg aatcgatcga ttatgatgcg gccgactcar 120
cggcccccgg cagcactaac cagtagtgat ttccactttg cagtgaccgg accaaaactt 180
cgaaattcga attgtaaagt gacagttcat ttcccgccaa gtgttgtgcc agtgtcatgt 240
cgatatttat tttattttct tttttgtagg aaaatgctga gcgaaattaa taatataagt 300
ggtgtactat cgtcgtccat gaagttattt tgcgaatgat actttgtttt gtatgtgctg 360
tgtgttgtgt ggacttttgc tgtgcgttgc tgtttgcgat ggaaggacta ttgtgtcgtc 420
gccacgctgg actattcggt gagtggtaga ataatatttt atctatttca tcgcggtaca 480
attgactttt tattactact cactgctatg gaggaatctc aggaacatcg taa 533

<210> SEQ ID NO 147
<211> LENGTH: 611
<212> TYPE: DNA
<213> ORGANISM: artificial
<220> FEATURE:
<223> OTHER INFORMATION: Bombyx-dsx fragment (Fig 6)

<400> SEQUENCE: 147
gcgattattt aattctatat atttttcaaa ttcagtttct attccactaa caatgtacac 60
tacacgtaca catacacaca acaaaatagt gaatcgataa attagtgtgt cataacacat 120
taacaacatt gttacacacc cacacataca aatttgctaa gttgatagtc gaataatcgg 180
aatggttcgc atcacactac taaccagtcg tgatttccac tttacagtga ccggacgaag 240
gtggagaaat tcgaaattta aatataaaag tgacaattcg aatttccacg cgcgcgctct 300
agtgatgtgc cagtgtgtga atatcaatat tattttttat tttctttttt gtaggaaaat 360
gctggaaatt aataatataa gtggtgtact gtcttcgtca atgaagttat tttgcgaatg 420
atacttagtt ttacaagtgc cgtggtgtgt gttgacactt gctgtgcgat gctgtgcgaa 480
tttcaacgga aatatttgtt gtcgtaacat tggatctatg ggtaagttta gtataataac 540
tttactctgt tcacattagt gaaacataca tttgtaaaat ttgtgtttta ctaatgtgaa 600
atttattttt g 611

<210> SEQ ID NO 148
<211> LENGTH: 570
<212> TYPE: DNA
<213> ORGANISM: artificial
<220> FEATURE:
<223> OTHER INFORMATION: codling-dsx fragment (Fig 6)

<400> SEQUENCE: 148
ttacaaacaa tgtacggagc tacaacgttg caagttcggt ccccacacaa cacaatgtgt 60
cataacacat taacaacatt gttacacacc cacacataca aatttgctaa gttgataaaa 120
gagtggtgtg tccgacgaat cagaacatca ctaacccagt cgtgatttca tttccacagt 180
gaccggacga aggtggagaa gttcgaaatt taaaaaaagt gaccacattt tatttaatag 240
tgatgtgcaa gtgatactat ttttattttg tttttctttt gtaggaaaat gctgagcgaa 300
ataaataatt ttagtggtgt gctatcgtca tcgatgaagt tgttttgcga atgatactat 360
gttcttcaag tgctgtgttt tgtggactgt ggggtgactg ttcctgtaaa taagcttcgt 420
tggacattgt gtctcacaca tcggatctca tggtaagtgc tagtgctagc atyrmaactt 480

```
aactctctga gcgaattcct ttgactctaa agtcacacgr acagccatac aatcaaagct    540

acgctctaat tttaagatga cawtctgtaa                                     570


<210> SEQ ID NO 149
<211> LENGTH: 4389
<212> TYPE: DNA
<213> ORGANISM: artificial
<220> FEATURE:
<223> OTHER INFORMATION: DSX Minigene1 rom construct LA3491

<400> SEQUENCE: 149

acgacgaact tgtcaaacga tctcaatggc tcctggagaa gctgcgatac ccctgggaga     60

tgatgcccct gatgtacgtg atactgaaag gcgccgacgg agacgtcaat aaagcgcgcc    120

aacggattga cgaaggtatg gggttctta ccggttggga ctgtttccga ggtatcgatc    180

gggtgtcact cacttcctgg gtgctcccat tttgtaactg ctaacgctta ttattgagtt    240

tcaggacatc tgggatcttc ggtcgacgga gtctattccc aacagtgccc tggatcaaac    300

actgccatca tgcagtttcc gtagcctgtt gggctacgct ccccgacttg acatccccca    360

ttcttatcaa acaacaactc aaggcctgag acaacgagtg gtggaatttg cgcacgaagt    420

cattggtttg tcctggtaaa agttaaaagg gttaactgga gggttaattg acacggtttc    480

aactgatggc cttattgaca cacggatgaa agacttgcac gcttgacctt ctgtctgtac    540

taataaaagt tacgttggct gggttttggg gtcataatgg ccccaaaatc gaatcgtcat    600

aacttcttga aatacaactc acgtttaaga ccattcaaga gtattagatc atcgtctata    660

atagcagatt tgaaatttac ttcacatttc ggtattgcag tgccccttgc ttccacaatg    720

gaattaggtc ggtggtgcgt cgatcgtcgc aagtttatcg ttaaacagtc aataaaatga    780

gcattttata tcgtgataca tatgagaaga tagaggtttc aattaaaaca aatccacatg    840

gtgtcgctaa taaaattgtg cattttaagc gagttatatc ctctgatcaa gataaaatag    900

aaaattcgat ttttgaatat tcaattataa gagcctgaat aactacaaca tgtagtgaat    960

cgaaactgat ttatgacggt ttgtgaaggt tacacgtcct aagcatttgg attcaagaaa   1020

agcaagagat atgacgaatg taaactttat cgtatcaatg aagtaactag cgtccagaac   1080

agtacaaacc aacatcgtac cgtcgtattc cactccggtc gttgcaatat ctctaggtcc   1140

accgaaaaac actcatgacc aagatcgtgt cgtcgatctt ggtccaccga aacaccgatg   1200

tccatatcgt ttcgtcgaac ttggaccaac gattcatgca actgatgaca acgcggcccc   1260

cgggtcgtac caatatccga aaaatccaac tgttcttctc tgcctcgcag gtcaagccgt   1320

ggtcaatgaa tactcacgat tgcacaatct gaacatgttc gacggtgtag agttgcgcag   1380

tacgacgcgc cagtccggat gatagacttt ttacacgatc agcacgaccc actgcgctgc   1440

ggcaaaggtc gaaccgaaac aagaataaac cacgaagatc agatcgattc gacggaagaa   1500

gcaatcgaat gcaaagaaga atcggaacga agaaaactct aaagcatcgc atatttacaa   1560

agcataacgg aaaacccgca agttcaaact agtgattagt gtaagatgaa gcaaagcaga   1620

aatgtagtat ctagattttt cgacgttagt ttacaaagat aaaaaatgag gttggacata   1680

caatcgtggg tattcgtctg agttcgtcac aactgcaccg gaaactgtga aacagaatag   1740

agccaacctg tgcgcggaga atgttgaggt cattataagc ttccttagca tccacgggtg   1800

aaagtcgatc gacggaagcc tgcaagactc tgtcgatggg ctttcgtcct agaagaataa   1860

gattaaacct gaaatgtatt ctcccgtgga atggtttcat ttgagtaatt ctgtatcttc   1920
```

-continued

```
tccttcccaa ttccacgaac gcgacgaact ctaatacaaa caacataatg accacagtgc   1980
aaatgctgtt taacgataat agcgacatgc agccattctg gggctaccac gtgtagctct   2040
acttgtgaga cagcgttcct aaagagtgtg aaagtgcaaa caagtgatga aaccaatagt   2100
gcaaagcaag tttagaggga aaatttaaaa aatgcaaaac agcagtagta cttaactttt   2160
aagattgtgt ttcgaaagcc gaagtgaggc tgttccatct gccaccggaa aaaaacgacg   2220
acagcagaat catcaacaag caacatccat ccgaaaaaat ccgggaaacc ggatcttcaa   2280
ccaaccatcc tacaatctac aaaccagaga ttatatctct tcaatcgttt ccgacatcgg   2340
tcggtttcgg tgcccaaaat gatctgataa acacttatct ctctgtagct tgcatgccat   2400
tgcgagcgta ttttggtagc tggccgttgc caaacggctc cgacaggtac tgctattgga   2460
ggttgtgcac gaccacgttg agtttgcctt ttgagttgga gagtgtgtct tttcgtcata   2520
tattcggcct tttcaagggt gattttcagg ctacgtaatg attgtatagt ttaaccagct   2580
aaaacatatt gatgacaagt tctatttcag caccacaaac aagcctgtta atgtctctca   2640
ccgcaaccat tgttctgcgc gcgttataat cagcatagaa gtttattttc tttgggatga   2700
ttcaaatatt acgtgacgca aagtttgcca attttagaac ccctccctcc tccacgtaac   2760
ggcttttgtg tgaaaaattt aaattttgtg tatagaccgt agcatttcgg aagacccccct   2820
cccttactct gttgagttac gtaaaatttc aacgatcctt ttgtagttct gaattttata   2880
tcagcgtgca gtgttatgaa gatatccaca gtataaaata ttattttatt ttaaattcta   2940
tgctgattat caatgtgtta ctagtggctt ttcatactca tgttgcgagc tcgatttggc   3000
gcacggtact tatcaaggca tgtatgtatg ttgtttgaag caactgtata actgtttgaa   3060
actatctaat tggtgagctc gtttcattta gtatataata atgataattg ctatggagac   3120
gttatttact agcaagtgat ttgacgacct gaaatcggaa caaatagaca acgtttttat   3180
aaatacaata aatcagaact ttccattatt gggtacaaag agttgcgcta tttcgatact   3240
gtcagatcag attttccagc acaacgatac cttgatatgc gataacttag aattagacct   3300
tcaaatccat ctctccagct atgaacagtc atatagataa agccaatggc gttatgaggt   3360
agcggaaagc gtcatctttc caatgctatc taagtacata atttgctata gctttctatt   3420
aatcgtagtt tgagagatgc aaagtcagtt atctcgtatc aaggtttgat tgttttggaa   3480
attagctaaa cagttgacat tatcacccgt ctttagggga taagcgcata caaatgtgta   3540
tttagttgtt cattgaagta acgtaagata ggcaagtatg gaaacgagct caccaaacgt   3600
cgaaatacgt ctaataaatt tgtgttcagc aggatggttc aaaatttatt tgcatcacct   3660
caaaattaca gtacctagtg ctgtttgtga caaacatcaa aaggtaaaat caaactcgtg   3720
gcgtcgtgca atctccatag aatgaacaat ttctaaccgt atttgatgga aagacattga   3780
gtctactatc ctcttaacag cattgcactt gtctataaac aataaataat ttgttctttt   3840
ttacattttc tttccccact ttcgcccccc cccccccaa aaatcaatcc ctcaaacagg   3900
atacgacatt tgttgcatct actttccgaa gcgttccagc agacacagac actggccgga   3960
cgaggagaac atctccgtca cccgcactcc gtctgcgtca cggtcgccat gtgccgattt   4020
tcgtacccgg tcacagtcca gctcgccgga taacaacggt ggcgcgctca atctggacac   4080
gaaatctacc aaagcgacga ccgccaccac cgacgacgaa gaggttatgt acgagaaacg   4140
cagcccgaag tccattgaat ctaccgagtt gcggtgccgt ctggaggaag ccttacacag   4200
tggcgctgct gctgctgcgg ctgctgaaga acctctggcg ggcggaagcg gttcccactg   4260
gaagagagaa agtttcggct ctacggagga gattcccact cgacccgctc acagtgaacc   4320
```

```
ggaagataat ggatttgaaa acggattgga agcgcaccag tcccatattc tgcacagcat   4380

acatcggaa                                                           4389


<210> SEQ ID NO 150
<211> LENGTH: 2572
<212> TYPE: DNA
<213> ORGANISM: artificial
<220> FEATURE:
<223> OTHER INFORMATION: DSX Minigene2 from construct LA3534

<400> SEQUENCE: 150

ctcgatttcc cctcgtttcc aatttcagac gacgaacttg tcaaacgatc tcaatggctc     60

ctggagaagc tgcgataccc ctgggagatg atgcccctga tgtacgtgat actgaaaggc    120

gccgacggag acgtcaataa agcgcgccaa cggattgacg aaggtatggg ggttcttacc    180

ggttgggact gtttccgagg tatcgatcgg gtgtcactca cttcctgggt gctcccattt    240

tgtaactgct aacgcttatt attgagtttc aggacatctg ggatcttcgg tcgacggagt    300

ctattcccaa cagtgccctg gatcaaacac tgccatcatg cagtttccgt agcctgttgg    360

gctacgctcc ccgacttgac atcccccatt cttatcaaac aacaactcaa ggcctgagac    420

aacgagtggt ggaatttgcg cacgaagtca ttggtttgtc ctggtaaaag ttaaaagggt    480

taactggagg gttaattgac acggtttcaa ctgatggcct tattgacaca cggatgaaag    540

acttgcacgc ttgaccttct gtctgtacta ataaaagtta cgttggctgg gttttggggt    600

cataatggcc ccaaaatcga atcgtcataa cttcttgaaa tacaactcac gtttaagacc    660

attcaagagt attagatcat cgtctataat agcagatttg aaatttactt cacatttcgg    720

tattgcagtg ccccttgctt ccacaatgga attagttaaa gtttcgagag cattgtcaat    780

atcaagtgtt gttagcaaac aaatgctaac atcaagatta ctatcgatgt ttgattcaca    840

tgtattccaa tcagctcgta aaaaatggaa agtggagctg atagggttga ggtctcacgt    900

gctccaaatc atcacctcca agttagttct aatacactcc gttatatgaa atatggtggt    960

gcgtcgatcg tcgcaagttt atcgttaaac agtcaataaa atgagcattt tatatcgtga   1020

tacatatgag aagatagagg tttcaattaa aacaaatcca catggtgtcg ctaataaaat   1080

tgtgcatttt aagcgagtta tatcctctga tcaagataaa atagaaaatt cgatttttga   1140

atattcaatt ataagagcct gaataactac aacatgtagt gaatcgaaac tgatttatga   1200

cggtttgtga aggttacacg tcctaagcat ttggattcaa gaaaagcaag agatatgacg   1260

aatgtaaact ttatcgtatc aatgaagtaa ctagcgtcca gaacagtaca aaccaacatc   1320

gtaccgtcgt attccactcc ggtcgttgca atatctctag gtccaccgaa aaacactcat   1380

gaccaagatc gtgtcgtcga tcttggtcca ccgaaacacc gatgtccata tcgtttcgtc   1440

gaacttggac caacgattca tgcaactgat gacaacgcgg cccccgggtc gtaccaatat   1500

ccgaaaaatc caactgttct tctctgcctc gcaggtcaag ccgtggtcaa tgaatactca   1560

cgattgcaca atctgaacat gttcgacggt gtagagttgc gcagtacgac gcgccagtcc   1620

ggatgataga ctttttacac gatcagcacg acccactgcg ctgcggcaaa ggtcgaaccg   1680

aaacaagaat aaaccacgaa gatcagatcg attcgacgga agaagcaatc gaatgcaaag   1740

aagaatcgga atgaagaaaa ctctaaagca tcgcatattt acaaagcata acggaaaacc   1800

cgcaagttca aactagtgat tagtgtaaga tgaagcaaag cagaaatgta gtatctagat   1860

ttttcgacgt tagtttacaa agataagaaa tgaggttgga catacaatcg tgggtattcg   1920
```

tctgagttcg tcacaactgc accggaaact gtgaaacaga atagagccaa cctgtgcgcg 1980
gagaatgttg aggtcattat aagcttcctt agcatccacg ggtgaaagtc gatcgacgga 2040
agcctgcaag actctgtcga tgggctttcg tcctagaaga ataagattaa acctgaaatg 2100
tattctcccg tggaatggtt tcatttgagt aattctgtat cttctccttc ccaattccac 2160
gaacgcgacg aactctaata caaacaacat aatgaccaca gtgcaaatgc tgtttaacga 2220
taatagcgac atgcagccat tctggggcta ccacgtgtag ctctacttgt gagacagcgt 2280
tcctaaagag tgtgaaagtg caaacaagtg atgaaaccaa tagtgcaaag caagtttaga 2340
gggaaaattt aaaaaatgca aaacagcagt agtacttaac ttttaagatt gtgtttcgaa 2400
agccgaagtg tgttccatct gccaccggaa aaaaacgacg acagcagaat catcaacaag 2460
caacatccat ccgaaaaaat ccgggaaacc ggatcttcaa ccaaccatcc tacaatctac 2520
aaaccagaga ttatatctct tcaatcgttt ccgacatcgg tcggtttcgg tg 2572

<210> SEQ ID NO 151
<211> LENGTH: 18790
<212> TYPE: DNA
<213> ORGANISM: artificial
<220> FEATURE:
<223> OTHER INFORMATION: LA3619 whole plasmid sequence

<400> SEQUENCE: 151
cgcgcctaag atacattgat gagtttggac aaaccacaac tagaatgcag tgaaaaaaat 60
gctttatttg tgaaatttgt gatgctattg ctttatttgt aaccattata agctgcaata 120
aacaagttaa caacaacaat tgcattcatt ttatgtttca ggttcagggg gaggtgtggg 180
aggtttttta aagcaagtaa aacctctaca aatgtggtat ggctgattat gatcgttgca 240
cattccgatg tatgctgtgc agaatatggg actggtgcgc ttccaatccg ttttcaaatc 300
cattatcttc cggttcactg tgagcgggtc gagtgggaat ctcctccgta gagccgaaac 360
tttctctctt ccagtgggaa ccgcttccgc ccgccagagg ttcttcagca gccgcagcag 420
cagcagcgcc actgtgtaag gcttcctcca gacggcaccg caactcggta gattcaatgg 480
acttcgggct gcgtttctcg tacataacct cttcgtcgtc ggtggtggcg gtcgtcgctt 540
tggtagattt cgtgtccaga ttgagcgcgc caccgttgtt atccggcgag ctggactgtg 600
accgggtacg aaaatcggca catggcgacc gtgacgcaga cggagtgcgg gtgacggaga 660
tgttctcctc gtccggccag tgtctgtgtc tgctggaacg cttcggaaag tagatgcaac 720
aaatgtcgta tcctgtttga gggattgatt tttggggggg gggggggcga aagtggggaa 780
agaaaatgta aaaaagaaca aattatttat tgtttataga caagtgcaat gctgttaaga 840
ggatagtaga ctcaatgtct ttccatcaaa tacggttaga aattgttcat tctatggaga 900
ttgcacgacg ccacgagttt gattttacct tttgatgttt gtcacaaaca gcactaggta 960
ctgtaatttt gaggtgatgc aaataaattt tgaaccatcc tgctgaacac aaatttatta 1020
gacgtatttc gacgtttggt gagctcgttt ccatacttgc ctatcttacg ttacttcaat 1080
gaacaactaa atacacattt gtatgcgctt atcccctaaa gacgggtgat aatgtcaact 1140
gtttagctaa tttccaaaac aatcaaacct tgatacgaga taactgactt tgcatctctc 1200
aaactacgat taatagaaag ctatagcaaa ttatgtactt agatagcatt ggaaagatga 1260
cgctttccgc tacctcataa cgccattggc tttatctata tgactgttca tagctggaga 1320
gatggatttg aaggtctaat tctaagttat cgcatatcaa ggtatcgttg tgctggaaaa 1380
tctgatctga cagtatcgaa atagcgcaac tctttgtacc caataatgga aagttctgat 1440
ttattgtatt tataaaaacg ttgtctattt gttccgattt caggtcgtca aatcacttgc 1500
tagtaaataa cgtctccata gcaattatca ttattatata ctaaatgaaa cgagctcacc 1560
aattagatag tttcaaacag ttatacagtt gcttcaaaca acatacatac atgccttgat 1620
aagtaccgtg cgccaaatcg agctcgcaac atgagtatga aaagccacta gtaacacatt 1680
gataatcagc atagaattta aaataaaata atattttata ctgtggatat cttcataaca 1740
ctgcacgctg atataaaatt cagaactaca aaaggatcgt tgaaatttta cgtaactcaa 1800
cagagtaagg gagggggtct tccgaaatgc tacggtctat acacaaaatt taaatttttc 1860
acacaaaagc cgttacgtgg aggagggagg ggttctaaaa ttggcaaact ttgcgtcacg 1920
taatatttga atcatcccaa agaaaataaa cttctatgct gattataacg cgcgcagaac 1980
aatggttgcg gtgagagaca ttaacaggct tgtttgtggt gctgaaatag aacttgtcat 2040
caatatgttt tagctggtta aactatacaa tcattacgta gcctgaaaat caccccttgaa 2100
aaggccgaat atatgacgaa aagacacact ctccaactca aaaggcaaac tcaacgtggt 2160
cgtgcacaac ctccaatagc agtacctgtc ggagccgttt ggcaacggcc agctaccaaa 2220
atacgctcgc aatggcatgc aagctacaga gagataagtg tttatcagat cattttgggc 2280
accgaaaccg accgatgtcg gaaacgattg aagagatata atctctggtt tgtagattgt 2340
aggatggttg gttgaagatc cggtttcccg gatttttttcg gatggatgtt gcttgttgat 2400
gattctgctg tcgtcgtttt tttccggtgg cagatggaac agcctcactt cggctttcga 2460
aacacaatct taaaagttaa gtactactgc tgttttgcat tttttaaatt ttccctctaa 2520
acttgctttg cactattggt ttcatcactt gtttgcactt tcacactctt taggaacgct 2580
gtctcacaag tagagcttgc ggtggacaat caccggtgtt agccgccgta ctcatcgatg 2640
cccagggcgt cggtgaacat ctgctcgaac tcgaaatcgg ccatatccag ggcgccgtag 2700
ggggcgctat cgtgcggggt gaatcccggt cccgggctat cgccatcgcc cagcatgtcc 2760
aggtcgaagt cgtccagggc atcggcgtgg gccatcgcca catcctcgcc atccaggtgc 2820
agctcatcgc ccaggctcac gtcggtcggc ggggcggtcg acaggcggcg ggtgtgtccg 2880
gccggcagga agctcaggcg cggggcggcc aggcccgcct cctccggggc atcatcatcc 2940
ggcagatcca gcaggccctc gatggtgctg ccgtagttgt tcttggtgcg ggcgcggctg 3000
taggcggggc ccgagcccga ctcgcatttc agttgctttt ccaatccgca gataatcagc 3060
tccaagccga acaggaatgc cggctcggct ccttgatgat cgaacagctc gattgcctga 3120
cgcagcagtg gggcatcga atcggttgtt ggggtctcgc gctcctcttt tgcgacttga 3180
tgctcttggt cctccagcac gcagcccagg gtaaagtgac cgacggcgct cagagcgtag 3240
agagcatttt ccaggctgaa gccttgctgg cacaggaacg cgagctggtt ctccagtgtc 3300
tcgtattgct tttcggtcgg gcgcgtgccg agatggactt tggcaccgtc tcggtgggac 3360
agcagagcgc agcggaacga cttggcgtta ttgcggagga agtcctgcca ggactcgcct 3420
tccaacgggc aaaaatgcgt gtggtggcgg tcgagcatct cgatggccag ggcatccagc 3480
agcgcccgct tattcttcac gtgccagtag agggtgggct gctccacgcc cagcttctgc 3540
gccaacttgc gggtcgtcag tccctcaatg ccaacttcgt tcaacagctc caacgcggag 3600
ttgatgactt tggacttatc caggcggctg cccatggtgg ttttccagtg gcgccgcttc 3660
acgtggtagc cccagaatgg ctgcatgtcg ctattatcgt taaacagcat ttgcactgtg 3720
gtcattatgt tgtttgtatt agagttcgtc gcgttcgtgg aattgggaag gagaagatac 3780

```
agaattactc aaatgaaacc attccacggg agaatacatt tcaggtttaa tcttattctt   3840
ctaggacgaa agcccatcga cagagtcttg caggcttccg tcgatcgact ttcacccgtg   3900
gatgctaagg aagcttataa tgacctcaac attctccgcg cacaggttgg ctctattctg   3960
tttcacagtt tccggtgcag ttgtgacgaa ctcagacgaa tacccacgat tgtatgtcca   4020
acctcatttt ttatctttgt aaactaacgt cgaaaaatct agatactaca tttctgcttt   4080
gcttcatctt acactaatca ctagtttgaa cttgcgggtt ttccgttatg ctttgtaaat   4140
atgcgatgct ttagagtttt cttcgttccg attcttcttt gcattcgatt gcttcttccg   4200
tcgaatcgat ctgatcttcg tggtttattc ttgtttcggt tcgacctttg ccgcagcgca   4260
gtgggtcgtg ctgatcgtgt aaaaagtcta tcatccggac tggcgcgtcg tactgcgcaa   4320
ctctacaccg tcgaacatgt tcagattgtg caatcgtgag tattcattga ccacggcttg   4380
acctgcgagg cagagaagaa cagttggatt tttcggatat tggtacgacc cgggggccgc   4440
gttgtcatca gttgcatgaa tcgttggtcc aagttcgacg aaacgatatg gacatcggtg   4500
tttcggtgga ccaagatcga cgacacgatc ttggtcatga gtgtttttcg gtggacctag   4560
agatattgca acgaccggag tggaatacga cggtacgatg ttggtttgta ctgttctgga   4620
cgctagttac ttcattgata cgataaagtt tacattcgtc atatctcttg cttttcttga   4680
atccaaatgc ttaggacgtg taaccttcac aaaccgtcat aaatcagttt cgattcacta   4740
catgttgtag ttattcaggc tcttataatt gaatattcaa aaatcgaatt ttctatttta   4800
tcttgatcag aggatataac tcgcttaaaa tgcacaattt tattagcgac accatgtgga   4860
tttgttttaa ttgaaacctc tatcttctca tatgtatcac gatataaaat gctcatttta   4920
ttgactgttt aacgataaac ttgcgacgat cgacgcacca ccgacctaat tccattgtgg   4980
aagcaagggg cactgcaata ccgaaatgtg aagtaaattt caaatctgct attatagacg   5040
atgatctaat actcttgaat ggtcttaaac gtgagttgta tttcaagaag ttatgacgat   5100
tcgattttgg ggccattatg accccaaaac ccagccaacg taacttttat tagtacagac   5160
agaaggtcaa gcgtgcaagt ctttcatccg tgtgtcaata aggccatcag ttgaaaccgt   5220
gtcaattaac cctccagtta acccttttaa cttttaccag gacaaaccaa tgacttcgtg   5280
cgcaaattcc accactcgtt gtctcaggcc ttgagttgtt gtttgataag aatgggggat   5340
gtcaagtcgg ggagcgtagc ccaacaggct acggaaactg catgatggca gtgtttgatc   5400
cagggcactg ttgggaatag actccgtcga ccgaagatcc cagatgtcct gaaactcaat   5460
aataagcgtt agcagttaca aaatgggagc acccaggaag tgagtgacac ccgatcgata   5520
cctcggaaac agtcccaacc ggtaagaacc cccatacctt cgtcaatccg ttggcgcgct   5580
ttattgacgt ctccgtcggc gcctttcagt atcacgtaca tcaggggcac cacctcctag   5640
ggcagattgt ttagcttgtt cagctgcgct tgtttatttg cttagctttc gcttagcgac   5700
gtgttcactt tgcttgtttg aattgaattg tcgctccgta gacgaagcgc ctctatttat   5760
actccggcgc tcgttttcga gtttaccact ccctatcagt gatagagaaa agtgaaagtc   5820
gagtttacca ctccctatca gtgatagaga aaagtgaaag tcgagtttac cactccctat   5880
cagtgataga gaaaagtgaa agtcgagttt accactccct atcagtgata gagaaaagtg   5940
aaagtcgagt ttaccactcc ctatcagtga tagagaaaag tgaaagtcga gtttaccact   6000
ccctatcagt gatagagaaa agtgaaagtc gagtttacca ctccctatca gtgatagaga   6060
aaagtgaaag tcgaaacctg gcgcgccccg gccatcgaga aagagagaga gaagagaaga   6120
gagagaacat tcgagaaaga gagagagaag agaagagaga gaacatactc cctatcagtg   6180
```

-continued

```
atagagaagt ccctatcagt gatagagatg tccctatcag tgatagagag ttccctatca   6240
gtgatagaga cgtccctatc agtgatagag aagtccctat cagtgataga gagatcccta   6300
tcagtgatag agatttccct atcagtgata gagaggtccc tatcagtgat agagacttcc   6360
ctatcagtga tagagaaatc cctatcagtg atagagacat ccctatcagt gatagagaac   6420
tccctatcag tgatagagac ctccctatca gtgatagaga tcgatgcggc cgcgagcgcc   6480
ggagtataaa tagaggcgct tcgtctacgg agcgacaatt caattcaaac aagcaaagtg   6540
aacacgtcgc taagcgaaag ctaagcaaat aaacaagcgc agctgaacaa gctaaacaat   6600
ctgcaggtac cctggcggta agttgatcaa aggaaacgca aagttttcaa gaaaaaacaa   6660
aactaatttg atttataaca cctttagaaa gcggggctag ccaccatggg cagcgcctac   6720
agccgcgccc gtaccaagaa caactatggc agcaccatcg agggactgct ggacctgccg   6780
gatgacgatg ccccggagga agccggcctg gccgcccccc gcctgagctt cctgcccgcc   6840
ggacacacgc gccgcctgag caccgccccg ccgaccgatg tgagcctggg cgacgagctg   6900
cacctggatg gagaggatgt ggcaatggcc cacgccgacg ccctggacga tttcgacctg   6960
gatatgctgg gcgatggaga tagcccggga ccgggcttca cgccccacga tagcgccccg   7020
tacggcgccc tggacatggc cgacttcgag ttcgagcaaa tgttcaccga cgcgctgggc   7080
atcgatgagt atggcgggta ggtttaaact cgcgttaaga tacattgatg agtttggaca   7140
aaccacaact agaatgcagt gaaaaaaatg ctttatttgt gaaatttgtg atgctattgc   7200
tttatttgta accattataa gctgcaataa acaagttaac aacaacaatt gcattcattt   7260
tatgtttcag gttcaggggg aggtgtggga ggttttttaa agcaagtaaa acctctacaa   7320
atgtggtatg gctgattatg atcagttatc tagatccggt ggatcttacg ggtcctccac   7380
cttccgcttt ttcttgggtc gagatctcag gaacaggtgg tggcggccct cggtgcgctc   7440
gtactgctcc acgatggtgt agtcctcgtt gtgggaggtg atgtccagct tggcgtccac   7500
gtagtagtag ccgggcagct gcacgggctt cttggccatg tagatggact tgaactccac   7560
caggtagtgg ccgccgtcct tcagcttcag ggccttgtgg gtctcgccct tcagcacgcc   7620
gtcgcggggg tacaggcgct cggtggaggc ctcccagccc atggtcttct tctgcatcac   7680
ggggccgtcg gaggggaagt tcacgccgat gaacttcacc ttgtagatga agcagccgtc   7740
ctgcagggag gagtcctggg tcacggtcgc cacgccgccg tcctcgaagt tcatcacgcg   7800
ctcccacttg aagccctcgg ggaaggacag cttcttgtag tcggggatgt cggcggggtg   7860
cttcacgtac accttggagc cgtactggaa ctgggggggac aggatgtccc aggcgaaggg   7920
cagggggccg cccttggtca ccttcagctt cacggtgttg tggccctcgt aggggcggcc   7980
ctcgccctcg ccctcgatct cgaactcgtg gccgttcacg gtgccctcca tgcgcacctt   8040
gaagcgcatg aactcggtga tgacgttctc ggaggaggcc atggtggcga ccggtttgcg   8100
cttcttcttg ggtggggtgg gatctcccat ggtggcctga atctcaactt gcacctgaag   8160
gtagtgcagc aaggatgagc aaaagggaag aacccagaaa agaacgggaa aacttacccc   8220
aattagaatt gcttgtcgcc gccagtgtca acttgcaact gaaacaatat ccaacatgaa   8280
cgtcaattta tactgcccta atggcgaaca cgataacaat atttctttta ttatgccctc   8340
taaaaccaac gcggttatcg tttatttatt caaattagat atagaacatc cgccgacata   8400
caatgttaat gcaaaaacgc gtttggtgag cggatacgaa aacagtcggc cgataaacat   8460
taatctgagg tcgataacac cgtccttgaa cggaacacga ggagcgtacg tgatcagctg   8520
```

-continued

```
cattcgcgcg ccgcgccttt atcgagattt atttgcatac aacaagtaca ctgcgccgtt   8580
gggatttgtg gtaacgcgca cacatgcaga gctgcaagtg tggcacattt tgtctgtgcg   8640
caaaaccttt gaagccaaaa gtacgaggtc cgttacgggc atgctactag cgcacacgga   8700
caatggaccc gacaaattct acgccaagga tttaatgata atgtcgggca acgtatccgt   8760
tcattttatc aataacctac aaaaatgtcg cgcgcatcac aaagacatcg atatatttaa   8820
acatttatgt cccgaactgc aaatcgataa tagtgttgtg caacctcgag cgtccgtttg   8880
atttaacgta tagcttgcaa atgaattatt taattatcaa tcatgtttta cgcgtagaat   8940
tctacccgta aagcgagttt agttatgagc catgtgcaaa acatgacatc agcttttatt   9000
tttataacaa atgacatcat ttcttgattg tgttttacac gtagaattct actcgtaaag   9060
cgagttcagt tttgaaaaac aaatgacatc atctttttga ttgtgcttta caagtagaat   9120
tctacccgta aatcaagttc ggttttgaaa aacaaatgag tcatattgta tgatatcata   9180
ttgcaaaaca aatgactcat caatcgatcg tgcgttacac gtagaattct actcgtaaag   9240
cgagtttatg agccgtgtgc aaaacatgac atcatctcga tttgaaaaac aaatgacatc   9300
atccactgat cgtgcattac aagtagaatt ctactcgtaa agccagttcg gttatgagcc   9360
gtgtacaaaa catgacatca gattatgact catacttgat tgtgttttac gcgtagaatt   9420
ctactcgtaa agccagttca attttaaaaa caaatgacat catccaaatt aataaatgac   9480
aagcaatggg taccatgcgg cctggcctcg cgctcgcgcg actgacggtc gtaagcaccc   9540
gcgtacgtgt ccaccccggt cacaacccct tgtgtcatgt cggcgaccct acgcccccaa   9600
ctgagagaac tcaaaggtta ccccagttgg ggcactactc ccgaaaaccg cttctgacct   9660
gggaaaacgt gaagccccgg ggcatccgct gagggttgcc gccggggctt cggtgtgtcc   9720
gtcagtactt aattaacacc gaaatcgtaa ttcacggcat cattacaaaa tattttgacg   9780
ttttggacct cgtccctaat gacaccataa cggtggcctt gaagtatatt taaccctaga   9840
aagatagtct gcgtaaaatt gacgcatgca ttcttgaaat attgctctct ctttctaaat   9900
agcgcgaatc cgtcgctgtg catttaggac atctcagtcg ccgcttggag ctcccgtgag   9960
gcgtgcttgt caatgcggta agtgtcactg attttgaact ataacgaccg cgtgagtcaa  10020
aatgacgcat gattatcttt tacgtgactt ttaagattta actcatacga taattatatt  10080
gttatttcat gttctactta cgtgataact tattatatat atattttctt gttatagata  10140
tcgtgactaa tatataataa aatgggtagt tctttagacg atgagcatat cctctctgct  10200
cttctgcaaa gcgatgacga gcttgttggt gaggattctg acagtgaaat atcagatcac  10260
gtaagtgaag atgacctcga ggatccaagc ttatcgattt cgaaccctcg accgccggag  10320
tataaataga ggcgcttcgt ctacggagcg acaattcaat tcaaacaagc aaagtgaaca  10380
cgtcgctaag cgaaagctaa gcaaataaac aagcgcagct gaacaagcta aacaatcggg  10440
gtaccgctag agtcgatccc accccaccca agaagaagcg caaaccggta ccatggcctc  10500
ctccgagaac gtcatcaccg agttcatgcg cttcaaggtg cgcatggagg gcaccgtgaa  10560
cggccacgag ttcgagatcg agggcgaggg cgagggccgc ccctacgagg gccacaacac  10620
cgtgaagctg aaggtgacca agggcggccc cctgcccttc gcctgggaca tcctgtcccc  10680
ccagttccag tacggctcca aggtgtacgt gaagcacccc gccgacatcc ccgactacaa  10740
gaagctgtcc ttccccgagg gcttcaagtg ggagcgcgtg atgaacttcg aggacggcgg  10800
cgtggcgacc gtgacccagg actcctccct gcaggacggc tgcttcatct acaaggtgaa  10860
gttcatcggc gtgaacttcc cctccgacgg ccccgtgatg cagaagaaga ccatgggctg  10920
```

```
ggaggcctcc accgagcgcc tgtacccccg cgacggcgtg ctgaagggcg agacccacaa  10980
ggccctgaag ctgaaggacg gcggccacta cctggtggag ttcaagtcca tctacatggc  11040
caagaagccc gtgcagctgc ccggctacta ctacgtggac gccaagctgg acatcacctc  11100
ccacaacgag gactacacca tcgtggagca gtacgagcgc accgagggcc gccaccacct  11160
gttcctgtga tgatcataat cagccatacc acatttgtag aggttttact tgctttaaaa  11220
aacctcccac acctcccct gaacctgaaa cataaaatga atgcaattgt tgttgttaac  11280
ttgtttattg cagcttataa tggttacaaa taaagcaata gcatcacaaa tttcacaaat  11340
aaagcatttt tttcactgca ttctagttgt ggtttgtcca aactcatcaa tgtatcttaa  11400
cgcgagttaa ttacggccgc tcatttaaat ctggccggcc gcaaccattg tgggaaccgt  11460
gcgatcaaac aaacgcgaga taccggaagt actgaaaaac agtcgctcca ggccagtggg  11520
aacatcgatg ttttgttttg acggacccct tactctcgtc tcatataaac cgaagccagc  11580
taagatggta tacttattat catcttgtga tgaggatgct tctatcaacg aaagtaccgg  11640
taaaccgcaa atggttatgt attataatca aactaaaggc ggagtggaca cgctagacca  11700
aatgtgttct gtgatgacct gcagtaggaa gacgaatagg tggcctatgg cattattgta  11760
cggaatgata aacattgcct gcataaattc ttttattata tacagccata atgtcagtag  11820
caagggagaa aaggtccaaa gtcgcaaaaa atttatgaga aacctttaca tgagcctgac  11880
gtcatcgttt atgcgtaagc gtttagaagc tcctactttg aagagatatt tgcgcgataa  11940
tatctctaat attttgccaa atgaagtgcc tggtacatca gatgacagta ctgaagagcc  12000
agtaatgaaa aaacgtactt actgtactta ctgcccctct aaaataaggc gaaaggcaaa  12060
tgcatcgtgc aaaaaatgca aaaaagttat ttgtcgagag cataatattg atatgtgcca  12120
aagttgtttc tgactgacta ataagtataa tttgtttcta ttatgtataa gttaagctaa  12180
ttacttattt tataatacaa catgactgtt tttaaagtac aaaataagtt tatttttgta  12240
aaagagagaa tgtttaaaag ttttgttact ttatagaaga aattttgagt ttttgttttt  12300
ttttaataaa taaataaaca taaataaatt gtttgttgaa tttattatta gtatgtaagt  12360
gtaaatataa taaaacttaa tatctattca aattaataaa taaacctcga tatacagacc  12420
gataaaacac atgcgtcaat ttttacgcatg attatcttta acgtacgtca caatatgatt  12480
atctttctag ggttaaataa tagtttctaa tttttttatt attcagcctg ctgtcgtgaa  12540
taccgtatat ctcaacgctg tctgtgagat tgtcgtattc tagccttttt agtttttcgc  12600
tcatcgactt gatattgtcc gacacatttt cgtcgatttg cgttttgatc aaagacttga  12660
gcagagacac gttaatcaac tgttcaaatt gatccatatt aacgatatca acccgatgcg  12720
tatatggtgc gtaaaatata ttttttaacc ctcttatact ttgcactctg cgttaatacg  12780
cgttcgtgta cagacgtaat catgttttct tttttggata aaactcctac tgagtttgac  12840
ctcatattag accctcacaa gttgcaaaac gtggcatttt ttaccaatga agaatttaaa  12900
gttattttaa aaaatttcat cacagattta aagaagaacc aaaaattaaa ttatttcaac  12960
agtttaatcg accagttaat caacgtgtac acagacgcgt cggcaaaaaa cacgcagccc  13020
gacgtgttgg ctaaaattat taaatcaact tgtgttatag tcacggattt gccgtccaac  13080
gtgttcctca aaaagttgaa gaccaacaag tttacggaca ctattaatta tttgattttg  13140
ccccacttca ttttgtggga tcacaatttt gttatatttt aaacaaagct tggcactggc  13200
cgtcgtttta caacgtcgtg actgggaaaa ccctggcgtt acccaactta atcgccttgc  13260
```

```
agcacatccc cctttcgcca gctggcgtaa tagcgaagag gcccgcaccg atcgcccttc  13320
ccaacagttg cgcagcctga atggcgaatg gcgcctgatg cggtattttc tccttacgca  13380
tctgtgcggt atttcacacc gcatatggtg cactctcagt acaatctgct ctgatgccgc  13440
atagttaagc cagccccgac acccgccaac acccgctgac gcgccctgac gggcttgtct  13500
gctcccggca tccgcttaca gacaagctgt gaccgtctcc gggagctgca tgtgtcagag  13560
gttttcaccg tcatcaccga aacgcgcgag acgaaagggc ctcgtgatac gcctattttt  13620
ataggttaat gtcatgataa taatggtttc ttagacgtca ggtggcactt ttcggggaaa  13680
tgtgcgcgga acccctattt gtttattttt ctaaatacat tcaaatatgt atccgctcat  13740
gagacaataa ccctgataaa tgcttcaata atattgaaaa aggaagagta tgagtattca  13800
acatttccgt gtcgccctta ttcccttttt tgcggcattt tgccttcctg tttttgctca  13860
cccagaaacg ctggtgaaag taaaagatgc tgaagatcag ttgggtgcac gagtgggtta  13920
catcgaactg gatctcaaca gcggtaagat ccttgagagt tttcgccccg aagaacgttt  13980
tccaatgatg agcactttta aagttctgct atgtggcgcg gtattatccc gtattgacgc  14040
cgggcaagag caactcggtc gccgcataca ctattctcag aatgacttgg ttgagtactc  14100
accagtcaca gaaaagcatc ttacggatgg catgacagta agagaattat gcagtgctgc  14160
cataaccatg agtgataaca ctgcggccaa cttacttctg acaacgatcg gaggaccgaa  14220
ggagctaacc gcttttttgc acaacatggg ggatcatgta actcgccttg atcgttggga  14280
accggagctg aatgaagcca taccaaacga cgagcgtgac accacgatgc ctgtagcaat  14340
ggcaacaacg ttgcgcaaac tattaactgg cgaactactt actctagctt cccggcaaca  14400
attaatagac tggatggagg cggataaagt tgcaggacca cttctgcgct cggcccttcc  14460
ggctggctgg tttattgctg ataaatctgg agccggtgag cgtgggtctc gcggtatcat  14520
tgcagcactg gggccagatg gtaagccctc ccgtatcgta gttatctaca cgacggggag  14580
tcaggcaact atggatgaac gaaatagaca gatcgctgag ataggtgcct cactgattaa  14640
gcattggtaa ctgtcagacc aagtttactc atatatactt tagattgatt taaaacttca  14700
tttttaattt aaaaggatct aggtgaagat cctttttgat aatctcatga ccaaaatccc  14760
ttaacgtgag ttttcgttcc actgagcgtc agaccccgta gaaaagatca aaggatcttc  14820
ttgagatcct ttttttctgc gcgtaatctg ctgcttgcaa acaaaaaaac caccgctacc  14880
agcggtggtt tgtttgccgg atcaagagct accaactctt tttccgaagg taactggctt  14940
cagcagagcg cagataccaa atactgtcct tctagtgtag ccgtagttag gccaccactt  15000
caagaactct gtagcaccgc ctacatacct cgctctgcta atcctgttac cagtggctgc  15060
tgccagtggc gataagtcgt gtcttaccgg gttggactca agacgatagt taccggataa  15120
ggcgcagcgg tcgggctgaa cggggggttc gtgcacacag cccagcttgg agcgaacgac  15180
ctacaccgaa ctgagatacc tacagcgtga gcattgagaa agcgccacgc ttcccgaagg  15240
gagaaaggcg gacaggtatc cggtaagcgg cagggtcgga acaggagagc gcacgaggga  15300
gcttccaggg ggaaacgcct ggtatcttta tagtcctgtc gggtttcgcc acctctgact  15360
tgagcgtcga tttttgtgat gctcgtcagg ggggcggagc ctatggaaaa acgccagcaa  15420
cgcggccttt ttacggttcc tggccttttg ctggcctttt gctcacatgt tctttcctgc  15480
gttatcccct gattctgtgg ataaccgtat taccgccttt gagtgagctg ataccgctcg  15540
ccgcagccga acgaccgagc gcagcgagtc agtgagcgag gaagcggaag agcgcccaat  15600
acgcaaaccg cctctccccg cgcgttggcc gattcattaa tgcagctggc acgacaggtt  15660
```

tcccgactgg aaagcgggca gtgagcgcaa cgcaattaat gtgagttagc tcactcatta 15720
ggcaccccag gctttacact ttatgcttcc ggctcgtatg ttgtgtggaa ttgtgagcgg 15780
ataacaattt cacacaggaa acagctatga ccatgattac gaatttcgac ctgcaggcat 15840
gcaagcttgc atgcctgcag gtcgacgctc gcgcgacttg gtttgccatt ctttagcgcg 15900
cgtcgcgtca cacagcttgg ccacaatgtg gtttttgtca aacgaagatt ctatgacgtg 15960
tttaaagttt aggtcgagta aagcgcaaat ctttttaac cctagaaaga tagtctgcgt 16020
aaaattgacg catgcattct tgaaatattg ctctctcttt ctaaatagcg cgaatccgtc 16080
gctgtgcatt taggacatct cagtcgccgc ttggagctcc cgtgaggcgt gcttgtcaat 16140
gcggtaagtg tcactgattt tgaactataa cgaccgcgtg agtcaaaatg acgcatgatt 16200
atcttttacg tgacttttaa gatttaactc atacgataat tatattgtta tttcatgttc 16260
tacttacgtg ataacttatt atatatatat tttcttgtta tagatatcgt gactaatata 16320
taataaaatg ggtagttctt tagacgatga gcatatcctc tctgctcttc tgcaaagcga 16380
tgacgagctt gttggtgagg attctgacag tgaaatatca gatcacgtaa gtgaagatga 16440
cgtccagagc gatacagaag aagcgtttat agatgaggta catgaagtgc agccaacgtc 16500
aagcggtagt gaaatattag acgaacaaaa tgttattgaa caaccaggtt cttcattggc 16560
ttctaacaga atcttgacct tgccacagag gactattaga ggtaagaata aacattgttg 16620
gtcaacttca aagtccacga ggcgtagccg agtctctgca ctgaacattg tcagatcggc 16680
ccgctcgccc ggggaactag ttcaattaga gactaattca attagagcta attcaattag 16740
gatccaagct tatcgatttc gaaccctcga ccgccggagt ataaatagag gcgcttcgtc 16800
tacggagcga caattcaatt caaacaagca aagtgaacac gtcgctaagc gaaagctaag 16860
caaataaaca agcgcagctg aacaagctaa acaatcgggg taccgctaga gtcgatccca 16920
ccccacccaa gaagaagcgc aaaccggtcg ccaccatggc cctgtccaac aagttcatcg 16980
gcgacgacat gaagatgacc taccacatgg acggctgcgt gaacggccac tacttcaccg 17040
tgaagggcga gggcagcggc aagccctacg agggcaccca gacctccacc ttcaaggtga 17100
ccatggccaa cggcggcccc ctggccttct ccttcgacat cctgtccacc gtgttcatgt 17160
acggcaaccg ctgcttcacc gcctacccca ccagcatgcc cgactacttc aagcaggcct 17220
tccccgacgg catgtcctac gagagaacct tcacctacga ggacggcggc gtggccaccg 17280
ccagctggga gatcagcctg aagggcaact gcttcgagca caagtccacc ttccacggcg 17340
tgaacttccc cgccgacggc cccgtgatgg ccaagaagac caccggctgg gacccctcct 17400
tcgagaagat gaccgtgtgc gacggcatct tgaagggcga cgtgaccgcc ttcctgatgc 17460
tgcagggcgg cggcaactac agatgccagt tccacacctc ctacaagacc aagaagcccg 17520
tgaccatgcc ccccaaccac gtggtggagc accgcatcgc cagaaccgac ctggacaagg 17580
gcggcaacag cgtgcagctg accgagcacg ccgtggccca catcacctcc gtggtgccct 17640
tctccggact cagatcataa tcagccatac cacatttgta gaggttttac ttgctttaaa 17700
aaacctccca cacctccccc tgaacctgaa acataaaatg aatgcaattg ttgttgttaa 17760
cttgtttatt gcagcttata atggttacaa ataaagcaat agcatcacaa atttcacaaa 17820
taaagcattt ttttcactgc attctagttg tggtttgtcc aaactcatca atgtatctta 17880
ccgcggagtg gacacgctag accaaatgtg ttctgtgatg acctgcagta ggaagacgaa 17940
taggtggcct atggcattat tgtacggaat gataaacatt gcctgcataa attcttttat 18000

```
tatatacagc cataatgtca gtagcaaggg agaaaaggtc caaagtcgca aaaaatttat  18060

gagaaacctt tacatgagcc tgacgtcatc gtttatgcgt aagcgtttag aagctcctac  18120

tttgaagaga tatttgcgcg ataatatctc taatattttg ccaaatgaag tgcctggtac  18180

atcagatgac agtactgaag agccagtaat gaaaaaacgt acttactgta cttactgccc  18240

ctctaaaata aggcgaaagg caaatgcatc gtgcaaaaaa tgcaaaaaag ttatttgtcg  18300

agagcataat attgatatgt gccaaagttg tttctgactg actaataagt ataatttgtt  18360

tctattatgt ataagttaag ctaattactt attttataat acaacatgac tgtttttaaa  18420

gtacaaaata agtttatttt tgtaaaagag agaatgttta aaagttttgt tactttatag  18480

aagaaatttt gagtttttgt tttttttaa taaataaata aacataaata aattgtttgt  18540

tgaatttatt attagtatgt aagtgtaaat ataataaaac ttaatatcta ttcaaattaa  18600

taaataaacc tcgatataca gaccgataaa acacatgcgt caattttacg catgattatc  18660

tttaacgtac gtcacaatat gattatcttt ctagggttaa aatgaatgta agcactttat  18720

taacgaaatc tttgggaata tttcgctcat cagcatttta tttgagcagg agtccgagat  18780

gcccgggcgg                                                         18790
```

```
<210> SEQ ID NO 152
<211> LENGTH: 19053
<212> TYPE: DNA
<213> ORGANISM: artificial
<220> FEATURE:
<223> OTHER INFORMATION: LA3612 whole plasmid sequence

<400> SEQUENCE: 152

gggcatctcg gactcctgct caaataaaat gctgatgagc gaaatattcc caaagatttc     60

gttaataaag tgcttacatt cattttaacc ctagaaagat aatcatattg tgacgtacgt    120

taaagataat catgcgtaaa attgacgcat gtgttttatc ggtctgtata tcgaggttta    180

tttattaatt tgaatagata ttaagtttta ttatatttac acttacatac taataataaa    240

ttcaacaaac aatttattta tgtttattta tttattaaaa aaaaacaaaa actcaaaatt    300

tcttctataa agtaacaaaa cttttaaaca ttctctcttt tacaaaaata aacttatttt    360

gtactttaaa aacagtcatg ttgtattata aaataagtaa ttagcttaac ttatacataa    420

tagaaacaaa ttatacttat tagtcagtca gaaacaactt tggcacatat caatattatg    480

ctctcgacaa ataacttttt tgcatttttt gcacgatgca tttgcctttc gccttatttt    540

agaggggcag taagtacagt aagtacgttt tttcattact ggctcttcag tactgtcatc    600

tgatgtacca ggcacttcat ttggcaaaat attagagata ttatcgcgca aatatctctt    660

caaagtagga gcttctaaac gcttacgcat aaacgatgac gtcaggctca tgtaaaggtt    720

tctcataaat tttttgcgac tttggacctt ttctcccttg ctactgacat tatggctgta    780

tataataaaa gaatttatgc aggcaatgtt tatcattccg tacaataatg ccataggcca    840

cctattcgtc ttcctactgc aggtcatcac agaacacatt tggtctagcg tgtccactcc    900

gcggtaagat acattgatga gtttggacaa accacaacta gaatgcagtg aaaaaaatgc    960

tttatttgtg aaatttgtga tgctattgct ttatttgtaa ccattataag ctgcaataaa   1020

caagttaaca acaacaattg cattcatttt atgtttcagg ttcaggggga ggtgtgggag   1080

gtttttttaaa gcaagtaaaa cctctacaaa tgtggtatgg ctgattatga tctgagtccg   1140

gagaagggca ccacggaggt gatgtgggcc acggcgtgct cggtcagctg cacgctgttg   1200

ccgcccttgt ccaggtcggt tctggcgatg cggtgctcca ccacgtggtt ggggggcatg   1260
```

-continued gtcacgggct tcttggtctt gtaggaggtg tggaactggc atctgtagtt gccgccgccc 1320
tgcagcatca ggaaggcggt cacgtcgccc ttcaagatgc cgtcgcacac ggtcatcttc 1380
tcgaaggagg ggtcccagcc ggtggtcttc ttggccatca cggggccgtc ggcggggaag 1440
ttcacgccgt ggaaggtgga cttgtgctcg aagcagttgc ccttcaggct gatctcccag 1500
ctggcggtgg ccacgccgcc gtcctcgtag gtgaaggttc tctcgtagga catgccgtcg 1560
gggaaggcct gcttgaagta gtcgggcatg ctggtggggt aggcggtgaa gcagcggttg 1620
ccgtacatga acacggtgga caggatgtcg aaggagaagg ccaggggggcc gccgttggcc 1680 atggtcacct tgaaggtgga ggtctgggtg ccctcgtagg gcttgccgct gccctcgccc 1740
ttcacggtga agtagtggcc gttcacgcag ccgtccatgt ggtaggtcat cttcatgtcg 1800
tcgccgatga acttgttgga cagggccatg gtggcgaccg gtttgcgctt cttcttgggt 1860
ggggtgggat cgactctagc ggtaccccga ttgtttagct tgttcagctg cgcttgttta 1920
tttgcttagc tttcgcttag cgacgtgttc actttgcttg tttgaattga attgtcgctc 1980
cgtagacgaa gcgcctctat ttatactccg gcggtcgagg gttcgaaatc gataagcttg 2040
gatcctaatt gaattagctc taattgaatt agtctctaat tgaactagtt ccccgggcga 2100
gcgggccgat ctgacaatgt tcagtgcaga gactcggcta cgcctcgtgg actttgaagt 2160
tgaccaacaa tgtttattct tacctctaat agtcctctgt ggcaaggtca agattctgtt 2220
agaagccaat gaagaacctg gttgttcaat aacattttgt tcgtctaata tttcactacc 2280
gcttgacgtt ggctgcactt catgtacctc atctataaac gcttcttctg tatcgctctg 2340
gacgtcatct tcacttacgt gatctgatat ttcactgtca gaatcctcac caacaagctc 2400
gtcatcgctt tgcagaagag cagagaggat atgctcatcg tctaaagaac tacccatttt 2460
attatatatt agtcacgata tctataacaa gaaaatatat atataataag ttatcacgta 2520
agtagaacat gaaataacaa tataattatc gtatgagtta aatcttaaaa gtcacgtaaa 2580
agataatcat gcgtcatttt gactcacgcg gtcgttatag ttcaaaatca gtgacactta 2640
ccgcattgac aagcacgcct cacgggagct ccaagcggcg actgagatgt cctaaatgca 2700
cagcgacgga ttcgcgctat ttagaaagag agagcaatat ttcaagaatg catgcgtcaa 2760
ttttacgcag actatctttc tagggttaaa aaagatttgc gctttactcg acctaaactt 2820
taaacacgtc atagaatctt cgtttgacaa aaaccacatt gtggccaagc tgtgtgacgc 2880
gacgcgcgct aaagaatggc aaaccaagtc gcgcgagcgt cgacctgcag gcatgcaagc 2940
ttgcatgcct gcaggtcgaa attcgtaatc atggtcatag ctgtttcctg tgtgaaattg 3000
ttatccgctc acaattccac acaacatacg agccggaagc ataaagtgta aagcctgggg 3060
tgcctaatga gtgagctaac tcacattaat tgcgttgcgc tcactgcccg ctttccagtc 3120
gggaaacctg tcgtgccagc tgcattaatg aatcggccaa cgcgcgggga gaggcggttt 3180
gcgtattggg cgctcttccg cttcctcgct cactgactcg ctgcgctcgg tcgttcggct 3240
gcggcgagcg gtatcagctc actcaaaggc ggtaatacgg ttatccacag aatcagggga 3300
taacgcagga aagaacatgt gagcaaaagg ccagcaaaag gccaggaacc gtaaaaaggc 3360
cgcgttgctg gcgtttttcc ataggctccg cccccctgac gagcatcaca aaaatcgacg 3420
ctcaagtcag aggtggcgaa acccgacagg actataaaga taccaggcgt ttccccctgg 3480
aagctccctc gtgcgctctc ctgttccgac cctgccgctt accggatacc tgtccgcctt 3540
tctcccttcg ggaagcgtgg cgctttctca atgctcacgc tgtaggtatc tcagttcggt 3600

-continued

```
gtaggtcgtt cgctccaagc tgggctgtgt gcacgaaccc cccgttcagc ccgaccgctg   3660
cgccttatcc ggtaactatc gtcttgagtc caacccggta agacacgact tatcgccact   3720
ggcagcagcc actggtaaca ggattagcag agcgaggtat gtaggcggtg ctacagagtt   3780
cttgaagtgg tggcctaact acggctacac tagaaggaca gtatttggta tctgcgctct   3840
gctgaagcca gttaccttcg gaaaaagagt tggtagctct tgatccggca aacaaaccac   3900
cgctggtagc ggtggttttt ttgtttgcaa gcagcagatt acgcgcagaa aaaaaggatc   3960
tcaagaagat cctttgatct tttctacggg gtctgacgct cagtggaacg aaaactcacg   4020
ttaagggatt ttggtcatga gattatcaaa aaggatcttc acctagatcc ttttaaatta   4080
aaaatgaagt tttaaatcaa tctaaagtat atatgagtaa acttggtctg acagttacca   4140
atgcttaatc agtgaggcac ctatctcagc gatctgtcta tttcgttcat ccatagttgc   4200
ctgactcccc gtcgtgtaga taactacgat acgggagggc ttaccatctg gccccagtgc   4260
tgcaatgata ccgcgagacc cacgctcacc ggctccagat ttatcagcaa taaaccagcc   4320
agccggaagg gccgagcgca gaagtggtcc tgcaacttta tccgcctcca tccagtctat   4380
taattgttgc cgggaagcta gagtaagtag ttcgccagtt aatagtttgc gcaacgttgt   4440
tgccattgct acaggcatcg tggtgtcacg ctcgtcgttt ggtatggctt cattcagctc   4500
cggttcccaa cgatcaaggc gagttacatg atcccccatg ttgtgcaaaa aagcggttag   4560
ctccttcggt cctccgatcg ttgtcagaag taagttggcc gcagtgttat cactcatggt   4620
tatggcagca ctgcataatt ctcttactgt catgccatcc gtaagatgct tttctgtgac   4680
tggtgagtac tcaaccaagt cattctgaga atagtgtatg cggcgaccga gttgctcttg   4740
cccggcgtca atacgggata ataccgcgcc acatagcaga actttaaaag tgctcatcat   4800
tggaaaacgt tcttcggggc gaaaactctc aaggatctta ccgctgttga gatccagttc   4860
gatgtaaccc actcgtgcac ccaactgatc ttcagcatct tttactttca ccagcgtttc   4920
tgggtgagca aaaacaggaa ggcaaaatgc cgcaaaaaag ggaataaggg cgacacggaa   4980
atgttgaata ctcatactct tcctttttca atattattga agcatttatc agggttattg   5040
tctcatgagc ggatacatat ttgaatgtat ttagaaaaat aaacaaatag gggttccgcg   5100
cacatttccc cgaaaagtgc cacctgacgt ctaagaaacc attattatca tgacattaac   5160
ctataaaaat aggcgtatca cgaggccctt tcgtctcgcg cgtttcggtg atgacggtga   5220
aaacctctga cacatgcagc tcccggagac ggtcacagct tgtctgtaag cggatgccgg   5280
gagcagacaa gcccgtcagg gcgcgtcagc gggtgttggc gggtgtcggg gctggcttaa   5340
ctatgcggca tcagagcaga ttgtactgag agtgcaccat atgcggtgtg aaataccgca   5400
cagatgcgta aggagaaaat accgcatcag gcgccattcg ccattcaggc tgcgcaactg   5460
ttgggaaggg cgatcggtgc gggcctcttc gctattacgc cagctggcga aaggggggatg   5520
tgctgcaagg cgattaagtt gggtaacgcc agggttttcc cagtcacgac gttgtaaaac   5580
gacggccagt gccaagcttt gtttaaaata taacaaaatt gtgatcccac aaaatgaagt   5640
ggggcaaaat caaataatta atagtgtccg taaacttgtt ggtcttcaac tttttgagga   5700
acacgttgga cggcaaatcc gtgactataa cacaagttga tttaataatt ttagccaaca   5760
cgtcgggctg cgtgtttttt gccgacgcgt ctgtgtacac gttgattaac tggtcgatta   5820
aactgttgaa ataatttaat ttttggttct tctttaaatc tgtgatgaaa ttttttaaaa   5880
taactttaaa ttcttcattg gtaaaaaatg ccacgttttg caacttgtga gggtctaata   5940
tgaggtcaaa ctcagtagga gttttatcca aaaaagaaaa catgattacg tctgtacacg   6000
```

-continued

```
aacgcgtatt aacgcagagt gcaaagtata agagggttaa aaaatatatt ttacgcacca   6060
tatacgcatc gggttgatat cgttaatatg gatcaatttg aacagttgat taacgtgtct   6120
ctgctcaagt ctttgatcaa aacgcaaatc gacgaaaatg tgtcggacaa tatcaagtcg   6180
atgagcgaaa aactaaaaag gctagaatac gacaatctca cagacagcgt tgagatatac   6240
ggtattcacg acagcaggct gaataataaa aaaattagaa actattattt aaccctagaa   6300
agataatcat attgtgacgt acgttaaaga taatcatgcg taaaattgac gcatgtgttt   6360
tatcggtctg tatatcgagg tttatttatt aatttgaata gatattaagt tttattatat   6420
ttacacttac atactaataa taaattcaac aaacaattta tttatgttta tttatttatt   6480
aaaaaaaaac aaaaactcaa aatttcttct ataaagtaac aaaactttta aacattctct   6540
cttttacaaa aataaactta ttttgtactt taaaaacagt catgttgtat tataaaataa   6600
gtaattagct taacttatac ataatagaaa caaattatac ttattagtca gtcagaaaca   6660
actttggcac atatcaatat tatgctctcg acaaataact tttttgcatt ttttgcacga   6720
tgcatttgcc tttcgcctta ttttagaggg gcagtaagta cagtaagtac gttttttcat   6780
tactggctct tcagtactgt catctgatgt accaggcact tcatttggca aaatattaga   6840
gatattatcg cgcaaatatc tcttcaaagt aggagcttct aaacgcttac gcataaacga   6900
tgacgtcagg ctcatgtaaa ggtttctcat aaattttttg cgactttgga ccttttctcc   6960
cttgctactg acattatggc tgtatataat aaaagaattt atgcaggcaa tgtttatcat   7020
tccgtacaat aatgccatag gccacctatt cgtcttccta ctgcaggtca tcacagaaca   7080
catttggtct agcgtgtcca ctccgccttt agtttgatta taatacataa ccatttgcgg   7140
tttaccggta ctttcgttga tagaagcatc ctcatcacaa gatgataata agtataccat   7200
cttagctggc ttcggtttat atgagacgag agtaaggggt ccgtcaaaac aaaacatcga   7260
tgttcccact ggcctggagc gactgttttt cagtacttcc ggtatctcgc gtttgtttga   7320
tcgcacggtt cccacaatgg ttgcggccgg ccagatttaa atgagcggcc gtaattaact   7380
cgcgttaaga tacattgatg agtttggaca aaccacaact agaatgcagt gaaaaaaatg   7440
ctttatttgt gaaatttgtg atgctattgc tttatttgta accattataa gctgcaataa   7500
acaagttaac aacaacaatt gcattcattt tatgtttcag gttcaggggg aggtgtggga   7560
ggttttttaa agcaagtaaa acctctacaa atgtggtatg gctgattatg atcatcacag   7620
gaacaggtgg tggcggccct cggtgcgctc gtactgctcc acgatggtgt agtcctcgtt   7680
gtgggaggtg atgtccagct tggcgtccac gtagtagtag ccgggcagct gcacgggctt   7740
cttggccatg tagatggact tgaactccac caggtagtgg ccgccgtcct tcagcttcag   7800
ggccttgtgg gtctcgccct tcagcacgcc gtcgcggggg tacaggcgct cggtggaggc   7860
ctcccagccc atggtcttct tctgcatcac ggggccgtcg gaggggaagt tcacgccgat   7920
gaacttcacc ttgtagatga agcagccgtc ctgcagggag gagtcctggg tcacggtcgc   7980
cacgccgccg tcctcgaagt tcatcacgcg ctcccacttg aagccctcgg ggaaggacag   8040
cttcttgtag tcggggatgt cggcggggtg cttcacgtac accttggagc cgtactggaa   8100
ctggggggac aggatgtccc aggcgaaggg cagggggccg cccttggtca ccttcagctt   8160
cacggtgttg tggccctcgt aggggcggcc ctcgccctcg ccctcgatct cgaactcgtg   8220
gccgttcacg gtgccctcca tgcgcacctt gaagcgcatg aactcggtga tgacgttctc   8280
ggaggaggcc atggtaccgg tttgcgcttc ttcttgggtg gggtgggatc gactctagcg   8340
```

```
gtaccccgat tgtttagctt gttcagctgc gcttgtttat ttgcttagct ttcgcttagc   8400
gacgtgttca ctttgcttgt ttgaattgaa ttgtcgctcc gtagacgaag cgcctctatt   8460
tatactccgg cggtcgaggg ttcgaaatcg ataagcttgg atcctcgagg tcatcttcac   8520
ttacgtgatc tgatatttca ctgtcagaat cctcaccaac aagctcgtca tcgctttgca   8580
gaagagcaga gaggatatgc tcatcgtcta aagaactacc cattttatta tatattagtc   8640
acgatatcta taacaagaaa atatatatat aataagttat cacgtaagta gaacatgaaa   8700
taacaatata attatcgtat gagttaaatc ttaaaagtca cgtaaaagat aatcatgcgt   8760
cattttgact cacgcggtcg ttatagttca aaatcagtga cacttaccgc attgacaagc   8820
acgcctcacg ggagctccaa gcggcgactg agatgtccta aatgcacagc gacggattcg   8880
cgctatttag aaagagagag caatatttca agaatgcatg cgtcaatttt acgcagacta   8940
tctttctagg gttaaatata cttcaaggcc accgttatgg tgtcattagg gacgaggtcc   9000
aaaacgtcaa aatattttgt aatgatgccg tgaattacga tttcggtgtt aattaagtac   9060
tgacggacac accgaagccc cggcggcaac cctcagcgga tgccccgggg cttcacgttt   9120
tcccaggtca gaagcggttt tcgggagtag tgccccaact ggggtaacct ttgagttctc   9180
tcagttgggg gcgtagggtc gccgacatga cacaaggggt tgtgaccggg gtggacacgt   9240
acgcgggtgc ttacgaccgt cagtcgcgcg agcgcgaggc caggccgcat ggtacccatt   9300
gcttgtcatt tattaatttg gatgatgtca tttgttttta aaattgaact ggctttacga   9360
gtagaattct acgcgtaaaa cacaatcaag tatgagtcat aatctgatgt catgttttgt   9420
acacggctca taaccgaact ggctttacga gtagaattct acttgtaatg cacgatcagt   9480
ggatgatgtc atttgttttt caaatcgaga tgatgtcatg ttttgcacac ggctcataaa   9540
ctcgctttac gagtagaatt ctacgtgtaa cgcacgatcg attgatgagt catttgtttt   9600
gcaatatgat atcatacaat atgactcatt tgtttttcaa aaccgaactt gatttacggg   9660
tagaattcta cttgtaaagc acaatcaaaa agatgatgtc atttgttttt caaaactgaa   9720
ctcgctttac gagtagaatt ctacgtgtaa aacacaatca agaaatgatg tcatttgtta   9780
taaaaataaa agctgatgtc atgttttgca catggctcat aactaaactc gctttacggg   9840
tagaattcta cgcgtaaaac atgattgata attaaataat tcatttgcaa gctatacgtt   9900
aaatcaaacg gacgctcgag gttgcacaac actattatcg atttgcagtt cgggacataa   9960
atgtttaaat atatcgatgt ctttgtgatg cgcgcgacat tttgtaggt tattgataaa  10020
atgaacggat acgttgcccg acattatcat taaatccttg gcgtagaatt tgtcgggtcc  10080
attgtccgtg tgcgctagta gcatgcccgt aacggacctc gtacttttgg cttcaaaggt  10140
tttgcgcaca gacaaaatgt gccacacttg cagctctgca tgtgtgcgcg ttaccacaaa  10200
tcccaacggc gcagtgtact tgttgtatgc aaataaatct cgataaaggc gcggcgcgcg  10260
aatgcagctg atcacgtacg ctcctcgtgt tccgttcaag gacggtgtta tcgacctcag  10320
attaatgttt atcggccgac tgttttcgta tccgctcacc aaacgcgttt ttgcattaac  10380
attgtatgtc ggcggatgtt ctatatctaa tttgaataaa taaacgataa ccgcgttggt  10440
tttagagggc ataataaaag aaatattgtt atcgtgttcg ccattagggc agtataaatt  10500
gacgttcatg ttggatattg tttcagttgc aagttgacac tggcggcgac aagcaattct  10560
aattggggta agttttcccg ttcttttctg ggttcttccc ttttgctcat ccttgctgca  10620
ctaccttcag gtgcaagttg agattcaggc caccatggga gatcccaccc cacccaagaa  10680
gaagcgcaaa ccggtcgcca ccatggcctc ctccgagaac gtcatcaccg agttcatgcg  10740
```

```
cttcaaggtg cgcatggagg gcaccgtgaa cggccacgag ttcgagatcg agggcgaggg  10800
cgagggccgc ccctacgagg gccacaacac cgtgaagctg aaggtgacca agggcggccc  10860
cctgcccttc gcctgggaca tcctgtcccc ccagttccag tacggctcca aggtgtacgt  10920
gaagcacccc gccgacatcc ccgactacaa gaagctgtcc ttccccgagg gcttcaagtg  10980
ggagcgcgtg atgaacttcg aggacggcgg cgtggcgacc gtgacccagg actcctccct  11040
gcaggacggc tgcttcatct acaaggtgaa gttcatcggc gtgaacttcc cctccgacgg  11100
ccccgtgatg cagaagaaga ccatgggctg ggaggcctcc accgagcgcc tgtacccccg  11160
cgacggcgtg ctgaagggcg agacccacaa ggccctgaag ctgaaggacg gcggccacta  11220
cctggtggag ttcaagtcca tctacatggc caagaagccc gtgcagctgc ccggctacta  11280
ctacgtggac gccaagctgg acatcacctc ccacaacgag gactacacca tcgtggagca  11340
gtacgagcgc accgagggcc gccaccacct gttcctgaga tctcgaccca agaaaaagcg  11400
gaaggtggag gacccgtaag atccaccgga tctagataac tgatcataat cagccatacc  11460
acatttgtag aggttttact tgctttaaaa aacctcccac acctccccct gaacctgaaa  11520
cataaaatga atgcaattgt tgttgttaac ttgtttattg cagcttataa tggttacaaa  11580
taaagcaata gcatcacaaa tttcacaaat aaagcatttt tttcactgca ttctagttgt  11640
ggtttgtcca aactcatcaa tgtatcttaa cgcgagttta aacctacccg ccatactcat  11700
cgatgcccag cgcgtcggtg aacatttgct cgaactcgaa gtcggccatg tccagggcgc  11760
cgtacggggc gctatcgtgg ggcgtgaagc ccggtcccgg gctatctcca tcgcccagca  11820
tatccaggtc gaaatcgtcc agggcgtcgg cgtgggccat tgccacatcc tctccatcca  11880
ggtgcagctc gtcgcccagg ctcacatcgg tcggcggggc ggtgctcagg cggcgcgtgt  11940
gtccggcggg caggaagctc aggcgggggg cggccaggcc ggcttcctcc ggggcatcgt  12000
catccggcag gtccagcagt ccctcgatgg tgctgccata gttgttcttg gtacgggcgc  12060
ggctgtaggc gctgcccatg gtggctagcc ccgctttcta aaggtgttat aaatcaaatt  12120
agttttgttt tttcttgaaa actttgcgtt tcctttgatc aacttaccgc cagggtacct  12180
gcagattgtt tagcttgttc agctgcgctt gtttatttgc ttagctttcg cttagcgacg  12240
tgttcacttt gcttgtttga attgaattgt cgctccgtag acgaagcgcc tctatttata  12300
ctccggcgct cgcggccgca tcgatctcta tcactgatag ggaggtctct atcactgata  12360
gggagttctc tatcactgat agggatgtct ctatcactga tagggatttc tctatcactg  12420
atagggaagt ctctatcact gatagggacc tctctatcac tgatagggaa atctctatca  12480
ctgataggga tctctctatc actgataggg acttctctat cactgatagg gacgtctcta  12540
tcactgatag ggaactctct atcactgata gggacatctc tatcactgat agggacttct  12600
ctatcactga tagggagtat gttctctctc ttctcttctc tctctctttc tcgaatgttc  12660
tctctcttct cttctctctc tctttctcga tggccggggc gcgccaggtt tcgactttca  12720
cttttctcta tcactgatag ggagtggtaa actcgacttt cacttttctc tatcactgat  12780
agggagtggt aaactcgact ttcacttttc tctatcactg atagggagtg gtaaactcga  12840
ctttcacttt tctctatcac tgatagggag tggtaaactc gactttcact tttctctatc  12900
actgataggg agtggtaaac tcgactttca cttttctcta tcactgatag ggagtggtaa  12960
actcgacttt cacttttctc tatcactgat agggagtggt aaactcgaaa acgagcgccg  13020
gagtataaat agaggcgctt cgtctacgga gcgacaattc aattcaaaca agcaaagtga  13080
```

-continued

```
acacgtcgct aagcgaaagc taagcaaata aacaagcgca gctgaacaag ctaaacaatc  13140
tgccctagga tctcagtggc tcctggagaa gctgcgatac ccctgggaga tgatgcccct  13200
gatgtacgtg atactgaaag gcgccgacgg agacgtcaat aaagcgcgcc aacggattga  13260
cgaaggtatg gggttcttta ccggttggga ctgtttccga ggtatcgatc gggtgtcact  13320
cacttcctgg gtgctcccat tttgtaactg ctaacgctta ttattgagtt tcaggacatc  13380
tgggatcttc ggtcgacgga gtctattccc aacagtgccc tggatcaaac actgccatca  13440
tgcagtttcc gtagcctgtt gggctacgct ccccgacttg acatccccca ttcttatcaa  13500
acaacaactc aaggcctgag acaacgagtg gtggaatttg cgcacgaagt cattggtttg  13560
tcctggtaaa agttaaaagg gttaactgga gggttaattg acacggtttc aactgatggc  13620
cttattgaca cacggatgaa agacttgcac gcttgacctt ctgtctgtac taataaaagt  13680
tacgttggct gggttttggg gtcataatgg ccccaaaatc gaatcgtcat aacttcttga  13740
aatacaactc acgtttaaga ccattcaaga gtattagatc atcgtctata atagcagatt  13800
tgaaatttac ttcacatttc ggtattgcag tgccccttgc ttccacaatg gaattaggtc  13860
ggtggtgcgt cgatcgtcgc aagtttatcg ttaaacagtc aataaaatga gcattttata  13920
tcgtgataca tatgagaaga tagaggtttc aattaaaaca aatccacatg gtgtcgctaa  13980
taaaattgtg cattttaagc gagttatatc ctctgatcaa gataaaatag aaaattcgat  14040
ttttgaatat tcaattataa gagcctgaat aactacaaca tgtagtgaat cgaaactgat  14100
ttatgacggt ttgtgaaggt tacacgtcct aagcatttgg attcaagaaa agcaagagat  14160
atgacgaatg taaactttat cgtatcaatg aagtaactag cgtccagaac agtacaaacc  14220
aacatcgtac cgtcgtattc cactccggtc gttgcaatat ctctaggtcc accgaaaaac  14280
actcatgacc aagatcgtgt cgtcgatctt ggtccaccga aacaccgatg tccatatcgt  14340
ttcgtcgaac ttggaccaac gattcatgca actgatgaca acgcggcccc cgggtcgtac  14400
caatatccga aaaatccaac tgttcttctc tgcctcgcag gtcaagccgt ggtcaatgaa  14460
tactcacgat tgcacaatct gaacatgttc gacggtgtag agttgcgcag tacgacgcgc  14520
cagtccggat gatagacttt ttacacgatc agcacgaccc actgcgctgc ggcaaaggtc  14580
gaaccgaaac aagaataaac cacgaagatc agatcgattc gacggaagaa gcaatcgaat  14640
gcaaagaaga atcggaacga agaaaactct aaagcatcgc atatttacaa agcataacgg  14700
aaaacccgca agttcaaact agtgattagt gtaagatgaa gcaaagcaga aatgtagtat  14760
ctagattttt cgacgttagt ttacaaagat aaaaaatgag gttggacata caatcgtggg  14820
tattcgtctg agttcgtcac aactgcaccg gaaactgtga aacagaatag agccaacctg  14880
tgcgcggaga atgttgaggt cattataagc ttccttagca tccacgggtg aaagtcgatc  14940
gacggaagcc tgcaagactc tgtcgatggg ctttcgtcct agaagaataa gattaaacct  15000
gaaatgtatt ctcccgtgga atggtttcat ttgagtaatt ctgtatcttc tccttcccaa  15060
ttccacgaac gcgacgaact ctaatacaaa caacataatg accacagtgc aaatgctgtt  15120
taacgataat agcgacatgc agccattctg gggctaccac gtgtggctct acttgcgatc  15180
caaaatgcag atcttcgtca agaccctgac cggcaagacc atcaccctgg aggtggagcc  15240
gagcgatacc atcgagaacg tgaaggccaa gatccaggac aaggagggca tcccgccgga  15300
tcagcagcgc ctgatcttcg ccggacgcca gctggaggat ggccgcaccc tgagcgacta  15360
caacatccag aaggagagca ccctgcacct ggtgctgcgc ctgcgcggtg gtatggtcag  15420
ccgcctggat aagtccaaag tcatcaactc cgcgttggag ctgttgaacg aagttggcat  15480
```

```
tgagggactg acgacccgca agttggcgca gaagctgggc gtggagcagc ccaccctcta  15540
ctggcacgtg aagaataagc gggcgctgct ggatgccctg gccatcgaga tgctcgaccg  15600
ccaccacacg catttttgcc cgttggaagg cgagtcctgg caggacttcc tccgcaataa  15660
cgccaagtcg ttccgctgcg ctctgctgtc ccaccgagac ggtgccaaag tccatctcgg  15720
cacgcgcccg accgaaaagc aatacgagac actggagaac cagctcgcgt tcctgtgcca  15780
gcaaggcttc agcctggaaa atgctctcta cgctctgagc gccgtcggtc actttaccct  15840
gggctgcgtg ctggaggacc aagagcatca agtcgcaaaa gaggagcgcg agaccccaac  15900
aaccgattcg atgcccccac tgctgcgtca ggcaatcgag ctgttcgatc atcaaggagc  15960
cgagccggca ttcctgttcg gcttggagct gattatctgc ggattggaaa agcaactgaa  16020
atgcgagtcg ggctcgggcc ccgcctacag ccgcgcccgc accaagaaca actacggcag  16080
caccatcgag ggcctgctgg atctgccgga tgatgatgcc ccggaggagg cgggcctggc  16140
cgccccgcgc ctgagcttcc tgccggccgg acacacccgc cgcctgtcga ccgccccgcc  16200
gaccgacgtg agcctgggcg atgagctgca cctggatggc gaggatgtgg cgatggccca  16260
cgccgatgcc ctggacgact tcgacctgga catgctgggc gatggcgata gcccgggacc  16320
gggattcacc ccgcacgata gcgcccccta cggcgccctg gatatggccg atttcgagtt  16380
cgagcagatg ttcaccgacg ccctgggcat cgatgagtac ggcggctaac accggtgatt  16440
gtccaccgca agctctactt gtgagacagc gttcctaaag agtgtgaaag tgcaaacaag  16500
tgatgaaacc aatagtgcaa agcaagttta gagggaaaat ttaaaaaatg caaaacagca  16560
gtagtactta acttttaaga ttgtgtttcg aaagccgaag tgaggctgtt ccatctgcca  16620
ccggaaaaaa acgacgacag cagaatcatc aacaagcaac atccatccga aaaaatccgg  16680
gaaaccggat cttcaaccaa ccatcctaca atctacaaac cagagattat atctcttcaa  16740
tcgtttccga catcggtcgg tttcggtgcc caaaatgatc tgataaacac ttatctctct  16800
gtagcttgca tgccattgcg agcgtatttt ggtagctggc cgttgccaaa cggctccgac  16860
aggtactgct attggaggtt gtgcacgacc acgttgagtt tgccttttga gttggagagt  16920
gtgtcttttc gtcatatatt cggccttttc aagggtgatt ttcaggctac gtaatgattg  16980
tatagtttaa ccagctaaaa catattgatg acaagttcta tttcagcacc acaaacaagc  17040
ctgttaatgt ctctcaccgc aaccattgtt ctgcgcgcgt tataatcagc atagaagttt  17100
attttctttg ggatgattca aatattacgt gacgcaaagt ttgccaattt tagaacccct  17160
ccctcctcca cgtaacggct tttgtgtgaa aaatttaaat tttgtgtata gaccgtagca  17220
tttcggaaga ccccctccct tactctgttg agttacgtaa aatttcaacg atccttttgt  17280
agttctgaat tttatatcag cgtgcagtgt tatgaagata tccacagtat aaaatattat  17340
tttattttaa attctatgct gattatcaat gtgttactag tggcttttca tactcatgtt  17400
gcgagctcga tttggcgcac ggtacttatc aaggcatgta tgtatgttgt ttgaagcaac  17460
tgtataactg tttgaaacta tctaattggt gagctcgttt catttagtat ataataatga  17520
taattgctat ggagacgtta tttactagca agtgatttga cgacctgaaa tcggaacaaa  17580
tagacaacgt ttttataaat acaataaatc agaactttcc attattgggt acaaagagtt  17640
gcgctatttc gatactgtca gatcagattt tccagcacaa cgataccttg atatgcgata  17700
acttagaatt agaccttcaa atccatctct ccagctatga acagtcatat agataaagcc  17760
aatggcgtta tgaggtagcg gaaagcgtca tctttccaat gctatctaag tacataattt  17820
```

```
gctatagctt tctattaatc gtagtttgag agatgcaaag tcagttatct cgtatcaagg  17880

tttgattgtt ttggaaatta gctaaacagt tgacattatc acccgtcttt aggggataag  17940

cgcatacaaa tgtgtattta gttgttcatt gaagtaacgt aagataggca agtatggaaa  18000

cgagctcacc aaacgtcgaa atacgtctaa taaatttgtg ttcagcagga tggttcaaaa  18060

tttatttgca tcacctcaaa attacagtac ctagtgctgt ttgtgacaaa catcaaaagg  18120

taaaatcaaa ctcgtggcgt cgtgcaatct ccatagaatg aacaatttct aaccgtattt  18180

gatggaaaga cattgagtct actatcctct taacagcatt gcacttgtct ataaacaata  18240

aataatttgt tcttttttac attttctttc cccactttcg cccccccccc ccccaaaaat  18300

caatccctca aacaggatac gacatttgtt gcatctactt tccgaagcgt tccagcagac  18360

acagacactg gccggacgag gagaacatct ccgtcacccg cactccgtct gcgtcacggt  18420

cgccatgtgc cgattttcgt acccggtcac agtccagctc gccggataac aacggtggcg  18480

cgctcaatct ggacacgaaa tctaccaaag cgacgaccgc caccaccgac gacgaagagg  18540

ttatgtacga gaaacgcagc ccgaagtcca ttgaatctac cgagttgcgg tgccgtctgg  18600

aggaagcctt acacagtggc gctgctgctg ctgcggctgc tgaagaacct ctggcgggcg  18660

gaagcggttc ccactggaag agagaaagtt tcggctctac ggaggagatt cccactcgac  18720

ccgctcacag tgaaccggaa gataatggat ttgaaaacgg attggaagcg caccagtccc  18780

atattctgca cagcatacat cggaatgtgc aacgatcata atcagccata ccacatttgt  18840

agaggtttta cttgctttaa aaaacctccc acacctcccc ctgaacctga aacataaaat  18900

gaatgcaatt gttgttgtta acttgtttat tgcagcttat aatggttaca aataaagcaa  18960

tagcatcaca aatttcacaa ataaagcatt tttttcactg cattctagtt gtggtttgtc  19020

caaactcatc aatgtatctt aggcgcgccg ccc                               19053
```

<210> SEQ ID NO 153
<211> LENGTH: 10540
<212> TYPE: DNA
<213> ORGANISM: artificial
<220> FEATURE:
<223> OTHER INFORMATION: LA3491 plasmid sequence

<400> SEQUENCE: 153

```
ctaggcttta cgagtagaat tctacgcgta aaacacaatc aagtatgagt cataatctga     60

tgtcatgttt tgtacacggc tcataaccga actggcttta cgagtagaat tctacttgta    120

atgcacgatc agtggatgat gtcatttgtt tttcaaatcg agatgatgtc atgttttgca    180

cacggctcat aaactcgctt tacgagtaga attctacgtg taacgcacga tcgattgatg    240

agtcatttgt tttgcaatat gatatcatac aatatgactc atttgttttt caaaaccgaa    300

cttgatttac gggtagaatt ctacttgtaa agcacaatca aaaagatgat gtcatttgtt    360

tttcaaaact gaactcgctt tacgagtaga attctacgtg taaaacacaa tcaagaaatg    420

atgtcatttg ttataaaaat aaaagctgat gtcatgtttt gcacatggct cataactaaa    480

ctcgctttac gggtagaatt ctacgcgtaa aacatgattg ataattaaat aattcatttg    540

caagctatac gttaaatcaa acggacgctc gaggttgcac aacactatta tcgatttgca    600

gttcgggaca taaatgttta aatatatcga tgtctttgtg atgcgcgcga catttttgta    660

ggttattgat aaaatgaacg gatacgttgc ccgacattat cattaaatcc ttggcgtaga    720

atttgtcggg tccattgtcc gtgtgcgcta gcatgcccgt aacggacctc gtacttttgg    780

cttcaaaggt tttgcgcaca gacaaaatgt gccacacttg cagctctgca tgtgtgcgcg    840
```

-continued ttaccacaaa tcccaacggc gcagtgtact tgttgtatgc aaataaatct cgataaaggc 900
gcggcgcgcg aatgcagctg atcacgtacg ctcctcgtgt tccgttcaag gacggtgtta 960
tcgacctcag attaatgttt atcggccgac tgttttcgta tccgctcacc aaacgcgttt 1020
ttgcattaac attgtatgtc ggcggatgtt ctatatctaa tttgaataaa taaacgataa 1080
ccgcgttggt tttagagggc ataataaaag aaatattgtt atcgtgttcg ccattagggc 1140
agtataaatt gacgttcatg ttggatattg tttcagttgc aagttgacac tggcggcgac 1200
aagcaattct aattggggta agttttcccg ttcttttctg ggttcttccc ttttgctcat 1260
ccttgctgca ctaccttcag gtgcaagttg agattcaggc caccatggga gcttcacgac 1320
gaacttgtca aacgatctca atggctcctg gagaagctgc gataccccctg ggagatgatg 1380
cccctgatgt acgtgatact gaaaggcgcc gacggagacg tcaataaagc gcgccaacgg 1440
attgacgaag gtatgggggt tcttaccggt tgggactgtt tccgaggtat cgatcgggtg 1500
tcactcactt cctgggtgct cccattttgt aactgctaac gcttattatt gagtttcagg 1560
acatctggga tcttcggtcg acggagtcta ttcccaacag tgccctggat caaacactgc 1620
catcatgcag tttccgtagc ctgttgggct acgctccccg acttgacatc ccccattctt 1680
atcaaacaac aactcaaggc ctgagacaac gagtggtgga atttgcgcac gaagtcattg 1740
gtttgtcctg gtaaaagtta aaagggttaa ctggagggtt aattgacacg gtttcaactg 1800
atggccttat tgacacacgg atgaaagact tgcacgcttg accttctgtc tgtactaata 1860
aaagttacgt tggctgggtt ttggggtcat aatggcccca aaatcgaatc gtcataactt 1920
cttgaaatac aactcacgtt taagaccatt caagagtatt agatcatcgt ctataatagc 1980
agatttgaaa tttacttcac atttcggtat tgcagtgccc cttgcttcca caatggaatt 2040
aggtcggtgg tgcgtcgatc gtcgcaagtt tatcgttaaa cagtcaataa aatgagcatt 2100
ttatatcgtg atacatatga gaagatagag gtttcaatta aaacaaatcc acatggtgtc 2160
gctaataaaa ttgtgcattt taagcgagtt atatcctctg atcaagataa aatagaaaat 2220
tcgatttttg aatattcaat tataagagcc tgaataacta caacatgtag tgaatcgaaa 2280
ctgatttatg acggtttgtg aaggttacac gtcctaagca tttggattca agaaaagcaa 2340
gagatatgac gaatgtaaac tttatcgtat caatgaagta actagcgtcc agaacagtac 2400
aaaccaacat cgtaccgtcg tattccactc cggtcgttgc aatatctcta ggtccaccga 2460
aaaacactca tgaccaagat cgtgtcgtcg atcttggtcc accgaaacac cgatgtccat 2520
atcgtttcgt cgaacttgga ccaacgattc atgcaactga tgacaacgcg gcccccgggt 2580
cgtaccaata tccgaaaaat ccaactgttc ttctctgcct cgcaggtcaa gccgtggtca 2640
atgaatactc acgattgcac aatctgaaca tgttcgacgg tgtagagttg cgcagtacga 2700
cgcgccagtc cggatgatag actttttaca cgatcagcac gacccactgc gctgcggcaa 2760
aggtcgaacc gaaacaagaa taaaccacga agatcagatc gattcgacgg aagaagcaat 2820
cgaatgcaaa gaagaatcgg aacgaagaaa actctaaagc atcgcatatt tacaaagcat 2880
aacggaaaac ccgcaagttc aaactagtga ttagtgtaag atgaagcaaa gcagaaatgt 2940
agtatctaga tttttcgacg ttagtttaca aagataaaaa atgaggttgg acatacaatc 3000
gtgggtattc gtctgagttc gtcacaactg caccggaaac tgtgaaacag aatagagcca 3060
acctgtgcgc ggagaatgtt gaggtcatta taagcttcct tagcatccac gggtgaaagt 3120
cgatcgacgg aagcctgcaa gactctgtcg atgggctttc gtcctagaag aataagatta 3180

-continued

```
aacctgaaat gtattctccc gtggaatggt ttcatttgag taattctgta tcttctcctt   3240
cccaattcca cgaacgcgac gaactctaat acaaacaaca taatgaccac agtgcaaatg   3300
ctgtttaacg ataatagcga catgcagcca ttctggggct accacgtgta gctctacttg   3360
tgagacagcg ttcctaaaga gtgtgaaagt gcaaacaagt gatgaaacca atagtgcaaa   3420
gcaagtttag agggaaaatt taaaaaatgc aaaacagcag tagtacttaa cttttaagat   3480
tgtgtttcga aagccgaagt gaggctgttc catctgccac cggaaaaaaa cgacgacagc   3540
agaatcatca acaagcaaca tccatccgaa aaaatccggg aaaccggatc ttcaaccaac   3600
catcctacaa tctacaaacc agagattata tctcttcaat cgtttccgac atcggtcggt   3660
ttcggtgccc aaaatgatct gataaacact tatctctctg tagcttgcat gccattgcga   3720
gcgtattttg gtagctggcc gttgccaaac ggctccgaca ggtactgcta ttggaggttg   3780
tgcacgacca cgttgagttt gccttttgag ttggagagtg tgtcttttcg tcatatattc   3840
ggccttttca agggtgattt tcaggctacg taatgattgt atagtttaac cagctaaaac   3900
atattgatga caagttctat ttcagcacca caaacaagcc tgttaatgtc tctcaccgca   3960
accattgttc tgcgcgcgtt ataatcagca tagaagttta ttttctttgg gatgattcaa   4020
atattacgtg acgcaaagtt tgccaatttt agaacccctc cctcctccac gtaacggctt   4080
ttgtgtgaaa aatttaaatt ttgtgtatag accgtagcat ttcggaagac cccctccctt   4140
actctgttga gttacgtaaa atttcaacga tccttttgta gttctgaatt ttatatcagc   4200
gtgcagtgtt atgaagatat ccacagtata aaatattatt ttattttaaa ttctatgctg   4260
attatcaatg tgttactagt ggcttttcat actcatgttg cgagctcgat ttggcgcacg   4320
gtacttatca aggcatgtat gtatgttgtt tgaagcaact gtataactgt ttgaaactat   4380
ctaattggtg agctcgtttc atttagtata taataatgat aattgctatg gagacgttat   4440
ttactagcaa gtgatttgac gacctgaaat cggaacaaat agacaacgtt tttataaata   4500
caataaatca gaactttcca ttattgggta caaagagttg cgctatttcg atactgtcag   4560
atcagatttt ccagcacaac gataccttga tatgcgataa cttagaatta gaccttcaaa   4620
tccatctctc cagctatgaa cagtcatata gataaagcca atggcgttat gaggtagcgg   4680
aaagcgtcat ctttccaatg ctatctaagt acataatttg ctatagcttt ctattaatcg   4740
tagtttgaga gatgcaaagt cagttatctc gtatcaaggt ttgattgttt tggaaattag   4800
ctaaacagtt gacattatca cccgtcttta ggggataagc gcatacaaat gtgtatttag   4860
ttgttcattg aagtaacgta agataggcaa gtatggaaac gagctcacca aacgtcgaaa   4920
tacgtctaat aaatttgtgt tcagcaggat ggttcaaaat ttatttgcat cacctcaaaa   4980
ttacagtacc tagtgctgtt tgtgacaaac atcaaaaggt aaaatcaaac tcgtggcgtc   5040
gtgcaatctc catagaatga acaatttcta accgtatttg atggaaagac attgagtcta   5100
ctatcctctt aacagcattg cacttgtcta taaacaataa ataatttgtt ctttttttaca   5160
ttttctttcc ccactttcgc cccccccccc cccaaaaatc aatccctcaa acaggatacg   5220
acatttgttg catctacttt ccgaagcgtt ccagcagaca cagacactgg ccggacgagg   5280
agaacatctc cgtcacccgc actccgtctg cgtcacggtc gccatgtgcc gattttcgta   5340
cccggtcaca gtccagctcg ccggataaca acggtggcgc gctcaatctg gacacgaaat   5400
ctaccaaagc gacgaccgcc accaccgacg acgaagaggt tatgtacgag aaacgcagcc   5460
cgaagtccat tgaatctacc gagttgcggt gccgtctgga ggaagcctta cacagtggcg   5520
ctgctgctgc tgcggctgct gaagaacctc tggcgggcgg aagcggttcc cactggaaga   5580
```

gagaaagttt cggctctacg gaggagattc ccactcgacc cgctcacagt gaaccggaag 5640
ataatggatt tgaaaacgga ttggaagcgc accagtccca tattctgcac agcatacatc 5700
ggaatgtgca acgatcataa tcagccatac cacatttgta gaggttttac ttgctttaaa 5760
aaacctccca cacctccccc tgaacctgaa acataaaatg aatgcaattg ttgttgttaa 5820
cttgtttatt gcagcttata atggttacaa ataaagcaat agcatcacaa atttcacaaa 5880
taaagcattt ttttcactgc attctagttg tggtttgtcc aaactcatca atgtatctta 5940
gggccgccac cgcggtggag ctccagcttt tgttcccttt agtgagggtt aattgcgcgc 6000
ttggcgtaat catggtcata gctgtttcct gtgtgaaatt gttatccgct cacaattcca 6060
cacaacatac gagccggaag cataaagtgt aaagcctggg gtgcctaatg agtgagctaa 6120
ctcacattaa ttgcgttgcg ctcactgccc gctttccagt cgggaaacct gtcgtgccag 6180
ctgcattaat gaatcggcca acgcgcgggg agaggcggtt tgcgtattgg gcgctcttcc 6240
gcttcctcgc tcactgactc gctgcgctcg gtcgttcggc tgcggcgagc ggtatcagct 6300
cactcaaagg cggtaatacg gttatccaca gaatcagggg ataacgcagg aaagaacatg 6360
tgagcaaaag gccagcaaaa ggccaggaac cgtaaaaagg ccgcgttgct ggcgtttttc 6420
cataggctcc gcccccctga cgagcatcac aaaaatcgac gctcaagtca gaggtggcga 6480
aacccgacag gactataaag ataccaggcg tttccccctg gaagctccct cgtgcgctct 6540
cctgttccga ccctgccgct taccggatac ctgtccgcct ttctcccttc gggaagcgtg 6600
gcgctttctc atagctcacg ctgtaggtat ctcagttcgg tgtaggtcgt tcgctccaag 6660
ctgggctgtg tgcacgaacc ccccgttcag cccgaccgct gcgccttatc cggtaactat 6720
cgtcttgagt ccaacccggt aagacacgac ttatcgccac tggcagcagc cactggtaac 6780
aggattagca gagcgaggta tgtaggcggt gctacagagt tcttgaagtg gtggcctaac 6840
tacggctaca ctagaaggac agtatttggt atctgcgctc tgctgaagcc agttaccttc 6900
ggaaaaagag ttggtagctc ttgatccggc aaacaaacca ccgctggtag cggtggtttt 6960
tttgtttgca agcagcagat tacgcgcaga aaaaaaggat ctcaagaaga tcctttgatc 7020
ttttctacgg ggtctgacgc tcagtggaac gaaaactcac gttaagggat tttggtcatg 7080
agattatcaa aaaggatctt cacctagatc cttttaaatt aaaaatgaag ttttaaatca 7140
atctaaagta tatatgagta aacttggtct gacagttacc aatgcttaat cagtgaggca 7200
cctatctcag cgatctgtct atttcgttca tccatagttg cctgactccc cgtcgtgtag 7260
ataactacga tacgggaggg cttaccatct ggccccagtg ctgcaatgat accgcgagac 7320
ccacgctcac cggctccaga tttatcagca ataaaccagc cagccggaag ggccgagcgc 7380
agaagtggtc ctgcaacttt atccgcctcc atccagtcta ttaattgttg ccgggaagct 7440
agagtaagta gttcgccagt taatagtttg cgcaacgttg ttgccattgc tacaggcatc 7500
gtggtgtcac gctcgtcgtt tggtatggct tcattcagct ccggttccca acgatcaagg 7560
cgagttacat gatcccccat gttgtgcaaa aaagcggtta gctccttcgg tcctccgatc 7620
gttgtcagaa gtaagttggc cgcagtgtta tcactcatgg ttatggcagc actgcataat 7680
tctcttactg tcatgccatc cgtaagatgc ttttctgtga ctggtgagta ctcaaccaag 7740
tcattctgag aatagtgtat gcggcgaccg agttgctctt gcccggcgtc aatacgggat 7800
aataccgcgc cacatagcag aactttaaaa gtgctcatca ttggaaaacg ttcttcgggg 7860
cgaaaactct caaggatctt accgctgttg agatccagtt cgatgtaacc cactcgtgca 7920

-continued

```
cccaactgat cttcagcatc ttttactttc accagcgttt ctgggtgagc aaaaacagga   7980
aggcaaaatg ccgcaaaaaa gggaataagg gcgacacgga aatgttgaat actcatactc   8040
ttcctttttc aatattattg aagcatttat cagggttatt gtctcatgag cggatacata   8100
tttgaatgta tttagaaaaa taaacaaata ggggttccgc gcacatttcc ccgaaaagtg   8160
ccacctaaat tgtaagcgtt aatattttgt taaaattcgc gttaaatttt tgttaaatca   8220
gctcattttt taaccaatag gccgaaatcg gcaaaatccc ttataaatca aaagaataga   8280
ccgagatagg gttgagtgtt gttccagttt ggaacaagag tccactatta aagaacgtgg   8340
actccaacgt caaagggcga aaaaccgtct atcagggcga tggcccacta cgtgaaccat   8400
caccctaatc aagttttttg gggtcgaggt gccgtaaagc actaaatcgg aaccctaaag   8460
ggagcccccg atttagagct tgacggggaa agccggcgaa cgtggcgaga aaggaaggga   8520
agaaagcgaa aggagcgggc gctagggcgc tggcaagtgt agcggtcacg ctgcgcgtaa   8580
ccaccacacc cgccgcgctt aatgcgccgc tacagggcgc gtcccattcg ccattcaggc   8640
tgcgcaactg ttgggaaggg cgatcggtgc gggcctcttc gctattacgc cagctggcga   8700
aagggggatg tgctgcaagg cgattaagtt gggtaacgcc agggttttcc cagtcacgac   8760
gttgtaaaac gacggccagt gagcgcgcgt aatacgactc actatagggc gaattgggta   8820
ccgggcccaa gcttatcgat accgtcgaca tgcccgccgt gaccgtcgag aacccgctga   8880
cgctgccccg cgtatccgca cccgccgacg ccgtcgcacg tcccgtgctc accgtgacca   8940
ccgcgcccag cggtttcgag ggcgagggct tcccggtgcg ccgcgcgttc gccgggatca   9000
actaccgcca cctcgacccg ttcatcatga tggaccagat gggtgaggtg gagtacgcgc   9060
ccggggagcc caagggcacg ccctggcacc cgcaccgcgg cttcgagacc gtgacctaca   9120
tcgtcgacct cgaggggggg cccccccctcg aggttcccac aatggttaat tcgagctcgc   9180
ccggggatct aattcaatta gagactaatt caattagagc taattcaatt aggatccaag   9240
cttatcgatt tcgaaccctc gaccgccgga gtataaatag aggcgcttcg tctacggagc   9300
gacaattcaa ttcaaacaag caaagtgaac acgtcgctaa gcgaaagcta agcaaataaa   9360
caagcgcagc tgaacaagct aaacaatcgg ggtaccgcta gagtcgatcc caccccaccc   9420
aagaagaagc gcaaaccggt cgccaccatg gcctcctccg agaacgtcat caccgagttc   9480
atgcgcttca aggtgcgcat ggagggcacc gtgaacggcc acgagttcga gatcgagggc   9540
gagggcgagg gccgccccta cgagggccac aacaccgtga agctgaaggt gaccaagggc   9600
ggcccccctgc ccttcgcctg ggacatcctg tccccccagt tccagtacgg ctccaaggtg   9660
tacgtgaagc accccgccga catccccgac tacaagaagc tgtccttccc cgagggcttc   9720
aagtgggagc gcgtgatgaa cttcgaggac ggcggcgtgg cgaccgtgac ccaggactcc   9780
tccctgcagg acggctgctt catctacaag gtgaagttca tcggcgtgaa cttcccctcc   9840
gacggccccg tgatgcagaa gaagaccatg ggctgggagg cctccaccga gcgcctgtac   9900
ccccgcgacg gcgtgctgaa gggcgagacc cacaaggccc tgaagctgaa ggacggcggc   9960
cactacctgg tggagttcaa gtccatctac atggccaaga agcccgtgca gctgcccggc  10020
tactactacg tggacgccaa gctggacatc acctcccaca acgaggacta caccatcgtg  10080
gagcagtacg agcgcaccga gggccgccac cacctgttcc tgagatctcg acccaagaaa  10140
aagcggaagg tggaggaccc gtaagatcca ccggatctag ataactgatc ataatcagcc  10200
ataccacatt tgtagaggtt ttacttgctt taaaaaacct cccacacctc cccctgaacc  10260
tgaaacataa aatgaatgca attgttgttg ttaacttgtt tattgcagct tataatggtt  10320
```

```
acaaataaag caatagcatc acaaatttca caaataaagc attttttca ctgcattcta  10380

gttgtggttt gtccaaactc atcaatgtat cttatcatgt ctggatcccg tttgacggta  10440

tcgataagct tgatggggat ccggaaccct taattaccgt tcgtataatg tatgctatac  10500

gaagttatta ggtccctcga cctgcagccc gggggatcca                       10540
```

<210> SEQ ID NO 154
<211> LENGTH: 4446
<212> TYPE: DNA
<213> ORGANISM: artificial
<220> FEATURE:
<223> OTHER INFORMATION: LA3515 plasmid sequence

<400> SEQUENCE: 154

```
ggccgccacc gcggtggagc tccagctttt gttcccttta gtgagggtta attgcgcgct     60

tggcgtaatc atggtcatag ctgtttcctg tgtgaaattg ttatccgctc acaattccac    120

acaacatacg agccggaagc ataaagtgta aagcctgggg tgcctaatga gtgagctaac    180

tcacattaat tgcgttgcgc tcactgcccg ctttccagtc gggaaacctg tcgtgccagc    240

tgcattaatg aatcggccaa cgcgcgggga gaggcggttt gcgtattggg cgctcttccg    300

cttcctcgct cactgactcg ctgcgctcgg tcgttcggct gcggcgagcg gtatcagctc    360

actcaaaggc ggtaatacgg ttatccacag aatcagggga taacgcagga aagaacatgt    420

gagcaaaagg ccagcaaaag gccaggaacc gtaaaaaggc cgcgttgctg gcgtttttcc    480

ataggctccg cccccctgac gagcatcaca aaaatcgacg ctcaagtcag aggtggcgaa    540

acccgacagg actataaaga taccaggcgt ttccccctgg aagctccctc gtgcgctctc    600

ctgttccgac cctgccgctt accggatacc tgtccgcctt tctcccttcg ggaagcgtgg    660

cgctttctca tagctcacgc tgtaggtatc tcagttcggt gtaggtcgtt cgctccaagc    720

tgggctgtgt gcacgaaccc cccgttcagc ccgaccgctg cgccttatcc ggtaactatc    780

gtcttgagtc caacccggta agacacgact tatcgccact ggcagcagcc actggtaaca    840

ggattagcag agcgaggtat gtaggcggtg ctacagagtt cttgaagtgg tggcctaact    900

acggctacac tagaaggaca gtatttggta tctgcgctct gctgaagcca gttaccttcg    960

gaaaaagagt tggtagctct tgatccggca aacaaaccac cgctggtagc ggtggttttt   1020

ttgtttgcaa gcagcagatt acgcgcagaa aaaaaggatc tcaagaagat cctttgatct   1080

tttctacggg gtctgacgct cagtggaacg aaaactcacg ttaagggatt ttggtcatga   1140

gattatcaaa aaggatcttc acctagatcc ttttaaatta aaaatgaagt tttaaatcaa   1200

tctaaagtat atatgagtaa acttggtctg acagttacca atgcttaatc agtgaggcac   1260

ctatctcagc gatctgtcta tttcgttcat ccatagttgc ctgactcccc gtcgtgtaga   1320

taactacgat acgggagggc ttaccatctg gccccagtgc tgcaatgata ccgcgagacc   1380

cacgctcacc ggctccagat ttatcagcaa taaaccagcc agccggaagg gccgagcgca   1440

gaagtggtcc tgcaacttta tccgcctcca tccagtctat taattgttgc cgggaagcta   1500

gagtaagtag ttcgccagtt aatagtttgc gcaacgttgt tgccattgct acaggcatcg   1560

tggtgtcacg ctcgtcgttt ggtatggctt cattcagctc cggttcccaa cgatcaaggc   1620

gagttacatg atcccccatg ttgtgcaaaa aagcggttag ctccttcggt cctccgatcg   1680

ttgtcagaag taagttggcc gcagtgttat cactcatggt tatggcagca ctgcataatt   1740

ctcttactgt catgccatcc gtaagatgct tttctgtgac tggtgagtac tcaaccaagt   1800
```

-continued

```
cattctgaga atagtgtatg cggcgaccga gttgctcttg cccggcgtca atacgggata   1860
ataccgcgcc acatagcaga actttaaaag tgctcatcat tggaaaacgt tcttcggggc   1920
gaaaactctc aaggatctta ccgctgttga gatccagttc gatgtaaccc actcgtgcac   1980
ccaactgatc ttcagcatct tttactttca ccagcgtttc tgggtgagca aaaacaggaa   2040
ggcaaaatgc cgcaaaaaag ggaataaggg cgacacggaa atgttgaata ctcatactct   2100
tcctttttca atattattga agcatttatc agggttattg tctcatgagc ggatacatat   2160
ttgaatgtat ttagaaaaat aaacaaatag gggttccgcg cacatttccc cgaaaagtgc   2220
cacctaaatt gtaagcgtta atattttgtt aaaattcgcg ttaaattttt gttaaatcag   2280
ctcatttttt aaccaatagg ccgaaatcgg caaaatccct tataaatcaa aagaatagac   2340
cgagataggg ttgagtgttg ttccagtttg gaacaagagt ccactattaa agaacgtgga   2400
ctccaacgtc aaagggcgaa aaaccgtcta tcagggcgat ggcccactac gtgaaccatc   2460
accctaatca agttttttgg ggtcgaggtg ccgtaaagca ctaaatcgga accctaaagg   2520
gagcccccga tttagagctt gacggggaaa gccggcgaac gtggcgagaa aggaagggaa   2580
gaaagcgaaa ggagcgggcg ctagggcgct ggcaagtgta gcggtcacgc tgcgcgtaac   2640
caccacaccc gccgcgctta atgcgccgct acagggcgcg tcccattcgc cattcaggct   2700
gcgcaactgt tgggaagggc gatcggtgcg ggcctcttcg ctattacgcc agctggcgaa   2760
agggggatgt gctgcaaggc gattaagttg ggtaacgcca gggttttccc agtcacgacg   2820
ttgtaaaacg acggccagtg agcgcgcgta atacgactca ctatagggcg aattgggtac   2880
cgggcccccc ctcgaggtcg acgatgtagg tcacggtctc gaagccgcgg tgcgggtgcc   2940
agggcgtgcc cttgggctcc ccgggcgcgt actccacctc acccatctgg tccatcatga   3000
tgaacgggtc gaggtggcgg tagttgatcc cggcgaacgc gcggcgcacc gggaagccct   3060
cgccctcgaa accgctgggc gcggtggtca cggtgagcac gggacgtgcg acggcgtcgg   3120
cgggtgcgga tacgcggggc agcgtcagcg ggttctcgac ggtcacggcg ggcatgtcga   3180
cggtatcgat aagcttgggc ccccccctcga ggttcccaca atggttaatt cgagctcgcc   3240
cggggatcta attcaattag agactaattc aattagagct aattcaatta ggatccaagc   3300
ttatcgattt cgaaccctcg accgccggag tataaataga ggcgcttcgt ctacggagcg   3360
acaattcaat tcaaacaagc aaagtgaaca cgtcgctaag cgaaagctaa gcaaataaac   3420
aagcgcagct gaacaagcta aacaatcggg gtaccgctag agtcgatccc accccaccca   3480
agaagaagcg caaaccggta ccatggcctc ctccgagaac gtcatcaccg agttcatgcg   3540
cttcaaggtg cgcatggagg gcaccgtgaa cggccacgag ttcgagatcg agggcgaggg   3600
cgagggccgc ccctacgagg gccacaacac cgtgaagctg aaggtgacca agggcggccc   3660
cctgcccttc gcctgggaca tcctgtcccc ccagttccag tacggctcca aggtgtacgt   3720
gaagcacccc gccgacatcc ccgactacaa gaagctgtcc ttccccgagg gcttcaagtg   3780
ggagcgcgtg atgaacttcg aggacggcgg cgtggcgacc gtgacccagg actcctccct   3840
gcaggacggc tgcttcatct acaaggtgaa gttcatcggc gtgaacttcc cctccgacgg   3900
ccccgtgatg cagaagaaga ccatgggctg ggaggcctcc accgagcgcc tgtacccccg   3960
cgacggcgtg ctgaagggcg agacccacaa ggccctgaag ctgaaggacg gcggccacta   4020
cctggtggag ttcaagtcca tctacatggc caagaagccc gtgcagctgc ccggctacta   4080
ctacgtggac gccaagctgg acatcacctc ccacaacgag gactacacca tcgtggagca   4140
gtacgagcgc accgagggcc gccaccacct gttcctgtga tgatcataat cagccatacc   4200
```

acatttgtag aggttttact tgctttaaaa aacctcccac acctcccct gaacctgaaa 4260 cataaaatga atgcaattgt tgttgttaac ttgtttattg cagcttataa tggttacaaa 4320
taaagcaata gcatcacaaa tttcacaaat aaagcatttt tttcactgca ttctagttgt 4380
ggtttgtcca aactcatcaa tgtatcttaa cgcgagttaa ttaaggccgc tcatttaaat 4440
ctggcc 4446

<210> SEQ ID NO 155
<211> LENGTH: 12991
<212> TYPE: DNA
<213> ORGANISM: artificial
<220> FEATURE:
<223> OTHER INFORMATION: LA3545 Plasmid sequence

<400> SEQUENCE: 155
gggcggccgt ttttcttgaa atattgctct ctctttctaa atagcgcgaa tccgtcgctg 60
tgcatttagg acatctcagt cgccgcttgg agctcccaaa cgcgccagtg gtagtacaca 120
gtactgtggg tgttcagttt gaaatcctct tgcttctcca ttgtctcggt tacctttggt 180
caaatccatg ggttctattg cctatatact cttgcgatta ccagtgattg cgctattagc 240
tattagatgg attgttggcc aaacttgtcg cttaagtggc tgggaattgt aaccgtaggc 300
ccgagtgtaa tgatccccca taaaaagttt tcgcaatgcc tttatttttt gttgcaaatc 360
tctctttatt ctgcggtatt cttcattatt gcggggatgg ggaaagtgtt tatatagaag 420
caacttacga ttgaacccaa atgcacctga caagcaaggt caaagggcca gatttttaaa 480
tatattattt agtcttagga ctctctattt gcaattaaat tactttgcta cctgagggtt 540
aaatcttccc cattgataat aataattcca ctatatgttc aattgggttt caccgcgctt 600
agttacatga cgagccctaa tgagccgtcg gtggtctata aactgtgcct tacaaatact 660
tgcaactctt ctcgttttga agtcagcaga gttattgcta attgctaatt gctaattgct 720
tttaactgat ttcttcgaaa ttggtgctat gtttatggcg ctattaacaa gtatgaatgt 780
caggtttaac caggggatgc ttaattgtgt tctcaacttc aaaggcagaa atgtttactc 840
ttgaccatgg gtttaggtat aatgttatca agctcctcga gttaacgtta cgttaacgtt 900
aacgttcgag gtcgactcta gcactgggaa gttgacgttg atatagagcc gaattgaact 960
tcaccgctgc ttggtaatta ctctacaagt tcatttagga gaaccggatt cgaaagatga 1020
ttttccagcg tttagctttc agatggccgc atacattttg caccaccaaa ccgaaactca 1080
ctagcgtatc caatcgttcg ttttttggtg ccggtgtgtt acgaacttta gctatcaagc 1140
taaagcaatt tgctctggtc ttccgtgcta aaaagaaaaa aaaactgttt tttttttggt 1200
tttgatattt gcgctatttt tacttgggcc ttaattgaac aaacttttga aagtttccac 1260
agcgaaatcg ttttcgacga tgccattttt ggtaacattt gcattttctt gctcaaattg 1320
cttgcaaaac ccgtgaaaga cattaatatt cgatagtgtc atccaaaatc acgaaaatga 1380
ttgttgcaaa acgttgaaca atttacacat gtaaaaaaca accatcgatt aatgtttatt 1440
caaacttttt acaagaaggg ttattctgat caatgtcacc ccgctgatga atgttacccc 1500
ggattacact tctcgaaaag tggttcaaaa tgctacttga gaatttttat ctgtcaaagg 1560
aagcaaattc gagtcgaatt aaatggtata gtcctgaatt aggtttccat ttacttacag 1620
gtattccact aaatagctgg aagatttatt ttacacaata atgataattc gtaccccaaa 1680
gagtgtagcc ctactttttt ctctcttttt tttttgtaaa ttttcatcgc tgcgtgccag 1740

```
cttaccgaca tgtcgcgaca gcataaagag cctgtcaaga gatgaagaaa aatgacaagg   1800
agtcagtggt caggtctctg tatcaatatt tgacgtcctg actttccaat ataccttttcc   1860
ttaaagagta gagatcatgc gatacgtgaa taaatatcgt ttggacttcg aaatagaaca   1920
taatttaagg tagctgatca gtagttgaac atcttcagac ttctgggaca agaagtgttt   1980
ttttgtttgt agaaaaggtt tttgttaaat tatatttgta agataattca atgaatatat   2040
ctctgattca gtaatcaatc cgtaccacgc accgtttaag aaacaccctg taggtttgca   2100
tcacgtctca gacaaaagtg tatcgatgtg cgaacactgc ataccggcgc tttgcaaata   2160
atgccaaatt tagatatgca ttacattgtc acttcgcaaa acacacactc ccaaatgcgt   2220
cggaaacctc acccgaacgc acgatcgtaa cgcgatcgat cgccgattga ttgatcggaa   2280
ttaactatct caatcgatcc ttctatggac tgatgcatgg gccggcactt ccgagtataa   2340
aaccccggta aacccaagga atcactcaca atcggatttt gacgctcgct ctggtacagt   2400
tcgatacggt ctagtgaaac cgaggataac gacgaaggtt tttccccatt gatccaggtc   2460
ggtgtttatg attggtggaa aaagactcga gaaaagttcc atcgaagccg ttggaaatgt   2520
gccgtcttcc tgtgacgtct tgtggatcca gttccttgtt cacgtctggt gatcgtgtaa   2580
aatgtgctgt cttgtggcgt catatgtgtt ccagatccag tgattacgat ccgatgtgat   2640
gttgatccct tgtgaacgtc ttatcctgtt ccgtgtgcac catgcataat gtcgtattac   2700
gtaagttctg aagtgaaaca gaagagtgaa ttgaaagttt ttttattcaa catcaaccta   2760
aatatggact ttactttcca agaaaattat gcctgatcaa ctgtggatag ttacaaaaaa   2820
aaaaggttta ttaattaaat tttatgatta cataatgtgt tgaaaagaac aactgaaatt   2880
ttagaagaag atcttttcgt gcatcaggct ttgccaatta attgatgata aattatcata   2940
gcaaattaac gtagagacta aaaggtatat cgtcaaatag ggcttctttt gacactattt   3000
tggcattctt gctctttgag aacttgcaac cctaaaatgg gatcttcatc agcctagtgg   3060
ttagattcag cagctacaaa gcaaaaccat gctgaagggt tcgattcccg gtcgtttcag   3120
gatcttttcg taattgaaat atccttgact accctaagta tcattgtgct tgccatttac   3180
gaatatacat attacgatat acgaatgaga aaatgacaac tttggaaaat aaagctctca   3240
atgtttcaat aagaaataaa tactacatca gtattgaagg ctaataacaa ttacagatta   3300
gaacctttaa acatcatttc tgcaacaggc tggataaagt acagttggag gattaaatta   3360
tgcgattttg caattttttc cgattaaatt catatttatt cctggtttgg tttttacaaa   3420
aaatattttt acatgacgtt tgaccccgat tccctcaact ttgattgtta tattttttttt   3480
tggacaggtt gagtttgtgg gttttttcct agtgttgctt tgctttatgg gctctggtta   3540
tttaaaatta aaatttgaca atcttactac acactccgaa aaaatcatgc gattttacgt   3600
cttttggatg cacataaaag aagcgagcca aatgaggtga atttgtgtca cattttaaat   3660
acgatggtgt ctgattcggg aaatgtcaat gatagtgtca ttcaatcata atgtgaatta   3720
cgtccgcagt aattttcatt atttttaaga gtgtactact atttacacta caaaaatttt   3780
gataccccag gggggaacga ggtcccggat gtccagctgg ccagattgtt ggcaacgagc   3840
cctgtaccta ttgatcgagt caccaaagca ctcctcaagt gttttaatct cgaccagacg   3900
gtggacctcg gttgttctca ttctcggagg gcgatttcgc aatcattagt accaaccaca   3960
tgtcgaagtc gggagatgtt ataaaattat aaccaattat tcaaaaaatg acatcattca   4020
atttgaacaa acgttcgata gaaattatat atgatttcac atgatattaa actacgaaga   4080
aaattttaca taaggaagtg gtataaaacg taatatgctt aataaaaact ttaacccttt   4140
```

tgggaggata atattcagaa gttctgattc agaaccatct ctcatgttat gttcgttttt 4200
tgttgcttgt cctttatatg ccacatgaac aataacacca atatctatcc catttccagg 4260
acctaacgga ccttgaagcg gcgccactag taaaccacca tgggcagccg cctggataag 4320
tccaaagtca tcaactccgc gttggagctg ttgaacgaag ttggcattga gggactgacg 4380
acccgcaagt tggcgcagaa gctgggcgtg gagcagccca ccctctactg gcacgtgaag 4440
aataagcggg cgctgctgga tgccctggcc atcgagatgc tcgaccgcca ccacacgcat 4500
ttttgcccgt tggaaggcga gtcctggcag gacttcctcc gcaataacgc caagtcgttc 4560
cgctgcgctc tgctgtccca ccgagacggt gccaaagtcc atctcggcac gcgcccgacc 4620
gaaaagcaat acgagacact ggagaaccag ctcgcgttcc tgtgccagca aggcttcagc 4680
ctggaaaatg ctctctacgc tctgagcgcc gtcggtcact ttaccctggg ctgcgtgctg 4740
gaggaccaag agcatcaagt cgcaaaagag gagcgcgaga ccccaacaac cgattcgatg 4800
cccccactgc tgcgtcaggc aatcgagctg ttcgatcatc aaggagccga gccggcattc 4860
ctgttcggct tggagctgat tatctgcgga ttggaaaagc aactgaaatg cgagtcgggc 4920
tcgggccccg cctacagccg cgcccgcacc aagaacaact acggcagcac catcgagggc 4980
ctgctggatc tgccggatga tgatgccccg gaggaggcgg gcctggccgc cccgcgcctg 5040
agcttcctgc cggccggaca cacccgccgc ctgtcgaccg ccccgccgac cgacgtgagc 5100
ctgggcgatg agctgcacct ggatggcgag gatgtggcga tggcccacgc cgatgccctg 5160
gacgacttcg acctggacat gctgggcgat ggcgatagcc cgggaccggg attcaccccg 5220
cacgatagcg ccccctacgg cgccctggat atggccgatt tcgagttcga gcagatgttc 5280
accgacgccc tgggcatcga tgagtacggc ggctaacacc ggaaactcgc gttaagatac 5340
attgatgagt ttggacaaac cacaactaga atgcagtgaa aaaaatgctt tatttgtgaa 5400
atttgtgatg ctattgcttt atttgtaacc attataagct gcaataaaca agttaacaac 5460
aacaattgca ttcattttat gtttcaggtt cagggggagg tgtgggaggt tttttaaagc 5520
aagtaaaacc tctacaaatg tggtatggct gattatgatc agttatctag atccggtgga 5580
tcttacgggt cctccacctt ccgctttttc ttgggtcgag atctcaggaa caggtggtgg 5640
cggccctcgg tgcgctcgta ctgctccacg atggtgtagt cctcgttgtg ggaggtgatg 5700
tccagcttgg cgtccacgta gtagtagccg ggcagctgca cgggcttctt ggccatgtag 5760
atggacttga actccaccag gtagtggccg ccgtccttca gcttcagggc cttgtgggtc 5820
tcgcccttca gcacgccgtc gcgggggtac aggcgctcgg tggaggcctc ccagcccatg 5880
gtcttcttct gcatcacggg gccgtcggag gggaagttca cgccgatgaa cttcaccttg 5940
tagatgaagc agccgtcctg cagggaggag tcctgggtca cggtcgccac gccgccgtcc 6000
tcgaagttca tcacgcgctc ccacttgaag ccctcgggga aggacagctt cttgtagtcg 6060
gggatgtcgg cggggtgctt cacgtacacc ttggagccgt actggaactg gggggacagg 6120
atgtcccagg cgaagggcag ggggccgccc ttggtcacct tcagcttcac ggtgttgtgg 6180
ccctcgtagg ggcggccctc gccctcgccc tcgatctcga actcgtggcc gttcacggtg 6240
ccctccatgc gcaccttgaa gcgcatgaac tcggtgatga cgttctcgga ggaggccatg 6300
gtggcgaccg gtttgcgctt cttcttgggt ggggtgggat ctcccatggt ggcctgaatc 6360
tcaacttgca cctgaaggta gtgcagcaag gatgagcaaa agggaagaac ccagaaaaga 6420
acgggaaaac ttaccccaat tagaattgct tgtcgccgcc agtgtcaact tgcaactgaa 6480

-continued

```
acaatatcca acatgaacgt caatttatac tgccctaatg gcgaacacga taacaatatt   6540
tcttttatta tgccctctaa aaccaacgcg gttatcgttt atttattcaa attagatata   6600
gaacatccgc cgacatacaa tgttaatgca aaaacgcgtt tggtgagcgg atacgaaaac   6660
agtcggccga taaacattaa tctgaggtcg ataacaccgt ccttgaacgg aacacgagga   6720
gcgtacgtga tcagctgcat tcgcgcgccg cgcctttatc gagatttatt tgcatacaac   6780
aagtacactg cgccgttggg atttgtggta acgcgcacac atgcagagct gcaagtgtgg   6840
cacattttgt ctgtgcgcaa aacctttgaa gccaaaagta cgaggtccgt tacgggcatg   6900
ctagcgcaca cggacaatgg acccgacaaa ttctacgcca aggatttaat gataatgtcg   6960
ggcaacgtat ccgttcattt tatcaataac ctacaaaaat gtcgcgcgca tcacaaagac   7020
atcgatatat ttaaacattt atgtcccgaa ctgcaaatcg ataatagtgt tgtgcaacct   7080
cgagcgtccg tttgatttaa cgtatagctt gcaaatgaat tatttaatta tcaatcatgt   7140
tttacgcgta gaattctacc cgtaaagcga gtttagttat gagccatgtg caaaacatga   7200
catcagcttt tatttttata acaaatgaca tcatttcttg attgtgtttt acacgtagaa   7260
ttctactcgt aaagcgagtt cagttttgaa aaacaaatga catcatcttt ttgattgtgc   7320
tttacaagta gaattctacc cgtaaatcaa gttcggtttt gaaaaacaaa tgagtcatat   7380
tgtatgatat catattgcaa aacaaatgac tcatcaatcg atcgtgcgtt acacgtagaa   7440
ttctactcgt aaagcgagtt tatgagccgt gtgcaaaaca tgacatcatc tcgatttgaa   7500
aaacaaatga catcatccac tgatcgtgca ttacaagtag aattctactc gtaaagccag   7560
ttcggttatg agccgtgtac aaaacatgac atcagattat gactcatact tgattgtgtt   7620
ttacgcgtag aattctactc gtaaagccag ttcaatttta aaaacaaatg acatcatcca   7680
aattaataaa tgacaagcaa tgggtaccat gcggccgctc atttaaatct ggccggcctg   7740
gccgatctga caatgttcag tgcagagact cggctacgcc tcgtggactt tgaagttgac   7800
caacaatgtt tattcttacc tctaatagtc ctctgtggca aggtcaagat tctgttagaa   7860
gccaatgaag aacctggttg ttcaataaca ttttgttcgt ctaatatttc actaccgctt   7920
gacgttggct gcacttcatg tacctcatct ataaacgctt cttctgtatc gctctggacg   7980
tcatcttcac ttacgtgatc tgatatttca ctgtcagaat cctcaccaac aagctcgtca   8040
tcgctttgca gaagagcaga gaggatatgc tcatcgtcta aagaactacc cattttatta   8100
tatattagtc acgatatcta taacaagaaa atatatatat aataagttat cacgtaagta   8160
gaacatgaaa taacaatata attatcgtat gagttaaatc ttaaaagtca cgtaaaagat   8220
aatcatgcgt cattttgact cacgcggtcg ttatagttca aaatcagtga cacttaccgc   8280
attgacaagc acgcctcacg ggagctccaa gcggcgactg agatgtccta aatgcacagc   8340
gacggattcg cgctatttag aaagagagag caatatttca agaatgcatg cgtcaatttt   8400
acgcagacta tctttctagg gttaaaaaag atttgcgctt tactcgacct aaactttaaa   8460
cacgtcatag aatcttcgtt tgacaaaaac cacattgtgg ccaagctgtg tgacgcgacg   8520
cgcgctaaag aatggcaaac caagtcgcgc gagcgtcgac ctgcaggcat gcaagcttgc   8580
atgcctgcag gtcgaaattc gtaatcatgg tcatagctgt ttcctgtgtg aaattgttat   8640
ccgctcacaa ttccacacaa catacgagcc ggaagcataa agtgtaaagc ctggggtgcc   8700
taatgagtga gctaactcac attaattgcg ttgcgctcac tgcccgcttt ccagtcggga   8760
aacctgtcgt gccagctgca ttaatgaatc ggccaacgcg cggggagagg cggtttgcgt   8820
attgggcgct cttccgcttc ctcgctcact gactcgctgc gctcggtcgt tcggctgcgg   8880
```

```
cgagcggtat cagctcactc aaaggcggta atacggttat ccacagaatc aggggataac    8940
gcaggaaaga acatgtgagc aaaaggccag caaaaggcca ggaaccgtaa aaaggccgcg    9000
ttgctggcgt ttttccatag gctccgcccc cctgacgagc atcacaaaaa tcgacgctca    9060
agtcagaggt ggcgaaaccc gacaggacta taaagatacc aggcgtttcc ccctggaagc    9120
tccctcgtgc gctctcctgt tccgaccctg ccgcttaccg gatacctgtc cgcctttctc    9180
ccttcgggaa gcgtggcgct ttctcaatgc tcacgctgta ggtatctcag ttcggtgtag    9240
gtcgttcgct ccaagctggg ctgtgtgcac gaaccccccg ttcagcccga ccgctgcgcc    9300
ttatccggta actatcgtct tgagtccaac ccggtaagac acgacttatc gccactggca    9360
gcagccactg gtaacaggat tagcagagcg aggtatgtag gcggtgctac agagttcttg    9420
aagtggtggc ctaactacgg ctacactaga aggacagtat ttggtatctg cgctctgctg    9480
aagccagtta ccttcggaaa aagagttggt agctcttgat ccggcaaaca aaccaccgct    9540
ggtagcggtg gtttttttgt ttgcaagcag cagattacgc gcagaaaaaa aggatctcaa    9600
gaagatcctt tgatcttttc tacggggtct gacgctcagt ggaacgaaaa ctcacgttaa    9660
gggattttgg tcatgagatt atcaaaaagg atcttcacct agatcctttt aaattaaaaa    9720
tgaagtttta aatcaatcta aagtatatat gagtaaactt ggtctgacag ttaccaatgc    9780
ttaatcagtg aggcacctat ctcagcgatc tgtctatttc gttcatccat agttgcctga    9840
ctccccgtcg tgtagataac tacgatacgg gagggcttac catctggccc cagtgctgca    9900
atgataccgc gagacccacg ctcaccggct ccagatttat cagcaataaa ccagccagcc    9960
ggaagggccg agcgcagaag tggtcctgca actttatccg cctccatcca gtctattaat   10020
tgttgccggg aagctagagt aagtagttcg ccagttaata gtttgcgcaa cgttgttgcc   10080
attgctacag gcatcgtggt gtcacgctcg tcgtttggta tggcttcatt cagctccggt   10140
tcccaacgat caaggcgagt tacatgatcc cccatgttgt gcaaaaaagc ggttagctcc   10200
ttcggtcctc cgatcgttgt cagaagtaag ttggccgcag tgttatcact catggttatg   10260
gcagcactgc ataattctct tactgtcatg ccatccgtaa gatgcttttc tgtgactggt   10320
gagtactcaa ccaagtcatt ctgagaatag tgtatgcggc gaccgagttg ctcttgcccg   10380
gcgtcaatac gggataatac cgcgccacat agcagaactt taaaagtgct catcattgga   10440
aaacgttctt cggggcgaaa actctcaagg atcttaccgc tgttgagatc cagttcgatg   10500
taacccactc gtgcacccaa ctgatcttca gcatctttta ctttcaccag cgtttctggg   10560
tgagcaaaaa caggaaggca aaatgccgca aaaaagggaa taagggcgac acggaaatgt   10620
tgaatactca tactcttcct ttttcaatat tattgaagca tttatcaggg ttattgtctc   10680
atgagcggat acatatttga atgtatttag aaaaataaac aaataggggt tccgcgcaca   10740
tttccccgaa aagtgccacc tgacgtctaa gaaaccatta ttatcatgac attaacctat   10800
aaaaataggc gtatcacgag gccctttcgt ctcgcgcgtt tcggtgatga cggtgaaaac   10860
ctctgacaca tgcagctccc ggagacggtc acagcttgtc tgtaagcgga tgccgggagc   10920
agacaagccc gtcagggcgc gtcagcgggt gttggcgggt gtcggggctg gcttaactat   10980
gcggcatcag agcagattgt actgagagtg caccatatat gcggtgtgaa ataccgcaca   11040
gatgcgtaag gagaaaatac cgcatcaggc gccattcgcc attcaggctg cgcaactgtt   11100
gggaagggcg atcggtgcgg gcctcttcgc tattacgcca gctggcgaaa gggggatgtg   11160
ctgcaaggcg attaagttgg gtaacgccag ggttttccca gtcacgacgt tgtaaaacga   11220
```

cggccagtgc caagctttgt ttaaaatata acaaaattgt gatcccacaa aatgaagtgg 11280
ggcaaaatca aataattaat agtgtccgta aacttgttgg tcttcaactt tttgaggaac 11340
acgttggacg gcaaatccgt gactataaca caagttgatt taataatttt agccaacacg 11400
tcgggctgcg tgtttttgc cgacgcgtct gtgtacacgt tgattaactg gtcgattaaa 11460
ctgttgaaat aatttaattt ttggttcttc tttaaatctg tgatgaaatt ttttaaaata 11520
actttaaatt cttcattggt aaaaaatgcc acgttttgca acttgtgagg gtctaatatg 11580
aggtcaaact cagtaggagt tttatccaaa aaagaaaaca tgattacgtc tgtacacgaa 11640
cgcgtattaa cgcagagtgc aaagtataag agggttaaaa aatatatttt acgcaccata 11700
tacgcatcgg gttgatatcg ttaatatgga tcaatttgaa cagttgatta acgtgtctct 11760
gctcaagtct ttgatcaaaa cgcaaatcga cgaaaatgtg tcggacaata tcaagtcgat 11820
gagcgaaaaa ctaaaaaggc tagaatacga caatctcaca gacagcgttg agatatacgg 11880
tattcacgac agcaggctga ataataaaaa aattagaaac tattatttaa ccctagaaag 11940
ataatcatat tgtgacgtac gttaaagata atcatgcgta aaattgacgc atgtgtttta 12000
tcggtctgta tatcgaggtt tatttattaa tttgaataga tattaagttt tattatattt 12060
acacttacat actaataata aattcaacaa acaatttatt tatgtttatt tatttattaa 12120
aaaaaaacaa aaactcaaaa tttcttctat aaagtaacaa aacttttaaa cattctctct 12180
tttacaaaaa taaacttatt ttgtacttta aaaacagtca tgttgtatta taaaataagt 12240
aattagctta acttatacat aatagaaaca aattatactt attagtcagt cagaaacaac 12300
tttggcacat atcaatatta tgctctcgac aaataacttt tttgcatttt ttgcacgatg 12360
catttgcctt tcgccttatt ttagaggggc agtaagtaca gtaagtacgt tttttcatta 12420
ctggctcttc agtactgtca tctgatgtac caggcacttc atttggcaaa atattagaga 12480
tattatcgcg caaatatctc ttcaaagtag gagcttctaa acgcttacgc ataaacgatg 12540
acgtcaggct catgtaaagg tttctcataa attttttgcg actttggacc ttttctccct 12600
tgctactgac attatggctg tatataataa aagaatttat gcaggcaatg tttatcattc 12660
cgtacaataa tgccataggc cacctattcg tcttcctact gcaggtcatc acagaacaca 12720
tttggtctag cgtgtccact ccgcctttag tttgattata atacataacc atttgcggtt 12780
taccggtact ttcgttgata gaagcatcct catcacaaga tgataataag tataccatct 12840
tagctggctt cggtttatat gagacgagag taaggggtcc gtcaaaacaa aacatcgatg 12900
ttcccactgg cctggagcga ctgtttttca gtacttccgg tatctcgcgt ttgtttgatc 12960
gcacggttcc cacaatggtt gcggccagcc c 12991

<210> SEQ ID NO 156
<211> LENGTH: 18411
<212> TYPE: DNA
<213> ORGANISM: artificial
<220> FEATURE:
<223> OTHER INFORMATION: LA3604 Plasmid sequence

<400> SEQUENCE: 156
ttaaaatgaa tgtaagcact ttattaacga aatctttggg aatatttcgc tcatcagcat 60
tttatttgag caggagtccg agatgcccgg gcggcgcgaa actcccctgc aggataactt 120
cgtatagcat acattatacg aagttatcct agggaagttc ctatactttc tagagaatag 180
gaacttcgga ataggaactt cttcgaacgg ccaaaaaggc cggccggggc acgggcgccg 240
tttttcttga aatattgctc tctctttcta aatagcgcga atccgtcgct gtgcatttag 300

-continued

```
gacatctcag tcgccgcttg gagctcccaa acgcgccagt ggtagtacac agtactgtgg    360
gtgttcagtt tgaaatcctc ttgcttctcc attgtctcgg ttacctttgg tcaaatccat    420
gggttctatt gcctatatac tcttgcgatt accagtgatt gcgctattag ctattagatg    480
gattgttggc caaacttgtc gcttaagtgg ctgggaattg taaccgtagg cccgagtgta    540
atgatccccc ataaaaagtt ttcgcaatgc ctttattttt tgttgcaaat ctctctttat    600
tctgcggtat tcttcattat tgcggggatg gggaaagtgt ttatatagaa gcaacttacg    660
attgaaccca aatgcacctg acaagcaagg tcaaagggcc agatttttaa atatattatt    720
tagtcttagg actctctatt tgcaattaaa ttactttgct acctgagggt taaatcttcc    780
ccattgataa taataattcc actatatgtt caattgggtt tcaccgcgct tagttacatg    840
acgagcccta atgagccgtc ggtggtctat aaactgtgcc ttacaaatac ttgcaactct    900
tctcgttttg aagtcagcag agttattgct aattgctaat tgctaattgc ttttaactga    960
tttcttcgaa attggtgcta tgtttatggc gctattaaca agtatgaatg tcaggtttaa   1020
ccaggggatg cttaattgtg ttctcaactt caaaggcaga aatgtttact cttgaccatg   1080
ggtttaggta taatgttatc aagctcctcg agttaacgtt acgttaacgt taacgttcga   1140
ggtcgactct agacaccggt gttagccgcc gtactcatcg atgcccaggg cgtcggtgaa   1200
catctgctcg aactcgaaat cggccatatc cagggcgccg tagggggcgc tatcgtgcgg   1260
ggtgaatccc ggtcccgggc tatcgccatc gcccagcatg tccaggtcga agtcgtccag   1320
ggcatcggcg tgggccatcg ccacatcctc gccatccagg tgcagctcat cgcccaggct   1380
cacgtcggtc ggcggggcgg tcgacaggcg gcgggtgtgt ccggccggca ggaagctcag   1440
gcgcggggcg gccaggcccg cctcctccgg ggcatcatca tccggcagat ccagcaggcc   1500
ctcgatggtg ctgccgtagt tgttcttggt gcgggcgcgg ctgtaggcgg ggcccgagcc   1560
cgactcgcat ttcagttgct tttccaatcc gcagataatc agctccaagc cgaacaggaa   1620
tgccggctcg gctccttgat gatcgaacag ctcgattgcc tgacgcagca gtgggggcat   1680
cgaatcggtt gttggggtct cgcgctcctc ttttgcgact tgatgctctt ggtcctccag   1740
cacgcagccc agggtaaagt gaccgacggc gctcagagcg tagagagcat tttccaggct   1800
gaagccttgc tggcacagga acgcgagctg gttctccagt gtctcgtatt gcttttcggt   1860
cgggcgcgtg ccgagatgga ctttggcacc gtctcggtgg gacagcagag cgcagcggaa   1920
cgacttggcg ttattgcgga ggaagtcctg ccaggactcg ccttccaacg ggcaaaaatg   1980
cgtgtggtgg cggtcgagca tctcgatggc cagggcatcc agcagcgccc gcttattctt   2040
cacgtgccag tagagggtgg gctgctccac gcccagcttc tgcgccaact tgcgggtcgt   2100
cagtccctca atgccaactt cgttcaacag ctccaacgcg gagttgatga ctttggactt   2160
atccaggcgg ctgaccatac caccgcgcag gcgcagcacc aggtgcaggg tgctctcctt   2220
ctggatgttg tagtcgctca gggtgcggcc atcctccagc tggcgtccgg cgaagatcag   2280
gcgctgctga tccggcggga tgccctcctt gtcctggatc ttggccttca cgttctcgat   2340
ggtatcgctc ggctccacct ccagggtgat ggtcttgccg gtcagggtct tgacgaagat   2400
ctgcatcgag ctagccgtca cacgttttgg cgccgcttca aggtccgtta ggtcctggaa   2460
atgggataga tattggtgtt attgttcatg tggcatataa aggacaagca acaaaaaacg   2520
aacataacat gagagatggt tctgaatcag aacttctgaa tattatcctc ccaaaagggt   2580
taaagttttt attaagcata ttacgtttta taccacttcc ttatgtaaaa ttttcttcgt   2640
```

-continued

```
agtttaatat catgtgaaat catatataat ttctatcgaa cgtttgttca aattgaatga   2700
tgtcattttt tgaataattg gttataattt tataacatct cccgacttcg acatgtggtt   2760
ggtactaatg attgcgaaat cgccctccga gaatgagaac aaccgaggtc caccgtctgg   2820
tcgagattaa aacacttgag gagtgctttg gtgactcgat caataggtac agggctcgtt   2880
gccaacaatc tggccagctg gacatccggg acctcgttcc cccctggggt atcaaaattt   2940
ttgtagtgta aatagtagta cactcttaaa aataatgaaa attactgcgg acgtaattca   3000
cattatgatt gaatgacact atcattgaca tttcccgaat cagacaccat cgtatttaaa   3060
atgtgacaca aattcacctc atttggctcg cttcttttat gtgcatccaa aagacgtaaa   3120
atcgcatgat tttttcggag tgtgtagtaa gattgtcaaa ttttaatttt aaataaccag   3180
agcccataaa gcaaagcaac actaggaaaa aacccacaaa ctcaacctgt ccaaaaaaaa   3240
atataacaat caaagttgag ggaatcgggg tcaaacgtca tgtaaaaata ttttttgtaa   3300
aaaccaaacc aggaataaat atgaatttaa tcggaaaaaa ttgcaaaatc gcataattta   3360
atcctccaac tgtactttat ccagcctgtt gcagaaatga tgtttaaagg ttctaatctg   3420
taattgttat tagccttcaa tactgatgta gtatttattt cttattgaaa cattgagagc   3480
tttattttcc aaagttgtca ttttctcatt cgtatatcgt aatatgtata ttcgtaaatg   3540
gcaagcacaa tgatactcag ggcagtcaag gatatttcaa ttacgaaaag atcctgaaac   3600
gaccgggaat cgaacccttc agcatggctt tgctttgtag ctgctgaatc taaccactag   3660
gctgatgaag atcccatttt agggttgcaa gttctcaaag agcaagaatg ccaaaatagt   3720
gtcaaaagaa gccctatttg acgatatacc ttttagtctc tacgttaatt tgctatgata   3780
atttatcatc aattaattgg caaagcctga tgcacgaaaa gatcttcttc taaaatttca   3840
gttgttcttt tcaacacatt atgtaatcat aaaatttata ataaaccttt ttttttgta    3900
actatccaca gttgatcagg cataattttc ttggaaagta aagtccatat ttaggttgat   3960
gttgaataaa aaaactttca attcactctt ctgtttcact tcagaactta cgtaatacga   4020
cattatgcat ggtgcacacg gaacaggata agacgttcac aagggatcaa catcacatcg   4080
gatcgtaatc actggatctg gaacacatat gacgccacaa gacagcacat tttacacgat   4140
caccagacgt gaacaaggaa ctggatccac aagacgtcac aggaagacgg cacatttcca   4200
acggcttcga tggaactttt ctcgagtctt tttccaccaa tcataaacac cgacctggat   4260
caatggggaa aaaccttcgt cgttatcctc ggtttccatg gtggcggtcc gtatcgaact   4320
gtaccagagc gagcgtcaaa atccgattgt gagtgattcc ttgggtttac cggggtttta   4380
tactcggaag tgccggccca tgcatcagtc catagaagga tcgattgaga tagttaattc   4440
cgatcaatca atcggcgatc gatcgcgtta cgatcgtgcg ttcgggtgag gtttccgacg   4500
catttgggag tgtgtgtttt gcgaagtgac aatgtaatgc atatctaaat ttggcattat   4560
ttgcaaagcg ccggtatgca gtgttcgcac atcgatacac ttttgtctga gacgtgatgc   4620
aaacctacag ggtgtttctt aaacggtgcg tggtacggat tgattactga atcagagata   4680
tattcattga attatcttac aaatataatt taacaaaaac cttttctaca aacaaaaaaa   4740
cacttcttgt cccagaagtc tgaagatgtt caactactga tcagctacct taaattatgt   4800
tctatttcga agtccaaacg atatttattc acgtatcgca tgatctctac tctttaagga   4860
aaggtatatt ggaaagtcag gacgtcaaat attgatacag agacctgacc actgactcct   4920
tgtcattttt cttcatctct tgacaggctc tttatgctgt cgcgacatgt cggtaagctg   4980
gcacgcagcg atgaaaattt acaaaaaaaa aagagagaaa aaagtagggc tacactcttt   5040
```

ggggtacgaa ttatcattat tgtgtaaaat aaatcttcca gctatttagt ggaatacctg 5100
taagtaaatg gaaacctaat tcaggactat accatttaat tcgactcgaa tttgcttcct 5160
ttgacagata aaaattctca agtagcattt tgaaccactt ttcgagaagt gtaatccggg 5220
gtaacattca tcagcggggt gacattgatc agaataaccc ttcttgtaaa aagtttgaat 5280
aaacattaat cgatggttgt tttttacatg tgtaaattgt tcaacgtttt gcaacaatca 5340
ttttcgtgat tttggatgac actatcgaat attaatgtct ttcacgggtt ttgcaagcaa 5400
tttgagcaag aaaatgcaaa tgttaccaaa aatggcatcg tcgaaaacga tttcgctgtg 5460
gaaactttca aaagtttgtt caattaaggc ccaagtaaaa atagcgcaaa tatcaaaacc 5520
aaaaaaaaaa cagttttttt ttctttttag cacggaagac cagagcaaat tgctttagct 5580
tgatagctaa agttcgtaac acaccggcac caaaaaacga acgattggat acgctagcga 5640
gtttcggttt ggtggtgcaa aatgtatgcg gccatctgaa agctaaacgc tggaaaatca 5700
tctttcgaat ccggttctcc taaatgaact tgtagagtaa ttaccaagca gcggtgaagt 5760
tcaattcggc tctatatcaa cgtcaacttc ccagtgcgcg ccccggccat cgagaaagag 5820
agagagaaga gaagagagag aacattcgag aaagagagag agaagagaag agagagaaca 5880
tactccctat cagtgataga gaagtcccta tcagtgatag agatgtccct atcagtgata 5940
gagagttccc tatcagtgat agagacgtcc ctatcagtga tagagaagtc cctatcagtg 6000
atagagagat ccctatcagt gatagagatt tccctatcag tgatagagag gtccctatca 6060
gtgatagaga cttccctatc agtgatagag aaatccctat cagtgataga gacatcccta 6120
tcagtgatag agaactccct atcagtgata gagacctccc tatcagtgat agagatcgat 6180
gcggccgcga gcgccggagt ataaatagag gcgcttcgtc tacggagcga caattcaatt 6240
caaacaagca aagtgaacac gtcgctaagc gaaagctaag caaataaaca agcgcagctg 6300
aacaagctaa acaatctgca ggtaccctgg cggtaagttg atcaaaggaa acgcaaagtt 6360
ttcaagaaaa aacaaaacta atttgattta taacaccttt agaaagcggg gctagccacc 6420
atgggcagcg cctacagccg cgcccgtacc aagaacaact atggcagcac catcgaggga 6480
ctgctggacc tgccggatga cgatgccccg gaggaagccg gcctggccgc cccccgcctg 6540
agcttcctgc ccgccggaca cacgcgccgc ctgagcaccg ccccgccgac cgatgtgagc 6600
ctgggcgacg agctgcacct ggatggagag gatgtggcaa tggcccacgc cgacgccctg 6660
gacgatttcg acctggatat gctgggcgat ggagatagcc cgggaccggg cttcacgccc 6720
cacgatagcg ccccgtacgg cgccctggac atggccgact tcgagttcga gcaaatgttc 6780
accgacgcgc tgggcatcga tgagtatggc gggtaggttt aaactcgcgt taagatacat 6840
tgatgagttt ggacaaacca caactagaat gcagtgaaaa aaatgcttta tttgtgaaat 6900
ttgtgatgct attgctttat ttgtaaccat tataagctgc aataaacaag ttaacaacaa 6960
caattgcatt cattttatgt ttcaggttca gggggaggtg tgggaggttt tttaaagcaa 7020
gtaaaacctc tacaaatgtg gtatggctga ttatgatcag ttatctagat ccggtggatc 7080
ttacgggtcc tccaccttcc gctttttctt gggtcgagat ctcaggaaca ggtggtggcg 7140
gccctcggtg cgctcgtact gctccacgat ggtgtagtcc tcgttgtggg aggtgatgtc 7200
cagcttggcg tccacgtagt agtagccggg cagctgcacg ggcttcttgg ccatgtagat 7260
ggacttgaac tccaccaggt agtggccgcc gtccttcagc ttcagggcct tgtgggtctc 7320
gcccttcagc acgccgtcgc gggggtacag gcgctcggtg gaggcctccc agcccatggt 7380

```
cttcttctgc atcacggggc cgtcggaggg gaagttcacg ccgatgaact tcaccttgta   7440
gatgaagcag ccgtcctgca gggaggagtc ctgggtcacg gtcgccacgc cgccgtcctc   7500
gaagttcatc acgcgctccc acttgaagcc ctcggggaag gacagcttct tgtagtcggg   7560
gatgtcggcg gggtgcttca cgtacacctt ggagccgtac tggaactggg gggacaggat   7620
gtcccaggcg aagggcaggg ggccgccctt ggtcaccttc agcttcacgg tgttgtggcc   7680
ctcgtagggg cggccctcgc cctcgccctc gatctcgaac tcgtggccgt tcacggtgcc   7740
ctccatgcgc accttgaagc gcatgaactc ggtgatgacg ttctcggagg aggccatggt   7800
ggcgaccggt ttgcgcttct tcttgggtgg ggtgggatct cccatggtgg cctgaatctc   7860
aacttgcacc tgaaggtagt gcagcaagga tgagcaaaag ggaagaaccc agaaaagaac   7920
gggaaaactt accccaatta gaattgcttg tcgccgccag tgtcaacttg caactgaaac   7980
aatatccaac atgaacgtca atttatactg ccctaatggc gaacacgata acaatatttc   8040
ttttattatg ccctctaaaa ccaacgcggt tatcgtttat ttattcaaat tagatataga   8100
acatccgccg acatacaatg ttaatgcaaa aacgcgtttg gtgagcggat acgaaaacag   8160
tcggccgata aacattaatc tgaggtcgat aacaccgtcc ttgaacggaa cacgaggagc   8220
gtacgtgatc agctgcattc gcgcgccgcg cctttatcga gatttatttg catacaacaa   8280
gtacactgcg ccgttgggat ttgtggtaac gcgcacacat gcagagctgc aagtgtggca   8340
cattttgtct gtgcgcaaaa cctttgaagc caaaagtacg aggtccgtta cgggcatgct   8400
actagcgcac acggacaatg gacccgacaa attctacgcc aaggatttaa tgataatgtc   8460
gggcaacgta tccgttcatt ttatcaataa cctacaaaaa tgtcgcgcgc atcacaaaga   8520
catcgatata tttaaacatt tatgtcccga actgcaaatc gataatagtg ttgtgcaacc   8580
tcgagcgtcc gtttgattta acgtatagct tgcaaatgaa ttatttaatt atcaatcatg   8640
ttttacgcgt agaattctac ccgtaaagcg agtttagtta tgagccatgt gcaaaacatg   8700
acatcagctt ttattttat aacaaatgac atcatttctt gattgtgttt tacacgtaga   8760
attctactcg taaagcgagt tcagttttga aaaacaaatg acatcatctt tttgattgtg   8820
ctttacaagt agaattctac ccgtaaatca agttcggttt tgaaaaacaa atgagtcata   8880
ttgtatgata tcatattgca aaacaaatga ctcatcaatc gatcgtgcgt tacacgtaga   8940
attctactcg taaagcgagt ttatgagccg tgtgcaaaac atgacatcat ctcgatttga   9000
aaaacaaatg acatcatcca ctgatcgtgc attacaagta gaattctact cgtaaagcca   9060
gttcggttat gagccgtgta caaaacatga catcagatta tgactcatac ttgattgtgt   9120
tttacgcgta gaattctact cgtaaagcca gttcaatttt aaaaacaaat gacatcatcc   9180
aaattaataa atgacaagca atgggtacca tgcggcctgg cctcgcgctc gcgcgactga   9240
cggtcgtaag cacccgcgta cgtgtccacc ccggtcacaa ccccttgtgt catgtcggcg   9300
accctacgcc cccaactgag agaactcaaa ggttacccca gttggggcac tactcccgaa   9360
aaccgcttct gacctgggaa aacgtgaagc cccggggcat ccgctgaggg ttgccgccgg   9420
ggcttcggtg tgtccgtcag tacttaatta acaccgaaat cgtaattcac ggcatcatta   9480
caaaatattt tgacgttttg gacctcgtcc ctaatgacac cataacggtg gccttgaagt   9540
atatttaacc ctagaaagat agtctgcgta aaattgacgc atgcattctt gaaatattgc   9600
tctctctttc taaatagcgc gaatccgtcg ctgtgcattt aggacatctc agtcgccgct   9660
tggagctccc gtgaggcgtg cttgtcaatg cggtaagtgt cactgatttt gaactataac   9720
gaccgcgtga gtcaaaatga cgcatgatta tcttttacgt gacttttaag atttaactca   9780
```

tacgataatt atattgttat ttcatgttct acttacgtga taacttatta tatatatatt 9840
ttcttgttat agatatcgtg actaatatat aataaaatgg gtagttcttt agacgatgag 9900
catatcctct ctgctcttct gcaaagcgat gacgagcttg ttggtgagga ttctgacagt 9960
gaaatatcag atcacgtaag tgaagatgac ctcgaggatc caagcttatc gatttcgaac 10020
cctcgaccgc cggagtataa atagaggcgc ttcgtctacg gagcgacaat tcaattcaaa 10080
caagcaaagt gaacacgtcg ctaagcgaaa gctaagcaaa taaacaagcg cagctgaaca 10140
agctaaacaa tcggggtacc gctagagtcg atcccacccc acccaagaag aagcgcaaac 10200
cggtaccatg gcctcctccg agaacgtcat caccgagttc atgcgcttca aggtgcgcat 10260
ggagggcacc gtgaacggcc acgagttcga gatcgagggc gagggcgagg gccgccccta 10320
cgagggccac aacaccgtga agctgaaggt gaccaagggc ggcccccctgc ccttcgcctg 10380 ggacatcctg tccccccagt tccagtacgg ctccaaggtg tacgtgaagc accccgccga 10440
catccccgac tacaagaagc tgtccttccc cgagggcttc aagtgggagc gcgtgatgaa 10500
cttcgaggac ggcggcgtgg cgaccgtgac ccaggactcc tccctgcagg acggctgctt 10560
catctacaag gtgaagttca tcggcgtgaa cttcccctcc gacggccccg tgatgcagaa 10620
gaagaccatg ggctgggagg cctccaccga gcgcctgtac ccccgcgacg gcgtgctgaa 10680
gggcgagacc cacaaggccc tgaagctgaa ggacggcggc cactacctgg tggagttcaa 10740
gtccatctac atggccaaga agcccgtgca gctgcccggc tactactacg tggacgccaa 10800
gctggacatc acctcccaca acgaggacta caccatcgtg gagcagtacg agcgcaccga 10860
gggccgccac cacctgttcc tgtgatgatc ataatcagcc ataccacatt tgtagaggtt 10920
ttacttgctt taaaaaacct cccacacctc cccctgaacc tgaaacataa aatgaatgca 10980
attgttgttg ttaacttgtt tattgcagct tataatggtt acaaataaag caatagcatc 11040
acaaatttca caaataaagc atttttttca ctgcattcta gttgtggttt gtccaaactc 11100
atcaatgtat cttaacgcga gttaattacg gccgctcatt taaatctggc cggccgcaac 11160
cattgtggga accgtgcgat caaacaaacg cgagataccg gaagtactga aaaacagtcg 11220
ctccaggcca gtgggaacat cgatgttttg ttttgacgga ccccttactc tcgtctcata 11280
taaaccgaag ccagctaaga tggtatactt attatcatct tgtgatgagg atgcttctat 11340
caacgaaagt accggtaaac cgcaaatggt tatgtattat aatcaaacta aaggcggagt 11400
ggacacgcta gaccaaatgt gttctgtgat gacctgcagt aggaagacga ataggtggcc 11460
tatggcatta ttgtacggaa tgataaacat tgcctgcata aattctttta ttatatacag 11520
ccataatgtc agtagcaagg gagaaaaggt ccaaagtcgc aaaaaattta tgagaaacct 11580
ttacatgagc ctgacgtcat cgtttatgcg taagcgttta gaagctccta ctttgaagag 11640
atatttgcgc gataatatct ctaatatttt gccaaatgaa gtgcctggta catcagatga 11700
cagtactgaa gagccagtaa tgaaaaaacg tacttactgt acttactgcc cctctaaaat 11760
aaggcgaaag gcaaatgcat cgtgcaaaaa atgcaaaaaa gttatttgtc gagagcataa 11820
tattgatatg tgccaaagtt gtttctgact gactaataag tataatttgt ttctattatg 11880
tataagttaa gctaattact tattttataa tacaacatga ctgtttttaa agtacaaaat 11940
aagtttattt ttgtaaaaga gagaatgttt aaaagttttg ttactttata gaagaaattt 12000
tgagtttttg ttttttttta ataaataaat aaacataaat aaattgtttg ttgaatttat 12060
tattagtatg taagtgtaaa tataataaaa cttaatatct attcaaatta ataaataaac 12120

```
ctcgatatac agaccgataa aacacatgcg tcaattttac gcatgattat ctttaacgta  12180
cgtcacaata tgattatctt tctagggtta aataatagtt tctaattttt ttattattca  12240
gcctgctgtc gtgaataccg tatatctcaa cgctgtctgt gagattgtcg tattctagcc  12300
tttttagttt ttcgctcatc gacttgatat tgtccgacac attttcgtcg atttgcgttt  12360
tgatcaaaga cttgagcaga gacacgttaa tcaactgttc aaattgatcc atattaacga  12420
tatcaacccg atgcgtatat ggtgcgtaaa atatattttt taaccctctt atactttgca  12480
ctctgcgtta atacgcgttc gtgtacagac gtaatcatgt tttctttttt ggataaaact  12540
cctactgagt ttgacctcat attagaccct cacaagttgc aaaacgtggc atttttttacc  12600
aatgaagaat ttaaagttat tttaaaaaat ttcatcacag atttaaagaa gaaccaaaaa  12660
ttaaattatt tcaacagttt aatcgaccag ttaatcaacg tgtacacaga cgcgtcggca  12720
aaaaacacgc agcccgacgt gttggctaaa attattaaat caacttgtgt tatagtcacg  12780
gatttgccgt ccaacgtgtt cctcaaaaag ttgaagacca acaagtttac ggacactatt  12840
aattatttga ttttgcccca cttcattttg tgggatcaca attttgttat attttaaaca  12900
aagcttggca ctggccgtcg ttttacaacg tcgtgactgg gaaaaccctg gcgttaccca  12960
acttaatcgc cttgcagcac atccccccttt cgccagctgg cgtaatagcg aagaggcccg  13020
caccgatcgc ccttcccaac agttgcgcag cctgaatggc gaatggcgcc tgatgcggta  13080
ttttctcctt acgcatctgt gcggtatttc acaccgcata tggtgcactc tcagtacaat  13140
ctgctctgat gccgcatagt taagccagcc ccgacacccg ccaacacccg ctgacgcgcc  13200
ctgacgggct tgtctgctcc cggcatccgc ttacagacaa gctgtgaccg tctccgggag  13260
ctgcatgtgt cagaggtttt caccgtcatc accgaaacgc gcgagacgaa agggcctcgt  13320
gatacgccta tttttatagg ttaatgtcat gataataatg gtttcttaga cgtcaggtgg  13380
cacttttcgg ggaaatgtgc gcggaacccc tatttgttta tttttctaaa tacattcaaa  13440
tatgtatccg ctcatgagac aataaccctg ataaatgctt caataatatt gaaaaaggaa  13500
gagtatgagt attcaacatt tccgtgtcgc ccttattccc ttttttgcgg cattttgcct  13560
tcctgttttt gctcacccag aaacgctggt gaaagtaaaa gatgctgaag atcagttggg  13620
tgcacgagtg ggttacatcg aactggatct caacagcggt aagatccttg agagttttcg  13680
ccccgaagaa cgttttccaa tgatgagcac ttttaaagtt ctgctatgtg gcgcggtatt  13740
atcccgtatt gacgccgggc aagagcaact cggtcgccgc atacactatt ctcagaatga  13800
cttggttgag tactcaccag tcacagaaaa gcatcttacg gatggcatga cagtaagaga  13860
attatgcagt gctgccataa ccatgagtga taacactgcg gccaacttac ttctgacaac  13920
gatcggagga ccgaaggagc taaccgcttt tttgcacaac atgggggatc atgtaactcg  13980
ccttgatcgt tgggaaccgg agctgaatga agccatacca aacgacgagc gtgacaccac  14040
gatgcctgta gcaatggcaa caacgttgcg caaactatta actggcgaac tacttactct  14100
agcttcccgg caacaattaa tagactggat ggaggcggat aaagttgcag gaccacttct  14160
gcgctcggcc cttccggctg gctggtttat tgctgataaa tctggagccg gtgagcgtgg  14220
gtctcgcggt atcattgcag cactggggcc agatggtaag ccctcccgta tcgtagttat  14280
ctacacgacg gggagtcagg caactatgga tgaacgaaat agacagatcg ctgagatagg  14340
tgcctcactg attaagcatt ggtaactgtc agaccaagtt tactcatata tactttagat  14400
tgatttaaaa cttcattttt aatttaaaag gatctaggtg aagatccttt ttgataatct  14460
catgaccaaa atcccttaac gtgagttttc gttccactga gcgtcagacc ccgtagaaaa  14520
```

gatcaaagga tcttcttgag atcctttttt tctgcgcgta atctgctgct tgcaaacaaa 14580
aaaaccaccg ctaccagcgg tggtttgttt gccggatcaa gagctaccaa ctctttttcc 14640
gaaggtaact ggcttcagca gagcgcagat accaaatact gtccttctag tgtagccgta 14700
gttaggccac cacttcaaga actctgtagc accgcctaca tacctcgctc tgctaatcct 14760
gttaccagtg gctgctgcca gtggcgataa gtcgtgtctt accgggttgg actcaagacg 14820
atagttaccg gataaggcgc agcggtcggg ctgaacgggg ggttcgtgca cacagcccag 14880
cttggagcga acgacctaca ccgaactgag atacctacag cgtgagcatt gagaaagcgc 14940
cacgcttccc gaagggagaa aggcggacag gtatccggta agcggcaggg tcggaacagg 15000
agagcgcacg agggagcttc cagggggaaa cgcctggtat ctttatagtc ctgtcgggtt 15060
tcgccacctc tgacttgagc gtcgattttt gtgatgctcg tcaggggggc ggagcctatg 15120
gaaaaacgcc agcaacgcgg cctttttacg gttcctggcc ttttgctggc cttttgctca 15180
catgttcttt cctgcgttat cccctgattc tgtggataac cgtattaccg cctttgagtg 15240
agctgatacc gctcgccgca gccgaacgac cgagcgcagc gagtcagtga gcgaggaagc 15300
ggaagagcgc ccaatacgca aaccgcctct ccccgcgcgt tggccgattc attaatgcag 15360
ctggcacgac aggtttcccg actggaaagc gggcagtgag cgcaacgcaa ttaatgtgag 15420
ttagctcact cattaggcac cccaggcttt acactttatg cttccggctc gtatgttgtg 15480
tggaattgtg agcggataac aatttcacac aggaaacagc tatgaccatg attacgaatt 15540
tcgacctgca ggcatgcaag cttgcatgcc tgcaggtcga cgctcgcgcg acttggtttg 15600
ccattcttta gcgcgcgtcg cgtcacacag cttggccaca atgtggtttt tgtcaaacga 15660
agattctatg acgtgtttaa agtttaggtc gagtaaagcg caaatctttt ttaaccctag 15720
aaagatagtc tgcgtaaaat tgacgcatgc attcttgaaa tattgctctc tctttctaaa 15780
tagcgcgaat ccgtcgctgt gcatttagga catctcagtc gccgcttgga gctcccgtga 15840
ggcgtgcttg tcaatgcggt aagtgtcact gattttgaac tataacgacc gcgtgagtca 15900
aaatgacgca tgattatctt ttacgtgact tttaagattt aactcatacg ataattatat 15960
tgttatttca tgttctactt acgtgataac ttattatata tatattttct tgttatagat 16020
atcgtgacta atatataata aaatgggtag ttctttagac gatgagcata tcctctctgc 16080
tcttctgcaa agcgatgacg agcttgttgg tgaggattct gacagtgaaa tatcagatca 16140
cgtaagtgaa gatgacgtcc agagcgatac agaagaagcg tttatagatg aggtacatga 16200
agtgcagcca acgtcaagcg gtagtgaaat attagacgaa caaaatgtta ttgaacaacc 16260
aggttcttca ttggcttcta acagaatctt gaccttgcca cagaggacta ttagaggtaa 16320
gaataaacat tgttggtcaa cttcaaagtc cacgaggcgt agccgagtct ctgcactgaa 16380
cattgtcaga tcggcccgct cgcccgggga actagttcaa ttagagacta attcaattag 16440
agctaattca attaggatcc aagcttatcg atttcgaacc ctcgaccgcc ggagtataaa 16500
tagaggcgct tcgtctacgg agcgacaatt caattcaaac aagcaaagtg aacacgtcgc 16560
taagcgaaag ctaagcaaat aaacaagcgc agctgaacaa gctaaacaat cggggtaccg 16620
ctagagtcga tcccacccca cccaagaaga agcgcaaacc ggtcgccacc atggccctgt 16680
ccaacaagtt catcggcgac gacatgaaga tgacctacca catggacggc tgcgtgaacg 16740
gccactactt caccgtgaag ggcgagggca gcggcaagcc ctacgagggc acccagacct 16800
ccaccttcaa ggtgaccatg gccaacggcg gcccccctggc cttctccttc gacatcctgt 16860
ccaccgtgtt catgtacggc aaccgctgct tcaccgccta ccccaccagc atgcccgact 16920
acttcaagca ggccttcccc gacggcatgt cctacgagag aaccttcacc tacgaggacg 16980
gcggcgtggc caccgccagc tgggagatca gcctgaaggg caactgcttc gagcacaagt 17040
ccaccttcca cggcgtgaac ttccccgccg acggccccgt gatggccaag aagaccaccg 17100
gctgggaccc ctccttcgag aagatgaccg tgtgcgacgg catcttgaag ggcgacgtga 17160
ccgccttcct gatgctgcag ggcggcggca actacagatg ccagttccac acctcctaca 17220
agaccaagaa gcccgtgacc atgcccccca accacgtggt ggagcaccgc atcgccagaa 17280
ccgacctgga caagggcggc aacagcgtgc agctgaccga gcacgccgtg gcccacatca 17340
cctccgtggt gcccttctcc ggactcagat cataatcagc cataccacat ttgtagaggt 17400
tttacttgct ttaaaaaacc tcccacacct ccccctgaac ctgaaacata aaatgaatgc 17460
aattgttgtt gttaacttgt ttattgcagc ttataatggt tacaaataaa gcaatagcat 17520
cacaaatttc acaaataaag catttttttc actgcattct agttgtggtt tgtccaaact 17580
catcaatgta tcttaccgcg gagtggacac gctagaccaa atgtgttctg tgatgacctg 17640
cagtaggaag acgaataggt ggcctatggc attattgtac ggaatgataa acattgcctg 17700
cataaattct tttattatat acagccataa tgtcagtagc aagggagaaa aggtccaaag 17760
tcgcaaaaaa tttatgagaa acctttacat gagcctgacg tcatcgttta tgcgtaagcg 17820
tttagaagct cctactttga agagatattt gcgcgataat atctctaata ttttgccaaa 17880
tgaagtgcct ggtacatcag atgacagtac tgaagagcca gtaatgaaaa aacgtactta 17940
ctgtacttac tgcccctcta aaataaggcg aaaggcaaat gcatcgtgca aaaaatgcaa 18000
aaaagttatt tgtcgagagc ataatattga tatgtgccaa agttgtttct gactgactaa 18060
taagtataat ttgtttctat tatgtataag ttaagctaat tacttatttt ataatacaac 18120
atgactgttt ttaaagtaca aaataagttt atttttgtaa aagagagaat gtttaaaagt 18180
tttgttactt tatagaagaa attttgagtt tttgtttttt tttaataaat aaataaacat 18240
aaataaattg tttgttgaat ttattattag tatgtaagtg taaatataat aaaacttaat 18300
atctattcaa attaataaat aaacctcgat atacagaccg ataaaacaca tgcgtcaatt 18360
ttacgcatga ttatctttaa cgtacgtcac aatatgatta tctttctagg g 18411

<210> SEQ ID NO 157
<211> LENGTH: 18073
<212> TYPE: DNA
<213> ORGANISM: artificial
<220> FEATURE:
<223> OTHER INFORMATION: LA3646 Plasmid sequence

<400> SEQUENCE: 157
ctaggtaaga tacattgatg agtttggaca aaccacaact agaatgcagt gaaaaaaatg 60
ctttatttgt gaaatttgtg atgctattgc tttatttgta accattataa gctgcaataa 120
acaagttaac aacaacaatt gcattcattt tatgtttcag gttcaggggg aggtgtggga 180
ggttttttaa agcaagtaaa acctctacaa atgtggtatg gctgattatg atcagttatc 240
tagatccggt ggatcttacg ggtcctccac cttccgcttt ttcttgggtc gagatctcag 300
gaacaggtgg tggcggccct cggtgcgctc gtactgctcc acgatggtgt agtcctcgtt 360
gtgggaggtg atgtccagct tggcgtccac gtagtagtag ccgggcagct gcacgggctt 420
cttggccatg tagatggact tgaactccac caggtagtgg ccgccgtcct tcagcttcag 480
ggccttgtgg gtctcgccct tcagcacgcc gtcgcggggg tacaggcgct cggtggaggc 540

```
ctcccagccc atggtcttct tctgcatcac ggggccgtcg gaggggaagt tcacgccgat    600
gaacttcacc ttgtagatga agcagccgtc ctgcagggag gagtcctggg tcacggtcgc    660
cacgccgccg tcctcgaagt tcatcacgcg ctcccacttg aagccctcgg ggaaggacag    720
cttcttgtag tcggggatgt cggcggggtg cttcacgtac accttggagc cgtactggaa    780
ctggggggac aggatgtccc aggcgaaggg caggggggccg cccttggtca ccttcagctt    840
cacggtgttg tggccctcgt aggggcggcc ctcgccctcg ccctcgatct cgaactcgtg    900
gccgttcacg gtgccctcca tgcgcacctt gaagcgcatg aactcggtga tgacgttctc    960
ggaggaggcc atggtggcga ccggtttgcg cttcttcttg ggtggggtgg gatctcccat   1020
ggtggcctga atctcaactt gcacctgaag gtagtgcagc aaggatgagc aaaagggaag   1080
aacccagaaa agaacgggaa aacttacccc aattagaatt gcttgtcgcc gccagtgtca   1140
acttgcaact gaaacaatat ccaacatgaa cgtcaattta tactgcccta atggcgaaca   1200
cgataacaat atttctttta ttatgccctc taaaaccaac gcggttatcg tttatttatt   1260
caaattagat atagaacatc cgccgacata caatgttaat gcaaaaaacgc gtttggtgag   1320
cggatacgaa aacagtcggc cgataaacat taatctgagg tcggtaacac cgtccttgaa   1380
cggaacacga ggagcgtacg tgatcagctg cattcgcgcg ccgcgccttt atcgagattt   1440
atttgcatac aacaagtaca ctgcgccgtt gggatttgtg gtaacgcgca cacatgcaga   1500
gctgcaagtg tggcacattt tgtctgtgcg caaaaccttt gaagccaaaa gtacgaggtc   1560
cgttacgggc atgctagcgc acacggacaa tggacccgac aaattctacg ccaaggattt   1620
aatgataatg tcgggcaacg tatccgttca ttttatcaat aacctacaaa aatgtcgcgc   1680
gcatcacaaa gacatcgata tatttaaaca tttatgtccc gaactgcaaa tcgataatag   1740
tgttgtgcaa cctcgagcgt ccgtttgatt taacgtatag cttgcaaatg aattatttaa   1800
ttatcaatca tgttttacgc gtagaattct acccgtaaag cgagtttagt tatgagccat   1860
gtgcaaaaca tgacatcagc ttttattttt ataacaaatg acatcatttc ttgattgtgt   1920
tttacacgta gaattctact cgtaaagcga gttcagtttt gaaaaacaaa tgacatcatc   1980
tttttgattg tgctttacaa gtagaattct acccgtaaat caagttcggt tttgaaaaac   2040
aaatgagtca tattgtatga tatcatattg caaaacaaat gactcatcaa tcgatcgtgc   2100
gttacacgta gaattctact cgtaaagcga gtttatgagc cgtgtgcaaa acatgacatc   2160
atctcgattt gaaaaacaaa tgacatcatc cactgatcgt gcattacaag tagaattcta   2220
ctcgtaaagc cagttcggtt atgagccgtg tacaaaacat gacatcagat tatgactcat   2280
acttgattgt gttttacgcg tagaattcta ctcgtaaagc cagttcaatt ttaaaaacaa   2340
atgacgcggc cgcattaaca ccgaaatcgt aattcacggc atcattacaa aatattttga   2400
cgttttggac ctcgtcccta atgacaccat aacggtggcc ttgaagtata tttaacccta   2460
gaaagatagt ctgcgtaaaa ttgacgcatg cattcttgaa atattgctct ctctttctaa   2520
atagcgcgaa tccgtcgctg tgcatttagg acatctcagt cgccgcttgg agctcccgtg   2580
aggcgtgctt gtcaatgcgg taagtgtcac tgattttgaa ctataacgac cgcgtgagtc   2640
aaaatgacgc atgattatct tttacgtgac ttttaagatt taactcatac gataattata   2700
ttgttatttc atgttctact tacgtgataa cttattatat atatattttc ttgttataga   2760
tatcgtgact aatatataat aaaatgggta gttctttaga cgatgagcat atcctctctg   2820
ctcttctgca aagcgatgac gagcttgttg gtgaggattc tgacagtgaa atatcagatc   2880
```

acgtaagtga agatgacctc gaggatccaa gcttatcgat ttcgaaccct cgaccgccgg 2940
agtataaata gaggcgcttc gtctacggag cgacaattca attcaaacaa gcaaagtgaa 3000
cacgtcgcta agcgaaagct aagcaaataa acaagcgcag ctgaacaagc taaacaatcg 3060
gggtaccgct agagtcgatc ccaccccacc caagaagaag cgcaaaccgg taccatggcc 3120
tcctccgaga acgtcatcac cgagttcatg cgcttcaagg tgcgcatgga gggcaccgtg 3180
aacggccacg agttcgagat cgagggcgag ggcgagggcc gcccctacga gggccacaac 3240
accgtgaagc tgaaggtgac caagggcggc cccctgccct tcgcctggga catcctgtcc 3300
ccccagttcc agtacggctc caaggtgtac gtgaagcacc ccgccgacat ccccgactac 3360
aagaagctgt ccttccccga gggcttcaag tgggagcgcg tgatgaactt cgaggacggc 3420
ggcgtggcga ccgtgaccca ggactcctcc ctgcaggacg gctgcttcat ctacaaggtg 3480
aagttcatcg gcgtgaactt cccctccgac ggccccgtga tgcagaagaa gaccatgggc 3540
tgggaggcct ccaccgagcg cctgtacccc cgcgacggcg tgctgaaggg cgagacccac 3600
aaggccctga agctgaagga cggcggccac tacctggtgg agttcaagtc catctacatg 3660
gccaagaagc ccgtgcagct gcccggctac tactacgtgg acgccaagct ggacatcacc 3720
tcccacaacg aggactacac catcgtggag cagtacgagc gcaccgaggg ccgccaccac 3780
ctgttcctgt gatgatcata atcagccata ccacatttgt agaggtttta cttgctttaa 3840
aaaacctccc acacctcccc ctgaacctga aacataaaat gaatgcaatt gttgttgtta 3900
acttgtttat tgcagcttat aatggttaca aataaagcaa tagcatcaca aatttcacaa 3960
ataaagcatt tttttcactg cattctagtt gtggtttgtc caaactcatc aatgtatctt 4020
aacgcgagtt aattacggcc gctcatttaa atctggccgg ccgcaaccat tgtgggaacc 4080
gtgcgatcaa acaaacgcga gataccggaa gtactgaaaa acagtcgctc caggccagtg 4140
ggaacatcga tgttttgttt tgacggaccc cttactctcg tctcatataa accgaagcca 4200
gctaagatgg tatacttatt atcatcttgt gatgaggatg cttctatcaa cgaaagtacc 4260
ggtaaaccgc aaatggttat gtattataat caaactaaag gcggagtgga cacgctagac 4320
caaatgtgtt ctgtgatgac ctgcagtagg aagacgaata ggtggcctat ggcattattg 4380
tacggaatga taaacattgc ctgcataaat tcttttatta tatacagcca taatgtcagt 4440
agcaagggag aaaaggtcca aagtcgcaaa aaatttatga gaaaccttta catgagcctg 4500
acgtcatcgt ttatgcgtaa gcgtttagaa gctcctactt tgaagagata tttgcgcgat 4560
aatatctcta atattttgcc aaatgaagtg cctggtacat cagatgacag tactgaagag 4620
ccagtaatga aaaaacgtac ttactgtact tactgcccct ctaaaataag gcgaaaggca 4680
aatgcatcgt gcaaaaaatg caaaaaagtt atttgtcgag agcataatat tgatatgtgc 4740
caaagttgtt tctgactgac taataagtat aatttgtttc tattatgtat aagttaagct 4800
aattacttat tttataatac aacatgactg tttttaaagt acaaaataag tttatttttg 4860
taaaagagag aatgtttaaa agttttgtta ctttatagaa gaaattttga gtttttgttt 4920
ttttttaata aataaataaa cataaataaa ttgtttgttg aatttattat tagtatgtaa 4980
gtgtaaatat aataaaactt aatatctatt caaattaata aataaacctc gatatacaga 5040
ccgataaaac acatgcgtca attttacgca tgattatctt taacgtacgt cacaatatga 5100
ttatctttct agggttaaat aatagtttct aatttttta ttattcagcc tgctgtcgtg 5160
aataccgtat atctcaacgc tgtctgtgag attgtcgtat tctagccttt ttagtttttc 5220
gctcatcgac ttgatattgt ccgacacatt ttcgtcgatt tgcgttttga tcaaagactt 5280

-continued

```
gagcagagac acgttaatca actgttcaaa ttgatccata ttaacgatat caacccgatg   5340
cgtatatggt gcgtaaaata tattttttaa ccctcttata ctttgcactc tgcgttaata   5400
cgcgttcgtg tacagacgta atcatgtttt cttttttgga taaaactcct actgagtttg   5460
acctcatatt agaccctcac aagttgcaaa acgtggcatt ttttaccaat gaagaattta   5520
aagttatttt aaaaaatttc atcacagatt taaagaagaa ccaaaaaatta aattatttca   5580
acagtttaat cgaccagtta atcaacgtgt acacagacgc gtcggcaaaa aacacgcagc   5640
ccgacgtgtt ggctaaaatt attaaatcaa cttgtgttat agtcacggat ttgccgtcca   5700
acgtgttcct caaaaagttg aagaccaaca agtttacgga cactattaat tatttgattt   5760
tgccccactt cattttgtgg gatcacaatt ttgttatatt ttaaacaaag cttggcactg   5820
gccgtcgttt tacaacgtcg tgactgggaa aaccctggcg ttacccaact taatcgcctt   5880
gcagcacatc ccccttttcgc cagctggcgt aatagcgaag aggcccgcac cgatcgccct   5940
tcccaacagt tgcgcagcct gaatggcgaa tggcgcctga tgcggtattt tctccttacg   6000
catctgtgcg gtatttcaca ccgcatatgg tgcactctca gtacaatctg ctctgatgcc   6060
gcatagttaa gccagccccg acacccgcca acacccgctg acgcgccctg acgggcttgt   6120
ctgctcccgg catccgctta cagacaagct gtgaccgtct ccgggagctg catgtgtcag   6180
aggttttcac cgtcatcacc gaaacgcgcg agacgaaagg gcctcgtgat acgcctattt   6240
ttataggtta atgtcatgat aataatggtt tcttagacgt caggtggcac ttttcgggga   6300
aatgtgcgcg gaacccctat ttgtttattt ttctaaatac attcaaatat gtatccgctc   6360
atgagacaat aaccctgata aatgcttcaa taatattgaa aaaggaagag tatgagtatt   6420
caacatttcc gtgtcgccct tattcccttt tttgcggcat tttgccttcc tgtttttgct   6480
cacccagaaa cgctggtgaa agtaaaagat gctgaagatc agttgggtgc acgagtgggt   6540
tacatcgaac tggatctcaa cagcggtaag atccttgaga gttttcgccc cgaagaacgt   6600
tttccaatga tgagcacttt taaagttctg ctatgtggcg cggtattatc ccgtattgac   6660
gccgggcaag agcaactcgg tcgccgcata cactattctc agaatgactt ggttgagtac   6720
tcaccagtca cagaaaagca tcttacggat ggcatgacag taagagaatt atgcagtgct   6780
gccataacca tgagtgataa cactgcggcc aacttacttc tgacaacgat cggaggaccg   6840
aaggagctaa ccgctttttt gcacaacatg ggggatcatg taactcgcct tgatcgttgg   6900
gaaccggagc tgaatgaagc cataccaaac gacgagcgtg acaccacgat gcctgtagca   6960
atggcaacaa cgttgcgcaa actattaact ggcgaactac ttactctagc ttcccggcaa   7020
caattaatag actggatgga ggcggataaa gttgcaggac cacttctgcg ctcggccctt   7080
ccggctggct ggtttattgc tgataaatct ggagccggtg agcgtgggtc tcgcggtatc   7140
attgcagcac tggggccaga tggtaagccc tcccgtatcg tagttatcta cacgacgggg   7200
agtcaggcaa ctatggatga acgaaataga cagatcgctg agataggtgc ctcactgatt   7260
aagcattggt aactgtcaga ccaagtttac tcatatatac tttagattga tttaaaactt   7320
catttttaat ttaaaaggat ctaggtgaag atcctttttg ataatctcat gaccaaaatc   7380
ccttaacgtg agttttcgtt ccactgagcg tcagaccccg tagaaaagat caaaggatct   7440
tcttgagatc cttttttttct gcgcgtaatc tgctgcttgc aaacaaaaaa accaccgcta   7500
ccagcggtgg tttgtttgcc ggatcaagag ctaccaactc tttttccgaa ggtaactggc   7560
ttcagcagag cgcagatacc aaatactgtc cttctagtgt agccgtagtt aggccaccac   7620
```

-continued

```
ttcaagaact ctgtagcacc gcctacatac ctcgctctgc taatcctgtt accagtggct   7680
gctgccagtg gcgataagtc gtgtcttacc gggttggact caagacgata gttaccggat   7740
aaggcgcagc ggtcgggctg aacggggggt tcgtgcacac agcccagctt ggagcgaacg   7800
acctacaccg aactgagata cctacagcgt gagcattgag aaagcgccac gcttcccgaa   7860
gggagaaagg cggacaggta tccggtaagc ggcagggtcg gaacaggaga gcgcacgagg   7920
gagcttccag ggggaaacgc ctggtatctt tatagtcctg tcgggtttcg ccacctctga   7980
cttgagcgtc gatttttgtg atgctcgtca ggggggcgga gcctatggaa aaacgccagc   8040
aacgcggcct ttttacggtt cctggccttt tgctggcctt ttgctcacat gttctttcct   8100
gcgttatccc ctgattctgt ggataaccgt attaccgcct ttgagtgagc tgataccgct   8160
cgccgcagcc gaacgaccga gcgcagcgag tcagtgagcg aggaagcgga agagcgccca   8220
atacgcaaac cgcctctccc cgcgcgttgg ccgattcatt aatgcagctg gcacgacagg   8280
tttcccgact ggaaagcggg cagtgagcgc aacgcaatta atgtgagtta gctcactcat   8340
taggcacccc aggctttaca ctttatgctt ccggctcgta tgttgtgtgg aattgtgagc   8400
ggataacaat ttcacacagg aaacagctat gaccatgatt acgaatttcg acctgcaggc   8460
atgcaagctt gcatgcctgc aggtcgacgc tcgcgcgact tggtttgcca ttctttagcg   8520
cgcgtcgcgt cacacagctt ggccacaatg tggtttttgt caaacgaaga ttctatgacg   8580
tgtttaaagt ttaggtcgag taaagcgcaa atctttttta accctagaaa gatagtctgc   8640
gtaaaattga cgcatgcatt cttgaaatat tgctctctct ttctaaatag cgcgaatccg   8700
tcgctgtgca tttaggacat ctcagtcgcc gcttggagct cccgtgaggc gtgcttgtca   8760
atgcggtaag tgtcactgat tttgaactat aacgaccgcg tgagtcaaaa tgacgcatga   8820
ttatctttta cgtgactttt aagatttaac tcatacgata attatattgt tatttcatgt   8880
tctacttacg tgataactta ttatatatat attttcttgt tatagatatc gtgactaata   8940
tataataaaa tgggtagttc tttagacgat gagcatatcc tctctgctct tctgcaaagc   9000
gatgacgagc ttgttggtga ggattctgac agtgaaatat cagatcacgt aagtgaagat   9060
gacgtccaga gcgatacaga agaagcgttt atagatgagg tacatgaagt gcagccaacg   9120
tcaagcggta gtgaaatatt agacgaacaa aatgttattg aacaaccagg ttcttcattg   9180
gcttctaaca gaatcttgac cttgccacag aggactatta gaggtaagaa taaacattgt   9240
tggtcaactt caaagtccac gaggcgtagc cgagtctctg cactgaacat tgtcagatcg   9300
gcccgctcgc ccggggaact agttcaatta gagactaatt caattagagc taattcaatt   9360
aggatccaag cttatcgatt tcgaaccctc gaccgccgga gtataaatag aggcgcttcg   9420
tctacggagc gacaattcaa ttcaaacaag caaagtgaac acgtcgctaa gcgaaagcta   9480
agcaaataaa caagcgcagc tgaacaagct aaacaatcgg ggtaccgcta gagtcgatcc   9540
caccccaccc aagaagaagc gcaaaccggt cgccaccatg gccctgtcca acaagttcat   9600
cggcgacgac atgaagatga cctaccacat ggacggctgc gtgaacggcc actacttcac   9660
cgtgaagggc gagggcagcg gcaagcccta cgagggcacc cagacctcca ccttcaaggt   9720
gaccatggcc aacggcggcc ccctggcctt ctccttcgac atcctgtcca ccgtgttcat   9780
gtacggcaac cgctgcttca ccgcctaccc caccagcatg cccgactact tcaagcaggc   9840
cttccccgac ggcatgtcct acgagagaac cttcacctac gaggacggcg gcgtggccac   9900
cgccagctgg gagatcagcc tgaagggcaa ctgcttcgag cacaagtcca ccttccacgg   9960
cgtgaacttc cccgccgacg gccccgtgat ggccaagaag accaccggct gggacccctc  10020
```

```
cttcgagaag atgaccgtgt gcgacggcat cttgaagggc gacgtgaccg ccttcctgat  10080
gctgcagggc ggcggcaact acagatgcca gttccacacc tcctacaaga ccaagaagcc  10140
cgtgaccatg ccccccaacc acgtggtgga gcaccgcatc gccagaaccg acctggacaa  10200
gggcggcaac agcgtgcagc tgaccgagca cgccgtggcc cacatcacct ccgtggtgcc  10260
cttctccgga ctcagatcat aatcagccat accacatttg tagaggtttt acttgcttta  10320
aaaaacctcc cacacctccc cctgaacctg aaacataaaa tgaatgcaat tgttgttgtt  10380
aacttgttta ttgcagctta taatggttac aaataaagca atagcatcac aaatttcaca  10440
aataaagcat ttttttcact gcattctagt tgtggtttgt ccaaactcat caatgtatct  10500
taccgcggag tggacacgct agaccaaatg tgttctgtga tgacctgcag taggaagacg  10560
aataggtggc ctatggcatt attgtacgga atgataaaca ttgcctgcat aaattctttt  10620
attatataca gccataatgt cagtagcaag ggagaaaagg tccaaagtcg caaaaaattt  10680
atgagaaacc tttacatgag cctgacgtca tcgtttatgc gtaagcgttt agaagctcct  10740
actttgaaga gatatttgcg cgataatatc tctaatattt tgccaaatga agtgcctggt  10800
acatcagatg acagtactga agagccagta atgaaaaaac gtacttactg tacttactgc  10860
ccctctaaaa taaggcgaaa ggcaaatgca tcgtgcaaaa aatgcaaaaa agttatttgt  10920
cgagagcata atattgatat gtgccaaagt tgtttctgac tgactaataa gtataatttg  10980
tttctattat gtataagtta agctaattac ttattttata atacaacatg actgttttta  11040
aagtacaaaa taagtttatt tttgtaaaag agagaatgtt taaaagtttt gttactttat  11100
agaagaaatt ttgagttttt gttttttttt aataaataaa taaacataaa taaattgttt  11160
gttgaattta ttattagtat gtaagtgtaa atataataaa acttaatatc tattcaaatt  11220
aataaataaa cctcgatata cagaccgata aaacacatgc gtcaatttta cgcatgatta  11280
tctttaacgt acgtcacaat atgattatct ttctagggtt aaaatgaatg taagcacttt  11340
attaacgaaa tctttgggaa tatttcgctc atcagcattt tatttgagca ggagtccgag  11400
atgcccgggc ggcgcgccga attcttaatt aacgccctag ccgcgatcgc atccgccgcg  11460
gtggcggccc taagatacat tgatgagttt ggacaaacca caactagaat gcagtgaaaa  11520
aaatgcttta tttgtgaaat ttgtgatgct attgctttat ttgtaaccat tataagctgc  11580
aataaacaag ttaacaacaa caattgcatt cattttatgt ttcaggttca gggggaggtg  11640
tgggaggttt tttaaagcaa gtaaaacctc tacaaatgtg gtatggctga ttatgatcgt  11700
tgcacattcc gatgtatgct gtgcagaata tgggactggt gcgcttccaa tccgttttca  11760
aatccattat cttccggttc actgtgagcg ggtcgagtgg gaatctcctc cgtagagccg  11820
aaactttctc tcttccagtg ggaaccgctt ccgcccgcca gaggttcttc agcagccgca  11880
gcagcagcag cgccactgtg taaggcttcc tccagacggc accgcaactc ggtagattca  11940
atggacttcg ggctgcgttt ctcgtacata acctcttcgt cgtcggtggt ggcggtcgtc  12000
gctttggtag atttcgtgtc cagattgagc gcgccaccgt tgttatccgg cgagctggac  12060
tgtgaccggg tacgaaaatc ggcacatggc gaccgtgacg cagacggagt gcgggtgacg  12120
gagatgttct cctcgtccgg ccagtgtctg tgtctgctgg aacgcttcgg aaagtagatg  12180
caacaaatgt cgtatcctgt ttgagggatt gatttttggg gggggggggg gcgaaagtgg  12240
ggaaagaaaa tgtaaaaaag aacaaattat ttattgttta tagacaagtg caatgctgtt  12300
aagaggatag tagactcaat gtctttccat caaatacggt tagaaattgt tcattctatg  12360
```

gagattgcac gacgccacga gtttgatttt accttttgat gtttgtcaca aacagcacta 12420
ggtactgtaa ttttgaggtg atgcaaataa attttgaacc atcctgctga acacaaattt 12480
attagacgta tttcgacgtt tggtgagctc gtttccatac ttgcctatct tacgttactt 12540
caatgaacaa ctaaatacac atttgtatgc gcttatcccc taaagacggg tgataatgtc 12600
aactgtttag ctaatttcca aaacaatcaa accttgatac gagataactg actttgcatc 12660
tctcaaacta cgattaatag aaagctatag caaattatgt acttagatag cattggaaag 12720
atgacgcttt ccgctacctc ataacgccat tggctttatc tatatgactg ttcatagctg 12780
gagagatgga tttgaaggtc taattctaag ttatcgcata tcaaggtatc gttgtgctgg 12840
aaaatctgat ctgacagtat cgaaatagcg caactctttg tacccaataa tggaaagttc 12900
tgatttattg tatttataaa aacgttgtct atttgttccg atttcaggtc gtcaaatcac 12960
ttgctagtaa ataacgtctc catagcaatt atcattatta tatactaaat gaaacgagct 13020
caccaattag atagtttcaa acagttatac agttgcttca aacaacatac atacatgcct 13080
tgataagtac cgtgcgccaa atcgagctcg caacatgagt atgaaaagcc actagtaaca 13140
cattgataat cagcatagaa tttaaaataa aataatattt tatactgtgg atatcttcat 13200
aacactgcac gctgatataa aattcagaac tacaaaagga tcgttgaaat tttacgtaac 13260
tcaacagagt aagggagggg gtcttccgaa atgctacggt ctatacacaa aatttaaatt 13320
tttcacacaa aagccgttac gtggaggagg gaggggttct aaaattggca aactttgcgt 13380
cacgtaatat ttgaatcatc ccaaagaaaa taaacttcta tgctgattat aacgcgcgca 13440
gaacaatggt tgcggtgaga gacattaaca ggcttgtttg tggtgctgaa atagaacttg 13500
tcatcaatat gttttagctg gttaaactat acaatcatta cgtagcctga aaatcaccct 13560
tgaaaaggcc gaatatatga cgaaaagaca cactctccaa ctcaaaaggc aaactcaacg 13620
tggtcgtgca caacctccaa tagcagtacc tgtcggagcc gtttggcaac ggccagctac 13680
caaaatacgc tcgcaatggc atgcaagcta cagagagata agtgtttatc agatcatttt 13740
gggcaccgaa accgaccgat gtcggaaacg attgaagaga tataatctct ggtttgtaga 13800
ttgtaggatg gttggttgaa gatccggttt cccggatttt ttcggatgga tgttgcttgt 13860
tgatgattct gctgtcgtcg ttttttttccg gtggcagatg gaacagcctc acttcggctt 13920
tcgaaacaca atcttaaaag ttaagtacta ctgctgtttt gcattttttta aattttccct 13980
ctaaacttgc tttgcactat tggtttcata gccgccgtac tcatcgatgc ccagggcgtc 14040
ggtgaacatc tgctcgaact cgaaatcggc catatccagg gcgccgtagg gggcgctatc 14100
gtgcggggtg aatcccggtc ccgggctatc gccatcgccc agcatgtcca ggtcgaagtc 14160
gtccagggca tcggcgtggg ccatcgccac atcctcgcca tccaggtgca gctcatcgcc 14220
caggctcacg tcggtcggcg gggcggtcga caggcggcgg gtgtgtccgg ccggcaggaa 14280
gctcaggcgc ggggcggcca ggcccgcctc ctccggggca tcatcatccg gcagatccag 14340
caggccctcg atggtgctgc cgtagttgtt cttggtgcgg gcgcggctgt aggcggggcc 14400
cgagcccgac tcgcatttca gttgcttttc caatccgcag ataatcagct ccaagccgaa 14460
caggaatgcc ggctcggctc cttgatgatc gaacagctcg attgcctgac gcagcagtgg 14520
gggcatcgaa tcggttgttg gggtctcgcg ctcctctttt gcgacttgat gctcttggtc 14580
ctccagcacg cagcccaggg taaagtgacc gacggcgctc agagcgtaga gagcattttc 14640
caggctgaag ccttgctggc acaggaacgc gagctggttc tccagtgtct cgtattgctt 14700
ttcggtcggg cgcgtgccga gatggacttt ggcaccgtct cggtgggaca gcagagcgca 14760

```
gcggaacgac ttggcgttat tgcggaggaa gtcctgccag gactcgcctt ccaacgggca  14820
aaaatgcgtg tggtggcggt cgagcatctc gatggccagg gcatccagca gcgcccgctt  14880
attcttcacg tgccagtaga gggtgggctg ctccacgccc agcttctgcg ccaacttgcg  14940
ggtcgtcagt ccctcaatgc caacttcgtt caacagctcc aacgcggagt tgatgacttt  15000
ggacttatcc aggcggctgc ccatggtcac ttgtttgcac tttcacactc tttaggaacg  15060
ctgtctcaca agtagagcta cacgtggtag ccccagaatg gctgtatgtc gctattatcg  15120
ttaaacagta tttgcactgt ggtcattatg ttgtttgtat tagagttcgt cgcgttcgtg  15180
gaattgggaa ggagaagata cagaattact caaatgaaac cattccacgg gagaatacat  15240
ttcaggttta atcttattct tctaggacga aagcccatcg acagagtctt gcaggcttcc  15300
gtcgatcgac tttcacccgt ggatgctaag gaagcttata atgacctcaa cattctccgc  15360
gcacaggttg gctctattct gtttcacagt ttccggtgca gttgtgacga actcagacga  15420
atacccacga ttgtatgtcc aacctcattt tttatctttg taaactaacg tcgaaaaatc  15480
tagatactac atttctgctt tgcttcatct tacactaatc actagtttga acttgcgggt  15540
tttccgttat gctttgtaaa tatgcgatgc tttagagttt tcttcgttcc gattcttctt  15600
tgcattcgat tgcttcttcc gtcgaatcga tctgatcttc gtggtttatt cttgtttcgg  15660
ttcgaccttt gccgcagcgc agtgggtcgt gctgatcgtg taaaaagtct atcatccgga  15720
ctggcgcgtc gtactgcgca actctacacc gtcgaacatg ttcagattgt gcaatcgtga  15780
gtattcattg accacggctt gacctgcgag gcagagaaga acagttggat ttttcggata  15840
ttggtacgac ccgggggccg cgttgtcatc agttgcatga atcgttggtc caagttcgac  15900
gaaacgatat ggacatcggt gtttcggtgg accaagatcg acgacacgat cttggtcatg  15960
agtgtttttc ggtggaccta gagatattgc aacgaccgga gtggaatacg acggtacgat  16020
gttggtttgt actgttctgg acgctagtta cttcattgat acgataaagt ttacattcgt  16080
catatctctt gcttttcttg aatccaaatg cttaggacgt gtaaccttca caaaccgtca  16140
taaatcagtt tcgattcact acatgttgta gttattcagg ctcttataat tgaatattca  16200
aaaatcgaat tttctatttt atcttgatca gaggatataa ctcgcttaaa atgcacaatt  16260
ttattagcga caccatgtgg atttgtttta attgaaacct ctatcttctc atatgtatca  16320
cgatataaaa tgctcatttt attgactgtt taacgataaa cttgcgacga tcgacgcacc  16380
accgacctaa ttccattgtg gaagcaaggg gcactgcaat accgaaatgt gaagtaaatt  16440
tcaaatctgc tattatagac gatgatctaa tactcttgaa tggtcttaaa cgtgagttgt  16500
atttcaagaa gttatgacga ttcgattttg gggccattat gaccccaaaa cccagccaac  16560
gtaactttta ttagtacaga cagaaggtca agcgtgcaag tctttcatcc gtgtgtcaat  16620
aaggccatca gttgaaaccg tgtcaattaa ccctccagtt aaccctttta acttttacca  16680
ggacaaacca atgacttcgt gcgcaaattc caccactcgt tgtctcaggc cttgagttgt  16740
tgtttgataa gaatgggggga tgtcaagtcg gggagcgtag cccaacaggc tacggaaact  16800
gcatgatggc agtgtttgat ccagggcact gttgggaata gactccgtcg accgaagatc  16860
ccagatgtcc tgaaactcaa taataagcgt tagcagttac aaaatgggag cacccaggaa  16920
gtgagtgaca cccgatcgat acctcggaaa cagtcccaac cggtaagaac ccccatacct  16980
tcgtcaatcc gttggcgcgc tttattgacg tctccgtcgg cgcctttcag tatcacgtac  17040
gtcaggggcg tcgtctccca ggggtatcgc agcttctcca ggagccgttg agatcgtttg  17100
```

acaagttcgt cgtggtacct ggcctgaatc tcaacttgca cctgaaggta gtgcagcaag 17160
gatgagcaaa agggaagaac ccagaaaaga acgggaaaac ttaccccaat tagaattggc 17220
tagcgcagat tgtttagctt gttcagctgc gcttgtttat ttgcttagct ttcgcttagc 17280
gacgtgttca ctttgcttgt ttgaattgaa ttgtcgctcc gtagacgaag cgcctctatt 17340
tatactccgg cgctcgtttt cgagtttacc actccctatc agtgatagag aaaagtgaaa 17400
gtcgagttta ccactcccta tcagtgatag agaaaagtga aagtcgagtt taccactccc 17460
tatcagtgat agagaaaagt gaaagtcgag tttaccactc cctatcagtg atagagaaaa 17520
gtgaaagtcg agtttaccac tccctatcag tgatagagaa aagtgaaagt cgagtttacc 17580
actccctatc agtgatagag aaaagtgaaa gtcgagttta ccactcccta tcagtgatag 17640
agaaaagtga aagtcgaaac ctggcgcgcc ccggccatcg agaaagagag agagaagaga 17700
agagagagaa cattcgagaa agagagagag aagagaagag agagaacata ctccctatca 17760
gtgatagaga agtccctatc agtgatagag atgtccctat cagtgataga gagttcccta 17820
tcagtgatag agacgtccct atcagtgata gagaagtccc tatcagtgat agagagatcc 17880
ctatcagtga tagagatttc cctatcagtg atagagaggt ccctatcagt gatagagact 17940
tccctatcag tgatagagaa atccctatca gtgatagaga catccctatc agtgatagag 18000
aactccctat cagtgataga gacctcccta tcagtgatag agatcgatgc ggccgcggcg 18060
gatgcgatcg cgg 18073

<210> SEQ ID NO 158
<211> LENGTH: 13293
<212> TYPE: DNA
<213> ORGANISM: artificial
<220> FEATURE:
<223> OTHER INFORMATION: LA3054 plasmid sequence

<400> SEQUENCE: 158
gggcgccgtt tttcttgaaa tattgctctc tctttctaaa tagcgcgaat ccgtcgctgt 60
gcatttagga catctcagtc gccgcttgga gctcccaaac gcgccagtgg tagtacacag 120
tactgtgggt gttcagtttg aaatcctctt gcttctccat tgtctcggtt acctttggtc 180
aaatccatgg gttctattgc ctatatactc ttgcgattac cagtgattgc gctattagct 240
attagatgga ttgttggcca aacttgtcgc ttaagtggct gggaattgta accgtaggcc 300
cgagtgtaat gatcccccat aaaaagtttt cgcaatgcct ttattttttg ttgcaaatct 360
ctctttattc tgcggtattc ttcattattg cggggatggg gaaagtgttt atatagaagc 420
aacttacgat tgaacccaaa tgcacctgac aagcaaggtc aaagggccag atttttaaat 480
atattattta gtcttaggac tctctatttg caattaaatt actttgctac ctgagggtta 540
aatcttcccc attgataata ataattccac tatatgttca attgggtttc accgcgctta 600
gttacatgac gagccctaat gagccgtcgg tggtctataa actgtgcctt acaaatactt 660
gcaactcttc tcgttttgaa gtcagcagag ttattgctaa ttgctaattg ctaattgctt 720
ttaactgatt tcttcgaaat tggtgctatg tttatggcgc tattaacaag tatgaatgtc 780
aggtttaacc aggggatgct taattgtgtt ctcaacttca aaggcagaaa tgtttactct 840
tgaccatggg tttaggtata atgttatcaa gctcctcgac gcgcctctta ctagaactac 900
ccaccgtact cgtcaattcc aagggcatcg gtaaacatct gctcaaactc gaagtcggcc 960
atatccagag cgccgtaggg ggcggagtcg tggggggtaa atcccggacc cggggaatcc 1020
ccgtccccca acatgtccag atcgaaatcg tctagcgcgt cggcatgcgc catcgccacg 1080

-continued

```
tcctcgccgt ctaagtggag ctcgtccccc aggctgacat cggtcggggg ggccgtcgac   1140
agtctgcgcg tgtgtcccgc ggggagaaag gacaggcgcg gagccgccag ccccgcctct   1200
tcgggggcgt cgtcgtccgg gagatcgagc aggccctcga tggtagaccc gtaattgttt   1260
ttcgtacgcg cgcggctgta cgcggggccc gagcccgact cgcatttcag ttgcttttcc   1320
aatccgcaga taatcagctc caagccgaac aggaatgccg gctcggctcc ttgatgatcg   1380
aacagctcga ttgcctgacg cagcagtggg ggcatcgaat cggttgttgg ggtctcgcgc   1440
tcctcttttg cgacttgatg ctcttggtcc tccagcacgc agcccagggt aaagtgaccg   1500
acggcgctca gagcgtagag agcattttcc aggctgaagc cttgctggca caggaacgcg   1560
agctggttct ccagtgtctc gtattgcttt tcggtcgggc gcgtgccgag atggactttg   1620
gcaccgtctc ggtgggacag cagagcgcag cggaacgact tggcgttatt gcggaggaag   1680
tcctgccagg actcgccttc caacgggcaa aaatgcgtgt ggtggcggtc gagcatctcg   1740
atggccaggg catccagcag cgcccgctta ttcttcacgt gccagtagag ggtgggctgc   1800
tccacgccca gcttctgcgc caacttgcgg gtcgtcagtc cctcaatgcc aacttcgttc   1860
aacagctcca acgcggagtt gatgactttg gacttatcca ggcggctgcc accacggaga   1920
cgaaggacca agtgaagggt ggactccttc tggatgttgt aatcggacag ggtgcgtcca   1980
tcctcaagct gcttgccggc gaagatcaga cgctgctgat ctggggggat tccctcctta   2040
tcctgaatct tggccttcac attctcaatg gtgtccgaag gctctacctc gagggtgatg   2100
gtctttccgg tcaaagtctt cacgaaaatc tgcatcgagc tagccagagg ctttgagcct   2160
tcacctatag ataccataga tgtatggatt agtatcatat acatacaaag gctatttttg   2220
ggacatatta atattaacaa tttccgtgat agttttcacc atttttgttg aatgttacgt   2280
tgaaaattta aatttgtttt aaattaattt taccagtcat gtgttcttaa aagtttttat   2340
gattgaaacg gcataaagtg gttcaaaaat ttatcaagaa aggctttcct tttttaaatc   2400
ttatcttttt ctcttaaaaa tcactagtca attcattatt aatttgttaa cttgaatttg   2460
gaatgtctat ttactttcag ataaattaaa gcaagaaact taatattcga aaaaaattga   2520
ttctaaatgg aatttcactt gatcttcatg tatgcatatc aatttttatt tacattgtat   2580
aataagtttc gagttgattg ttgtaatcca caggtgtccc agagaattaa attccaaatt   2640
acccaagttt attgaatgtt gattgtagtt tcagttgctt tgttgctgca acaatggctt   2700
gttgattgta gatattttcc ctttccttgg tttacttatt acatagactg aaaaagaggt   2760
ttactttttt gatacttatg aaaaatttct attagtgatt actaaccaat cgctatatgt   2820
ttactagaaa acaaataaac tctttacatt aacattcaat aatgtttgct ctgtaaccga   2880
caattgaagg cgttacagca acagtaatat aactagcttc ttaaccctca tctattaacc   2940
ccatcgttta aaacactatg ttaaatggtc taacaaatct agatactaat agatgtctta   3000
ttacttagca gccacagctg caacatccaa gacaattttt gaaacttctt attgagctct   3060
tggcagcaga aatgttggta tttttcacag ctttctgaaa gaccggcacc ttcctccggt   3120
tcccgtttct gaattcaaga ggatttccga cccccaatta atcccgaaac aaataaggta   3180
tattcaaaat gatggaaaag tcatggctgc tgaccttatt tttattccta ttgatagaat   3240
attattcccc ttttaaatac actgtactaa gaggtccggc tataatttta ctcacttgtc   3300
gattatccca tagaatgttg attgtagttg gttgcttttc caggtgagag ttgatcaagt   3360
cacaaaagtt agcgtgtgtt gattgtagat ttgaaggtaa aataattttt gcacccattc   3420
```

```
atcgggtaaa acgttctcca tagaatacat ttccatcgat aattgataac ttatgaattt   3480
caaagaaaaa aatatgcttt taaaattacc aaatctacgt ttaataacaa cagatctcag   3540
gaacaggtgg tggcggccct cggtgcgctc gtactgctcc acgatggtgt agtcctcgtt   3600
gtgggaggtg atgtccagct tggcgtccac gtagtagtag ccgggcagct gcacgggctt   3660
cttggccatg tagatggact tgaactccac caggtagtgg ccgccgtcct tcagcttcag   3720
ggccttgtgg gtctcgccct tcagcacgcc gtcgcggggg tacaggcgct cggtggaggc   3780
ctcccagccc atggtcttct tctgcatcac ggggccgtcg gaggggaagt tcacgccgat   3840
gaacttcacc ttgtagatga agcagccgtc ctgcagggag gagtcctggg tcacggtcgc   3900
cacgccgccg tcctcgaagt tcatcacgcg ctcccacttg aagccctcgg ggaaggacag   3960
cttcttgtag tcggggatgt cggcggggtg cttcacgtac accttggagc cgtactggaa   4020
ctggggggac aggatgtccc aggcgaaggg cagggggccg cccttggtca ccttcagctt   4080
cacggtgttg tggccctcgt aggggcggcc ctcgccctcg ccctcgatct cgaactcgtg   4140
gccgttcacg gtgccctcca tgcgcacctt gaagcgcatg aactcggtga tgacgttctc   4200
ggaggaggcc atggtggcga ccggtttgcg cttcttcttg ggtggggtgg gatccaccag   4260
agacaggttg cggcggcggt tggatggcgt gggcgcgttg gcgttgttgg accggctcat   4320
gttgtgtcgc tgtaacagat gctgttcaac tgtgtttacc agatcgttgc gggctgtatt   4380
tataggcgcg ataagcggga cgggcgcctc gtgtccggtc acgcgcatga gataacgcgc   4440
ggctgatatg gaggcgcgtc ctgttccgat aaggagttgc gtccggctgc ggttagcaac   4500
acaggaagct ggcgtcctgt cacgataaga caacactcgt ccggtccgat aatgtgattc   4560
gtacgtgaca ggacgcgacc cgataaggcc ggcctacgtg actgccgaca cgtacttttt   4620
tgcactgcaa aaaggttcaa tgtgtggtag tgtatttgga gcgtatacaa cggtgtagac   4680
tatttatgta aaatagtcta cgaaacgtag agtttgtact atgtatgggc ccgcgtgcaa   4740
aagcgtgttt ttttgcagtg caaaaaagtt ggtggtgggg aggccaccga gtatggtacc   4800
gcagattgtt tagcttgttc agctgcgctt gtttatttgc ttagctttcg cttagcgacg   4860
tgttcacttt gcttgtttga attgaattgt cgctccgtag acgaagcgcc tctatttata   4920
ctccggcgct cgttttcgag tttaccactc cctatcagtg atagagaaaa gtgaaagtcg   4980
agtttaccac tccctatcag tgatagagaa aagtgaaagt cgagtttacc actccctatc   5040
agtgatagag aaaagtgaaa gtcgagttta ccactcccta tcagtgatag agaaaagtga   5100
aagtcgagtt taccactccc tatcagtgat agagaaaagt gaaagtcgag tttaccactc   5160
cctatcagtg atagagaaaa gtgaaagtcg agtttaccac tccctatcag tgatagagaa   5220
aagtgaaagt cgaaacctgg cgcgccccgg ccatcgagaa agagagagag aagagaagag   5280
agagaacatt cgagaaagag agagagaaga gaagagagag aacatactcc ctatcagtga   5340
tagagaagtc cctatcagtg atagagatgt ccctatcagt gatagagagt tccctatcag   5400
tgatagagac gtccctatca gtgatagaga agtccctatc agtgatagag agatccctat   5460
cagtgataga gatttcccta tcagtgatag agaggtccct atcagtgata gagacttccc   5520
tatcagtgat agagaaatcc ctatcagtga tagagacatc cctatcagtg atagagaact   5580
ccctatcagt gatagagacc tccctatcag tgatagagat cgatgcggcc gcatggtacc   5640
cattgcttgt catttattaa tttggatgat gtcatttgtt tttaaaattg aactggcttt   5700
acgagtagaa ttctacgcgt aaaacacaat caagtatgag tcataatctg atgtcatgtt   5760
ttgtacacgg ctcataaccg aactggcttt acgagtagaa ttctacttgt aatgcacgat   5820
```

-continued

```
cagtggatga tgtcatttgt ttttcaaatc gagatgatgt catgttttgc acacggctca   5880
taaactcgct ttacgagtag aattctacgt gtaacgcacg atcgattgat gagtcatttg   5940
ttttgcaata tgatatcata caatatgact catttgtttt tcaaaaccga acttgattta   6000
cgggtagaat tctacttgta aagcacaatc aaaaagatga tgtcatttgt ttttcaaaac   6060
tgaactcgct ttacgagtag aattctacgt gtaaaacaca atcaagaaat gatgtcattt   6120
gttataaaaa taaaagctga tgtcatgttt tgcacatggc tcataactaa actcgcttta   6180
cgggtagaat tctacgcgta aaacatgatt gataattaaa taattcattt gcaagctata   6240
cgttaaatca aacggacgct cgaggttgca caacactatt atcgatttgc agttcgggac   6300
ataaatgttt aaatatatcg atgtctttgt gatgcgcgcg acatttttgt aggttattga   6360
taaaatgaac ggatacgttg cccgacatta tcattaaatc cttggcgtag aatttgtcgg   6420
gtccattgtc cgtgtgcgct agcatgcccg taacggacct cgtacttttg gcttcaaagg   6480
ttttgcgcac agacaaaatg tgccacactt gcagctctgc atgtgtgcgc gttaccacaa   6540
atcccaacgg cgcagtgtac ttgttgtatg caaataaatc tcgataaagg cgcggcgcgc   6600
gaatgcagct gatcacgtac gctcctcgtg ttccgttcaa ggacggtgtt atcgacctca   6660
gattaatgtt tatcggccga ctgttttcgt atccgctcac caaacgcgtt tttgcattaa   6720
cattgtatgt cggcggatgt tctatatcta atttgaataa ataaacgata accgcgttgg   6780
ttttagaggg cataataaaa gaaatattgt tatcgtgttc gccattaggg cagtataaat   6840
tgacgttcat gttggatatt gtttcagttg caagttgaca ctggcggcga caagcaattc   6900
taattggggt aagttttccc gttcttttct gggttcttcc cttttgctca tccttgctgc   6960
actaccttca ggtgcaagtt gagattcagg ccaccatggg agatcccacc ccacccaaga   7020
agaagcgcaa accggtcgcc accatggcct cctccgagaa cgtcatcacc gagttcatgc   7080
gcttcaaggt gcgcatggag ggcaccgtga acggccacga gttcgagatc gagggcgagg   7140
gcgagggccg cccctacgag ggccacaaca ccgtgaagct gaaggtgacc aagggcggcc   7200
ccctgccctt cgcctgggac atcctgtccc cccagttcca gtacggctcc aaggtgtacg   7260
tgaagcaccc cgccgacatc cccgactaca agaagctgtc cttccccgag ggcttcaagt   7320
gggagcgcgt gatgaacttc gaggacggcg gcgtggcgac cgtgacccag gactcctccc   7380
tgcaggacgg ctgcttcatc tacaaggtga agttcatcgg cgtgaacttc ccctccgacg   7440
gccccgtgat gcagaagaag accatgggct gggaggcctc caccgagcgc ctgtaccccc   7500
gcgacggcgt gctgaagggc gagacccaca aggccctgaa gctgaaggac ggcggccact   7560
acctggtgga gttcaagtcc atctacatgg ccaagaagcc cgtgcagctg cccggctact   7620
actacgtgga cgccaagctg gacatcacct cccacaacga ggactacacc atcgtggagc   7680
agtacgagcg caccgagggc cgccaccacc tgttcctgag atctcgaccc aagaaaaagc   7740
ggaaggtgga ggacccgtaa gatccaccgg atctagataa ctgatcataa tcagccatac   7800
cacatttgta gaggttttac ttgctttaaa aaacctccca cacctccccc tgaacctgaa   7860
acataaaatg aatgcaattg ttgttgttaa cttgtttatt gcagcttata atggttacaa   7920
ataaagcaat agcatcacaa atttcacaaa taaagcattt ttttcactgc attctagttg   7980
tggtttgtcc aaactcatca atgtatctta acgcgagtta attaaggccg ctcatttaaa   8040
tctggccggc cgcaaccatt gtgggaaccg tgcgatcaaa caaacgcgag ataccggaag   8100
tactgaaaaa cagtcgctcc aggccagtgg gaacatcgat gttttgtttt gacggacccc   8160
```

```
ttactctcgt ctcatataaa ccgaagccag ctaagatggt atacttatta tcatcttgtg   8220
atgaggatgc ttctatcaac gaaagtaccg gtaaaccgca aatggttatg tattataatc   8280
aaactaaagg cggagtggac acgctagacc aaatgtgttc tgtgatgacc tgcagtagga   8340
agacgaatag gtggcctatg gcattattgt acggaatgat aaacattgcc tgcataaatt   8400
cttttattat atacagccat aatgtcagta gcaagggaga aaaggtccaa agtcgcaaaa   8460
aatttatgag aaacctttac atgagcctga cgtcatcgtt tatgcgtaag cgtttagaag   8520
ctcctacttt gaagagatat ttgcgcgata atatctctaa tattttgcca aatgaagtgc   8580
ctggtacatc agatgacagt actgaagagc cagtaatgaa aaaacgtact tactgtactt   8640
actgcccctc taaaataagg cgaaaggcaa atgcatcgtg caaaaaatgc aaaaaagtta   8700
tttgtcgaga gcataatatt gatatgtgcc aaagttgttt ctgactgact aataagtata   8760
atttgtttct attatgtata agttaagcta attacttatt ttataataca acatgactgt   8820
ttttaaagta caaaataagt ttatttttgt aaaagagaga atgtttaaaa gttttgttac   8880
tttatagaag aaattttgag tttttgtttt tttttaataa ataaataaac ataaataaat   8940
tgtttgttga atttattatt agtatgtaag tgtaaatata ataaaactta atatctattc   9000
aaattaataa ataaacctcg atatacagac cgataaaaca catgcgtcaa ttttacgcat   9060
gattatcttt aacgtacgtc acaatatgat tatctttcta gggttaaata atagtttcta   9120
attttttat tattcagcct gctgtcgtga ataccgtata tctcaacgct gtctgtgaga   9180
ttgtcgtatt ctagcctttt tagtttttcg ctcatcgact tgatattgtc cgacacattt   9240
tcgtcgattt gcgttttgat caaagacttg agcagagaca cgttaatcaa ctgttcaaat   9300
tgatccatat taacgatatc aacccgatgc gtatatggtg cgtaaaatat atttttaac   9360
cctcttatac tttgcactct gcgttaatac gcgttcgtgt acagacgtaa tcatgttttc   9420
tttttggat aaaactccta ctgagtttga cctcatatta gaccctcaca agttgcaaaa   9480
cgtggcattt tttaccaatg aagaatttaa agttatttta aaaaatttca tcacagattt   9540
aaagaagaac caaaaattaa attatttcaa cagtttaatc gaccagttaa tcaacgtgta   9600
cacagacgcg tcggcaaaaa acacgcagcc cgacgtgttg gctaaaatta ttaaatcaac   9660
ttgtgttata gtcacggatt tgccgtccaa cgtgttcctc aaaaagttga agaccaacaa   9720
gtttacggac actattaatt atttgatttt gccccacttc attttgtggg atcacaattt   9780
tgttatattt taaacaaagc ttggcactgg ccgtcgtttt acaacgtcgt gactgggaaa   9840
accctggcgt tacccaactt aatcgccttg cagcacatcc ccctttcgcc agctggcgta   9900
atagcgaaga ggcccgcacc gatcgccctt cccaacagtt gcgcagcctg aatggcgaat   9960
ggcgcctgat gcggtatttt ctccttacgc atctgtgcgg tatttcacac cgcatatggt  10020
gcactctcag tacaatctgc tctgatgccg catagttaag ccagccccga cacccgccaa  10080
cacccgctga cgcgccctga cgggcttgtc tgctcccggc atccgcttac agacaagctg  10140
tgaccgtctc cgggagctgc atgtgtcaga ggttttcacc gtcatcaccg aaacgcgcga  10200
gacgaaaggg cctcgtgata cgcctatttt tataggttaa tgtcatgata ataatggttt  10260
cttagacgtc aggtggcact tttcggggaa atgtgcgcgg aacccctatt tgtttatttt  10320
tctaaataca ttcaaatatg tatccgctca tgagacaata accctgataa atgcttcaat  10380
aatattgaaa aaggaagagt atgagtattc aacatttccg tgtcgccctt attccctttt  10440
ttgcggcatt ttgccttcct gtttttgctc acccagaaac gctggtgaaa gtaaaagatg  10500
ctgaagatca gttgggtgca cgagtgggtt acatcgaact ggatctcaac agcggtaaga  10560
```

tccttgagag ttttcgcccc gaagaacgtt ttccaatgat gagcactttt aaagttctgc 10620
tatgtggcgc ggtattatcc cgtattgacg ccgggcaaga gcaactcggt cgccgcatac 10680
actattctca gaatgacttg gttgagtact caccagtcac agaaaagcat cttacggatg 10740
gcatgacagt aagagaatta tgcagtgctg ccataaccat gagtgataac actgcggcca 10800
acttacttct gacaacgatc ggaggaccga aggagctaac cgcttttttg cacaacatgg 10860
gggatcatgt aactcgcctt gatcgttggg aaccggagct gaatgaagcc ataccaaacg 10920
acgagcgtga caccacgatg cctgtagcaa tggcaacaac gttgcgcaaa ctattaactg 10980
gcgaactact tactctagct tcccggcaac aattaataga ctggatggag gcggataaag 11040
ttgcaggacc acttctgcgc tcggcccttc cggctggctg gtttattgct gataaatctg 11100
gagccggtga gcgtgggtct cgcggtatca ttgcagcact ggggccagat ggtaagccct 11160
cccgtatcgt agttatctac acgacgggga gtcaggcaac tatggatgaa cgaaatagac 11220
agatcgctga gataggtgcc tcactgatta agcattggta actgtcagac caagtttact 11280
catatatact ttagattgat ttaaaacttc atttttaatt taaaaggatc taggtgaaga 11340
tcctttttga taatctcatg accaaaatcc cttaacgtga gttttcgttc cactgagcgt 11400
cagaccccgt agaaaagatc aaaggatctt cttgagatcc tttttttctg cgcgtaatct 11460
gctgcttgca aacaaaaaaa ccaccgctac cagcggtggt ttgtttgccg gatcaagagc 11520
taccaactct ttttccgaag gtaactggct tcagcagagc gcagatacca aatactgtcc 11580
ttctagtgta gccgtagtta ggccaccact tcaagaactc tgtagcaccg cctacatacc 11640
tcgctctgct aatcctgtta ccagtggctg ctgccagtgg cgataagtcg tgtcttaccg 11700
ggttggactc aagacgatag ttaccggata aggcgcagcg gtcgggctga acggggggtt 11760
cgtgcacaca gcccagcttg gagcgaacga cctacaccga actgagatac ctacagcgtg 11820
agcattgaga aagcgccacg cttcccgaag ggagaaaggc ggacaggtat ccggtaagcg 11880
gcagggtcgg aacaggagag cgcacgaggg agcttccagg gggaaacgcc tggtatcttt 11940
atagtcctgt cgggtttcgc cacctctgac ttgagcgtcg atttttgtga tgctcgtcag 12000
gggggcggag cctatggaaa aacgccagca acgcggcctt tttacggttc ctggcctttt 12060
gctggccttt tgctcacatg ttctttcctg cgttatcccc tgattctgtg gataaccgta 12120
ttaccgcctt tgagtgagct gataccgctc gccgcagccg aacgaccgag cgcagcgagt 12180
cagtgagcga ggaagcggaa gagcgcccaa tacgcaaacc gcctctcccc gcgcgttggc 12240
cgattcatta atgcagctgg cacgacaggt ttcccgactg gaaagcgggc agtgagcgca 12300
acgcaattaa tgtgagttag ctcactcatt aggcacccca ggctttacac tttatgcttc 12360
cggctcgtat gttgtgtgga attgtgagcg gataacaatt tcacacagga aacagctatg 12420
accatgatta cgaatttcga cctgcaggca tgcaagcttg catgcctgca ggtcgacgct 12480
cgcgcgactt ggtttgccat tctttagcgc gcgtcgcgtc acacagcttg gccacaatgt 12540
ggtttttgtc aaacgaagat tctatgacgt gtttaaagtt taggtcgagt aaagcgcaaa 12600
tctttttaa ccctagaaag atagtctgcg taaaattgac gcatgcattc ttgaaatatt 12660
gctctctctt tctaaatagc gcgaatccgt cgctgtgcat ttaggacatc tcagtcgccg 12720
cttggagctc ccgtgaggcg tgcttgtcaa tgcggtaagt gtcactgatt ttgaactata 12780
acgaccgcgt gagtcaaaat gacgcatgat tatcttttac gtgactttta agatttaact 12840
catacgataa ttatattgtt atttcatgtt ctacttacgt gataacttat tatatatata 12900

```
ttttcttgtt atagatatcg tgactaatat ataataaaat gggtagttct ttagacgatg  12960

agcatatcct ctctgctctt ctgcaaagcg atgacgagct tgttggtgag gattctgaca  13020

gtgaaatatc agatcacgta agtgaagatg acgtccagag cgatacagaa gaagcgttta  13080

tagatgaggt acatgaagtg cagccaacgt caagcggtag tgaaatatta gacgaacaaa  13140

atgttattga acaaccaggt tcttcattgg cttctaacag aatcttgacc ttgccacaga  13200

ggactattag aggtaagaat aaacattgtt ggtcaacttc aaagtccacg aggcgtagcc  13260

gagtctctgc actgaacatt gtcagatcgg ccc                               13293
```

<210> SEQ ID NO 159
<211> LENGTH: 13515
<212> TYPE: DNA
<213> ORGANISM: artificial
<220> FEATURE:
<223> OTHER INFORMATION: LA3056 plasmid sequence

<400> SEQUENCE: 159

```
gggcgccgtt tttcttgaaa tattgctctc tctttctaaa tagcgcgaat ccgtcgctgt     60

gcatttagga catctcagtc gccgcttgga gctcccaaac gcgccagtgg tagtacacag    120

tactgtgggt gttcagtttg aaatcctctt gcttctccat tgtctcggtt acctttggtc    180

aaatccatgg gttctattgc ctatatactc ttgcgattac cagtgattgc gctattagct    240

attagatgga ttgttggcca aacttgtcgc ttaagtggct gggaattgta accgtaggcc    300

cgagtgtaat gatcccccat aaaaagtttt cgcaatgcct ttattttttg ttgcaaatct    360

ctctttattc tgcggtattc ttcattattg cggggatggg gaaagtgttt atatagaagc    420

aacttacgat tgaacccaaa tgcacctgac aagcaaggtc aaagggccag atttttaaat    480

atattattta gtcttaggac tctctatttg caattaaatt actttgctac ctgagggtta    540

aatcttcccc attgataata ataattccac tatatgttca attgggtttc accgcgctta    600

gttacatgac gagccctaat gagccgtcgg tggtctataa actgtgcctt acaaatactt    660

gcaactcttc tcgttttgaa gtcagcagag ttattgctaa ttgctaattg ctaattgctt    720

ttaactgatt tcttcgaaat tggtgctatg tttatggcgc tattaacaag tatgaatgtc    780

aggtttaacc aggggatgct taattgtgtt ctcaacttca aaggcagaaa tgtttactct    840

tgaccatggg tttaggtata atgttatcaa gctcctcgac gcgcctctta ctagaactac    900

ccaccgtact cgtcaattcc aagggcatcg gtaaacatct gctcaaactc gaagtcggcc    960

atatccagag cgccgtaggg ggcggagtcg tgggggggtaa atcccggacc cggggaatcc   1020

ccgtccccca acatgtccag atcgaaatcg tctagcgcgt cggcatgcgc catcgccacg   1080

tcctcgccgt ctaagtggag ctcgtccccc aggctgacat cggtcggggg ggccgtcgac   1140

agtctgcgcg tgtgtcccgc ggggagaaag gacaggcgcg gagccgccag ccccgcctct   1200

tcgggggcgt cgtcgtccgg gagatcgagc aggccctcga tggtagaccc gtaattgttt   1260

ttcgtacgcg cgcggctgta cgcggggccc gagcccgact cgcatttcag ttgcttttcc   1320

aatccgcaga taatcagctc caagccgaac aggaatgccg gctcggctcc ttgatgatcg   1380

aacagctcga ttgcctgacg cagcagtggg ggcatcgaat cggttgttgg ggtctcgcgc   1440

tcctcttttg cgacttgatg ctcttggtcc tccagcacgc agcccagggt aaagtgaccg   1500

acggcgctca gagcgtagag agcattttcc aggctgaagc cttgctggca caggaacgcg   1560

agctggttct ccagtgtctc gtattgcttt tcggtcgggc gcgtgccgag atggactttg   1620

gcaccgtctc ggtgggacag cagagcgcag cggaacgact tggcgttatt gcggaggaag   1680
```

```
tcctgccagg actcgccttc caacgggcaa aaatgcgtgt ggtggcggtc gagcatctcg   1740
atggccaggg catccagcag cgcccgctta ttcttcacgt gccagtagag ggtgggctgc   1800
tccacgccca gcttctgcgc caacttgcgg gtcgtcagtc cctcaatgcc aacttcgttc   1860
aacagctcca acgcggagtt gatgactttg gacttatcca ggcggctgcc accacggaga   1920
cgaaggacca agtgaagggt ggactccttc tggatgttgt aatcggacag ggtgcgtcca   1980
tcctcaagct gcttgccggc gaagatcaga cgctgctgat ctggggggat tccctcctta   2040
tcctgaatct tggccttcac attctcaatg gtgtccgaag gctctacctc gagggtgatg   2100
gtctttccgg tcaaagtctt cacgaaaatc tgcatcgagc tagcaaatcg ttctgggctg   2160
ctggaatcct tttaaaaaaa atgatttttt ttttgctata aagctatgaa gtagttcact   2220
tactgtcgat ttgtgacgct ctttgcgcca ttgatttcaa cctcctcttt actgttgtta   2280
ctccgatctt taggctgtgt ttcaaaatga gcacccacat tacttacaac attatcaggg   2340
tttacaacga tgtcgtcgcg ttgaaacaga ggctttgagc cttcacctat agataccata   2400
gatgtatgga ttagtatcat atacatacaa aggctatttt tgggacatat taatattaac   2460
aatttccgtg atagttttca ccatttttgt tgaatgttac gttgaaaatt taaatttgtt   2520
ttaaattaat tttaccagtc atgtgttctt aaaagttttt atgattgaaa cggcataaag   2580
tggttcaaaa atttatcaag aaaggctttc ctttttaaa tcttatcttt ttctcttaaa   2640
aatcactagt caattcatta ttaatttgtt aacttgaatt tggaatgtct atttactttc   2700
agataaatta aagcaagaaa cttaatattc gaaaaaaatt gattctaaat ggaatttcac   2760
ttgatcttca tgtatgcata tcaattttta tttacattgt ataataagtt tcgagttgat   2820
tgttgtaatc cacaggtgtc ccagagaatt aaattccaaa ttacccaagt ttattgaatg   2880
ttgattgtag tttcagttgc tttgttgctg caacaatggc ttgttgattg tagatatttt   2940
ccctttcctt ggtttactta ttacatagac tgaaaaagag gtttactttt ttgatactta   3000
tgaaaaattt ctattagtga ttactaacca atcgctatat gtttactaga aaacaaataa   3060
actctttaca ttaacattca ataatgtttg ctctgtaacc gacaattgaa ggcgttacag   3120
caacagtaat ataactagct tcttaaccct catctattaa ccccatcgtt taaaacacta   3180
tgttaaatgg tctaacaaat ctagatacta atagatgtct tattacttag cagccacagc   3240
tgcaacatcc aagacaattt ttgaaacttc ttattgagct cttggcagca gaaatgttgg   3300
tatttttcac agctttctga aagaccggca ccttcctccg gttcccgttt ctgaattcaa   3360
gaggatttcc gacccccaat taatcccgaa acaaataagg tatattcaaa atgatggaaa   3420
agtcatggct gctgacctta tttttattcc tattgataga atattattcc ccttttaaat   3480
acactgtact aagaggtccg gctataattt tactcacttg tcgattatcc catagaatgt   3540
tgattgtagt tggttgcttt tccaggtgag agttgatcaa gtcacaaaag ttagcgtgtg   3600
ttgattgtag atttgaaggt aaaataattt ttgcacccat tcatcgggta aaacgttctc   3660
catagaatac atttccatcg ataattgata acttatgaat ttcaaagaaa aaaatatgct   3720
tttaaaatta ccaaatctac gtttaataac aacagatctc aggaacaggt ggtggcggcc   3780
ctcggtgcgc tcgtactgct ccacgatggt gtagtcctcg ttgtgggagg tgatgtccag   3840
cttggcgtcc acgtagtagt agccgggcag ctgcacgggc ttcttggcca tgtagatgga   3900
cttgaactcc accaggtagt ggccgccgtc cttcagcttc agggccttgt gggtctcgcc   3960
cttcagcacg ccgtcgcggg ggtacaggcg ctcggtggag gcctcccagc ccatggtctt   4020
```

-continued

```
cttctgcatc acggggccgt cggaggggaa gttcacgccg atgaacttca ccttgtagat   4080
gaagcagccg tcctgcaggg aggagtcctg ggtcacggtc gccacgccgc cgtcctcgaa   4140
gttcatcacg cgctcccact tgaagccctc ggggaaggac agcttcttgt agtcggggat   4200
gtcggcgggg tgcttcacgt acaccttgga gccgtactgg aactgggggg acaggatgtc   4260
ccaggcgaag ggcagggggc cgcccttggt caccttcagc ttcacggtgt tgtggccctc   4320
gtaggggcgg ccctcgccct cgccctcgat ctcgaactcg tggccgttca cggtgccctc   4380
catgcgcacc ttgaagcgca tgaactcggt gatgacgttc tcggaggagg ccatggtggc   4440
gaccggtttg cgcttcttct tgggtggggt gggatccacc agagacaggt tgcggcggcg   4500
gttggatggc gtgggcgcgt tggcgttgtt ggaccggctc atgttgtgtc gctgtaacag   4560
atgctgttca actgtgttta ccagatcgtt gcgggctgta tttataggcg cgataagcgg   4620
gacgggcgcc tcgtgtccgg tcacgcgcat gagataacgc gcggctgata tggaggcgcg   4680
tcctgttccg ataaggagtt gcgtccggct gcggttagca acacaggaag ctggcgtcct   4740
gtcacgataa gacaacactc gtccggtccg ataatgtgat tcgtacgtga caggacgcga   4800
cccgataagg ccggcctacg tgactgccga cacgtacttt tttgcactgc aaaaaggttc   4860
aatgtgtggt agtgtatttg gagcgtatac aacggtgtag actatttatg taaaatagtc   4920
tacgaaacgt agagtttgta ctatgtatgg gcccgcgtgc aaaagcgtgt ttttttgcag   4980
tgcaaaaaag ttggtggtgg ggaggccacc gagtatggta ccgcagattg tttagcttgt   5040
tcagctgcgc ttgtttattt gcttagcttt cgcttagcga cgtgttcact ttgcttgttt   5100
gaattgaatt gtcgctccgt agacgaagcg cctctattta tactccggcg ctcgttttcg   5160
agtttaccac tccctatcag tgatagagaa aagtgaaagt cgagtttacc actccctatc   5220
agtgatagag aaaagtgaaa gtcgagttta ccactcccta tcagtgatag agaaaagtga   5280
aagtcgagtt taccactccc tatcagtgat agagaaaagt gaaagtcgag tttaccactc   5340
cctatcagtg atagagaaaa gtgaaagtcg agtttaccac tccctatcag tgatagagaa   5400
aagtgaaagt cgagtttacc actccctatc agtgatagag aaaagtgaaa gtcgaaacct   5460
ggcgcgcccc ggccatcgag aaagagagag agaagagaag agagagaaca ttcgagaaag   5520
agagagagaa gagaagagag agaacatact ccctatcagt gatagagaag tccctatcag   5580
tgatagagat gtccctatca gtgatagaga gttccctatc agtgatagag acgtccctat   5640
cagtgataga gaagtcccta tcagtgatag agagatccct atcagtgata gagatttccc   5700
tatcagtgat agagaggtcc ctatcagtga tagagacttc cctatcagtg atagagaaat   5760
ccctatcagt gatagagaca tccctatcag tgatagagaa ctccctatca gtgatagaga   5820
cctccctatc agtgatagag atcgatgcgg ccgcatggta cccattgctt gtcatttatt   5880
aatttggatg atgtcatttg tttttaaaat tgaactggct ttacgagtag aattctacgc   5940
gtaaaacaca atcaagtatg agtcataatc tgatgtcatg ttttgtacac ggctcataac   6000
cgaactggct ttacgagtag aattctactt gtaatgcacg atcagtggat gatgtcattt   6060
gtttttcaaa tcgagatgat gtcatgtttt gcacacggct cataaactcg ctttacgagt   6120
agaattctac gtgtaacgca cgatcgattg atgagtcatt tgttttgcaa tatgatatca   6180
tacaatatga ctcatttgtt tttcaaaacc gaacttgatt tacgggtaga attctacttg   6240
taaagcacaa tcaaaaagat gatgtcattt gtttttcaaa actgaactcg ctttacgagt   6300
agaattctac gtgtaaaaca caatcaagaa atgatgtcat ttgttataaa aataaaagct   6360
gatgtcatgt tttgcacatg gctcataact aaactcgctt tacgggtaga attctacgcg   6420
```

taaaacatga ttgataatta aataattcat ttgcaagcta tacgttaaat caaacggacg 6480
ctcgaggttg cacaacacta ttatcgattt gcagttcggg acataaatgt ttaaatatat 6540
cgatgtcttt gtgatgcgcg cgacattttt gtaggttatt gataaaatga acggatacgt 6600
tgcccgacat tatcattaaa tccttggcgt agaatttgtc gggtccattg tccgtgtgcg 6660
ctagcatgcc cgtaacggac ctcgtacttt tggcttcaaa ggttttgcgc acagacaaaa 6720
tgtgccacac ttgcagctct gcatgtgtgc gcgttaccac aaatcccaac ggcgcagtgt 6780
acttgttgta tgcaaataaa tctcgataaa ggcgcggcgc gcgaatgcag ctgatcacgt 6840
acgctcctcg tgttccgttc aaggacggtg ttatcgacct cagattaatg tttatcggcc 6900
gactgttttc gtatccgctc accaaacgcg tttttgcatt aacattgtat gtcggcggat 6960
gttctatatc taatttgaat aaataaacga taaccgcgtt ggttttagag ggcataataa 7020
aagaaatatt gttatcgtgt tcgccattag ggcagtataa attgacgttc atgttggata 7080
ttgtttcagt tgcaagttga cactggcggc gacaagcaat tctaattggg gtaagttttc 7140
ccgttctttt ctgggttctt cccttttgct catccttgct gcactacctt caggtgcaag 7200
ttgagattca ggccaccatg ggagatccca ccccacccaa gaagaagcgc aaaccggtcg 7260
ccaccatggc ctcctccgag aacgtcatca ccgagttcat gcgcttcaag gtgcgcatgg 7320
agggcaccgt gaacggccac gagttcgaga tcgagggcga gggcgagggc cgcccctacg 7380
agggccacaa caccgtgaag ctgaaggtga ccaagggcgg cccccctgccc ttcgcctggg 7440 acatcctgtc cccccagttc cagtacggct ccaaggtgta cgtgaagcac cccgccgaca 7500
tccccgacta caagaagctg tccttccccg agggcttcaa gtgggagcgc gtgatgaact 7560
tcgaggacgg cggcgtggcg accgtgaccc aggactcctc cctgcaggac ggctgcttca 7620
tctacaaggt gaagttcatc ggcgtgaact tcccctccga cggccccgtg atgcagaaga 7680
agaccatggg ctgggaggcc tccaccgagc gcctgtaccc ccgcgacggc gtgctgaagg 7740
gcgagaccca caaggccctg aagctgaagg acggcggcca ctacctggtg gagttcaagt 7800
ccatctacat ggccaagaag cccgtgcagc tgcccggcta ctactacgtg gacgccaagc 7860
tggacatcac ctcccacaac gaggactaca ccatcgtgga gcagtacgag cgcaccgagg 7920
gccgccacca cctgttcctg agatctcgac ccaagaaaaa gcggaaggtg gaggacccgt 7980
aagatccacc ggatctagat aactgatcat aatcagccat accacatttg tagaggtttt 8040
acttgcttta aaaaacctcc cacacctccc cctgaacctg aaacataaaa tgaatgcaat 8100
tgttgttgtt aacttgttta ttgcagctta taatggttac aaataaagca atagcatcac 8160
aaatttcaca aataaagcat ttttttcact gcattctagt tgtggtttgt ccaaactcat 8220
caatgtatct taacgcgagt taattaaggc cgctcattta aatctggccg gccgcaacca 8280
ttgtgggaac cgtgcgatca aacaaacgcg agataccgga agtactgaaa aacagtcgct 8340
ccaggccagt gggaacatcg atgttttgtt ttgacggacc ccttactctc gtctcatata 8400
aaccgaagcc agctaagatg gtatacttat tatcatcttg tgatgaggat gcttctatca 8460
acgaaagtac cggtaaaccg caaatggtta tgtattataa tcaaactaaa ggcggagtgg 8520
acacgctaga ccaaatgtgt tctgtgatga cctgcagtag gaagacgaat aggtggccta 8580
tggcattatt gtacggaatg ataaacattg cctgcataaa ttcttttatt atatacagcc 8640
ataatgtcag tagcaaggga gaaaaggtcc aaagtcgcaa aaaatttatg agaaaccttt 8700
acatgagcct gacgtcatcg tttatgcgta agcgtttaga agctcctact ttgaagagat 8760

```
atttgcgcga taatatctct aatattttgc caaatgaagt gcctggtaca tcagatgaca   8820
gtactgaaga gccagtaatg aaaaaacgta cttactgtac ttactgcccc tctaaaataa   8880
ggcgaaaggc aaatgcatcg tgcaaaaaat gcaaaaaagt tatttgtcga gagcataata   8940
ttgatatgtg ccaaagttgt ttctgactga ctaataagta taatttgttt ctattatgta   9000
taagttaagc taattactta ttttataata caacatgact gtttttaaag tacaaaataa   9060
gtttattttt gtaaaagaga gaatgtttaa aagttttgtt actttataga agaaattttg   9120
agtttttgtt ttttttaat aaataaataa acataaataa attgtttgtt gaatttatta   9180
ttagtatgta agtgtaaata taataaaact taatatctat tcaaattaat aaataaacct   9240
cgatatacag accgataaaa cacatgcgtc aattttacgc atgattatct ttaacgtacg   9300
tcacaatatg attatctttc tagggttaaa taatagtttc taattttttt attattcagc   9360
ctgctgtcgt gaataccgta tatctcaacg ctgtctgtga gattgtcgta ttctagcctt   9420
tttagttttt cgctcatcga cttgatattg tccgacacat tttcgtcgat ttgcgttttg   9480
atcaaagact tgagcagaga cacgttaatc aactgttcaa attgatccat attaacgata   9540
tcaacccgat gcgtatatgg tgcgtaaaat atatttttta accctcttat actttgcact   9600
ctgcgttaat acgcgttcgt gtacagacgt aatcatgttt tctttttgg ataaaactcc   9660
tactgagttt gacctcatat tagaccctca caagttgcaa aacgtggcat tttttaccaa   9720
tgaagaattt aaagttattt taaaaaattt catcacagat ttaaagaaga accaaaaatt   9780
aaattatttc aacagtttaa tcgaccagtt aatcaacgtg tacacagacg cgtcggcaaa   9840
aaacacgcag cccgacgtgt tggctaaaat tattaaatca acttgtgtta tagtcacgga   9900
tttgccgtcc aacgtgttcc tcaaaaagtt gaagaccaac aagtttacgg acactattaa   9960
ttatttgatt ttgccccact tcattttgtg ggatcacaat tttgttatat tttaaacaaa  10020
gcttggcact ggccgtcgtt ttacaacgtc gtgactggga aaaccctggc gttacccaac  10080
ttaatcgcct tgcagcacat ccccctttcg ccagctggcg taatagcgaa gaggcccgca  10140
ccgatcgccc ttcccaacag ttgcgcagcc tgaatggcga atggcgcctg atgcggtatt  10200
ttctccttac gcatctgtgc ggtatttcac accgcatatg gtgcactctc agtacaatct  10260
gctctgatgc cgcatagtta agccagcccc gacacccgcc aacacccgct gacgcgccct  10320
gacgggcttg tctgctcccg gcatccgctt acagacaagc tgtgaccgtc tccgggagct  10380
gcatgtgtca gaggttttca ccgtcatcac cgaaacgcgc gagacgaaag ggcctcgtga  10440
tacgcctatt tttataggtt aatgtcatga taataatggt ttcttagacg tcaggtggca  10500
cttttcgggg aaatgtgcgc ggaacccta tttgtttatt tttctaaata cattcaaata  10560
tgtatccgct catgagacaa taaccctgat aaatgcttca ataatattga aaaaggaaga  10620
gtatgagtat tcaacatttc cgtgtcgccc ttattccctt ttttgcggca ttttgccttc  10680
ctgtttttgc tcacccagaa acgctggtga aagtaaaaga tgctgaagat cagttgggtg  10740
cacgagtggg ttacatcgaa ctggatctca acagcggtaa gatccttgag agttttcgcc  10800
ccgaagaacg ttttccaatg atgagcactt ttaaagttct gctatgtggc gcggtattat  10860
cccgtattga cgccgggcaa gagcaactcg gtcgccgcat acactattct cagaatgact  10920
tggttgagta ctcaccagtc acagaaaagc atcttacgga tggcatgaca gtaagagaat  10980
tatgcagtgc tgccataacc atgagtgata acactgcggc caacttactt ctgacaacga  11040
tcggaggacc gaaggagcta accgcttttt tgcacaacat gggggatcat gtaactcgcc  11100
ttgatcgttg ggaaccggag ctgaatgaag ccataccaaa cgacgagcgt gacaccacga  11160
```

```
tgcctgtagc aatggcaaca acgttgcgca aactattaac tggcgaacta cttactctag  11220
cttcccggca acaattaata gactggatgg aggcggataa agttgcagga ccacttctgc  11280
gctcggccct tccggctggc tggtttattg ctgataaatc tggagccggt gagcgtgggt  11340
ctcgcggtat cattgcagca ctggggccag atggtaagcc ctcccgtatc gtagttatct  11400
acacgacggg gagtcaggca actatggatg aacgaaatag acagatcgct gagataggtg  11460
cctcactgat taagcattgg taactgtcag accaagttta ctcatatata ctttagattg  11520
atttaaaact tcatttttaa tttaaaagga tctaggtgaa gatccttttt gataatctca  11580
tgaccaaaat cccttaacgt gagttttcgt tccactgagc gtcagacccc gtagaaaaga  11640
tcaaaggatc ttcttgagat cctttttttc tgcgcgtaat ctgctgcttg caaacaaaaa  11700
aaccaccgct accagcggtg gtttgtttgc cggatcaaga gctaccaact ctttttccga  11760
aggtaactgg cttcagcaga gcgcagatac caaatactgt ccttctagtg tagccgtagt  11820
taggccacca cttcaagaac tctgtagcac cgcctacata cctcgctctg ctaatcctgt  11880
taccagtggc tgctgccagt ggcgataagt cgtgtcttac cgggttggac tcaagacgat  11940
agttaccgga taaggcgcag cggtcgggct gaacgggggg ttcgtgcaca cagcccagct  12000
tggagcgaac gacctacacc gaactgagat acctacagcg tgagcattga gaaagcgcca  12060
cgcttcccga agggagaaag gcggacaggt atccggtaag cggcagggtc ggaacaggag  12120
agcgcacgag ggagcttcca gggggaaacg cctggtatct ttatagtcct gtcgggtttc  12180
gccacctctg acttgagcgt cgatttttgt gatgctcgtc aggggggcgg agcctatgga  12240
aaaacgccag caacgcggcc tttttacggt tcctggcctt ttgctggcct tttgctcaca  12300
tgttctttcc tgcgttatcc cctgattctg tggataaccg tattaccgcc tttgagtgag  12360
ctgataccgc tcgccgcagc cgaacgaccg agcgcagcga gtcagtgagc gaggaagcgg  12420
aagagcgccc aatacgcaaa ccgcctctcc ccgcgcgttg gccgattcat taatgcagct  12480
ggcacgacag gtttcccgac tggaaagcgg gcagtgagcg caacgcaatt aatgtgagtt  12540
agctcactca ttaggcaccc caggctttac actttatgct tccggctcgt atgttgtgtg  12600
gaattgtgag cggataacaa tttcacacag gaaacagcta tgaccatgat tacgaatttc  12660
gacctgcagg catgcaagct tgcatgcctg caggtcgacg ctcgcgcgac ttggtttgcc  12720
attctttagc gcgcgtcgcg tcacacagct tggccacaat gtggtttttg tcaaacgaag  12780
attctatgac gtgtttaaag tttaggtcga gtaaagcgca aatctttttt aaccctagaa  12840
agatagtctg cgtaaaattg acgcatgcat tcttgaaata ttgctctctc tttctaaata  12900
gcgcgaatcc gtcgctgtgc atttaggaca tctcagtcgc cgcttggagc tcccgtgagg  12960
cgtgcttgtc aatgcggtaa gtgtcactga ttttgaacta taacgaccgc gtgagtcaaa  13020
atgacgcatg attatctttt acgtgacttt taagatttaa ctcatacgat aattatattg  13080
ttatttcatg ttctacttac gtgataactt attatatata tattttcttg ttatagatat  13140
cgtgactaat atataataaa atgggtagtt ctttagacga tgagcatatc ctctctgctc  13200
ttctgcaaag cgatgacgag cttgttggtg aggattctga cagtgaaata tcagatcacg  13260
taagtgaaga tgacgtccag agcgatacag aagaagcgtt tatagatgag gtacatgaag  13320
tgcagccaac gtcaagcggt agtgaaatat tagacgaaca aaatgttatt gaacaaccag  13380
gttcttcatt ggcttctaac agaatcttga ccttgccaca gaggactatt agaggtaaga  13440
ataaacattg ttggtcaact tcaaagtcca cgaggcgtag ccgagtctct gcactgaaca  13500
```

ttgtcagatc ggccc 13515

<210> SEQ ID NO 160
<211> LENGTH: 9423
<212> TYPE: DNA
<213> ORGANISM: artificial
<220> FEATURE:
<223> OTHER INFORMATION: LA3488 plasmid sequence

<400> SEQUENCE: 160
cggcgcgccg gctttacgag tagaattcta cgcgtaaaac acaatcaagt atgagtcata 60
atctgatgtc atgttttgta cacggctcat aaccgaactg gctttacgag tagaattcta 120
cttgtaatgc acgatcagtg gatgatgtca tttgtttttc aaatcgagat gatgtcatgt 180
tttgcacacg gctcataaac tcgctttacg agtagaattc tacgtgtaac gcacgatcga 240
ttgatgagtc atttgttttg caatatgata tcatacaata tgactcattt gtttttcaaa 300
accgaacttg atttacgggt agaattctac ttgtaaagca caatcaaaaa gatgatgtca 360
tttgtttttc aaaactgaac tcgctttacg agtagaattc tacgtgtaaa acacaatcaa 420
gaaatgatgt catttgttat aaaaataaaa gctgatgtca tgttttgcac atggctcata 480
actaaactcg ctttacgggt agaattctac gcgtaaaaca tgattgataa ttaaataatt 540
catttgcaag ctatacgtta aatcaaacgg acgctcgagg ttgcacaaca ctattatcga 600
tttgcagttc gggacataaa tgtttaaata tatcgatgtc tttgtgatgc gcgcgacatt 660
tttgtaggtt attgataaaa tgaacggata cgttgcccga cattatcatt aaatccttgg 720
cgtagaattt gtcgggtcca ttgtccgtgt gcgctagcat gcccgtaacg gacctcgtac 780
ttttggcttc aaaggttttg cgcacagaca aaatgtgcca cacttgcagc tctgcatgtg 840
tgcgcgttac cacaaatccc aacggcgcag tgtacttgtt gtatgcaaat aaatctcgat 900
aaaggcgcgg cgcgcgaatg cagctgatca cgtacgctcc tcgtgttccg ttcaaggacg 960
gtgttatcga cctcagatta atgtttatcg gccgactgtt ttcgtatccg ctcaccaaac 1020
gcgtttttgc attaacattg tatgtcggcg gatgttctat atctaatttg aataaataaa 1080
cgataaccgc gttggtttta gagggcataa taaaagaaat attgttatcg tgttcgccat 1140
tagggcagta taaattgacg ttcatgttgg atattgtttc agttgcaagt tgacactggc 1200
ggcgacaagc aattctaatt ggggtaagtt ttcccgttct tttctgggtt cttccctttt 1260
gctcatcctt gctgcactac cttcaggtgc aagttgagat tcaggccacc atgggagatc 1320
ccaccccacc caagaagaag cgcaaaccgg tcgccaccat ggagagcgac gagagcggcc 1380
tgcccgccat ggagatcgag tgccgcatca ccggcaccct gaacggcgtg gagttcgagc 1440
tggtgggcgg cggagagggc acccccgagc agggccgcat gaccaacaag atgaagagca 1500
ccaaaggcgc cctgaccttc agcccctacc tgctgagcca cgtgatgggc tacggcttct 1560
accacttcgg cacctacccc agcggctacg agaacccctt cctgcacgcc atcaacaacg 1620
gcggctacac caacacccgc atcgagaagt acgaggacgg cggcgtgctg cacgtgagct 1680
tcagctaccg ctacgaggcc ggccgcgtga tcggcgactt caaggtgatg ggcaccggct 1740
tccccgagga cagcgtgatc ttcaccgaca agatcatccg cagcaacgcc accgtggagc 1800
acctgcaccc catgggcgat aacgatctgg atggcagctt cacccgcacc ttcagcctgc 1860
gcgacggcgg ctactacagc tccgtggtgg acagccacat gcacttcaag agcgccatcc 1920
accccagcat cctgcagaac gggggcccca tgttcgcctt ccgccgcgtg gaggaggatc 1980
acagcaacac cgagctgggc atcgtggagt accagcacgc cttcaagacc ccggatgcag 2040

-continued

```
atgccggtga agaaagatct cgacccaaga aaaagcggaa ggtggaggac ccgtctggag   2100
gcggtggatc cggcggtgga ggcatgcaga tctttgtgaa gactttgacc ggaaagacca   2160
tcaccctcga ggtagagcca tcggacacca ttgagaatgt aaaggccaag attcaggata   2220
aggagggaat ccccccagat cagcagcgtc tgatcttcgc tggtaatttt aaaagcatat   2280
tttttctttt gaaattcata agttatcaat tatcgatgga aatgtattct atggagaacg   2340
ttttacccga tgaatgggtg caaaaattat tttaccttca aatctacaat caacacacgc   2400
taacttttgt gacttgatca actctcacct ggaaaagcaa ccaactacaa tcaacattct   2460
atgggataat cgacaagtga gtaaaattat agccggacct cttagtacag tgtatttaaa   2520
aggggaataa tattctatca ataggaataa aaataaggtc agcagccatg acttttccat   2580
cattttgaat ataccttatt tgtttcggga ttaattgggg gtcggaaatc ctcttgaatt   2640
cagaaacggg aaccggagga aggtgccggt ctttcagaaa gctgtgaaaa ataccaacat   2700
ttctgctgcc aagagctcaa taagaagttt caaaaattgt cttggatgtt gcagctgtgg   2760
ctgctaagta ataagacatc tattagtatc tagatttgtt agaccattta acatagtgtt   2820
ttaaacgatg gggttaatag atgagggtta agaagctagt tatattactg ttgctgtaac   2880
gccttcaatt gtcggttaca gagcaaacat tattgaatgt taatgtaaag agtttatttg   2940
ttttctagta aacatatagc gattggttag taatcactaa tagaaatttt tcataagtat   3000
caaaaaagta aacctctttt tcagtctatg taataagtaa accaaggaaa gggaaaatat   3060
ctacaatcaa caagccattg ttgcagcaac aaagcaactg aaactacaat caacattcaa   3120
taaacttggg taatttggaa tttaattctc tgggacacct gtggattaca acaatcaact   3180
cgaaacttat tatacaatgt aaataaaaat tgatatgcat acatgaagat caagtgaaat   3240
tccatttaga atcaattttt ttcgaatatt aagtttcttg ctttaattta tctgaaagta   3300
aatagacatt ccaaattcaa gttaacaaat taataatgaa ttgactagtg atttttaaga   3360
gaaaaagata agatttaaaa aaggaaagcc tttcttgata aatttttgaa ccactttatg   3420
ccgtttcaat cataaaaact tttaagaaca catgactggt aaaattaatt taaaacaaat   3480
ttaaattttc aacgtaacat tcaacaaaaa tggtgaaaac tatcacggaa attgttaata   3540
ttaatatgtc ccaaaaatag cctttgtatg tatatgatac taatccatac atctatggta   3600
tctataggta agcaactgga agacggacgc accctgtccg attacaacat ccagaaggag   3660
tccacccttc acttggtcct tcgtctccgc ggtggcatgc agatcgggga tcccacccca   3720
cccaagaaga agcgcaaacc ggtcgccacc atggcctcct ccgagaacgt catcaccgag   3780
ttcatgcgct tcaaggtgcg catggagggc accgtgaacg gccacgagtt cgagatcgag   3840
ggcgagggcg agggccgccc ctacgagggc cacaacaccg tgaagctgaa ggtgaccaag   3900
ggcggccccc tgcccttcgc ctgggacatc ctgtcccccc agttccagta cggctccaag   3960
gtgtacgtga agcaccccgc cgacatcccc gactacaaga agctgtcctt ccccgagggc   4020
ttcaagtggg agcgcgtgat gaacttcgag gacggcggcg tggcgaccgt gacccaggac   4080
tcctccctgc aggacggctg cttcatctac aaggtgaagt tcatcggcgt gaacttcccc   4140
tccgacggcc ccgtgatgca gaagaagacc atgggctggg aggcctccac cgagcgcctg   4200
tacccccgcg acggcgtgct gaagggcgag acccacaagg ccctgaagct gaaggacggc   4260
ggccactacc tggtggagtt caagtccatc tacatggcca agaagcccgt gcagctgccc   4320
ggctactact acgtggacgc caagctggac atcacctccc acaacgagga ctacaccatc   4380
```

```
gtggagcagt acgagcgcac cgagggccgc caccacctgt tcctgagatc tcgacccaag   4440
aaaaagcgga aggtggagga cccgtaagat ccaccgggtc tagataactg atcataatca   4500
gccataccac atttgtagag gttttacttg ctttaaaaaa cctcccacac ctccccctga   4560
acctgaaaca taaaatgaat gcaattgttg ttgttaactt gtttattgca gcttataatg   4620
gttacaaata aagcaatagc atcacaaatt tcacaaataa agcatttttt tcactgcatt   4680
ctagttgtgg tttgtccaaa ctcatcaatg tatcttaacg cgagttaatt aagaggcgcg   4740
gtaaaccgca aatggttatg tattataatc aaactaaagg cggagtggac acgctagacc   4800
aaatgtgttc tgtgatgacc tgcagtagga agacgaatag gtggcctatg gcattattgt   4860
acggaatgat aaacattgcc tgcataaatt cttttattat atacagccat aatgtcagta   4920
gcaagggaga aaaggtccaa agtcgcaaaa aatttatgag aaacctttac atgagcctga   4980
cgtcatcgtt tatgcgtaag cgtttagaag ctcctacttt gaagagatat ttgcgcgata   5040
atatctctaa tattttgcca aatgaagtgc ctggtacatc agatgacagt actgaagagc   5100
cagtaatgaa aaaacgtact tactgtactt actgcccctc taaaataagg cgaaaggcaa   5160
atgcatcgtg caaaaaatgc aaaaaagtta tttgtcgaga gcataatatt gatatgtgcc   5220
aaagttgttt ctgactgact aataagtata atttgtttct attatgtata agttaagcta   5280
attacttatt ttataataca acatgactgt ttttaaagta caaaataagt ttatttttgt   5340
aaaagagaga atgtttaaaa gttttgttac tttatagaag aaattttgag tttttgtttt   5400
tttttaataa ataaataaac ataaataaat tgtttgttga atttattatt agtatgtaag   5460
tgtaaatata ataaaactta atatctattc aaattaataa ataaacctcg atatacagac   5520
cgataaaaca catgcgtcaa ttttacgcat gattatcttt aacgtacgtc acaatatgat   5580
tatctttcta gggttaaata atagtttcta attttttat tattcagcct gctgtcgtga   5640
ataccgtata tctcaacgct gtctgtgaga ttgtcgtatt ctagcctttt tagtttttcg   5700
ctcatcgact tgatattgtc cgacacattt tcgtcgattt gcgttttgat caaagacttg   5760
agcagagaca cgttaatcaa ctgttcaaat tgatccatat taacgatatc aacccgatgc   5820
gtatatggtg cgtaaaatat attttttaac cctcttatac tttgcactct gcgttaatac   5880
gcgttcgtgt acagacgtaa tcatgttttc ttttttggat aaaactccta ctgagtttga   5940
cctcatatta gaccctcaca agttgcaaaa cgtggcattt tttaccaatg aagaatttaa   6000
agttatttta aaaaatttca tcacagattt aaagaagaac caaaaattaa attatttcaa   6060
cagtttaatc gaccagttaa tcaacgtgta cacagacgcg tcggcaaaaa acacgcagcc   6120
cgacgtgttg gctaaaatta ttaaatcaac ttgtgttata gtcacggatt tgccgtccaa   6180
cgtgttcctc aaaaagttga agaccaacaa gtttacggac actattaatt atttgatttt   6240
gccccacttc attttgtggg atcacaattt tgttatattt taaacaaagc ttggcactgg   6300
ccgtcgtttt acaacgtcgt gactgggaaa accctggcgt tacccaactt aatcgccttg   6360
cagcacatcc ccctttcgcc agctggcgta atagcgaaga ggcccgcacc gatcgccctt   6420
cccaacagtt gcgcagcctg aatggcgaat ggcgcctgat gcggtatttt ctccttacgc   6480
atctgtgcgg tatttcacac cgcatatatg gtgcactctc agtacaatct gctctgatgc   6540
cgcatagtta agccagcccc gacacccgcc aacacccgct gacgcgccct gacgggcttg   6600
tctgctcccg gcatccgctt acagacaagc tgtgaccgtc tccgggagct gcatgtgtca   6660
gaggttttca ccgtcatcac cgaaacgcgc gagacgaaag ggcctcgtga tacgcctatt   6720
tttataggtt aatgtcatga taataatggt ttcttagacg tcaggtggca cttttcgggg   6780
```

aaatgtgcgc ggaacccta tttgtttatt tttctaaata cattcaaata tgtatccgct 6840
catgagacaa taaccctgat aaatgcttca ataatattga aaaaggaaga gtatgagtat 6900
tcaacatttc cgtgtcgccc ttattccctt ttttgcggca ttttgccttc ctgtttttgc 6960
tcacccagaa acgctggtga aagtaaaaga tgctgaagat cagttgggtg cacgagtggg 7020
ttacatcgaa ctggatctca acagcggtaa gatccttgag agttttcgcc ccgaagaacg 7080
ttttccaatg atgagcactt ttaaagttct gctatgtggc gcggtattat cccgtattga 7140
cgccgggcaa gagcaactcg gtcgccgcat acactattct cagaatgact tggttgagta 7200
ctcaccagtc acagaaaagc atcttacgga tggcatgaca gtaagagaat tatgcagtgc 7260
tgccataacc atgagtgata acactgcggc caacttactt ctgacaacga tcggaggacc 7320
gaaggagcta accgcttttt tgcacaacat gggggatcat gtaactcgcc ttgatcgttg 7380
ggaaccggag ctgaatgaag ccataccaaa cgacgagcgt gacaccacga tgcctgtagc 7440
aatggcaaca acgttgcgca aactattaac tggcgaacta cttactctag cttcccggca 7500
acaattaata gactggatgg aggcggataa agttgcagga ccacttctgc gctcggccct 7560
tccggctggc tggtttattg ctgataaatc tggagccggt gagcgtgggt ctcgcggtat 7620
cattgcagca ctggggccag atggtaagcc ctcccgtatc gtagttatct acacgacggg 7680
gagtcaggca actatggatg aacgaaatag acagatcgct gagataggtg cctcactgat 7740
taagcattgg taactgtcag accaagttta ctcatatata ctttagattg atttaaaact 7800
tcatttttaa tttaaaagga tctaggtgaa gatccttttt gataatctca tgaccaaaat 7860
cccttaacgt gagttttcgt tccactgagc gtcagacccc gtagaaaaga tcaaaggatc 7920
ttcttgagat cctttttttc tgcgcgtaat ctgctgcttg caaacaaaaa aaccaccgct 7980
accagcggtg gtttgtttgc cggatcaaga gctaccaact ctttttccga aggtaactgg 8040
cttcagcaga gcgcagatac caaatactgt ccttctagtg tagccgtagt taggccacca 8100
cttcaagaac tctgtagcac cgcctacata cctcgctctg ctaatcctgt taccagtggc 8160
tgctgccagt ggcgataagt cgtgtcttac cgggttggac tcaagacgat agttaccgga 8220
taaggcgcag cggtcgggct gaacgggggg ttcgtgcaca cagcccagct tggagcgaac 8280
gacctacacc gaactgagat acctacagcg tgagcattga gaaagcgcca cgcttcccga 8340
agggagaaag gcggacaggt atccggtaag cggcagggtc ggaacaggag agcgcacgag 8400
ggagcttcca gggggaaacg cctggtatct ttatagtcct gtcgggtttc gccacctctg 8460
acttgagcgt cgatttttgt gatgctcgtc aggggggcgg agcctatgga aaaacgccag 8520
caacgcggcc tttttacggt tcctggcctt ttgctggcct tttgctcaca tgttctttcc 8580
tgcgttatcc cctgattctg tggataaccg tattaccgcc tttgagtgag ctgataccgc 8640
tcgccgcagc cgaacgaccg agcgcagcga gtcagtgagc gaggaagcgg aagagcgccc 8700
aatacgcaaa ccgcctctcc ccgcgcgttg gccgattcat taatgcagct ggcacgacag 8760
gtttcccgac tggaaagcgg gcagtgagcg caacgcaatt aatgtgagtt agctcactca 8820
ttaggcaccc caggctttac actttatgct tccggctcgt atgttgtgtg gaattgtgag 8880
cggataacaa tttcacacag gaaacagcta tgaccatgat tacgaatttc gacgctcgcg 8940
cgacttggtt tgccattctt tagcgcgcgt cgcgtcacac agcttggcca caatgtggat 9000
gtcgacttaa ccctagaaag atagtctgcg taaaattgac gcatgcattc ttgaaatatt 9060
gctctctctt tctaaatagc gcgaatccgt cgctgtgcat ttaggacatc tcagtcgccg 9120

```
cttggagctc ccgtgaggcg tgcttgtcaa tgcggtaagt gtcactgatt ttgaactata   9180

acgaccgcgt gagtcaaaat gacgcatgat tatcttttac gtgactttta agatttaact   9240

catacgataa ttatattgtt atttcatgtt ctacttacgt gataacttat tatatatata   9300

ttttcttgtt atagatatct accggtcata ctcggtggcc tccccaccac caactttttt   9360

gcactgcaaa aaaacacgct tttgcacgcg ggcccggcgc gccatctgcc ggccgcatgg   9420

tac                                                                 9423
```

<210> SEQ ID NO 161
<211> LENGTH: 17781
<212> TYPE: DNA
<213> ORGANISM: artificial
<220> FEATURE:
<223> OTHER INFORMATION: LA3641plasmid sequence

<400> SEQUENCE: 161

```
ttaaaatgaa tgtaagcact ttattaacga aatctttggg aatatttcgc tcatcagcat     60

tttatttgag caggagtccg agatgccccc ttcccttaag tcaatattac aaacaatgtg    120

gttttccgcc aaccacagtg tggttaaatt ttatcaccga tgatatgaaa tttctagctg    180

caacatgtcc acaagaaata ccataattct catggttgct taacaactgt taattataca    240

tcaggcaaag tattcactgg ttttcttaat atatctggga ataattactt caaggaccgg    300

gttaacaaga taaggtaacc gctctccaac ttaatgtccg tgataaatata caaatatgcg    360

tgttgtaaca cgtatagcac atataaaact aggtaaagtc cggaatagcc cactcgggtc    420

ctctcgggtc gggctcgggt cggcctcggg cctactcggg tttggccgaa gtagatggct    480

cagtgggctc gtgcgccgtc tgtcgcggcg cggtgtgggg ctacaagtgc gctggcggcg    540

gcgagcgcat gagcggcacg ggcaggtgcg gcgcgtactc gcgcgacagc acatagcgcg    600

gcgagcagca aaacgactct ttgcgcgctt gcagctccag cagcgagcac agtgagcgct    660

cgtacagccg ccactggtgc accacccagg aggctggaat taacaagaca ggtttaaata    720

aaaactacac aaaaaacaaa taccctgcct acatgcccac caagcacttc cacgtgacct    780

gggaaaacta gaaagccaat ttgaatgtac attttgatat ctaaattatg taattttgtt    840

attttgtatt aaatatgcat aacacattac aaattataac aaaatgacct tgttgatgtc    900

acaacgtaag aattggccgt cgtatcgcgt tatcacgttt ttcgatttaa atcgaggctt    960

taacgtagrc ttaggtacga aagaagcact ctaagcgaat taccttgacg ctgacgcttg   1020

cagcgttgag cgtaaaaact ataactgagt cacacgaact cgccgcgaaa aagctggcct   1080

aatacaagaa aacagagtga gtagaagttt tgtagtcact ctaatttctt tgtattacaa   1140

tttgtagcaa cgaattgtat tatctatatc cagatataga tatatgttac atgaatattc   1200

ctgtcaaatt gttacagawt gtcatcttaa aattagagcg tagctttgat tgtatggctg   1260

tycgtgtgac tttagagtca aaggaattcg ctcagagagt taagttkyra tgctagcact   1320

agcacttacc atgagatccg atgtgtgaga cacaatgtcc aacgaagctt atttacagga   1380

acagtcaccc cacagtccac aaaacacagc acttgaagaa catagtatca ttcgcaaaac   1440

aacttcatcg atgacgatag cacaccacta aaattattta tttcgctcag cattttccta   1500

caaaagaaaa acaaaataaa aatagtatca cttgcacatc actattaaat aaaatgtggt   1560

cacttttttt aaatttcgaa cttctccacc ttcgtccggt cactgtggaa atgaaatcac   1620

gactgggtta gtgatgttct gattcgtcgg acacaccact cttttatcaa cttagcaaat   1680

ttgtatgtgt gggtgtgtaa caatgttgtt aatgtgttat gacacattgt gttgtgtggg   1740
```

-continued

```
gaccgaactt gcaacgttgt agctccgtac attgtttgta aacggcaggc tacgttacta   1800
tacgtagtac gtaagcgacg taagcgtgac tcaacttctt atcgattaca gcgtctttat   1860
aaatgtaagt tatttataat acagtggaac ctcgataagg cgaaaataaa acgctgtctc   1920
gctccgctca caccagtgag agtgagagtg agagaagaac ctgaactcgc ggcgccttaa   1980
cggtccccag caagctcggt tgtaagtaaa cgatggatgg attgtgtgaa agaggatatg   2040
agaaagaaag gagtgagaag agaggaacat gttgtgccga ccccacataa cgtgggataa   2100
gagcaggagg aagaagagca agctaacgta gttacgctct cattttaaaa cgactagcta   2160
aattgctctg aaactttgta ctaacaatag gattaggcat atcggagtcg cctttaagag   2220
cttattaccc ctccgtcgaa ataccacggc caatagtcat atgtattgtt tggactgacg   2280
tttaactgac atatttgctc ctcccccgta aaatcgttgt acagagaatt acagacaagg   2340
tgtttccagt tgttaaatcc tccaagtcta aggctgtaat tagtttatgt agcctcagat   2400
accaagtata aactaatttc agccctagac atacctcatg tcattgtatg tgcaaagttc   2460
cattacaatc caacacgcag ttttataatg agaacgaaac tccgtttgta tgtgaaattc   2520
agccgagctt accattgcta gttttaggaa taaggggtta aaatttgcaa attcggtcta   2580
agtgtgtgta aaaaacaaag gtcggtttcc gaacagaatt ttggtttctt tttgagtgtt   2640
tctaacggtt ttgagatgat ttaaatggaa ccttactttg agacttgctt aggttgcggt   2700
gggcgttttt catcgccatc cgaaatggag ttagccgccg tattcatcga tgcccagggc   2760
gtcggtgaac atctgctcga actcgaaatc ggccatatcc agggcgccgt agggggcgct   2820
atcgtgcggg gtgaatcccg gtcccgggct atcgccatcg cccagcatgt ccaggtcgaa   2880
gtcgtccagg gcatcggcgt gggccatcgc cacatcctcg ccatccaggt gcagctcatc   2940
gcccaggctc acgtcggtcg gcggggcggt cgacaggcgg cgggtgtgtc cggccggcag   3000
gaagctcagg cgcggggcgg ccaggcccgc ctcctccggg gcatcatcat ccggcagatc   3060
cagcaggccc tcgatggtgc tgccgtagtt gttcttggtg cgggcgcggc tgtaggcggg   3120
gcccgagccc gactcgcatt tcagttgctt ttccaatccg cagataatca gctccaagcc   3180
gaacaggaat gccggctcgg ctccttgatg atcgaacagc tcgattgcct gacgcagcag   3240
tgggggcatc gaatcggttg ttggggtctc gcgctcctct tttgcgactt gatgctcttg   3300
gtcctccagc acgcagccca gggtaaagtg accgacggcg ctcagagcgt agagagcatt   3360
ttccaggctg aagccttgct ggcacaggaa cgcgagctgg ttctccagtg tctcgtattg   3420
cttttcggtc gggcgcgtgc cgagatggac tttggcaccg tctcggtggg acagcagagc   3480
gcagcggaac gacttggcgt tattgcggag gaagtcctgc caggactcgc cttccaacgg   3540
gcaaaaatgc gtgtggtggc ggtcgagcat ctcgatggcc agggcatcca gcagcgcccg   3600
cttattcttc acgtgccagt agagggtggg ctgctccacg cccagcttct gcgccaactt   3660
gcgggtcgtc agtccctcaa tgccaacttc gttcaacagc tccaacgcgg agttgatgac   3720
tttggactta tccaggcggc tgaccatttt gcctggggac aacggaaatc gcacagtttg   3780
aacgttcgct tggcggcgcg gagactgcat tttggagaac acgtacatgt atcgggcgat   3840
aaaaaaaacy ttgtcattgt ttcattatga ccatgacaaa ttaaggtggg ttattttttg   3900
ctacttgaat ttaattgtcg aamagtaaaa aaaaacgatg caactttttt atattgaaat   3960
tgactgatta caaaatgcag ccttgcttta taatagacac aacatacacg gaggaatgga   4020
ctaggaacat ctattttatg taaccttgta cataactaag acctaggtta aaataacgat   4080
```

```
gtgttaatat aatatataga gaacaatata aagcattttg taccatttgg cgttgaaact   4140
tttttgcagc aacgaagcgt ttggtatacg tactcgtaaa tggtgaccga aaagctggcg   4200
gcttcctcgc acaagtaatt ccgccagcat ccttagtaca atgcctgaag ggtatatttt   4260
agatttagct aatttattaa tttagtttag tatttgtaca gttactgcaa tacctctgta   4320
ccggaactcc agctgtgacc ttgacttgtt tcatgtgtca actcgccaca gtcccaactt   4380
gcttaccttc atcaatcttc cgtaacaaaa aagtctcggc gaatccctgg gctttgctcc   4440
aatctaagta ctctgcgttt tcgtaatcgt ttcgtgtccg cgagtttacc catattaata   4500
ctccgtacga cataagtgaa tggaagtgag cgtagtatac ggatcttaaa gtatcactat   4560
cagaagacgg cggcatcaac ggcggtggca gaataacagc gtccgttgct agaattcttt   4620
agcgcactct acaaaattat atcctggtgg attagccgag tcacattccc tttcaattcg   4680
tctgtaagca ttgttatgta cttaaattta aacttacctt cgtcaatctt ccgcgaggcc   4740
tcctccaggt cggagccggc gtagttgagg atgaccagca cgagcggcac cacctcccaa   4800
ctgttctagg gcagattgtt tagcttgttc agctgcgctt gtttatttgc ttagctttcg   4860
cttagcgacg tgttcacttt gcttgtttga attgaattgt cgctccgtag acgaagcgcc   4920
tctatttata ctccggcgct cgttttcgag tttaccactc cctatcagtg atagagaaaa   4980
gtgaaagtcg agtttaccac tccctatcag tgatagagaa aagtgaaagt cgagtttacc   5040
actccctatc agtgatagag aaaagtgaaa gtcgagttta ccactcccta tcagtgatag   5100
agaaaagtga aagtcgagtt taccactccc tatcagtgat agagaaaagt gaaagtcgaa   5160
acctggcgcg ccccggccat cgagaaagag agagagaaga gaagagagag aacattcgag   5220
aaagagagag agaagagaag agagagaaca tactccctat cagtgataga gaagtcccta   5280
tcagtgatag agatgtccct atcagtgata gagagttccc tatcagtgat agagacgtcc   5340
ctatcagtga tagagaagtc cctatcagtg atagagagat ccctatcagt gatagagatt   5400
tccctatcag tgatagagag gtccctatca gtgatagaga cttccctatc agtgatagag   5460
aaatccctat cagtgataga gacatcccta tcagtgatag agaactccct atcagtgata   5520
gagacctccc tatcagtgat agagatcgat gcggccgcga gcgccggagt ataaatagag   5580
gcgcttcgtc tacggagcga caattcaatt caaacaagca aagtgaacac gtcgctaagc   5640
gaaagctaag caaataaaca agcgcagctg aacaagctaa acaatctgca ggtaccctgg   5700
cggtaagttg atcaaaggaa acgcaaagtt ttcaagaaaa aacaaaacta atttgattta   5760
taacaccttt agaaagcggg gctagccacc atgggcagcg cctacagccg cgcccgtacc   5820
aagaacaact atggcagcac catcgaggga ctgctggacc tgccggatga cgatgccccg   5880
gaggaagccg gcctggccgc cccccgcctg agcttcctgc ccgccggaca cacgcgccgc   5940
ctgagcaccg ccccgccgac cgatgtgagc ctgggcgacg agctgcacct ggatggagag   6000
gatgtggcaa tggcccacgc cgacgccctg gacgatttcg acctggatat gctgggcgat   6060
ggagatagcc cgggaccggg cttcacgccc cacgatagcg ccccgtacgg cgccctggac   6120
atggccgact tcgagttcga gcaaatgttc accgacgcgc tgggcatcga tgagtatggc   6180
gggtaggttt aaactcgcgt taagatacat tgatgagttt ggacaaacca caactagaat   6240
gcagtgaaaa aaatgcttta tttgtgaaat ttgtgatgct attgctttat ttgtaaccat   6300
tataagctgc aataaacaag ttaacaacaa caattgcatt cattttatgt ttcaggttca   6360
gggggaggtg tgggaggttt tttaaagcaa gtaaaacctc tacaaatgtg gtatggctga   6420
ttatgatcag ttatctagat ccggtggatc ttacgggtcc tccaccttcc gctttttctt   6480
```

```
gggtcgagat ctcaggaaca ggtggtggcg gccctcggtg cgctcgtact gctccacgat   6540
ggtgtagtcc tcgttgtggg aggtgatgtc cagcttggcg tccacgtagt agtagccggg   6600
cagctgcacg ggcttcttgg ccatgtagat ggacttgaac tccaccaggt agtggccgcc   6660
gtccttcagc ttcagggcct tgtgggtctc gcccttcagc acgccgtcgc gggggtacag   6720
gcgctcggtg gaggcctccc agcccatggt cttcttctgc atcacggggc cgtcggaggg   6780
gaagttcacg ccgatgaact tcaccttgta gatgaagcag ccgtcctgca gggaggagtc   6840
ctgggtcacg gtcgccacgc cgccgtcctc gaagttcatc acgcgctccc acttgaagcc   6900
ctcggggaag gacagcttct tgtagtcggg gatgtcggcg gggtgcttca cgtacacctt   6960
ggagccgtac tggaactggg gggacaggat gtcccaggcg aagggcaggg ggccgccctt   7020
ggtcaccttc agcttcacgg tgttgtggcc ctcgtagggg cggccctcgc cctcgccctc   7080
gatctcgaac tcgtggccgt tcacggtgcc ctccatgcgc accttgaagc gcatgaactc   7140
ggtgatgacg ttctcggagg aggccatggt ggcgaccggt ttgcgcttct tcttgggtgg   7200
ggtgggatct cccatggtgg cctgaatctc aacttgcacc tgaaggtagt gcagcaagga   7260
tgagcaaaag ggaagaaccc agaaaagaac gggaaaactt accccaatta gaattgcttg   7320
tcgccgccag tgtcaacttg caactgaaac aatatccaac atgaacgtca atttatactg   7380
ccctaatggc gaacacgata acaatatttc ttttattatg ccctctaaaa ccaacgcggt   7440
tatcgtttat ttattcaaat tagatataga acatccgccg acatacaatg ttaatgcaaa   7500
aacgcgtttg gtgagcggat acgaaaacag tcggccgata aacattaatc tgaggtcgat   7560
aacaccgtcc ttgaacggaa cacgaggagc gtacgtgatc agctgcattc gcgcgccgcg   7620
cctttatcga gatttatttg catacaacaa gtacactgcg ccgttgggat ttgtggtaac   7680
gcgcacacat gcagagctgc aagtgtggca cattttgtct gtgcgcaaaa cctttgaagc   7740
caaaagtacg aggtccgtta cggcatgct actagcgcac acggacaatg gacccgacaa   7800
attctacgcc aaggatttaa tgataatgtc gggcaacgta tccgttcatt ttatcaataa   7860
cctacaaaaa tgtcgcgcgc atcacaaaga catcgatata tttaaacatt tatgtcccga   7920
actgcaaatc gataatagtg ttgtgcaacc tcgagcgtcc gtttgattta acgtatagct   7980
tgcaaatgaa ttatttaatt atcaatcatg ttttacgcgt agaattctac ccgtaaagcg   8040
agtttagtta tgagccatgt gcaaaacatg acatcagctt ttattttat aacaaatgac   8100
atcatttctt gattgtgttt tacacgtaga attctactcg taaagcgagt tcagttttga   8160
aaaacaaatg acatcatctt tttgattgtg ctttacaagt agaattctac ccgtaaatca   8220
agttcggttt tgaaaaacaa atgagtcata ttgtatgata tcatattgca aaacaaatga   8280
ctcatcaatc gatcgtgcgt tacacgtaga attctactcg taaagcgagt ttatgagccg   8340
tgtgcaaaac atgacatcat ctcgatttga aaaacaaatg acatcatcca ctgatcgtgc   8400
attacaagta gaattctact cgtaaagcca gttcggttat gagccgtgta caaaacatga   8460
catcagatta tgactcatac ttgattgtgt tttacgcgta gaattctact cgtaaagcca   8520
gttcaatttt aaaaacaaat gacatcatcc aaattaataa atgacaagca atgggtacca   8580
tgcggcctgg cctcgcgctc gcgcgactga cggtcgtaag cacccgcgta cgtgtccacc   8640
ccggtcacaa ccccttgtgt catgtcggcg accctacgcc cccaactgag agaactcaaa   8700
ggttacccca gttggggcac tactcccgaa aaccgcttct gacctgggaa aacgtgaagc   8760
cccggggcat ccgctgaggg ttgccgccgg ggcttcggtg tgtccgtcag tacttaatta   8820
```

-continued

```
acaccgaaat cgtaattcac ggcatcatta caaaatattt tgacgttttg gacctcgtcc   8880
ctaatgacac cataacggtg gccttgaagt atatttaacc ctagaaagat agtctgcgta   8940
aaattgacgc atgcattctt gaaatattgc tctctctttc taaatagcgc gaatccgtcg   9000
ctgtgcattt aggacatctc agtcgccgct tggagctccc gtgaggcgtg cttgtcaatg   9060
cggtaagtgt cactgatttt gaactataac gaccgcgtga gtcaaaatga cgcatgatta   9120
tcttttacgt gacttttaag atttaactca tacgataatt atattgttat ttcatgttct   9180
acttacgtga taacttatta tatatatatt ttcttgttat agatatcgtg actaatatat   9240
aataaaatgg gtagttcttt agacgatgag catatcctct ctgctcttct gcaaagcgat   9300
gacgagcttg ttggtgagga ttctgacagt gaaatatcag atcacgtaag tgaagatgac   9360
ctcgaggatc caagcttatc gatttcgaac cctcgaccgc cggagtataa atagaggcgc   9420
ttcgtctacg gagcgacaat tcaattcaaa caagcaaagt gaacacgtcg ctaagcgaaa   9480
gctaagcaaa taaacaagcg cagctgaaca agctaaacaa tcggggtacc gctagagtcg   9540
atcccacccc acccaagaag aagcgcaaac cggtaccatg gcctcctccg agaacgtcat   9600
caccgagttc atgcgcttca aggtgcgcat ggagggcacc gtgaacggcc acgagttcga   9660
gatcgagggc gagggcgagg gccgccccta cgagggccac aacaccgtga agctgaaggt   9720
gaccaagggc ggcccccctgc ccttcgcctg ggacatcctg tccccccagt tccagtacgg   9780
ctccaaggtg tacgtgaagc accccgccga catccccgac tacaagaagc tgtccttccc   9840
cgagggcttc aagtgggagc gcgtgatgaa cttcgaggac ggcggcgtgg cgaccgtgac   9900
ccaggactcc tccctgcagg acggctgctt catctacaag gtgaagttca tcggcgtgaa   9960
cttcccctcc gacggccccg tgatgcagaa gaagaccatg ggctgggagg cctccaccga  10020
gcgcctgtac ccccgcgacg gcgtgctgaa gggcgagacc cacaaggccc tgaagctgaa  10080
ggacggcggc cactacctgg tggagttcaa gtccatctac atggccaaga agcccgtgca  10140
gctgcccggc tactactacg tggacgccaa gctggacatc acctcccaca acgaggacta  10200
caccatcgtg gagcagtacg agcgcaccga gggccgccac cacctgttcc tgtgatgatc  10260
ataatcagcc ataccacatt tgtagaggtt ttacttgctt taaaaaacct cccacacctc  10320
cccctgaacc tgaaacataa aatgaatgca attgttgttg ttaacttgtt tattgcagct  10380
tataatggtt acaaataaag caatagcatc acaaatttca caaataaagc atttttttca  10440
ctgcattcta gttgtggttt gtccaaactc atcaatgtat cttaacgcga gttaattacg  10500
gccgctcatt taaatctggc cggccgcaac cattgtggga accgtgcgat caaacaaacg  10560
cgagataccg gaagtactga aaaacagtcg ctccaggcca gtgggaacat cgatgttttg  10620
ttttgacgga cccttactc tcgtctcata taaaccgaag ccagctaaga tggtatactt  10680
attatcatct tgtgatgagg atgcttctat caacgaaagt accggtaaac cgcaaatggt  10740
tatgtattat aatcaaacta aaggcggagt ggacacgcta gaccaaatgt gttctgtgat  10800
gacctgcagt aggaagacga ataggtggcc tatggcatta ttgtacggaa tgataaacat  10860
tgcctgcata aattctttta ttatatacag ccataatgtc agtagcaagg gagaaaaggt  10920
ccaaagtcgc aaaaaattta tgagaaacct ttacatgagc ctgacgtcat cgtttatgcg  10980
taagcgttta gaagctccta ctttgaagag atatttgcgc gataatatct ctaatatttt  11040
gccaaatgaa gtgcctggta catcagatga cagtactgaa gagccagtaa tgaaaaaacg  11100
tacttactgt acttactgcc cctctaaaat aaggcgaaag gcaaatgcat cgtgcaaaaa  11160
atgcaaaaaa gttatttgtc gagagcataa tattgatatg tgccaaagtt gtttctgact  11220
```

```
gactaataag tataatttgt ttctattatg tataagttaa gctaattact tattttataa  11280
tacaacatga ctgtttttaa agtacaaaat aagtttattt ttgtaaaaga gagaatgttt  11340
aaaagttttg ttactttata gaagaaattt tgagtttttg ttttttttta ataaataaat  11400
aaacataaat aaattgtttg ttgaatttat tattagtatg taagtgtaaa tataataaaa  11460
cttaatatct attcaaatta ataaataaac ctcgatatac agaccgataa aacacatgcg  11520
tcaattttac gcatgattat ctttaacgta cgtcacaata tgattatctt tctagggtta  11580
aataatagtt tctaattttt ttattattca gcctgctgtc gtgaataccg tatatctcaa  11640
cgctgtctgt gagattgtcg tattctagcc tttttagttt ttcgctcatc gacttgatat  11700
tgtccgacac attttcgtcg atttgcgttt tgatcaaaga cttgagcaga gacacgttaa  11760
tcaactgttc aaattgatcc atattaacga tatcaacccg atgcgtatat ggtgcgtaaa  11820
atatattttt taaccctctt atactttgca ctctgcgtta atacgcgttc gtgtacagac  11880
gtaatcatgt tttctttttt ggataaaact cctactgagt ttgacctcat attagaccct  11940
cacaagttgc aaaacgtggc attttttacc aatgaagaat ttaaagttat tttaaaaaat  12000
ttcatcacag atttaaagaa gaaccaaaaa ttaaattatt tcaacagttt aatcgaccag  12060
ttaatcaacg tgtacacaga cgcgtcggca aaaaacacgc agcccgacgt gttggctaaa  12120
attattaaat caacttgtgt tatagtcacg gatttgccgt ccaacgtgtt cctcaaaaag  12180
ttgaagacca acaagtttac ggacactatt aattatttga ttttgcccca cttcattttg  12240
tgggatcaca attttgttat attttaaaca aagcttggca ctggccgtcg ttttacaacg  12300
tcgtgactgg gaaaaccctg gcgttaccca acttaatcgc cttgcagcac atcccccttt  12360
cgccagctgg cgtaatagcg aagaggcccg caccgatcgc ccttcccaac agttgcgcag  12420
cctgaatggc gaatggcgcc tgatgcggta ttttctcctt acgcatctgt gcggtatttc  12480
acaccgcata tggtgcactc tcagtacaat ctgctctgat gccgcatagt taagccagcc  12540
ccgacacccg ccaacacccg ctgacgcgcc ctgacgggct tgtctgctcc cggcatccgc  12600
ttacagacaa gctgtgaccg tctccgggag ctgcatgtgt cagaggtttt caccgtcatc  12660
accgaaacgc gcgagacgaa agggcctcgt gatacgccta tttttatagg ttaatgtcat  12720
gataataatg gtttcttaga cgtcaggtgg cacttttcgg ggaaatgtgc gcggaacccc  12780
tatttgttta tttttctaaa tacattcaaa tatgtatccg ctcatgagac aataaccctg  12840
ataaatgctt caataatatt gaaaaaggaa gagtatgagt attcaacatt tccgtgtcgc  12900
ccttattccc ttttttgcgg cattttgcct tcctgttttt gctcacccag aaacgctggt  12960
gaaagtaaaa gatgctgaag atcagttggg tgcacgagtg ggttacatcg aactggatct  13020
caacagcggt aagatccttg agagttttcg ccccgaagaa cgttttccaa tgatgagcac  13080
ttttaaagtt ctgctatgtg gcgcggtatt atcccgtatt gacgccgggc aagagcaact  13140
cggtcgccgc atacactatt ctcagaatga cttggttgag tactcaccag tcacagaaaa  13200
gcatcttacg gatggcatga cagtaagaga attatgcagt gctgccataa ccatgagtga  13260
taacactgcg gccaacttac ttctgacaac gatcggagga ccgaaggagc taaccgcttt  13320
tttgcacaac atgggggatc atgtaactcg ccttgatcgt tgggaaccgg agctgaatga  13380
agccatacca aacgacgagc gtgacaccac gatgcctgta gcaatggcaa caacgttgcg  13440
caaactatta actggcgaac tacttactct agcttcccgg caacaattaa tagactggat  13500
ggaggcggat aaagttgcag gaccacttct gcgctcggcc cttccggctg gctggtttat  13560
```

-continued

```
tgctgataaa tctggagccg gtgagcgtgg gtctcgcggt atcattgcag cactggggcc  13620
agatggtaag ccctcccgta tcgtagttat ctacacgacg gggagtcagg caactatgga  13680
tgaacgaaat agacagatcg ctgagatagg tgcctcactg attaagcatt ggtaactgtc  13740
agaccaagtt tactcatata tactttagat tgatttaaaa cttcattttt aatttaaaag  13800
gatctaggtg aagatccttt ttgataatct catgaccaaa atcccttaac gtgagttttc  13860
gttccactga gcgtcagacc ccgtagaaaa gatcaaagga tcttcttgag atcctttttt  13920
tctgcgcgta atctgctgct tgcaaacaaa aaaaccaccg ctaccagcgg tggtttgttt  13980
gccggatcaa gagctaccaa ctctttttcc gaaggtaact ggcttcagca gagcgcagat  14040
accaaatact gtccttctag tgtagccgta gttaggccac cacttcaaga actctgtagc  14100
accgcctaca tacctcgctc tgctaatcct gttaccagtg gctgctgcca gtggcgataa  14160
gtcgtgtctt accgggttgg actcaagacg atagttaccg gataaggcgc agcggtcggg  14220
ctgaacgggg ggttcgtgca cacagcccag cttggagcga acgacctaca ccgaactgag  14280
atacctacag cgtgagcatt gagaaagcgc cacgcttccc gaagggagaa aggcggacag  14340
gtatccggta agcggcaggg tcggaacagg agagcgcacg agggagcttc caggggggaaa  14400
cgcctggtat ctttatagtc ctgtcgggtt tcgccacctc tgacttgagc gtcgattttt  14460
gtgatgctcg tcaggggggc ggagcctatg gaaaaacgcc agcaacgcgg cctttttacg  14520
gttcctggcc ttttgctggc cttttgctca catgttcttt cctgcgttat cccctgattc  14580
tgtggataac cgtattaccg cctttgagtg agctgatacc gctcgccgca gccgaacgac  14640
cgagcgcagc gagtcagtga gcgaggaagc ggaagagcgc ccaatacgca aaccgcctct  14700
ccccgcgcgt tggccgattc attaatgcag ctggcacgac aggtttcccg actggaaagc  14760
gggcagtgag cgcaacgcaa ttaatgtgag ttagctcact cattaggcac cccaggcttt  14820
acactttatg cttccggctc gtatgttgtg tggaattgtg agcggataac aatttcacac  14880
aggaaacagc tatgaccatg attacgaatt tcgacctgca ggcatgcaag cttgcatgcc  14940
tgcaggtcga cgctcgcgcg acttggtttg ccattcttta gcgcgcgtcg cgtcacacag  15000
cttggccaca atgtggtttt tgtcaaacga agattctatg acgtgtttaa agtttaggtc  15060
gagtaaagcg caaatctttt ttaaccctag aaagatagtc tgcgtaaaat tgacgcatgc  15120
attcttgaaa tattgctctc tctttctaaa tagcgcgaat ccgtcgctgt gcatttagga  15180
catctcagtc gccgcttgga gctcccgtga ggcgtgcttg tcaatgcggt aagtgtcact  15240
gattttgaac tataacgacc gcgtgagtca aaatgacgca tgattatctt ttacgtgact  15300
tttaagattt aactcatacg ataattatat tgttatttca tgttctactt acgtgataac  15360
ttattatata tatattttct tgttatagat atcgtgacta atatataata aaatgggtag  15420
ttctttagac gatgagcata tcctctctgc tcttctgcaa agcgatgacg agcttgttgg  15480
tgaggattct gacagtgaaa tatcagatca cgtaagtgaa gatgacgtcc agagcgatac  15540
agaagaagcg tttatagatg aggtacatga agtgcagcca acgtcaagcg gtagtgaaat  15600
attagacgaa caaaatgtta ttgaacaacc aggttcttca ttggcttcta acagaatctt  15660
gaccttgcca cagaggacta ttagaggtaa gaataaacat tgttggtcaa cttcaaagtc  15720
cacgaggcgt agccgagtct ctgcactgaa cattgtcaga tcggcccgct cgcccgggga  15780
actagttcaa ttagagacta attcaattag agctaattca attaggatcc aagcttatcg  15840
atttcgaacc ctcgaccgcc ggagtataaa tagaggcgct tcgtctacgg agcgacaatt  15900
caattcaaac aagcaaagtg aacacgtcgc taagcgaaag ctaagcaaat aaacaagcgc  15960
```

```
agctgaacaa gctaaacaat cggggtaccg ctagagtcga tcccacccca cccaagaaga  16020
agcgcaaacc ggtcgccacc atggccctgt ccaacaagtt catcggcgac gacatgaaga  16080
tgacctacca catggacggc tgcgtgaacg gccactactt caccgtgaag ggcgagggca  16140
gcggcaagcc ctacgagggc acccagacct ccaccttcaa ggtgaccatg gccaacggcg  16200
gcccccctggc cttctccttc gacatcctgt ccaccgtgtt catgtacggc aaccgctgct  16260
tcaccgccta ccccaccagc atgcccgact acttcaagca ggccttcccc gacggcatgt  16320
cctacgagag aaccttcacc tacgaggacg gcggcgtggc caccgccagc tgggagatca  16380
gcctgaaggg caactgcttc gagcacaagt ccaccttcca cggcgtgaac ttccccgccg  16440
acggccccgt gatggccaag aagaccaccg gctgggaccc ctccttcgag aagatgaccg  16500
tgtgcgacgg catcttgaag ggcgacgtga ccgccttcct gatgctgcag ggcggcggca  16560
actacagatg ccagttccac acctcctaca agaccaagaa gcccgtgacc atgcccccca  16620
accacgtggt ggagcaccgc atcgccagaa ccgacctgga caagggcggc aacagcgtgc  16680
agctgaccga gcacgccgtg gcccacatca cctccgtggt gcccttctcc ggactcagat  16740
cataatcagc cataccacat ttgtagaggt tttacttgct ttaaaaaacc tcccacacct  16800
ccccctgaac ctgaaacata aaatgaatgc aattgttgtt gttaacttgt ttattgcagc  16860
ttataatggt tacaaataaa gcaatagcat cacaaatttc acaaataaag catttttttc  16920
actgcattct agttgtggtt tgtccaaact catcaatgta tcttaccgcg gagtggacac  16980
gctagaccaa atgtgttctg tgatgacctg cagtaggaag acgaataggt ggcctatggc  17040
attattgtac ggaatgataa acattgcctg cataaattct tttattatat acagccataa  17100
tgtcagtagc aagggagaaa aggtccaaag tcgcaaaaaa tttatgagaa acctttacat  17160
gagcctgacg tcatcgttta tgcgtaagcg tttagaagct cctactttga agagatattt  17220
gcgcgataat atctctaata ttttgccaaa tgaagtgcct ggtacatcag atgacagtac  17280
tgaagagcca gtaatgaaaa aacgtactta ctgtacttac tgcccctcta aaataaggcg  17340
aaaggcaaat gcatcgtgca aaaaatgcaa aaaagttatt tgtcgagagc ataatattga  17400
tatgtgccaa agttgtttct gactgactaa taagtataat ttgtttctat tatgtataag  17460
ttaagctaat tacttatttt ataatacaac atgactgttt ttaaagtaca aaataagttt  17520
atttttgtaa aagagagaat gtttaaaagt tttgttactt tatagaagaa attttgagtt  17580
tttgtttttt tttaataaat aaataaacat aaataaattg tttgttgaat ttattattag  17640
tatgtaagtg taaatataat aaaacttaat atctattcaa attaataaat aaacctcgat  17700
atacagaccg ataaaacaca tgcgtcaatt ttacgcatga ttatctttaa cgtacgtcac  17760
aatatgatta tctttctagg g                                             17781
```

<210> SEQ ID NO 162
<211> LENGTH: 15482
<212> TYPE: DNA
<213> ORGANISM: artificial
<220> FEATURE:
<223> OTHER INFORMATION: LA3570 plasmid sequence
<220> FEATURE:
<221> NAME/KEY: misc_feature
<222> LOCATION: (1875)..(1875)
<223> OTHER INFORMATION: n is a, c, g, or t

<400> SEQUENCE: 162

```
gggcggccgt tttcttgaa atattgctct ctctttctaa atagcgcgaa tccgtcgctg     60
```

```
tgcatttagg acatctcagt cgccgcttgg agctcccaaa cgcgccagtg gtagtacaca    120
gtactgtggg tgttcagttt gaaatcctct tgcttctcca ttgtctcggt tacctttggt    180
caaatccatg ggttctattg cctatatact cttgcgatta ccagtgattg cgctattagc    240
tattagatgg attgttggcc aaacttgtcg cttaagtggc tgggaattgt aaccgtaggc    300
ccgagtgtaa tgatccccca taaaaagttt tcgcaatgcc tttatttttt gttgcaaatc    360
tctctttatt ctgcggtatt cttcattatt gcggggatgg ggaaagtgtt tatatagaag    420
caacttacga ttgaacccaa atgcacctga caagcaaggt caaagggcca gatttttaaa    480
tatattattt agtcttagga ctctctattt gcaattaaat tactttgcta cctgagggtt    540
aaatcttccc cattgataat aataattcca ctatatgttc aattgggttt caccgcgctt    600
agttacatga cgagccctaa tgagccgtcg gtggtctata aactgtgcct tacaaatact    660
tgcaactctt ctcgttttga agtcagcaga gttattgcta attgctaatt gctaattgct    720
tttaactgat ttcttcgaaa ttggtgctat gtttatggcg ctattaacaa gtatgaatgt    780
caggtttaac caggggatgc ttaattgtgt tctcaacttc aaaggcagaa atgtttactc    840
ttgaccatgg gtttaggtat aatgttatca agctcctcga gttaacgtta cgttaacgtt    900
aacgttcgag gtcgactcta gggcctctct agatttacag gtctattttg agctctttgt    960
cagacactgt ttgcttgaaa ttcaagtctg tcagcacctt aaaaccaaaa ataaaaagaa   1020
taataaatga aatagtactt acttcccgcg gcgcaggttc gcatcgctac aagtgcgcgg   1080
gcggcgggga tgatctctgc gtggtaagcg gcagaggcaa caggtgtggc gcgtactcgg   1140
gcgcgatgac gtagcggggt gagcagcaca ccgagtacgt ccctttgcgc gcttgcagct   1200
ccaggagcga gcacagcgac cgctcgtaca tccgccactg gtggaccacc caatgtgcac   1260
ccaatgtgct gcaaggaagg cggggttaag tcgtcgagaa gtgatacaag aaatcggtct   1320
ttaaagtcgt aaggtccatt acctttaaaa atcgaaaacc cttaaactac tgtgtctaga   1380
aatctggacc ttacgaggtt aagtcgttag agaattgaaa gaaagcataa agaaactaga   1440
ccatatcatc gccttgtagc gaaaccacgt aagcgttttt ttgaaaatca aattaaaaac   1500
attctgatac gattttcttc aacaaaattt cattacaggt aaaaattaag accacraatt   1560
attgcctggg ttgaattgaa acaagcttgt ctattgtgtg gttttattaa caaaaatcac   1620
atccgaaggc gcttrtgtgg gtttcattat aaagccacga tatacagtct atacatttag   1680
ctgttcaagt tacaggtgaa tcgcaacctc caaggttaca agcggtataa aattwatatt   1740
gttaataatg tcaaatgtac caactatagt tttacattgg tcaaatgagc aatgtacggc   1800
cgtaaaatgg ccagtcgcag tgccagtaat gtagtttttt aaatccgtaa aaattaagtg   1860
ccatacyttt tttanctacc ttaaaataca aaaatattgg gaacmcacga acaccccaat   1920
aatagtgttt aaacagtcgt tgtcataaaa cgatatcaat aatctttgat gttataaaaa   1980
tatatgtttt tctttatttt aattgcccgg tagtcatgtt gtatacgagt attgtataaa   2040
gcaatcgttc tacaaatgac tcgttacgat gttcctgaga ttcctccata gcagtgagta   2100
gtaataaaaa gtcaattgta ccgcgatgaa atagataaaa tattattcta ccactcaccg   2160
aatagtccag cgtggcgacg acacaatagt ccttccatcg caaacagcaa cgcacagcaa   2220
aagtccacac aacacacagc acatacaaaa caaagtatca ttcgcaaaat aacttcatgg   2280
acgacgatag tacaccactt atattattaa tttcgctcag cattttccac cggtgttagc   2340
cgccgtactc atcgatgccc agggcgtcgg tgaacatctg ctcgaactcg aaatcggcca   2400
tatccagggc gccgtagggg gcgctatcgt gcggggtgaa tcccggtccc gggctatcgc   2460
```

```
catcgcccag catgtccagg tcgaagtcgt ccagggcatc ggcgtgggcc atcgccacat   2520
cctcgccatc caggtgcagc tcatcgccca ggctcacgtc ggtcggcggg gcggtcgaca   2580
ggcggcgggt gtgtccggcc ggcaggaagc tcaggcgcgg ggcggccagg cccgcctcct   2640
ccggggcatc atcatccggc agatccagca ggccctcgat ggtgctgccg tagttgttct   2700
tggtgcgggc gcggctgtag gcggggcccg agcccgactc gcatttcagt tgcttttcca   2760
atccgcagat aatcagctcc aagccgaaca ggaatgccgg ctcggctcct tgatgatcga   2820
acagctcgat tgcctgacgc agcagtgggg gcatcgaatc ggttgttggg gtctcgcgct   2880
cctcttttgc gacttgatgc tcttggtcct ccagcacgca gcccagggta aagtgaccga   2940
cggcgctcag agcgtagaga gcattttcca ggctgaagcc ttgctggcac aggaacgcga   3000
gctggttctc cagtgtctcg tattgctttt cggtcgggcg cgtgccgaga tggactttgg   3060
caccgtctcg gtgggacagc agagcgcagc ggaacgactt ggcgttattg cggaggaagt   3120
cctgccagga ctcgccttcc aacgggcaaa aatgcgtgtg gtggcggtcg agcatctcga   3180
tggccagggc atccagcagc gcccgcttat tcttcacgtg ccagtagagg gtgggctgct   3240
ccacgcccag cttctgcgcc aacttgcggg tcgtcagtcc ctcaatgcca acttcgttca   3300
acagctccaa cgcggagttg atgactttgg acttatccag gcggctgccc atggtggttt   3360
cggtccgtta gcgagtcgag ttcctcagct cgtggccatc gaagatgttc agattgtgct   3420
tcctcgcgta ctcgttgatg atcatcttcc ctggaaacat atgacgctag ctttacattc   3480
gcacagcggg gtatgaggaa ctgcatttat tacaatttat tatactatta ttataattcc   3540
cgtcgtcata attgtcgtcg gtcatgtcgt atcaggaggt gaaggatttg gtaggaagaa   3600
gagaggaatg gcgattactc caccgacaag agcgcagctc ttaaaaaaaa agagagataa   3660
ttcccgtgac cttaatataa gcatcatggc ttcataacct cgtgagaaaa cgcacataat   3720
ttcccgagaa atgcgtttcg gaggtgacct aaccagccca atacctgtgt tgtttgcctt   3780
cgggttggaa ggtcagatag gcattcaatt ctgtaatgaa ccggacctgt caaatcttca   3840
ggctaagtac agaaattata ccatcaaata aggtaacata attttgatca gatttcttta   3900
ttatttattt atctttagaa gacagagaga tgaggaggaa gggtgcagac aacattgcat   3960
cctacgtgca ctcaagaaca agtagaatgt ctacttgtat ttactaccta aaatacattt   4020
tattggacct cctagattta attacagttt tgaaatctct aacatctaaa ataatagccc   4080
cgggccttca attattgtaa aaggggaatg aatcttatgt tactataggt agtttcgcct   4140
cgagaggcat tcgcaacttg accgaacaaa cggtttcttc ctttagcgaa tgtattataa   4200
ttatccaaca cacaagactg cacgcagtac aagtaggtaa taatgcaata gattgacata   4260
aacggcaatt aacgaacgac agacgtacct accgcggtgt agagttgtag acctatgatt   4320
attcttcacg gagtttttta ttacaaactg tggtaaaacc tttataaacc accgtaatat   4380
acaagaataa agaacgaaac taattatgta taaacaactt atataaatac cactgctgga   4440
cgcagacgtc ccctcaatca actggacagg gaagatcgta ctccaccacg ctgcttcgtt   4500
acgggttggt agagaattaa ataaatgaat tgtatgaaaa aaaaaacgta agtaaacata   4560
taaaaaatgt aagttttcta tcaaaaactt cacctcgtat tcaaagaacg caaagaactt   4620
gtaatcaatc agtaattatc gtaccttcat caatttttcc agaagcctcg tcgaggccta   4680
gggcagattg tttagcttgt tcagctgcgc ttgtttattt gcttagcttt cgcttagcga   4740
cgtgttcact ttgcttgttt gaattgaatt gtcgctccgt agacgaagcg cctctattta   4800
```

-continued

```
tactccggcg ctcgttttcg agtttaccac tccctatcag tgatagagaa aagtgaaagt   4860
cgagtttacc actccctatc agtgatagag aaaagtgaaa gtcgagttta ccactcccta   4920
tcagtgatag agaaaagtga aagtcgagtt taccactccc tatcagtgat agagaaaagt   4980
gaaagtcgag tttaccactc cctatcagtg atagagaaaa gtgaaagtcg agtttaccac   5040
tccctatcag tgatagagaa aagtgaaagt cgagtttacc actccctatc agtgatagag   5100
aaaagtgaaa gtcgaaacct ggcgcgcccc ggccatcgag aaagagagag agaagagaag   5160
agagagaaca ttcgagaaag agagagagaa gagaagagag agaacatact ccctatcagt   5220
gatagagaag tccctatcag tgatagagat gtccctatca gtgatagaga gttccctatc   5280
agtgatagag acgtccctat cagtgataga gaagtcccta tcagtgatag agagatccct   5340
atcagtgata gagatttccc tatcagtgat agagaggtcc ctatcagtga tagagacttc   5400
cctatcagtg atagagaaat ccctatcagt gatagagaca tccctatcag tgatagagaa   5460
ctccctatca gtgatagaga cctccctatc agtgatagag atcgatgcgg ccgcgagcgc   5520
cggagtataa atagaggcgc ttcgtctacg gagcgacaat tcaattcaaa caagcaaagt   5580
gaacacgtcg ctaagcgaaa gctaagcaaa taaacaagcg cagctgaaca agctaaacaa   5640
tctgcaggta ccctggcggt aagttgatca aaggaaacgc aaagttttca agaaaaaaca   5700
aaactaattt gatttataac acctttagaa agcggggcta gccaccatgg gcagcgccta   5760
cagccgcgcc cgtaccaaga acaactatgg cagcaccatc gagggactgc tggacctgcc   5820
ggatgacgat gccccggagg aagccggcct ggccgccccc cgcctgagct tcctgcccgc   5880
cggacacacg cgccgcctga gcaccgcccc gccgaccgat gtgagcctgg gcgacgagct   5940
gcacctggat ggagaggatg tggcaatggc ccacgccgac gccctggacg atttcgacct   6000
ggatatgctg ggcgatggag atagcccggg accgggcttc acgccccacg atagcgcccc   6060
gtacggcgcc ctggacatgg ccgacttcga gttcgagcaa atgttcaccg acgcgctggg   6120
catcgatgag tatggcgggt aggtttaaac tcgcgttaag atacattgat gagtttggac   6180
aaaccacaac tagaatgcag tgaaaaaaat gctttatttg tgaaatttgt gatgctattg   6240
ctttatttgt aaccattata agctgcaata aacaagttaa caacaacaat tgcattcatt   6300
ttatgtttca ggttcagggg gaggtgtggg aggtttttta aagcaagtaa aacctctaca   6360
aatgtggtat ggctgattat gatcagttat ctagatccgg tggatcttac gggtcctcca   6420
ccttccgctt tttcttgggt cgagatctca ggaacaggtg gtggcggccc tcggtgcgct   6480
cgtactgctc cacgatggtg tagtcctcgt tgtgggaggt gatgtccagc ttggcgtcca   6540
cgtagtagta gccgggcagc tgcacgggct tcttggccat gtagatggac ttgaactcca   6600
ccaggtagtg gccgccgtcc ttcagcttca gggccttgtg ggtctcgccc ttcagcacgc   6660
cgtcgcgggg gtacaggcgc tcggtggagg cctcccagcc catggtcttc ttctgcatca   6720
cggggccgtc ggaggggaag ttcacgccga tgaacttcac cttgtagatg aagcagccgt   6780
cctgcaggga ggagtcctgg gtcacggtcg ccacgccgcc gtcctcgaag ttcatcacgc   6840
gctcccactt gaagccctcg gggaaggaca gcttcttgta gtcggggatg tcggcggggt   6900
gcttcacgta caccttggag ccgtactgga actgggggga caggatgtcc caggcgaagg   6960
gcagggggcc gcccttggtc accttcagct tcacggtgtt gtggccctcg taggggcggc   7020
cctcgccctc gccctcgatc tcgaactcgt ggccgttcac ggtgccctcc atgcgcacct   7080
tgaagcgcat gaactcggtg atgacgttct cggaggaggc catggtggcg accggtttgc   7140
gcttcttctt gggtggggtg ggatctccca tggtggcctg aatctcaact tgcacctgaa   7200
```

-continued

```
ggtagtgcag caaggatgag caaaagggaa gaacccagaa aagaacggga aaacttaccc   7260
caattagaat tgcttgtcgc cgccagtgtc aacttgcaac tgaaacaata tccaacatga   7320
acgtcaattt atactgccct aatggcgaac acgataacaa tatttctttt attatgccct   7380
ctaaaaccaa cgcggttatc gtttatttat tcaaattaga tatagaacat ccgccgacat   7440
acaatgttaa tgcaaaaacg cgtttggtga gcggatacga aaacagtcgg ccgataaaca   7500
ttaatctgag gtcgataaca ccgtccttga acggaacacg aggagcgtac gtgatcagct   7560
gcattcgcgc gccgcgcctt tatcgagatt tatttgcata caacaagtac actgcgccgt   7620
tgggatttgt ggtaacgcgc acacatgcag agctgcaagt gtggcacatt ttgtctgtgc   7680
gcaaaacctt tgaagccaaa agtacgaggt ccgttacggg catgctacta gcgcacacgg   7740
acaatggacc cgacaaattc tacgccaagg atttaatgat aatgtcgggc aacgtatccg   7800
ttcattttat caataaccta caaaaatgtc gcgcgcatca caaagacatc gatatattta   7860
aacatttatg tcccgaactg caaatcgata atagtgttgt gcaacctcga gcgtccgttt   7920
gatttaacgt atagcttgca aatgaattat ttaattatca atcatgtttt acgcgtagaa   7980
ttctacccgt aaagcgagtt tagttatgag ccatgtgcaa aacatgacat cagcttttat   8040
ttttataaca aatgacatca tttcttgatt gtgttttaca cgtagaattc tactcgtaaa   8100
gcgagttcag ttttgaaaaa caaatgacat catctttttg attgtgcttt acaagtagaa   8160
ttctacccgt aaatcaagtt cggttttgaa aaacaaatga gtcatattgt atgatatcat   8220
attgcaaaac aaatgactca tcaatcgatc gtgcgttaca cgtagaattc tactcgtaaa   8280
gcgagtttat gagccgtgtg caaaacatga catcatctcg atttgaaaaa caaatgacat   8340
catccactga tcgtgcatta caagtagaat tctactcgta aagccagttc ggttatgagc   8400
cgtgtacaaa acatgacatc agattatgac tcatacttga ttgtgtttta cgcgtagaat   8460
tctactcgta aagccagttc aattttaaaa acaaatgaca tcatccaaat taataaatga   8520
caagcaatgg gtaccatgcg gcctggcctc gcgctcgcgc gactgacggt cgtaagcacc   8580
cgcgtacgtg tccaccccgg tcacaacccc ttgtgtcatg tcggcgaccc tacgcccccca   8640
actgagagaa ctcaaaggtt accccagttg gggcactact cccgaaaacc gcttctgacc   8700
tgggaaaacg tgaagccccg gggcatccgc tgagggttgc cgccggggct tcggtgtgtc   8760
cgtcagtact taattaacac cgaaatcgta attcacggca tcattacaaa atattttgac   8820
gttttggacc tcgtccctaa tgacaccata acggtggcct tgaagtatat ttaaccctag   8880
aaagatagtc tgcgtaaaat tgacgcatgc attcttgaaa tattgctctc tctttctaaa   8940
tagcgcgaat ccgtcgctgt gcatttagga catctcagtc gccgcttgga gctcccgtga   9000
ggcgtgcttg tcaatgcggt aagtgtcact gattttgaac tataacgacc gcgtgagtca   9060
aaatgacgca tgattatctt ttacgtgact tttaagattt aactcatacg ataattatat   9120
tgttatttca tgttctactt acgtgataac ttattatata tatattttct tgttatagat   9180
atcgtgacta atatataata aaatgggtag ttctttagac gatgagcata tcctctctgc   9240
tcttctgcaa agcgatgacg agcttgttgg tgaggattct gacagtgaaa tatcagatca   9300
cgtaagtgaa gatgacgtcc aggaaatctg gccggccgca accattgtgg gaaccgtgcg   9360
atcaaacaaa cgcgagatac cggaagtact gaaaaacagt cgctccaggc cagtgggaac   9420
atcgatgttt tgttttgacg gaccccttac tctcgtctca tataaaccga agccagctaa   9480
gatggtatac ttattatcat cttgtgatga ggatgcttct atcaacgaaa gtaccggtaa   9540
```

-continued

```
accgcaaatg gttatgtatt ataatcaaac taaaggcgga gtggacacgc tagaccaaat   9600
gtgttctgtg atgacctgca gtaggaagac gaataggtgg cctatggcat tattgtacgg   9660
aatgataaac attgcctgca taaattcttt tattatatac agccataatg tcagtagcaa   9720
gggagaaaag gtccaaagtc gcaaaaaatt tatgagaaac ctttacatga gcctgacgtc   9780
atcgtttatg cgtaagcgtt tagaagctcc tactttgaag agatatttgc gcgataatat   9840
ctctaatatt ttgccaaatg aagtgcctgg tacatcagat gacagtactg aagagccagt   9900
aatgaaaaaa cgtacttact gtacttactg cccctctaaa ataaggcgaa aggcaaatgc   9960
atcgtgcaaa aaatgcaaaa aagttatttg tcgagagcat aatattgata tgtgccaaag  10020
ttgtttctga ctgactaata agtataattt gtttctatta tgtataagtt aagctaatta  10080
cttattttat aatacaacat gactgttttt aaagtacaaa ataagtttat ttttgtaaaa  10140
gagagaatgt ttaaaagttt tgttacttta tagaagaaat tttgagtttt tgtttttttt  10200
taataaataa ataaacataa ataaattgtt tgttgaattt attattagta tgtaagtgta  10260
aatataataa aacttaatat ctattcaaat taataaataa acctcgatat acagaccgat  10320
aaaacacatg cgtcaatttt acgcatgatt atctttaacg tacgtcacaa tatgattatc  10380
tttctagggt taaataatag tttctaattt ttttattatt cagcctgctg tcgtgaatac  10440
cgtatatctc aacgctgtct gtgagattgt cgtattctag cctttttagt ttttcgctca  10500
tcgacttgat attgtccgac acattttcgt cgatttgcgt tttgatcaaa gacttgagca  10560
gagacacgtt aatcaactgt tcaaattgat ccatattaac gatatcaacc cgatgcgtat  10620
atggtgcgta aaatatattt tttaaccctc ttatactttg cactctgcgt taatacgcgt  10680
tcgtgtacag acgtaatcat gtttctttt ttggataaaa ctcctactga gtttgacctc  10740
atattagacc ctcacaagtt gcaaaacgtg gcattttta ccaatgaaga atttaaagtt  10800
attttaaaaa atttcatcac agatttaaag aagaaccaaa aattaaatta tttcaacagt  10860
ttaatcgacc agttaatcaa cgtgtacaca gacgcgtcgg caaaaaacac gcagcccgac  10920
gtgttggcta aaattattaa atcaacttgt gttatagtca cggatttgcc gtccaacgtg  10980
ttcctcaaaa agttgaagac caacaagttt acggacacta ttaattattt gattttgccc  11040
cacttcattt tgtgggatca caattttgtt atattttaaa caaagcttgg cactggccgt  11100
cgttttacaa cgtcgtgact gggaaaaccc tggcgttacc caacttaatc gccttgcagc  11160
acatcccccct ttcgccagct ggcgtaatag cgaagaggcc cgcaccgatc gcccttccca  11220
acagttgcgc agcctgaatg gcgaatggcg cctgatgcgg tattttctcc ttacgcatct  11280
gtgcggtatt tcacaccgca tatggtgcac tctcagtaca atctgctctg atgccgcata  11340
gttaagccag ccccgacacc cgccaacacc cgctgacgcg ccctgacggg cttgtctgct  11400
cccggcatcc gcttacagac aagctgtgac cgtctccggg agctgcatgt gtcagaggtt  11460
ttcaccgtca tcaccgaaac gcgcgagacg aaagggcctc gtgatacgcc tatttttata  11520
ggttaatgtc atgataataa tggtttctta gacgtcaggt ggcacttttc ggggaaatgt  11580
gcgcggaacc cctatttgtt tatttttcta aatacattca aatatgtatc cgctcatgag  11640
acaataaccc tgataaatgc ttcaataata ttgaaaaagg aagagtatga gtattcaaca  11700
tttccgtgtc gcccttattc cctttttgc ggcattttgc cttcctgttt ttgctcaccc  11760
agaaacgctg gtgaaagtaa aagatgctga agatcagttg ggtgcacgag tgggttacat  11820
cgaactggat ctcaacagcg gtaagatcct tgagagtttt cgccccgaag aacgttttcc  11880
aatgatgagc acttttaaag ttctgctatg tggcgcggta ttatcccgta ttgacgccgg  11940
```

gcaagagcaa ctcggtcgcc gcatacacta ttctcagaat gacttggttg agtactcacc 12000
agtcacagaa aagcatctta cggatggcat gacagtaaga gaattatgca gtgctgccat 12060
aaccatgagt gataacactg cggccaactt acttctgaca acgatcggag gaccgaagga 12120
gctaaccgct tttttgcaca acatgggga tcatgtaact cgccttgatc gttgggaacc 12180
ggagctgaat gaagccatac caaacgacga gcgtgacacc acgatgcctg tagcaatggc 12240
aacaacgttg cgcaaactat taactggcga actacttact ctagcttccc ggcaacaatt 12300
aatagactgg atggaggcgg ataaagttgc aggaccactt ctgcgctcgg cccttccggc 12360
tggctggttt attgctgata aatctggagc cggtgagcgt gggtctcgcg gtatcattgc 12420
agcactgggg ccagatggta agccctcccg tatcgtagtt atctacacga cggggagtca 12480
ggcaactatg gatgaacgaa atagacagat cgctgagata ggtgcctcac tgattaagca 12540
ttggtaactg tcagaccaag tttactcata tatactttag attgatttaa aacttcattt 12600
ttaatttaaa aggatctagg tgaagatcct ttttgataat ctcatgacca aaatccctta 12660
acgtgagttt tcgttccact gagcgtcaga ccccgtagaa aagatcaaag gatcttcttg 12720
agatcctttt tttctgcgcg taatctgctg cttgcaaaca aaaaaaccac cgctaccagc 12780
ggtggtttgt ttgccggatc aagagctacc aactcttttt ccgaaggtaa ctggcttcag 12840
cagagcgcag ataccaaata ctgtccttct agtgtagccg tagttaggcc accacttcaa 12900
gaactctgta gcaccgccta catacctcgc tctgctaatc ctgttaccag tggctgctgc 12960
cagtggcgat aagtcgtgtc ttaccgggtt ggactcaaga cgatagttac cggataaggc 13020
gcagcggtcg ggctgaacgg ggggttcgtg cacacagccc agcttggagc gaacgaccta 13080
caccgaactg agatacctac agcgtgagca ttgagaaagc gccacgcttc ccgaagggag 13140
aaaggcggac aggtatccgg taagcggcag ggtcggaaca ggagagcgca cgagggagct 13200
tccaggggga aacgcctggt atctttatag tcctgtcggg tttcgccacc tctgacttga 13260
gcgtcgattt ttgtgatgct cgtcaggggg gcggagccta tggaaaaacg ccagcaacgc 13320
ggccttttta cggttcctgg ccttttgctg gccttttgct cacatgttct ttcctgcgtt 13380
atcccctgat tctgtggata accgtattac cgcctttgag tgagctgata ccgctcgccg 13440
cagccgaacg accgagcgca gcgagtcagt gagcgaggaa gcggaagagc gcccaatacg 13500
caaaccgcct ctccccgcgc gttggccgat tcattaatgc agctggcacg acaggtttcc 13560
cgactggaaa gcgggcagtg agcgcaacgc aattaatgtg agttagctca ctcattaggc 13620
accccaggct ttacacttta tgcttccggc tcgtatgttg tgtggaattg tgagcggata 13680
acaatttcac acaggaaaca gctatgacca tgattacgaa tttcgacctg caggcatgca 13740
agcttgcatg cctgcaggtc gacgctcgcg cgacttggtt tgccattctt tagcgcgcgt 13800
cgcgtcacac agcttggcca caatgtggtt tttgtcaaac gaagattcta tgacgtgttt 13860
aaagtttagg tcgagtaaag cgcaaatctt ttttaaccct agaaagatag tctgcgtaaa 13920
attgacgcat gcattcttga aatattgctc tctctttcta aatagcgcga atccgtcgct 13980
gtgcatttag gacatctcag tcgccgcttg gagctcccgt gaggcgtgct tgtcaatgcg 14040
gtaagtgtca ctgattttga actataacga ccgcgtgagt caaaatgacg catgattatc 14100
ttttacgtga cttttaagat ttaactcata cgataattat attgttattt catgttctac 14160
ttacgtgata acttattata tatatatttt cttgttatag atatcgtgac taatatataa 14220
taaaatgggt agttctttag acgatgagca tatcctctct gctcttctgc aaagcgatga 14280

-continued

```
cgagcttgtt ggtgaggatt ctgacagtga aatatcagat cacgtaagtg aagatgacgt  14340

ccagagcgat acagaagaag cgtttataga tgaggtacat gaagtgcagc caacgtcaag  14400

cggtagtgaa atattagacg aacaaaatgt tattgaacaa ccaggttctt cattggcttc  14460

taacagaatc ttgaccttgc cacagaggac tattagaggt aagaataaac attgttggtc  14520

aacttcaaag tccacgaggc gtagccgagt ctctgcactg aacattgtca gatcggcccg  14580

gcggagtgga cacgctagac caaatgtgtt ctgtgatgac ctgcagtagg aagacgaata  14640

ggtggcctat ggcattattg tacggaatga taaacattgc ctgcataaat tcttttatta  14700

tatacagcca taatgtcagt agcaagggag aaaaggtcca aagtcgcaaa aaatttatga  14760

gaaaccttta catgagcctg acgtcatcgt ttatgcgtaa gcgtttagaa gctcctactt  14820

tgaagagata tttgcgcgat aatatctcta atattttgcc aaatgaagtg cctggtacat  14880

cagatgacag tactgaagag ccagtaatga aaaaacgtac ttactgtact tactgcccct  14940

ctaaaataag gcgaaaggca aatgcatcgt gcaaaaaatg caaaaaagtt atttgtcgag  15000

agcataatat tgatatgtgc caaagttgtt tctgactgac taataagtat aatttgtttc  15060

tattatgtat aagttaagct aattacttat tttataatac aacatgactg tttttaaagt  15120

acaaaataag tttatttttg taaaagagag aatgtttaaa agttttgtta ctttatagaa  15180

gaaattttga gtttttgttt ttttttaata aataaataaa cataaataaa ttgtttgttg  15240

aatttattat tagtatgtaa gtgtaaatat aataaaactt aatatctatt caaattaata  15300

aataaacctc gatatacaga ccgataaaac acatgcgtca attttacgca tgattatctt  15360

taacgtacgt cacaatatga ttatctttct agggttaaaa tgaatgtaag cactttatta  15420

acgaaatctt tgggaatatt tcgctcatca gcattttatt tgagcaggag tccgagatgc  15480

cc                                                                 15482
```

<210> SEQ ID NO 163
<211> LENGTH: 10
<212> TYPE: DNA
<213> ORGANISM: Artificial Sequence
<220> FEATURE:
<223> OTHER INFORMATION: LA3077 flanking sequence

<400> SEQUENCE: 163
aacgaagttg 10

<210> SEQ ID NO 164
<211> LENGTH: 11
<212> TYPE: DNA
<213> ORGANISM: Artificial Sequence
<220> FEATURE:
<223> OTHER INFORMATION: LA3077 flanking sequence.

<400> SEQUENCE: 164
gtattgagtg g 11

<210> SEQ ID NO 165
<211> LENGTH: 10
<212> TYPE: DNA
<213> ORGANISM: Artificial Sequence
<220> FEATURE:
<223> OTHER INFORMATION: LA1188 flanking sequence

<400> SEQUENCE: 165
ctactggcac 10

-continued

```
<210> SEQ ID NO 166
<211> LENGTH: 10
<212> TYPE: DNA
<213> ORGANISM: Artificial Sequence
<220> FEATURE:
<223> OTHER INFORMATION: LA1188 flanking sequence

<400> SEQUENCE: 166

gtgaagaata                                                              10


<210> SEQ ID NO 167
<211> LENGTH: 10
<212> TYPE: DNA
<213> ORGANISM: Artificial Sequence
<220> FEATURE:
<223> OTHER INFORMATION: native flanking sequence

<400> SEQUENCE: 167

cgtagatttg                                                              10


<210> SEQ ID NO 168
<211> LENGTH: 10
<212> TYPE: DNA
<213> ORGANISM: Artificial Sequence
<220> FEATURE:
<223> OTHER INFORMATION: native flanking sequence

<400> SEQUENCE: 168

gtgaaggctc                                                              10
```

GENE EXPRESSION SYSTEM USING ALTERNATIVE SPLICING IN INSECTS

CROSS-REFERENCE TO RELATED APPLICATIONS

This application is a continuation of U.S. application Ser. No. 12/278,849, filed Mar. 6, 2009, which is a U.S. national stage application of International Application No. PCT/GB2007/000488, filed Feb. 12, 2007 and published in English on Aug. 16, 2007 as WO 2007/091099, which claims benefit of priority to United Kingdom Application GB 0621234.4, filed Oct. 25, 2006, and U.S. application Ser. No. 11/352,177, filed Feb. 10, 2006. All of the above applications are hereby incorporated by reference in their entirety to the extent not inconsistent with the disclosure herein.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750402000501SeqList.txt, date recorded: Jan. 8, 2016, size: 556,596 bytes).

All references cited herein are hereby incorporated by reference, unless otherwise apparent.

INTRODUCTION

The present invention relates to a gene expression system, in combination with splice control sequences, said control sequences providing a mechanism for alternative splicing.

Alternative splicing involves the removal of one or more introns and ligation of the flanking exons. This reaction is catalyzed by the spliceosome, a macromolecular machine composed of five RNAs and hundreds of proteins (Jurica, M. S. & Moore, M. J. (2003) *Mol. Cell* 12, 5-14). Alternative splicing generates multiple mRNAs from a single gene, thus increasing proteome diversity (Graveley, B. R. (2001) *Trends Genet.* 17, 100-107).

Alternative splicing also plays a key role in the regulation of gene expression in many developmental processes ranging from sex determination to apoptosis (Black, D. L. (2003) *Annu. Rev. Biochem.* 72, 291-336), and defects in alternative splicing have been linked to many human disorders (Caceres, J. F. & Kornblihtt, A. R. (2002) *Trends Genet.* 18, 186-193). In general, alternative splicing is regulated by proteins that associate with the pre-mRNA and function to either enhance or repress the ability of the spliceosome to recognize the splice site(s) flanking the regulated exon (Smith, C. W. & Valcarcel, J. (2000) *Trends Biochem. Sci.* 25, 381-388).

Whether a particular alternative exon will be included or excluded from a mature RNA in each cell is thought to be determined by the relative concentration of a number of positive and negative splicing regulators and the interactions of these factors with the pre-mRNA and components of the spliceosome (Smith, C. W. & Valcarcel, J. (2000) *Trends Biochem. Sci.* 25, 381-388).

Spliceosomes are large complexes of small nuclear RNA and protein particles (snRNPs) which assemble with pre-mRNA to achieve RNA splicing, by removing introns from eukaryotic nuclear RNAs, thereby producing mRNA which is then translated to protein in ribosomes.

Although at least 74% of human genes encode alternatively spliced mRNAs (Johnson, J. M., Castle, J., Garrett-Engele, P., Kan, Z., Loerch, P. M., Armour C. D., Santos, R., Schadt, E. E., Stoughton, R. & Shoemaker, D. D. (2003) *Science* 302, 2141-2144), relatively few splicing regulators have been identified.

SUMMARY OF THE INVENTION

Thus, in a first aspect, the present invention provides a polynucleotide expression system comprising:

at least one heterologous polynucleotide sequence encoding a functional protein, defined between a start codon and a stop codon, and/or polynucleotides for interference RNA (RNAi), to be expressed in an organism;

at least one promoter operably linked thereto; and at least one splice control sequence which, in cooperation with a spliceosome, is capable of (i) mediating splicing of an RNA transcript of the coding sequence to yield a first spliced messenger RNA (mRNA) product, and (ii) mediating at least one alternative splicing of said RNA transcript to yield an alternative spliced mRNA product;

wherein, when the at least one heterologous polynucleotide sequence encodes a functional protein, at least one of the mature mRNA products comprising a continuous Open Reading Frame (ORF) extending from said start codon to said stop codon, thereby defining a protein, which is said functional protein, or is related to said functional protein by at least one amino acid deletion, and which is functional when translated and, optionally, has undergone post-translational modification;

the mediation being selected from the group consisting of: sex-specific mediation, stage-specific mediation, germline-specific mediation, tissue-specific mediation, and combinations thereof.

The expression system may be DNA or RNA or a hybrid or combination of both. It is envisaged that the system comprises both ribo- and deoxy-ribonucleotides, i.e. portions of DNA and portions of RNA. These could correspond to different genetic elements, such that the system is a DNA/RNA hybrid, with some functional elements provided by DNA and others by RNA.

Preferably, the mediation is in a sex-specific, stage-specific, germline-specific or tissue-specific manner. In particular, sex-specific mediation is particularly preferred. However, it is also preferred that a combination of these four manners of mediation can be utilised. It is particularly preferred that, when a combination of these modes is used, that this includes sex-specific mediation. A particularly preferred example of such a combination is a combination of sex-specific, tissue-specific and stage-specific mediation of alternative splicing.

The system may be adapted for expression of a gene. Preferably, the polynucleotide sequence to be expressed comprises a coding sequence for a protein or polypeptide, i.e. at least one exon, and preferably 2 or more exons, capable of encoding a polypeptide, such as a protein or fragment thereof.

It will be understood that an exon is any region of DNA within a gene, that is present in a mature RNA molecule derived from that gene, rather than being spliced out from the transcribed RNA molecule. For protein coding genes, mature RNA molecules correspond to mature mRNA molecules, which may encode one or more proteins or polypeptides. Exons of many eukaryotic genes interleave with segments of non-coding DNA.

The at least one heterologous polynucleotide sequence may encode a functional protein, defined between a start codon and a stop codon to be expressed in an organism.

Alternatively, or in addition, the at least one heterologous polynucleotide sequence encodes or comprises polynucleotides for interference RNA (RNAi), to be expressed in an organism.

These sequences, to be expressed in the organism, may also be referred to as sequences, the expression of which is to be regulated in said organism.

Preferably, the polynucleotide sequence to be expressed comprises two or more coding exons, being segments or sequences of polynucleotides that encode amino acids when translated from mRNA. Preferably, the different exons are differentially spliced together to provide alternative mRNAs. Preferably, said alternative spliced mRNAs have different coding potential, i.e. encode different proteins or polypeptide sequences. Thus, the expression of the coding sequence is regulated by alternative splicing in the above-mentioned manners of mediation.

The polynucleotide sequence to be expressed may comprise polynucleotides for interference RNA (RNAi). Such sequences are capable of providing, for instance, one or more stretches of double-stranded RNA (dsRNA), preferably in the form of a primary transcript, which in turn is capable of processing by the RNA Pol III-like enzyme "Dicer." Such stretches include, for instance, stretches of single-stranded RNA that can form loops, such as those found in short-hairpin RNA (shRNA), or with longer regions that are substantially self-complementary.

Thus, where the system is DNA, the polynucleotides for interference RNA are deoxyribonucleotides that, when transcribed into pre-RNA ribonucleotides, provide a stretch of dsRNA, as discussed above.

Polynucleotides for interference RNA are particularly preferred when said polynucleotides are positioned to minimise interference with alternative splicing. This may be achieved by distal positioning of these polynucleotides from the alternative splicing control sequences, preferably 3' to the control sequences. In another preferred embodiment, substantially self-complementary regions may be separated from each other by one or more splice control sequences, such as an intron, that mediate alternative splicing. Preferably, the self-complementary regions are arranged as a series of two or more inverted repeats, each inverted repeat separated by splice control sequence, preferably an intron, as defined elsewhere.

In this configuration, different alternatively spliced transcripts may have their substantially self-complementary regions separated by different lengths of non-self-complementary sequence in the mature (post-alternative-splicing) transcript. It will be appreciated that regions that are substantially self-complementary are those that are capable of forming hairpins, for instance, as portions of the sequence are capable of base-pairing with other portions of the sequence. These two portions do not have to be exactly complementary to each other, as there can be some mismatching or toleration of stretches in each portion that do not base-pair with each other. Such stretches may not have an equivalent in the other portion, such that symmetry is lost and "bulges" form, as is known with base-pair complementation in general.

In another preferred embodiment, one or more segment of sequence substantially complementary to another section of the primary transcript is positioned, relative to the at least one splice control sequence, so that it is not included in all of the transcripts produced by alternative splicing of the primary transcript. By this method, some transcripts are produced that tend to produce dsRNA while others do not; by mediation of the alternative splicing, e.g. sex-specific mediation, stage-specific mediation, germline-specific mediation, tissue-specific mediation, and combinations thereof, dsRNA may be produced in a sex-specific, stage-specific, germline-specific or tissue-specific manner, or combinations thereof.

The system is preferably capable of expressing at least one protein of interest, i.e. said functional protein to be expressed in an organism. Said at least one protein of interest may have a therapeutic effect or may, preferably, be a marker, for instance DsRed, Green Fluorescent Protein (GFP) or one or more of their mutants or variants, or other markers that are well known in the art.

Most preferably, the functional protein to be expressed in an organism has a lethal, deleterious or sterilizing effect. Where reference is made herein to a lethal effect, it will be appreciated that this extends to a deleterious or sterilizing effect, such as an effect capable of killing the organism per se or its offspring, or capable of reducing or destroying the function of certain tissues thereof, of which the reproductive tissues are particularly preferred, so that the organism or its offspring are sterile. Therefore, some lethal effects, such as poisons, will kill the organism or tissue in a short time-frame relative to their life-span, whilst others may simply reduce the organism's ability to function, for instance reproductively.

A lethal effect resulting in sterilization is particularly preferred, as this allows the organism to compete in the natural environment ("in the wild") with wild-type organisms, but the sterile insect cannot then produce viable offspring. In this way, the present invention achieve a similar result to techniques such as the Sterile Insect Technique (SIT) in insects, without the problems associated with SIT, such as the cost, danger to the user, and reduced competitiveness of the irradiated organism.

Preferably, the system comprises at least one positive feedback mechanism, namely at least functional protein to be differentially expressed, via alternative splicing, and at least one promoter therefor, wherein a product of a gene to be expressed serves as a positive transcriptional control factor for the at least one promoter, and whereby the product, or the expression of the product, is controllable. Preferably, an enhancer is associated with the promoter, the gene product serving to enhance activity of the promoter via the enhancer. Preferably, the control factor is the tTA gene product or an analogue thereof, and wherein one or more tetO operator units is operably linked with the promoter and is the enhancer, tTA or its analogue serving to enhance activity of the promoter via tetO. It is preferred that functional protein encodes the tTAV or tTAF product and preferably, the promoter is substantially inactive in the absence of the positive transcriptional control factor. Suitable, preferably minimal, promoters for this system can be selected from: hsp70, a P minimal promoter, a CMV minimal promoter, an Act5C-based minimal promoter, a BmA3 promoter fragment, a promoter fragment from hunchback, an Adh core promoter, and an Act5C minimal promoter, or combinations thereof.

In one embodiment, the functional protein is preferably an apoptosis-inducing factor, such as the AIF protein described for instance in Candé et al (*Journal of Cell Science* 115, 4727-4734 (2002)) or homologues thereof. AIF homologues are found in mammals and even in invertebrates, including insects, nematodes, fungi, and plants, meaning that the AIF gene has been conserved throughout the eukaryotic kingdom. Also preferred is Hid, the protein product of the head involution defective gene of *Drosophila melanogaster*, or Reaper (Rpr), the product of the reaper gene of *Drosophila*, or mutants thereof. Use of Hid was described by Heinrich and Scott (*Proc. Natl Acad. Sci USA* 97, 8229-8232 (2000). Use of a mutant derivative, $Hid^{Ala5}$ was described by Horn and Wimmer (*Nature Biotechnology* 21, 64-70 (2003)). Use of a mutant derivative of Rpr, $Rpr^{KR}$, is described herein (see also White et al 1996, Wing et al., 2001, and Olson et al., 2003). Both Rpr and Hid are pro-apoptotic proteins, thought to bind to IAP1. IAP1 is a well-conserved anti-apoptotic protein. Hid and Rpr are therefore expected to work across a wide phylogenetic range (Huang et al., 2002, Vernooy et al., 2000) even though their own sequence is not well conserved.

Also preferred is Nipp1Dm, the *Drosophila* homologue of mammalian Nipp1 (Parker et al *Biochemical Journal* 368, 789-797 (2002); Bennett et al., *Genetics* 164, 235-245 (2003)). Nipp1Dm is another example of a protein with lethal effect if expressed at a suitable level, as would be understood by the skilled person. Indeed, many other examples of proteins with a lethal effect will be known to the person skilled in the art.

It is also preferred that the functional protein itself a transcriptional trans activator, such as the tTAV system described above.

It is preferred that the promoter can be activated by environmental conditions, for instance the presence or absence of a particular factor such as tetracycline in the tet system described herein, such that the expression of the gene of interest can be easily manipulated by the skilled person. Alternatively, a preferred example of a suitable promoter is the hsp70 heat shock promoter, allowing the user to control expression by variation of the environmental temperature to which the hosts are exposed in a lab or in the field, for instance. Another preferred example of temperature control is described in Fryxell and Miller (*Journal of Economic Entomology* 88, 1221-1232 (1995)).

Also preferred as a promoter is the sryα embryo-specific promoter (Horn & Wimmer (2003) from *Drosophila melanogaster*, or its homologues, or promoters from other embryo-specific or embryo-active genes, such as that of the *Drosophila* gene slow as molasses (slam), or its homologues from other species.

It is also preferred that the system comprises other upstream, 5' factors and/or downstream 3' factors for controlling expression. Examples include enhancers such as the fat-body enhancers from the *Drosophila* yolk protein genes, and the homology region (hr) enhancers from baculoviruses, for example AcMNPV. It will also be appreciated that the RNA products will include suitable 5' and 3' UTRs, for instance.

The splice control sequence allows an additional level of control of protein expression, in addition to the promoter and/or enhancer of the gene. For instance, tissue or sex-specific expression in insect embryos only would be extremely difficult by conventional methods. Promoters with this specificity are unknown, even in *Drosophila*. However, using combinatorial control according to the present invention, an embryo-specific promoter, for example sryα, can be combined with a suitable alternative splicing system.

It is preferred that any combination of promoter and alternative splicing mechanism is envisaged. The promoter is preferably specific to a particular protein having a short temporal or confined spatial effect, for example a cell-autonomous effect.

Alternatively, it is preferred that the promoter may be specific for a broader class of proteins or a specific protein that has a long-term and/or wide system effect, such as a hormone, positive or negative growth factor, morphogen or other secreted or cell-surface signalling molecule. This would allow, for instance, a broader expression pattern so that a combination of a morphogen promoter with a stage-specific alternative splicing mechanism could result in the morphogen being expressed only once a certain life-cycle stage was reached, but the effect of the morphogen would still be felt (i.e. the morphogen can still act and have an effect) beyond that life-cycle stage. Preferred examples would be the morphogen/signaling molecules Hedgehog, Wingless/WNTs, TGFβ/BMPs, EGF and their homologues, which are well-known evolutionarily-conserved signalling molecules.

It is also envisaged that a promoter that is activated by a range of protein factors, for instance transactivators, or which has a broad systemic effect, such as a hormone or morphogen, could be used in combination with an alternative splicing mechanism to achieve a tissue and sex-specific control or sex and stage-specific control, or other combinations of stage-, tissue, germ-line- and sex-specific control.

It is also envisaged that more than one promoter, and optionally an enhancer therefor, can be used in the present system, either as alternative means for initiating transcription of the same protein or by virtue of the fact that the genetic system comprises more than one gene expression system (i.e. more than one gene and its accompanying promoter).

In a further aspect, the present invention provides a method of transformation, comprising expressing two or more RNA molecules, derived from a single primary transcript, or substantially similar primary transcripts, by alternative splicing, said two or more RNA molecules preferably encoding different proteins or polypeptides, in an organism by contacting the organism with the expression system and preferably inducing expression of the expression system. Methods of introduction or transformation of the gene system and induction of expression are well known in the art with respect to the relevant organism.

Also provided are organisms (i.e. transformants) transformed by the present system.

Where reference to a particular nucleotide or protein sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

Figures 33, 34:
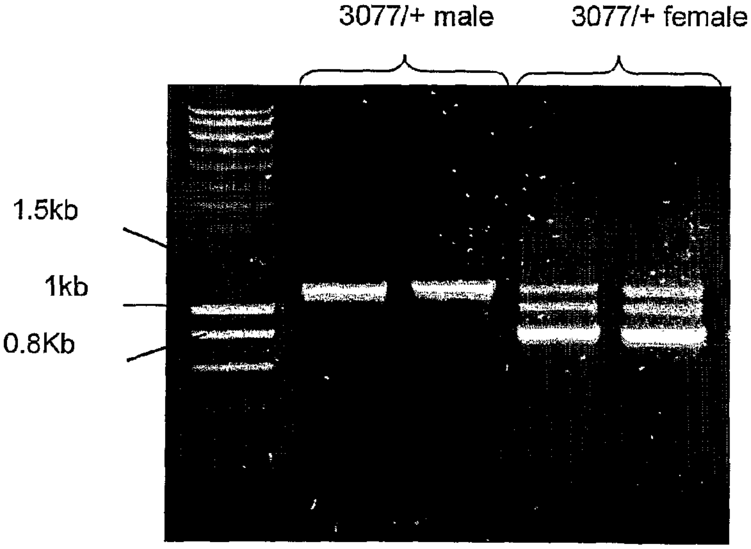

The sequences provided can tolerate some sequence variation and still splice correctly. There are a few nucleotides known to be important. These are the ones required for all splicing, e.g. as shown in FIG. 34 below. The initial GU and the final AG of the intron are particularly important and therefore preferred, as discussed elsewhere, though ~5% of introns start GC instead. This consensus sequence is preferred, although it applies to all splicing, not specifically to alternative splicing. In FIG. 34, Pu=A or G; Py=C or U.

Preferably, the system is or comprises a plasmid. As mentioned above, this can be either DNA, RNA or a mixture of both. If the system comprises RNA, then it may be preferable to reverse-translate the RNA into DNA by means of a Reverse Transcriptase. If reverse transcription is required, then the system may also comprise a coding sequence for the RT protein and a suitable promoter therefor. Alternatively, the RTase and promoter therefore may be provided on a separate system, such as a virus. In this case, the system would only be activated following infection with that virus. The need to include suitable cis-acting sequences for the reverse transcriptase or RNA-dependent RNA polymerase would be apparent to the person skilled in the art.

However, it is particularly preferred that the system is predominantly DNA and more preferably consists only of DNA, at least with respect to the sequences to be expressed in the organism.

Whilst in some embodiments the at least one heterologous polynucleotide sequence to be expressed in an organism is a polynucleotide sequence for interference RNA (RNAi), it is particularly preferred that it is a polynucleotide sequence capable off encoding a functional protein. The description will predominantly focus on polynucleotide sequences encoding a functional protein, but it will be understood that this also refers to polynucleotides for interference RNA (RNAi), unless otherwise apparent.

It will be understood that reference is made to start and stop codons between which the polynucleotide sequence to be expressed in an organism is defined, but that this does not exclude positioning of the at least one splice control sequence, elements thereof, or other sequences, such as introns, in this region. In fact, it will be apparent form the present description that the splice control sequence, can, in some embodiments, be positioned in this region.

Furthermore, the splice control sequence, for instance, can overlap with the start codon at least, in the sense that the G of the ATG can be, in some embodiments, be the initial 5' G of the splice control sequence. Thus, the term "between" can be thought of as referring to from the beginning (3' to the initial nucleotide, i.e. A) of the start codon, preferably 3' to the second nucleotide of the start codon (i.e. T), up to the 5' side of the first nucleotide of the stop codon. Alternatively, as will be apparent by a simple reading of a polynucleotide sequence, the stop codon may also be included.

The at least one heterologous polynucleotide sequence to be expressed in an organism is a heterologous sequence. By "heterologous", it would be understood that this refers to a sequence that would not, in the wild type, be normally found in association with, or linked to, at least one element or component of the at least one splice control sequence. For example, where the splice control sequence is derived from a particular organism, and the heterologous polynucleotide is a coding sequence for a protein or polypeptide, i.e. is a polynucleotide sequence encoding a functional protein, then the coding sequence could be derived, in part or in whole, from a gene from the same organism, provided that that the origin of at least some part of the transcribed polynucleotide sequence was not the same as the origin of the at least one splice control sequence. Alternatively, the coding sequence could be from a different organism and, in this context, could be thought of as "exogenous". The heterologous polynucleotide could also be thought of as "recombinant", in that the coding sequence for a protein or polypeptide are derived from different locations, either within the same genome (i.e. the genome of a single species or sub-species) or from different genomes (i.e. genomes from different species or subspecies).

Heterologous can refer to a sequence other than the splice control sequence and can, therefore, relate to the fact the promoter, and other sequences such as 5' UTR and/or 3'UTR can be heterologous to the polynucleotide sequence to be expressed in the organism, provided that said polynucleotide sequence is not found in association or operably linked to the promoter, 5' UTR and/or 3'UTR, in the wildtype, i.e. the natural context of said polynucleotide sequence, if any.

It will be understood that heterologous also applies to "designer" or hybrid sequences that are not derived from a particular organism but are based on a number of components from different organisms, as this would also satisfy the requirement that the sequence and at least one component of the splice control sequence are not linked or found in association in the wildtype, even if one part or element of the hybrid sequence is so found, as long as at least one part or element is not. Preferably, a portion of at least 50 nucleotides of the hybrid sequence is not found in association with the at least one component of the splice control sequence, more preferably 200 nucleotides and most preferably 500 nucleotides.

It will also be understood that synthetic versions of naturally occurring sequences are envisioned. Such synthetic sequences are also considered as heterologous, unless they are of identical sequence to a sequence which would, in the wild type or natural context, be normally found in association with, or linked to, at least one element or component of the at least one splice control sequence.

This applies equally to where the heterologous polynucleotide is a polynucleotide for interference RNA.

In one embodiment, where the polynucleotide sequence to be expressed comprises a coding sequence for a protein or polypeptide, it will be understood that reference to expression in an organism refers to the provision of one or more transcribed RNA sequences, preferably mature mRNAs, but this may, preferably, also refer to translated polypeptides in said organism.

RT-PCR, which demonstrates the presence of a transcript, not of a protein, may be used to identify transcribed RNA sequences. This is also particularly useful when the protein itself is not translated or is not functional or not identifiable by antibodies raised against the naturally-occurring or wild-type protein, due to RNAi, post-translational modification or distorted folding.

In another embodiment, where the polynucleotide sequence to be expressed comprises polynucleotides for interference RNA, it will also be understood that reference to expression in an organism refers to the interaction of the polynucleotides for interference RNA, or transcripts thereof, in the RNAi pathway, for instance by binding of Dicer or formation of small interfering RNA (siRNA). Indeed, it is particularly preferred that the polynucleotides for interference RNA comprise siRNA sequences and are, therefore, preferably 20-25 nucleotides long, especially where the organism is mammalian.

In insects and nematodes especially, it is preferred to provide portion of dsRNA, for instance by hairpin formation, which can then be processed by the Dicer system. Mammalian cells generally produce an interferon response against long dsRNA sequences, so for mammalian cells it is more common to provide shorter sequences, such as siRNAs. Antisense sequences or sequences having homology to microRNAs that are naturally occurring RNA molecules targeting protein 3' UTRs are also envisaged as sequences for RNAi according to an embodiment of the present invention.

Each splice control sequence in the system comprises at least one splice acceptor site and at least one splice donor site. The number of donor and acceptor sites may vary, depending on the number of segments of sequence that are to be spliced together. Preferably, branch sites are included in each splice control sequence. A branch site is the sequence to which the splice donor is initially joined, see FIG. 32, which shows that splicing occurs in two stages, in which the 5' exon is separated and then is joined to the 3' exon.

Referring to said figure, the A is the only essential nucleotide, and is, therefore, preferably included. Without being bound by theory, it is believed that pre-mRNA splicing proceeds via a lariat intermediate, just as it does in group II self-splicing. First, cleavage occurs at the 5' junction—sometimes called the splice donor site. The phosphate at the 5' end of the intron then becomes linked to the 2' OH of an adenine approximately 25 nucleotides upstream of the 3' end of the intron, which is sometimes called the acceptor site. This A residue is called the branch point. The next step is that cleavage occurs at the 3' splice junction and the 5' phosphate of the downstream exon is joined to the 3' OH of the upstream exon.

It is particularly preferred that the manner or mechanism of alternative splicing is sex-specific. Preferably, the splice control sequence is derived from a tra intron. However, it is particularly preferred that the alternative splicing mechanism is derived from the Medfly transformer gene Cctra, or from another ortholog or homolog of the *Drosophila transformer* gene, preferably from *C. rosa*, or *B. zonata* especially one derived from a tephritid fruit fly.

It is also preferred that the splice control sequence is derived from the alternative splicing mechanism of the Actin-4 gene, in particular that from *Aedes* spp. and most preferably from AaActin-4, which is a gene from *Aedes/Stegomyia aegypti* which shows tissue, stage and sex-specific splicing.

Preferably, alternative splicing, particularly that mediated by Actin-4, may add sequences that affect RNA translation or stability, for instance.

It is also preferred that the splicing mechanism comprises at least a fragment of the doublesex (dsx) gene, preferably that derived from *Drosophila, B. mori*, Pink Boll Worm, Codling Moth, or a mosquito, in particular *A. gambiae* or especially *A. aegypti.*

It is preferred that the splice control sequence and the heterologous polynucleotide sequence encoding a functional protein, defined between a start codon and a stop codon, and/or polynucleotides for interference RNA (RNAi), to be expressed in an organism, are provided in the form of a minigene construct or a cassette exon.

This is particularly preferred when the splice control sequence is derived from dsx (preferably minigene 1 as described in the Examples and represented in SEQ ID NO. 149 (exons are present at positions 1-135, 1311-2446 and 3900-4389 of SEQ ID NO. 149) which was included in construct LA3491) or Actin-4.

Particularly preferred examples of the present invention are provided in the Examples, and can be selected from the group consisting of the plasmids or constructs, in particular any of those according to any one of FIGS. 19-31, especially any of the plasmids shown in FIGS. 16-18, 22-24, 26-32, 49, 52-55, and 61-69, and/or SEQ ID NOs 46-48, 50-56, 143-145 and 151-162.

Preferably, the functional protein to be expressed in an organism is tTAV, tTAV2 or tTAV3.

Further proteins to be expressed in the organism are, or course envisaged, in combination with said functional protein, preferably a lethal gene as discussed elsewhere.

A continuous ORF may be also be thought of as an uninterrupted ORF, i.e. a polynucleotide sequence in mature mRNA, which does not include non-coding nucleotides, for instance those having the potential to be translated into amino acids. In this definition, it is preferred that the stop codon is not included.

In some embodiments, the at least one splice control sequence regulates the alternative splicing by means of both intronic and exonic nucleotides. However, in one embodiment, it is particularly preferred that the at least one splice control sequence is an intronic splice control sequence. In other words, it is preferred that the at least one splice control sequence is substantially derived from polynucleotides that form part of an intron and are thus excised from the primary transcript by splicing, such that these nucleotides are not retained in the mature mRNA sequence.

Therefore, intronic sequences can be thought of as distinct from "exonic" sequences, which are retained in the processed (post-splicing) RNA molecule. Where the processed RNA molecule encodes a protein or polypeptide sequence, and is capable of being translated, i.e. has the correct structure and modifications such as a cap, and a polyadenylation signal, for instance, it is known as mature or processed mRNA and some of the exonic sequences then code for amino acids, when translated.

It will be understood that in alternative splicing, sequences may be intronic under some circumstances (i.e. in some alternative splicing variants), but exonic under other circumstances (i.e. in other variants). Thus, the at least one splice control sequence of the present invention is preferably substantially derived from polynucleotides that form part of an intron in at least one alternative splicing variant, i.e. in either the first spliced mRNA product or the at least one alternatively spliced mRNA product. Thus, introns or intronic sequences can be viewed as spliced out in at least one transcript or transcript type.

For example, consider the tra intron from *C. capitata* (Cctra intron), which is a particularly preferred example of an at least one splice control sequence according to the present invention. According to FIG. 2A of Pane et al, reproduced as FIG. 33, all 8 of the putative Tra/Tra2 binding sites highlighted are in intronic sequence in the sense that they are in portions of sequence spliced out in transcript F1, but on the other hand 6 out of the 8 are exonic in the sense that they are in exons that are included or retained in either transcript M1 or M2, or both. Thus, these Tra/Tra2 binding sites are intronic in the present sense as they are capable of controlling alternative splicing, but are spliced out, i.e. not present, in at least one alternative splicing variant, i.e. at least one mRNA that has been spliced in an alternative manner from pre-RNA.

In "normal" (non-alternative) splicing and in alternative splicing, introns are generally removed from the pre-RNA to form a spliced mRNA, which may then be translated into a polypeptide, such as a protein or protein fragment, having an amino acid sequence. Thus, it will be readily apparent to the skilled person how to determine those sequences of the present system that are to be considered intronic, rather than exonic.

It will, of course be appreciated that only part of an mRNA is actually translated, i.e. typically the part between the start codon and the stop codon, although it will be understood that sometimes multiple starts and stops are present. Thus, when reference is made herein to translation of an mRNA sequence, it will be appreciated that this is referring to translation of the portion starting at the first nucleotide of the start codon and ending after the last nucleotide before the start of the stop codon, which may be considered as the coding portion.

As mentioned above, exonic sequences may be involved in the mediation of the control of alternative splicing, but it is preferred that at least some intronic control sequences are involved in the mediation of the alternative splicing. In other words, the gene expression system of the present invention may also include splice control sequences present in exons, as long as there is some intronic involvement of control. Particularly preferred examples of these are splice control sequences derived from or containing elements of the dsx gene, where, without being bound by theory, it is thought that exonic sequences assist in the mechanism of alternative splicing.

Thus, in some embodiments, the at least one splice control sequence does comprise exonic sequence and it will be understood that this is envisaged by definitions used to describe the present invention. Thus, as will be apparent, it is possible for some nucleotides to be encompassed within the definition of the at least one splice control sequence and also within the definition of a polynucleotide sequence encoding a functional protein. In other words, the definition of these elements can overlap, such that certain nucleotides can be covered by the definition of more than one element.

However, the skilled person will recognise that this is not unusual in molecular biology, as nucleotides can often perform more than one role. For instance, in the present invention, a nucleotide can form part of a coding sequence for a functional protein, but could also form part of a sequence recognised and bound by a splicing factor, an example of which the TRA protein or TRA/TRA complex, as discussed elsewhere. This is not unusual as, for instance, some viruses have highly concentrated genome where the same stretch of polynucleotides can code for two or even three different proteins, each read in a different frame.

Of course, it may also be that the splice control sequence or sequences are solely intronic, i.e. with no exonic influence. Indeed, this is particularly preferred.

In some embodiments, it is preferred that the at least one splice control sequence is capable of being removed from the pre-RNA, by splicing. Preferably, the at least one splice control sequence does not result in a frameshift in at least one splice variant. Preferably this is a splice variant encoding a full-length functional protein. In other words, at least the one splice control sequence preferably does not mediate the removal of nucleotides that form part, or were intended to form part of, the polynucleotide sequence encoding a functional protein, defined between a start codon and a stop codon, and/or polynucleotides for interference RNA (RNAi), to be expressed in an organism. By this it is meant that nucleotides that are excised by splicing, in at least one splice variant, are not nucleotides that encode amino acids in the wild type form of the protein or gene. One or more splice variants may have said nucleotides excised, but at least one variant must retain these nucleotides, so that a frameshift is not induced in the at least one variant. These removed nucleotides are those that are removed in addition to the sequences that are normally spliced out such as the intron.

However, in view of the above, it is also envisaged that different splice variants may result in the same sequence being read in different frames.

Interaction of the at least one splice control sequence with cellular splicing machinery, e.g. the spliceosome, leads to or mediates the removal of a series of, preferably, at least 50 consecutive nucleotides from the primary transcript and ligation (splicing) together of nucleotide sequences that were not consecutive in the primary transcript (because they, or their complement if the antisense sequence is considered, were not consecutive in the original template sequence from which the primary transcript was transcribed). Said series of at least 50 consecutive nucleotides comprises an intron. This mediation acts preferably in a sex-specific, stage-specific, germline-specific or tissue-specific manner, or combination thereof, such that equivalent primary transcripts in different sexes, stages, tissue types, etc, tend to remove introns of different size or sequence, or in some cases may remove an intron in one case but not another. This phenomenon, the removal of introns of different size or sequence in different circumstances, or the differential removal of introns of a given size or sequence, in different circumstances, is known as alternative splicing. Alternative splicing is a well-known phenomenon in nature, and many instances are known, see above.

In some preferred embodiments, the at least one splice control sequence is associated with a heterologous open reading frame such that, in at least one splice variant, the heterologous open reading frame is disrupted, e.g. by a stop codon or frameshift, while in at least one alternative splice variant the heterologous open reading frame is not disrupted. Transcripts of the second type encode or potentially encode a functional protein, whereas those of the first type encode a protein with altered, disrupted or even no function, activity or stability relative to those of the second type.

In general, it will be apparent to the person skilled in the art that the heterologous open reading frame may itself be a composite or fusion of sequences from various sources. Splicing to produce a functional protein may still produce an altered protein relative to the prototype heterologous open reading frame, for example if the inserted alternatively spliced intron includes sequence that is exonic in all alternative splicing forms, and therefore retained in mature mRNAs of the second type. However, it is particularly preferred that at least one transcript removes all, or substantially all, of the inserted alternatively spliced sequence, such that the heterologous open reading frame is restored, or substantially restored, to intact form, with little or no sequence endogenously associated with the intron remaining in the mature mRNA. Endogenous is used here in contrast to heterologous, so it will be understood that this refers to a sequence that would, in the wild type, be normally found in association with, or linked to, at least one element or component of the at least one splice control sequence.

Alternatively, one or more transcripts may remove additional nucleotides, so that the heterologous open reading frame is disrupted, not by the insertion of extra nucleotides (for example stop codon or frame shift, but also potentially coding sequence that disrupts the function), but rather by deletion of nucleotides from the heterologous open reading frame, for example in such a way as to induce a frameshift. One or more splice variants may have said nucleotides excised, but at least one variant must retain these nucleotides, so that a frameshift is not induced in the at least one variant. These removed nucleotides are those that are removed in addition to the sequences that are normally spliced out such as the intron, where an intronic sequence may be considered as one that forms part of an intron in at least one alternative splicing variant of the natural analogue.

When exonic nucleotides are to be removed, then these must be removed in multiples of three, if it is desired to avoid to avoid a frameshift, but as a single nucleotide or multiples of two (that are not also multiples of three) if it is desired to induce a frameshift. It will be appreciated that if only one or certain multiples of two nucleotides are removed, then this could lead to a completely different protein sequence being encoded at or around the splice junction of the mRNA.

This is particularly the case in an embodiment of the system where cassette exons are used to interrupt an open reading frame in some splice variants but not others, such as in, for example, tra, especially Cctra.

In another preferred embodiment of the present invention, all or part of an open reading frame is on a cassette exon, for example some Dsx embodiments derived from *Aedes*, are provided with, for instance, a tTAV coding region on a cassette exon that is only present in female-specific splice variants.

Where mediation of alternative splicing is sex-specific, it is preferred that the splice variant encoding a functional protein to be expressed in an organism is the F1 splice variant, i.e. a splice variant found only or predominantly in females, and preferably is the most abundant variant found in females, although this is not essential. Correspondingly for configurations where all or part of a functional open reading frame is on a cassette exon, it is preferred that this cassette exon is included in transcripts found only or predominantly in females, and preferably such transcripts are, individually or in combination, the most abundant variants found in females, although this is not essential.

In one preferred embodiment, sequences are included in a hybrid or recombinant sequence or construct which are derived from naturally occurring intronic sequences which are themselves subject to alternative splicing, in their native or original context. Therefore, an intronic sequence may be considered as one that forms part of an intron in at least one alternative splicing variant of the natural analogue. Thus, sequences corresponding to single contiguous stretches of naturally occurring intronic sequence are envisioned, but also hybrids of such sequences, including hybrids from two different naturally occurring intronic sequences, and also sequences with deletions or insertions relative to single contiguous stretches of naturally occurring intronic sequence, and hybrids thereof. Said sequences derived from naturally occurring intronic sequences may themselves be associated, in the invention, with sequences not themselves part of any naturally occurring intron. If such sequences are transcribed, and preferably retained in the mature RNA in at least one splice variant, they may then be considered exonic.

It will also be appreciated that reference to a "frame shift" could also refer to the direct coding of a stop codon, which is also likely to lead to a non-functioning protein as would a disruption of the spliced mRNA sequence caused by insertion or deletion of nucleotides. Production from different splice variants of two or more different proteins or polypeptide sequences of differential function is also envisioned, in addition to the production of two or more different proteins or polypeptide sequences of which one or more has no predicted or discernable function. Also envisioned is the production from different splice variants of two or more different proteins or polypeptide sequences of similar function, but differing subcellular location, stability or capacity to bind to or associate with other proteins or nucleic acids.

Preferably, the at least one splice control sequence is intronic and comprises on its 5' end a guanine (G) nucleotide. In other words, the 5' nucleotide of the splice control sequence, 3' to the splice donor site, and preferably at the interface or junction of the exon with the splice control sequence, is Guanine (G), in the pre-RNA, or C in an antisense DNA sequence corresponding thereto.

Furthermore, the adjacent nucleotide (3' to said G) is preferably Cytosine (C) in the pre-RNA, or a corresponding G in a DNA sequence, but is most preferably Uracil (U) in the pre-RNA, or a corresponding A in a DNA antisense sequence. Thus, the two 5' nucleotides of the splice control sequence are preferably 5'GT with respect to the DNA sense strand, 5'-GU in the primary transcript.

Preferably, at least one intronic splice control sequence also comprises on its 3' end a 3' Guanine nucleotide and preferably AG-3' at the junction of the splice acceptor site with the exon, for instance, see FIG. 34.

Preferably, the flanking sequence 5' to the splice donor site in the system comprises 5'-TG, so that the sequence can be represented 5'-TG-*-splice control sequence-**-3', where * represents the splice donor site and ** represents the splice acceptor site.

Preferably, the splice control sequence is also flanked on its 3' side by a G nucleotide, and most preferably by GT nucleotides, such that the sequence could be represented as: 5'-TG-*-splice control sequence-**-GT-3'. It will be appreciated that this is the sense strand DNA sequence (TG). Thus, the transcribed pre-RNA will read UG for instance, where U replaces T.

Derivatives of Guanine or Thymine having the same function are also envisaged.

It is particularly preferred that the splicing is sex-specific and further mediated or controlled by binding of the TRA protein or TRA/TRA2 protein complex, or homologues thereof. In insects, for instance, the TRA protein is differentially expressed in different sexes. In particular, the TRA protein is known to be present largely in females and, therefore, mediates alternative splicing in such a way that a coding sequence is expressed in a sex-specific manner, i.e. that in some cases a protein is expressed only in females or at a much higher level in females than in males or, alternatively, in other cases a protein is expressed only in males, or at a much higher level in males than in females. Whilst it is preferred that the protein is expressed only in males, it is particularly preferred that the protein is expressed only in females, however. The mechanism for achieving this sex-specific alternative splicing mediated by the TRA protein or the TRA/TRA-2 complex is known and is discussed, for instance, in Pane et al (Development 129, 3715-3725 (2002)).

Preferably, the at least one splice control sequence comprises, and more preferably consists of, the tra intron derived from the tra gene of *Ceratitis capitata* (Cctra), which has one alternatively spliced region. In the F1 transcript, as illustrated by FIG. 33 (FIG. 2A of Pane et al (2002) supra), this is the first intron. Homologues of the tra gene in other species, such as *Bactrocera oleae, Ceratitis rosa, Bactrocera zonata* and *Drosophila melanogaster* also have alternatively spliced regions in a similar location within the tra coding sequence. tra introns derived from these insects are also particularly preferred.

The splicing pattern in Cctra in particular is well conserved, with those transcripts found in males containing additional exonic material relative to the F1 transcript, such that these transcripts do not encode full-length, functional Tra protein. By contrast, the F1 transcript does encode full-length, functional Tra protein; this transcript is substantially female-specific at most life-cycle stages, though it is speculated that very early embryos of both sexes may contain a small amount of this transcript. We describe the sequence spliced out of the F1 transcript, but not the male-specific or non-sex-specific transcripts, as the tra intron, or even the tra F1 intron. Thus the version of this sequence found in the Cctra gene is the Cctra intron.

Thus the tra gene is regulated in part by sex-specific alternative splicing, while its key product, the Tra protein, is itself involved in alternative splicing. In insects, sex-specific alternative splicing mediated by the TRA protein, or a complex comprising the TRA and TRA2 proteins, include Dipteran splice control sequences derived from the doublesex (dsx) gene and also the tra intron itself, although this would exclude the tra intron from *Drosophila* (Dmtra), which is principally mediated by the Sxl gene product in *Drosophila*, rather than TRA or the TRA/TRA2 complex.

Outside of *Drosophila*, the Sxl gene product is not differentially expressed in the different sexes. Sxl is not thought to act in the mediation of sex-specific alternative splicing in non-Drosophilid insects.

Examples of the TRA protein that binds to the binding protein sites (the nucleotide sequences specifically recognised by the TRA protein) in the tra intron are preferably from Diptera, preferably from the family Tephritidae, more preferably from the genera *Ceratitis, Anastrepha* or *Bactrocera*. However, it is also envisaged that other Dipterans, such as Drosophilids or mosquitoes of the various forms discussed below, are also capable of providing the TRA protein or homologues thereof that are capable of binding to the appropriate sites on the splice control sequences derived from dsx gene, the tra gene or the tra intron, i.e. the alternatively spliced tra intron completely removed in the F1 transcript, even in those cases, such as *Drosophila*, where the natural tra gene (Dmtra) is not itself regulated by TRA protein. In some embodiments, the "tra intron" may be defined as a splice control sequence wherein alternative splicing of the RNA transcript is regulated by TRA, for instance binding thereof, alone or in combination (i.e. when complexed) with TRA2. This excludes the tra intron from *Drosophila*.

It is particularly preferred that the splice control sequences are derived from the tra intron. Said tra intron may be derived, as discussed elsewhere, from *Ceratitis, Anastrepha* or *Bactrocera*. The *Ceratitis capitata* tra intron from the transformer gene was initially characterised by Pane et al (2002), supra. However, it will be appreciated that homologues exist in other species, and can be easily identified in said species and also in their various genera. Thus, when reference is made to tra it will be appreciated that this also relates to tra homologues in other species, especially in *Ceratitis, Anastrapha* or *Bactrocera* species.

By "derived" it will be understood that, using reference to the tra intron, this refers to sequences that approximate to or replicate exactly the tra intron, as described in the art, in this case by Pane et al (2002), supra. However, it will be appreciated that, as these are intronic sequences, that some nucleotides can be added or deleted or substituted without a substantial loss in function.

Preferred examples of this include the dsx intron, preferably provided in the form of a minigene. In this instance, it may be preferable to delete, as we have done in the Examples, sizable amounts from alternatively spliced introns, e.g. 90% or more of an intron in some cases, whilst still retaining the alternative splicing function. Thus, whilst large deletions are envisioned, it is also envisaged that smaller, e.g. even single nucleotide insertions, substitutions or deletions are also preferred.

The exact length of the splice control sequence derived from the tra intron is not essential, provided that it is capable of mediating alternative splicing. In this regard, it is thought that around 55 to 60 nucleotides is the minimum length for a modified tra intron, although the wild type tra intron (F1 splice variant) from *C. capitata* is in the region of 1345 nucleotides long.

It is particularly preferred that the full length 1345 ntd sequence of Cctra is used.

As with all nucleotide sequences discussed herein, it is preferred that a certain degree of sequence homology is envisaged, unless otherwise apparent. Thus, it is preferred that the splice control sequence has at least 80% sequence homology with the reference SEQ ID NO., preferably at least 80% sequence homology with the reference SEQ ID NO., preferably at least 80% sequence homology with the reference SEQ ID NO., more preferably at least 90% sequence homology with the reference SEQ ID NO., more preferably at least 95% sequence homology with the reference SEQ ID NO., even more preferably at least 99% sequence homology with the reference SEQ ID NO., and most preferably at least 99.9% sequence homology with the reference SEQ ID NO. A suitable algorithm such as BLAST may be used to ascertain sequence homology. If large amounts of sequence are deleted cf the wildtype, then the sequence comparison may be over the full length of the wildtype or over aligned sequences of similar homology.

However, it will be understood that despite the above sequence homology, certain elements, in particular the flanking nucleotides and splice branch site must be retained, for efficient functioning of the system. In other words, whilst portions may be deleted or otherwise altered, alternative splicing functionality or activity, to at least 30%, preferably 50%, preferably 70%, more preferably 90%, and most preferably 95% compared to the wildtype should be retained. This could be increased cf the wildtype, as well, by suitably engineering the sites that bind alternative splicing factors or interact with the spliceosome, for instance.

In particular, it is preferred that where the splice control sequence comprises a modified TRA intron, this comprises at least 20 to 40 base pairs from the 5' and, preferably, so the 3' end of said intron. Furthermore, it is preferred that at least 3 or 4 and most preferably, at least 5, preferably 6, more preferably 7 and most preferably all 8 of the 8 putative TRA binding domains of the *C. capitata* tra intron, as taught by Pane et al (2002), or homologues thereof, are provided. Of course, if further such sites are discovered in due course, then it is envisaged that the splice control sequence could include more than 8 sites. In fact, it is envisaged that the more than 8 sites may be engineered in to the splice control sequence and that alternative splicing may be regulated in this way, especially if some sites are bound with differing affinities leading to different alternative splicing outcomes.

A consensus sequence for the putative TRA binding domains of the *C. capitata* tra intron is given below as SEQ ID NO 1, a DNA sequence, although the corresponding RNA equivalent is also preferred.

The preferred consensus sequences is 1: TC WWCRATCAACA (SEQ ID NO. 1), where W=A or T and R=A or G.

Similar considerations apply to doublesex, where the consensus sequence for the TRA protein is also that given in SEQ ID NO. 1, as a protein complex comprising the Tra and TRA2 proteins is a key regulator of alternative splicing of doublesex, as it is for tra homologues (though not the tra homologues found in Drosophilids).

As mentioned above, the splice control sequences are preferably derived from the tra intron, preferably from the family Tephritidae. It is particularly preferred that the tra intron is derived from *B. zonata* or, preferably, from other non-Drosophilid fruit flies. However, it is particularly preferred that the tra intron is derived from the *Ceratitis* genus, in particular *C. rosa* and, most preferably, *C. capitata*. These are more widely known as the Natal and Mediterranean fruit flies, respectively.

With regard to the tra intron derived from *B. zonata*, we have shown that this can lead to sex-specific alternative splicing in transgenic Mexfly (*Anastrapha ludens*) and in transgenic Medfly (*C. capitata*). We have also shown that a variety of proteins can be expressed in a sex-specific manner via alternative splicing, including tTAV 3 and Rpr.

In relation to the tra intron derived from *C. rosa*, we have successfully provided alternative splicing in a sex-specific manner of a transgene in Medfly.

With regard to the tra intron derived from *C. capitata* (Medfly), we have shown that this can mediate sex-specific splicing in transgenic Medfly, and other Tephritids, and other Tephritids such as *A. ludens* (Mexfly). Not only that, we have shown that this intron can work successfully across a whole range of insects and, in particular, Dipterans. Indeed, we have shown that the TRA intron from *C. capitata* (referred to as Cctra) can provide sex-specific alternative splicing in transgenic *Drosophila*, which is not a Tephritid, and also in the mosquito *Aedes aegypti*. Although mosquitoes are Diptera, they diverged from *Drosophila* and the Tephritids about 250 million years ago and, therefore, are much more distantly related than Drosophilids are to Tephritids, for which the divergence time has been estimated as 120-150 million years. Thus, this shows the broad applicability of the present invention across a wide range of insects.

With regard to splice control sequences derived from the dsx intron, we have also shown that this can be used to alternatively splice, in a sex-specific manner, in a broad range of insects. Accordingly, it is particularly preferred that the dsx is derived from *Bombyx mori* (silk moth), *Pectinophora gossypiella* (Pink Bollworm) *Pectinophora gossypiella, Cydia. pomonella* (codling moth), *Drosophila*, and mosquitoes such as *Anopheles* sp., for instance *A. gambiae*. Particularly preferred mosquitoes include *Stegomyia* spp., particularly *S. aegypti* (also known as *Aedes aegypti*).

Indeed, in *A. aegypti*, we have shown a considerable number of DNA constructs, which are capable of providing sex-specific alternative splicing.

It will be appreciated that the system or construct is preferably administered as a plasmid, but generally tested after integrating into the genome. Administration can be by known methods in the art, such as parenterally, intra-venous intra-muscularly, orally, transdermally, delivered across a mucous membrane, and so forth. Injection into embryos is particularly preferred. The plasmid may be linearised before or during administration, and not all of the plasmid may be integrated into the genome. Where only part of the plasmid is integrated into the genome, it is preferred that this part include the at least one splice control sequence capable of mediating alternative splicing.

Preferably, the polynucleotide expression system is a recombinant dominant lethal genetic system, the lethal effect of which is conditional. Suitable conditions include temperature, so that the system is expressed at one temperature but not, or to a lesser degree, at another temperature, for example. The lethal genetic system may act on specific cells or tissues or impose its effect on the whole organism. Systems that are not strictly lethal but impose a substantial fitness cost are also envisioned, for example leading to blindness, flightlessness (for organisms that could normally fly), or sterility. Systems that interfere with sex determination are also envisioned, for example transforming or tending to transform all or part of an organism from one sexual type to another. It will be understood that all such systems and consequences are encompassed by the term lethal as used herein. Similarly, "killing", and similar terms refer to the effective expression of the lethal system and thereby the imposition of a deleterious or sex-distorting phenotype, for example death.

More preferably, the polynucleotide expression system is a recombinant dominant lethal genetic system, the lethal effect of which is conditional and is not expressed under permissive conditions requiring the presence of a substance which is absent from the natural environment of the organism, such that the lethal effect of the lethal system occurs in the natural environment of the organism.

In other words, the coding sequences encode a lethal linked to a system such as the tet system described in WO 01/39599 and/or WO2005/012534.

Indeed it is preferred that the expression of said lethal gene is under the control of a repressible transactivator protein. It is also preferred that the gene whose expression is regulated by alternative splicing encode a transactivator protein such as tTA. This is not incompatible with the regulated protein being a lethal. Indeed, it is particularly preferred that it is both. In this regard, we particularly prefer that the system includes a positive feedback system as taught in WO2005/012534.

Preferably, the lethal effect of the dominant lethal system is conditionally suppressible.

Suitable organisms under which the present system can be used include mammals such as mice, rats and farm animals. Also preferred are fish, such as salmon and trout. Plants are also preferred, but it is particularly preferred that the host organism is an insect, preferably a Dipteran or tephritid. Preferably, the organism is not a human, preferably non-mammalian, preferably not a bird, preferably an invertebrate, preferably an arthropod.

In particular, it is preferred that the insect is from the Order Diptera, especially higher Diptera and particularly that it is a tephritid fruit fly, preferably Medfly (*Ceratitis capitata*), preferably Mexfly (*Anastrepha ludens*), preferably Oriental fruit fly (*Bactrocera dorsalis*), Olive fruit fly (*Bactrocera oleae*), Melon fly (*Bactrocera cucuritae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*). It is also particularly preferred that the host organism is a mosquito, preferably from the genera *Stegomyia, Aedes, Anopheles* or *Culex*. Particularly preferred are *Stegomyia aegyptae*, also known as *Aedes aegypti, Stegomyia albopicta* (also known as *Aedes albopictus*), *Anopheles stephensi, Anopheles albimanus* and *Anopheles gambiae.*

Within Diptera, another preferred group is Calliphoridae, particularly the New world screwworm (*Cochliomyia hominivorax*), Old world screwworm (*Chrysomya bezziana*) and Australian sheep blowfly (*Lucilia cuprina*). Lepidoptera and Coleoptera are also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially Heliothinae. Among Coleoptera, Japanese beetle (*Popilla japonica*), White-fringed beetle (*Graphognatus* spp.), Boll weevil (*Anthonomous grandis*), corn root worm (*Diabrotica* spp) and Colorado potato beetle (*Leptinotarsa decemlineata*) are particularly preferred.

Preferably, the insect is not a Drosphilid, especially Dm. Thus, in some embodiments, expression in Drosophilids, especially Dm is excluded. In other embodiments, the splice control sequence is not derived from the tra intron of a Drosphilid, especially Dm.

It is preferred that the expression of the heterologous polynucleotide sequence leads to a phenotypic consequence in the organism. It is particularly preferred that the functional protein is not beta-galactosidase, but can be associated with visible markers (including fluorescence), viability, fertility, fecundity, fitness, flight ability, vision, and behavioural differences. It will be appreciated, of course, that, in some embodiments, the expression systems are typically conditional, with the phenotype being expressed only under some, for instance restrictive, conditions.

In a further aspect, there is also provided a method of population control of an organism in a natural environment therefor, comprising:

i) breeding a stock of the organism, the organism carrying a gene expression system comprising a system according to the present invention which is a dominant lethal genetic system, ii) distributing the said stock animals into the environment at a locus for population control; and iii) achieving population control through early stage lethality by expression of the lethal system in offspring that result from interbreeding of the said stock individuals with individuals of the opposite sex of the wild population.

Preferably, the early stage lethality is embryonic or before sexual maturity, preferably early in development, most preferably in the early larval or embryonic life stages.

Preferably, the lethal effect of the lethal system is conditional and occurs in the said natural environment via the expression of a lethal gene, the expression of said lethal gene being under the control of a repressible transactivator protein, the said breeding being under permissive conditions in the presence of a substance, the substance being absent from the said natural environment and able to repress said transactivator.

Preferably, the lethal effect is expressed in the embryos of said offspring. Preferably, the organism is an invertebrate multicellular animal or is as discussed elsewhere.

Also provided is a method of biological control, comprising:

i) breeding a stock of males and female organisms transformed with the expression system according to the present invention under permissive conditions, allowing the survival of males and females, to give a dual sex biological control agent;

ii) optionally before the next step imposing or permitting restrictive conditions to cause death of individuals of one sex and thereby providing a single sex biological control agent comprising individuals of the other sex carrying the conditional lethal genetic system;

iii) releasing the dual sex or single sex biological control agent into the environment at a locus for biological control; and iv) achieving biological control through expression of the genetic system in offspring resulting from interbreeding of the individuals of the biological control agent with individuals of the opposite sex of the wild population.

Preferably, there is sex-separation prior to organism distribution by expression of a sex specific lethal genetic system.

Preferably, the lethal effect results in killing of greater than 90% of the target class of the progeny of matings between released organisms and the wild population.

Also provided is a method of sex separation comprising:

i) breeding a stock of male and female organisms transformed with the gene expression system under permissive or restrictive conditions, allowing the survival of males and females; and ii) removing the permissive or restrictive conditions to induce the lethal effect of the lethal gene in one sex and not the other by sex-specific alternative splicing of the lethal gene.

Preferably, the lethal effect results in killing of greater than 90% of the target class of the progeny of matings between released organisms and the wild population.

Also provided is a method or biological or population control comprising:

i) breeding a stock of male and female organisms transformed with the gene expression system under permissive or restrictive conditions, allowing the survival of males and females;

ii) removing the permissive or restrictive conditions to induce the lethal effect of the lethal gene in one sex and not the other by sex-specific alternative splicing of the lethal gene to achieve sex separation;

iii) sterilising or partially sterilising the separated individuals and iv) achieving said control through release of the separated sterile or partially sterile individuals in to the natural environment of the organism.

Preferably, the sterilising is achieved through the use of ionising radiation. In general, however, methods avoiding irradiation, as used in the Sterile Insect Technique (SIT) are especially preferred and have many cost and health advantages over methods associated with or followed by the use of radiation.

Also provided is a method to selectively eliminate females from a population. The equivalent for males is also envisaged.

Methods of sex separation are hugely important commercially in, for example silk worms, where males produce more and better silk than females. Thus, methods of sex separation that eliminate females and, in particular female silk worms are particularly preferred.

It is also envisaged that the functional protein may be a expressed differentially, but detectably in more than one splice variant and preferably, therefore, in both sexes, for instance. Such examples include a fluorescent protein, such as eGFP, CopGFP and DsRed2. This may be used in a method of non-lethal sex separation or sorting, so that one can separate the two types without killing either of them.

We have also surprisingly discovered that the positioning of the splice control sequence can be altered and better results obtained. Preferably, the splice control sequence is the “first” splice control sequence, when read from the promoter, in 5' to 3' direction We have found that in certain constructs with an intron in the 5' UTR of the system that this leads to reduced levels or alternatively spliced protein expression mediated by the splice control sequence of the present invention.

Preferably, the splice control sequence is 3' to the start codon. Preferably, the splice control sequence is inserted within the first exon, i.e. the stretch of sequence immediately 3' to the transcription start site. It will be understood that such terms may refer to the DNA sequence which encodes the transcript, or to the RNA transcript itself.

Where the splice control sequence is 3' to the start codon, it is preferred that it is also 5' to the first in-frame stop codon (that is 3' to and in frame with the start codon), so that alternative splicing yields transcripts that encode different protein or polypeptide sequences. Thus in a preferred embodiment, the construct or polynucleotide sequence comprises the following elements in 5' to 3' order, with respect to the sense strand or primary transcript: transcription start, translation start, intron capable of alternative splicing, coding sequence for all or part of a protein, stop codon.

The splice control sequence may be defined as preferably up to and including the 5' G (GT/C) and its 3' G equivalent, especially in tra, but as mentioned above, this can include some exonic sequence and therefore, could include the 3' most (last) nucleotide of the exon (i.e. G).

It is particularly preferred that the splice control sequence is immediately adjacent, in the 3' direction, the start codon, so that the G of the ATG is 5' to the start (5' end) of the splice control sequence. This is particularly advantageous as it allows the G of the ATG start codon to be the 5'G flanking sequence to the splice control sequence.

Alternatively, the splice control sequence is 3' to the start codon but within 1000 exonic bp, preferably 500 exonic bp, preferably 300 exonic bp, preferably 200 exonic bp, preferably 150 exonic bp, preferably 100 exonic bp, more preferably 75 exonic bp, more preferably 50 exonic bp, more preferably 30 exonic bp, more preferably 20 exonic bp, and most preferably 10 or even 5, 4, 3, 2, or 1 exonic bp.

The present invention is an improvement on the system defined as LA1188 in WO2005/012534. This plasmid had a number of defects, principal of which is that exonic nucleotides were excised with the Cctra intron used therein, thereby resulting in an induced frameshift in the transcript. Specifically, in addition to the sequence derived from Cctra (the Cctra intron), 4 nucleotides of tTAV sequence were removed in the female-specific transcript. Therefore, though several alternatively spliced transcripts were produced, including one female-specific transcript, none were capable of encoding functional tTAV protein. Therefore, this construct was not capable of providing sex-specific expression of functional tTAV protein.

Since splicing was not directed to the splice donor sequence (5'-GT . . . ) normally used in the Cctra intron, clearly this construct did not contain all of the regulatory sequences necessary to direct splicing in the form of the Cctra intron in “its native context.” However, this highlights another issue. Probably the only thing missing was the flanking TG . . . GT, of which it is possible that only the 5'G mattered.

A key benefit of the present invention is, in particular in relation to tra, that the requirements for exonic sequence are so minimal (e.g. 2 nucleotides at each end) that they can easily be designed into most coding sequences, using the redundancy in the genetic code. So the “extra” exonic nucleotides can both be part of the heterologous protein sequence, and the flanking sequence of the intron in its native context at the same time.

Furthermore, the Cctra intron in LA1188 was +132 bp 3' to the G of the ATG start codon (to the last exonic nucleotide). Indeed, although the Cctra intron in LA1188 is the first intron read in the 5' to 3; direction from the ATG start codon, it is not the “first” intron when read in the 5' to 3' direction from promoter. In fact, it is the $2^{nd}$ intron, as there is a further intron (derived from the *Drosophila melanogaster* Adh gene) upstream of the ATG start codon. This information is included in the Table 3.

It will be understood that where reference is made to ATG start codons or flanking G, or 5'-TG . . . GT-3' sequences, that this is in relation to a DNA sequence, but this is also covers the corresponding DNA antisense sequence and, equally, the corresponding RNA sequence.

DESCRIPTION OF THE SEQUENCES OF THE PRESENT INVENTION

SEQ ID NO. 1 tra consensus sequence
SEQ ID NO. 2 LA3097 5' flanking sequence
SEQ ID NO. 3 LA3097 3' flanking sequence
SEQ ID NO. 4 primer 688—ie1-transcr
SEQ ID NO. 5 primer 790—Aedsx-m-r2
SEQ ID NO. 6 primer 761—Aedsx-fem-r
SEQ ID NO. 7 primer AedsxR1
SEQ ID NO. 8 Pane et al consensus sequence
SEQ ID NO. 9 Scali et al 2005 consensus sequence
SEQ ID NOS. 10-33 and 107-138 consensus sequences of putative Tra/Tra2 binding sites deduced for *Drosophila* (see Table 2).
SEQ ID NO. 34: Open reading frame of tTAV
SEQ ID NO. 35: Protein sequence of tTAV
SEQ ID NO. 36: Open reading frame of tTAV2
SEQ ID NO. 37: Protein sequence of tTAV2
SEQ ID NO. 38: Open reading frame of tTAV3
SEQ ID NO. 39: Protein sequence of tTAV3
SEQ ID NO. 40: Pink Bollworm dsx female specific sequence fragment 1
SEQ ID NO. 41: Pink Bollworm (PBW, *Pectinophora gossypiella*) dsx female specific sequence fragment 2
SEQ ID NO. 42: Pink Bollworm (PBW, *Pectinophora gossypiella*) dsx male specific sequence
SEQ ID NO. 43: Partial gene sequence of *Aedes aegypti* dsx. All exonic sequence is included, but only partial intronic sequence—see FIGS. 47 and 48 for annotation.
SEQ ID NO. 44: Codling moth (*Cydia pomonella*) dsx female gene sequence: includes a stretch of unknown nucleotides, preferably than then 100, preferably less than 50, more preferably less than 20, more preferably less than 10, and most preferably less than 5.
SEQ ID NO. 45: Codling moth (*Cydia pomonella*) dsx-male sequence.
SEQ ID NO. 46: Sequence of pLA3435-*Bombyx mori*-dsx construct/plasmid.
SEQ ID NO. 47: Sequence of pLA3359-*Anopheles gambiae* dsx construct.
SEQ ID NO. 48: Sequence of pLA3433-Agdsx (*Anopheles gambiae*) construct with exon 2 included.
SEQ ID NO. 49: Sequence of pLA1188-cctra intron construct
SEQ ID NO. 50: Sequence of pLA3077-a Cctra intron-tTAV construct.
SEQ ID NO. 51: Sequence of pLA3097-a Cctra intron-tTAV construct.
SEQ ID NO. 52: Sequence of pLA3233-Cctra-intron-tTAV2 construct.
SEQ ID NO 53: Sequence of pLA3014-Cctra-intron-Ubiquitin-reaperKR construct.
SEQ ID NO. 54: Sequence of pLA3166-Cctra intron-Ubiquitin-reaperKR construct.
SEQ ID NO. 55: Sequence of pLA3376-Bztra intron-reaperKR and Bztra-intron-tTAV3.
SEQ ID NO. 56: Sequence of pLA3242-Crtra intron-reaperKR construct.
SEQ ID NO. 57: Partial sequence of a male transcript generated in *Drosophila melanogaster* from LA3077 transformants that differs to the sequence generated in Medfly LA3077 lines. This sequence corresponds to the M3 transcript depicted in FIG. 36.
SEQ ID NO. 58: Partial sequence of *Bactrocera zonata* tra homologue. Sequence of intron predicted to be spliced out in a female-specific transcript of *B. zonata* tra (+3 to +970 bp in sequence). Exonic flanking nucleotides are at positions 1-2 and 971-972, i.e. at the 5' and 3' ends of the intronic sequence. In fact, it is worth noting that the intronic sequence is flanked on its 5' end by a Guanine nucleotide, which is thought critical for a clean exit of the intron.

SEQ ID NO 59: Partial sequence of *Ceratitis rosa* tra homologue. Sequence of intron predicted to be spliced out in a female-specific transcript of *C. rosa* tra (+3 to 1311 bp in sequence). Exonic flanking nucleotides are present at positions 1-2 and 1312-3. Again, it is noteworthy that the intronic sequence is flanked on its 5' end by a Guanine nucleotide, which is thought critical for a clean exit of the intron.

SEQ ID NOS. 60-70: Primers as referred to in FIGS. 44-46 and 50-51.

SEQ ID NO. 71: Pink Bollworm (PBW, *Pectinophora gossypiella*) dsx female specific fragment 3.

SEQ ID NO. 72: Open reading frame of *Drosophila melanogaster* ubiquitin.

SEQ ID NO. 73: Protein sequence of *Drosophila melanogaster* Ubiquitin.

SEQ ID NOS. 74-105 are primers as discussed above in the Examples.

SEQ ID NO. 106 is the LA1172 nucleotide sequence, including plasmid backbone.

SEQ ID NOs 107-138 are described above.

SEQ ID NO. 139 HSP primer

SEQ ID NO. 140 VP16 primer

SEQ ID NO. 141 primer Agexon1F

SEQ ID NO. 142 primer TETRR1

SEQ ID NO. 143 LA3576 plasmid sequence

SEQ ID NO. 144 LA3582 plasmid sequence

SEQ ID NO. 145 LA3596 plasmid sequence

SEQ ID NO. 146 PBW-dsx (FIG. 6A and FIG. 6B)

SEQ ID NO. 147 *bombyx*-dsx (FIG. 6A and FIG. 6B)

SEQ ID NO. 148 codling-dsx (FIG. 6A and FIG. 6B)

SEQ ID NO. 149 DSX Minigene1 from construct LA3491

SEQ ID NO. 150 DSX Minigene2 from construct LA3534

SEQ ID NO. 151 LA3619 whole plasmid sequence

SEQ ID NO. 152 LA3612 whole plasmid sequence

SEQ ID NO. 153 LA3491 plasmid sequence

SEQ ID NO. 154 LA3515 plasmid sequence

SEQ ID NO. 155 LA3545 plasmid sequence

SEQ ID NO. 156 LA3604 plasmid sequence

SEQ ID NO. 157 LA3646 plasmid sequence

SEQ ID NO. 158 LA3054 plasmid sequence

SEQ ID NO. 159 LA3056 plasmid sequence

SEQ ID NO. 160 LA3488 plasmid sequence

SEQ ID NO. 161 LA3641 plasmid sequence

SEQ ID NO. 162 LA3570 plasmid sequence

The invention will now be described by reference to the following, non-limiting Examples.

EXAMPLES

Transformer

Example 1—*Ceratitis capitata* Tra Intron

We have prepared an insertion of a Cctra intron cassette into a synthetic open reading frame (ORF). Two versions of this splice correctly in Medfly, in other words the splicing of the Cctra intron cassette faithfully recapitulates what it would normally do in the context of the endogenous Cctra gene. This is to produce 3 (major or only) splice variants in females, one of which is female-specific (called F1), while the other two are found in both males and females (called M1 and M2). Since each of the non-sex-specific transcripts contains additional exonic material with stop codons, we have also arranged this so that only the female splice variant produces functional protein.

Each of these constructs (LA3077 and LA3097) has the Cctra intron flanked by TG and GT (to give 5' . . . TG¦intron¦GT . . . 3'. An older construct, which does not work perfectly, is LA1188. LA1188 is quite well characterized—splicing is exactly as above except that an additional 4 nucleotides are removed. The intron is in the context 5' . . . TGGCAC¦intron¦GT . . . 3'; splicing removes an additional 4 bases, i.e. 5' . . . TG¦GCACintron¦GT . . . 3' (FIG. 33).

In all cases the intron is invariant, and is simply the complete Cctra intron sequence. As is normal for introns, it begins GT and ends AG. Almost all introns start with GT, so the use of the rare alternative GC in LA1188 is surprising [GC-AG introns are a known alternative—in one large-scale survey, 0.5% of all introns were reported to use GC-AG (Burset et al., 2001), though this may be an underestimate, particularly for alternatively spliced introns, of which perhaps 5% might use GC-AG (Thanaraj and Clark, 2001)].

RT-PCR analysis was performed on LA3077, (a positive feedback construct with the CcTRA intron in the tTAV open reading frame). Transformed adult flies of both sexes were reared on diet substantially free of tetracycline ("off tetracycline") for 7 days. Flies were then collected for RNA extraction and RT PCR using primers (HSP—SEQ ID NO. 104 and VP16 SEQ ID NO. 105) were used to analyse the splicing pattern of the CcTRA intron (FIG. 34). In two female samples we found the correct splice pattern of the Cctra (776 bp, corresponding to precise removal of the Cctra intron) and saw no such band in males.

We found that LA3077 and LA3097 correspondingly gave repressible female-specific lethality. LA3077 was tested phenotypically through crossing flies heterozygous for LA3077 to wild type, on and off tetracycline. Female lethality ranged from 50 to 70%. LA3097 (a modified version of LA3077 whereby the Cctra intron immediately follows the start codon in the tTAV ORF), demonstrated a much higher level of female specific lethality, peaking at 100% (FIG. 35). The Cctra intron was also inserted in tTAV2 at the same position as LA3097, in construct LA3233, and this gave a similar phenotypic result as LA3097 (FIG. 35).

Figure 36:
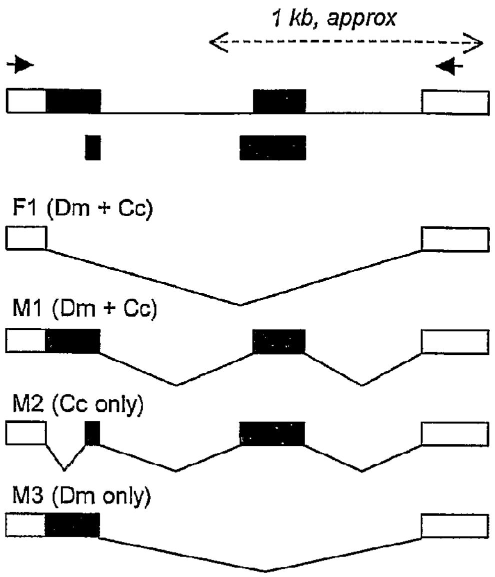

We have also prepared transformants of LA3077 in *Drosophila*. Phenotypically, the construct works perfectly, which is to say it is a highly effective female-specific lethal. However, sequencing of the splice variants of one of these insertions has shown that the splicing of this construct in *Drosophila* is not quite the same as it is in Medfly (SEQ ID NO. 57). The critical transcript, the female-specific one, is the same in both, but at least one of the non-sex-specific transcripts is different. It still incorporates extra exonic sequence, with stop codons, but the splice junctions are not quite the same (FIG. 36). This observation is extremely important in that it shows that this method (regulation of gene expression by use of alternatively spliced introns) can be used across quite a wide phylogenetic range.

A simple test to determine whether an as yet uncharacterized exonic splice regulator (such as enhancers and suppressors) may be modifying the function of the alternatively spliced intron, could include making the construct and introducing it into a target tissue, then examining its splice pattern. In many cases this will not require germline transformation, so the test can be quite rapid, for instance by transient expression in suitable tissue culture cells or in vivo. For instance, in vivo testing in insects could be achieved by delivering the DNA by microinjection. However, as the skilled person will appreciate, microinjection coupled with electroporation, or electroporation, chemical transformation, ballistic methods, for instance, have all been used in a number of various contexts and such methods of plasmid introduction and protein expression therefrom are well known in the art.

Figures 37, 38:
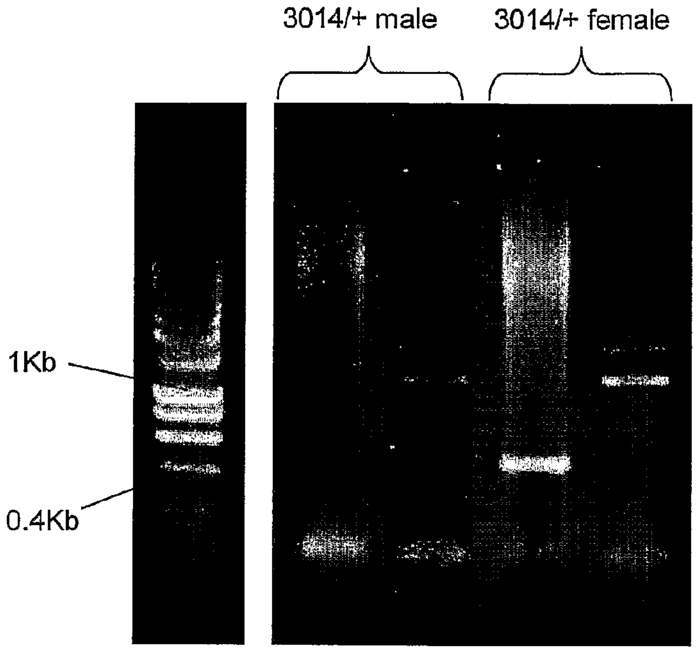

We have also recently made, and have obtained transgenics with, the Cctra intron in a different gene (LA3014) (all the above examples are in tTAV). LA3014 contains a ubiquitin-reaper$^{KR}$ fusion downstream of a Cctra intron. Phenotypic data (FIG. 35) shows that LA3014 transgenic Medfly gave repressible female-specific lethality. RT-PCR analysis on RNA extracted from adult males and females raised off tetracycline, using primers (HSP, SEQ ID NO 74) and ReaperKR (SEQ ID NO. 75), demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly (FIG. 35).

We have also recently made, and have obtained transgenics with, 'intron-only' Cctra-based constructs with the intron in a different gene (all the above examples are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above.

In order to demonstrate the phylogenetic range of the Cctra intron we generated transgenic LA3097 and LA3233 *Anastrepha ludens*. LA3097 and LA3233 were selected for injection into *Anastrepha ludens* as they demonstrated the best female specific lethality in *Ceratitis capitata* (see Example 13). Phenotypic data was generated for 4 independent LA3097 lines and 1 LA3233 line (see FIG. 38). Female specific lethality was generally somewhat lower in *Anastrepha ludens* when compared to *C. capitata* but reached 100% in one line.

Figure 39:
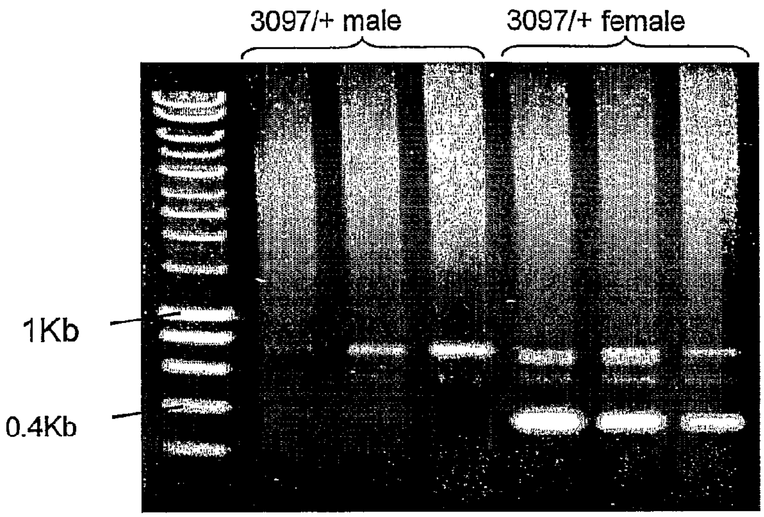

*Anastrepha ludens* transformed with LA3097 and raised on tetracycline until eclosion were isolated and maintained off tetracycline for 7 days. RNA was then extracted and RT-PCR analysis was performed using primers HSP (SEQ ID NO. 76) and TETRR1 (SEQ ID NO. 77). The correct female specific (F1-like) splice pattern was observed RNA isolated from in females (348 bp) but not from males demonstrating the function of the Cctra intron in a different species (FIG. 39)

The brightest male band and the female specific band were purified and precipitated for sequencing. The female specific transcript was found to be correctly spliced in Mexfly females as expected for LA3097:

```
LA3097:
AGCCACCATG ⌊⌊ GT . . . intron . . . AG ⌊ GTCAGCCGCC
```

The two flanking sequences above are SEQ ID NOS. 2 and 3, respectively.

Example 2—*Bactocera zonata* Tra Intron

We isolated the tra intron from *Bactocera zonata* (*B. zonata*) (SEQ ID NO. 58) using primers ROSA1 (SEQ ID NO. 78), ROSA2 (SEQ ID NO. 79), and ROSA3 (SEQ ID NO. 80).

Figure 31:
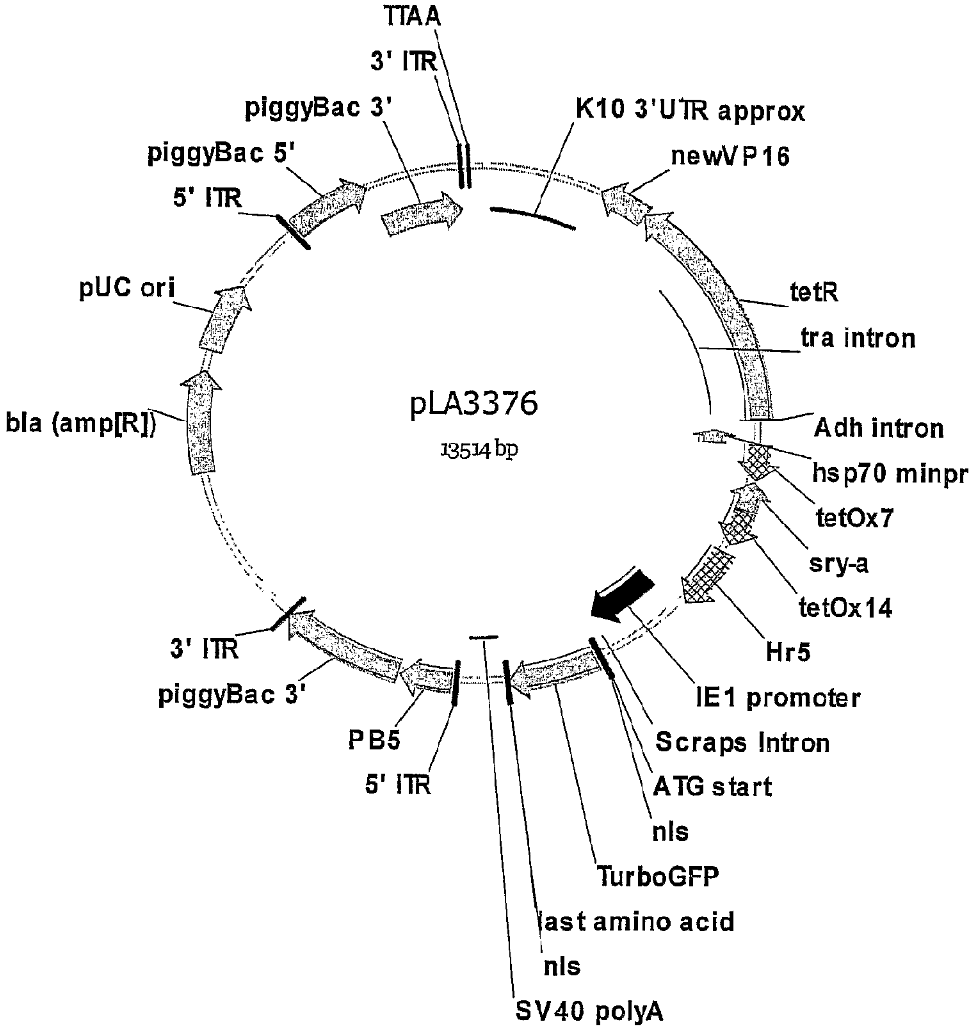

These primer sequences were designed based on conserved coding sequence of *Ceratitis capitata* and *Bactrocera oleae* tra homologs. Using ROSA2 and ROSA3 or ROSA1 and ROSA3 as primers, the tra intron and its flanking coding region were amplified from *Bactrocera zonata* genomic DNA. Then we used these PCR products as a template and amplified the tra intron fragment to make the construct-LA3376 (FIG. 31 and SEQ ID NO. 55). The primers (BZNHE—SEQ ID NO. 81 and BZR-SEQ ID NO. 82) were used for making the constructs; these primers contain additional sequences for cloning purposes. The Bztra intron in LA3376 is cloned into the ORF of tTAV3 and also of reaper$^{KR}$. Medfly transformants were generated and RNA extracted from male and female flies.

Figure 40:
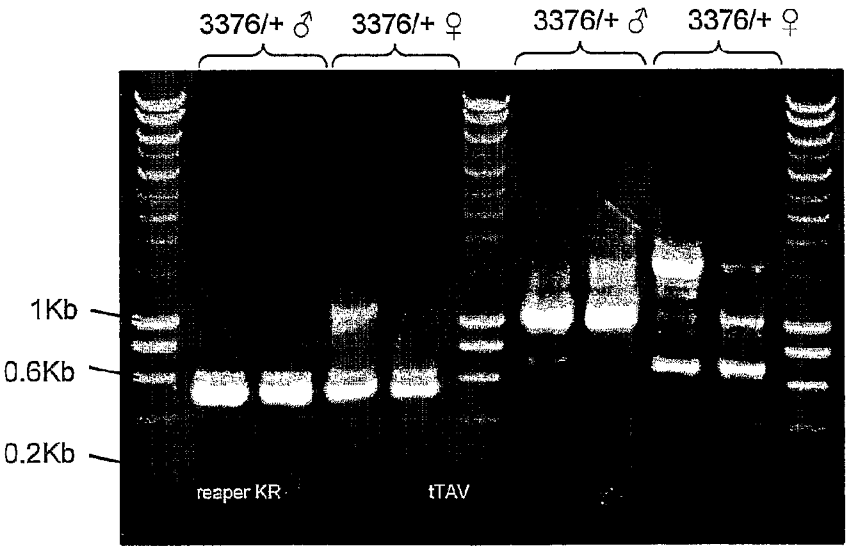

RT-PCR was then performed on both the reaper$^{KR}$ (HB—SEQ ID NO. 83) and Reaper KR—SEQ ID NO. 84) and tTAV3 (SRY—SEQ ID NO. 85) and AV3F—SEQ ID NO. 86) splice. The expected fragments of 200 bp for reaper$^{KR}$ and 670 bp for tTAV3, corresponding to splicing in a pattern equivalent to the F1 transcript of Cctra (Pane et al., 2002), were generated in females (FIG. 40).

Figure 41:
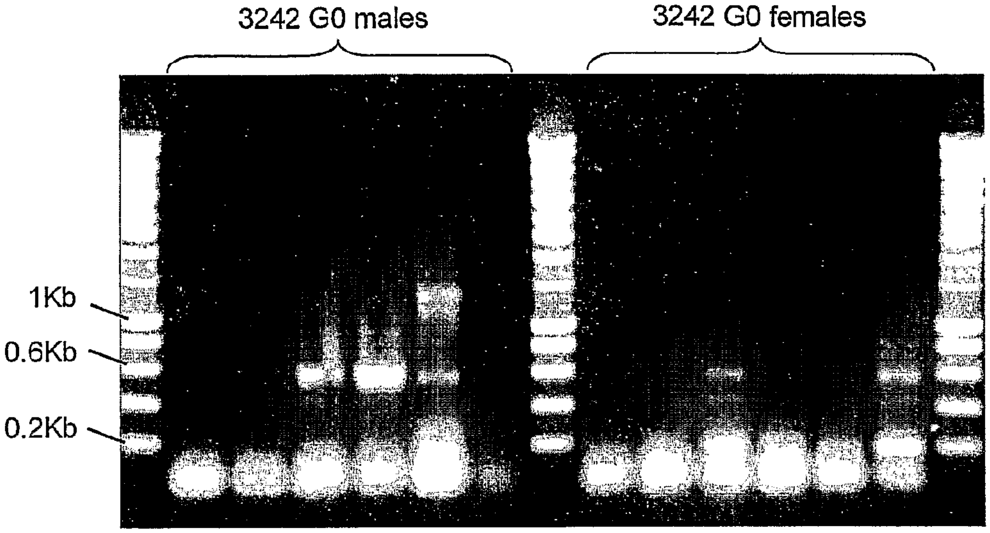

Example 3—Isolation and Splicing of the *Ceratitis rosa* (*C. rosa*, Natal Fruit Fly) Tra Intron Primers ROSA2 (SEQ ID NO. 87) and ROSA3 (SEQ ID NO. 88) were designed based on conserved coding sequence of *Ceratitis capitata* and *Bactrocera oleae* Using ROSA2 and ROSA3 as primers, the tra intron and its flanking coding region were amplified from *Ceratitis rosa* genomic DNA (SEQ ID NO. 59). We then used the PCR products as a template and amplified the tra intron fragment to make constructs. The primers (CRNHE—SEQ ID NO 89 and CRR SEQ ID NO 90) were used during the construction of LA3242 (SEQ ID NO. 56 and FIG. 32. LA3242 contains the *C. rosa* intron at the 5' end of the reaper$^{KR}$ ORF. *Ceratitis capitata* embryos were injected with DNA of LA3242, injected embryos were raised to adulthood on a diet substantially free of tetracycline. RNA was extracted from adult males and females; this was used as a template for RT PCR using primers HB (SEQ ID NO. 91) and ReaperKR (SEQ ID NO. 92). The expected female-specific splice band (200 bp), corresponding to splicing in the equivalent pattern to that of transcript F1 of Cctra, was observed in females and not males (FIG. 41).

Double-Sex

Example 4—*Bombyx mori* Dsx in PBW

The sequence of a *Bombyx mori* (silk moth) homolog of *Drosophila* Dsx (Bmdsx) has been previously described and a male- and a female-specific splice product have been identified (Suzuki et al, 2001). Both males and females use the same 3' polyA, and there are two female specific exons. One paper has suggested that the sex-specific splicing is not dependent on tra/tra2, in other words even though the pattern looks the same, the underlying mechanism may be different (Suzuki et al., 2001), though their data, principally the lack of recognisable tra-tra2 binding sites, however, is not compelling. In addition, a *B. mori* dsx mini-gene construct (containing exonic sequence and truncated intronic sequence) has been transformed into *B. mori* and the germline transformants show sex-specific splicing (Funaguma et al., 2005).

Figure 22:
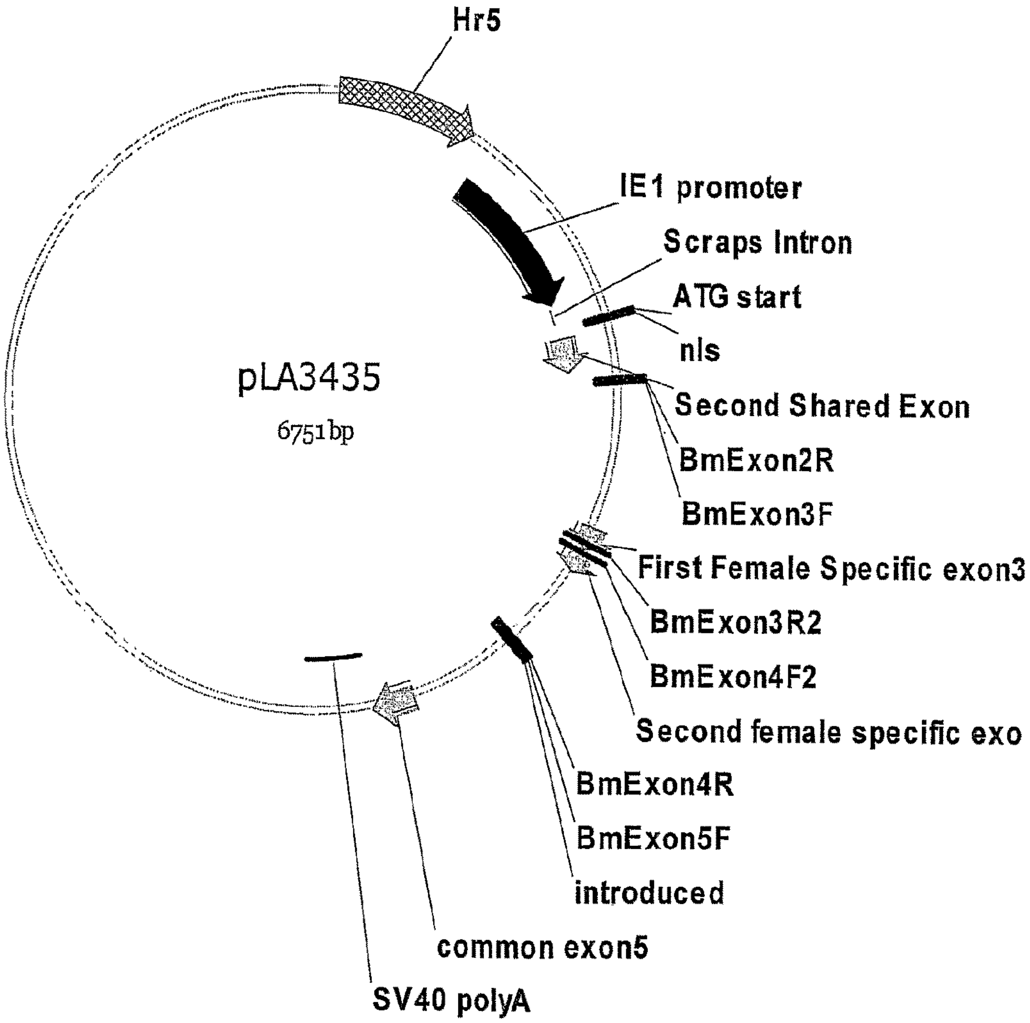

We have generated a Bmdsx minigene based on the sequence used in the Funaguma et al paper, with some significant changes, and injected this into the moth Pink Bollworm to ascertain if one can obtain sex-specific splicing in a divergent species. The mini-gene construct we generated does not included exon 1, which is present in both males and females. In addition, we removed the intron between exon 3 and 4 (the two female specific exons), included a heterologous sequence (containing multiple cloning sites, MCS), used the Hr5-IE1 enhancer/promoter sequence from the baculovirus AcNPV and used a 3' transcriptional termination sequence derived from SV40 (see FIG. 42 for a schematic). The individual exon/flanking intron fragments used were amplified and recombined together by PCR and ligated into a construct carrying a Hr5/IE1 enhancer promoter fragment and SV40 3'UTR (FIG. 22 and SEQ ID NO. 22).

Figure 43:
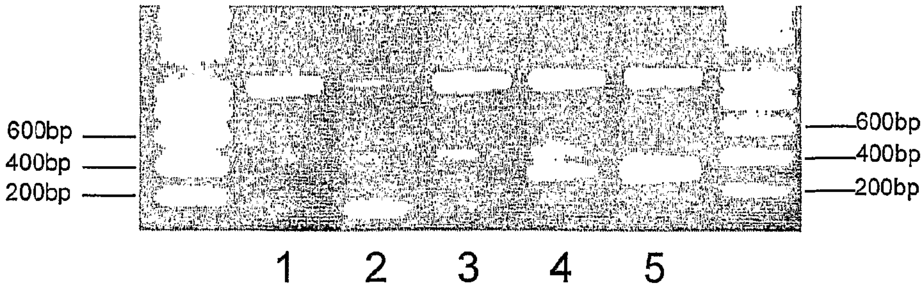

LA3435 was injected into pink bollworm (*Pectinophora gossypiella*) embryos. First instar larvae were collected after 5-7 days and analysed individually by RT-PCR (using primers IE1 transcr—SEQ ID NO. 93 and SV40-RT-P2—SEQ ID NO. 94) to determine if BMdsx can undergo male and female specific splicing (FIG. 43). Our analysis detected the male specific band (predicted to be 442 bp) in 4 samples (Lanes 1, 2, 3 and 4) and the female specific band (predicted to be 612 bp) in 1 sample (Lane 5).

The correct splicing of *B. mori* dsx in PBW demonstrates that we can achieve (have achieved) sex-specific expression of a heterologous sequence (here, the MCS) in a Lepidopteran by utilizing an alternative splicing system. Furthermore, since this splicing system was derived from a heterologous species, this suggests that such constructs might work over a wide phylogenetic range. However, the identification of alternative splicing systems in the species of interest is also envisioned, and methods for identifying such alternative splicing systems are provided herein or will be known to the person skilled in the art. By providing a MCS in our Example (see FIG. 42), the expression of a sequence of interest, for example a coding region for a protein of interest could readily be achieved by inserting said sequence. If said sequence encoded a suitable protein, a sex-specific phenotype, for example conditional sex-specific lethality, could thereby be introduced, for example into pink bollworm.

Example 5—Isolation of Codling Moth Dsx

The dsx gene from Codling moth (*Cydia pomonella*) was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using the TT7T25 primer (SEQ ID NO. 95).

PCR was performed using the primers ds1c (SEQ ID NO. 96) and TT7 (SEQ ID NO. 97). Two rounds of nested PCR were then performed on the product of the first PCR using the primers codling2a (SEQ ID NO. 98) and TT7 (SEQ ID NO. 99) and the product of the second round of PCR using Codling2b (SEQ ID NO. 100) and TT7. The isolated male and female specific sequences share sequence similarity to previously isolated dsx homologues (Male-SEQ ID NO. 43 and Female—SEQ ID NO. 42).

Example 6—Isolation of PBW Dsx

The dsx gene from pink bollworm was isolated by performing 3' RACE using primers which were based on sequence alignments from *B. oleae, B. tyroni, C. capitata, D. melanogaster, B. mori*, and *A. gambiae*. RNA was isolated from a male and female codling moth and 3' RACE, to generate cDNA, was performed using TT7T25 (sequence defined herein). PCR was performed using the primers Pbwdsx2 (SEQ ID NO. 101) and TT7 (SEQ ID NO. 102). Nested PCR was then performed on the product of the first PCR using the primers Pbwdsx3 (SEQ ID NO. 103) and TT7. Three female specific sequences were isolated: PBWdsx-F1 (SEQ ID NO. 40), PBWdsx-F2 (FIG. 10), and PBWdsx-F3 (SEQ ID NO. 71) and one male specific sequence (SEQ ID NO. 42). The isolated male and female specific sequences share sequence similarity to previously isolated dsx homologues.

Example 7—Dsx in *Anopheles gambiae*

Figure 44:
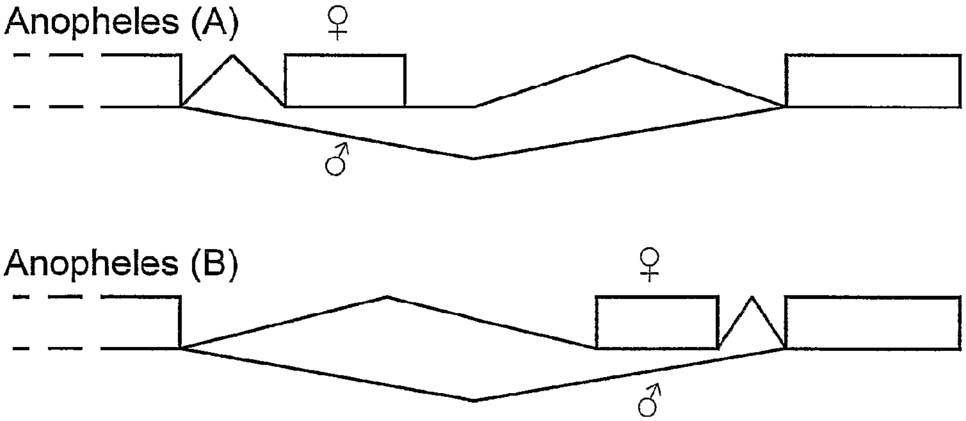

The sequence of the dsx gene of *Anopheles gambiae* has previously been described (Scali et al 2005). However, when we have tried to repeat the work described in the paper we find that there are some differences in the splicing that occurs. When we tried to repeat the amplification of the female specific transcript using primers designed from the mRNA sequence (Accession; AY903308 for female coding sequence and AY903307 for male coding sequence), the amplification failed. However, when Scali and colleagues showed that there was a shared exon, which had previously not been described, we designed primers to amplify the entire dsx transcript and gene. Using these primers and primers designed from genomic DNA sequence (Accession; GI:19611767) we find that the splicing of the female transcript is different from that described by Scali et al 2005 (FIG. 44). The transcript showed that the female exon was in a different position. There are several explanations for these differences, but the most likely are either some sort of strain difference in the *Anopheles* that we used to get the data from, or the published sequence is not from *Anopheles gambiae*, or there is more than one female isoform as shown for *Stegomyia aegypti* in Example 20.

Figure 45:
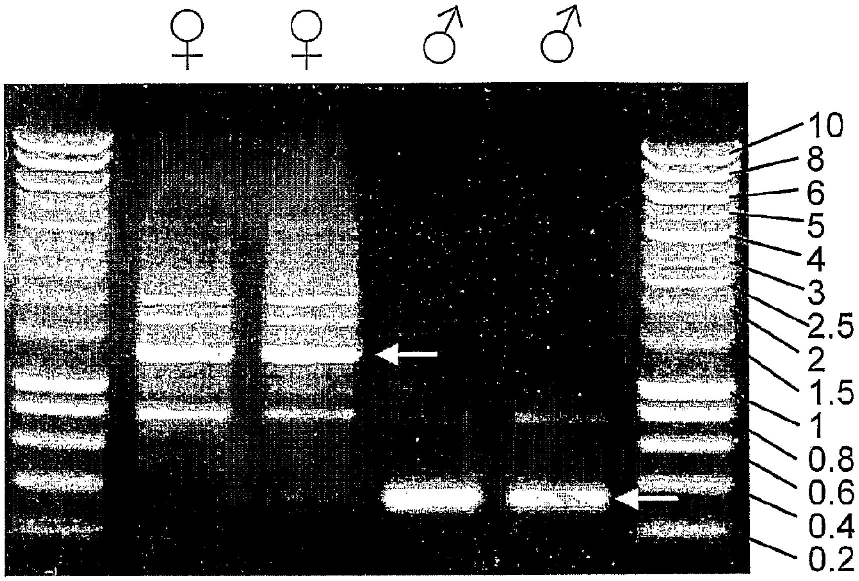

We have also successfully used primers, designed around our version of the *Anopheles gambiae* dsx splicing, that are able to distinguish between males and females of *Anopheles gambiae* (FIG. 45). This provides good evidence that the system will be functional as a sex-specific splicing mechanism when fused to a protein of interest, such as tTAV or a killer.

Figure 23:
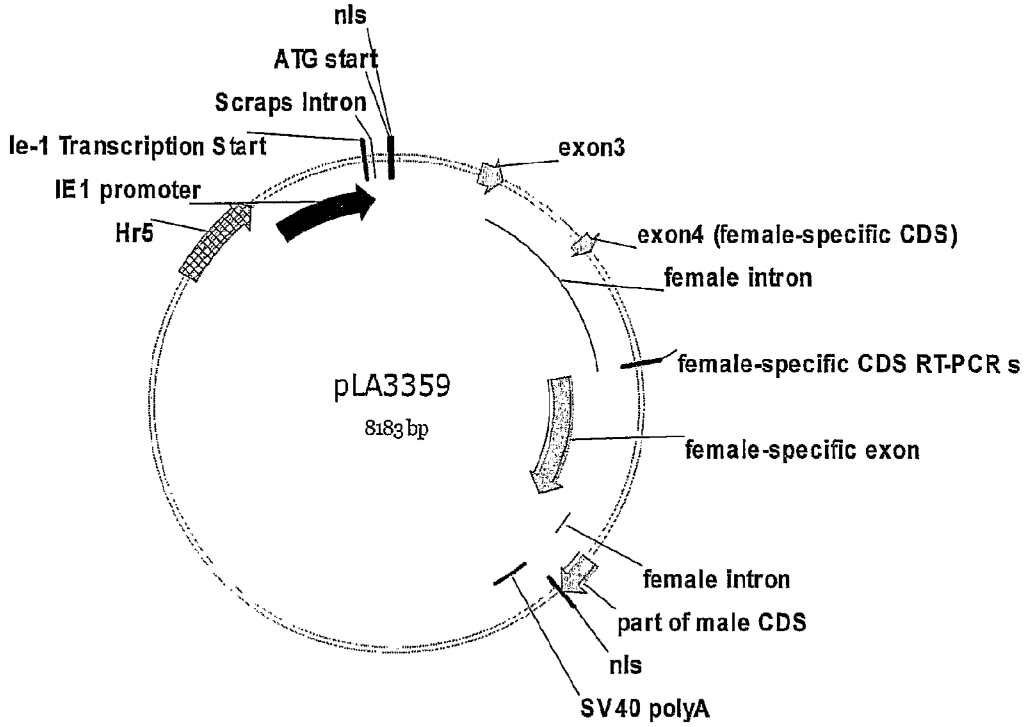
Figure 24:
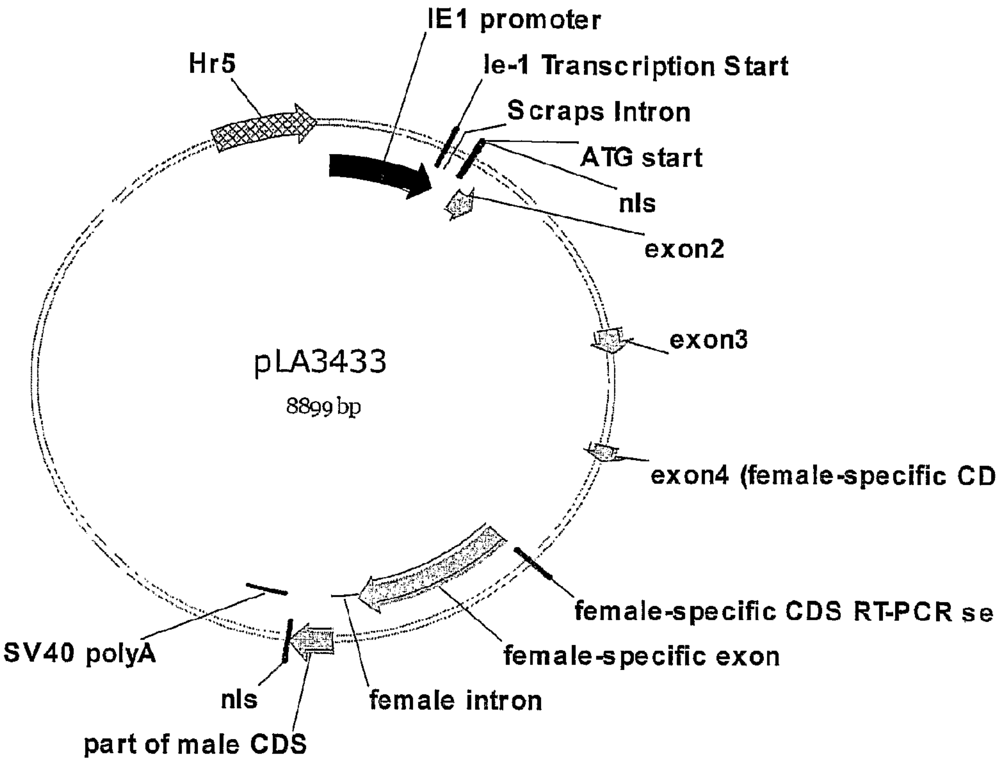

The *Anopheles gambiae* dsx gene that we have isolated from genomic DNA, which has several changes in nucleotide sequence compared to the reported genomic sequence, was cloned into LA3359 (SEQ ID NO. 47) and LA3433 (SEQ ID NO. 48), schematics can be found in FIG. 23 and FIG. 24, respectively.

Example 8—Dsx in *Stegomyia aegypti*

Figure 46:
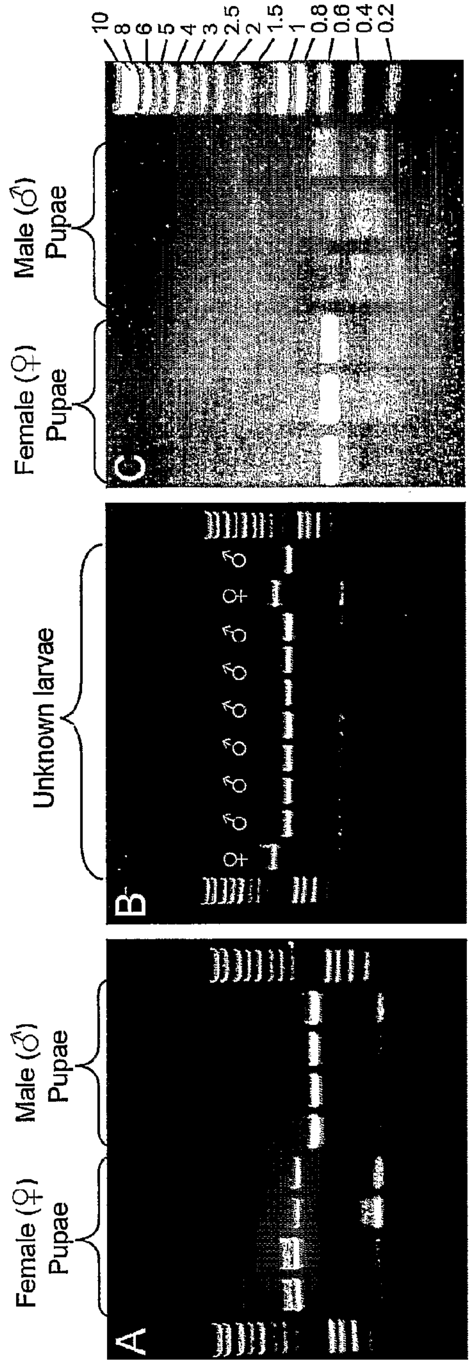

The splicing of the gene appears to be similar to *Anopheles gambiae* dsx (Scali et al 2005). The *Stegomyia aegypti* dsx gene is illustrated diagrammatically in FIG. 47 or 48. A male-specific transcript (M1) is produced which does not include exons 5a or 5b. Two female specific splice variants (F1 and F2) have the following structure; F1 comprises exons 1-4, 5a, 6 and 7 but not 5b, F2 comprises exons 1-4 and 5b (FIG. 46). In addition, a further transcript (C1) is present in both males and females; this comprises exons 1-4 and 7, but not exons 5a, 5b or 6.

The splicing of the gene appears to be similar to *Anopheles gambiae* dsx (Scali et al 2005). The *Stegomyia aegypti* dsx gene is illustrated diagrammatically in FIG. 47 or 48.

Actin 4

Example 9—*Stegomyia aegypti* Actin-4 Gene

One way to get sex-, tissue- and stage-specific expression of a gene of interest is to link it with the *Stegomyia aegypti* Actin-4 (AeAct-4) gene. This gene is only expressed in the developing flight muscles of female *Stegomyia aegypti* (Munoz et al 2004). They used in-situ hybridisation to an RNA to detect the expression profile of AeAct-4. We have taken a fragment of the *Stegomyia aegypti* Actin-4 gene, comprising a putative promoter region, an alternatively spliced intron, and a section of 5' untranslated region (UTR) and placed it in front of sequence coding for tTAV (FIG. 49) to test the function of the sex specific splicing when fused to tTAV.

Figure 50:
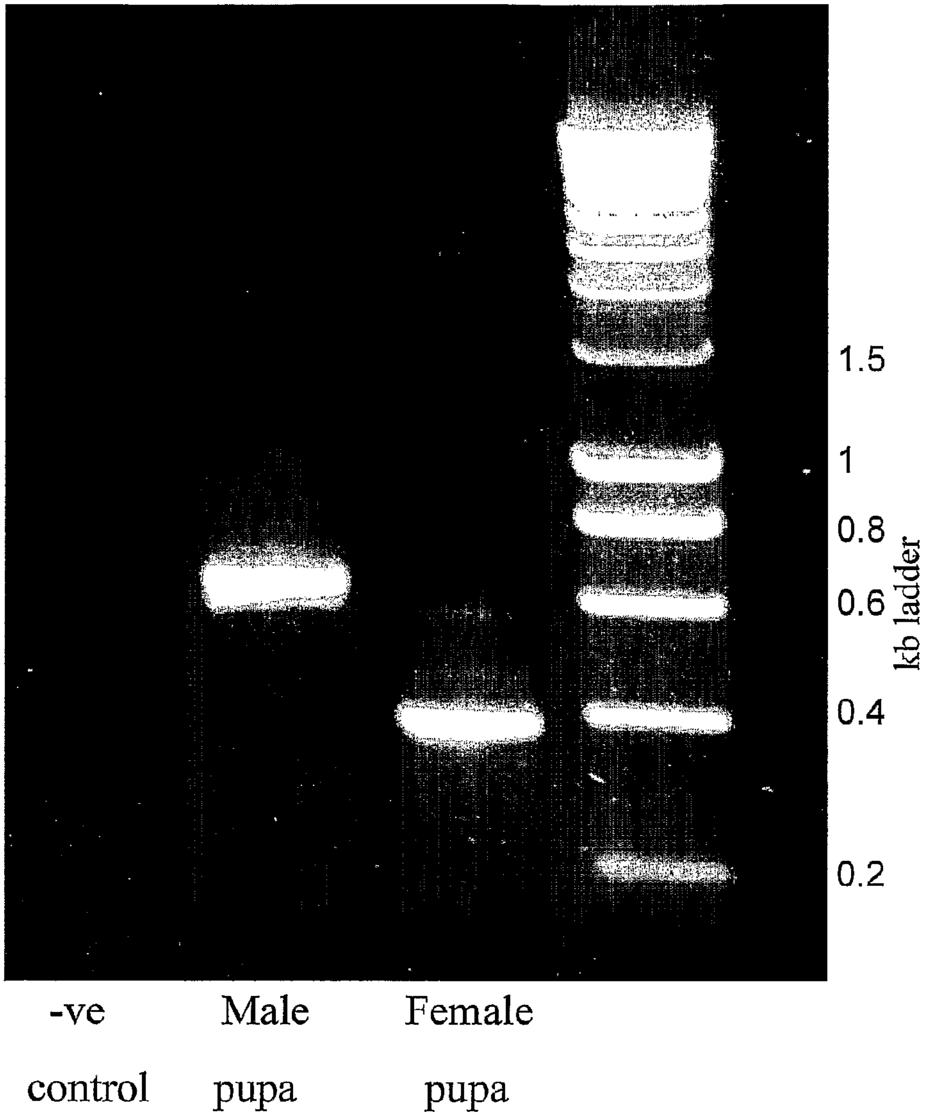
Figure 51:
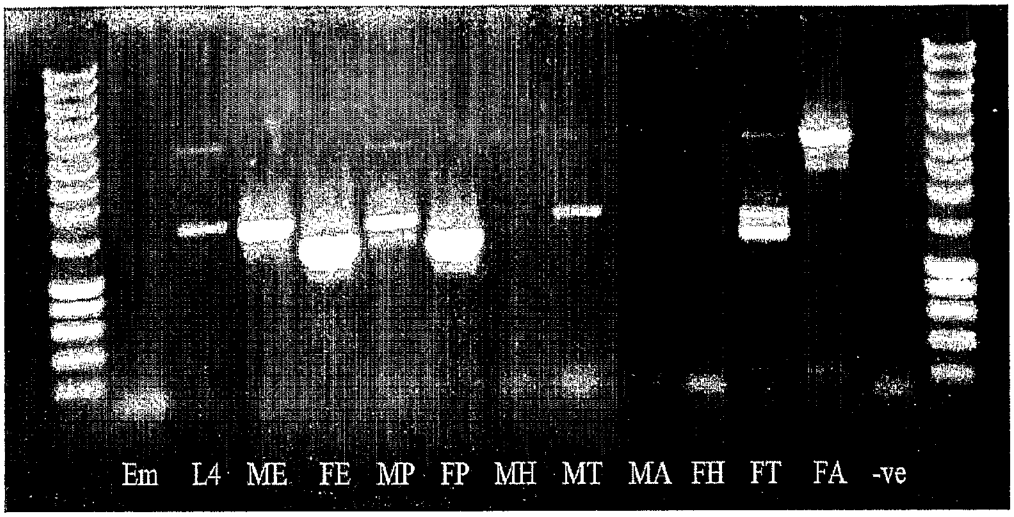

We integrated LA1172 into the *Stegomyia aegypti* genome using piggyBac. Two independent lines were generated (lines 2 and 8). Both of these lines show the correct splicing of the Actin-4-tTAV gene (FIGS. 50 and 51). The Actin-4 promoter and alternatively spliced intron can therefore be used successfully to provide sex-, tissue- and stage-specific splicing of a gene of interest in *Stegomyia aegypti.*

Description of the Figures and Sequence Listings of Examples 1-9

Figure 19:
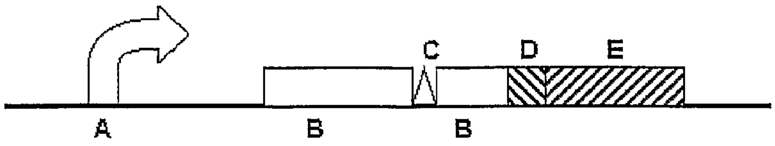

FIG. 19: One use of the P element in generating germline-specific expression of a gene of interest (Gene E).

Insertion of the P element IVS3 and flanking exonic sequences upstream of an ubiquitin-Gene E fusion with allow germline-specific expression of Gene E under a germline active promoter. A—Germline active promoter; B—P-element open reading frame; C—P intron 'IVS3'; D—Ubiquitin; E—Coding region for protein of Interest e.g. tTAV.

Figure 20:
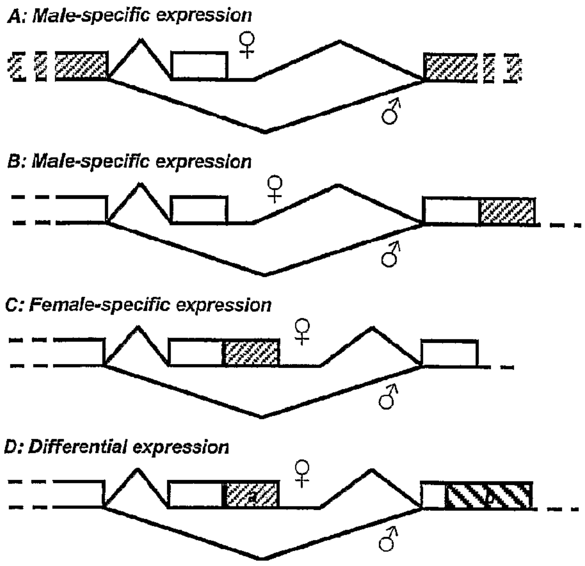

FIG. 20: Sex-specific expression using dsx.

A: Intron used as Cctra intron above, but giving male-specific expression. A fragment of dsx (here the *Anopheles* version) is inserted into a heterologous coding region (shaded boxes). The intron is completely removed in males, but in females the coding region is prematurely terminated.

B: An alternative approach to male-specific expression, in which a heterologous coding region is fused to a fragment of dsx.

C: Female-specific expression: the heterologous coding region is inserted into the female-specific exon, either as an in-frame fusion to a fragment of Dsx, or with its own start and stop codons.

D: Differential expression: designs B and C can be combined to give expression of gene a in females and b in males.

Figure 21:
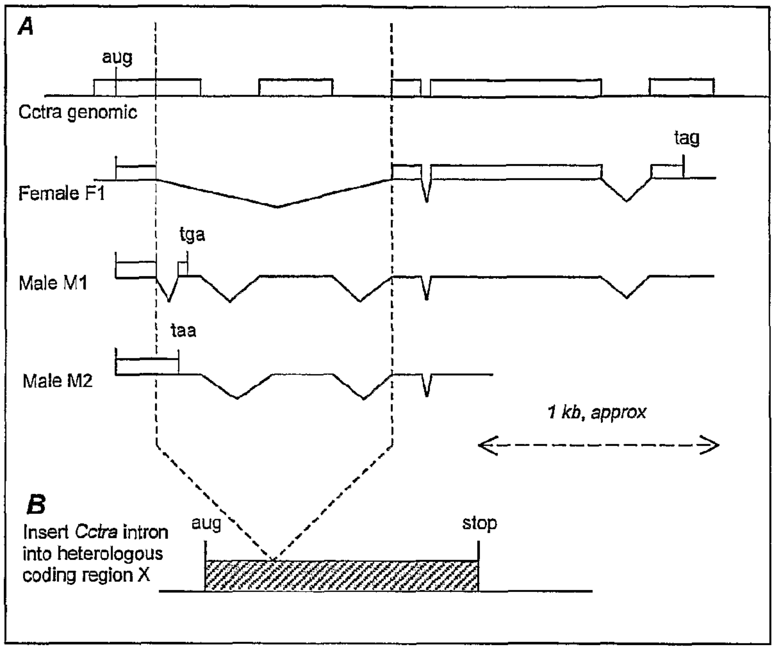

FIG. 21: Sex-specific alternative splicing of Cctra

A: Cctra is spliced in females to produce three transcripts: F1, which encodes functional Tra protein, and M1 and M2, which do not, because they include additional exons with stop codons (redrawn from Pane et al. 2002). Males produce only transcripts M1 and M2 and therefore do not produce functional Tra protein at all.

B: If this intron were to function similarly in a heterologous coding region, this would similarly allow females, but not males, to produce functional protein X.

FIG. 22: Diagrammatic representation of pLA3435 construct/plasmid (SEQ ID NO. 46).

FIG. 23: Plasmid map of pLA3359 *Anopheles gambiae* dsx gene placed under the control of a Hr5-IE1 promoter for assessing splicing via transient expression.

FIG. 24: pLA3433-*Anopheles gambiae* dsx gene placed under the contron1 of a Hr5-IE1 promoter, with the addition of exon 2, for assessing splicing via transient expression.

Figure 25:
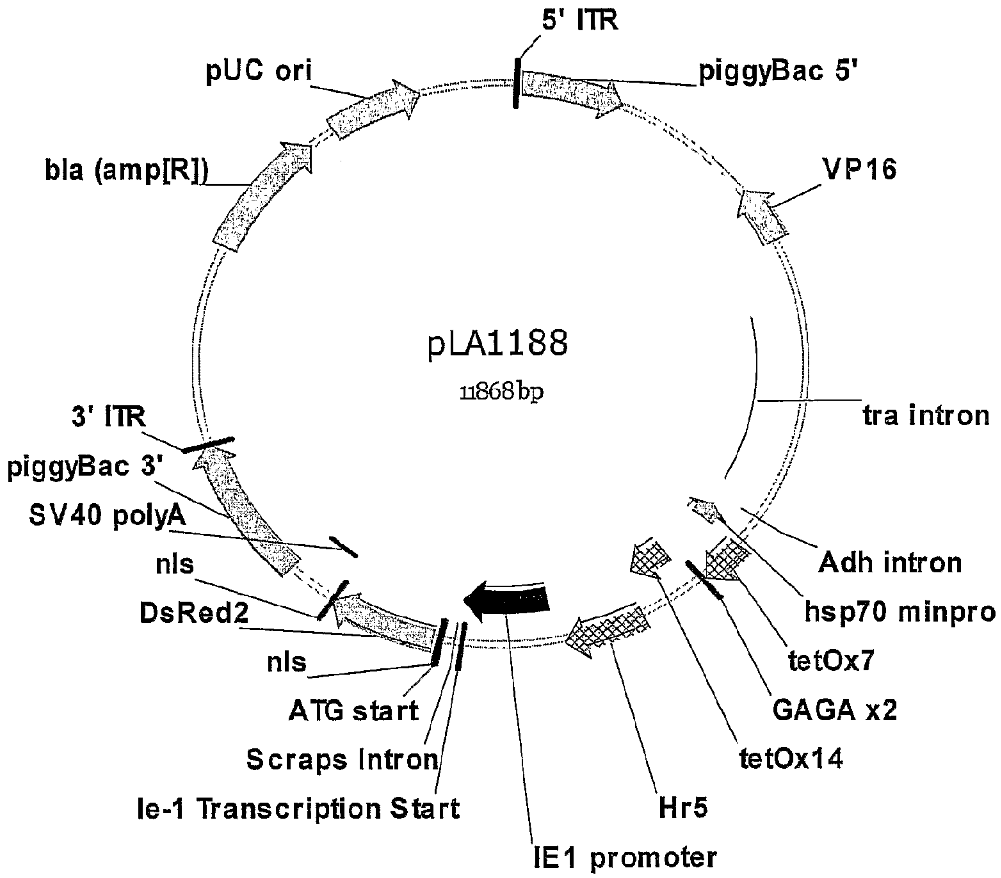

FIG. 25: Schematic representation of pLA1188 construct.

Figure 26:
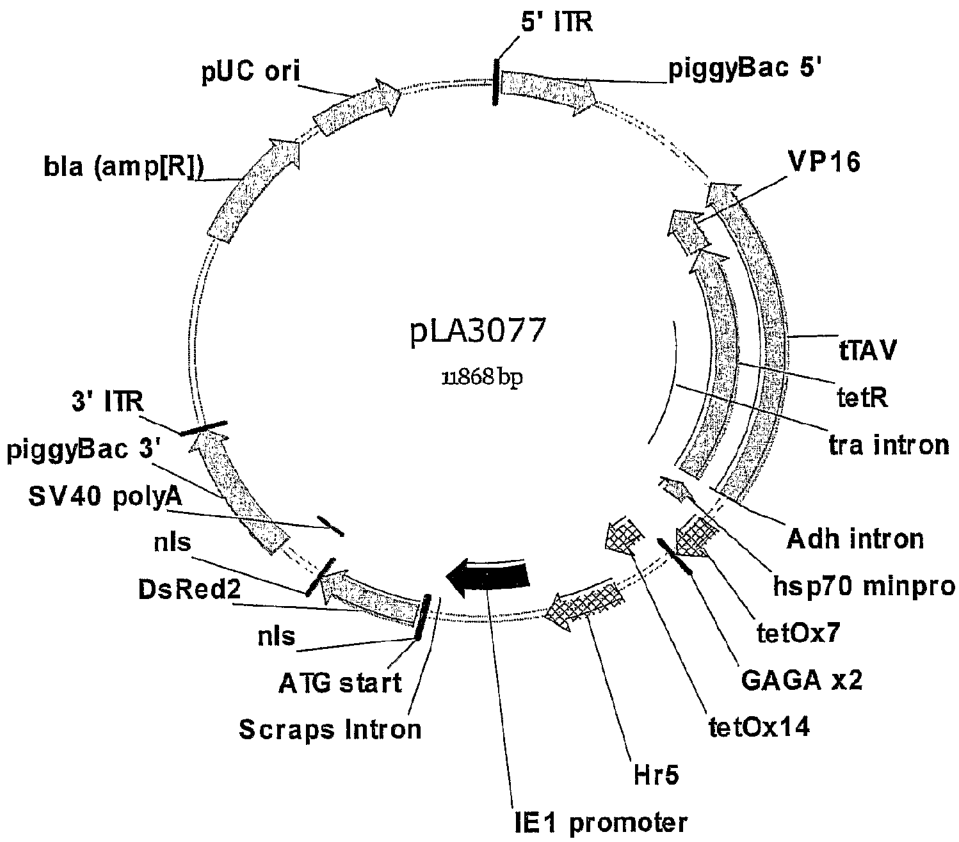

FIG. 26: Schematic diagram of pLA3077 construct.

Figure 27:
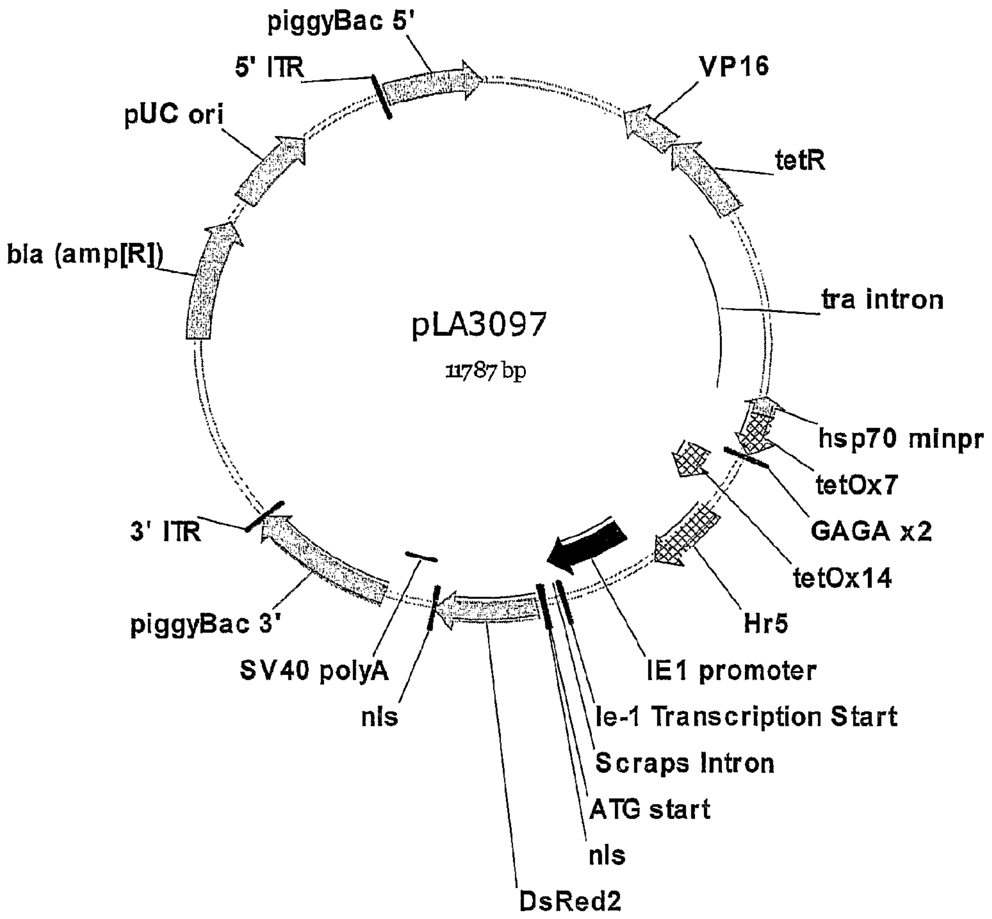

FIG. 27: Schematic diagram of pLA3097 construct.

Figure 28:
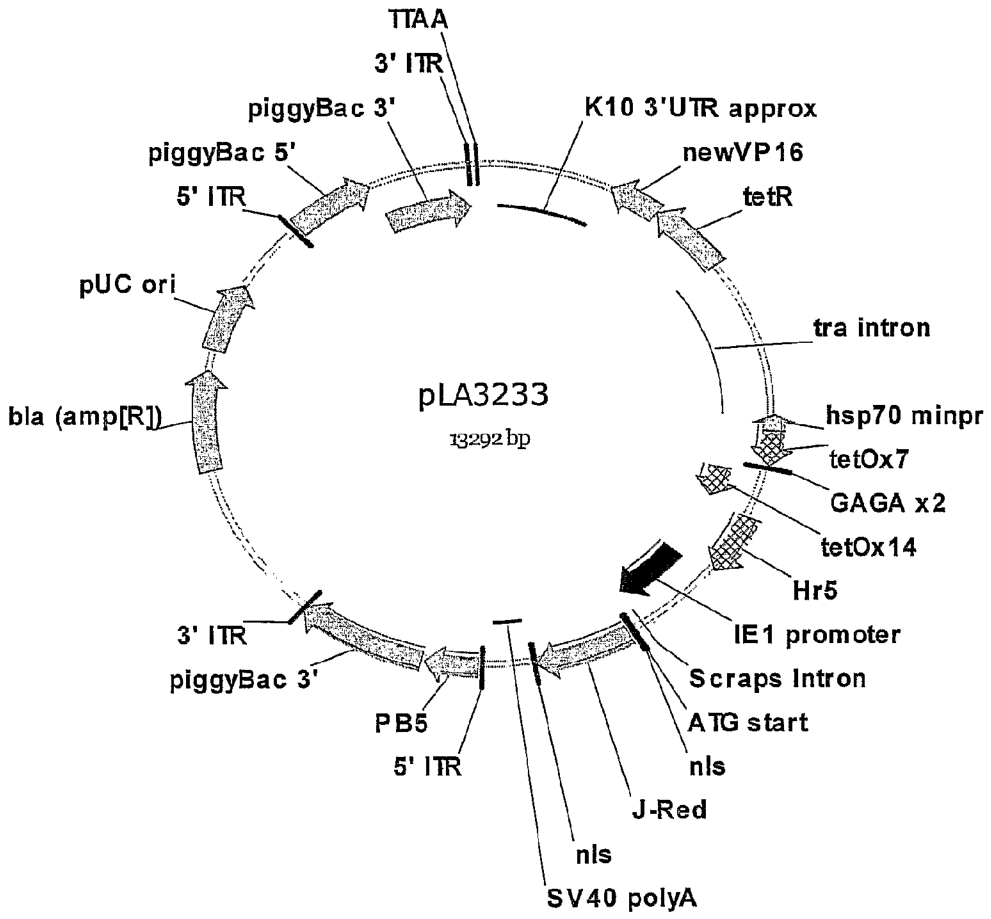

FIG. 28: Schematic diagram of pLA3233 construct.

Figure 29:
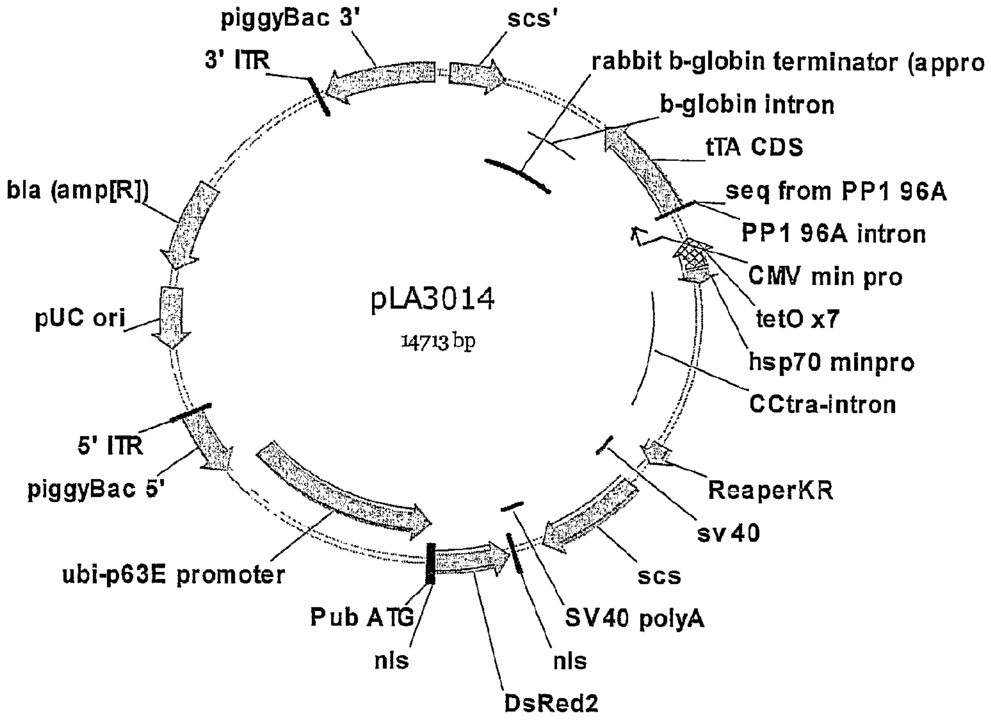

FIG. 29: Schematic diagram of pLA3014 construct.

Figure 30:
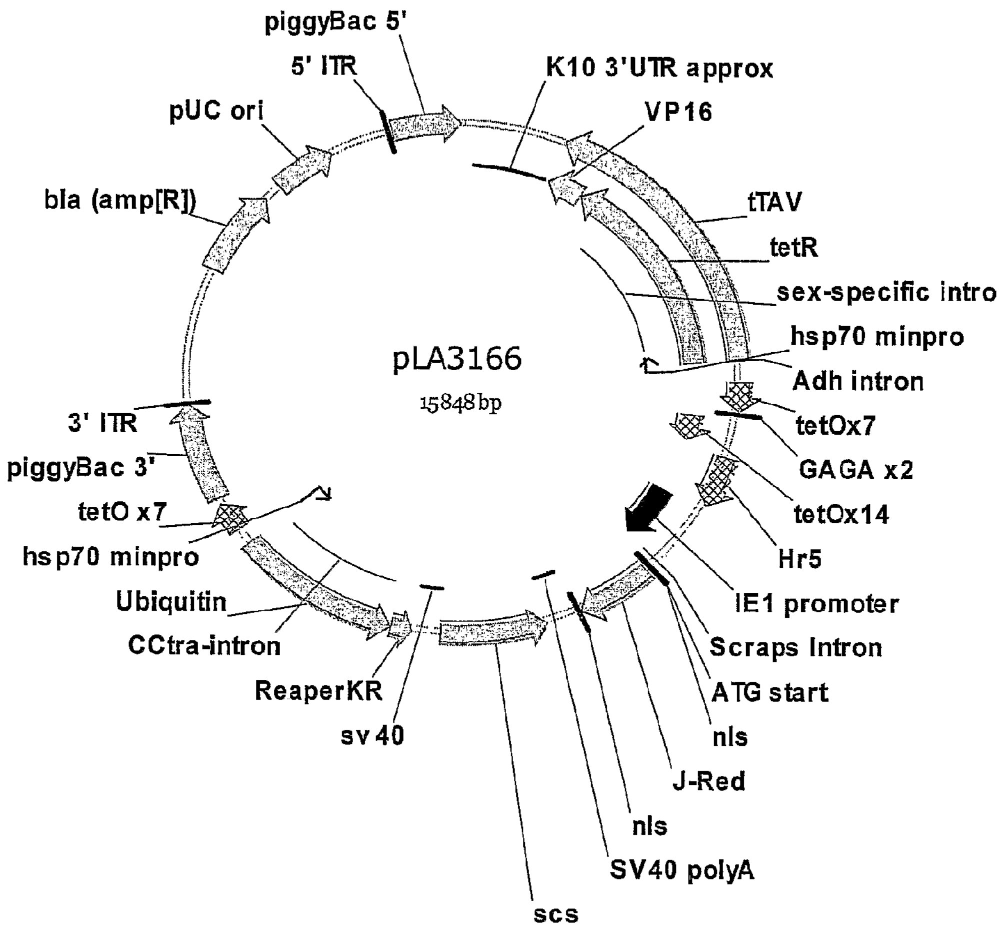

FIG. 30: Schematic diagram of pLA3166 construct.

FIG. 31: Schematic diagram of pLA3376 construct.

Figure 32:
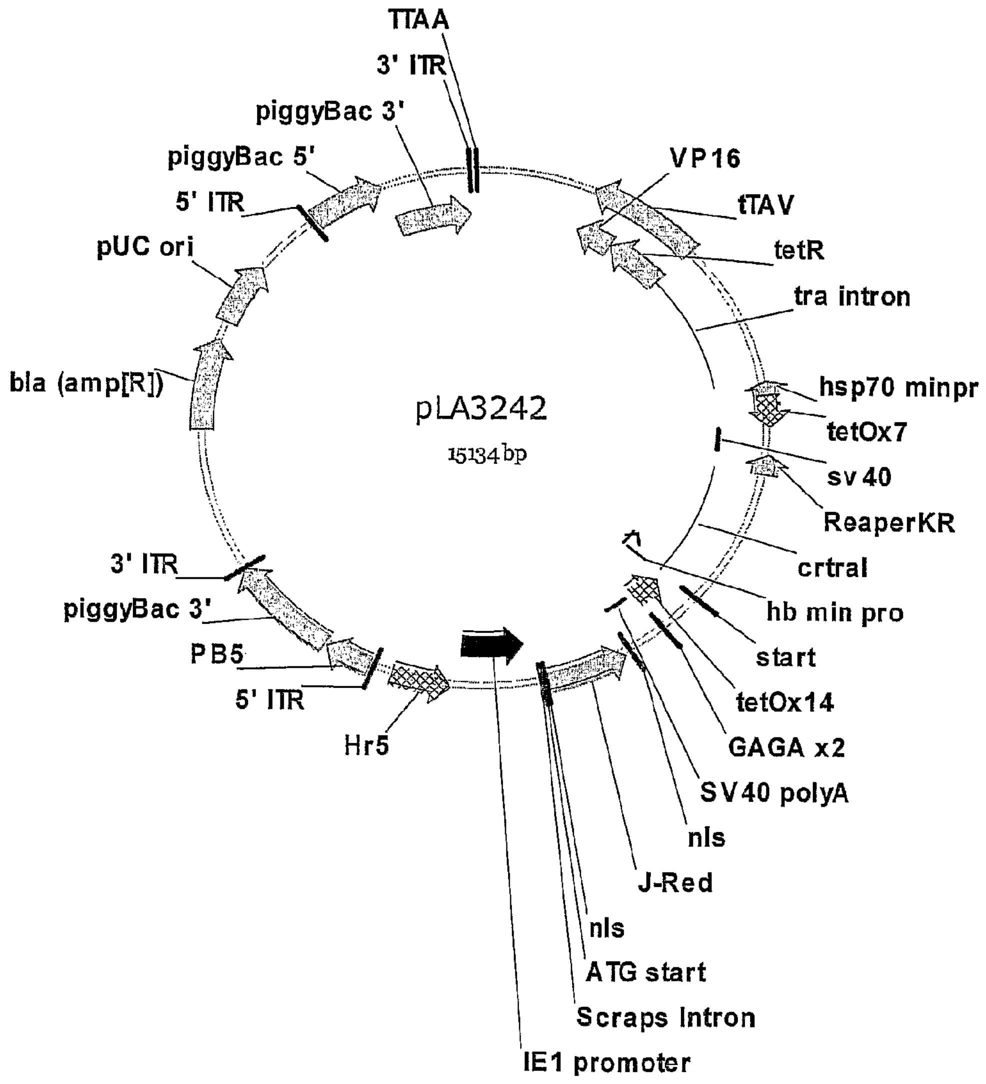

FIG. 32: Schematic diagram of pLA3242 construct.

FIG. 33: Flanking sequence of Cctra

Splicing of the Cctra intron in LA3077 and LA3097 is exactly as you would see in the native Cctra intron. Splicing in LA1188 results in the removal of 4 additional nucleotides. In all cases the introns are flanked by 5' exonic TG and 3' GT. The sequences flanking the "GT . . . intron . . . AG" in LA3097 are given in SEQ ID NO:2 and SEQ ID NO:3. The sequences flanking the "GT . . . intron . . . AG" in LA3077 are given in SEQ ID NO:163 and SEQ ID NO:164, the sequences flanking the "GT . . . intron . . . AG" in LA1188 are given in SEQ ID NO:165 and SEQ ID NO:166, and the sequences flanking the "GT . . . intron . . . AG" in the native are given in SEQ ID NO: 167 and 168.

FIG. 34: Gel showing correct sex-specific splicing of intron(s) derived from CcTra (776 bp band in females) in *Ceratitis capitata* transformed with LA3077. Lane 1: Marker (SmartLadder™ from Eurogentec, bands of approx 0.8, 1.0 and 1.5 kb are indicated); Lanes 2 and 3: *Ceratitis capitata* LA3077/+ males; Lanes 4 and 5: *Ceratitis capitata* LA3077/+ females.

FIG. 35: Phenotypic data for transformed female specific constructs in *Ceratitis capitata*. Column 1: Construct designation LA#, e.g. LA3077, LA3097, LA3233, etc, is indicated by number, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

FIG. 36: Transcripts of Cctra intron constructs in *Drosophila* and *Ceratitis capitata.*

The top line represents the construct DNA containing tra intron flanked by desired gene (the open box). The red box represents the male specific exons. Introns are represented by solid lines. Arrow above the first line represents the positions of the oligonucleotides used in the RT-PCR experiments. The bar indicates the scale of the figure.

FIG. 37: Gel showing correct female specific splicing of CcTRA-derived sequence (508 bp band) in female *Ceratitis capitata* transformed with LA3014. Lane 1: Marker (SmartLadder™ from Eurogentec, bands of approx 0.4 and 1.0 kb are indicated); Lane 2 *Ceratitis capitata* LA3014/+ male; Lane 4: *Ceratitis capitata* LA3014/+ female; Lanes 3 and 5: no reverse transcriptase negative controls (background bands, probably from genomic DNA, can be seen in lanes 2 and 4).

FIG. 38: Phenotypic data for transgenic *Anastrepha ludens* transformed with LA3097 or LA3233. Column 1: Construct LA# (LA3097 or LA3233) indicated, with independent insertion lines referred to by letter; Columns 2 and 3: Non-tetracycline (NT) results for each transformed line given in total males (2) and total females (3). Columns 4 and 5: Tetracycline (TET) results for each transformed line given in total males (4) and total females (5).

FIG. 39: Gel showing correct sex-specific splicing of CcTRA splicing (348 bp band in females) in *Anastrepha*

*ludens* transformed with LA3097. Lane 1: Marker (SmartLadder™ from Eurogentec, bands of approx 0.4 and 1.0 kb are indicated); Lanes 2, 3 and 4*: A. ludens* LA3097/+ males; Lanes 5, 6 and 7*: A. ludens* LA3097/+ females.

FIG. 40: Gel showing correct sex-specific splicing of BzTRA in reaperKR (200 bp band in females) and tTAV3 (670 bp band in females) regions of LA3376, in *Ceratitis capitata* transformed with LA3376. Lane 1: Marker (SmartLadder™ from Eurogentec, bands of approx 0.2, 0.6 and 1.0 kb are indicated); Lanes 2 and 3: *C. capitata* LA3376/+ males tested for splicing in reaperKR; Lanes 4 and 5: *C. capitata* LA3376/+ females tested for splicing in reaperKR; Lane 6: SmartLadder™; Lanes 7 and 8: *C. capitata* LA3376/+ males tested for splicing in tTAV; Lanes 9 and 10: *C. capitata* LA3376/+ females tested for splicing in tTAV; Lane 11: SmartLadder™

FIG. 41: Gel showing correct sex-specific CrTRA splicing in CrTRA-reaperKR (200 bp band in females) in *Ceratitis capitata* injected with LA3242. Lane 1: Marker (SmartLadder™ from Eurogentec, bands of approx 0.2, 0.6 and 1.0 kb are indicated); Lanes 2-7*: C. capitata* wild type males injected with LA3242; Lane 8: SmartLadder™; Lanes 9-14: *C. capitata* wild type females injected with LA3242; Lane 15: SmartLadder™.

Figure 42:
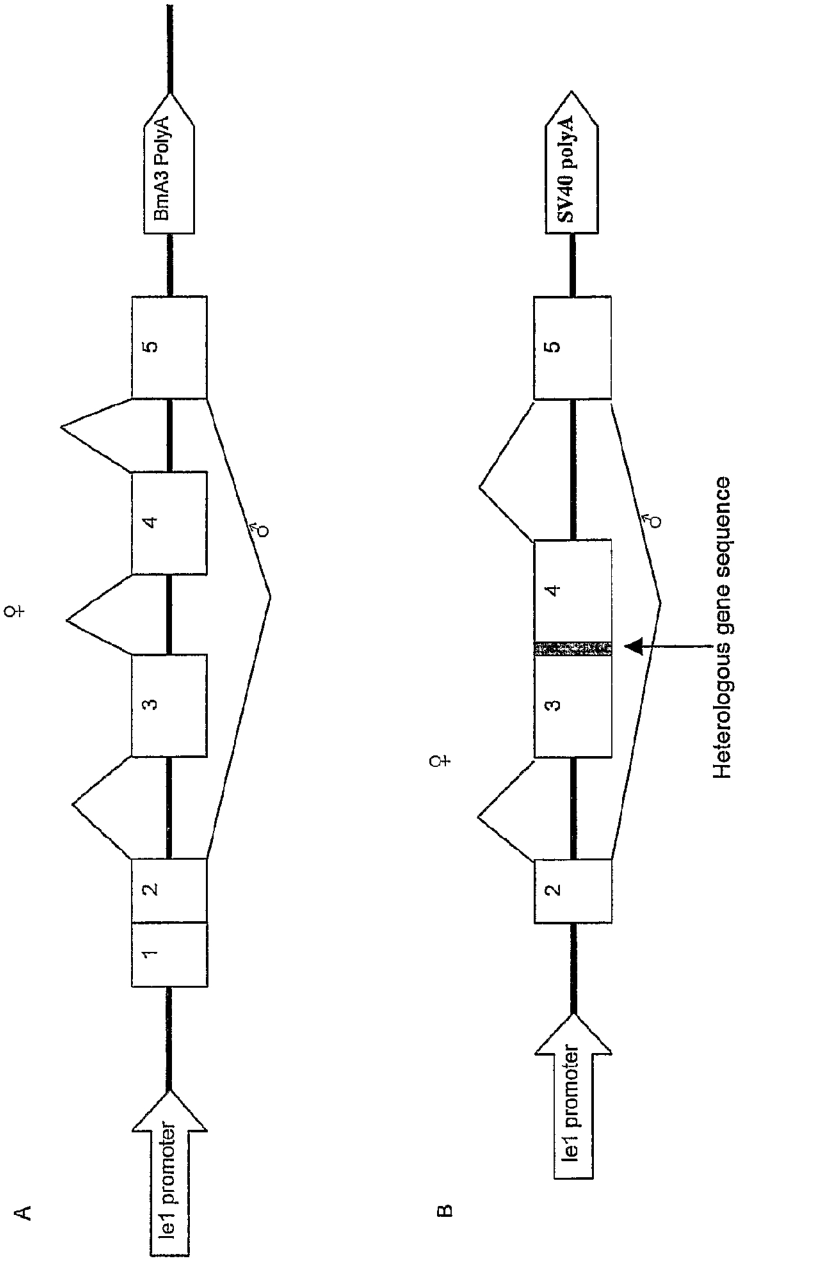

FIG. 42: Schematic representation of Bmdsx minigene constructs.

Two minigene constructs derived from the *Bombyx mori* dsx gene are illustrated diagrammatically, together with the predicted alternative splicing of these constructs (female pattern shown above the construct, male pattern below). (A) is the *Bombyx mori* dsx mini-gene construct used in Funaguma et al., 2005) (B) is pLA3435. A and B differ from each other in several ways: (i) Exon 1 is excluded from pLA3435, (ii) the intron between female specific exons 3 and 4 has been removed and a short heterologous sequence has been inserted in pLA3435 (iii) Funaguma et al., use the ie1 promoter from the baculovirus BmNPV and a BmA3 3'UTR compared with pLA3435 which uses the hr5-IE1 enhancer/promoter from the baculovirus AcNPV and a 3' SV40 3'UTR. (iv) pLA3435 uses slightly longer intron sequences when compared with (A) (see FIG. 15 for sequence). Two minigene constructs derived from the *Bombyx mori* dsx gene are illustrated diagrammatically, together with the predicted alternative splicing of these constructs (female pattern shown above the construct, male pattern below).

FIG. 43: Sex-specific splicing of BMdsx mini-gene construct in PBW.

Analysis of transient expression from pLA3435 using RT-PCR show the presence of a 442 bp fragment (Lanes 1,2,3 and 4) in males and a 612 bp fragment in females (Lane 5), showing that the BMdsx mini-gene with a heterologous fragment inserted between exon 3 and 4 is able to splice correctly in the divergent moth, PBW. Markers are SmartLadder™ from Eurogentec; bands of approx 0.2, 0.4 and 0.6 kb are indicated FIG. 44: Sex-specific splicing of *Anopheles gambiae* dsx.

*Anopheles* (A) shows the splicing that was reported by Scali et al 2005. However, when RT-PCR was performed using our primers (spl-agdsx-e3 (SEQ ID NO. 60) and spl-agdsx-m (SEQ ID NO. 61)) a different splicing pattern for females was revealed, represented by *Anopheles* (B).

FIG. 45: Identification of male and female *Anopheles gambiae* using dsx primers.

RNA was extracted from male and female *Anopheles gambiae* and the dsx transcripts were amplified by RT-PCR using the primers spl-agdsx-e3 (SEQ ID NO. 62) and spl-agdsx-m (SEQ ID NO. 63); the resulting banding pattern is shown in the gel above. The expected bands for the male and female transcripts are indicated by the white arrows, the bands have been cloned and sequenced and are identical to the predicted sequence of our version of the dsx transcript (see SEQ ID NO. 47 (LA3359) and SEQ ID NO. 48 (LA3433)). The molecular weight markers are shown in kb (SmartLadder™ from Eurogentec; sizes are approximate).

FIG. 46: Identification of male and female *Stegomyia aegypti* using dsx primers.

Figure 56:
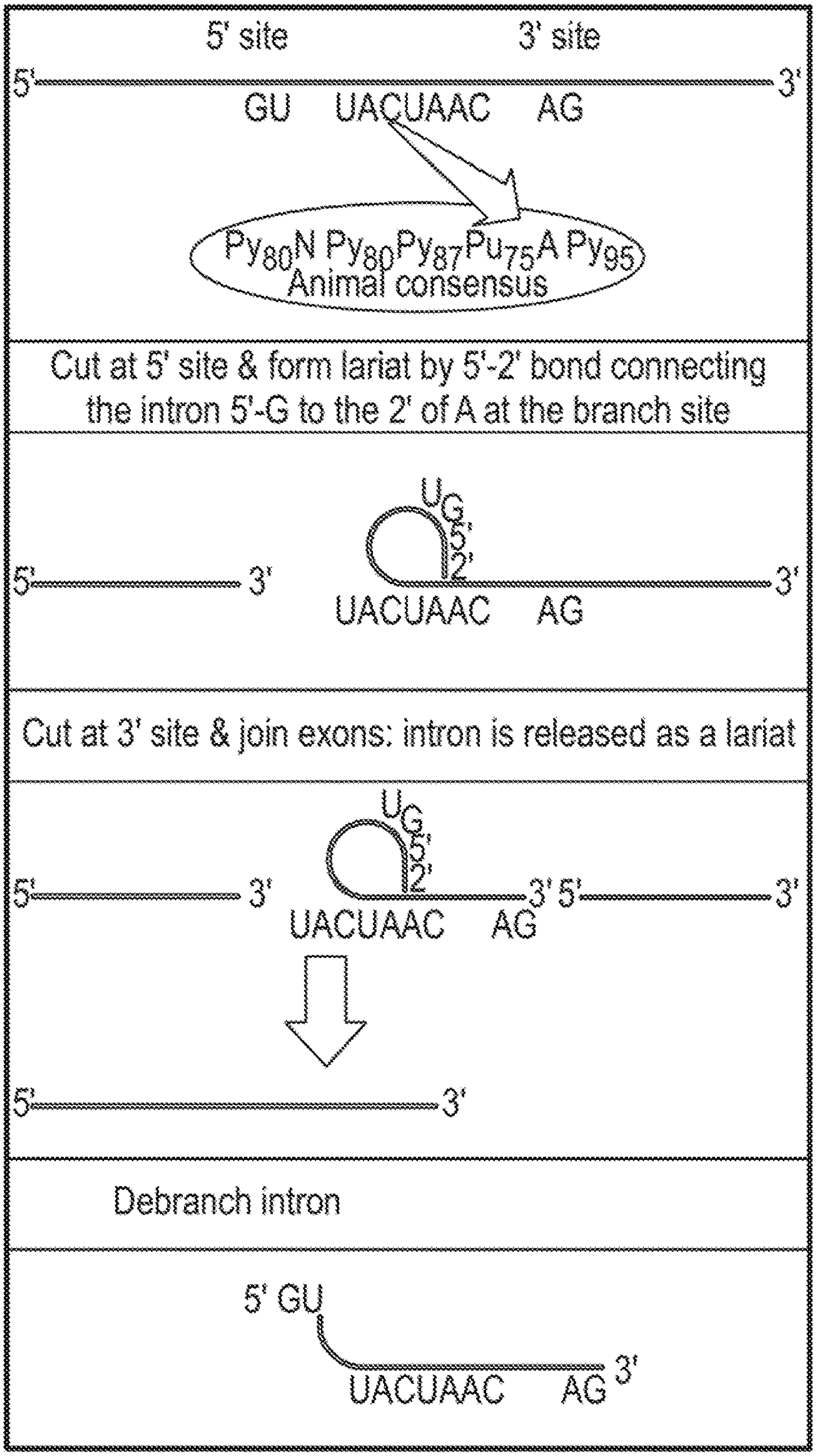
Figure 57:
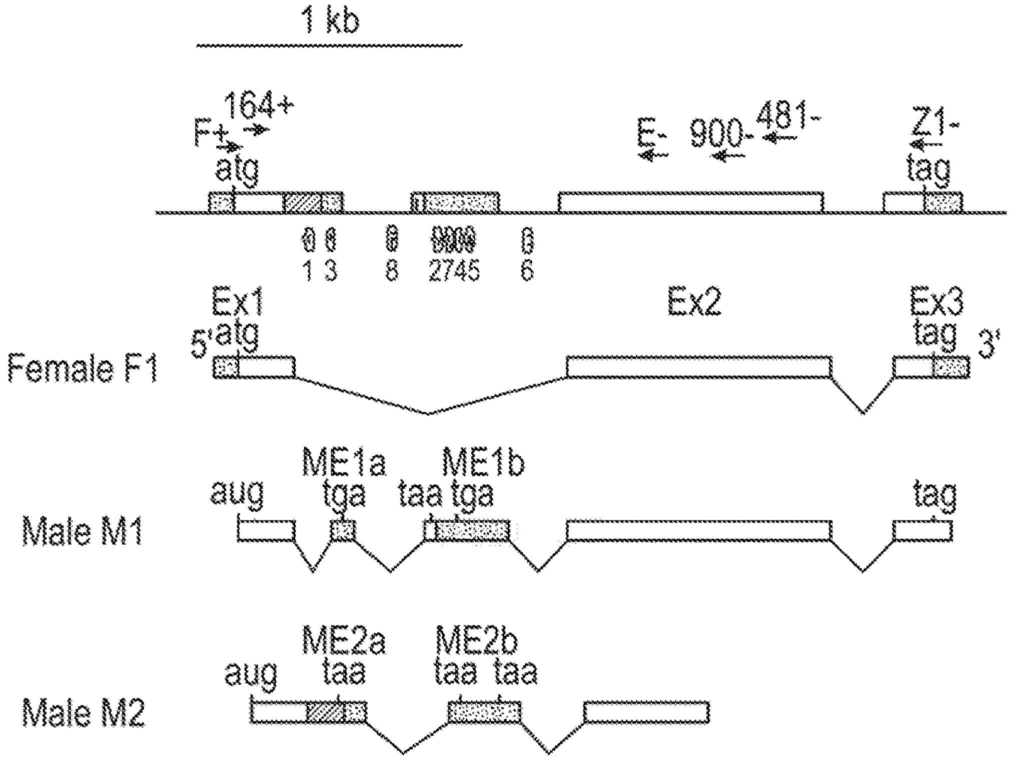

The primers for the *Stegomyia aegypti* RT-PCR for A and B were aedesxF1 (SEQ ID NO. 64) and aedesxR5 (SEQ ID NO. 65) were tested initially on pupae, a life stage of *Stegomyia aegypti* that can be sexed conveniently and accurately; the resulting RT-PCR amplification is shown on gel image (A). The male and female pupae show a distinctive sex specific band. Then the primers were tested on RNA extractions from larvae, which can not be readily sexed by their morphology and the resulting RT-PCR amplification shown on gel image (B). The larvae show a clear banding pattern which distinguishes males from females unambiguously. Gel image (C) shows an approximately 600 bp band from RT-PCR using the primers aedessxF1 and aedesxR2 (SEQ ID NO. 66) from individual male and female pupa. Sequencing of this band showed a female specific splice variant which does not appear to possess the male shared exon to which aedesxR5 is predicted to anneal (exon 7, see FIG. 56). The molecular weight markers are shown in kb (SmartLadder™ from Eurogentec; sizes are approximate).

Figure 47:
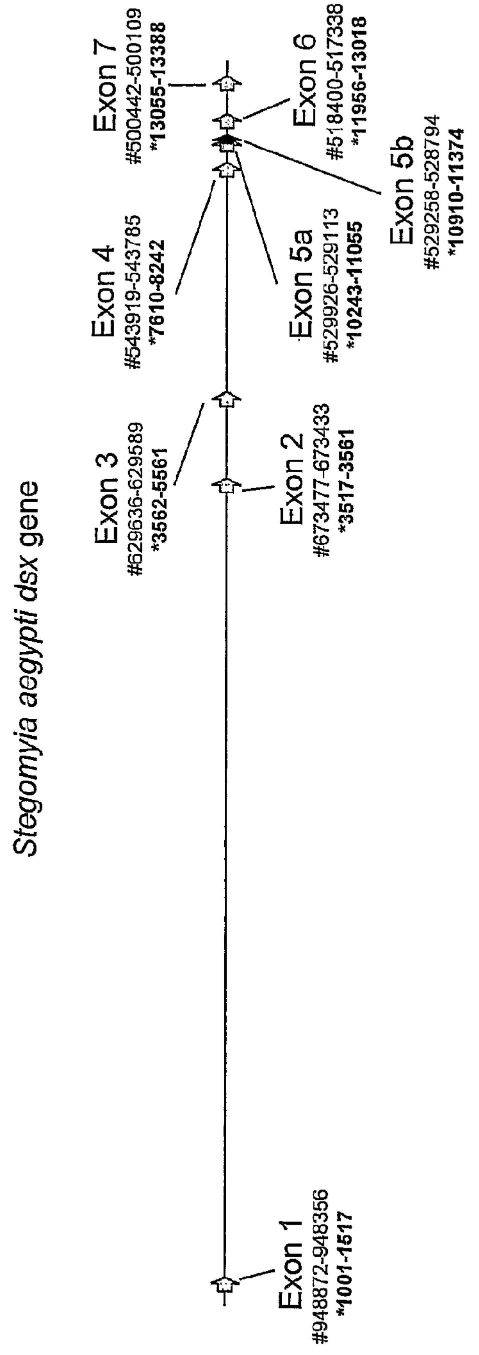

FIG. 47: Diagrammatic representation of part of the *Stegomyia aegypti* dsx gene (not to scale).

A fragment of the *Stegomyia aegypti* dsx gene is represented above. Exons 5a and 5b are female specific and exon 6 is a male specific exon. Two female-specific splice variants have been found (F1 and F2) which comprise exons 1-4,5b,6 and 7 (F1) or 1-4,5a (F2); transcripts in males (M1) comprise exons 1-4,6 and 7 but not exon 5a or 5b and a transcript (C1) of 1-4 and 7 but not exons 5a, 5b or 6 is shown in males and females. The numbers for each of the exons after #relates to contig 1.370, see internet address broad.mit.edu/annotation/disease_vector/aedes_aegypti/, which reads in the opposite orientation, and after * relate to the nucleotide sequence shown in SEQ ID NO. 43.

Figure 48:
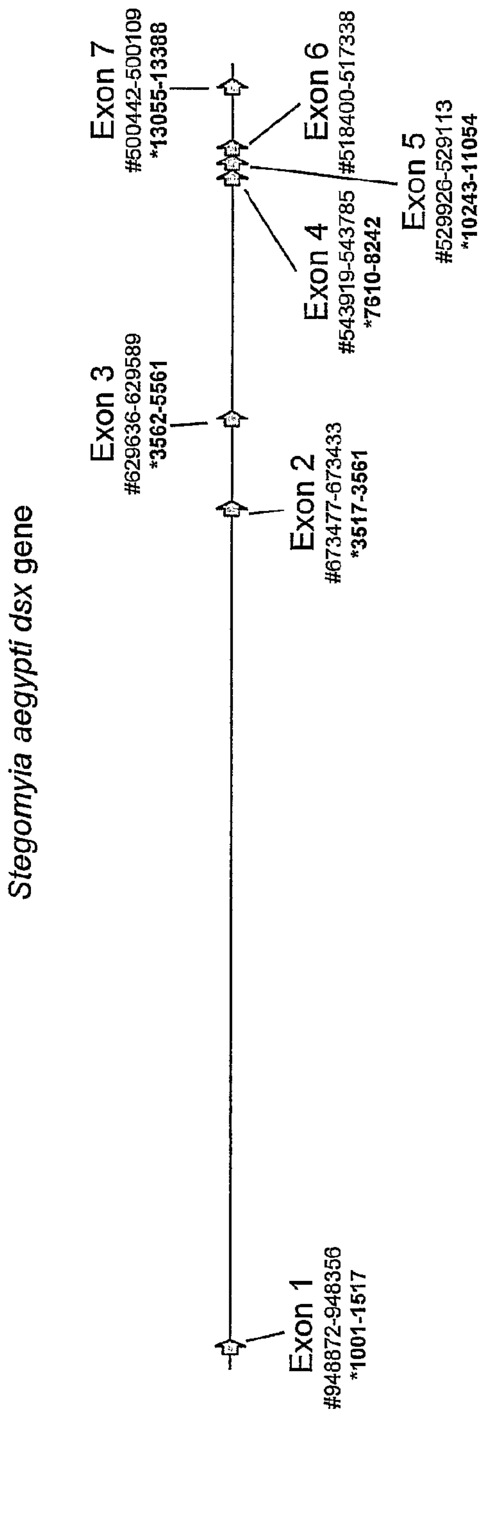

FIG. 48: Diagrammatic representation of the *Stegomyia aegypti* dsx gene.

The entire *Stegomyia aegypti* dsx gene is represented above Exon 5 is the female specific exon and exon 6 is a putative male specific exon. In principle, transcripts in females comprise exons 1, 2, 3, 4, 5, and 7, and males comprise exons 1, 2, 3, 4, 6, and 7. The numbers for each of the exons after #relates to contig 1.370, see internet address broad.mit.edu/annotation/disease_vector/aedes_aegypti/, reading in the opposite orientation, and after * relate to FIG. 12.

Figure 49:
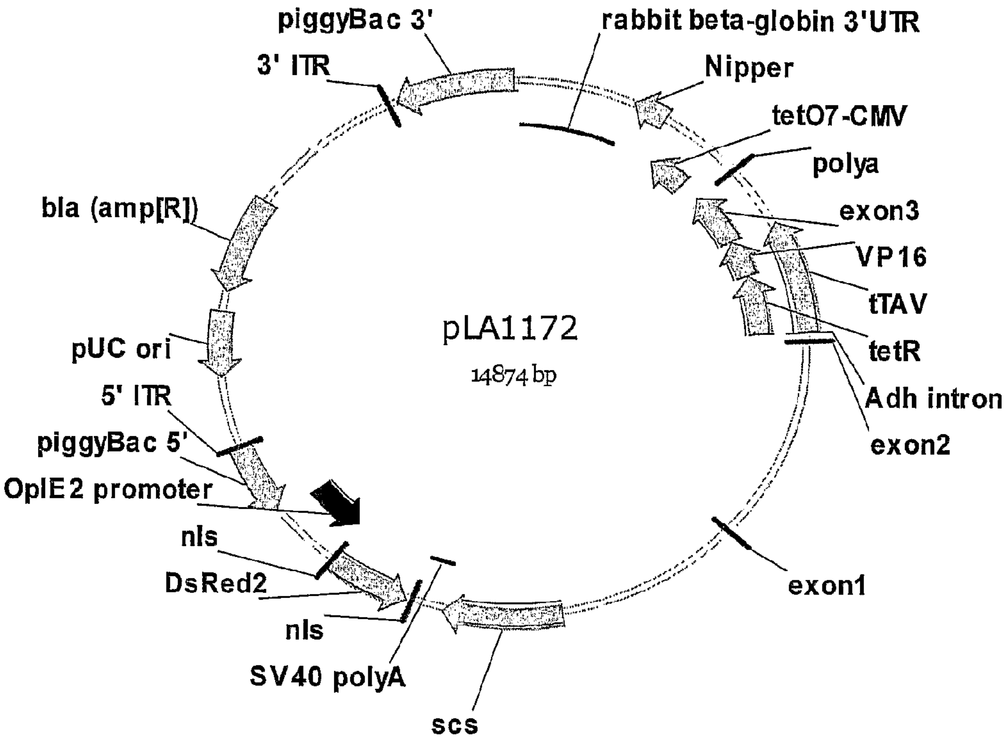

FIG. 49: Plasmid map of pLA 1172.

A coding region for tTAV has been placed under the control of a fragment from the *Stegomyia aegypti* actin-4 gene (Munoz et al 2005) which includes the 5' UTR, first intron, and upstream sequences (putative promoter). The construct also contains a $tetO_7$ Nipper sequence. The construct has piggyBac ends and a DsRed2 marker for stable integration into a genome.

FIG. 50: Sex-specific splicing of tTAV in LA1172 transformants.

Gel image of RT-PCR of RNA extracted from LA1172 line 2 male and female pupa. The primers used were Agexon1 (SEQ ID NO. 67) and Tra (tTAV) seq+ (SEQ ID NO. 68). Sequencing of the RT-PCR bands showed the expected splicing occurring in males and females. The data shown in the above diagram is for LA1172 line 2, line 8 showed exactly the same results (data not shown). Markers are SmartLadder™ from Eurogentec; approximate sizes are indicated, in kb).

FIG. 51: RT-PCR of wild type samples, showing sex-specific splice variants of the *Stegomyia aegypti* Actin-4 gene.

Gel image of RT-PCR of RNA extracted from different developmental stages, and dissections of adults, of LA1172 line 8. The primers used were Agexon1 (SEQ ID NO. 69) and Exon 3 (SEQ ID NO. 70). The gel image shows that strong expression from the Actin-4 gene only occurs at the pupal stage, and that adult expression is generally limited to the female thorax where the flight muscles are found. Table 17, below show the contents of each lane.

TABLE 1

| |
|---|
| E = pool of ~100 embryos |
| L4 = $4^{th}$ instar larva |
| ME = early male pupa (<4 hours old) |
| FE = early female pupa (<4 hours old) |
| MP = male pupa |
| FP = female pupae |
| MH = head from male adult |
| MT = thorax from male adult |
| MA = abdomen from male adult |
| FH = head from female adult |
| FT = thorax from female adult |
| FA = abdomen from female adult |
| −ve = water control |

FURTHER EXAMPLES

Example 10: Moths

We have newly made constructs based on our transient expression data using a recombinant minigene construct derived from *Bombyx mori*. This is discussed further below in the section entitled "Moth dsx sequence alignment and conserved motifs"

Example 11: Use of Bztra

Figure 15:
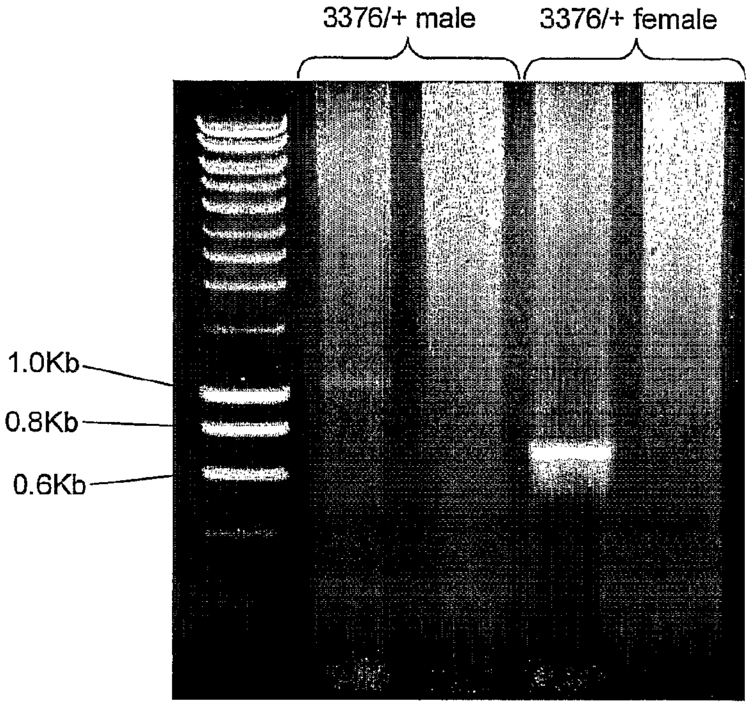
Figure 16:
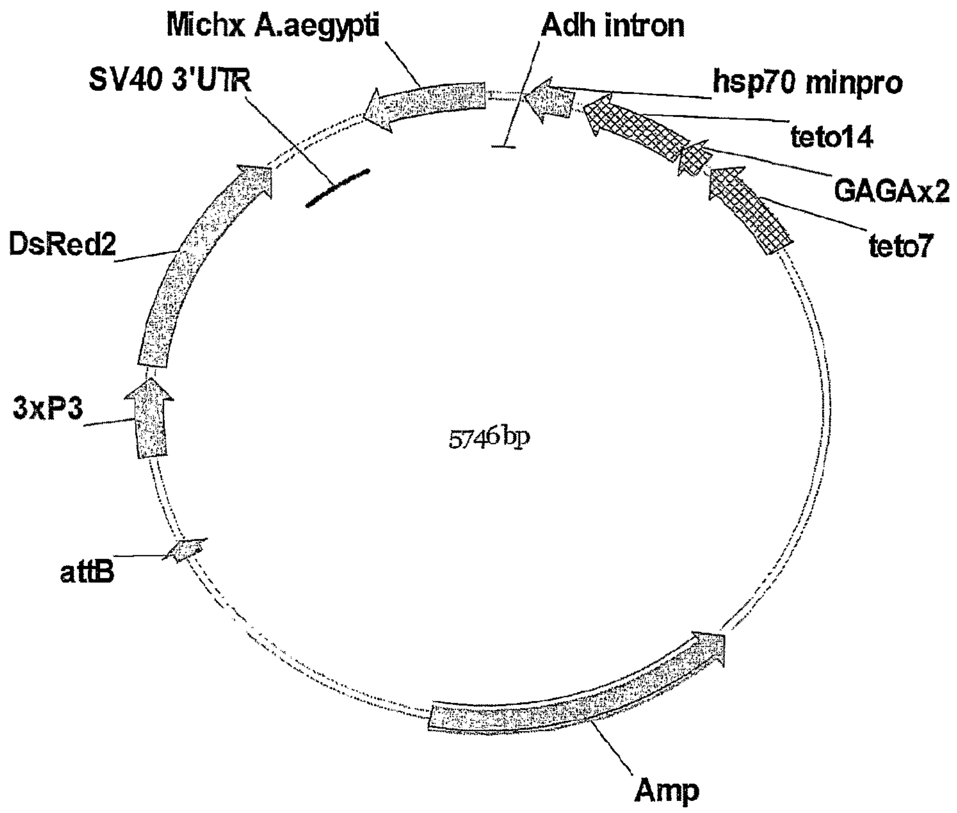
Figure 17:
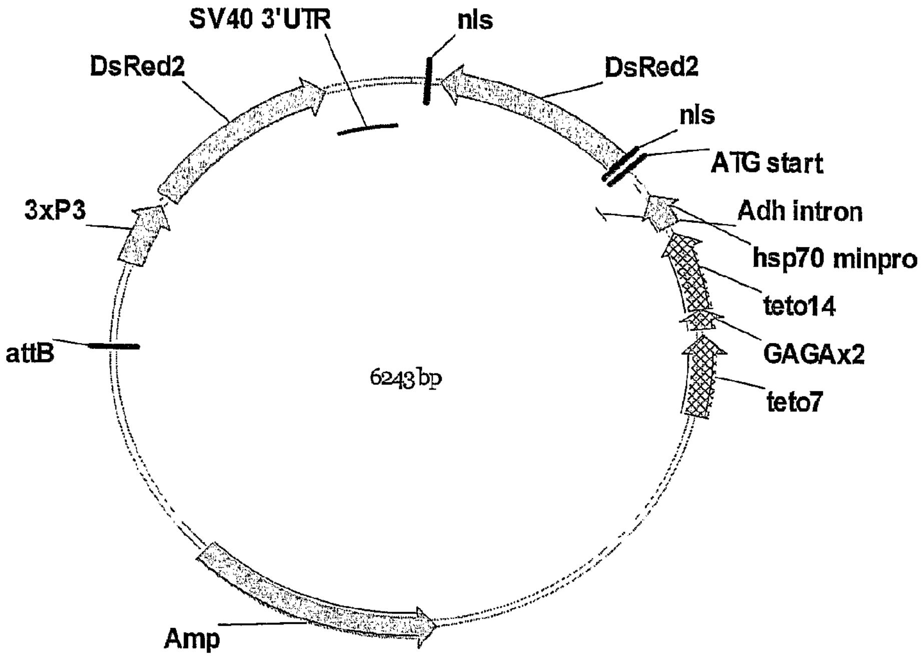

We have newly made two Bztra-based constructs, expressed in Mexfly (LA3376). LA3376 gives repressible female-specific lethality. LA3376 we have previously shown to function and splice correctly in Medfly. Transformants in Mexfly (*Anastrepha ludens*) were also generated with LA3376. These were analysed for correct splicing of the Bztra intron in order to demonstrate the phylogenetic range of the Bztra intron by RT-PCR using primers SRY and AV3F (FIG. 15 and "Medfly RT-PCR gels" section above). This shows correct splicing of the Bztra intron in Mexfly.

Example 12: Dmdsx in Medfly (DmDsx in Transgenic Medfly Example: Nipper Fusion in #797)

We also have newly made data on a Dmdsx construct in Medfly. The construct used a fragment of the *Drosophila melanogaster* gene doublesex to give sex-specific expression of a fragment of the *Drosophila melanogaster* gene Nipp1Dm (we call this fragment "nipper"). We didn't see clear sex-specific splicing. However, the phenotypic data shows some sex-specificity; we saw increased lethality of females, to about 75% penetration. Of course this incomplete penetrance could be due to expression level, lack of toxicity of nipper in Medfly, etc. We also had a significant reduction in the number of males, but the tTA source, LA670, used in this experiment could itself be killing some of the males.

We have tested three independent Medfly transgenic lines that carry a fusion of nipper to DmDsx sequence that was intended to be expressed specifically in females. This construct may not have worked perfectly possibly due to essential sequence for correct alternative splicing and/or the Sxl binding sites required by DmDsx, and since Medfly do not use Sxl in the sex-determining pathway, DmDsx may be unable to completely splice this fusion in the correct way in Medfly. However, we were successful in reproducibly causing increased lethality in females compared to males across all three lines at a very similar efficiency (approximately 75% more lethality observed in females than in males). This demonstrates the dsx system can work across quite distantly related species (evolutionary separation is around 120-150 Million years), and if the Ccdsx sequence were used it may have well worked due to the Sxl requirement of Dmdsx.

The 797 results are shown below, using a Tet014 dsx splice nipper (Pub EGFP) system. They show that this system is lethal at the larval stage (50%), and is likely to be acting more successfully in females (75%). 797 is marked with green (G), 670 with red (R). 670 is a tTAV source, so one expects to see a phenotype in the R+G flies; G (and R) only are controls. NF—non-fluorescent (i.e. wild type) is also a control where included. All progeny reared on tet-free media.

All three Independent Lines seem to act in similar way.

797A/797A M2×670A/+:

| | Pupae | Adults | Males:Females |
|---|---|---|---|
| G | 184 | 176 | 85:91 |
| R + G | 74 | 57 | 44:13 |

797C/797C M1×670A/+:

| | Pupae | Adults | Males:Females |
|---|---|---|---|
| G | 169 | 157 | 89:68 |
| R + G | 94 | 67 | 54:13 |

797C/797C M2×670A/+:

| | Pupae | Adults | Males:Females |
|---|---|---|---|
| G | 406 | 377 | 179:198 |
| R + G | 171 | 147 | 121:26 |

670A/+×797C/+M2:

| | Pupae | Adults | Males:Females |
|---|---|---|---|
| NF | 198 | 192 | 92:100 |
| G | 162 | 147 | 67:80 |
| R | 149 | 72 | 43:29 |
| R + G | 45 | 22 | 20:2 |

Average of all 3 lines: number of R+G females=21% of the number of R+G males, therefore substantial excess mortality in R+G females relative to males. This effect is not seen in R only or G only control females, nor in wild type.

Examples 13-15

We have newly demonstrated:

(5) sex-specific splicing in recombinant Aadsx-based minigene constructs;

(6) sex-specific phenotype from a Cctra-based construct; and (7) sex-specific splicing in *Aedes*-Actin4-based constructs.

At least some of each of these examples not only shows minigenes, but actually shows splicing to generate tTAV/tTAV2 or ubi-tTAV2.

Example 13: *Aedes* Doublesex (Dsx) Minigenes

See also section entitled *Aedes* dsx Tra2 binding sites. We have isolated the *Aedes aegypti* dsx gene (Aadsx) and identified 6 transcripts from this region (FIG. 1). These are: 2 male-specific transcripts (M1 and M2), 3 female-specific transcripts (F1, F2 and F3) and a transcript found in both males and females (MF). We made two minigene constructs. In these constructs, the large majority of the intronic sequence was deleted. For example, DSX minigene1 is approximately 4.4 kb in length, whereas its terminal sequences are separated by approximately 26 kb in its natural context, i.e. in the genomic DNA of *Aedes aegypti.*

The splicing in minigene2 of FIG. 1 is illustrative as splicing occurs in the "female" form in both males and females. This may mean that this system depends on alternative splice acceptor use. In this model, there is competition between alternative splice acceptors, with some sex-specific factor biasing this, the sex-specific factor probably being Tra. But deleting the M1 and M2 3' splice acceptors forces splicing in the F forms, by removing the alternative.

Therefore, it is preferred that one or more of the female-specific (F1 and/or F2) 3' splice acceptors are provided together with an additional 3' splice acceptor. Most preferably, said additional splice acceptor is the 3' splice acceptor of M1 or M2 splice variant (or both), although it is envisaged that this is not essential as other known 3' splice acceptors are likely to function.

FIG. 1 illustrates the various transcripts produced by alternative splicing of the *Aedes aegypti* doublesex gene (Aadsx). It will be appreciated that *Aedes aegypti* is also known as *Stegomyia aegypti*. The figure shows the Aadsx gene from the fourth exon, which is not alternatively spliced, i.e. is present in all transcripts discussed here. Numbering is from the first nucleotide of the fourth exon (acgacgaact, nucleotides 1-10 of SEQ ID NO:1, nucleotides 1316-1325 of SEQ ID NO:153). Note that the diagram is not to scale—the introns are much longer than the exons. The total alternatively spliced region comprises over 43 kb.

This minigene fragment was included in an expression construct (LA3515). Transgenic *Aedes aegypti* were generated by site-specific recombination into an attP site, using the method of Nimmo et al (2006: Nimmo, D. D., Alphey, L. Meredith, J. M. and Eggleston, P (2006). High efficiency site-specific genetic engineering of the mosquito genome. Insect Molecular Biology, 15: 129-136).

A second, smaller minigene was constructed similarly (DSX minigene2) and an expression construct for this was inserted into the same attP site as DSX minigene1, to allow direct comparison (LA3534). DSX minigene2 did not show sex-specific splicing. This indicates that sequences present in DSX minigene1 but not in DSX minigene2 (approx 2029 bp, see FIG. 1 and SEQ ID NO. 150, where exons are found at positions 29-163 and 1535-2572) are essential for correct alternative splicing, even though the first alternatively spliced intron, and the exonic sequence immediately flanking it, is present in both constructs.

We have produced two transgenic lines (LA3491 and LA3534) using minigene constructs of *Aedes aegypti* dsx gene. LA3491 is a fusion of shared exon4, the female-specific cassette exons, and part of the first shared 3' exon (exon 5 in transcript M1).

Figure 2:
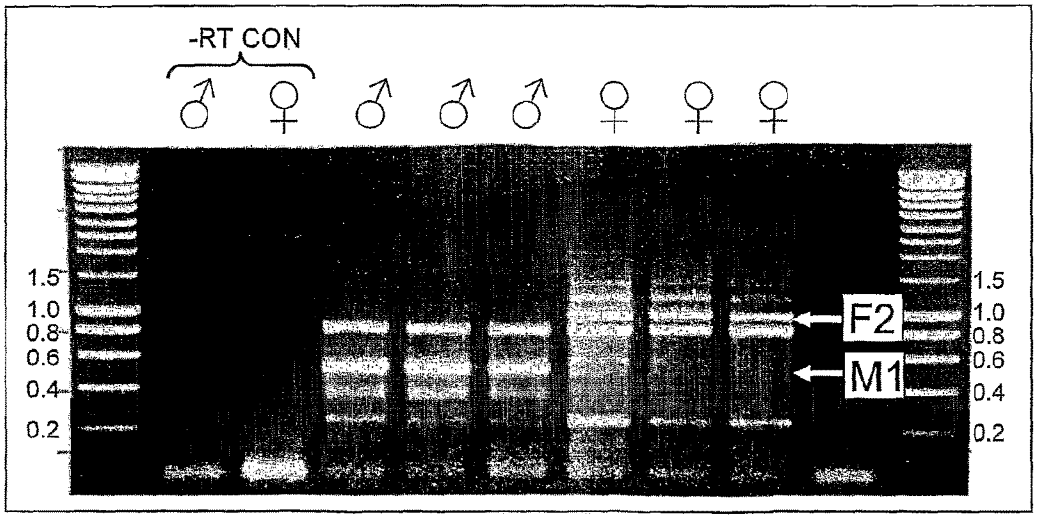

Transcripts from the minigene region of LA3491 were analysed by reverse transcriptase PCR (RT-PCR) and sequencing. Transcripts corresponding to alternative splicing in the F2 form were found in females but not in males (FIGS. 2 and 3) and in the F1 form there was some male expression but it was very low (FIG. 4). While transcripts corresponding to the M1 form were detected in males but not in females (FIG. 2). Since the minigene did not contain the 3' splice acceptor of the M2 variant, this transcript was not possible from this construct. This minigene does not contain any exogenous sequence, though it clearly demonstrates sex-specific splicing of an Aadsx fragment, indeed a highly deleted "minigene" fragment.

It will be apparent that certain sequences are important for controlling splicing and should therefor be retained, as discussed elsewhere. This can be easily established by deletion of certain portions and testing for alternative splicing by RT-PCR for instance.

FIG. 2 shows RT-PCR of males and females from LA3491 *Aedes aegypti* transgenic line using the primers 688—ie1-transcr (SEQ ID NO. 4) and 790—Aedsx-m-r2 (SEQ ID NO. 5). Using these primers, splicing in the F2 pattern would give a band of approximately 985 bp while splicing in the M1 pattern would give a band of approximately 516 bp. A band of approx 985 bp (F2) appeared only in lanes representing females and a band of approx 516 bp male specific transcript 1 (M1) appeared only in males. These bands have been sequenced and show that correct splicing had occurred, i.e. F2-type and M1-type respectively. The absence of bands in the no RT controls (-RT CON) shows that there was no genomic DNA contamination in the samples. Lanes 1 and 11 are Marker (SmartLadder™ from Eurogentec, bands from 1.5 kb to 0.2 kb are indicated). Lanes 2 and 3 are negative controls (no reverse transcriptase) and lanes 2-9 represent reactions performed on extracts from males or females as marked.

Figure 3:
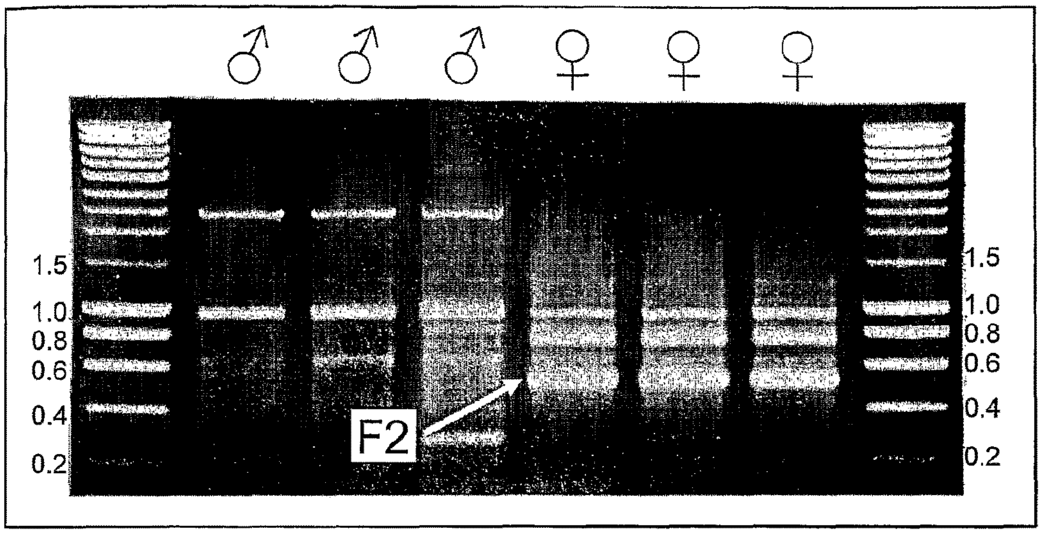
Figure 4:
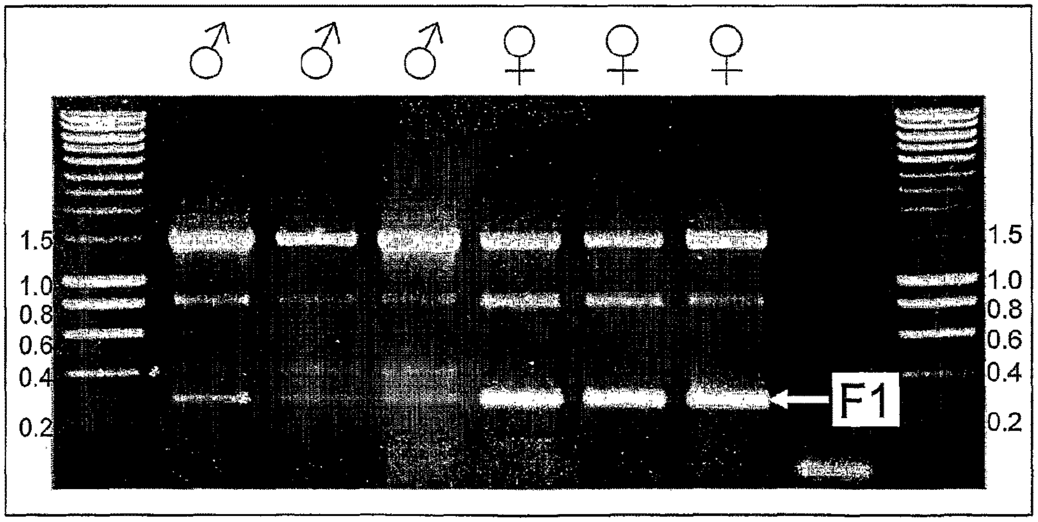

FIG. 3 shows RT-PCR of males and females from LA3491 *Aedes aegypti* transgenic lines using the primers 688—ie1-transcr (SEQ ID NO. 4) and 761—Aedsx-fem-r (SEQ ID NO. 6). Using these primers, splicing in the F2 pattern would give a band of approximately 525 bp. A band of approximately 525 bp was present in reactions on extracts from females, but not from corresponding reactions on extracts from males. Sequencing of this 525 bp band confirmed that correct, i.e. F2-type splicing had occurred. Marker (SmartLadder™ from Eurogentec, bands from 1.5 kb to 0.2 kb are indicated).

FIG. 4 shows RT-PCR of males and females from LA3491 *Aedes aegypti* transgenic lines using the primers 688—ie1-transcr (SEQ ID NO. 4) and AedsxR1 (SEQ ID NO. 4). Using these primers splicing in the F1 pattern would give a band of 283 bp. A band of approximately 283 bp is present predominantly in females, although there is evidence of a small amount of splicing in males. Sequencing confirmed that this band did indeed correspond to splicing in the F1 pattern. Marker (SmartLadder™ from Eurogentec, bands from 1.5 kb to 0.2 kb are indicated).

LA3534 is identical to LA3491 except for a 3' deletion of approx 2 kb. This construct showed no differential splicing between male and females (FIG. 1, minigene 2). RT-PCR gels have not been shown for this case. Based on these results several constructs have been designed to incorporate the sex-specific splicing of LA3491 (FIG. 1, minigene 1)

into a positive-feedback system. LA3612 (FIG. 5), which incorporates a fusion of ubiquitin and tTAV2 into the dsx coding region, is designed so that when the F2 female transcript is produced, the ubiquitin is cleaved and the tTAV2 is released to initiate and sustain the positive feedback system. LA3619 (FIG. 5) has tTAV2 without ubiquitin and using its own translation start codon. LA3646 (FIG. 5) is identical to LA3619 except the start codons for the dsx gene have been mutated; this should improve the quantity of tTAV2 produced by removing non-specific translation.

Figure 5:
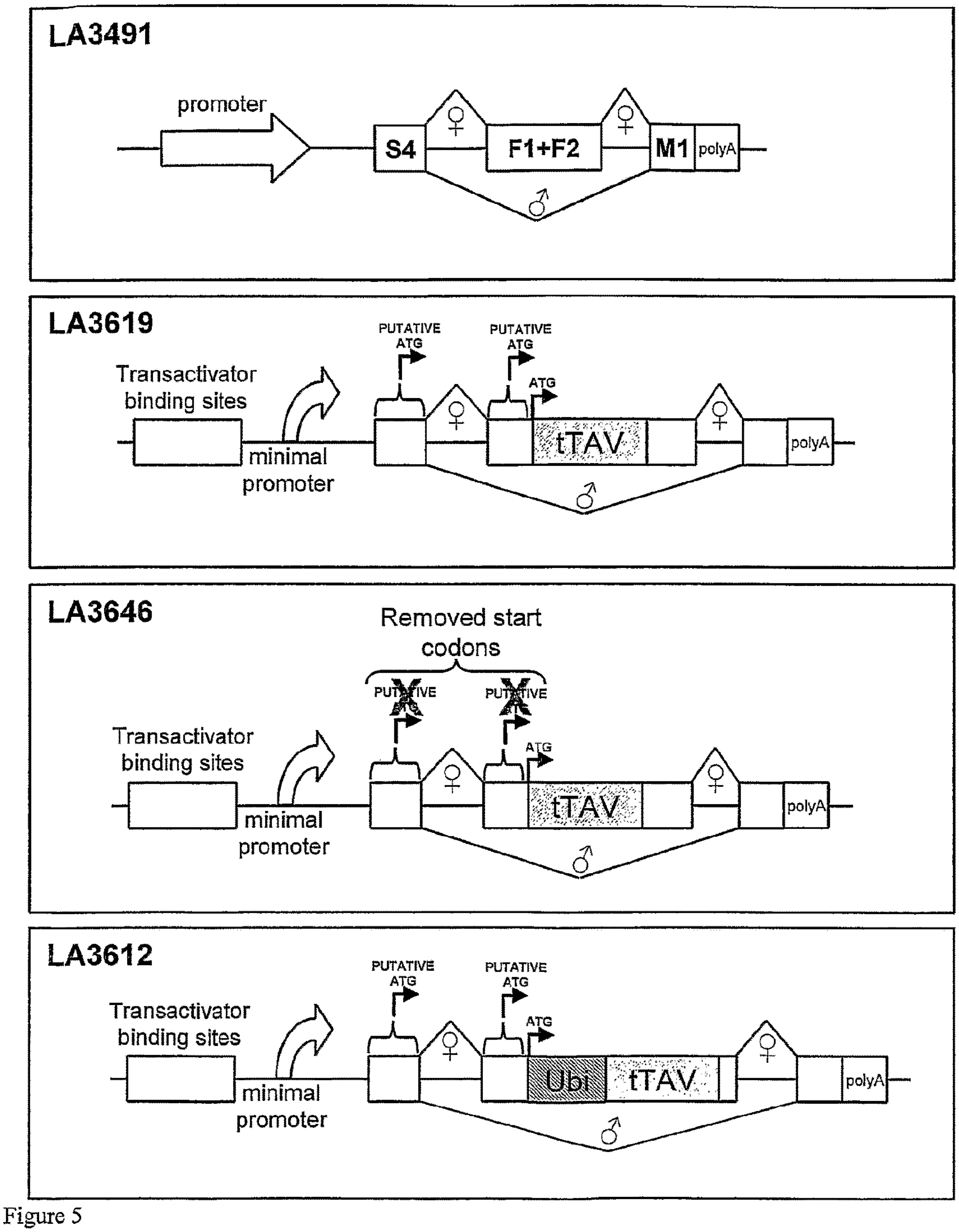

FIG. 5 is a diagrammatic representation of plasmids based around the splicing in *Aedes aegypti* dsx minigene. For clarity it will be understood that the first female intron represents any of F1, F2 or F3 splicing, and tTAV in the diagram refers to tTAV2 (it will be appreciated that other proteins or other versions of tTA or tTAV could alternatively be used). In each of these plasmids, apart from LA3491, heterologous sequence has been added to the F2 exon. "Putative ATG" represents any ATG triplet sequence in exonic sequence located 5' relative to the heterologous DNA. In LA3646 these putative translation start codons ("putative ATG") were removed or modified. In the case of construct LA3612, translation from an upstream (5') ATG that is in frame with the ubi-tTAV coding region will still (assuming no intervening stop codon) produce functional tTAV, following separation of the ubiquitin and tTAV moieties by protease action. The various alternative splicing cassettes are operably linked to a suitable promoter, transcriptional terminator and other regulatory sequences.

This example shows sex-specific splicing of a highly compressed "minigene" fragment in a heterologous context (i.e. heterologous promoter, 5' UTR and 3'UTR). Although it does not show differential expression of a non-*Aedes* sequence, as the alternatively spliced exons are derived from the Aadsx gene and do not contain additional material, it does clearly illustrate the feasibility of this approach. In any case, the promoter, 5' UTR and 3'UTR are heterologous. We have additional constructs which illustrate several different methods for obtaining differential (sex-specific) expression of a heterologous protein by this dsx.

TRA Sequence Alignment

Pane et al. (2002) suggested that certain sequences related to the known binding sites of the Tra/Tra-2 complex in *Drosophila* might be important in regulating the splicing of Cctra, and this also known for *Drosophila* dsx and has also been suggested for *Anopheles gambiae* dsx (Scali et al 2005). The consensus sequence is variously described as UC(U/A)(U/A)C(A/G)AUCAACA (Pane et al), SEQ ID NO. 8, or UC(U/A)(U/A)CAAUCAACA (Scali et al 2005), SEQ ID NO. 9.

It is noteworthy that these definitions are extremely similar. Pane et al identify 8 partial matches to this consensus in the Cctra sequence (7 or more nucleotides matching the 13 nucleotide consensus sequence. Scali et al identify 6 matches in Agdsx (9/13 or better). Such sequences are also known to regulate the alternative splicing of the *Drosophila* gene fruitless; Scali et al review 3 matches in that sequence (12/13 or better). Correct splicing of dsx may also require a purine-rich region, as discussed by Scali et al.

Figure 7:
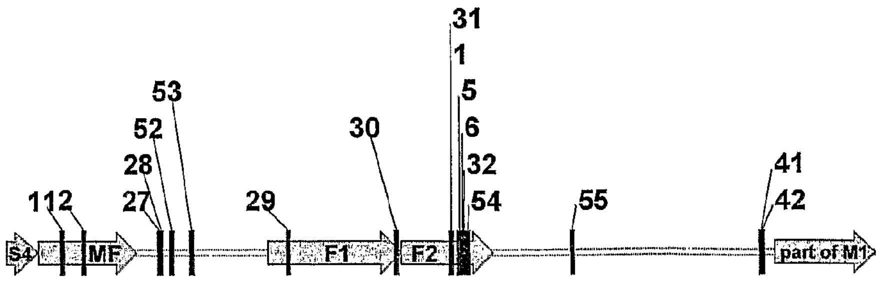

As can be seen from the Table 2 and FIG. 7, we have identified what are thought to be significant clusters of binding sites for Tra/Tra2 in our *Aedes aegypti* dsx minigene1.

Moth Dsx Sequence Alignment and Conserved Motifs

FIG. 6A and FIG. 6B show an alignment of the second female-specific exons and flanking sequences of dsx genes from pink bollworm (*Pectinophora gossypiella*, PBW-dsx, SEQ ID NO. 146), silk worm (*Bombyx mori, bombyx*-dsx, SEQ ID NO. 147) and codling moth (*Cydia pomonella*, codling-dsx, SEQ ID NO. 148). The second female-specific exon is shown in bold. We identified multiple copies of a short, repeated nucleotide sequence, conserved in sequence and approximate location between these relatively distantly related moths; these are located just 5' to the female-specific exon. The conserved repeats AGTGAC/T are underlined. Asterisks (*) represent identical nucleotides, dashes (-) represent gaps for best alignment. The exons are represented in the SEQ ID NOS. by the following nucleotide numbering: SEQ ID NO. 146 289-439; SEQ ID NO. 147 339-492; and SEQ ID NO. 148 285-439.

*Aedes* Dsx Tra2 Binding Sites.

In females of *Drosophila melanogaster*, Tra and a product from the constitutively active gene tra2, act as splicing regulators by binding to splice enhancer sites on the pre-mRNA of dsx, which activates the weak 3' acceptor site of the female-specific exon (Scali et al). In males there is no expression of TRA and the weak 3' acceptor site is not recognised and splicing occurs at the male exon. To look for putative Tra/Tra2 binding sites we used the consensus sequence of these binding sites deduced for *Drosophila* Tra/Tra2 and looked for the distribution of these in the *Aedes aegypti* dsx gene sequence. This is shown in Table 2, below.

TABLE 2

| Name | Sequence w = T or A r = A or G | Present in Minigene1 | Position | Identity with consensus | Identity with wwcrat | SEQ ID NO. |
|---|---|---|---|---|---|---|
| Consensus | tc**wwcrat**caaca | / | / | /13 | /6 | 138 |
| 1 | tcaacaagcaaca | Y | 14917 | 12 | 5 | 10 |
| 2 | ttatcaaacaaca | Y | 364 | 11 | 5 | 11 |
| 3 | tcatcaattaaaa | | 1015 | 11 | 6 | 12 |
| 4 | tcatcaatcaaac | | 6502 | 11 | 6 | 13 |
| 5 | tcttcaaccaacc | Y | 14958 | 11 | 5 | 14 |
| 6 | cctacaatctaca | Y | 14973 | 11 | 6 | 15 |
| 7 | tcttagatcaaaa | | 16553 | 11 | 5 | 16 |
| 8 | tcttcgatcatta | | 17386 | 11 | 6 | 17 |

TABLE 2-continued

| Name | Sequence w = T or A r = A or G | Present in Minigene1 | Position | Identity with consensus | Identity with wwcrat | SEQ ID NO. |
|---|---|---|---|---|---|---|
| 9 | ccaacaatctaca | | 28802 | 11 | 6 | 18 |
| 10 | tcaaagatcacca | | 42096 | 11 | 5 | 19 |
| 11 | tcttcggtcgacg | Y | 256 | 11 | 5 | 20 |
| 12 | tcgacaaacaaaa | | 1277 | 11 | <5 | 21 |
| 13 | tattcaaacaacg | | 4061 | 11 | 5 | 22 |
| 14 | ttttcgataaaaa | | 4380 | 10 | 6 | 23 |
| 15 | tcttcagtctgca | | 5399 | 10 | 5 | 24 |
| 16 | gattcaatcatca | | 7723 | 10 | 6 | 25 |
| 17 | ttatcgagcaaaa | | 8137 | 10 | 5 | 26 |
| 18 | tcataactcaaga | | 9062 | 10 | <5 | 27 |
| 19 | tcagaaatcaaaa | | 9126 | 10 | <5 | 28 |
| 20 | tctttaatttaca | | 10639 | 10 | 5 | 29 |
| 21 | tttacaatcctca | | 10646 | 10 | 6 | 30 |
| 22 | tcatagatcagga | | 11214 | 10 | 5 | 31 |
| 23 | acctcaaacaaca | | 11989 | 10 | <5 | 32 |
| 24 | tcatcgaacaccc | | 12020 | 10 | 5 | 33 |
| 25 | tcaataatcgtca | | 12199 | 10 | 5 | 107 |
| 26 | tcatcaaacgtca | | 13287 | 10 | 5 | 108 |
| 27 | ttatcgttaaaca | Y | 13439 | 10 | 5 | 109 |
| 28 | taaacagtcaata | Y | 13446 | 10 | 5 | 110 |
| 29 | tacacgatcagca | Y | 14096 | 10 | 5 | 111 |
| 30 | aatacaaacaaca | Y | 14637 | 10 | 5 | 112 |
| 31 | tcatcaacaagca | Y | 14914 | 10 | 5 | 113 |
| 32 | tctacaaaccaga | Y | 14980 | 10 | 5 | 114 |
| 33 | acatcgattcaca | | 16085 | 10 | 6 | 115 |
| 34 | cgctcaatcaaca | | 16175 | 10 | 5 | 116 |
| 35 | tctaccataaaaa | | 16511 | 10 | 5 | 117 |
| 36 | aaatgaatcaaca | | 20044 | 10 | 5 | 118 |
| 37 | acatcgttcaacg | | 21374 | 10 | 5 | 119 |
| 38 | tcttgattcacca | | 21580 | 10 | <5 | 120 |
| 39 | tctgcagacaaca | | 22408 | 10 | <5 | 121 |
| 40 | tcttcggtaatca | | 23285 | 10 | 5 | 122 |
| 41 | tctataaacaata | Y | 25436 | 10 | <5 | 123 |
| 42 | taaacaataaata | Y | 25440 | 10 | 6 | 124 |
| 43 | taaacaagcaaaa | | 28242 | 10 | 5 | 125 |
| 44 | tcaacgatcggcg | | 30309 | 10 | 6 | 126 |
| 45 | tgatccatcatca | | 30910 | 10 | 5 | 127 |
| 46 | tcaacatgcaaga | | 32295 | 10 | <5 | 128 |

TABLE 2-continued

| Name | Sequence w = T or A r = A or G | Present in Minigene1 | Position | Identity with consensus | Identity with wwcrat | SEQ ID NO. |
|---|---|---|---|---|---|---|
| 47 | tcttaaataaaga | | 32862 | 10 | 5 | 129 |
| 48 | tcaaagatctata | | 40551 | 10 | 5 | 130 |
| 49 | taatgaattaaca | | 40847 | 10 | 5 | 131 |
| 50 | tttaccatcaact | | 41712 | 10 | 5 | 132 |
| 51 | taatgaaacaaca | | 43380 | 10 | <5 | 133 |
| 52* | gtttcaattaaaa | Y | 13500 | 9 | 6 | 134 |
| 53* | tattcaattataa | Y | 13602 | 9 | 6 | 135 |
| 54* | tcttcaatcgttt | Y | 15002 | 9 | 6 | 136 |
| 55* | tcaacgatccttt | Y | 15533 | 9 | 6 | 137 |

* = in 3491, only 9/13 but 6/6 in core. This table does not include 9/13 identities apart from the ones that are in 3491 with 6/6 identity with core sequence of wwcrat. This consensus core sequence (WWCRAT) is particularly preferred.

FIG. 7 is a diagrammatic representation of putative Tra/Tra2 binding sites within the dsx coding region of plasmid LA3491. This diagram is approximately to scale and represents a sequence of approximately 4 kb. We can calculate the chance of a random match to the Tra/Tra2 consensus sequence. Assuming all 4 nucleotides occur at equal frequency, the chances of any given nucleotide in a random sequence being the first nucleotide of a 10/13 or better match to the consensus is approx $7\times10^{-4}$. Therefore, one would expect slightly less than one such match per 1000 nucleotides of such random sequence. The calculation for this is below:

Sex-Specific Splicing: Probabilities

Questions

A binding site consensus sequence consists of 13 bases. Ten of those (fixed) positions (call this set X) must each be one specific base. The other three (call this set Y) can each be one of two specific bases. Assuming that each possible base A, G, C and T is equally likely and that the base at each position is independent of the bases at the other positions, what is the probability of a 13-base sequence selected at random exactly matching this sequence? What are the probabilities of such a sequence being a near mismatch (allowing for up to one, two, three or four differences)? The answers are provided in Table 2 below and the workings are shown thereafter.

Answers

TABLE 3

| No. of positions mismatched | Probability (fraction) | Probability (to 3 d.p.) |
|---|---|---|
| none, i.e. exact match | $\frac{1}{2^{23}}$ | $1.192\times10^{-7}$ |
| up to 1, i.e. at least 12 positions match | $\frac{17}{2^{22}}$ | $4.053\times10^{-6}$ |
| up to 2, i.e. at least 11 positions match | $\frac{133}{2^{21}}$ | $6.342\times10^{-5}$ |
| up to 3, i.e. at least 10 positions match | $\frac{23}{2^{15}}$ | $7.019\times10^{-4}$ |

TABLE 3-continued

| No. of positions mismatched | Probability (fraction) | Probability (to 3 d.p.) |
|---|---|---|
| up to 4, i.e. at least 9 positions match | $\frac{33863}{2^{23}}$ | $4.037\times10^{-3}$ |

Workings:

$$P(\text{exact match}) = P_0 = \left(\frac{1}{4}\right)^{10}\left(\frac{1}{2}\right)^{3} =$$

$$\frac{1}{4^{10}\times2^{3}} = \frac{1}{2^{23}} = 1.192\times10^{-7} \text{ to 3 } d.p. \text{ (3 } d.p. \text{ all below)}$$

$P(\text{mismatch in exactly 1 position}) =$ $$P(\text{mismatch at one of the 10 } X \text{ positions or mismatch at one of the 3 } Y \text{ positions}) = P_1 =$$

$$10\left(\frac{1}{4}\right)^{9}\left(\frac{3}{4}\right)\left(\frac{1}{2}\right)^{3} + 3\left(\frac{1}{4}\right)^{10}\left(\frac{1}{2}\right)^{3} = \frac{(10\times3)+3}{4^{10}\times2^{3}} = \frac{33}{2^{23}} = 3.934\times10^{-6}$$

$P(\text{mismatch in exactly 2 positions}) =$ $$P(\text{mismatches at 2 of the 10 } X \text{ or mismatch at 1 of the 10 } X \text{ and 1 of the 3 } Y \text{ or mismatches at 2 of the 3 Y}) =$$

$$P_2 = \frac{10!}{2!8!}\left(\frac{1}{4}\right)^{8}\left(\frac{3}{4}\right)^{2}\left(\frac{1}{2}\right)^{3} + 10\times3\left(\frac{1}{4}\right)^{9}\left(\frac{3}{4}\right)\left(\frac{1}{2}\right)^{3} + 3\left(\frac{1}{4}\right)^{10}\left(\frac{1}{2}\right)^{3} =$$

$$\frac{((45\times3^2)+(30\times3)+3)}{2^{23}} = \frac{498}{2^{23}} = \frac{249}{2^{22}} = 5.937\times10^{-5}$$

$P(\text{mismatch in exactly 3 positions}) =$ $$P(\text{mismatches at 3 of the 10 } X \text{ or mismatches at 2 of the 10 } X \text{ and 1 of the 3 } Y \text{ or mismatches at 1 of the 10 X and 2 of the 3 Y or mismatches at 3 of the 3 Y}) = P_3 =$$

$$\frac{10!}{3!7!}\left(\frac{1}{4}\right)^{7}\left(\frac{3}{4}\right)^{3}\left(\frac{1}{2}\right)^{3} + \frac{10!}{2!8!}3\left(\frac{1}{4}\right)^{8}\left(\frac{3}{4}\right)^{2}\left(\frac{1}{2}\right)^{3} + 10\times3\left(\frac{1}{4}\right)^{9}\left(\frac{3}{4}\right)\left(\frac{1}{2}\right)^{3} +$$

$$\left(\frac{1}{4}\right)^{10}\left(\frac{1}{2}\right)^{3} = \frac{((120\times3^3)+(45\times3^3)+(30\times3)+1)}{2^{23}} =$$

$$\frac{5356}{2^{23}} = \frac{1339}{2^{21}} = 6.385\times10^{-4}$$

-continued $$P(\text{mismatch in exactly 4 positions}) =$$

$$P(\text{mismatches at 4 of the 10 } X \text{ or mismatches at 3 of the 10 } X \text{ and 1 of the 3 } Y \text{ or mismatches at 2 of the 10 X and 2 of the 3 Y or mismatches at 1 of the 10 X and 3 of the 3 Y}) =$$

$$P_4 = \frac{10!}{4!6!}\left(\frac{1}{4}\right)^6\left(\frac{3}{4}\right)^4\left(\frac{1}{2}\right)^3 + \frac{10!}{3!7!}3\left(\frac{1}{4}\right)^7\left(\frac{3}{4}\right)^3\left(\frac{1}{2}\right)^3 + \frac{10!}{2!8!}3\left(\frac{1}{4}\right)^8\left(\frac{3}{4}\right)^2\left(\frac{1}{2}\right)^3 + 10\left(\frac{1}{4}\right)^9\left(\frac{3}{4}\right)\left(\frac{1}{2}\right)^3 = \frac{((210\times 3^4) + (120\times 3^4) + (45\times 3^3) + (10\times 3))}{2^{23}} = \frac{27975}{2^{23}} = 3.335\times 10^{-3}$$

$$P(\text{mismatch in up to 1 position}) = P_0 + P_1 = \frac{1+33}{2^{23}} = \frac{17}{2^{22}} = 4.053\times 10^{-6}$$

$$P(\text{mismatch in up to 2 positions}) =$$

$$P_0 + P_1 + P_2 = \frac{1+33+498}{2^{23}} = \frac{532}{2^{23}} = \frac{133}{2^{21}} = 6.342\times 10^{-5}$$

$$P(\text{mismatch in up to 3 positions}) =$$

$$P_0 + P_1 + P_2 + P_3 = \frac{1+33+498+5356}{2^{23}} = \frac{5888}{2^{23}} = \frac{23}{2^{15}} = 7.019\times 10^{-4}$$

$$P(\text{mismatch in up to 4 positions}) = P_0 + P_1 + P_2 + P_3 + P_4 = \frac{1+33+498+5356+27975}{2^{23}} = \frac{33863}{2^{23}} = 4.037\times 10^{-3}$$

Experiment 14: Cctra

We have one line of LA3097 (LA3097A) which shows very good expression of its fluorescent marker; it is unknown if this line is a single integration event. This line does show evidence of sex-specific splicing, when reared off tetracycline all the females die as embryos, and when it is on 30 μg/ml of tetracycline both males and females survive.

This example is important. It shows that Cctra provides sex-specific alternative splicing in *Aedes*, and that this can be used to give sex-specific lethality. This, therefore, provides evidence of the phylogenetic range for Cctra splicing. Thus, it is entirely plausible that the present invention can be applied to all Diptera, as we have shown that Cctra works in *Drosophila*, tephritids and mosquitoes, which essentially spans the whole Dipteran Order.

It is surprising that Cctra works in *Aedes*, given the rapid sequence evolution of tra.

We transformed *Aedes aegypti* with construct LA3097. Heterozygous males from the resultant transgenic line were crossed to wild type and the progeny reared in aqueous medium supplemented with tetracycline to a final concentration of 30 μg/ml. Adults were recovered as follows: 14 males and one female, thus showing significant female-specific lethality.

This species and strain normally has a sex ratio of approximately 1:1, therefore this construct gave female-specific lethality in *Aedes aegypti*. Equivalent constructs which did not contain the Cctra intronic sequence gave non-sex-specific lethality. Therefore, the Cctra intron can be used to provide differential (i.e. sex-specific) regulation of gene expression in mosquitoes, and this can further be used to provide sex-specific lethality and a method for the selective elimination of females from a population.

In more detail: on 0 μg/ml tetracycline, males survive only to pupae, i.e. don't make it to adult. Females die so early that we don't see them, probably as embryos, so there is still a differential effect between the sexes. However, the pupal lethality in males suggests that the system is not completely switched off in males. The single insertion line that we recovered is unusual, in that it shows extremely strong expression of the marker; other insertions with more typical expression levels might well not show male lethality.

Splicing in LA3097A

Analysis of splicing of LA3097 from LA3097A transgenic mosquitoes by RT-PCR showed that males and females shared two transcripts, an approximately 950 bp band and a fainter band of approximately 800 bp (FIG. 59). Sequencing of these bands showed that the ~900 bp band corresponds to a non-sex-specific splice variant (AeM2, —920 bp), and the fainter band was a mixture of a non-sex-specific splice variant (AeM1, —804 bp) and the female form (AeF1, ~765 bp), see FIG. 60. The splicing of the AeF1 transcript was identical to that shown for this construct in Medfly (FIG. 33). The splicing of the M transcripts differs somewhat from that seen in the native context (Cctra splicing in Medfly, either the native gene or as we observed from LA3097 in transgenic Medfly); in AeM1 the second alternatively spliced exon (ME1b) is not included in the mature AeM1 transcript and in AeM2 the second alternatively spliced exon (ME2b) is similarly not included in the mature AeM2 transcript. In other words, for each of these transcripts the first but not the second cassette exon is present, relative to the Medfly prototype. Note that, as a consequence of the absence of the second cassette exon in AeM1, and the reading frame of tTAV2 relative to the first cassette exon in this construct, splicing in the AeM1 pattern does not lead to interruption of the tTAV2 open reading frame, but rather to the addition of 39 nucleotides (corresponding to 13 amino acids) between the ATG and the rest of the tTAV2 open reading frame. It is likely that this variant of tTAV2 may retain some activity, relative to normal or prototypic tTAV2 (as encoded by the F1 splice variant). In the absence of tetracycline, a phenotypic effect was observed in males as well as in females, though weaker in males than females. Production of a partially active variant of tTAV2 from the AeM1 transcript in males (and females) may explain this.

FIG. 59—shows RT-PCR of males and females from LA3097A *Aedes aegypti* transgenic line using the primers HSP (SEQ ID NO. 139) and VP16 (SEQ ID NO. 140). Using these primers, splicing in the CcF1 pattern (i.e. corresponding to the F1 variant of *Ceratitis capitata*) would give a band of approximately 765 bp and splicing in the CcM1 1005 bp and CcM2 1094 bp. In both males and females, a strong band of approximately 950 bp (1) was observed along with a fainter band of approximately 800 bp (2). Marker (SmartLadder™ from Eurogentec, bands from 1.5 kb to 0.4 kb are indicated).

Sequence analysis of several clones from band 2 (i.e. AeM1/AeF1 splice variants) from males and females showed that one of five clones from females showed AeM2 splicing (20%), whereas in males three of the four clones showed AeM2 splicing (75%); all the other clones showed AeF1 splicing. This indicates that there is more AeF1 transcript present in females than in males and this would explain the differential killing effect seen between them.

Figure 60:
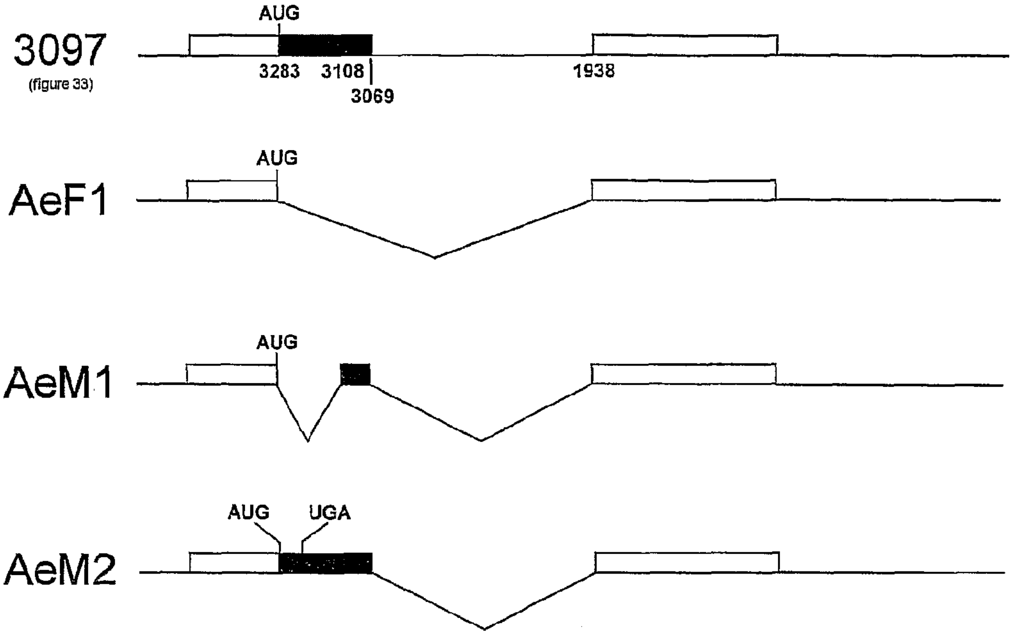
Figure 61:
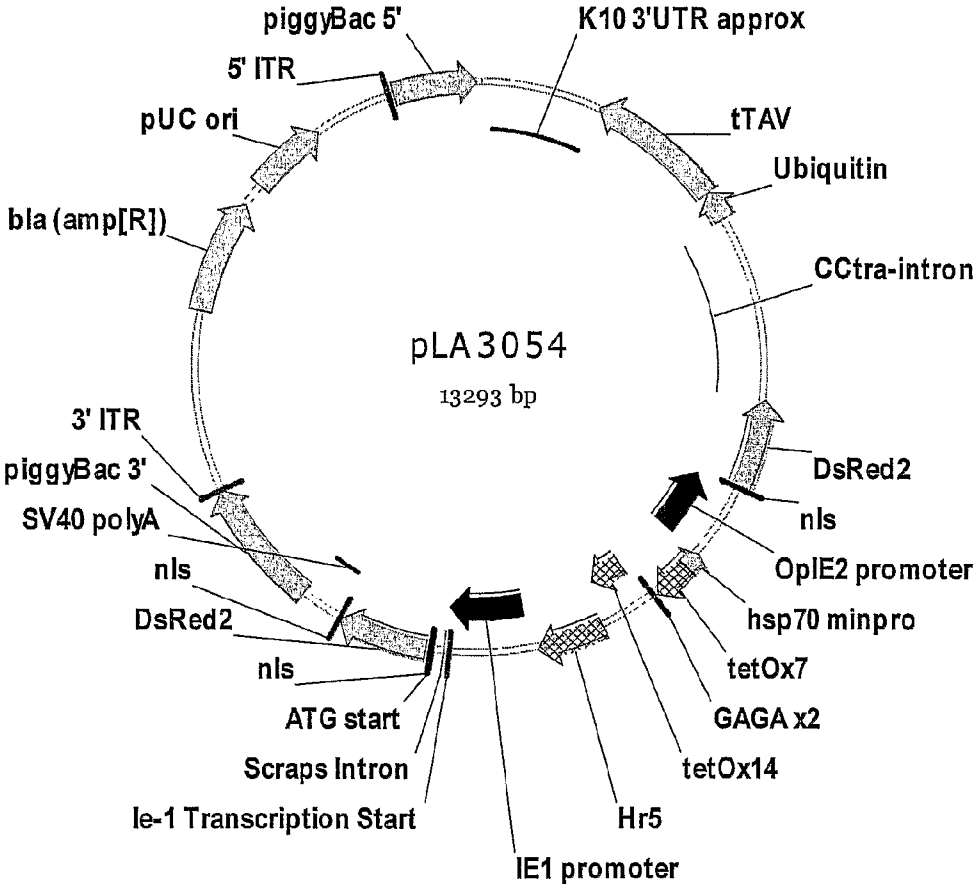
Figure 62:
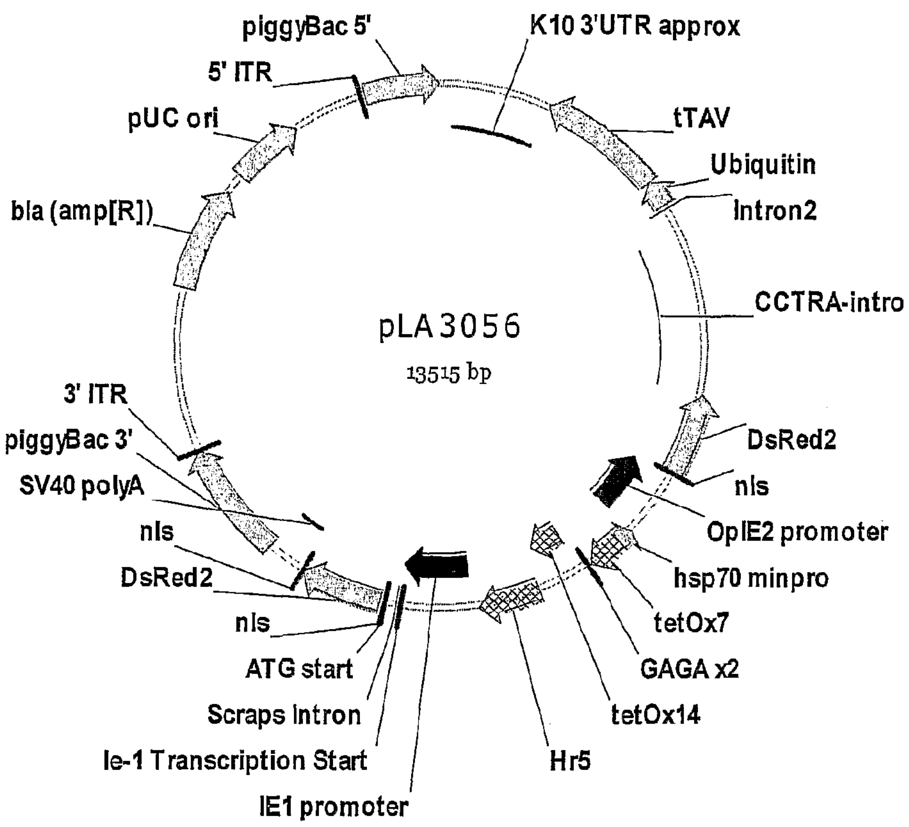
Figure 63:
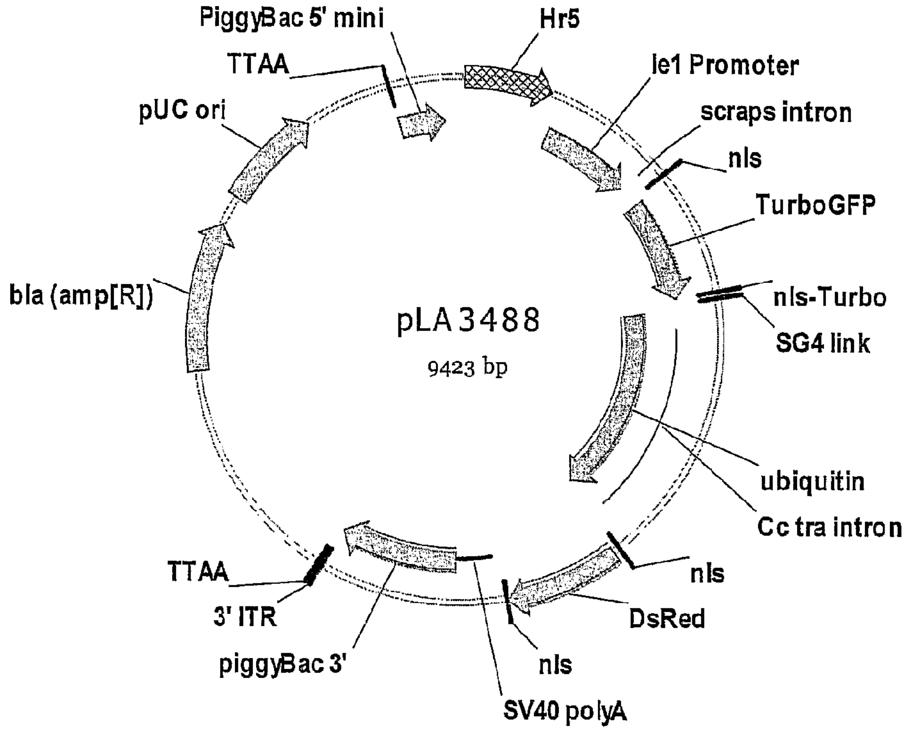
Figure 64:
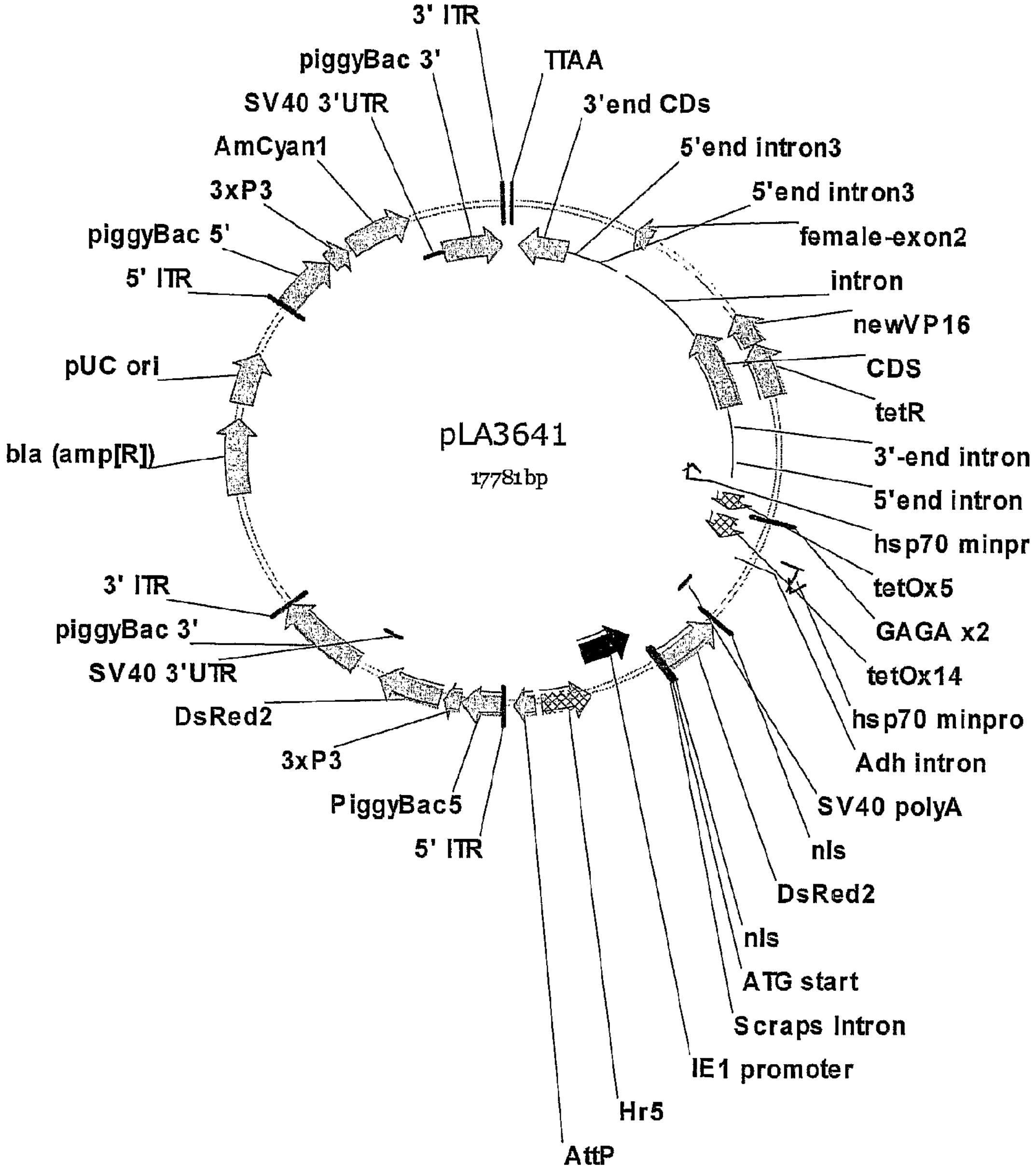
Figure 65:
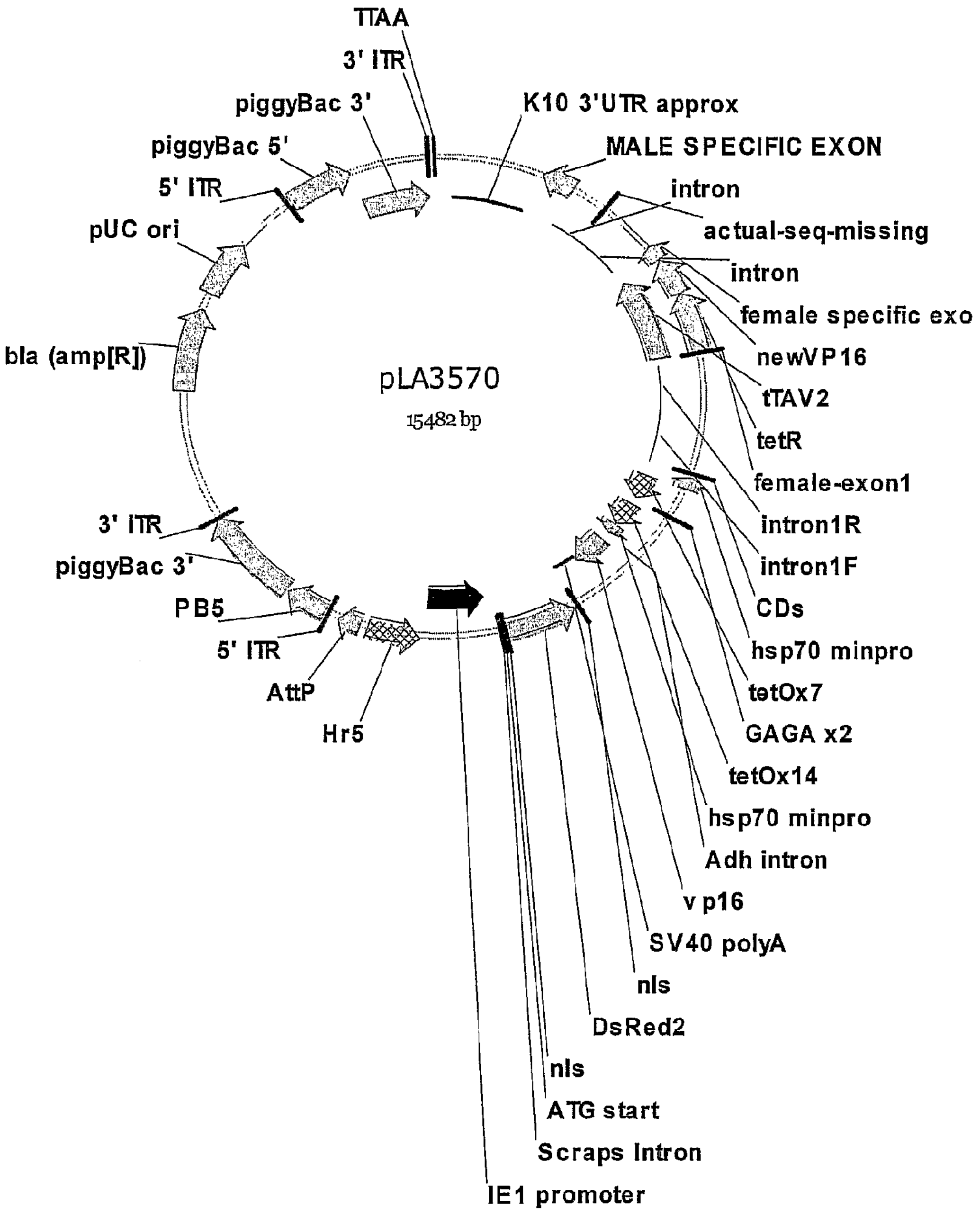
Figure 66:
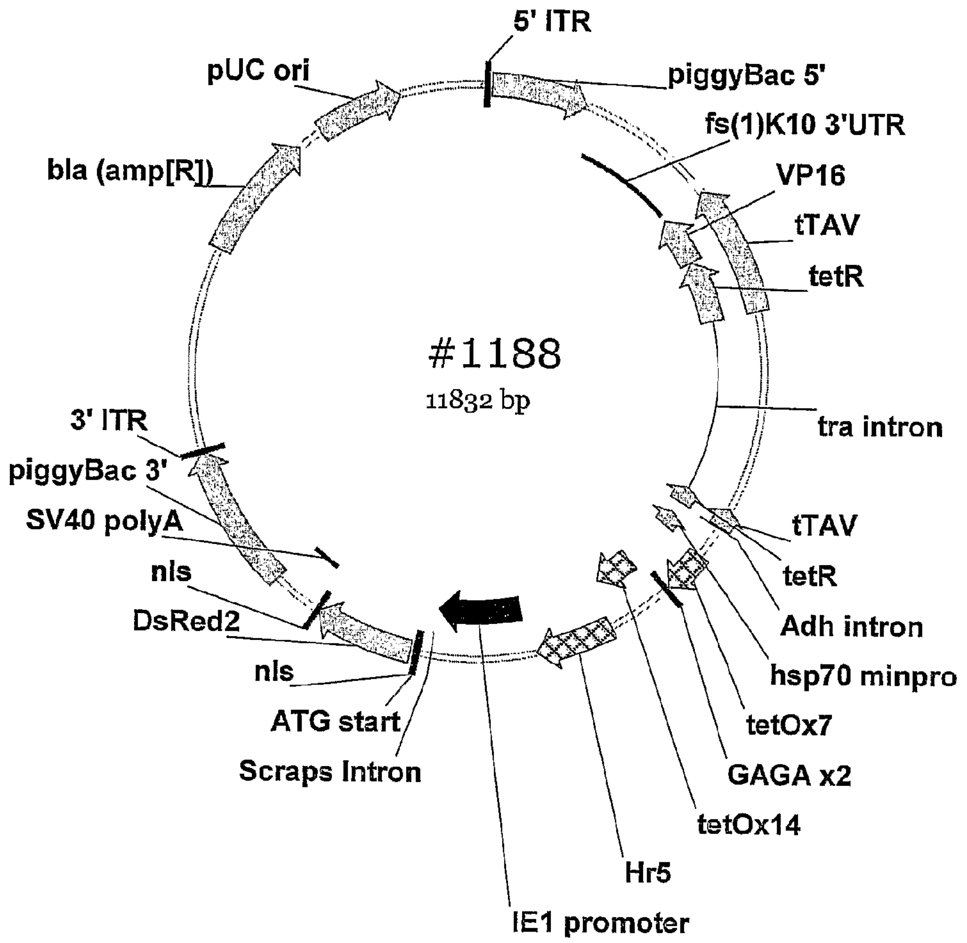

FIG. 60 Illustrates the various transcripts produced by alternative splicing of Cctra from LA3097A *Aedes aegypti* transgenic line. 3097 represents the DNA sequence of Cctra and the numbers relate to figure described elsewhere. Shading and boxes also relate to FIG. 33. Note that the diagram is not to scale.

Example 15*: Aedes* Actin-4

Figure 10:
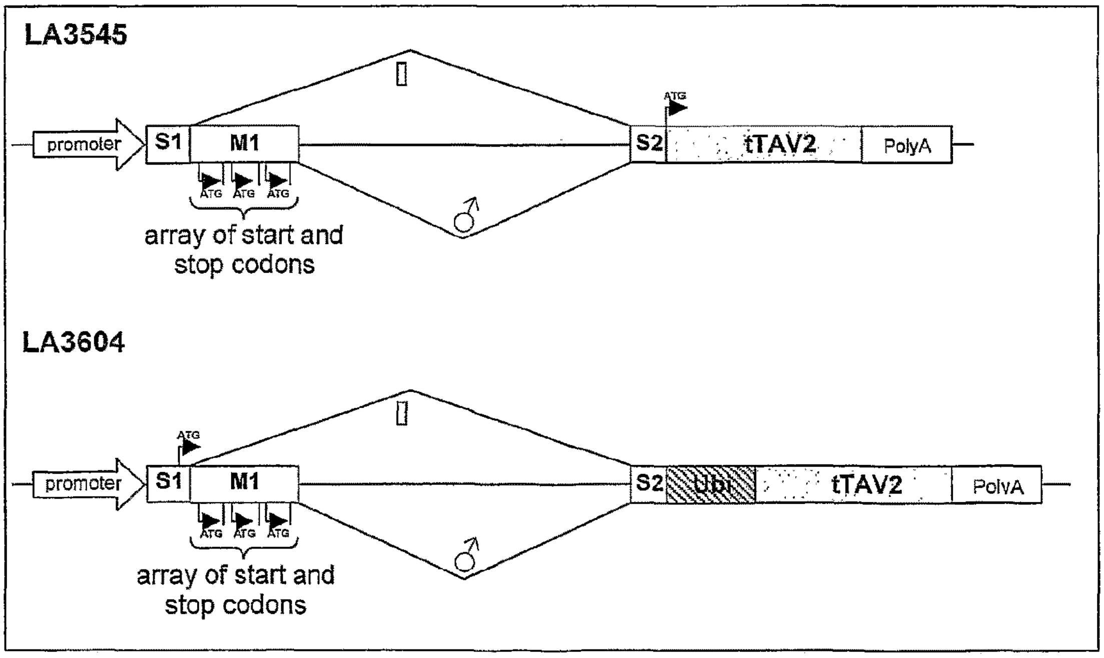

We have eleven lines of LA3545, which uses the *Aedes* actin-4 gene (AeAct-4 or AaAct4) to drive expression of tTAV2. In construct LA3545, a sequence encoding tTAV2 has been inserted into the second exon of AaAct4 (FIG. 10). For transcripts spliced in the pattern characteristic of AaAct4 splicing in females, the ATG of the tTAV2 coding region will be the first (5'-most) ATG of the transcript. Splicing in the pattern characteristic of AaAct4 splicing in males introduces an array of start and stop codons before the tTAV2 sequence which tends to inhibit or interfere with translation from the ATG of the tTAV2 coding region. These lines should only express tTAV2 in female pupae. The splicing is shown in FIG. 8, below.

Figure 8:
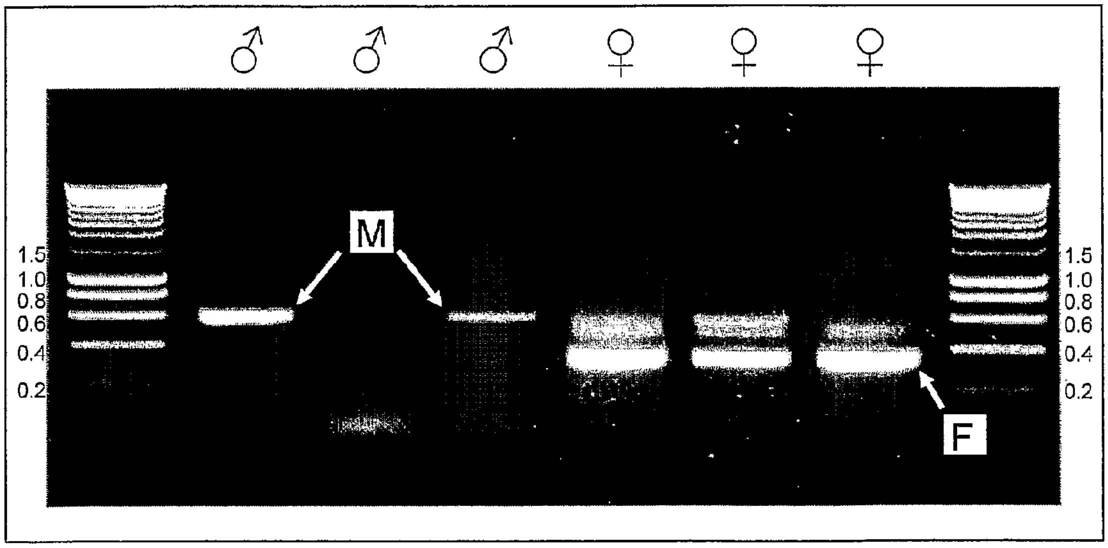

FIG. 8 shows RT-PCR of male and female adults from LA3545AeC *Aedes aegypti* transgenic line using the primers Agexon1F (SEQ ID NO. 141) and TETRR1 (SEQ ID NO. 142). Using these primers, splicing in a pattern equivalent to that of the native AaAct4 gene would give bands of approx 347 bp for the female-type splice variant and of approx 595 bp for the male-type splice variant. A band of approx 347 bp band (F) was found only in reactions on extracts from females; a band of approx 595 bp (M) was found in both males and females. Sequencing has confirmed that the correct splicing occurred in males and females. Marker (SmartLadder™ from Eurogentec, bands from 1.5 kb to 0.2 kb are indicated).

We also have transgenic *Aedes aegypti* carrying construct LA3604, which is similar to LA3545 except it has an engineered start codon in the portion of exon 1 that is present in both male-type and female-type transcripts (FIG. 10). This is arranged to be the first ATG in either transcript type. LA3604 encodes tTAV2 fused to ubiquitin (LA3545 codes tTAV, while LA3604 codes ubi-tTAV2). This construct should produce a fully functional tTAV2 protein in females only, even if the male form is expressed in females the extra male exon contains several start and stop codons that would prevent translation of the Ubi-tTAV2 fusion protein.

The alternative splicing of AaAct4 occurs in the 5' UTR (of the native gene). It may or may not have a regulatory role in the native gene. One possibility is as follows: in the female-specific splice variant, the start codon of the AaAct4 coding region is the first ATG of the transcript. However, in the male-specific splice variant there are several additional ATG sequences 5' to the start codon of the AaAct4 coding region; most of these have in-frame stop codons a short distance 3'. This sequence arrangement may interfere with the efficient translation of the AaAct4 protein and thereby reduce expression of the protein in males as compared with females. This is the arrangement in LA3545.

However, a greater differential effect between males and females would be expected if the intron was included in coding region (rather than 5' UTR), i.e. inserted between the start and stop codons of the polynucleotide for expression in the organism. In this case, the male-specific cassette exon would change the coding potential of the transcript, rather than simply interfering with translation.

This is achieved in construct LA3604. We modified the shared first exon to include an ATG sequence in a suitable sequence context for translational initiation. In this modified sequence, this is the first ATG in either the male-type (M) or female-type (F) splice variants. Following splicing in the F form, this (engineered) 5' ATG is in frame with the ubi-tTAV coding region. F-type transcripts would therefore encode a fusion protein, comprising sections encoded by (i) part of what is normally Act4 5' UTR (but here obviously translated, and so not UTR at all), (ii) ubiquitin coding region and (iii) tTAV2 coding region.

Activity of cellular ubiquitin proteases will release the tTAV2 protein. Translation from the engineered 5' ATG would be terminated by in-frame stop codons in the additional sequence (cassette exon) present in transcripts spliced in the M form. This would therefore prevent expression of functional tTAV2 in males, thereby giving sex-specific expression of tTAV2. Obviously, this gives a general method for sex-specific expression of a protein, by replacing the tTAV2 segment with another protein or sequence of interest. Using this strategy we have provided transgenics and shown sex-specific splicing (FIG. 9).

Figure 9:
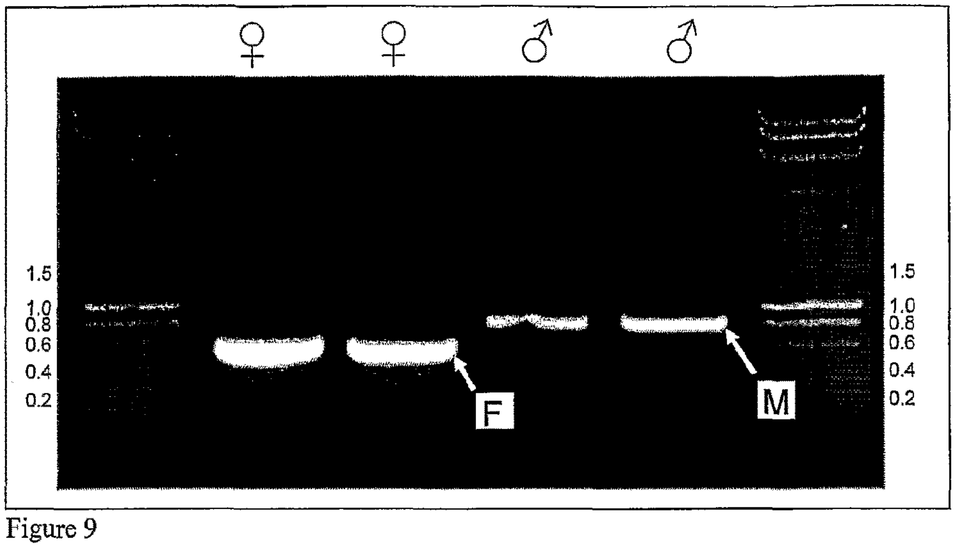

FIG. 9 shows RT-PCR of males and females from LA3604AeA *Aedes aegypti* transgenic line using the primers Agexon1F (SEQ ID NO. 141) and TETRR1 (SEQ ID NO. 142). Using these primers, splicing in the female form would give a band of approximately 575 bp, while inclusion of the male-specific cassette exon would increase this to approximately 823 bp. A band of approx 575 bp was seen from each female analyzed, while a band of approx 823 bp was seen from each male analyzed. These bands appear to be substantially specific to the respective sexes. Sequencing of these bands showed the correct splicing had occurred in males and females. Marker: SmartLadder™ from Eurogentec, bands from 1.5 kb to 0.2 kb are indicated.

FIG. 10, below, is a diagrammatic representation of plasmids LA3545 and LA3604. S1: shared exon 1; M1: additional sequence included in male-specific exon 1; S2: shared exon 2 (5' end only); ubi: sequence encoding ubiquitin; tTAV2: sequence encoding tTAV2.

In several of the LA3545 transgenic lines a sex- and tissue-specific effect was observed: females are flightless. Two of the lines show a 90-100% female flightless phenotype one line shows 70% flightless and another 50%. This phenotype is presumably due to female-specific expression of tTAV2 in the developing flight muscles. The difference in the phenotypes between the lines is due to positional effects on the expression of the AaAct4 promoter. Due to a genes position in the genome expression can be influenced by a number of factors (heterochromatic or euchromatin regions, enhancer and suppressor elements, proximity to other genes) which can be seen readily in the fluorescent markers used to identify transgenics. All eleven lines of LA3545 were identified because they have different fluorescent profiles, even though they have the same promoters and marker. This variation is due to positional effects. This would then mean that we would expect some lines of LA3545 to express more tTAV2 than other because of positional effects, and those lines that do express more would give a female-specific flightless phenotype.

To test this hypothesis we developed a separate *Aedes aegypti* line with a tetO-DsRed2 reporter gene (LA3576 see FIG. 17 and SEQ ID NO. 143), when crossed with the different LA3545 lines this would allow the visualisation of where and when the Actin4-tTAV2 was expressing. Out of 8 LA3545 lines crossed to LA3576 all showed female-specific indirect flight muscle fluorescence in late L4 larvae, pupae and adults. In four of the lines DsRed2 expression appeared to be specific (i.e. exclusive) to the female indirect flight muscles; in the other four additional tissues showed expression of DsRed2. This phenomenon, where expression of a transgene depends in part on the region or point in the genome into which it has inserted, is called position effect, and will be well known and understood by the person skilled in the art.

Using LA3576 proved that the expression of tTAV2 in LA3604 was female-specific, occurs mainly in the indirect flight muscles and is stage-specific. Several different tetO-effector constructs were then constructed to analyse their effects. The tetO-MichelobX transgenics (LA3582, see FIG. 15 and SEQ ID NO. 144) when crossed to LA3545 all showed female-specific flightless phenotypes that could be repressed by tetracycline. This proves that Actin4 can be used to drive an effector gene in a stage, tissue and sex-specific manner.

Because some lines of LA3545 had a female-specific flightless phenotype without the presence of an induced effector gene, this showed that tTAV2 could act as an effector molecule. tTAV2 is composed of a tTA, a tetO binding domain and VP16, a herpes simplex virus protein. VP16 activates transcription of immediate early viral genes by using its amino-terminal sequences to attach to one or more host-encoded proteins that recognise DNA sequences in their promoters. In LA3604 a tetO-VP16 effector gene has been added to enhance the effect of tTAV2. In three transgenic lines of LA3604 this has caused a 100% female-specific flightless phenotype when reared without tetracycline, showing that VP16 is an effective effector molecule. Note that LA3604 has a potential start codon (ATG) engineered 5' to the alternatively spliced intron. Therefore, in this construct, the male-specific exon is expected to interrupt the open reading frame encoding tTAV (ubi-tTAV); since the male-specific sequence contains several stop codons, this will tend to reduce or eliminate production of functional tTAV in males. By way of comparison, the male-specific exon is 5' to the start codon of tTAV in LA3545. However, by inserting a number of start codons 5' to the start codon of tTAV (which is the first ATG of the female transcript but not of the male transcript), none of these additional start codons being suitable for efficient production of functional tTAV due to being out of frame or having intervening stop codons, this arrangement will also tend to reduce or eliminate production of functional tTAV in males, consistent with the phenotypic data above.

Example 16: Use of Ubiquitin and Intron Positioning

We have newly made Cctra-based constructs with the Cctra intron cassette in a variety of different contexts, i.e. flanked by different sequences. Various lines of transgenic Medfly carrying these have been constructed. This shows that the system is general and robust, i.e. that it will work for a wide range of heterologous sequences of interest.

We also have at least one newly made example of a Cctra-ubi-tTAV fusion giving correct splicing (DsRed-cctra-ubi-tTAV).

Preferred examples of the functional protein place the coding sequence for either ubiquitin or tTA, or their functional mutants and or variants such as tTAV, tTAV2 or tTAV3, 3' to the intron. These are arranged so that these elements are substantially adjacent to the 3' end of the intron, more preferably such that the coding region starts within 20 nucleotides or less of the 3' intron boundary), and most preferably, immediately adjacent the 3' end of the intron, although this is less relevant if the Ubiquitin system is used.

Preferred examples of constructs according to the present invention are listed in Table 4, below. It will be appreciated that LA1188 is not within the scope of the present invention, as it does not encode a functional protein, i.e. it doesn't work properly. This is thought to be because of the unexpected use of a splice donor 4 bp 5' to the junction with Cctra intron sequence, leading to a frameshift that is induced in all splices. It is, therefore, included for the sake of information only.

TABLE 4

| Construct NO. (FIGS #.) | Species tra intron is from | position from ATG (bp) | tra intron is fused to- |
|---|---|---|---|
| LA1188 (80) | Medfly | +132 | tTAV |
| LA3014 (29) | Medfly | +22 | ubiquitin |
| LA3166 (30) | Medfly | +136 | ubiquitin |
| LA3097 (27) | Medfly | +0 | tTAV |
| LA3077 (26) | Medfly | +61 | tTAV |
| LA3233 (28) | Medfly | +0 | tTAV2 |
| LA3376 (31) | Medfly | +0 | tTAV2 |
| LA3376 (31) | *B. zonata* | +3 | reaper KR |
| LA3376 (31) | *B. zonata* | +0 | tTAV3 |
| LA3242 (32) | *C. rosa* | +3 | reaperKR |
| LA1038 (14) | Medfly | +21 | Nipp1 (nipper) |
| LA3054 (61) | Medfly | +811 | DsRed-ubiquitin |
| LA3056 (62) | Medfly | +811 | DsRed-ubiquitin |
| LA3488 (63) | Medfly | +949 | Ubiquitin |
| LA3596 (67) | Medfly | +949 | Ubiquitin |

Table 4 shows constructs which contain a splice control sequence which is derived from a tra intron. The introns were derived from *C. capitata* (Medfly), *B. zonata* or *C. rosa* (see column 2). Said intron was inserted within the coding region such that the distance between the putative initiator ATG and the last nucleotide of the exon immediately preceding the tra intron was as should be indicated in column 3. Intron is inserted into or adjacent to coding region for either ubiquitin, tTAV, reaper$^{KR}$, nipper or ubiquitin-DsRed as shown in column 4 These were generated and shown to successfully splice, by RT-PCR or phenotypically in Medfly and, in some cases, also either in *Drosophila melanogaster* (LA3077) or *Anastrepha ludens* (LA3097, LA3233, LA3376). In addition, the distance between the ATG and the end of the exon immediately preceding the tra intron (assuming splicing in F1-like form) can range from 0 bp to at least +949 bp without adverse consequences to splicing (see Table 4, column 3). Thus, it is reasonable to assume that this distance can be up to at least 900 and preferably up to at least 949 bp.

Further information on these examples is summarized in Table 5. The preferred option is to use no endogenous sequence to achieve correct alternative splicing control of expression (+0 bp in table 4). We prefer to insert the tra intron between the flanking dinucleotides TG . . . GT in the coding region of the protein of interest to be alternatively spliced to ensure correct splicing as this may be important, however we will not restrict ourselves to this if necessary as other flanking nucleotides may function correctly as well. Examples LA1038, LA3054 and LA3056 include some endogenous flanking exonic sequence from the natural Cctra gene. In Table 5, if 6 nucleotides or less (including the ATG start codon) are included of particular fusions to the 3' or 5' of the splice junction, for the summary purposes of this table these will not be considered to be part of the fusion. Table 4 can be correlated with table 3 to find which tra intron (Cctra, Bztra or Crtra) is used in each example. Again, LA1188 is included only for the purposes of information and falls outside the present invention.

TABLE 5

| Construct NO. (FIGS #.) | tra intron is fused to 5' | tra intron is fused to 3' | exonic tra sequence fused to 5' (bp) | exonic tra sequence fused to 3' (bp) |
|---|---|---|---|---|
| LA1188 (80) | Hsp70-tTAV | tTAV | +0 bp | +0 bp |
| LA3014 (29) | Hsp70-ubiquitin | ubiquitin-reaperKR-sv40 | +0 bp | +0 bp |
| LA3166 (30) | Hsp70-ubiquitin- | ubiquitin-reaperKR-sv40 | +0 bp | +0 bp |
| LA3097 (27) | Hsp70 | tTAV-K10 | +0 bp | +0 bp |
| LA3077 (26) | Hsp70-tTAV | tTAV-K10 | +0 bp | +0 bp |
| LA3233 (28) | Hsp70 | tTAV2-K10 | +0 bp | +0 bp |
| LA3376 (31) | Hsp70 | tTAV2-K10 | +0 bp | +0 bp |
| LA3376 (31) | Sry-a | tTAV3-sv40 | +0 bp | +0 bp |
| LA3376 (31) | HB | reaperKR-sv40 | +0 bp | +0 bp |
| LA3242 (32) | HB | reaperKR-sv40 | +0 bp | +0 bp |
| LA1038 (14) | Hsp70-tra | Tra-Nipp1 (nipper)-sv40 | +22 bp | +20 bp |
| LA3054 (61) | Opie2-nls-DsRed-tra | tra-ubiquitin-tTAV-sv40 | +22 bp | +20 bp |
| LA3056 (62) | Opie2-nls-DsRed-tra | tra-ubiquitin-tTAV-sv40 | +22 bp | +242 bp |
| LA3488 (63) | Ie1-nls-TurboGreen-nls-ubiquitin | ubiquitin-nls-DsRed-nls-sv40 | +0 bp | +0 bp |
| LA3596 (67) | Ie1-nls-TurboGreen-nls-ubiquitin | ubiquitin-nls-DsRed-nls-sv40 | +0 bp | +0 bp |

As mentioned above when an intron is placed 5' to a protein coding region (ORF-X), it is preferred to position or use ubiquitin 3' to the intron, 5' to ORF-X, thus and providing female-specific regulation of ORF-X, whilst introducing physical separation between that sequence and the tra intron, thereby reducing the chance that sequences within ORF-X will interfere with the splicing of the tra intron.

Composite constructs and sequences are also envisaged, for example of the form:

X-ubi-Y with the alternatively spliced intron inserted between coding region X and the region encoding ubiquitin (ubi), or within the ubiquitin coding region, or between the region encoding ubiquitin and coding region Y. Thus X will be expressed irrespective of the splicing of the intron, while Y will only be expressed when the intron is spliced in a suitable form. Further configurations and arrangements of this general type will be apparent to the person skilled in the art. Some examples of this are LA3014, LA3054, LA3056, LA3166, LA3488 and LA3596 which all use ubiquitin fusions in this way demonstrating the ability of this idea to be successfully applied in transgenic Medfly. Alternative examples in transgenic mosquitoes include LA3604 and LA3612, showing the wide phylogenetic applicability of this system in not only different species (mosquitoes and Medfly), but also in different contexts including AaActin4, Aadsx and Cctra.

LA3596 (see FIG. 67 and SEQ ID NO. 145) is of similar design to LA3488, intended to generate green fluorescence (by expression of nuclear localised TurboGreen fluorescent protein) in both sexes, but red fluorescence only in females (by expression of nuclear localised DsRed2 fluorescent protein). This is accomplished by the fusion of these two proteins, driven by the Hr5-Ie1 enhancer/promoter cassette, linked together with a short 11 amino acid linker (SG4 linker) and a coding region comprising ubiquitin (with one intended point mutation to stabilize the resulting protein by reducing its propensity to ubiquitin-mediated degradation) and the Cctra intron to limit DsRed2 expression to females. Transgenic Medfly were generated with this construct. Red fluorescence was limited to females in this line as expected, while green fluorescence was observed in all males and females. This could be used for sex separation by fluorescence screening for a particular fluorescent protein, in this case red fluorescence representing expression of DsRed2.

Example 17: Further Cctra Exemplification

Reference is also made to LA3014 and LA3166 and phenotypic data therefrom in other Examples.

We have previously made, and have obtained transgenics with, the Cctra intron in a functional protein other than tTAV, see LA3014 and LA3166. LA3014 contains a ubiquitin-reaper$^{KR}$ fusion downstream of a Cctra intron. Phenotypic data shows that LA3014 transgenic Medfly gave repressible female-specific lethality. RT-PCR analysis on RNA extracted from adult males and females raised off tetracycline, using primers and ReaperKR, demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly.

Figure 12:
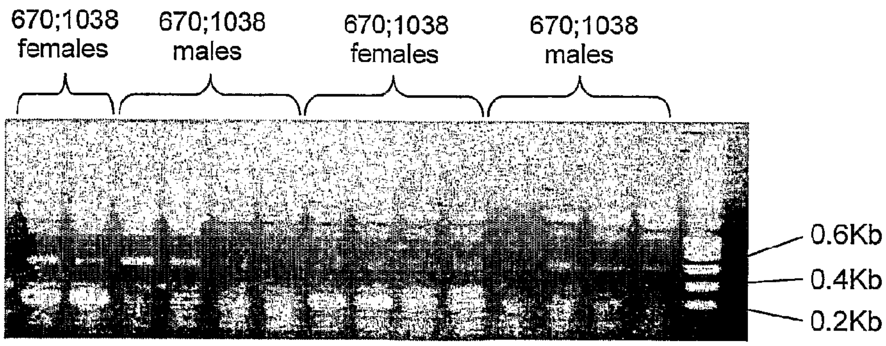

LA1038 is a new example of the use of the Cctra intron in a different sequence context, here placed in a fragment of Nipp1Dm called 'nipper' that also splices correctly in transgenic Medfly when analysed by RT-PCR (FIG. 12). LA670 was required as a source of tTAV to drive expression of the alternatively spliced nipper.

We have also newly made, and have obtained transgenics with, 'intron-only' Cctra-based constructs with the intron in a different gene (many of the above examples, unless otherwise apparent, are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above. The ubiquitin fusion method is further exemplified by RT-PCR analysis of LA3054, LA3056 and LA3488 (FIGS. 11, 13, 14), as described in Example 16, above.

Example 17: Further Cctra Exemplification

Reference is also made to LA3014 and LA3166 and phenotypic data therefrom in other Examples.

We have previously made, and have obtained transgenics with, the Cctra intron in a functional protein other than tTAV, see LA3014 and LA3166. LA3014 contains a ubiquitin-reaper$^{KR}$ fusion downstream of a Cctra intron. Phenotypic data shows that LA3014 transgenic Medfly gave repressible female-specific lethality. RT-PCR analysis on RNA extracted from adult males and females raised off tetracycline, using primers and ReaperKR, demonstrate that correct splicing was occurring in females (508 bp band) and no such band was found in males (FIG. 37). LA3166 is another construct with the Cctra intron placed inside the ubiquitin coding region fused to reaper$^{KR}$, but placed in a different position in ubiquitin. LA3166 also produces a dominant repressible female-specific lethal effect in Medfly.

LA1038 is a new example of the use of the Cctra intron in a different sequence context, here placed in a fragment of Nipp1Dm called 'nipper' that also splices correctly in transgenic Medfly when analysed by RT-PCR (FIG. 12). LA670 was required as a source of tTAV to drive expression of the alternatively spliced nipper.

We have also newly made, and have obtained transgenics with, 'intron-only' Cctra-based constructs with the intron in a different gene (many of the above examples, unless otherwise apparent, are in tTAV or one of its variants, i.e. tTAV2 or tTAV3). These constructs work as predicted. This is an important result, thus showing that there are not essential exonic sequences in Cctra that we have simply duplicated (in function, if not necessarily in sequence) by chance, in tTAV. We also have ubi-rpr$^{KR}$ constructs of this type (LA3014 and LA3166), which also validates the ubiquitin fusion method described above. The ubiquitin fusion method is further exemplified by RT-PCR analysis of LA3054, LA3056 and LA3488 (FIGS. 11, 13, 14), and as described in Example 16, above.

Figure 11:
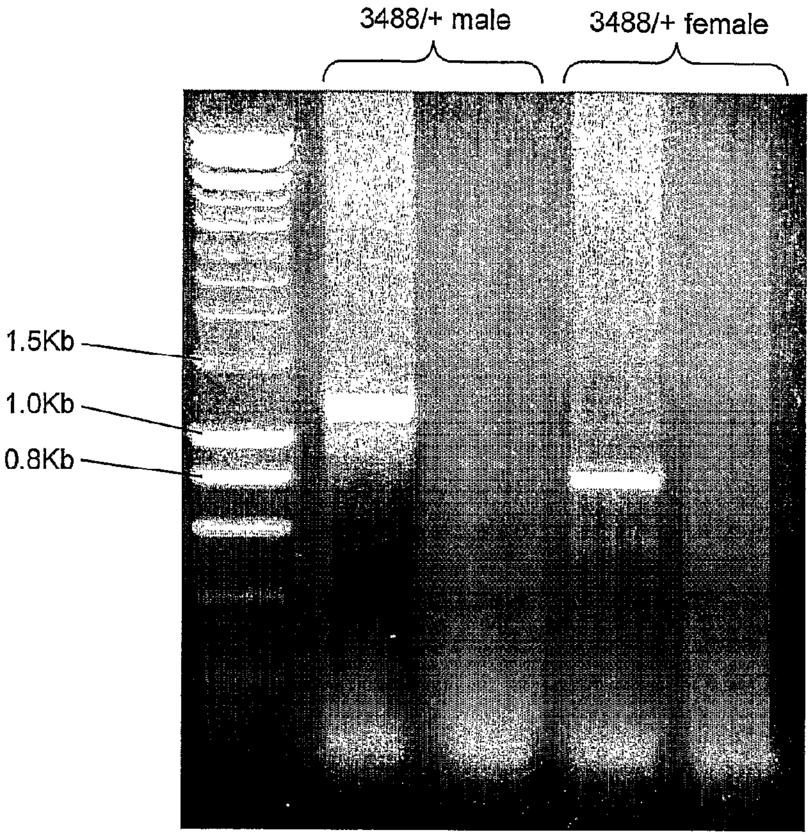

FIG. 11: Gel showing sex-specific splicing of intron(s) derived from Cctra (780 bp band in females) in *Ceratitis capitata* transformed with LA3488. Splicing in the F1 form would yield a product of approximately 780 bp. A band of this size is clearly visible from females (lane 4), but not from males, nor in the lanes with reactions from which the reverse transcriptase enzyme was omitted ("no RT"). Therefore, the Cctra-derived intron is capable of sex-specific alternative splicing in this novel sequence context. Lane 1: Marker (SmartLadder™ from Eurogentec, bands of approx 0.8, 1.0 and 1.5 kb are indicated); Lanes 2 and 3: *Ceratitis capitata* LA3488/+ males (RT and no RT control, respectively); Lanes 4 and 5: *Ceratitis capitata* LA3488/+ females (RT and noRT control, respectively).

FIG. 12: Gel showing sex-specific splicing of intron(s) derived from Cctra in *Ceratitis capitata* transformed with LA1038. Splicing in the F1 form would yield a product of approximately 230 bp. A band of this size is clearly visible from females (lanes 1, 2, 7, 8, 9 and 10), but not from males. Therefore, the Cctra-derived intron is capable of sex-specific alternative splicing in this novel sequence context. Lane 15: Marker (SmartLadder™ from Eurogentec, bands of approx 0.2, 0.4 and 0.6 kb are indicated); Lanes 1, 2, 7, 8, 9 and 10: *Ceratitis capitata* LA670; LA1038 females; Lanes 3, 4, 5, 6, 11, 12, 13 and 14: *Ceratitis capitata* LA670; LA1038 males.

Figure 13:
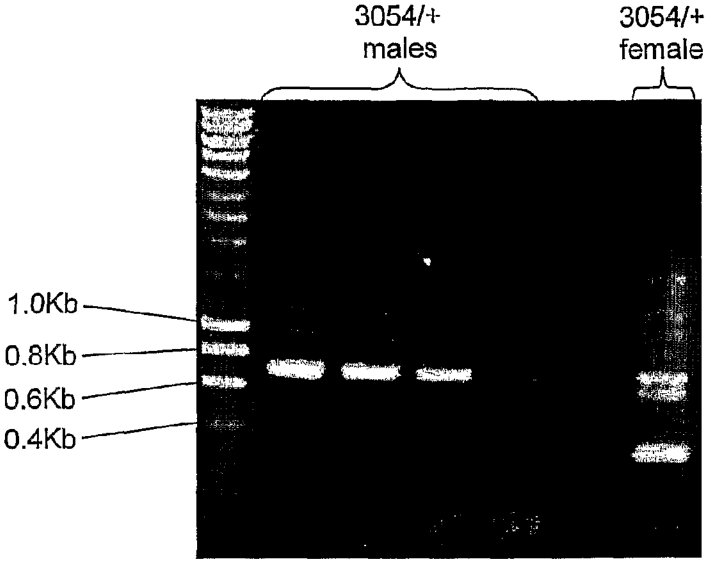

FIG. 13: Gel showing sex-specific splicing of intron(s) derived from CcTra in *Ceratitis capitata* transformed with LA3054. Splicing in the F1 form would yield a product of approximately 340 bp. A band of this size is clearly visible in lane 7, but not from males. Therefore, the Cctra-derived intron is capable of sex-specific alternative splicing in this novel sequence context. Lane 1: Marker (SmartLadder™ from Eurogentec, bands of approx 0.4, 0.6, 0.8 and 1.0 kb are indicated); Lanes 2-5: *Ceratitis capitata* LA3054 males; Lane 7: *Ceratitis capitata* LA3054 female.

Figure 14:
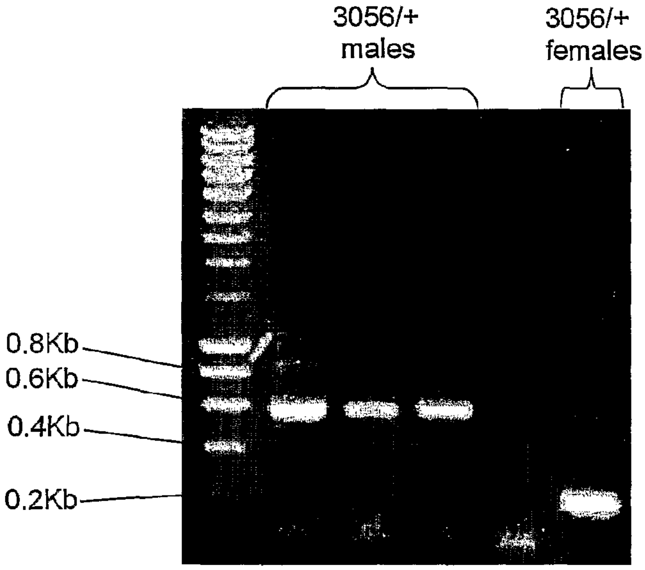

FIG. 14: Gel showing sex-specific splicing of intron(s) derived from Cctra in *Ceratitis capitata* transformed with LA3056. Splicing in the F1 form would yield a product of approximately 200 bp. A band of this size is clearly visible from a female (lane 6), but not from males (lanes 2-4). Therefore, the Cctra-derived intron is capable of sex-specific alternative splicing in this novel sequence context. Lane 1: Marker (SmartLadder™ from Eurogentec, bands of approx 0.2, 0.4, 0.6 and 0.8 kb are indicated); Lanes 2-5: *Ceratitis capitata* LA3056/+ males; Lanes 6-7: *Ceratitis capitata* LA3056/+ females.

FIG. 15: Gel showing sex-specific splicing of intron(s) derived from BzTra in *Anastrepha ludens* transformed with LA3376. Splicing in the F1 form would yield a product of approximately 672 bp. A band of this size is clearly visible from females (lane 4), but not from males, nor in the lanes with reactions from which the reverse transcriptase enzyme was omitted ("no RT"), primers used were SRY and AV3F. Therefore, the Bztra-derived intron is capable of sex-specific alternative splicing in this novel sequence context and species. Lane 1: Marker (SmartLadder™ from Eurogentec, bands of approx 0.6, 0.8, and 1.0 kb are indicated); Lanes 2 and 3*: Anastrepha ludens* LA3376/+ males (RT and no RT control, respectively); Lanes 4 and 5*: Anastrepha ludens* LA3376/+ females (RT and no RT control, respectively).

FIG. 18 and SE ID NOs 149 and 150 show DSX minigene1, DSX minigene2 sequences and LA3619 plasmid map.

Figure 67:
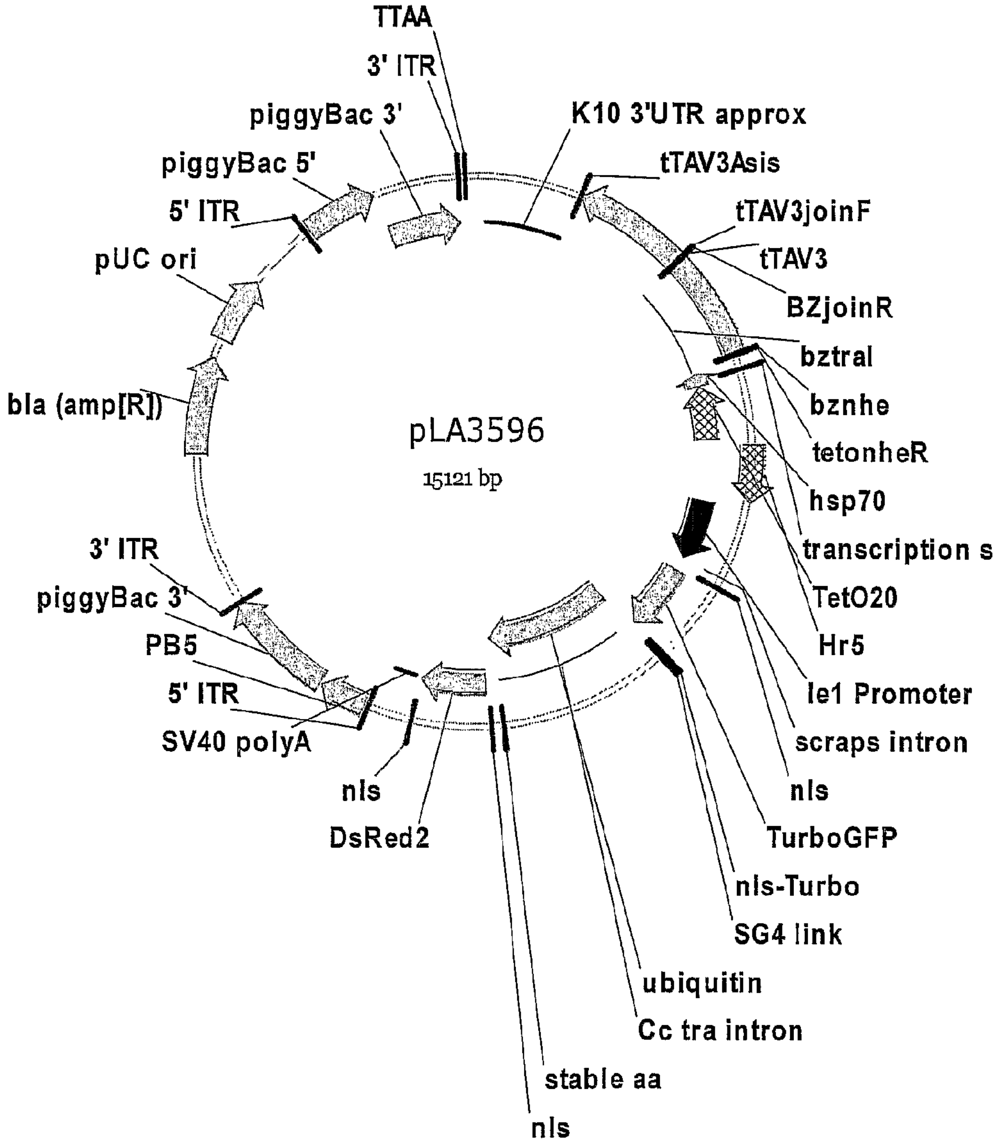
Figure 68:
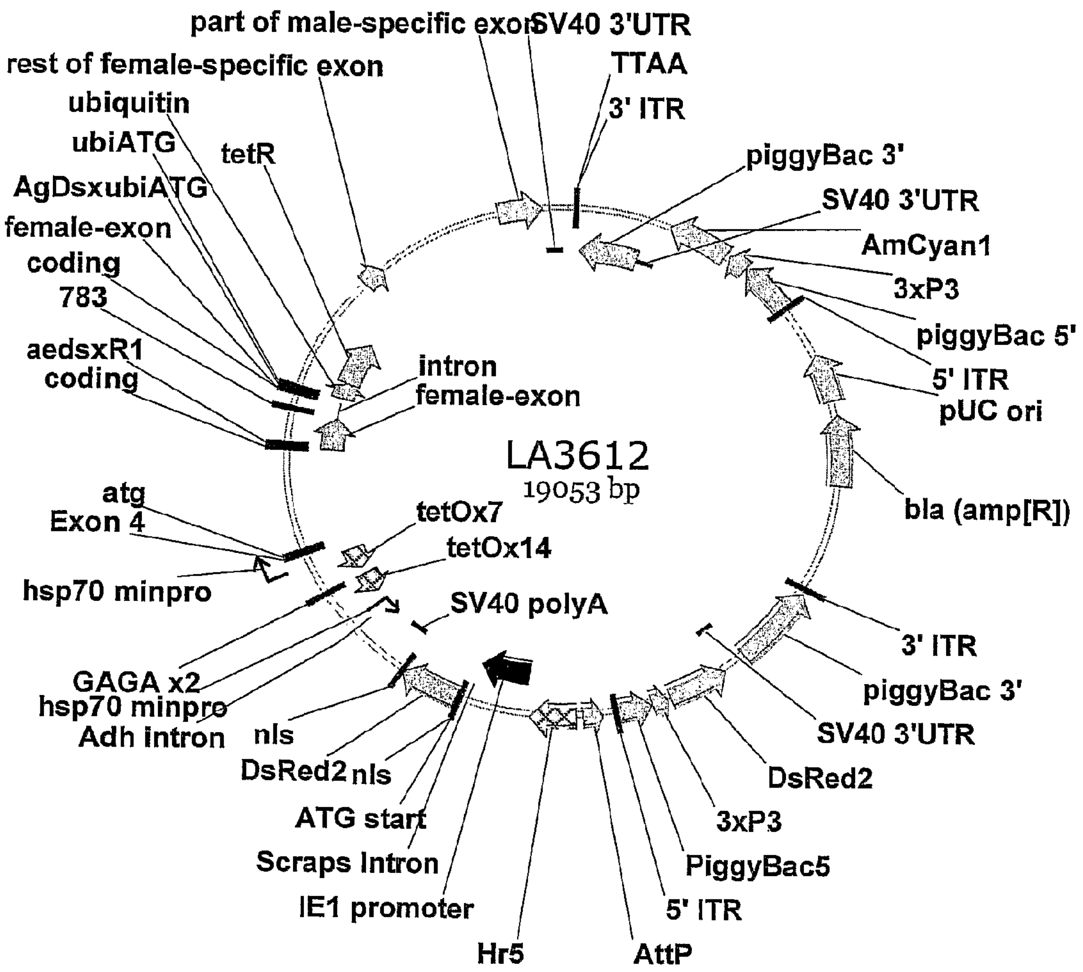
Figure 69:
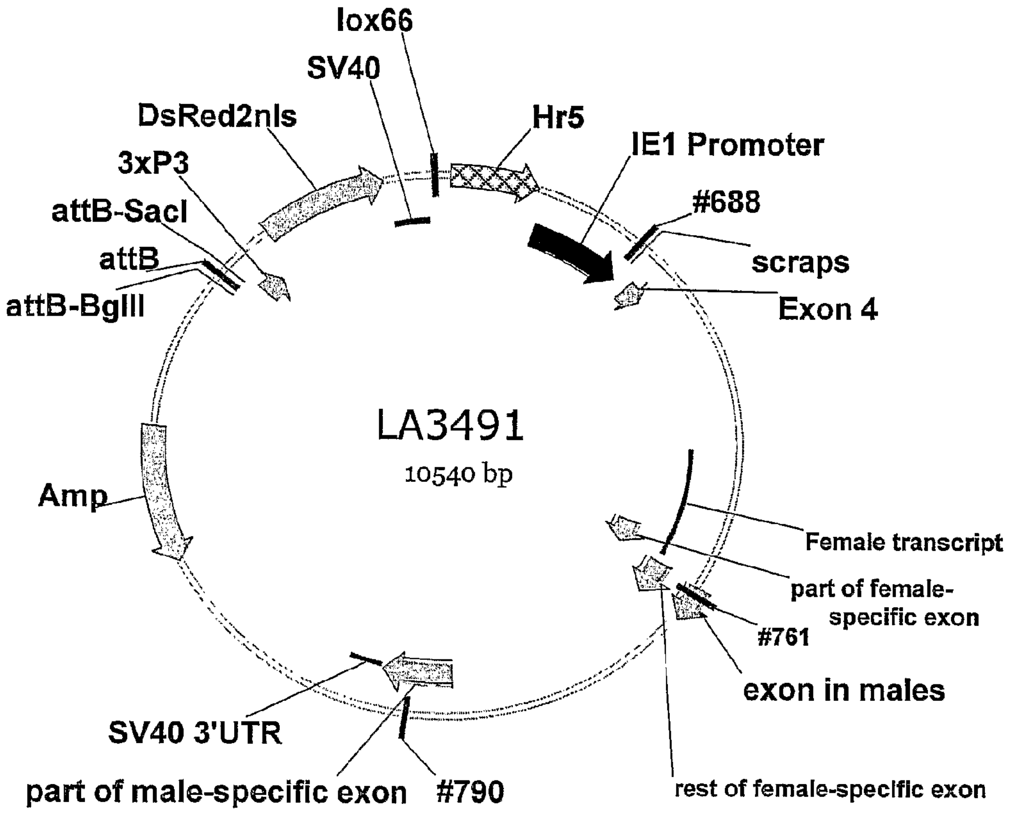

FIGS. 19-51 are as per Examples 1-9 above. FIGS. 52-58, 68 and 69 show various plasmid diagrams and sequences. FIGS. 59-60 are described above and FIGS. 61-66 show various further plasmid diagrams and sequences. FIG. 67 is pLA3596, as discussed elsewhere.

REFERENCES

Allen M L, Christensen B M. Related 2004 Flight muscle-specific expression of act88F: GFP in transgenic *Culex quinquefasciatus* Say (Diptera: Culicidae). Parasitol Int. 53(4):307-14.

Bennett D, Szoor B, Gross S, Vereshchagina N, Alphey L. 2003 Ectopic expression of inhibitors of protein phosphatase type 1 (PP1) can be used to analyze roles of PP1 in *Drosophila* development. Genetics. 164(1):235-45.

Black, D. (2003). Mechanisms of alternative pre-messenger RNA splicing. Annu Rev Biochem 72, 291-336.

Burset, M., Seledtsov, I., and Solovyev, V. (2001). SpliceDB: database of canonical and non-canonical splice sites in mammalian genomes. Nucleic Acids Research 29, 255-259.

Caceres J F, Kornblihtt A R. 2002 Alternative splicing: multiple control mechanisms and involvement in human disease. Trends Genet. 18(4):186-93.

Cande C, Cecconi F, Dessen P, Kroemer G. 2002 Apoptosis-inducing factor (AIF): key to the conserved caspase-independent pathways of cell death? J Cell Sci. 115(24): 4727-34.

Cartegni, L., Chew, S., and Krainer, A. (2002). Listening to silence and understanding nonsense: exonic mutations that affect splicing. Nature Reviews Genetics 3, 285-298.

Clark, F., and Thanaraj, T. (2002). Categorization and characterization of transcript-confirmed constitutively and alternatively spliced introns and exons from human. Human Molecular Genetics 11, 451-464.

Funaguma, S., Suzuki, M., Tamura, T., and Shimada, T. (2005). The Bmdsx transgene including trimmed introns is sex-specifically spliced in tissues of the silkworm, *Bombyx mori*. J Insect Sci 5, 17.

George, E. L., Ober, M. B. and Emerson Jr, C. P. (1989). Functional domains of the *Drosophila melanogaster* muscle myosin heavy-chain gene are encoded by alternatively spliced exons. Mol. Cell Biol. 9:2957-2974.

Graveley B R. 2001 Alternative splicing: increasing diversity in the proteomic world. Trends Genet. 17(2):100-7.

Hammes, A., Guo, J. K., Lutsch, G., Leheste, J. R., Landrock, D., Zeigler, U., Gubler, M. C. and Schedl, A. (2001). Two splice variants of the Wilms' Tumour 1 gene have distinct functions during sex determination and nephron formation. Cell 106:319-329.

Hastings, G. A. and Emerson Jr, C. P (1991). Myosin functional domains encoded by alternative exons are expressed in specific thoracic muscles of *Drosophila*. J. Cell Biol. 114: 263-276.

Hedley, M. L. and Maniatis (1991). Sex-specific splicing and polyadenylation of dsx pre-mRNA requires a sequence that binds specifically to a tra-2 protein in vivo. Cell 65:579-586.

Heinrich J. C. and Scott M. J. 2000 A repressible female-specific lethal genetic system for making transgenic insect strains suitable for a sterile-release program PNAS 97 (15): 8229-8232

Horn C, Wimmer E A. 2003 A transgene-based, embryo-specific lethality system for insect pest management. Nat Biotechnol. 21(1):64-70.

Hoshijima, K. K, Inoue, L., Higuchi, I., Sakamoto, H. and Shimura, Y. (1991). Control of doublesex alternative splicing by transformer and transformer-2 in *Drosophila*. Science 252:833-836.

Huang, Q., Deveraux, Q. L., Maeda, S., Salvesen, G. S., Stennicke, H. R., Hammock, B. D. and Reed, J. C. (2002). Evolutionary conservation of apoptosis mechanisms: Lepidopteran and baculoviral inhibitor of apoptosis proteins are inhibitor of mammalian caspase-9.Agricultural Sciences 97(4):1427-1432.

Ito, Y., Hirochicka, H. and Kurata, N. (2002). Organ-specific alternative transcripts of KNOX family class 2 homeobox genes of rice. Gene 288:41-47.

Johnson J M, Castle J, Garrett-Engele P, Kan Z, Loerch P M, Armour C D, Santos R, Schadt E E, Stoughton R, Shoemaker D D. 2003 Genome-wide survey of human alternative pre-mRNA splicing with exon junction microarrays. Science. 302(5653):2141-4.

Jurica M S, Moore M J. 2003 Pre-mRNA splicing: awash in a sea of proteins. Mol Cell. 12(1):5-14.

Kazzaz J A, Rozek C E. 1989 Tissue-specific expression of the alternately processed *Drosophila* myosin heavy-chain messenger RNAs. Dev Biol. 133(2):550-61.

Maniatis, T., and Tasic, B. (2002). Alternative pre-mRNA splicing and proteome expansion in metazoans. Nature 418, 236-243.

Muñoz, D., Jimenez, A., Marinotti, O., and James, A. (2004). The AeAct-4 gene is expressed in the developing flight muscles of females *Aedes aegypti*. Insect Molecular Biology 13, 563-568.

Nishiyama, R., Mizuno, H., Okada, S., Yamaguchi, T., Takenaka, M., Fukuzawa, H. and Ohyama, K. (1999). Two mRNA species encoding calcium-dependent protein kinases are differentially expressed in sexual organs of *Marchantia polymorpha* through alternative splicing. Plant Cell Physiol. 40(2):205-212.

Nishiyama, R., Yamato, K. T., Miura, K., Sakida, M., Okada, S., Kono, K., Takahama, M., Sone, T., Takenaka, M., Fukuzawa, H. and Ohyama, K. (2000). Comparison of expressed sequence tags from male and female sexual organs of *Marchantia polymorpha*. DNA Res. 7:165-174.

Olson, M. R., Holley, C. L., Ji Yoo, S., Huh, J. R, Hay, B. A. and Kornbluth, S. (2003). Reaper is regulated by IAP-mediated Ubiquitination. J. Biol. Chem., 278(6): 4028-4034.

Olson, M. R., Holley, C. L., Gan, E. C., Colon-Ramos, D. A., Kaplan, B. and Kornbluth, S. (2003). A GH3-like domain in reaper is required for mitochondrial localization and induction of IAP degradation. J. Biol. Chem. 278(45): 44758-44768.

Pan, Q., Shai, O., Misquitta, C., Zhang, W., Saltzman, A., Mohammad, N., Babak, T., Siu, H., Hughes, T., Morris, Q., et al. (2004). Revealing global regulatory features of mammalian alternative splicing using a quantitative microarray platform. Mol Cell 16, 929-941.

Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.

Park, J., Parisky, K., Celotto, A., Reenan, R., and Graveley, B. (2004). Identification of alternative splicing regulators by RNA interference in *Drosophila*. Proc Nat'l Acad Sci (USA) 101, 15974-15979.

Parker L, Gross S, Beullens M, Bollen M, Bennett D, Alphey L. 2002 Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1. Biochem J. 368(3): 789-97.

Raphael, K. A., Whyard, S., Shearman, D., An, X. and Frommer, M. (2004). *Bactrocera tyroni* and closely related pest-tephritids-molecular analysis and prospects for transgenic control strategies. Insect Biochem. Mol. Biol. 34:167-176.

Ryner, L. and Baker, B. S. (1991). Regulation of doublesex pre-mRNA processing occurs by 3'-splice site activation. Genes Dev. 5:2071-2085.

Saccone, G., Pane, A., and Polito, C. (2002). Sex determination in flies, fruitfles and butterflies. Genetica 116, 15-23.

Scali, C., Catteruccia, F., Li, Q., and Crisanti, A. (2005). Identification of sex-specific transcripts of the *Anopheles gambiae* doublesex gene. J Exp Biol 208, 3701-3709.

Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.

Seo, S-J., Cheon, H-M., Sun, J., Sappington, T. W. and Raikhel, A. S. (2003). Tissue- and stage-specific expression of two lipophorin receptor variants with seven and eight ligand-binding repeats in the adult mosquito. J. Biol. Chem. 278(43):41954-41962.

Siebel C W, Fresco L D, Rio D C. 1992 The mechanism of somatic inhibition of *Drosophila* P-element pre-mRNA splicing: multiprotein complexes at an exon pseudo-5' splice site control U1 snRNP binding. Genes Dev. 6(8): 1386-401.

Shivikrupa, Singh., R and Swarup, G. (1999). Identification of a novel splice variant of C3G which shows tissue-specific expression. DNA Cell Biol. 18: 701-708.

Smith, C., and Valcarcel, J. (2000). Alternative pre-mRNA splicing: the logic of combinatorial control. Trends Biochem Sci 25, 381-388.

Stoss, O., Stoilov, P., Hartmann, A. M., Nayler, O., and Stamm, S. (1999). The in vivo minigene approach to analyze tissue-specific splicing. Brain Research Protocols 4, 383-394.

Stoss, O., Olbrich, M, Hartmann, A. M., Konig, H., Memmott, J., Andreadis, A and Stamm, S. (2001). The STAR/GSG family protein rSLM-2 regulates the selection of alternative splice sites. J. Biol. Chem. 276(12):8665-8673.

Streuli, M. and Saito, H. (1989). Regulation of tissue-specific alternative splicing: exon-specific cis-elements govern the splicing of leukocyte common antigen pre-mRNA. EMBO J. 8(3): 787-796.

Suzuki, M., Ohbayashi, F., Mita, K., and Shimada, T. (2001). The mechanism of sex-specific splicing at the doublesex gene is different between *Drosophila melanogaster* and *Bombyx mori*. Insect Biochem Mol Biol 31, 1201-1211.

Thanaraj, T., and Clark, F. (2001). Human GC-AG alternative intron isoforms with weak donor sites show enhanced consensus at acceptor exon positions. Nucleic Acids Research 29, 2581-2593.

Thanaraj, T., Stamm, S., Clark, F., Reithoven, J., Le Texier, V., and Muilu, J. (2004). ASD: the Alternative Splicing Database. Nucleic Acids Research 32, D64-D69.

Varshaysky, A. (2000). Ubiquitin fusion technique and its descendants. Meth Enz 327.

Venables, J. (2002). Alternative splicing in the testes. Curr Opin Genet Dev 12, 615-619.

Venables J P. 2004 Aberrant and alternative splicing in cancer. Cancer Res. 64(21):7647-54.

Vernooy, S. Y., Copeland, J., Ghaboosi, N., Griffin, E. E., Yoo, S. J. and Hay, B. A. (2000). J. Cell Biol. 150(2): F69-F75.

White, K., Tahoaglu, E. and Steller, H. (1996). Cell killing by the *Drosophila* gene reaper. Science 271 (5250): 805-807.

Wing, J. P., Zhou, L., Schwartz, L. M. and Nambu, J. R. (2001) Distinct cell killing properties of the *Drosophila* reaper, head involution defective, and grim genes. Cell Death Diffn 5(11): 930-939

Yali Chiu A., and Pin Ouyang, A. B., (2006). Loss of Pnn expression attenuates expression levels of SR family splicing factors and modulates alternative pre-mRNA splicing in vivo. Bioch. Biophys. Res. Comm 341:663-671.

Yoshimura, K., Yabuta, Y., Ishikawa, T. and Shigeoka, S. (2002). Identification of a cis element for tissue-specific alternative splicing of chloroplast Ascorbate Peroxidase pre-mRNA in higher plants. J. Biol. Chem 277 (43): 40623-40632.

SEQUENCE ANNOTATIONS

The following relates to the various plasmids of the present and highlights the position of certain preferred elements therein.

<223> Sequence of pLA3359 (SED ID NO. 47).

<***> Key features include:

1. *Anopheles gambiae* dsx (Agdsx) mini-gene, [a mini-gene is a recombinant sequence derived from a particular gene (the Agdsx gene in this example) by ligating together non-contiguous segments while retaining original 5'-3' order; this is equivalent to deletion of some internal segments from a longer fragment of genomic sequence derived from the gene], (1-3135): including Agdsx part of exon3, exon 4a (female), exon 4b (female) and part of exon5 (male and female).

<***> Exons derived from Agdsx from positions 426 to 560 (part of exon 3); 1068 to 2755 (including part of exon 4, found in females); 1809 to 2755 (including part of exon 4, found in females); and 2914 to 3135 (including part of exon 5, found in males).

<***> Alternatively spliced transcript starts in segment derived from baculovirus AcMNPV Ie1 (immediate early 1) at position ~8031 (Ie1 fragment is from position 7431 to 8060).

<***> Included feature:

1. additional intron derived from *Drosophila* scraps gene ('scraps intron') upstream to Agdsx sequence from position 8075 to 8137.

<223> Sequence of pLA3433 (SED ID NO. 48).

<***> Key features include:

1. Agdsx mini-gene (778-4623): including Agdsx part of exon 2, exon3, exon 4a (female), exon 4b (female) and part of exon5 (male and female).

<***> Exons derived from Agdsx from position 778 to 908 (part of exon 2); 1913 to 2048 (part of exon 3); 2556 to 2642 (part of exon 4a); 3297 to 4243 (part of exon 4b) and 4402 to 4623 (part of exon 5).

<***> Alternatively spliced transcript starts in segment derived from baculovirus AcMNPV Ie1 (immediate early 1) at position ~606 (Ie1 fragment is from position 6 to 635).

<***> Included feature:

1. additional intron derived from *Drosophila* scraps gene ('scraps intron') upstream to Agdsx sequence from position 650 to 712.

<223> Sequence of pLA3491.

<***> Key features include:

1. *Aedes aegypti* dsx (Aadsx) mini-gene: including part of Aadsx exon 4, exon5a (female), exon 5b (female), and part of exon6 (male and female).

<***> Exons derived from Aadsx from position 1316 to 1450 (part of exon 4); 2626 to 3761 (part of exon 5a); 3293 to 3761 (part of exon 5b); and 5215 to 5704 (part of exon 6).

<***> Part of the F1 transcript is predicted to comprise nucleotides ~1174-1450, 2626-3761, 5215-~5850.

<***> Part of the F2 transcript is predicted to comprise nucleotides ~1174-1450, 3293-3761, 5215-~5850.

<***> Part of the F3 transcript is predicted to comprise nucleotides ~1174-1450, 2626-3083, 3293-3761, 5215-~5850.

<***> Part of the M1 transcript is predicted to comprise nucleotides ~1174-1450, 5215-~5850.

<***> Alternatively spliced transcript starts in segment derived from baculovirus AcMNPV Ie1 (immediate early 1) at position ~1174 (Ie1 fragment is from position 574 to 1203).

<***> Included feature:

1. additional intron derived from *Drosophila* scraps gene ('scraps intron') upstream to Aadsx sequence from position 1218 to 1280.

<223> Sequence of pLA3646.

<***> Key features include:

1. Aadsx mini-gene (17218-11707): including part of Aadsx exon 4 from position 17113 to 16979, exon 5a from position 15803 to 15025+14010 to 13650, exon 5b from position 15136 to 15025+14010 to 13650 and exon 6 from position 12196 to 11707 (note: reverse orientation).

<***> part of exon 4 contains 4 point mutations relative to wild type at positions 17087 (ATG-ACG), 17053 (ATG-ACG), 17050 (ATG-ACG) and 17041 (ATG-ACG) (note: reverse orientation); part of exon 5a and 5b contain 3 point mutations relative to wild type at positions 15129 (ATG-ATA), 15116 (ATG-ATA) and 15113 (ATG-ATA) (note: reverse orientation). All of these mutations are to eliminate ATG sequences.

<***> tTAV2 is inserted in the overlapping exons 5a and 5b from position 15024 to 14011 (note: reverse orientation).

<***> Alternatively spliced transcript starts in hsp70 derived fragment at position ~17312 (hsp70 fragment is from position 17354 to 17225); (note: reverse orientation).

<***> Included feature:

1. additional intron derived from *Drosophila* scraps gene ('scraps intron') upstream to Aadsx sequence from position 1107 to 1045 (note: reverse orientation)

Sequence of pLA3435 (SED ID NO. 46).

<223> Key features include:

1. *Bombyx mori* dsx (Bmdsx) minigene (1411-3161) with an exogenous linker between fused female exons 3 and 4.

<***> Fragment of shared exon two (1411 bp-1554 bp)

<***> Part of female specific exon three (2121 bp-2202) fused to part of female specific exon 4 (2225 bp-2290 bp) using an exogenous linker (2203 bp-2224 bp)

<***> Fragment of shared exon five (3007 bp-3161 bp)

<***> A female dsx mini-gene splicing product is encoded by 1411-1554+2121-2290+3007-3161.

<***> A male dsx mini-gene splicing product is encoded by 1411-1554+3007-3161.

<***> Transcription is predicted to start at approximately position ~1239 within the segment derived from baculovirus AcMNPV Ie1 (immediate early 1) promoter (639 bp-1268 bp).

<223> Sequence of pLA3534.

<***> Key features include:

1. Aadsx mini-gene (6996-4425): containing Aadsx exon 4, part of exon5a (female) and part of exon 56 (female), inclusive of Aadsx intron fragments.

<***> Exons derived from Aadsx from position 6968 to 6834 (part of exon 4), 5462 to 4425 (part of exon 5a) and 4795 to 4425 (part of exon 5b); (note reverse orientation).

<***> Part of the F1 transcript is predicted to comprise nucleotides ~7146-6834, 5462-4300 (note: reverse orientation).

<***> Part of the F2 transcript is predicted to comprise nucleotides ~7146-6834, 4795-4300 (note: reverse orientation).

<***> Part of the F3 transcript is predicted to comprise nucleotides ~7146-6834, 5462-5005, 4795-4300 (note: reverse orientation).

<***> Alternatively spliced transcript starts in segment derived from baculovirus AcMNPV Ie1 (immediate early 1) at position ~7146 (Ie1 fragment is from position 7746 to 7117, reverse orientation).

<223> Sequence of pLA3612.

<***> Key features include:

1. Ubiquitin-tTAV2 coding region inserted into a female exon of Aadsx gene.

<***> Ubiquitin-tTAV2 is from position 15185-16429 in Aadsx (ubiquitin is from 15185-15412; tTAV2 is from 15413-16429), inclusive of start and stop codon.

<***> Sequence derived from Aadsx: 13150-15184, 16438-18805.

<***> Aadsx-ubiquitin-tTAV2 alternatively spliced transcript starts in hsp70 derived segment (hsp70 fragment is from 13014-13143).

<223> Sequence of pLA3619.

<***> Key features include:

1. tTAV2 coding region inserted into a female exon of Aadsx gene.

<***> Sequence derived from Aadsx: 5635-3641, 2610-243 (note: reverse orientation).

<***> Aadsx-tTAV2 alternatively spliced transcript starts in hsp70 derived segment from 5642-5771 (note: reverse orientation).

<***> tTAV2 transcript is predicted to be translated between 2619-3635, inclusive of start and stop codon (note: reverse orientation).

<223> Sequence of pLA3545.

<***> Key features include:

1. AaActin4 promoter and 5' UTR including first intron regulates tTAV expression.

<***> Sequence derived from AaActin4 is from position 923-4285.

<***> Alternatively spliced transcript is predicted to start from approximately ~2366.

<***> The first intron from AaActin4 (female splice variant) is from 2458-4259.

<***> tTAV is predicted to be translated between 4300-5316, inclusive of start and stop codon.

<223> Sequence of pLA3604.

<***> Key features include:

1. AaActin4 promoter and 5' UTR regulates ubiquitin-tTAV2 expression.

<***> Sequence derived from AaActin4 is from position 5795-2407 (note: reverse orientation).

<***> Alternatively spliced transcript is predicted to start from approximately ~4353 (note: reverse orientation).

<***> The first intron from AaActin4 (female splice variant) is from 2455-4254 (note: reverse orientation).

<***> Ubquitin-tTAV2 transcript is predicted to be translated from a start codon engineered in the first exon of AaAct4 gene at 4299-4297 (ubiquitin is from 2406-2179; tTAV2 is from 2178-1162); (note: reverse orientation).

<223> Sequence of pLA3641.

<***> Key features include:

1. tTAV coding region inserted into a female exon of CodlingDsx gene.

<***> tTAV is from position 2731-3747 in CodlingDsx gene.

<***> Dsx-tTAV alternatively spliced transcript starts in hsp70 derived segment (hsp70 fragment is from 4811-4940).

<***> tTAV transcript is predicted to be translated between 2731-3747, inclusive of start and stop codon (note: reverse orientation).

<223> Sequence of pLA3570

<***> Key features include:

1. tTAV coding region inserted into a female exon of PBW-Dsx gene.

<***> tTAV coding region is from 2336-3352.

<***> Dsx-tTAV alternatively spliced transcript starts in hsp70 derived segment (hsp70 fragment is from 4683-4812).

<***> tTAV transcript is predicted to be translated between 2336-3352, inclusive of start and stop codon (note: reverse orientation).

<223> Sequence of pLA1188 (SED ID NO. 49)

<***> Key features include:

1. tTAV coding region with inserted Cctra intron.

<***> Cctra intron is from position 3905-2561 in tTAV (note: reverse orientation).

<***> tTAV alternatively spliced transcript starts in hsp70 derived segment at position 4217 (hsp70 fragment is from 4260-4131); (note: reverse orientation).

<***> tTAV F1 transcript is predicted to be translated between 4040-1679 (note: reverse orientation).

<***> Included feature:

1. Adh intron within predicted F1 transcript from position 4118-4049 (note: reverse orientation).

<223> Sequence of pLA3077 (SED ID NO. 50).

<***> Key features include:

1. tTAV coding region with inserted Cctra intron.

<***> Cctra intron is from position 3975-2631 in tTAV (note: reverse orientation).

<***> tTAV alternatively spliced transcript starts in hsp70 derived segment at position ~4217 (hsp70 fragment is from 4260-4131); (note: reverse orientation).

<***> tTAV F1 transcript is predicted to be translated between 4039-1678, inclusive of start and stop codon (note: reverse orientation).

<***> Included feature:

1. Adh intron within predicted F1 transcript from position 4117-4048 (note: reverse orientation).

<223> Sequence of pLA3097 (SED ID NO. 51).

<***> Key features include:

1. tTAV coding region with inserted Cctra intron.

<***> Cctra intron is from position 3282-1938 in tTAV (note: reverse orientation).

<***> tTAV alternatively spliced transcript starts in hsp70 derived segment at position ~3382 (hsp70 fragment is from 3425-3296); (note: reverse orientation).

<***> tTAV F1 transcript is predicted to be translated between 3285-924, inclusive of start and stop codon (note: reverse orientation).

<223> Sequence of pLA3233 (SED ID NO. 52).

<***> Key features include:

1. tTAV2 coding region with inserted Cctra intron.

<***> Cctra intron is from position 3289-1945 in tTAV2 (note: reverse orientation).

<***> tTAV2 alternatively spliced transcript starts in hsp70 derived segment at position ~3389 (hsp70 fragment is from 3432-3303); (note: reverse orientation).

<***> tTAV2 F1 transcript is predicted to be translated between 3292-931, inclusive of start and stop codon (note: reverse orientation).

<223> Sequence of pLA3014 (SED ID NO. 53).

<***> Key features include:

1. ubi-reaper[KR] coding region with inserted Cctra intron.

<***> Cctra intron is from position 3356-4700 in ubi-reaper [KR].

<***> ubi-reaper[KR] alternatively spliced transcript starts in hsp70 derived segment at position ~3234 (hsp70 fragment is from 3191-3320).

<***> ubi-reaper[KR] F1 transcript is predicted to be translated between 3331-5143, inclusive of start and stop codon (ubiquitin is from 3331-3355, 4701-4948; reaper[KR] is from 4949-5143).

<223> Sequence of pLA3166 (SED ID NO. 54).

<***> Key features include:

1. ubi-reaper[KR] coding region with inserted Cctra intron.

<***> Cctra intron is from position 9987-8643 in ubi-reaper [KR] (note: reverse orientation).

<***> ubi-reaper[KR] alternatively spliced transcript starts in hsp70 derived segment at position ~10227 (hsp70 fragment is from 10270-10141); (note: reverse orientation).

<***> ubi-reaper[KR] F1 transcript is predicted to be translated between 10126-8359, inclusive of start and stop codon (ubiquitin is from 10126-9988, 8642-8554; reaper[KR] is from 8553-8359); (note: reverse orientation).

<223> Sequence of pLA3376 (SED ID NO. 55).

<***> Key features include:

1. tTAV2 coding region with inserted Cctra intron.
2. tTAV3 coding region with inserted Bztra intron.
3. reaper[KR] coding region with inserted Bztra intron.

<***> Cctra intron is from position 3289-1945 in tTAV2 (note: reverse orientation).

<***> Bztra intron is from position 5981-5014 in tTAV3 (note: reverse orientation).

<***> Bztra intron is from position 16391-17358 in reaper [KR].

<***> tTAV2 alternatively spliced transcript starts in hsp70 derived segment at position ~3389 (hsp70 fragment is from 3432-3303); (note: reverse orientation).

<***> tTAV3 alternatively spliced transcript starts in sry-alpha derived segment at position ~6019 (sry-alpha fragment is from 6243-5999); (note: reverse orientation).

<***> reaper[KR] alternatively spliced transcript starts in hunchback derived segment at position ~16339 (hunchback fragment is from 16289-16372).

<***> tTAV2 F1 transcript is predicted to be translated between 3292-931, inclusive of start and stop codon (note: reverse orientation).

<***> tTAV3 F1 transcript is predicted to be translated between 5984-4006, inclusive of start and stop codon (note: reverse orientation).

<***> reaper[KR] F1 transcript is predicted to be translated between 16385-17550, inclusive of start and stop codon.

<223> Sequence of pLA3242 (SED ID NO. 56).

<***> Key features include:

1) tTAV coding region with inserted Cctra intron.
2) reaper[KR] coding region with inserted Crtra intron.

<***> Cctra intron is from position 3282-1938 in tTAV (note: reverse orientation).

<***> Crtra intron is from position 5488-4180 in reaperKR (note: reverse orientation).

<***> reaperKR alternatively spliced transcript starts in hunchback derived segment at position ~5540 (hunchback fragment is from 5590-5507); (note: reverse orientation).

<***> tTAV alternatively spliced transcript starts in hsp70 derived segment at position ~3382 (hsp70 fragment is from 3425-3296); (note: reverse orientation).

<***> reaperKR F1 transcript is predicted to be mainly translated between 4088-5494, inclusive of start and stop codon (note: reverse orientation).

<***> tTAV F1 transcript is predicted to be mainly translated between 924-3285, inclusive of start and stop codon (note: reverse orientation).

<223> Sequence of pLA1172 (SED ID NO. 106).

<***> Key features include:

1. tTAV coding region between AaActin4 derived fragments.

<***> AaActin4 derived fragments are from 7868-11257 and 12366-13100.

<***> tTAV transcript is predicted to be translated between 11342-12358, inclusive of start and stop codon.

<***> AaActin4-tTAV transcript is predicted to start at position ~9312.

<***> AaActin4 contains an intron (female-type splice variant) from position 9403-11204.

<223> Sequence of pLA1038 (FIG. 12).

<***> Key features include:

1. Fragment of Nipp1Dm ('nipper') coding region with inserted Cctra intron with flanking tra exonic sequence.

<***> Cctra intron is from position 3365-4709 in nipper.

<***> Cctra intron is flanked by Cctra exonic sequence at positions 3343-3364 and 4710-4729.

<***> nipper alternatively spliced transcript starts in hsp70 derived segment at position ~3243 (hsp70 fragment is from 3200-3329).

<***> nipper F1 transcript is predicted to be translated between 3340-5014, inclusive of start and stop codon.

<223> Sequence of pLA3054 (SED ID NO. 158).

<***> Key features include:

1. DsRed-ubi-tTAV coding region with inserted Cctra intron with flanking tra exonic sequence.

<***> Cctra intron is from position 3509-2165 in DsRed-ubi-tTAV (note: reverse orientation).

<***> Cctra intron is flanked by Cctra exonic sequence at positions 3531-3510 and 2164-2145 (note: reverse orientation).

<***> DsRed-ubi-tTAV alternatively spliced transcript starts either in hsp70 derived segment at position ~3243 (hsp70 fragment is from 4930-4801) or Opie2 derived segment at position ~4353 (Opie2 fragment is from 4795-4255); (note: reverse orientation).

<***> DsRed-ubi-tTAV F1 transcript is predicted to be translated between 4320-888, inclusive of start and stop codon (DsRed is from 4212-3538; ubiquitin is from 2135-1908; tTAV is from 1907-888); (note: reverse orientation).

<223> Sequence of pLA3056 (SED ID NO. 159).

<***> Key features include:

1. DsRed-ubi-tTAV coding region with inserted Cctra intron with flanking tra exonic sequence.

<***> Cctra intron is from position 3731-2387 in DsRed-ubi-tTAV (note: reverse orientation).

<***> Cctra intron is flanked by Cctra exonic sequence at positions 3753-3732 and 2386-2145 (note: reverse orientation).

<***> DsRed-ubi-tTAV alternatively spliced transcript starts either in hsp70 derived segment at position ~5109 (hsp70 fragment is from 5152-5023) or Opie2 derived segment at position ~4575 (Opie2 fragment is from 5017-4477); (note: reverse orientation).

<***> DsRed-ubi-tTAV F1 transcript is predicted to be translated between 4542-888, inclusive of start and stop codon (DsRed is from 4434-3760; ubiquitin is from 2135-1908; tTAV is from 1907-888); (note: reverse orientation).

<***> Included feature:

1. additional intron derived from Cctra gene (second intron of Cctra F1 transcript) within predicted F1 transcript from position 2222-2168 (note: reverse orientation).

<223> Sequence of pLA3488 (SED ID NO. 160).

<***> Key features include:

1. TurboGreen-ubi-DsRed coding region with inserted Cctra intron.

<***> Cctra intron is from position 2263-3607 in TurboGreen-ubi-DsRed.

<***> TurboGreen-ubi-DsRed alternatively spliced transcript starts in segment derived from baculovirus AcMNPV Ie1 (immediate early 1) at position ~1180 (Ie1 fragment is from 580-1209).

<***> TurboGreen-ubi-DsRed F1 transcript is predicted to be translated between 1311-4467, inclusive of start and stop codon (TurboGreen is from 1311-2093; SG4 linker is from 2094-2123; ubiquitin is from 2124-3696, inclusive of Cctra intron; DsRed is from 3697-4467).

<***> Included feature:

1. additional intron derived from *Drosophila* scraps gene ('scraps intron') within predicted F1 transcript from position 1224-1286.

<223> Sequence of pLA3596 (SED ID NO. 145).

<***> Key features include:

1. TurboGreen-ubi-DsRed2 coding region with inserted Cctra intron.

<***> Cctra intron is from position 5947-7291 in TurboGreen-ubi-DsRed2.

<***> TurboGreen-ubi-DsRed2 alternatively spliced transcript starts in segment derived from baculovirus AcMNPV Ie1 (immediate early 1) at position ~4864 (Ie1 fragment is from 4264-4893).

<***> TurboGreen-ubi-DsRed2 F1 transcript is predicted to be translated between 4995-8148, inclusive of start and stop codon (TurboGreen is from 4995-5777; SG4 linker is from 5778-5807; ubiquitin is from 5808-7380, inclusive of Cctra intron; DsRed2 is from 7381-8151).

<***> Included feature:

1. additional intron derived from *Drosophila* scraps gene ('scraps intron') within predicted F1 transcript from position 4908-4970.

2. intended amino acid mutation compared to LA3488 at position 7294-7296.

The invention claimed is:

1. A polynucleotide expression system capable of expressing a functional protein in an insect, comprising:

a heterologous polynucleotide sequence encoding a functional protein, the coding sequence of which is defined between a start codon and a stop codon;

a promoter capable of initiating transcription in the insect operably linked to the heterologous polynucleotide sequence; and a splice control sequence, which, in cooperation with a spliceosome in the insect or its offspring, is capable of sex-specifically mediating in the insect or its offspring (i) a first splicing of an RNA transcript of the polynucleotide sequence to produce a first spliced mRNA product, which does not comprise a continuous open reading frame extending from the start codon to the stop codon, and (ii) an alternative splicing of said RNA transcript to yield an alternatively spliced mRNA product, which comprises a continuous open reading frame extending from the start codon to the stop codon, wherein the splice control sequence comprises a core consensus sequence of WWCRAT, wherein W=A or T and R=A or G, or its RNA equivalent and said protein has a lethal effect.

2. The polynucleotide expression system of claim 1, wherein said coding sequence comprises two or more coding exons for the functional protein.

3. The polynucleotide expression system of claim 1, wherein said lethal effect is conditionally suppressible.

4. The polynucleotide expression system of claim 1, wherein said functional protein is selected from the group consisting of an apoptosis-inducing factor, Hid, Reaper (Rpr), and Nipp1Dm.

5. The polynucleotide expression system of claim 1, wherein the functional protein serves as a positive transcriptional control factor for the promoter, such that the functional protein or its expression is controlled by a positive feedback mechanism.

6. The polynucleotide expression system of claim 5, wherein the system further comprises an enhancer associated with said promoter, wherein the functional protein is capable of enhancing activity of the promoter via the enhancer.

7. The polynucleotide expression system of claim 6, wherein the functional protein is a tTA gene product or an analogue thereof and the enhancer comprises one or more tetO operator units operably linked with the promoter.

8. The polynucleotide expression system of claim 1, wherein said functional protein is a transcriptional transactivator selected from the group consisting of tTAV, tTAV2, and tTAV3.

9. The polynucleotide expression system of claim 1, wherein said promoter is activated by environmental conditions.

10. The polynucleotide expression system of claim 1, further comprising an enhancer.

11. The polynucleotide expression system of claim 1, wherein the splice control sequence is derived from a tra intron.

12. The polynucleotide expression system of claim 11, wherein said splice control sequence is derived from the Medfly transformer gene Cctra.

13. The polynucleotide expression system of claim 1, wherein said system comprises a nucleotide sequence selected from the group consisting of SEQ ID NOs: 46-48, 50-56, 106, 143-145, and 151-162.

14. The polynucleotide expression system of claim 1, wherein said splice control sequence is intronic and comprises, on its 5' end, guanine (G) nucleotide, in RNA.

15. The polynucleotide expression system of claim 1, wherein said splice control sequence is intronic and has UG nucleotides flanking its 5' end and GU nucleotides flanking its 3' end, in RNA.

16. The polynucleotide expression system of claim 1, wherein said sex-specific mediation is controlled by binding of a TRA protein, a TRA/TRA2 protein complex, or homolog or homologues thereof.

17. The polynucleotide expression system of claim 1, wherein the splice control sequence is not present in the alternatively spliced mRNA product.

18. The polynucleotide expression system of claim 1, wherein said insect is from the Order Diptera.

19. The polynucleotide expression system of claim 18, wherein said insect is a tephritid fruit fly selected from the group consisting of: Medfly (*Ceratitis capitata*), Mexfly (*Anastrepha ludens*), Oriental fruit fly (Bactrocera *dorsalis*), Olive fruit fly (*Bactrocera oleae*), Melon fly (*Bactrocera cucurbitae*), Natal fruit fly (*Ceratitis* rosa), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), and West Indian fruit fly (*Anastrepha obliqua*).

20. The polynucleotide expression system of claim 18, wherein said insect is a mosquito from the genera *Stegomyia, Aedes, Anopheles*, or *Culex.*

21. The polynucleotide expression system of claim 20, wherein said mosquito is selected from *Aedes aegypti, Aedes albopictus, Anopheles stephensi, Anopheles albimanus*, and *Anopheles gambiae.*

22. The polynucleotide expression system of claim 1, wherein said insect is selected from the group consisting of: the New World screwworm (*Cochliomyia hominivorax*), the Old World screwworm (*Chrysomya bezziana*), Australian sheep blowfly (*Lucilia cuprina*), codling moth (*Cydia pomonella*), the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*), the rice stem borer (*Tryporyza incertulas*), the noctuid moths, Heliothinae, the Japanese beetle (*Papilla japonica*), White-fringed beetle (*Graphognatus* spp.), Boll weevil (*Anthonomous grandis*), corn root worm (*Diabrotica* spp.), and Colorado potato beetle (*Leptinotarsa decemlineata*).

23. The polynucleotide expression system of claim 18, wherein said insect is not a Drosphilid.

24. A method of population control of an insect in a natural environment therefor, comprising:

i) breeding a stock of the insect, the insect carrying a gene expression system comprising the system of claim 1, wherein the effect of the protein is dominantly lethal; and ii) distributing the said stock insect into the environment, whereby individual stock insects breed with insects of the opposite sex to produce offspring expressing the functional protein.

25. The method of claim 24, wherein the method achieves population control through early stage lethality in one or more of the offspring, which lethality occurs early in development.

26. The method of claim 25, wherein said early stage lethality is embryonic or before sexual maturity.

27. The method of claim 24, wherein expression of the functional protein under the control of a repressible transactivator protein, wherein the breeding is carried out under permissive conditions in the presence of a substance that is absent from the natural environment and capable of repressing said transactivator, whereby the lethal effect is conditional.

28. A method of biological control, comprising:

i) breeding a stock of male and female insects transformed with the system of claim 1 under permissive conditions, allowing the survival of male and female insects from the stock; and ii) releasing insects from the stock into the environment at a locus for biological control, whereby individual insects breed with insects of the opposite sex in the wild-type population to produce offspring expressing the functional protein, thereby achieving biological control.

29. A method of sex separation comprising:

i) breeding a stock of male and female insects transformed with the expression system of claim 1 under permissive or restrictive conditions, allowing the survival of males and females; and ii) removing the permissive or restrictive conditions to induce the lethal effect of the lethal gene in one sex and not the other by sex-specific alternative splicing of the lethal gene.

30. A method or biological or population control comprising:

i) breeding a stock of male and female insects transformed with the gene expression system of claim 1 under permissive or restrictive conditions, allowing the survival of males and females;

ii) removing the permissive or restrictive conditions to induce the lethal effect of the lethal gene in one sex and not the other by sex-specific alternative splicing of the lethal gene to achieve sex separation;

iii) sterilising or partially sterilising the separated individuals; and iv) achieving said control through release of the separated sterile or partially sterile individuals in to the natural environment of the insect.

31. The polynucleotide expression system of claim 9, wherein the environmental conditions comprise (i) the presence or absence of tetracycline or (ii) temperature.

32. The polynucleotide expression system of claim 1, wherein the functional protein is capable of positively controlling transcription from the promoter.

33. The polynucleotide expression system of claim 1, wherein the splice control sequence comprises the portion of a tra gene that is spliced out in splicing to generate the tra F1 mRNA product.

34. The polynucleotide expression system of claim 33, wherein the tra gene is a non-Drosophilid tra gene.

35. The polynucleotide expression system of claim 34, wherein the tra gene is the Medfly transformer gene Cctra.

36. The polynucleotide expression system of claim 1, wherein:

the system further comprises a binding sequence for a repressible transactivator protein, which transactivator protein is repressible by tetracycline or an analog or derivative thereof, wherein the transactivator protein positively controls expression from the promoter; and the splice control sequence comprises the portion of a tra gene that is spliced out in splicing to generate the tra F1 mRNA product.

37. The polynucleotide of claim 36, wherein the tra gene is the Medfly transformer gene Cctra.

38. The polynucleotide expression system of claim 1, wherein the repressible transactivator protein is the functional protein.

39. The polynucleotide expression system of claim 1, wherein:

the functional protein is a tTA gene product or an analogue thereof;

the system further comprises a tetO operator unit operably linked with the promoter; and the splice control sequence comprises the portion of a tra gene that is spliced out in splicing to generate the tra F1 mRNA product.

40. The polynucleotide expression system of claim 39, wherein the tra gene is the Medfly transformer gene Cctra.

41. The polynucleotide expression system of claim 1, wherein the system comprises the sequence of SEQ ID NO: 51.

42. The method of claim 28, further comprising, prior to step (ii), imposing or permitting restrictive conditions to cause death of insects of one sex, whereby only insects of the other sex are released in step (ii).

43. The polynucleotide expression system of claim 1, wherein the splice control sequence comprises the nucleotide sequence of SEQ ID NO: 1 (TCWWCRATCAACA, wherein W =A or T and R=A or G) or its RNA equivalent.

* * * * *